US011332733B2

(12) United States Patent
Seth et al.

(10) Patent No.: US 11,332,733 B2
(45) **Date of Patent: *May 17, 2022**

(54) MODIFIED COMPOUNDS AND USES THEREOF

(71) Applicant: Ionis Pharmaceuticals, Inc., Carlsbad, CA (US)

(72) Inventors: Punit P. Seth, Carlsbad, CA (US); Michael Oestergaard, Carlsbad, CA (US); Michael T. Migawa, Carlsbad, CA (US); Xue-hai Liang, Del Mar, CA (US); Wen Shen, Carlsbad, CA (US); Stanley T. Crooke, Carlsbad, CA (US); Eric E. Swayze, Encinitas, CA (US)

(73) Assignee: Ionis Pharmaceuticals, Inc., Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/968,701

(22) PCT Filed: Feb. 12, 2019

(86) PCT No.: PCT/US2019/017725
§ 371 (c)(1),
(2) Date: Aug. 10, 2020

(87) PCT Pub. No.: WO2019/157531
PCT Pub. Date: Aug. 15, 2019

(65) Prior Publication Data

US 2021/0017513 A1 Jan. 21, 2021

Related U.S. Application Data

(60) Provisional application No. 62/746,511, filed on Oct. 16, 2018, provisional application No. 62/742,265, filed on Oct. 5, 2018, provisional application No. 62/739,088, filed on Sep. 28, 2018, provisional application No. 62/713,698, filed on Aug. 2, 2018, provisional application No. 62/686,632, filed on Jun. 18, 2018, provisional application No. 62/629,632, filed on Feb. 12, 2018.

(51) Int. Cl.
*C07H 21/04* (2006.01)
*C12N 15/10* (2006.01)
*C12N 15/113* (2010.01)

(52) U.S. Cl.
CPC ............ *C12N 15/10* (2013.01); *C12N 15/113* (2013.01); *C12N 2310/315* (2013.01); *C12N 2310/3231* (2013.01)

(58) Field of Classification Search
None
See application file for complete search history.

(56) References Cited

U.S. PATENT DOCUMENTS

| | | | |
|---|---|---|---|
| 3,687,808 | A | 8/1972 | Merigan et al. |
| 4,751,219 | A | 6/1988 | Kempen |
| 4,845,205 | A | 7/1989 | Huynh Dinh et al. |
| 5,034,506 | A | 7/1991 | Summerton et al. |
| 5,130,302 | A | 7/1992 | Spielvogel et al. |
| 5,134,066 | A | 7/1992 | Rogers et al. |
| 5,166,315 | A | 11/1992 | Summerton et al. |
| 5,175,273 | A | 12/1992 | Bischofberger et al. |
| 5,185,444 | A | 12/1993 | Summerton et al. |
| 5,367,066 | A | 11/1994 | Urdea et al. |
| 5,432,272 | A | 7/1995 | Benner |
| 5,434,257 | A | 7/1995 | Matteucci |
| 5,457,187 | A | 10/1995 | Gmelner et al. |
| 5,457,191 | A | 10/1995 | Cook et al. |
| 5,459,255 | A | 10/1995 | Cook et al. |
| 5,484,908 | A | 1/1996 | Froehler et al. |
| 5,502,177 | A | 3/1996 | Matteucci et al. |
| 5,525,711 | A | 6/1996 | Hawkins et al. |
| 5,552,540 | A | 9/1996 | Haralambidis |
| 5,587,469 | A | 12/1996 | Cook et al. |
| 5,587,470 | A | 12/1996 | Cook et al. |
| 5,594,121 | A | 1/1997 | Froehler et al. |
| 5,596,091 | A | 1/1997 | Switzer |
| 5,614,617 | A | 3/1997 | Cook et al. |
| 5,645,985 | A | 7/1997 | Froehler et al. |
| 5,681,941 | A | 10/1997 | Cook et al. |
| 5,698,685 | A | 12/1997 | Summerton et al. |
| 5,750,692 | A | 5/1998 | Cook et al. |

(Continued)

FOREIGN PATENT DOCUMENTS

| | | |
|---|---|---|
| WO | WO 1994/022890 | 10/1994 |
| WO | WO/1997/020563 | 6/1997 |

(Continued)

OTHER PUBLICATIONS

Albaek et al., "Analogues of a Locked Nucleic Acid with Three-Carbon 2',4'-Linkages: Synthesis by Ring-Closing Metathesis and Influence of Nucleic Acid Duplex Stability" J. Org. Chem. (2006) 71:7731-7740.
Biessen et al., "Novel hepatotrophic prodrugs of the antiviral nucleoside 9-(2-phosphonylmethoxyethyl)adenine with improved pharmacokinetics and antiviral activity" FASEB J. (2000) 14(12):1784-1792.
Biessen et al., "Synthesis of Cluster Galactosides with High Affinity for the Hepatic Asialoglycoprotein Receptor" J Med Chem (1995) 38(9):1538-1546.
Biessen et al., "The cholesterol derivative of a triantennary galactoside with high affinity for the hepatic asialoglycoprotein receptor: a potent cholesterol lowering agent" J Med Chem (1995) 38(11):1846-1852.

(Continued)

*Primary Examiner* — Kimberly Chong
(74) *Attorney, Agent, or Firm* — McNeill Baur PLLC

(57) ABSTRACT

The present disclosure provides oligomeric compound comprising a modified oligonucleotide having a central region comprising one or more modifications. In certain embodiments, the present disclosure provides oligomeric compounds having an improved therapeutic index or an increased maximum tolerated dose.

20 Claims, No Drawings

Specification includes a Sequence Listing.

(56) References Cited

U.S. PATENT DOCUMENTS

| | | | |
|---|---|---|---|
| 5,763,588 | A | 6/1998 | Matteucci et al. |
| 5,808,027 | A | 9/1998 | Cook et al. |
| 5,811,534 | A | 9/1998 | Cook et al. |
| 5,830,653 | A | 11/1998 | Froehler et al. |
| 5,948,903 | A | 9/1999 | Cook et al. |
| 5,994,517 | A | 11/1999 | Ts'O |
| 6,005,096 | A | 12/1999 | Matteucci et al. |
| 6,166,199 | A | 12/2000 | Cook et al. |
| 6,268,490 | B1 | 7/2001 | Imanishi et al. |
| 6,300,319 | B1 | 10/2001 | Manoharan |
| 6,383,812 | B1 | 5/2002 | Chen et al. |
| 6,525,031 | B2 | 2/2003 | Manoharan |
| 6,525,191 | B1 | 2/2003 | Ramasamy |
| 6,620,916 | B1 | 9/2003 | Takahara et al. |
| 6,660,720 | B2 | 12/2003 | Manoharan |
| 6,670,461 | B1 | 12/2003 | Wengel et al. |
| 6,770,748 | B2 | 8/2004 | Imanishi et al. |
| 6,794,499 | B2 | 9/2004 | Wengel et al. |
| 6,906,182 | B2 | 6/2005 | Ts'o et al. |
| 6,908,903 | B1 | 6/2005 | Theodore et al. |
| 7,034,133 | B2 | 4/2006 | Wengel et al. |
| 7,053,207 | B2 | 5/2006 | Wengel et al. |
| 7,262,177 | B2 | 8/2007 | Ts'o et al. |
| 7,399,845 | B2 | 7/2008 | Seth et al. |
| 7,427,672 | B2 | 9/2008 | Imanishi et al. |
| 7,491,805 | B2 | 2/2009 | Vargeese et al. |
| 7,547,684 | B2 | 6/2009 | Seth et al. |
| 7,569,686 | B1 | 8/2009 | Bhat et al. |
| 7,572,582 | B2 | 8/2009 | Wengel et al. |
| 7,582,744 | B2 | 9/2009 | Manoharan et al. |
| 7,666,854 | B2 | 2/2010 | Seth et al. |
| 7,696,345 | B2 | 4/2010 | Allerson et al. |
| 7,723,509 | B2 | 5/2010 | Manoharan et al. |
| 7,741,457 | B2 | 6/2010 | Swayze et al. |
| 7,750,131 | B2 | 7/2010 | Seth et al. |
| 7,851,615 | B2 | 12/2010 | Manoharan et al. |
| 7,875,733 | B2 | 1/2011 | Bhat et al. |
| 7,939,677 | B2 | 5/2011 | Bhat et al. |
| 8,022,193 | B2 | 9/2011 | Swayze et al. |
| 8,030,467 | B2 | 10/2011 | Seth et al. |
| 8,034,909 | B2 | 10/2011 | Wengel et al. |
| 8,080,644 | B2 | 12/2011 | Wengel et al. |
| 8,088,746 | B2 | 1/2012 | Seth et al. |
| 8,088,904 | B2 | 1/2012 | Swayze et al. |
| 8,106,022 | B2 | 1/2012 | Manoharan et al. |
| 8,124,745 | B2 | 2/2012 | Allerson et al. |
| 8,137,695 | B2 | 3/2012 | Rozema et al. |
| 8,153,365 | B2 | 4/2012 | Wengel et al. |
| 8,158,601 | B2 | 4/2012 | Chen et al. |
| 8,268,980 | B2 | 9/2012 | Seth et al. |
| 8,278,283 | B2 | 10/2012 | Seth et al. |
| 8,278,425 | B2 | 10/2012 | Prakash et al. |
| 8,278,426 | B2 | 10/2012 | Seth et al. |
| 8,313,772 | B2 | 11/2012 | Rozema et al. |
| 8,344,125 | B2 | 1/2013 | Manoharan et al. |
| 8,349,308 | B2 | 1/2013 | Yurkovetskiy et al. |
| 8,404,862 | B2 | 3/2013 | Manoharan et al. |
| 8,435,491 | B2 | 5/2013 | Wang et al. |
| 8,440,803 | B2 | 5/2013 | Swayze et al. |
| 8,450,467 | B2 | 5/2013 | Manoharan et al. |
| 8,501,805 | B2 | 8/2013 | Seth et al. |
| 8,501,930 | B2 | 8/2013 | Rozema et al. |
| 8,530,640 | B2 | 9/2013 | Seth et al. |
| 8,541,548 | B2 | 9/2013 | Rozema |
| 8,546,556 | B2 | 10/2013 | Seth et al. |
| 8,552,163 | B2 | 10/2013 | Lee et al. |
| RE44,779 | E | 2/2014 | Imanishi et al. |
| 8,642,752 | B2 | 2/2014 | Swayze et al. |
| 8,796,437 | B2 | 8/2014 | Swayze et al. |
| 8,957,200 | B2 | 2/2015 | Seth et al. |
| 9,005,906 | B2 | 4/2015 | Swayze et al. |
| 9,012,421 | B2 | 4/2015 | Migawa et al. |
| 9,175,291 | B2 | 11/2015 | MacLeod et al. |
| 9,523,094 | B2 | 12/2016 | Hung |
| 9,550,988 | B2 | 1/2017 | Swayze |
| 9,695,418 | B2 | 7/2017 | Seth et al. |
| 9,752,142 | B2 | 9/2017 | Oestergaard et al. |
| 9,914,922 | B2 | 3/2018 | Freier et al. |
| 9,926,556 | B2 | 3/2018 | Wan et al. |
| 10,017,764 | B2 | 7/2018 | Freier et al. |
| 10,202,599 | B2 | 2/2019 | Seth et al. |
| 10,415,038 | B2 | 9/2019 | Guo et al. |
| 10,426,789 | B2 | 10/2019 | Murray et al. |
| 11,149,264 | B2 | 10/2021 | Seth et al. |
| 2003/0077829 | A1 | 4/2003 | Maclachlan |
| 2003/0119724 | A1 | 6/2003 | Ts'o et al. |
| 2003/0158403 | A1 | 8/2003 | Manoharan et al. |
| 2003/0175906 | A1 | 9/2003 | Manoharan et al. |
| 2005/0164235 | A1 | 7/2005 | Manoharan et al. |
| 2006/0148740 | A1 | 7/2006 | Platenburg et al. |
| 2006/0183886 | A1 | 8/2006 | Ts'o et al. |
| 2008/0039618 | A1 | 2/2008 | Allerson et al. |
| 2008/0108801 | A1 | 5/2008 | Manoharan et al. |
| 2008/0206869 | A1 | 8/2008 | Smith et al. |
| 2008/0281041 | A1 | 11/2008 | Rozema et al. |
| 2008/0281044 | A1 | 11/2008 | Monahan et al. |
| 2009/0203132 | A1 | 8/2009 | Swayze et al. |
| 2009/0203135 | A1 | 8/2009 | Forst et al. |
| 2009/0286973 | A1 | 11/2009 | Manoharan et al. |
| 2010/0240730 | A1 | 9/2010 | Beigelman et al. |
| 2011/0097264 | A1 | 4/2011 | Wang et al. |
| 2011/0097265 | A1 | 4/2011 | Wang et al. |
| 2011/0123520 | A1 | 5/2011 | Manoharan et al. |
| 2011/0207799 | A1 | 8/2011 | Rozema et al. |
| 2011/0269814 | A1 | 11/2011 | Manoharan et al. |
| 2012/0035115 | A1 | 2/2012 | Manoharan et al. |
| 2012/0095075 | A1 | 4/2012 | Manoharan et al. |
| 2012/0101148 | A1 | 4/2012 | Aking et al. |
| 2012/0128760 | A1 | 5/2012 | Manoharan et al. |
| 2012/0136042 | A1 | 5/2012 | Manoharan et al. |
| 2012/0157509 | A1 | 6/2012 | Hadwiger et al. |
| 2012/0165393 | A1 | 6/2012 | Rozema et al. |
| 2012/0230938 | A1 | 9/2012 | Rozema et al. |
| 2013/0004427 | A1 | 1/2013 | El-Sayed et al. |
| 2013/0109817 | A1 | 5/2013 | Yurkovetskiy et al. |
| 2013/0121954 | A1 | 5/2013 | Wakefield et al. |
| 2013/0178512 | A1 | 7/2013 | Manoharan et al. |
| 2013/0203836 | A1 | 8/2013 | Rajeev et al. |
| 2013/0236968 | A1 | 9/2013 | Manoharan et al. |
| 2014/0107330 | A1 | 4/2014 | Freier et al. |
| 2014/0303235 | A1 * | 10/2014 | Oestergaard ......... C12N 15/113 514/44 A |
| 2014/0309279 | A1 | 10/2014 | Oestergaard et al. |
| 2014/0323707 | A1 | 10/2014 | Seth et al. |
| 2015/0051389 | A1 | 2/2015 | Swayze et al. |
| 2015/0184153 | A1 | 7/2015 | Freier et al. |
| 2015/0191727 | A1 | 7/2015 | Migawa et al. |
| 2015/0267195 | A1 | 9/2015 | Seth et al. |
| 2015/0276208 | A1 | 10/2015 | Oestergaard et al. |
| 2016/0160280 | A1 | 6/2016 | Burel |
| 2016/0186175 | A1 | 6/2016 | Seth et al. |
| 2017/0044526 | A1 | 2/2017 | Wan et al. |
| 2017/0191064 | A1 | 7/2017 | Costa et al. |
| 2017/0327824 | A1 | 11/2017 | Oestergaard et al. |
| 2018/0002701 | A1 | 1/2018 | Iacone et al. |
| 2018/0023081 | A1 | 1/2018 | Hagedorn et al. |
| 2018/0161356 | A1 | 6/2018 | Olson et al. |
| 2018/0273577 | A1 | 9/2018 | Revenko et al. |
| 2019/0055564 | A1 | 2/2019 | Sanchez et al. |
| 2019/0265230 | A1 | 8/2019 | Gubler et al. |
| 2019/0383797 | A1 | 12/2019 | Olson et al. |
| 2020/0010831 | A1 | 1/2020 | Hagedorn et al. |
| 2020/0109451 | A1 | 4/2020 | Gubler et al. |
| 2020/0354720 | A1 | 11/2020 | Olson et al. |
| 2020/0362337 | A1 | 11/2020 | Dodart et al. |
| 2020/0362347 | A1 | 11/2020 | Olson et al. |
| 2020/0385727 | A1 | 12/2020 | Moller et al. |
| 2021/0261945 | A1 | 8/2021 | Seth et al. |

FOREIGN PATENT DOCUMENTS

| | | |
|---|---|---|
| WO | WO/1997/046098 | 12/1997 |
| WO | WO/1998/013381 | 4/1998 |
| WO | WO/1999/014226 | 3/1999 |

(56) References Cited

FOREIGN PATENT DOCUMENTS

| | | |
|---|---|---|
| WO | WO/2002/043771 | 6/2002 |
| WO | WO/2004/024757 | 3/2004 |
| WO | WO/2004/101619 | 11/2004 |
| WO | WO/2004/106356 | 12/2004 |
| WO | WO/2007/134181 | 11/2007 |
| WO | WO/2008/098788 | 8/2008 |
| WO | WO/2008/101157 | 8/2008 |
| WO | WO/2009/082607 | 7/2009 |
| WO | WO/2009/126933 | 10/2009 |
| WO | WO/2009/134487 | 11/2009 |
| WO | WO/2010/054406 | 5/2010 |
| WO | WO/2010/088537 | 8/2010 |
| WO | WO/2010/129709 | 11/2010 |
| WO | WO/2010/144740 | 12/2010 |
| WO | WO/2010/148013 | 12/2010 |
| WO | WO/2011/038356 | 3/2011 |
| WO | WO/2011/100131 | 8/2011 |
| WO | WO/2011/120053 | 9/2011 |
| WO | WO/2011/133876 | 10/2011 |
| WO | WO/2011/163121 | 12/2011 |
| WO | WO/2012/037254 | 3/2012 |
| WO | WO/2012/068187 | 5/2012 |
| WO | WO/2012/083046 | 6/2012 |
| WO | WO/2012/083185 | 6/2012 |
| WO | WO/2012/089352 | 7/2012 |
| WO | WO/2012/089602 | 7/2012 |
| WO | WO 2012/170347 | 12/2012 |
| WO | WO/2012/177947 | 12/2012 |
| WO | WO 2013/022966 | 2/2013 |
| WO | WO 2013/022967 | 2/2013 |
| WO | WO 2013/022984 | 2/2013 |
| WO | WO 2013/022990 | 2/2013 |
| WO | WO/2013/033230 | 3/2013 |
| WO | WO/2013/075035 | 5/2013 |
| WO | WO/2013/165816 | 11/2013 |
| WO | WO/2013/166121 | 11/2013 |
| WO | WO 2014/059341 | 4/2014 |
| WO | WO/2014/179620 | 11/2014 |
| WO | WO 2015/021457 | 2/2015 |
| WO | WO/2015/106128 | 7/2015 |
| WO | WO/2017/015555 | 1/2017 |
| WO | WO 2018/165564 | 9/2018 |
| WO | WO 2019/032607 | 2/2019 |
| WO | WO 2019/032612 | 2/2019 |
| WO | WO 2019/138057 | 7/2019 |
| WO | WO 2019/157531 | 8/2019 |
| WO | WO 2019/169219 | 9/2019 |
| WO | WO 2019/200172 | 10/2019 |
| WO | WO 2019/245957 | 12/2019 |
| WO | WO 2020/160336 | 8/2020 |
| WO | WO 2020/201339 | 10/2020 |
| WO | WO 2020/219983 | 10/2020 |
| WO | WO 2020/227691 | 11/2020 |

OTHER PUBLICATIONS

Braasch et al., "Novel Antisense and Peptide Nucleic Acid Strategies for Controlling Gene Expression" Biochemistry (2002) 41(14):4503-4510.

Burel et al., "Hepatotoxicity of high affinity gapmer antisense oligonucleotides is mediated by Rnase H1 dependent promiscuous reduction of very long pre-mRNA transcripts" Nucleic Acids Research (2015) 44(5):2093-2109.

Connolly et al., "Binding and endocytosis of cluster glycosides by rabbit hepatocytes. Evidence for a short-circuit pathway that does not lead to degradation." J Biol Chem (1982) 257(2):939-945.

Crooke et al., "Pharmacokinetic Properties of Several Novel Oligonucleotide Analogs in mice" J. Pharmacol. Exp. Ther. (1996) 277(2):923-937.

Crooke S.T., Ed., "Antisense Drug Technology, Second Edition" CRC Press (2008) 163-166 and 442-443.

Dieckmann, et al. "A Sensitive In Vitro Approach to Assess the Hybridization-Dependent Toxic Potential of High Affinity Gapmer Oligonucleotides" Molecular Therapy: Nucleic Acids (2018) 10: 45-54.

Detmer et al., "Substrates for Investigation of DNA Polymerase Function: Synthesis and Properties of 4'-C-Alkylated Oligonucleotides" European J. Org. Chem (2003) 10:1837-1846.

Duff et al., "Intrabody tissue-specific delivery of antisense conjugates in animals: ligand-linker-antisense oligomer conjugates." Methods Enzymol (2000) 313:297-321.

Englisch et al., "Chemically Modified Oligonucleotides as Probes and Inhibitors" Agnew Chem. Int. Ed. Engl. (1991) 30:613-629.

Freier et al., "The ups and downs of nucleic acid duplex stability: structure-stability studies on chemically-modified DNA:RNA duplexes" Nucleic Acids Research (1997) 25(22):4429-4443.

Frieden et al., "Expanding the design horizon of antisense oligonucleotides with alpha-L-LNA" Nucleic Acids Research (2003) 31(21):6365-6372.

International Search Report for PCT/US2019/017725 dated Apr. 15, 2019.

Jayaprakash et al., "Non-Nucleoside Building Blocks for Copper-Assisted and Copper-Free Click Chemistry for the Efficient Synthesis of RNA Conjugates" Org Lett (2010) 12:5410-5413.

Kabanov et al., "A new class of antivirals: antisense oligonucleotides combined with a hydrophobic substituent effectively inhibit influenza virus reproduction and synthesis of virus-specific proteins in MDCK cells" FEBS Lett. (1990) 259: 327-330.

Kasuya et al., "Ribonuclease H1-dependent hepatotoxicity caused by locked nucleic acid-modified gapmer antisense oligonucleotides" Scientific Reports (2016) 6:30377, 1-12.

Kato et al., "N-acetylgalactosamine incorporation into a peptide containing consecutive threonine residues by UDP-N-acetyl-D-galactosaminide:polypeptide N-acetylgalactosaminyltransferases" Glycobiol (2001) 11:821-829.

Khorev et al., "Trivalent, Gal/GalNAc-containing ligands designed for the asialoglycoprotein receptor." Bioorg Med Chem (2008) 16:5216-5231.

Kim et al., "Oligomeric glycopeptidomimetics bearing the cancer related TN-antigen" Tetrahedron Lett (1997) 38:3487-3490.

Kornilova et al., "Development of a fluorescence polarization binding assay for asialoglycoprotein receptor" Analyt Biochem (2012) 425:43-46.

Koshkin et al., "LNA (locked nucleic acids): Synthesis of the adenine, cytosine, guanine, 5-methylcytosine, thymine and uracil bicyclonucleoside monomers, oligomerisation, and unprecedented nucleic acid recognition" Tetrahedron (1998) 54:3607-3630.

Kroschwitz, "Polynucleotides" Concise Encyclopedia of Polymer Science and Engineering (1990) John Wiley & Sons, NY pp. 858-859.

Kumar et al., "The first analogues of LNA (locked nucleic acids): phosphorothioate-LNA and 2'-thio-LNA" Bioorg Med Chem Lett. (1998) 8:2219-2222.

Kumar et al., "Design, synthesis, biophysical and primer extension studies of novel acyclic butyl nucleic acid (BuNA)" Org. Biomol. Chem. (2013) 11:5853-5865.

Lee et al., "New synthetic cluster ligands for galactose/N-acetylgalactosamine-specific lectin of mammalian liver" Biochem (1984) 23:4255-4261.

Lee et al., "Facile Synthesis of a High-Affinity Ligand for Mammalian Hepatic Lectin Containing Three Terminal N-Acetylgalactosamine Residues" Bioconjug Chem (1997) 8(5):762-765.

Lee et al., "Protein microarrays to study carbohydrate-recognition events" Bioorg Med Chem Lett (2006) 16(19):5132-5135.

Lee et al., "New and more efficient multivalent glyco-ligands for asialoglycoprotein receptor of mammalian hepatocytes" Bioorg Med Chem (2011) 19(8):2494-2500.

Lee et al., "Preparation of cluster glycosides ofN-acetylgalactosamine that have subnanomolar binding constants towards the mammalian hepatic Gal/GalNAc-specific receptor" Glycoconjugate J (1987) 4(4):317-328.

(56) References Cited

OTHER PUBLICATIONS

Lee et al., "Synthesis of Multivalent Neoglyconjugates of MUC1 by the Conjugation of Carbohydrate-Centered, Triazole-Linked Glycoclusters to MUC1 Peptides Using Click Chemistry" J Org Chem (2012) 77:7564-7571.
Lee et al., "Synthesis of peptide-based trivalent scaffold for preparation of cluster glycosides." Methods Enzymol (2003) 362:38-43.
Letsinger et al., "Cholesteryl-conjugated oligonucleotides: Synthesis, properties, and activity as inhibitors of replication of human immunodeficiency virus in cell culture" PNAS (1989) 86:6553-6556.
Leumann et al., "DNA Analogues: From Supramolecular Principles to Biological Properties" Bioorganic & Medicinal Chemistry (2002) 10:841-854.
Maier et al., "Synthesis of Antisense Oligonucleotides Conjugated to a Multivalent Carbohydrate Cluster for Cellular Targeting," Bioconjugate Chemistry (2003) 14, 18-29.
Maierhofer et al., "Probing multivalent carbohydrate-lectin interactions by an enzyme-linked lectin assay employing covalently immobilized carbohydrates" Bioorg Med Chem (2007) 15(24):7661-7676.
Manoharan et al., "Chemical Modifications to Improve Uptake and Bioavailability of Antisense Oligonucleotides" Ann. N.Y. Acad. Sci. (1992) 660: 306-309.
Manoharan et al., "Introduction of a Lipophilic Thioether Tether in the Minor Groove of Nucleic Acids for Antisense Applications" Bioorg. Med. Chem. Lett. (1993) 3(12):2765-2770.
Manoharan et al., "Cholic Acid-Oligonucleotide Conjugates for Antisense Applications" Bioorg. Med. Chem. Lett. (1994) 4:1053-1060.
Manoharan et al., "Oligonucleotide Conjugates: Alteration of the Pharmacokinetic Properties of Antisense Agents" Nucleosides & Nucleotides (1995) 14(3-5):969-973.
Manoharan et al., "Lipidic Nucleic Acids" Tetrahedron Lett. (1995) 36(21):3651-3654.
Manoharan, "Oligonucleotide conjugates as potential antisense drugs with improved uptake, biodistribution, targeted delivery, and mechanism of action." Antisense Nucleic Acid Drug Dev (2002) 12(2):103-128.
Merwin et al., "Targeted Delivery of DNA Using YEE(GalNAcAH)3, a Synthetic Glycopeptide Ligand for the Asialoglycoprotein Receptor" Bioconjug Chem (1994) 5(6):612-620.
Mishra et al., "Improved leishmanicidal effect of phosphorotioate antisense oligonucleotides by LDL-mediated delivery" Biochim. Biophys. Acta (1995) 1264:229-237.
Morvan et al., "Sugar modified oligonucleotides. III (1). Synthesis, nuclease resistance and base pairing properties of α- and β-L-octathymidylates" Biochem Biophys Res Commun. (1990) 172(2):537-543.
Nishina et al., "Chimeric Antisense Oligonucleotide Conjugated to α-Tocopherol" Molecular Therapy Nucleic Acids (2015) 4(1):e220.
Nishina et al., "Efficient in vivo delivery of siRNA to the liver by conjugation of alpha-tocopherol." Molecular Therapy (2008) 16(4):734-740.
Oberhauser et al., "Effective incorporation of 2'-O-methyl-oligoribonucleotides into liposomes and enhanced cell association through modifications with thiocholesterol" Nucl. Acids Res. (1992) 20(3):533-538.
Oestergaard et al., "Rational design of antisense oligonucleotides targeting single nucleotide polymorphisms for potent and allele selective suppression of mutant Huntingtin in the CNS" Nucleic Acids Research (2013) 41(21): 9634-9650.
Oka et al., "An Oxazaphospholidine Approach for the Stereocontrolled Synthesis of Oligonucleoside Phosphorothioates" JACS (2003) 125(27):8307-8317.
Pavia et al., "Synthetic TN glycopeptide related to human glycophorin AM. High-field proton and carbon-13 nuclear magnetic resonance study." Int J Pep Protein Res. (1983) 22(5):539-548.
Pujol et al., "A sulfur tripod glycoconjugate that releases a high-affinity copper chelator in hepatocytes." Angew Chemie Int Ed Engl. (2012) 51(30):7445-7448.
Rajur et al., "Covalent Protein-Oligonucleotide Conjugates for Efficient Delivery of Antisense Molecules" Bioconjug Chem. (1997) 8(6):935-940.
Rensen et al., "Design and Synthesis of Novel N-Acetylgalactosamine-Terminated Glycolipids for Targeting of Lipoproteins to the Hepatic Asiaglycoprotein Receptor," J. Med. Chem. (2004) 47:5798-5808.
Rensen et al., "Stimulation of liver-directed cholesterol flux in mice by novel N-acetylgalactosamine-terminated glycolipids with high affinity for the asialoglycoprotein receptor." Arterioscler Thromb Vasc Biol. (2006) 26(1):169-175.
Rensen et al., "Determination of the Upper Size Limit for Uptake and Processing of Ligands by the Asialoglycoprotein Receptor on Hepatocytesin Vitro and in Vivo" J Biol Chem. (2001) 276:37577-37584.
Saison-Behmoaras et al., "Short modified antisense oligonucleotides directed against Ha-ras point mutation induce selective cleavage of the mRNA and inhibit T24 cells proliferation" EMBO J. (1991) 10(5):1111-1118.
Sanghvi, Chapter 15, Antisense Research and Applications, Crooke and Lebleu ed., CRC Press (1993).
Sato et al., "Glycoinsulins: Dendritic Sialyloligosaccharide-Displaying Insulins Showing a Prolonged Blood-Sugar-Lowering Activity" J Am Chem Soc. (2004) 126(43):14013-14022.
Shea et al., "Synthesis, hybridization properties and antiviral activity of lipid-oligodeoxynucleotide conjugates" Nucl. Acids Res. (1990) 18(13):3777-3783.
Singh et al., "LNA (locked nucleic acids): synthesis and high-affinity nucleic acid recognition" Chem. Commun. (1998) 4: 455-456.
Singh et al., "Synthesis of 2'-amino-LNA: A novel conformationally restricted high-affinity oligonucleotide analogue with a handle" J. Org. Chem. (1998) 63: 10035-10039.
Sliedregt et al., "Design and Synthesis of Novel Amphiphilic Dendritic Galactosides for Selective Targeting of Liposomes to the Hepatic Asialoglycoprotein Receptor" J Med Chem. (1999) 42(4):609-618.
Srivastava et al., "Five- and Six-Membered Conformationally Locked 2',4'-Carbocyclic ribo-Thymidines: Synthesis, Structure, and Biochemical Studies" J. Am. Chem. Soc. (2007) 129(26):8362-8379.
Svinarchuk et al., "Inhibition of HIV proliferation in MT-4 cells by antisense oligonucleotide conjugated to lipophilic groups" Biochimie (1993) 75:49-54.
Tomiya et al., "Liver-targeting of primaquine-(poly-γ-glutamic acid) and its degradation in rat hepatocytes" Bioorg Med Chem. (2013) 21(17):5275-5281.
Toyokuni et al., "Synthetic vaccines: I. Synthesis of multivalent Tn antigen cluster-lysyllysine conjugates" Tetrahedron Lett. (1990) 31(19):2673-2676.
Valentin et al., "Solid-phase synthesis of lysine-based cluster galactosides with high affinity for the asialoglycoprotein Receptor" Tetrahedron (1997) 53:759-770.
Van Rossenberg et al., "Stable polyplexes based on arginine-containing oligopeptides for in vivo gene delivery." Gene Ther. (2004) 11(5):457-464.
Wan et al. "Synthesis, biophysical properties and biological activity of second generation antisense oligonucleotides containing chiral phosphorothioate linkages" Nucleic Acids Res. (2014) 42:13456-13468.
Wang et al., "Cytotoxic and Mutagenic Properties of C3'-Epimeric Lesions of 2'-Deoxyribonucleosides in *Escherichia coli* Cells" Biochemistry (2017) 56(29): 3725-3732.
Westerlind et al., "Ligands of the asialoglycoprotein receptor for targeted gene delivery, part 1: Synthesis of and binding studies with biotinylated cluster glycosides containing N-acetylgalactosamine." Glycoconj J. (2004) 21(5):227-241.
Zhou et al., "Fine Tuning of Electrostatics around the Internucleotidic Phosphate through Incorporation of Modified 2',4'-Carbocyclic-LNAs and -ENAs Leads to Significant Modulation of Antisense Properties" J. Org. Chem. (2009) 74:118-134.

(56) References Cited

OTHER PUBLICATIONS

Migawa et al., "Site-specific replacement of phosphorothioate with alkyl phosphonate linkages enhances the therapeutic profile of gapmer ASOs by modulating interactions with cellular proteins" Nucleic Acids Research (2019) 47(11): 5465-6479.
Shen et al., "Chemical modification of PS-ASO therapeutics reduces cellular protein-binding and improves the therapeutic index", Nature Biotechnology (2019) 37(6): 640-650.

* cited by examiner

MODIFIED COMPOUNDS AND USES THEREOF

SEQUENCE LISTING

The present application is being filed along with a Sequence Listing in electronic format. The Sequence Listing is provided as a file entitled CORE0148USASEQ_ST25.txt created Aug. 4, 2020 which is 368 kb in size. The information in the electronic format of the sequence listing is incorporated herein by reference in its entirety.

FIELD

The present disclosure provides oligomeric compounds comprising a modified oligonucleotide having a central region comprising one or more modifications. In certain embodiments, the present disclosure provides oligomeric compounds having an improved therapeutic index or an increased maximum tolerated dose.

BACKGROUND

The principle behind antisense technology is that an antisense compound hybridizes to a target nucleic acid and modulates the amount, activity, and/or function of the target nucleic acid. For example, in certain instances, antisense compounds result in altered transcription or translation of a target. Such modulation of expression can be achieved by, for example, target RNA degradation or occupancy-based inhibition. An example of modulation of RNA target function by degradation is RNase H-based degradation of the target RNA upon hybridization with a DNA-like antisense compound. Another example of modulation of gene expression by target degradation is RNA interference (RNAi). RNAi refers to antisense-mediated gene silencing through a mechanism that utilizes the RNA-induced silencing complex (RISC). An additional example of modulation of RNA target function is by an occupancy-based mechanism such as is employed naturally by microRNA. MicroRNAs are small non-coding RNAs that regulate the expression of protein-coding RNAs. The binding of an antisense compound to a microRNA prevents that microRNA from binding to its messenger RNA targets, and thus interferes with the function of the microRNA. MicroRNA mimics can enhance native microRNA function. Certain antisense compounds alter splicing of pre-mRNA. Regardless of the specific mechanism, sequence-specificity makes antisense compounds attractive as tools for target validation and gene functionalization, as well as therapeutics to selectively modulate the expression of genes involved in the pathogenesis of disease.

Antisense technology is an effective means for modulating the expression of one or more specific gene products and can therefore prove to be uniquely useful in a number of therapeutic, diagnostic, and research applications. Chemically modified nucleosides may be incorporated into antisense compounds to enhance one or more properties, such as nuclease resistance, pharmacokinetics, or affinity for a target nucleic acid.

SUMMARY

The present disclosure provides oligomeric compounds and methods of using oligomeric compounds that comprise a modified oligonucleotide consisting of 14-23 linked nucleosides, wherein the modified oligonucleotide comprises a gapmer consisting of a 5'-region, a central region, and a 3'-region wherein:

the 5'-region consists of 2-5 linked modified nucleosides, wherein each nucleoside of the 5'-region comprises a 2'-modified furanosyl sugar moiety;

the 3'-region consists of 1-5 linked modified nucleosides, wherein each nucleoside of the 3'-region comprises a 2'-modified furanosyl sugar moiety;

the central region consists of 7-10 linked nucleosides, where each nucleoside of the central region comprises a sugar moiety selected from an unmodified 2'-β-D-deoxyribosyl sugar moiety and a modified sugar moiety; wherein the 3'- and 5'-most nucleosides of the central region each comprise a sugar moiety independently selected from a 2'-deoxyfuranosyl sugar moiety or a sugar surrogate; and wherein the central region comprises:

at least one altered nucleotide, comprising a modified internucleoside linkage other than phosphorothioate and/or a modified nucleobase other than 5-methylcytosine and/or a modified sugar moiety; and at least 6 nucleosides each comprising an unmodified 2'-β-D-deoxyribosyl sugar moiety.

In certain embodiments, oligomeric compounds are provided comprising a single conjugate group linked to the 5'-end. In certain embodiments, oligomeric compounds are provided comprising a single conjugate group linked to the 3'-end.

In certain embodiments, the oligomeric compounds provided herein have an increased maximum tolerated dose when administered to an animal compared to an otherwise identical oligomeric compound except that the otherwise identical oligomeric compound lacks the altered nucleotide in the central region.

In certain embodiments, the oligomeric compounds provided herein have an increased therapeutic index compared to an otherwise identical oligomeric compound except that the otherwise identical oligomeric compound lacks the altered nucleotide in the central region.

In certain embodiments, methods of inhibiting target RNA are provided comprising contacting one or more cells, a tissue or an animal with an oligomeric compound as provided herein wherein said oligomeric compound is complementary to a target RNA.

In certain embodiments, the cells are in a human. In certain embodiments, the target RNA is human RNA. In certain embodiments, the target is human mRNA. In certain embodiments, the target RNA is cleaved, thereby inhibiting its function.

In certain embodiments, in vitro methods of inhibiting gene expression are provided comprising contacting one or more cells or a tissue with an oligomeric compound as provided herein.

In certain embodiments, oligomeric compounds are provided for use in an in vivo method of inhibiting gene expression wherein the method comprises contacting one or more cells, a tissue or an animal with an oligomeric compound as provided herein.

In certain embodiments, oligomeric compounds are provided for use in medical therapy.

DETAILED DESCRIPTION

It is to be understood that both the foregoing general description and the following detailed description are exemplary and explanatory only and are not restrictive of the embodiments, as claimed. Herein, the use of the singular includes the plural unless specifically stated otherwise. As used herein, the use of "or" means "and/or" unless stated otherwise. Furthermore, the use of the term "including" as well as other forms, such as "includes" and "included", is not limiting.

The section headings used herein are for organizational purposes only and are not to be construed as limiting the subject matter described. All documents, or portions of documents, cited in this application, including, but not limited to, patents, patent applications, articles, books, treatises, and GenBank and NCBI reference sequence records are hereby expressly incorporated by reference for the portions of the document discussed herein, as well as in their entirety.

It is understood that the sequence set forth in each SEQ ID NO contained herein is independent of any modification to a sugar moiety, an internucleoside linkage, or a nucleobase. As such, compounds defined by a SEQ ID NO may comprise, independently, one or more modifications to a sugar moiety, an internucleoside linkage, or a nucleobase. Although the sequence listing accompanying this filing identifies each sequence as either "RNA" or "DNA" as required, in reality, those sequences may be modified with any combination of chemical modifications. One of skill in the art will readily appreciate that such designation as "RNA" or "DNA" to describe modified oligonucleotides is, in certain instances, arbitrary. For example, an oligonucleotide comprising a nucleoside comprising a 2'-OH(H) sugar moiety and a thymine base could be described as a DNA having a modified sugar (2'-OH in place of one 2'-H of DNA) or as an RNA having a modified base (thymine (methylated uracil) in place of an uracil of RNA). Accordingly, nucleic acid sequences provided herein, including, but not limited to those in the sequence listing, are intended to encompass nucleic acids containing any combination of natural or modified RNA and/or DNA, including, but not limited to such nucleic acids having modified nucleobases. By way of further example and without limitation, an oligomeric compound having the nucleobase sequence "ATCGATCG" encompasses any oligomeric compounds having such nucleobase sequence, whether modified or unmodified, including, but not limited to, such compounds comprising RNA bases, such as those having sequence "AUCGAUCG" and those having some DNA bases and some RNA bases such as "AUCGATCG" and oligomeric compounds having other modified nucleobases, such as "AT$^{m}$CGAUCG," wherein $^{m}$C indicates a cytosine base comprising a methyl group at the 5-position.

As used herein, "2'-deoxyfuranosyl sugar moiety" or "2'-deoxyfuranosyl sugar" means a furanosyl sugar moiety having two hydrogens at the 2'-position. 2'-deoxyfuranosyl sugar moieties may be unmodified or modified and may be substituted at positions other than the 2'-position or unsubstituted. A β-D-2'-deoxyribosyl sugar moiety or 2'-β-D-deoxyribosyl sugar moiety in the context of an oligonucleotide is an unsubstituted, unmodified 2'-deoxyfuranosyl and is found in naturally occurring deoxyribonucleic acids (DNA).

As used herein, "2'-modified" in reference to a furanosyl sugar moiety or nucleoside comprising a furanosyl sugar moiety means the furanosyl sugar moiety comprises a substituent other than H or OH at the 2'-position of the furanosyl sugar moiety. 2'-modified furanosyl sugar moieties include non-bicyclic and bicyclic sugar moieties and may comprise, but are not required to comprise, additional substituents at other positions of the furanosyl sugar moiety.

As used herein, "2'-ribo-F" indicates a 2'-fluororibose.

As used herein, "2'-substituted" in reference to a furanosyl sugar moiety or nucleoside comprising a furanosyl sugar moiety means the furanosyl sugar moiety or nucleoside comprising the furanosyl sugar moiety comprises a substituent other than H or OH at the 2'-position and is a non-bicyclic furanosyl sugar moiety. 2'-substituted furanosyl sugar moieties do not comprise additional substituents at other positions of the furanosyl sugar moiety other than a nucleobase and/or internucleoside linkage(s) when in the context of an oligonucleotide.

As used herein, "4'-modified" in reference to a furanosyl sugar moiety or nucleoside comprising a furanosyl sugar moiety means the furanosyl sugar moiety comprises a substituent other than H at the 4'-position of the furanosyl sugar moiety. 4'-modified furanosyl sugar moieties include non-bicyclic and bicyclic sugar moieties and may but are not required to comprise additional substituents at other positions of the furanosyl sugar moiety.

As used herein, "4'-substituted" in reference to a furanosyl sugar moiety or nucleoside comprising a furanosyl sugar moiety means the furanosyl sugar moiety or nucleoside comprising the furanosyl sugar moiety comprises a substituent other than H at the 4'-position and is a non-bicyclic furanosyl sugar moiety. 4'-substituted furanosyl sugar moieties do not comprise additional substituents at other positions of the furanosyl sugar moiety other than a nucleobase and/or internucleoside linkage(s) when in the context of an oligonucleotide.

As used herein, "5'-modified" in reference to a furanosyl sugar moiety or nucleoside comprising a furanosyl sugar moiety means the furanosyl sugar moiety comprises a substituent other than H at the 5'-position of the furanosyl sugar moiety. 5'-modified furanosyl sugar moieties may but are not required to comprise additional substituents at other positions of the furanosyl sugar moiety.

As used herein, "5'-substituted" in reference to a furanosyl sugar moiety or nucleoside comprising a furanosyl sugar moiety means the furanosyl sugar moiety or nucleoside comprising the furanosyl sugar moiety comprises a substituent other than H at the 5'-position and is a non-bicyclic furanosyl sugar moiety. 5'-substituted furanosyl sugar moieties do not comprise additional substituents at other positions of the furanosyl sugar moiety other than a nucleobase and/or internucleoside linkage(s) when in the context of an oligonucleotide.

As used herein, "administration" or "administering" refers to routes of introducing a compound or composition provided herein to a subject to perform its intended function. Examples of routes of administration that can be used include, but are not limited to, administration by inhalation, subcutaneous injection, intrathecal injection, and oral administration.

As used herein, "administered concomitantly" or "co-administration" means administration of two or more compounds in any manner in which the pharmacological effects of both are manifest in the patient. Concomitant administration does not require that both compounds be administered in a single pharmaceutical composition, in the same dosage form, by the same route of administration, or at the same time. The effects of both compounds need not manifest themselves at the same time. The effects need only be overlapping for a period of time and need not be coextensive. Concomitant administration or co-administration encompasses administration in parallel, sequentially, separate, or simultaneous administration.

As used herein, "ALT" means alanine aminotransferase. As used herein, "AST" means aspartate transaminase. In certain embodiments, plasma levels of ALT and AST in a subject are measured in units per liter. As used herein, "units per liter" in the context of plasma ALT or plasma AST levels means international units per liter, the standard units for measurement of plasma ALT or plasma AST levels used by those of ordinary skill in the medical arts.

As used herein, "animal" refers to a human or non-human animal, including, but not limited to, mice, rats, rabbits, dogs, cats, pigs, and non-human primates, including, but not limited to, monkeys and chimpanzees.

As used herein, "antisense activity" means any detectable and/or measurable change attributable to the hybridization of an antisense compound to its target nucleic acid. In certain embodiments, antisense activity is a decrease in the amount or expression of a target nucleic acid or protein encoded by such target nucleic acid compared to target nucleic acid levels or target protein levels in the absence of the antisense compound.

As used herein, "antisense compound" means a compound comprising an antisense oligonucleotide and optionally one or more additional features, such as a conjugate group or terminal group.

As used herein, "antisense oligonucleotide" means an oligonucleotide having a nucleobase sequence that is at least partially complementary to a target nucleic acid.

As used herein, "ameliorate" in reference to a treatment means improvement in at least one symptom relative to the same symptom in the absence of the treatment. In certain embodiments, amelioration is the reduction in the severity or frequency of a symptom or the delayed onset or slowing of progression in the severity or frequency of a symptom.

As used herein, "bicyclic nucleoside" or "BNA" means a nucleoside comprising a bicyclic sugar moiety. As used herein, "bicyclic sugar" or "bicyclic sugar moiety" means a modified sugar moiety comprising two rings, wherein the second ring is formed via a bridge connecting two of the atoms in the first ring thereby forming a bicyclic structure. In certain embodiments, the first ring of the bicyclic sugar moiety is a furanosyl moiety, and the bicyclic sugar moiety is a modified furanosyl sugar moiety. In certain embodiments, the bicyclic sugar moiety does not comprise a furanosyl moiety.

As used herein, a "central nervous system target" is a target RNA that is expressed in the central nervous system.

As used herein, "cEt" or "constrained ethyl" means a bicyclic sugar moiety, wherein the first ring of the bicyclic sugar moiety is a ribosyl sugar moiety, the second ring of the bicyclic sugar is formed via a bridge connecting the 4'-carbon and the 2'-carbon, the bridge has the formula 4'-CH($CH_3$)—O-2', and the methyl group of the bridge is in the S configuration. A cEt bicyclic sugar moiety is in the β-D configuration.

As used herein, a "cEt nucleoside" or "cEt nucleotide" is a nucleoside or nucleotide comprising a cEt.

As used herein, "complementary" in reference to an oligonucleotide means that at least 70% of the nucleobases of such oligonucleotide or one or more regions thereof and the nucleobases of another nucleic acid or one or more regions thereof are capable of hydrogen bonding with one another when the nucleobase sequence of the oligonucleotide and the other nucleic acid are aligned in opposing directions. Complementary nucleobases are nucleobase pairs that are capable of forming hydrogen bonds with one another. Complementary nucleobase pairs include adenine (A) and thymine (T), adenine (A) and uracil (U), cytosine (C) and guanine (G), 5-methyl cytosine ($^{m}C$) and guanine (G). Complementary oligonucleotides and/or nucleic acids need not have nucleobase complementarity at each nucleoside. Rather, some mismatches are tolerated. As used herein, "fully complementary" or "100% complementary" in reference to oligonucleotides means that such oligonucleotides are complementary to another oligonucleotide or nucleic acid at each nucleoside of the oligonucleotide.

As used herein, "conjugate group" means a group of atoms that is directly or indirectly attached to an oligonucleotide. Conjugate groups may comprise a conjugate moiety and a conjugate linker that attaches the conjugate moiety to the oligonucleotide.

As used herein, "conjugate linker" means a group of atoms comprising at least one bond that connects a conjugate moiety to an oligonucleotide.

As used herein, "conjugate moiety" means a group of atoms that is attached to an oligonucleotide via a conjugate linker.

As used herein, "contiguous" or "adjacent" in the context of an oligonucleotide refers to nucleosides, nucleobases, sugar moieties, or internucleoside linkages that are immediately adjacent to each other independent of the other moieties of the oligonucleotide. For example, "contiguous nucleobases" means nucleobases that are immediately adjacent to each other in a sequence. Moieties that are "directly linked" are immediately adjacent to each other and not separated by any other type of moiety.

As used herein, "cytotoxic" or "cytotoxicity" in the context of an effect of an oligomeric compound or a parent oligomeric compound on cultured cells means an at least 2-fold increase in caspase activation following administration of 10 μM or less of the oligomeric compound or parent oligomeric compound to the cultured cells relative to cells cultured under the same conditions but that are not administered the oligomeric compound or parent oligomeric compound. In certain embodiments, cytotoxicity is measured using a standard in vitro cytotoxicity assay.

As used herein, "double-stranded antisense compound" means an antisense compound comprising two oligomeric compounds that are complementary to each other and form a duplex, and wherein one of the two said oligomeric compounds comprises an antisense oligonucleotide.

As used herein, "effective amount" means the amount of compound sufficient to effectuate a desired physiological outcome in a subject in need of the compound. The effective amount may vary among subjects depending on the health and physical condition of the subject to be treated, the taxonomic group of the subjects to be treated, the formulation of the composition, assessment of the subject's medical condition, and other relevant factors.

As used herein, "efficacy" means the ability to produce a desired effect.

As used herein, "expression" includes all the functions by which a gene's coded information is converted into structures present and operating in a cell. Such structures include, but are not limited to, the products of transcription and translation. As used herein, "modulation of expression" means any change in amount or activity of a product of transcription or translation of a gene. Such a change may be an increase or a reduction of any amount relative to the expression level prior to the modulation.

As used herein, "gapmer" means an oligonucleotide having a central region comprising a plurality of nucleosides that support RNase H cleavage positioned between a 5'-region and a 3'-region. Herein, the nucleosides of the 5'-region and 3'-region each comprise a 2'-modified furanosyl sugar moiety, and the 3'- and 5'-most nucleosides of the central region each comprise a sugar moiety independently selected from a 2'-deoxyfuranosyl sugar moiety or a sugar surrogate. The positions of the central region refer to the order of the nucleosides of the central region and are counted starting from the 5'-end of the central region. Thus, the 5'-most nucleoside of the central region is at position 1 of the central region. The "central region" may be referred to as a "gap", and the "5'-region" and "3'-region" may be referred to as "wings".

As used herein, "hepatotoxic" in the context of a mouse means a plasma ALT level that is above 300 units per liter. Hepatotoxicity of an oligomeric compound or parent oligomeric compound that is administered to a mouse is determined by measuring the plasma ALT level of the mouse 24 hours to 2 weeks following at least one dose of 1-150 mg/kg of the compound.

As used herein, "hepatotoxic" in the context of a human means a plasma ALT level that is above 150 units per liter. Hepatotoxicity of an oligomeric compound or parent oligomeric compound that is administered to a human is determined by measuring the plasma ALT level of the human 24 hours to 2 weeks following at least one dose of 10-300 mg of the compound.

As used herein, "hybridization" means the pairing or annealing of complementary oligonucleotides and/or nucleic acids. While not limited to a particular mechanism, the most common mechanism of hybridization involves hydrogen bonding, which may be Watson-Crick, Hoogsteen or reversed Hoogsteen hydrogen bonding, between complementary nucleobases.

As used herein, "inhibiting the expression or activity" refers to a reduction or blockade of the expression or activity relative to the expression or activity in an untreated or control sample and does not necessarily indicate a total elimination of expression or activity.

As used herein, the terms "internucleoside linkage" means a group or bond that forms a covalent linkage between adjacent nucleosides in an oligonucleotide. As used herein "modified internucleoside linkage" means any internucleoside linkage other than a naturally occurring, phosphodiester internucleoside linkage. "Phosphorothioate linkage" means a modified internucleoside linkage in which one of the non-bridging oxygen atoms of a phosphodiester is replaced with a sulfur atom. Modified internucleoside linkages may or may not contain a phosphorus atom. A "neutral internucleoside linkage" is a modified internucleoside linkage that does not have a negatively charged phosphate in a buffered aqueous solution at pH=7.0.

As used herein, "abasic nucleoside" means a sugar moiety in an oligonucleotide or oligomeric compound that is not directly connected to a nucleobase. In certain embodiments, an abasic nucleoside is adjacent to one or two nucleosides in an oligonucleotide.

As used herein, "LICA-1" is a conjugate group that is represented by the formula:

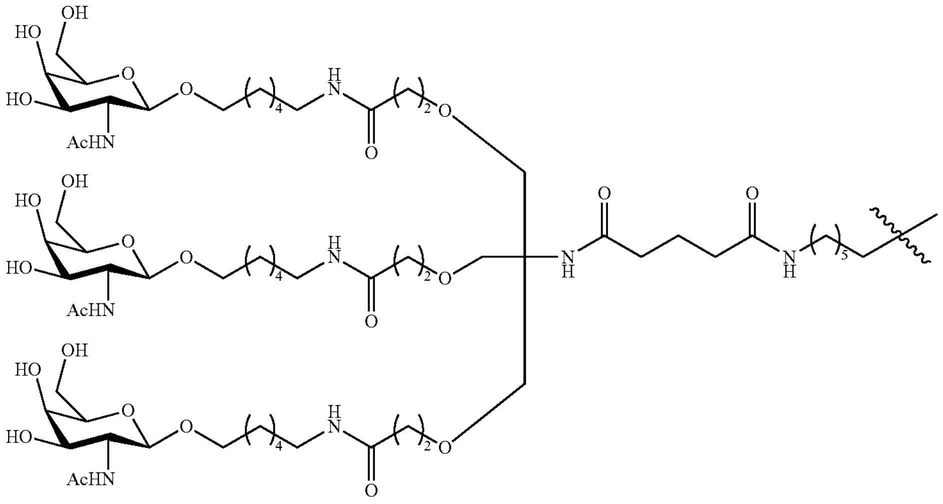

As used herein, "linker-nucleoside" means a nucleoside that links, either directly or indirectly, an oligonucleotide to a conjugate moiety. Linker-nucleosides are located within the conjugate linker of an oligomeric compound. Linker-nucleosides are not considered part of the oligonucleotide portion of an oligomeric compound even if they are contiguous with the oligonucleotide.

As used herein, "non-bicyclic sugar" or "non-bicyclic sugar moiety" means a sugar moiety that comprises fewer than 2 rings. Substituents of modified, non-bicyclic sugar moieties do not form a bridge between two atoms of the sugar moiety to form a second ring.

As used herein, "linked nucleosides" are nucleosides that are connected in a continuous sequence (i.e. no additional nucleosides are present between those that are linked).

As used herein, "liver target" is a target RNA expressed in the liver wherein modulation of the expression of the target RNA in the liver is desired for therapeutic benefit. In certain embodiments, a liver target is expressed in tissues other than the liver as well as in the liver. As used herein, modulation of the expression of a target RNA that is "not a liver target" is desired in a tissue that is not the liver for therapeutic benefit. In certain embodiments, a target RNA that is not a liver target is expressed in the liver and is modulated by an oligomeric compound in therapy.

As used herein, "mismatch" or "non-complementary" means a nucleobase of a first oligonucleotide that is not complementary with the corresponding nucleobase of a second oligonucleotide or target nucleic acid when the first and second oligomeric compound are aligned.

As used herein, "modulating" refers to changing or adjusting a feature in a cell, tissue, organ or organism.

As used herein, "MOE" means methoxyethyl. "2'-MOE" or "2'-O-methoxyethyl" means a 2'-$OCH_2CH_2OCH_3$ group at the 2'-position of a furanosyl ring. In certain embodiments, the 2'-$OCH_2CH_2OCH_3$ group is in place of the 2'-OH group of a ribosyl ring or in place of a 2'-H in a 2'-deoxyribosyl ring.

As used herein, "MOP" or "methoxypropyl internucleoside linkage" means the alkyl phosphonate internucleoside bond shown below:

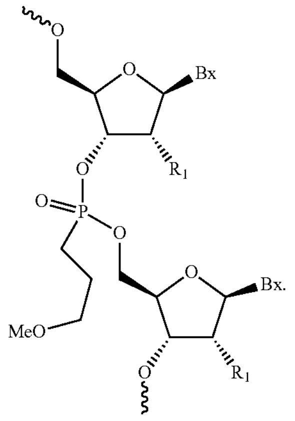

MOP
(alkyl phosphonate)

As used herein, "motif" means the pattern of unmodified and/or modified sugar moieties, nucleobases, and/or internucleoside linkages, in an oligonucleotide.

As used herein, "naturally occurring" means found in nature.

As used herein, "nucleobase" means an unmodified nucleobase or a modified nucleobase. As used herein an "unmodified nucleobase" is adenine (A), thymine (T), cytosine (C), uracil (U), or guanine (G). As used herein, a modified nucleobase is a group of atoms capable of pairing with at least one unmodified nucleobase. A universal base is a nucleobase that can pair with any one of the five unmodified nucleobases. 5-methylcytosine (NC) is one example of a modified nucleobase.

As used herein, "nucleobase sequence" means the order of contiguous nucleobases in a nucleic acid or oligonucleotide independent of any sugar moiety or internucleoside linkage modification.

As used herein, "nucleoside" means a moiety comprising a nucleobase and a sugar moiety. The nucleobase and sugar moiety are each, independently, unmodified or modified. As used herein, "modified nucleoside" means a nucleoside comprising a modified nucleobase and/or a modified sugar moiety.

As used herein, "oligomeric compound" means a compound consisting of an oligonucleotide and optionally one or more additional features, such as a conjugate group or terminal group.

As used herein, "oligonucleotide" means a strand of linked nucleosides connected via internucleoside linkages, wherein each nucleoside and internucleoside linkage may be modified or unmodified. Unless otherwise indicated, oligonucleotides consist of 8-50 linked nucleosides. As used herein, "modified oligonucleotide" means an oligonucleotide, wherein at least one nucleoside or internucleoside linkage is modified. As used herein, "unmodified oligonucleotide" means an oligonucleotide that does not comprise any nucleoside modifications or internucleoside modifications.

As used herein, "parent oligomeric compound" in the context of an oligomeric compound comprising at least one modification in the central region other than phosphorothioate or 5-methylcytosine means an oligomeric compound that is identical to the oligomeric compound comprising the at least one modification in the central region except that the parent oligomeric compound does not comprise at least one modified internucleoside linkage other than phosphorothioate and/or at least one modified nucleoside comprising a modified nucleobase other than 5-methylcytosine and/or a modified sugar moiety. A parent oligomeric compound and its counterpart oligomeric compound comprising at least one modification in the central region have identical nucleobase sequences or differ in nucleobase sequence only due to inclusion of a modified nucleobase other than 5-methylcytosine in the oligomeric compound comprising at least one modification in the central region.

As used herein, "pharmaceutically acceptable carrier or diluent" means any substance suitable for use in administering to an animal. Certain such carriers enable pharmaceutical compositions to be formulated as, for example, liquids, powders, or suspensions that can be aerosolized or otherwise dispersed for inhalation by a subject. In certain embodiments, a pharmaceutically acceptable carrier or diluent is sterile water; sterile saline; or sterile buffer solution.

As used herein "pharmaceutically acceptable salts" means physiologically and pharmaceutically acceptable salts of compounds, such as oligomeric compounds, i.e., salts that retain the desired biological activity of the compound and do not impart undesired toxicological effects thereto.

As used herein "pharmaceutical composition" means a mixture of substances suitable for administering to a subject. For example, a pharmaceutical composition may comprise an antisense compound and an aqueous solution.

As used herein, "RNAi compound" means an antisense compound that acts, at least in part, through RISC or Ago2 to modulate a target nucleic acid and/or protein encoded by a target nucleic acid. RNAi compounds include, but are not limited to double-stranded siRNA, single-stranded RNA (ssRNA), and microRNA, including microRNA mimics. In certain embodiments, an RNAi compound modulates the amount, activity, and/or splicing of a target nucleic acid. The term RNAi compound excludes antisense oligonucleotides that act through RNase H.

As used herein, the term "single-stranded" in reference to an antisense compound means such a compound consisting of one oligomeric compound that is not paired with a second oligomeric compound to form a duplex. "Self-complementary" in reference to an oligonucleotide means an oligonucleotide that at least partially hybridizes to itself. A compound consisting of one oligomeric compound, wherein the oligonucleotide of the oligomeric compound is self-complementary, is a single-stranded compound. A single-stranded antisense or oligomeric compound may be capable of binding to a complementary oligomeric compound to form a duplex, in which case the compound would no longer be single-stranded.

As used herein, "standard cell assay" means any of the assays described in Examples 1-9, and reasonable variations thereof.

As used herein, "standard in vitro activity assay" means a procedure, as described in Example 1 herein, wherein expression is measured by RT-PCR in cultured cells expressing the target RNA following administration of an oligomeric compound to the cultured cells.

As used herein, "standard in vitro cytotoxicity assay" means a procedure, as described in Example 8 herein, wherein activation of caspases 3 and 7 is measured in cultured 3T3-L1 cells following administration of an oligomeric compound to the cells.

As used herein, "standard in vivo experiment" means the procedure described in Example 10 and reasonable variations thereof.

As used herein, "stereorandom" in the context of a compound or moiety comprising a chiral center means the chiral center has a random stereochemical configuration. For example, in a population of molecules of identical formula comprising a stereorandom chiral center, the number of molecules having the (5) configuration of the stereorandom chiral center may be but is not necessarily the same as the number of molecules having the (R) configuration of the stereorandom chiral center. The stereochemical configuration of a chiral center is considered random when it is the result of a synthetic method that is not designed to control the stereochemical configuration.

As used herein, "subject" means a human or non-human animal selected for treatment or therapy.

As used herein, "sugar moiety" means an unmodified sugar moiety or a modified sugar moiety. As used herein, "unmodified sugar moiety" means a β-D-ribosyl moiety, as found in naturally occurring RNA, or a β-D-2'-deoxyribosyl sugar moiety as found in naturally occurring DNA. As used herein, "modified sugar moiety" or "modified sugar" means a sugar surrogate or a furanosyl sugar moiety other than a β-D-ribosyl or a β-D-2'-deoxyribosyl. Modified furanosyl sugar moieties may be modified or substituted at a certain position(s) of the sugar moiety, or unsubstituted, and they may or may not have a stereoconfiguration other than β-D-ribosyl. Modified furanosyl sugar moieties include bicyclic sugars and non-bicyclic sugars. As used herein, "sugar surrogate" means a modified sugar moiety that does not comprise a furanosyl or tetrahydrofuranyl ring (is not a "furanosyl sugar moiety") and that can link a nucleobase to another group, such as an internucleoside linkage, conjugate group, or terminal group in an oligonucleotide. Modified nucleosides comprising sugar surrogates can be incorporated into one or more positions within an oligonucleotide and such oligonucleotides are capable of hybridizing to complementary oligomeric compounds or nucleic acids.

As used herein, "susceptible" in the context of a disease, disorder, condition, or symptom such as degeneration, damage, or elevated apoptosis means that a subject has a higher risk than the average risk for the general population for the disease, disorder, condition, or symptom.

As used herein, "target nucleic acid," "target RNA," "target RNA transcript" and "nucleic acid target" mean a nucleic acid that an oligomeric compound, such as an antisense compound, is designed to affect. In certain embodiments, an oligomeric compound comprises an oligonucleotide having a nucleobase sequence that is complementary to more than one RNA, only one of which is the target RNA of the oligomeric compound. In certain embodiments, the target RNA is an RNA present in the species to which an oligomeric compound is administered. As used herein, a "liver target" is a target RNA that is expressed in the liver, and modulation of expression of the target RNA in the liver provides a therapeutic effect. As used herein a "central nervous system target" is a target RNA that is expressed in the central nervous system, and modulation of expression of the target RNA in the central nervous system provides a therapeutic effect.

The present disclosure provides certain individual cellular, tissue, or organ targets. For example, a "macrophage target" or a "liver target." For each such individual target, modulation of the expression of the target RNA in the individual cellular, tissue, or organ target is desired for therapeutic benefit. In certain embodiments, modulation of the target RNA in an individual cellular, tissue, or organ target provides a therapeutic effect. In certain embodiments, a cellular, tissue, or organ target is expressed in tissues other than in a particular type of cell, tissue, or organ as well as being expressed in a particular type of cell, tissue, or organ. For example, certain target RNAs may be expressed in both a macrophage and a hepatocyte.

As used herein, "therapeutically effective amount" means an amount of a compound, pharmaceutical agent, or composition that provides a therapeutic benefit to a subject.

As used herein, "treat" refers to administering a compound or pharmaceutical composition to an animal in order to effect an alteration or improvement of a disease, disorder, or condition in the animal.

As used herein, "maximum tolerated dose" means the highest dose of a compound that does not cause unacceptable side effects. In certain embodiments, the maximum tolerated dose is the highest dose of a modified oligonucleotide that does not cause an ALT elevation of three times the upper limit of normal as measured by a standard assay, e.g. the assay of Example 12 or Example 1. In certain embodiments, the maximum tolerated dose is the highest dose of a modified oligonucleotide that does not cause caspase elevation of greater than 30,000 RLU as measured by a standard assay, e.g. the assay of Example 13, Example 8, or Example 4.

As used herein, "DNA isomer" means a nucleoside that comprises a modified sugar moiety that is a stereoisomer of β-D-2'-deoxyribosyl. As used herein, a "DNA isomer" does not include β-D-2'-deoxyribosyl nucleosides. Seven such isomers of 2'-β-D-deoxyribosyl exist: 2'-β-D-deoxyxylosyl (β-D-XNA), 2'-α-D-deoxyribosyl (α-D-DNA), 2'-α-L-deoxyribosyl (α-L-DNA), 2'-β-L-deoxyribosyl (β-L-DNA), 2'-α-D-deoxyxylosyl (α-L-XNA), 1, 2'-α-L-deoxyxylosyl (α-L-XNA), 2'-β-L-deoxyxylosyl (β-L-XNA). In certain embodiments, a DNA isomer is 2'-α-D-deoxyribosyl, 2'-α-L-deoxyribosyl, 2'-β-L-deoxyribosyl, or 2'-β-D-deoxyxylosyl sugar moiety. As used herein, "DNA isomer" does not include any nonfuranosyl sugar moieties.

As used herein, "DNA nucleoside" means a nucleoside comprising a 2'-H(H)β-D-2'-deoxyribosyl sugar moiety, as found in naturally-occurring DNA. A "DNA nucleoside" may comprise a modified nucleobase or a uracil nucleobase. A DNA nucleoside may be linked to adjacent nucleosides through unmodified phosphodiester internucleoside linkages or through modified internucleoside linkages.

As used herein, a "2'-modified DNA isomer" means a nucleoside that comprises a modified sugar moiety that is selected from 2'-β-D-deoxyxylosyl (β-D-XNA), 2'-α-D-deoxyribosyl (α-D-DNA), 2'-α-L-deoxyribosyl (α-L-DNA), 2'-β-L-deoxyribosyl (β-L-DNA), 2'-α-D-deoxyxylosyl (α-L-XNA), 1, 2'-α-L-deoxyxylosyl (α-L-XNA), 2'-β-L-deoxyxylosyl (β-L-XNA), and that further comprises a 2'-substituent. In certain embodiments, the 2'-substituent is fluoro, alkoxy, or $C_1$-$C_{10}$ alkyl.

As used herein, "DNA mimic" means a nucleoside other than a DNA nucleoside wherein the nucleobase is directly linked to a carbon atom of a ring bound to a second carbon atom within the ring, wherein the second carbon atom comprises a bond to at least one hydrogen atom, wherein the nucleobase and at least one hydrogen atom are trans to one another relative to the bond between the two carbon atoms. In certain embodiments, a DNA mimic comprises a structure represented by the formula:

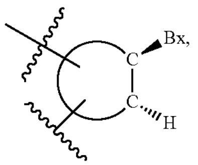

wherein Bx is a heterocylic base moiety, the ring contains 5-7 members, and the ring is attached at two positions to a hydroxyl, a phosphate, an internucleoside linking group, or a conjugate linker.

As used herein, a "standard RNase H cleavage assay" is an assay wherein a heteroduplex of the modified oligonucleotide and a complementary strand of unmodified RNA are incubated with each other to form a heteroduplex, and are then incubated with RNase H1 for specified time points before being analyzed on a polyacrylamide gel.

As used herein, a modified nucleoside "supports RNase H cleavage" when incorporated into an oligonucleotide if RNase H cleavage of the complementary RNA is observed within two nucleobases of the modified nucleoside in a standard RNase H cleavage assay.

As used herein, "therapeutic index" means a comparison of the amount of a compound that causes a therapeutic effect to the amount that causes toxicity. Compounds having a high therapeutic index have strong efficacy and low toxicity. In certain embodiments, increasing the therapeutic index of a compound increases the amount of the compound that can be safely administered. In certain embodiments, therapeutic index is the ratio of the amount of modulation of a target nucleic acid by a modified oligonucleotide compared to ALT elevation, wherein the ALT elevation is measured by a standard assay, e.g. the assay of Example 12 or Example 1. In certain embodiments, therapeutic index is the ratio of the amount of modulation of a target nucleic acid by a modified oligonucleotide compared to caspase elevation, wherein the caspase elevation is measured by a standard assay, e.g. the assay of Example 13, Example 8, or Example 4.

As used herein, an "altered nucleotide" is a nucleotide that comprises one or more modifications relative to a nucleotide comprising a 2'-β-D-deoxyribosyl sugar moiety, a nucleobase selected from adenine (A), thymine (T), cytosine (C), 5-methyl cytosine ($^{m}$C), uracil (U), or guanine (G), and a 5' to 3' internucleoside linkage selected from phosphodiester or stereorandom phosphorothioate. In certain embodiments, the altered nucleotide is an altered nucleoside attached to a phosphorothioate or phosphodiester internucleoside linkage. In certain embodiments, the altered nucleotide comprises a 2'-modified sugar moiety, or is a "2'-altered nucleotide". In certain embodiments, the altered nucleotide comprises a modified internucleoside linking group, and is a "linkage-altered nucleotide". Herein, a linkage-altered nucleotide comprises an internucleoside linking group other than phosphodiester or phosphorothioate attached to the 3' carbon of the sugar moiety, or the equivalent position for a sugar surrogate. The nucleotide on the 5'-end of an internucleoside linking group other than phosphodiester or phoshporothioate is not an "altered nucleotide", as used herein.

Certain embodiments are described in the numbered embodiments below:

1. An oligomeric compound comprising a modified oligonucleotide consisting of 14-23 linked nucleosides, wherein the modified oligonucleotide comprises a gapmer consisting of a 5'-region, a central region, and a 3'-region wherein:
   the 5'-region consists of 2-5 linked modified nucleosides, wherein each nucleoside of the 5'-region comprises a 2'-modified furanosyl sugar moiety;
   the 3'-region consists of 1-5 linked modified nucleosides, wherein each nucleoside of the 3'-region comprises a 2'-modified furanosyl sugar moiety;
   the central region consists of 7-10 linked nucleosides, where each nucleoside of the central region comprises a sugar moiety selected from an unmodified 2'-β-D-deoxyribosyl sugar moiety and a modified sugar moiety; wherein
   the 3'- and 5'-most nucleosides of the central region each comprise a sugar moiety independently selected from a 2'-deoxyfuranosyl sugar moiety or a sugar surrogate; and wherein the central region comprises:
   at least one modified internucleoside linkage other than phosphorothioate and/or at least one modified nucleoside comprising a modified nucleobase other than 5-methylcytosine and/or a modified sugar moiety; and
   at least 6 nucleosides each comprising an unmodified 2'-β-D-deoxyribosyl sugar moiety.
2. The oligomeric compound of embodiment 1, wherein the 5'-region consists of 2-4 linked nucleosides.
3. The oligomeric compound of embodiment 1, wherein the 5'-region consists of 2 linked nucleosides.
4. The oligomeric compound of embodiment 1, wherein the 5'-region consists of 3 linked nucleosides.
5. The oligomeric compound of embodiment 1, wherein the 5'-region consists of 4 linked nucleosides.
6. The oligomeric compound of embodiment 1, wherein the 5'-region consists of 5 linked nucleosides.
7. The oligomeric compound of any of embodiments 1-6, wherein each nucleoside of the 5'-region comprises a 2'-modified ribosyl sugar moiety.
8. The oligomeric compound of any of embodiments 1-7, wherein at least one nucleoside of the 5'-region comprises a bicyclic furanosyl sugar moiety.
9. The oligomeric compound of any of embodiments 1-8, wherein each nucleoside of the 5'-region comprises a bicyclic furanosyl sugar moiety.
10. The oligomeric compound of any of embodiments 1-8, wherein at least one nucleoside of the 5'-region comprises a non-bicyclic sugar moiety.
11. The oligomeric compound of embodiment 10, wherein the non-bicyclic sugar moiety of the at least one nucleoside of the 5'-region is a 2'-substituted ribosyl sugar moiety.
12. The oligomeric compound of any of embodiments 1-7 or 10-11, wherein each nucleoside of the 5'-region comprises a non-bicyclic sugar moiety.
13. The oligomeric compound of embodiment 12, wherein each nucleoside of the 5'-region comprises a 2'-substituted ribosyl sugar moiety.
14. The oligomeric compound of any of embodiments 1-7, wherein each nucleoside of the 5'-region comprises a 2'-modified furanosyl sugar moiety independently selected from a bicyclic sugar moiety and a non-bicyclic sugar moiety, 2'-substituted ribosyl sugar moiety.

15. The oligomeric compound of any of embodiments 8-11 or 14, wherein each bicyclic sugar moiety of the 5'-region is selected from among cEt, LNA, and ENA.

16. The oligomeric compound of any of embodiments 10-14, wherein each nonbicyclic sugar moiety of the 5'-region has a 2'-substituent selected from among 2'-MOE, 2'-OMe, and 2'-NMA.

17. The oligomeric compound of any of embodiments 1-16, wherein none of the nucleosides of the 5'-region comprise a sugar moiety having a 2'-F substituent.

18. The oligomeric compound of any of embodiments 1-17, wherein each nucleobase of the 5'-region is independently selected from among thymine, uracil, guanine, cytosine, 5-methylcytosine, and adenine.

19. The oligomeric compound of any of embodiments 1-18, wherein each internucleoside linkage of the 5'-region is selected from among phosphodiester and phosophorothioate internucleoside linkages.

20. The oligomeric compound of any of embodiments 1-19, wherein the 3'-region consists of 2-4 linked nucleosides.

21. The oligomeric compound of any of embodiments 1-19, wherein the 3'-region consists of 1 nucleoside.

22. The oligomeric compound of any of embodiments 1-19, wherein the 3'-region consists of 2 linked nucleosides.

23. The oligomeric compound of any of embodiments 1-19, wherein the 3'-region consists of 3 linked nucleosides.

24. The oligomeric compound of any of embodiments 1-19, wherein the 3'-region consists of 4 linked nucleosides.

25. The oligomeric compound of any of embodiments 1-19, wherein the 3'-region consists of 5 linked nucleosides.

26. The oligomeric compound of any of embodiments 1-25, wherein each nucleoside of the 3'-region comprises a 2'-modified ribosyl sugar moiety.

27. The oligomeric compound of any of embodiments 1-26, wherein at least one nucleoside of the 3'-region comprises a bicyclic furanosyl sugar moiety.

28. The oligomeric compound of any of embodiments 1-27, wherein each nucleoside of the 3'-region comprises a bicyclic furanosyl sugar moiety.

29. The oligomeric compound of any of embodiments 1-27, wherein at least one nucleoside of the 3'-region comprises a non-bicyclic sugar moiety.

30. The oligomeric compound of embodiment 29, wherein the non-bicyclic sugar moiety of the at least one nucleoside of the 3'-region is a 2'-substituted ribosyl sugar moiety.

31. The oligomeric compound of any of embodiments 1-26 or 29-30, wherein each nucleoside of the 3'-region comprises a non-bicyclic sugar moiety.

32. The oligomeric compound of embodiment 31, wherein each nucleoside of the 3'-region comprises a 2'-substituted ribosyl sugar moiety.

33. The oligomeric compound of any of embodiments 1-26, wherein each nucleoside of the 3'-region comprises a 2'-modified furanosyl sugar moiety independently selected from a bicyclic sugar moiety and a non-bicyclic sugar moiety, 2'-substituted ribosyl sugar moiety.

34. The oligomeric compound of any of embodiments 27-30 or 33, wherein each bicyclic sugar moiety of the 3'-region is selected from among cEt, LNA, and ENA.

35. The oligomeric compound of any of embodiments 29-33, wherein each nonbicyclic sugar moiety of the 3'-region has a 2'-substituent selected from among 2'-MOE, 2'-OMe, and 2'-NMA.

36. The oligomeric compound of any of embodiments 1-35, wherein none of the nucleosides of the 3'-region comprise a sugar moiety having a 2'-F substituent.

37. The oligomeric compound of any of embodiments 1-36, wherein each nucleobase of the 3'-region is independently selected from among thymine, uracil, guanine, cytosine, 5-methylcytosine, and adenine.

38. The oligomeric compound of any of embodiments 1-37, wherein each internucleoside linkage of the 3'-region is selected from among phosphodiester and phosophorothioate internucleoside linkages.

39. The oligomeric compound of any of embodiments 1-38, wherein the central region consists of 7 linked nucleosides.

40. The oligomeric compound of any of embodiments 1-38, wherein the central region consists of 8 linked nucleosides.

41. The oligomeric compound of any of embodiments 1-38, wherein the central region consists of 9 linked nucleosides.

42. The oligomeric compound of any of embodiments 1-38, wherein the central region consists of 10 linked nucleosides.

43. The oligomeric compound of any of embodiments 1-42, wherein each of the two internucleoside linkages connecting the central region to the 5'-region and 3'-region are independently selected from among phosphosdiester and phosphorothioate internucleoside linkages.

44. The oligomeric compound of any of embodiments 1-43, wherein the modified oligonucleotide consists of the gapmer.

45. The oligomeric compound of any of embodiments 1-43, comprising a conjugate group.

46. The oligomeric compound of any of embodiments 1-43 or 45, wherein the modified oligonucleotide comprises 1-3 linker nucleosides.

47. The oligomeric compound of embodiment 46, wherein the linker nucleosides are linked to the 5'-end or the 3'-end of the gapmer.

48. The oligomeric compound of any of embodiments 45-47, wherein the conjugate group comprises GalNAc.

49. The oligomeric compound of any of embodiments 45-47, comprising LICA-1.

50. The oligomeric compound of any of embodiments 1-49, wherein the central region comprises one, and no more than one, modified sugar moiety.

51. The oligomeric compound of embodiment 50, wherein the each internucleoside linkage within the central region is selected from among phosphodiester and phosophorothioate internucleoside linkages.

52. The oligomeric compound of any of embodiments 50-51, wherein each nucleobase of the central region is independently selected from among thymine, uracil, guanine, cytosine, 5-methylcytosine, and adenine.

53. The oligomeric compound of any of embodiments 1-50 or 52, wherein the central region comprises one, and no more than one, modified internucleoside linkage other than phosphorothioate.

54. The oligomeric compound of embodiment 53, wherein the modified internucleoside linkage other than phosphorothioate contains phosphorus.

55. The oligomeric compound of any of embodiments 53-54, wherein the modified internucleoside linkage other than phosphorothioate is a neutral internucleoside linkage.

56. The oligomeric compound of any of embodiments 1-50 or 52, wherein the central region comprises two, and no more than two, modified internucleoside linkages other than phosphorothioate.

57. The oligomeric compound of embodiment 56, wherein the two modified internucleoside linkages other than phosphorothioate each contain phosphorus.
58. The oligomeric compound of any of embodiments 56-57, wherein at least one of the modified internucleoside linkages other than phosphorothioate is a neutral internucleoside linkage.
59. The oligomeric compound of any of embodiments 56-57, wherein the two modified internucleoside linkages other than phosphorothioate are neutral internucleoside linkages.
60. The oligomeric compound of any of embodiments 1-51 or 53-59, wherein the central region comprises one, and no more than one, modified nucleobase other than 5-methylcytosine.
61. The oligomeric compound of any of embodiments 1-60, wherein each of the unmodified sugar moieties of the central region are 2'-β-D-deoxyribosyl sugar moieties.
62. The oligomeric compound of any of embodiments 50-61, wherein the one modified sugar moiety of the central region is at one of positions 2-9 of the central region.
63. The oligomeric compound of any of embodiments 50-61, wherein the one modified sugar moiety of the central region is at one of positions 1-6 of the central region.
64. The oligomeric compound of any of embodiments 50-61, wherein the one modified sugar moiety of the central region is at one of positions 1-4 of the central region.
65. The oligomeric compound of any of embodiments 50-61, wherein the one modified sugar moiety of the central region is at one of positions 2-4 of the central region.
66. The oligomeric compound of any of embodiments 50-61, wherein the one modified sugar moiety of the central region is at one of positions 3-4 of the central region.
67. The oligomeric compound of any of embodiments 50-66, wherein the one modified sugar moiety of the central region is a sugar surrogate, a bicyclic furanosyl sugar moiety, a non-bicyclic 2'-modified furanosyl sugar moiety, a non-bicyclic 4'-modified furanosyl sugar moiety, a non-bicyclic 5'-modified furanosyl sugar moiety, or a modified 2'-deoxyfuranosyl sugar moiety.
68. The oligomeric compound of embodiment 67, wherein the one modified sugar moiety of the central region is a bicyclic ribosyl sugar moiety, a non-bicyclic 2'-modified ribosyl sugar moiety, a non-bicyclic 4'-modified 2'-deoxyribosyl sugar moiety, a non-bicyclic 5'-modified 2'-deoxyribosyl sugar moiety, or a modified 2'-deoxyfuranosyl sugar moiety.
69. The oligomeric compound of embodiment 68, wherein the one modified sugar moiety of the central region is a bicyclic ribosyl sugar moiety, a non-bicyclic 2'-substituted ribosyl sugar moiety, a non-bicyclic 4'-substituted 2'-deoxyribosyl sugar moiety, a non-bicyclic 5'-substituted 2'-deoxyribosyl sugar moiety, or a modified, unsubstituted 2'-deoxyfuranosyl sugar moiety.
70. The oligomeric compound of any of embodiments 67-69, wherein the one modified sugar moiety of the central region is a 2'-substituted ribosyl sugar moiety.
71. The oligomeric compound of embodiment 70, wherein the 2'-substituted ribosyl sugar moiety is a 2'-F, 2'-MOE, or 2'-O-methyl substituted sugar moiety.
72. The oligomeric compound of any of embodiments 67-69, wherein the one modified sugar moiety of the central region is a 4'-alkyl substituted 2'-deoxyribosyl sugar moiety.
73. The oligomeric compound of embodiment 72, wherein the 4'-alkyl substituted ribosyl sugar moiety is a 4'-methyl substituted 2'-deoxyribosyl sugar moiety.
74. The oligomeric compound of any of embodiments 67-69, wherein the one modified sugar moiety of the central region is a 5'-alkyl substituted 2'-deoxyribosyl sugar moiety.
75. The oligomeric compound of embodiment 74, wherein the 5'-alkyl substituted ribosyl sugar moiety is a 5'-methyl, 5'-ethyl, or 5'-allyl substituted 2'-deoxyribosyl sugar moiety.
76. The oligomeric compound of any of embodiments 67-69, wherein the one modified sugar moiety of the central region is a modified, unsubstituted 2'-deoxyfuranosyl sugar moiety.
77. The oligomeric compound of embodiment 76, wherein the modified, unsubstituted 2'-deoxyfuranosyl sugar moiety is an unsubstituted α-D-2'-deoxyribosyl, α-L-2'-deoxyribosyl, β-L-2'-deoxyribosyl, or β-D-2'-deoxyxylosyl sugar moiety.
78. The oligomeric compound of any of embodiments 67-69, wherein the one modified sugar moiety of the central region is a bicyclic ribosyl sugar moiety.
79. The oligomeric compound of embodiment 78, wherein the bicyclic ribosyl sugar moiety is cEt, LNA, or ENA.
80. The oligomeric compound of any of embodiments 67-69, wherein the one modified sugar moiety of the central region is a morpholino, cEt, 2'-F, 2'-O-Methyl, 2'-MOE, 4'-Methyl, 5'-Methyl, 5'-allyl, 5'-ethyl, β-L-2'-deoxyribosyl, α-D-2'-deoxyribosyl, β-D-2'-deoxyxylosyl, or α-L-2'-deoxyribosyl sugar moiety.
81. The oligomeric compound of embodiment 62, wherein the one modified sugar moiety of the central region is a 2'-O-Methyl substituted ribosyl, unsubstituted α-D-2'-deoxyribosyl, unsubstituted α-L-2'-deoxyribosyl, or unsubstituted β-L-2'-deoxyribosyl sugar moiety.
82. The oligomeric compound of embodiment 81, wherein the one modified sugar moiety of the central region is a 2'-O-Methyl substituted ribosyl or unsubstituted β-L-2'-deoxyribosyl sugar moiety.
83. The oligomeric compound of embodiment 63, wherein the one modified sugar moiety of the central region is a morpholino, 2'-O-Methyl substituted ribosyl, unsubstituted α-D-2'-deoxyribosyl, or unsubstituted L-2'-deoxyribosyl sugar moiety sugar moiety.
84. The oligomeric compound of embodiment 64, wherein the one modified sugar moiety of the central region is a morpholino, unsubstituted α-D-2'-deoxyribosyl, or unsubstituted β-L-2'-deoxyribosyl sugar moiety sugar moiety.
85. The oligomeric compound of embodiment 65, wherein the one modified sugar moiety of the central region is a 2'-F substituted ribosyl, 2'-MOE substituted ribosyl, 2'-O-Methyl substituted ribosyl, 5'-(S)-Methyl substituted 2'-deoxyribosyl, 5'-allyl substituted 2'-deoxyribosyl, unsubstituted α-D-2'-deoxyribosyl, or cEt bicyclic sugar moiety.
86. The oligomeric compound of embodiment 85, wherein the one modified sugar moiety of the central region is a 2'-MOE substituted ribosyl, 2'-O-Methyl substituted ribosyl, or 5'-allyl substituted 2'-deoxyribosyl sugar moiety.

87. The oligomeric compound of embodiment 85 or 86, wherein the 5'-allyl substituted ribosyl sugar moiety is stereorandom at the 5'-position of the modified sugar moiety.
88. The oligomeric compound of embodiment 66, wherein the one modified sugar moiety of the central region is a 2'-F substituted ribosyl, 2'-MOE substituted ribosyl, 2'-O-Methyl substituted ribosyl, 4'-Methyl substituted 2'-deoxyribosyl, 5'-(S)-Methyl substituted 2'-deoxyribosyl, 5'-(R)-Methyl substituted 2'-deoxyribosyl, 5'-stereorandom Methyl substituted 2'-deoxyribosyl, 5'-(S)-Ethyl substituted 2'-deoxyribosyl, 5'-(R)-Ethyl substituted 2'-deoxyribosyl, 5'-stereorandom Ethyl 2'-deoxyribosyl, 5'-(S)-Allyl substituted 2'-deoxyribosyl, 5'-(R)-Allyl substituted 2'-deoxyribosyl, 5'-stereorandom allyl substituted 2'-deoxyribosyl, unsubstituted α-D-2'-deoxyribosyl, unsubstituted α-L-2'-deoxyribosyl, unsubstituted β-L-2'-deoxyribosyl, cEt, or morpholino sugar moiety.
89. The oligomeric compound of embodiment 88, wherein the one modified sugar moiety of the central region is a 2'-F substituted ribosyl, 2'-MOE substituted ribosyl, 2'-O-Methyl substituted ribosyl, 4'-Methyl substituted 2'-deoxyribosyl, 5'-(R)-Methyl substituted 2'-deoxyribosyl, 5'-(S)-Ethyl substituted 2'-deoxyribosyl, 5'-(R)-Ethyl substituted 2'-deoxyribosyl, 5'-(S)-Allyl substituted 2'-deoxyribosyl, 5'-(R)-Allyl substituted 2'-deoxyribosyl, 5'-stereorandom allyl substituted 2'-deoxyribosyl, unsubstituted β-L-2'-deoxyribosyl, cEt, or morpholino sugar moiety.
90. The oligomeric compound of any of embodiments 50-61 or 67-69, wherein the one modified sugar moiety of the central region is at position 1 of the central region.
91. The oligomeric compound of embodiment 90, wherein the one modified sugar moiety of the central region is a morpholino, unsubstituted β-L-2'-deoxyribosyl, or unsubstituted α-D-2'-deoxyribosyl sugar moiety.
92. The oligomeric compound of embodiment 90, wherein the one modified sugar moiety of the central region is a morpholino or unsubstituted α-D-2'-deoxyribosyl sugar moiety.
93. The oligomeric compound of any of embodiments 50-61 or 67-69, wherein the one modified sugar moiety of the central region is at position 2 of the central region.
94. The oligomeric compound of embodiment 93, wherein the one modified sugar moiety of the central region is a 2'-F substituted ribosyl, 2'-MOE substituted ribosyl, 2'-O-Methyl substituted ribosyl, 5'-(S)-Methyl substituted 2'-deoxyribosyl, 5'-Allyl substituted 2'-deoxyribosyl, unsubstituted α-D-2'-deoxyribosyl, or cEt sugar moiety.
95. The oligomeric compound of embodiment 93, wherein the one modified sugar moiety of the central region is a 2'-MOE substituted ribosyl, 2'-O-Methyl substituted ribosyl, 5'-(S)-Methyl substituted 2'-deoxyribosyl, 5'-Allyl substituted 2'-deoxyribosyl, or unsubstituted α-D-2'-deoxyribosyl sugar moiety.
96. The oligomeric compound of embodiment 94 or 95, wherein the 5'-allyl substituted 2'-deoxyribosyl sugar moiety is stereorandom at the 5'-position of the modified sugar moiety.
97. The oligomeric compound of any of embodiments 50-61 or 67-69, wherein the one modified sugar moiety of the central region is at position 3 of the central region.
98. The oligomeric compound of embodiment 97, wherein the one modified sugar moiety of the central region is a 2'-F substituted ribosyl, 2'-MOE substituted ribosyl, 2'-O-Methyl substituted ribosyl, 4'-Methyl substituted 2'-deoxyribosyl, 5'-(R)-Methyl substituted 2'-deoxyribosyl, 5'-(5)-Methyl substituted 2'-deoxyribosyl, 5'-(5)-Ethyl substituted 2'-deoxyribosyl, 5'-(R)-Ethyl substituted 2'-deoxyribosyl, 5'-(5)-Allyl substituted 2'-deoxyribosyl, 5'-(R)-Allyl substituted 2'-deoxyribosyl, 5'-stereorandom allyl substituted 2'-deoxyribosyl, unsubstituted β-L-2'-deoxyribosyl, unsubstituted β-D-2'-deoxyxylosyl, unsubstituted α-L-2'-deoxyribosyl, unsubstituted α-D-2'-deoxyribosyl, cEt, or morpholino sugar moiety.
99. The oligomeric compound of embodiment 97, wherein the one modified sugar moiety of the central region is a 2'-F substituted ribosyl, 2'-MOE substituted ribosyl, 2'-O-Methyl substituted ribosyl, 4'-Methyl substituted 2'-deoxyribosyl, 5'-(R)-Methyl substituted 2'-deoxyribosyl, 5'-(S)-Ethyl substituted 2'-deoxyribosyl, 5'-(R)-Ethyl substituted 2'-deoxyribosyl, 5'-(S)-Allyl substituted 2'-deoxyribosyl, 5'-(R)-Allyl substituted 2'-deoxyribosyl, 5'-stereorandom allyl substituted 2'-deoxyribosyl, unsubstituted β-L-2'-deoxyribosyl, unsubstituted β-D-2'-deoxyxylosyl, cEt, or morpholino sugar moiety.
100. The oligomeric compound of any of embodiments 50-61 or 67-69, wherein the one modified sugar moiety of the central region is at position 4 of the central region.
101. The oligomeric compound of embodiment 100, wherein the one modified sugar moiety of the central region is a 2'-F substituted ribosyl, 2'-MOE substituted ribosyl, 2'-O-Methyl substituted ribosyl, 4'-Methyl substituted 2'-deoxyribosyl, 5'-(R)-Methyl substituted 2'-deoxyribosyl, 5'-(S)-Methyl substituted 2'-deoxyribosyl, 5'-(S)-Ethyl substituted 2'-deoxyribosyl, 5'-(R)-Ethyl substituted 2'-deoxyribosyl, 5'-(S)-Allyl substituted 2'-deoxyribosyl, 5'-(R)-Allyl substituted 2'-deoxyribosyl, 5'-stereorandom allyl substituted 2'-deoxyribosyl, unsubstituted β-L-2'-deoxyribosyl, unsubstituted α-L-2'-deoxyribosyl, unsubstituted α-D-2'-deoxyribosyl, cEt, or morpholino sugar moiety.
102. The oligomeric compound of embodiment 100, wherein the one modified sugar moiety of the central region is a 2'-F substituted ribosyl, 2'-MOE substituted ribosyl, 2'-O-Methyl substituted ribosyl, 4'-Methyl substituted 2'-deoxyribosyl, 5'-(R)-Methyl substituted 2'-deoxyribosyl, 5'-(S)-Ethyl substituted 2'-deoxyribosyl, 5'-(R)-Ethyl substituted 2'-deoxyribosyl, 5'-(S)-Allyl substituted 2'-deoxyribosyl, 5'-(R)-Allyl substituted 2'-deoxyribosyl, 5'-stereorandom allyl substituted 2'-deoxyribosyl, unsubstituted L-2'-deoxyribosyl, unsubstituted α-L-2'-deoxyribosyl, unsubstituted α-D-2'-deoxyribosyl, cEt, or morpholino sugar moiety.
103. The oligomeric compound of any of embodiments 50-61 or 67-69, wherein the one modified sugar moiety of the central region is at position 5 of the central region.
104. The oligomeric compound of embodiment 103, wherein the one modified sugar moiety of the central region is a 2'-O-Methyl substituted ribosyl or unsubstituted β-L-2'-deoxyribosyl sugar moiety.
105. The oligomeric compound of embodiment 103, wherein the one modified sugar moiety of the central region is an unsubstituted β-L-2'-deoxyribosyl sugar moiety.
106. The oligomeric compound of any of embodiments 50-61 or 67-69, wherein the one modified sugar moiety of the central region is at position 6 of the central region.
107. The oligomeric compound of embodiment 106, wherein the one modified sugar moiety of the central region is a 2'-O-Methyl substituted ribosyl, unsubstituted β-L-2'-deoxyribosyl, unsubstituted α-D-2'-deoxyribosyl, or morpholino sugar moiety.

108. The oligomeric compound of any of embodiments 50-61 or 67-69, wherein the one modified sugar moiety of the central region is at position 7 of the central region.

109. The oligomeric compound of embodiment 108, wherein the one modified sugar moiety of the central region is a 2'-O-Methyl substituted ribosyl, unsubstituted β-L-2'-deoxyribosyl, or unsubstituted α-D-2'-deoxyribosyl sugar moiety.

110. The oligomeric compound of any of embodiments 50-61 or 67-69, wherein the one modified sugar moiety of the central region is at position 8 of the central region.

111. The oligomeric compound of embodiment 110, wherein the one modified sugar moiety of the central region is a 2'-O-Methyl substituted ribosyl, unsubstituted β-L-2'-deoxyribosyl, or unsubstituted α-D-2'-deoxyribosyl sugar moiety.

112. The oligomeric compound of any of embodiments 50-61 or 67-69, wherein the one modified sugar moiety of the central region is at position 9 of the central region.

113. The oligomeric compound of embodiment 112, wherein the one modified sugar moiety of the central region is a 2'-O-Methyl substituted ribosyl or unsubstituted β-L-2'-deoxyribosyl sugar moiety.

114. The oligomeric compound of any of embodiments 50-61 or 67-69, wherein the one modified sugar moiety of the central region is at position 10 of the central region.

115. The oligomeric compound of any of embodiments 50-61 or 67-69, wherein the one modified sugar moiety of the central region is a morpholino modified sugar moiety at position 1 of the central region.

116. The oligomeric compound of any of embodiments 50-61 or 67-69, wherein the one modified sugar moiety of the central region is a modified, unsubstituted 2'-deoxyfuranosyl sugar moiety at position 1 of the central region.

117. The oligomeric compound of embodiment 116, wherein the one modified sugar moiety of the central region is an unsubstituted β-L-2'-deoxyribosyl sugar moiety at position 1 of the central region.

118. The oligomeric compound of embodiment 116, wherein the one modified sugar moiety of the central region is an unsubstituted α-D-2'-deoxyribosyl sugar moiety 119. The oligomeric compound of any of embodiments 50-61 or 67-69, wherein the one modified sugar moiety of the central region is a 2'-substituted ribosyl sugar moiety at position 2 of the central region.

120. The oligomeric compound of embodiment 119, wherein the 2'-substituted ribosyl sugar moiety at position 2 of the central region is a 2'-F ribosyl sugar moiety.

121. The oligomeric compound of embodiment 119, wherein the 2'-substituted ribosyl sugar moiety at position 2 of the central region is a 2'-MOE ribosyl sugar moiety.

122. The oligomeric compound of embodiment 119, wherein the 2'-substituted ribosyl sugar moiety at position 2 of the central region is a 2'-O-methyl ribosyl sugar moiety.

123. The oligomeric compound of any of embodiments 50-61 or 67-69, wherein the one modified sugar moiety of the central region is a 5'-alkyl substituted 2'-deoxyribosyl sugar moiety at position 2 of the central region.

124. The oligomeric compound of embodiment 123, wherein the 5'-alkyl substituted 2'-deoxyribosyl sugar moiety at position 2 of the central region is a 5'-(S)Me 2'-deoxyribosyl sugar moiety.

125. The oligomeric compound of embodiment 123, wherein the 5'-alkyl substituted 2'-deoxyribosyl sugar moiety at position 2 of the central region is a 5'-allyl 2'-deoxyribosyl sugar moiety.

126. The oligomeric compound of embodiment 125, wherein the 5'-allyl 2'-deoxyribosyl sugar moiety is stereorandom at the 5'-position of the 5'-allyl 2'-deoxyribosyl sugar moiety.

127. The oligomeric compound of any of embodiments 50-61 or 67-69, wherein the one modified sugar moiety of the central region is a modified, unsubstituted 2'-deoxyfuranosyl sugar moiety at position 2 of the central region.

128. The oligomeric compound of embodiment 127, wherein the modified, unsubstituted 2'-deoxyfuranosyl sugar moiety at position 2 of the central region is a α-D-2'-deoxyribosyl modified sugar moiety.

129. The oligomeric compound of any of embodiments 50-61 or 67-69, wherein the one modified sugar moiety of the central region is a cEt or LNA sugar moiety at position 2 of the central region.

130. The oligomeric compound of any of embodiments 50-61 or 67-69, wherein the one modified sugar moiety of the central region is a 2'-substituted ribosyl sugar moiety at position 3 of the central region.

131. The oligomeric compound of embodiment 130, wherein the 2'-substituted ribosyl sugar moiety at position 3 of the central region is a 2'-F ribosyl sugar moiety.

132. The oligomeric compound of embodiment 130, wherein the 2'-substituted ribosyl sugar moiety at position 3 of the central region is a 2'-MOE ribosyl sugar moiety.

133. The oligomeric compound of embodiment 130, wherein the 2'-substituted ribosyl sugar moiety at position 3 of the central region is a 2'-O-methyl ribosyl sugar moiety.

134. The oligomeric compound of any of embodiments 50-61 or 67-69, wherein the one modified sugar moiety of the central region is a 4'-alkyl substituted 2'-deoxyribosyl sugar moiety at position 3 of the central region.

135. The oligomeric compound of embodiment 134, wherein the 4'-substituted 2'-deoxyribosyl sugar moiety at position 3 of the central region is a 4'-methyl 2'-deoxyribosyl sugar moiety.

136. The oligomeric compound of any of embodiments 50-61 or 67-69, wherein the one modified sugar moiety of the central region is a 5'-alkyl substituted 2'-deoxyribosyl sugar moiety at position 3 of the central region.

137. The oligomeric compound of embodiment 136, wherein the 5'-alkyl substituted 2'-deoxyribosyl sugar moiety at position 3 of the central region is a 5'-(R)-methyl 2'-deoxyribosyl sugar moiety.

138. The oligomeric compound of embodiment 136, wherein the 5'-alkyl substituted 2'-deoxyribosyl sugar moiety at position 3 of the central region is a 5'-(S)-methyl 2'-deoxyribosyl sugar moiety.

139. The oligomeric compound of embodiment 136, wherein the 5'-alkyl substituted 2'-deoxyribosyl sugar moiety at position 3 of the central region is a 5'-stereorandom methyl 2'-deoxyribosyl sugar moiety.

140. The oligomeric compound of embodiment 136, wherein the 5'-alkyl substituted 2'-deoxyribosyl sugar moiety at position 3 of the central region is a 5'-(R)-ethyl 2'-deoxyribosyl sugar moiety.

141. The oligomeric compound of embodiment 136, wherein the 5'-alkyl substituted 2'-deoxyribosyl sugar moiety at position 3 of the central region is a 5'-(S)-ethyl 2'-deoxyribosyl sugar moiety.

142. The oligomeric compound of embodiment 136, wherein the 5'-alkyl substituted 2'-deoxyribosyl sugar moiety at position 3 of the central region is a 5'-stereorandom ethyl 2'-deoxyribosyl sugar moiety.

143. The oligomeric compound of embodiment 136, wherein the 5'-alkyl substituted 2'-deoxyribosyl sugar moiety at position 3 of the central region is a 5'-(R)-allyl 2'-deoxyribosyl sugar moiety.

144. The oligomeric compound of embodiment 136, wherein the 5'-alkyl substituted 2'-deoxyribosyl sugar moiety at position 3 of the central region is a 5'-(S)-allyl 2'-deoxyribosyl sugar moiety.

145. The oligomeric compound of embodiment 136, wherein the 5'-alkyl substituted 2'-deoxyribosyl sugar moiety at position 3 of the central region is a 5'-stereorandom allyl 2'-deoxyribosyl sugar moiety.

146. The oligomeric compound of any of embodiments 50-61 or 67-69, wherein the one modified sugar moiety of the central region is a modified, unsubstituted 2'-deoxyfuranosyl sugar moiety at position 3 of the central region.

147. The oligomeric compound of embodiment 146, wherein the modified, unsubstituted 2'-deoxyfuranosyl sugar moiety at position 3 of the central region is an α-D-2'-deoxyribosyl modified sugar moiety.

148. The oligomeric compound of embodiment 146, wherein the modified, unsubstituted 2'-deoxyfuranosyl sugar moiety at position 3 of the central region is an α-L-2'-deoxyribosyl modified sugar moiety.

149. The oligomeric compound of embodiment 146, wherein the modified, unsubstituted 2'-deoxyfuranosyl sugar moiety at position 3 of the central region is an β-L-2'-deoxyribosyl modified sugar moiety.

150. The oligomeric compound of embodiment 146, wherein the modified, unsubstituted 2'-deoxyfuranosyl sugar moiety at position 3 of the central region is an β-D-2'-deoxyxylosyl modified sugar moiety.

151. The oligomeric compound of any of embodiments 50-61 or 67-69, wherein the one modified sugar moiety of the central region is a bicyclic ribosyl sugar moiety at position 3 of the central region.

152. The oligomeric compound of embodiment 151, wherein the bicyclic ribosyl sugar moiety at position 3 of the central region is a cEt or LNA sugar moiety.

153. The oligomeric compound of embodiment 151, wherein the bicyclic ribosyl sugar moiety at position 3 of the central region is a cEt sugar moiety.

154. The oligomeric compound of embodiment 151, wherein the bicyclic ribosyl sugar moiety at position 3 of the central region is a LNA sugar moiety.

155. The oligomeric compound of any of embodiments 50-61 or 67-69, wherein the one modified sugar moiety of the central region is a morpholino sugar moiety at position 3 of the central region.

156. The oligomeric compound of any of embodiments 50-61 or 67-69, wherein the one modified sugar moiety of the central region is a 2'-substituted ribosyl sugar moiety at position 4 of the central region.

157. The oligomeric compound of embodiment 156, wherein the 2'-substituted ribosyl sugar moiety at position 4 of the central region is a 2'-F ribosyl sugar moiety.

158. The oligomeric compound of embodiment 156, wherein the 2'-substituted ribosyl sugar moiety at position 4 of the central region is a 2'-MOE ribosyl sugar moiety.

159. The oligomeric compound of embodiment 156, wherein the 2'-substituted ribosyl sugar moiety at position 4 of the central region is a 2'-O-methyl ribosyl sugar moiety.

160. The oligomeric compound of any of embodiments 50-61 or 67-69, wherein the one modified sugar moiety of the central region is a 4'-alkyl substituted 2'-deoxyribosyl sugar moiety at position 4 of the central region.

161. The oligomeric compound of embodiment 160, wherein the 4'-substituted 2'-deoxyribosyl sugar moiety at position 4 of the central region is a 4'-methyl 2'-deoxyribosyl sugar moiety.

162. The oligomeric compound of any of embodiments 50-61 or 67-69, wherein the one modified sugar moiety of the central region is a 5'-alkyl substituted 2'-deoxyribosyl sugar moiety at position 4 of the central region.

163. The oligomeric compound of embodiment 162, wherein the 5'-alkyl substituted 2'-deoxyribosyl sugar moiety at position 4 of the central region is a 5'-(R)-methyl 2'-deoxyribosyl sugar moiety.

164. The oligomeric compound of embodiment 162, wherein the 5'-alkyl substituted 2'-deoxyribosyl sugar moiety at position 4 of the central region is a 5'-(S)-methyl 2'-deoxyribosyl sugar moiety.

165. The oligomeric compound of embodiment 162, wherein the 5'-alkyl substituted 2'-deoxyribosyl sugar moiety at position 4 of the central region is a 5'-stereorandom methyl 2'-deoxyribosyl sugar moiety.

166. The oligomeric compound of embodiment 162, wherein the 5'-alkyl substituted 2'-deoxyribosyl sugar moiety at position 4 of the central region is a 5'-(R)-ethyl 2'-deoxyribosyl sugar moiety.

167. The oligomeric compound of embodiment 162, wherein the 5'-alkyl substituted 2'-deoxyribosyl sugar moiety at position 4 of the central region is a 5'-(S)-ethyl 2'-deoxyribosyl sugar moiety.

168. The oligomeric compound of embodiment 162, wherein the 5'-alkyl substituted 2'-deoxyribosyl sugar moiety at position 4 of the central region is a 5'-stereorandom ethyl 2'-deoxyribosyl sugar moiety.

169. The oligomeric compound of embodiment 162, wherein the 5'-alkyl substituted 2'-deoxyribosyl sugar moiety at position 4 of the central region is a 5'-(R)-allyl 2'-deoxyribosyl sugar moiety.

170. The oligomeric compound of embodiment 162, wherein the 5'-alkyl substituted 2'-deoxyribosyl sugar moiety at position 4 of the central region is a 5'-(S)-allyl 2'-deoxyribosyl sugar moiety.

171. The oligomeric compound of embodiment 162, wherein the 5'-alkyl substituted 2'-deoxyribosyl sugar moiety at position 4 of the central region is a 5'-stereorandom allyl 2'-deoxyribosyl sugar moiety.

172. The oligomeric compound of any of embodiments 50-61 or 67-69, wherein the one modified sugar moiety of the central region is a modified, unsubstituted 2'-deoxyfuranosyl sugar moiety at position 4 of the central region.

173. The oligomeric compound of embodiment 172, wherein the modified, unsubstituted 2'-deoxyfuranosyl sugar moiety at position 4 of the central region is an α-D-2'-deoxyribosyl modified sugar moiety.

174. The oligomeric compound of embodiment 172, wherein the modified, unsubstituted 2'-deoxyfuranosyl sugar moiety at position 4 of the central region is an α-L-2'-deoxyribosyl modified sugar moiety.

175. The oligomeric compound of embodiment 172, wherein the modified, unsubstituted 2'-deoxyfuranosyl sugar moiety at position 4 of the central region is an β-L-2'-deoxyribosyl modified sugar moiety.

176. The oligomeric compound of any of embodiments 50-61 or 67-69, wherein the one modified sugar moiety of the central region is a bicyclic ribosyl sugar moiety at position 4 of the central region.

177. The oligomeric compound of embodiment 176, wherein the bicyclic ribosyl sugar moiety at position 4 of the central region is a cEt or LNA sugar moiety.

178. The oligomeric compound of embodiment 176, wherein the bicyclic ribosyl sugar moiety at position 4 of the central region is a cEt sugar moiety.

179. The oligomeric compound of embodiment 176, wherein the bicyclic ribosyl sugar moiety at position 4 of the central region is a LNA sugar moiety.

180. The oligomeric compound of any of embodiments 50-61 or 67-69, wherein the one modified sugar moiety of the central region is a morpholino sugar moiety at position 4 of the central region.

181. The oligomeric compound of any of embodiments 50-61 or 67-69, wherein the one modified sugar moiety of the central region is a 2'-O-methyl substituted ribosyl sugar moiety at position 5 of the central region.

182. The oligomeric compound of any of embodiments 50-61 or 67-69, wherein the one modified sugar moiety of the central region is a modified, unsubstituted 2'-deoxyfuranosyl sugar moiety at position 5 of the central region.

183. The oligomeric compound of embodiment 182, wherein the modified, unsubstituted 2'-deoxyfuranosyl sugar moiety at position 5 of the central region is a β-L-2'-deoxyribosyl sugar moiety.

184. The oligomeric compound of any of embodiments 50-61 or 67-69, wherein the one modified sugar moiety of the central region is a morpholino sugar moiety at position 6 of the central region.

185. The oligomeric compound of any of embodiments 50-61 or 67-69, wherein the one modified sugar moiety of the central region is a 2'-O-methyl substituted ribosyl sugar moiety at position 6 of the central region.

186. The oligomeric compound of any of embodiments 50-61 or 67-69, wherein the one modified sugar moiety of the central region is a modified, unsubstituted 2'-deoxyfuranosyl sugar moiety at position 6 of the central region.

187. The oligomeric compound of embodiment 186, wherein the modified, unsubstituted 2'-deoxyfuranosyl sugar moiety at position 6 of the central region is a β-L-2'-deoxyribosyl sugar moiety.

188. The oligomeric compound of embodiment 186, wherein the modified, unsubstituted 2'-deoxyfuranosyl sugar moiety at position 6 of the central region is an α-D-2'-deoxyribosyl sugar moiety.

189. The oligomeric compound of any of embodiments 50-61 or 67-69, wherein the one modified sugar moiety of the central region is a 2'-O-methyl substituted ribosyl sugar moiety at position 7 of the central region.

190. The oligomeric compound of any of embodiments 50-61 or 67-69, wherein the one modified sugar moiety of the central region is a modified, unsubstituted 2'-deoxyfuranosyl sugar moiety at position 7 of the central region.

191. The oligomeric compound of embodiment 190, wherein the modified, unsubstituted 2'-deoxyfuranosyl sugar moiety at position 7 of the central region is a β-L-2'-deoxyribosyl sugar moiety.

192. The oligomeric compound of embodiment 190, wherein the modified, unsubstituted 2'-deoxyfuranosyl sugar moiety at position 7 of the central region is an α-D-2'-deoxyribosyl sugar moiety.

193. The oligomeric compound of any of embodiments 50-61 or 67-69, wherein the one modified sugar moiety of the central region is a 2'-O-methyl substituted ribosyl sugar moiety at position 8 of the central region.

194. The oligomeric compound of any of embodiments 50-61 or 67-69, wherein the one modified sugar moiety of the central region is a modified, unsubstituted 2'-deoxyfuranosyl sugar moiety at position 8 of the central region.

195. The oligomeric compound of embodiment 194, wherein the modified, unsubstituted 2'-deoxyfuranosyl sugar moiety at position 8 of the central region is a β-L-2'-deoxyribosyl sugar moiety.

196. The oligomeric compound of embodiment 194, wherein the modified, unsubstituted 2'-deoxyfuranosyl sugar moiety at position 8 of the central region is an α-D-2'-deoxyribosyl sugar moiety.

197. The oligomeric compound of any of embodiments 50-61 or 67-69, wherein the one modified sugar moiety of the central region is a 2'-O-methyl substituted ribosyl sugar moiety at position 9 of the central region.

198. The oligomeric compound of any of embodiments 50-61 or 67-69, wherein the one modified sugar moiety of the central region is a modified, unsubstituted 2'-deoxyfuranosyl sugar moiety at position 9 of the central region.

199. The oligomeric compound of embodiment 198, wherein the modified, unsubstituted 2'-deoxyfuranosyl sugar moiety at position 9 of the central region is a β-L-2'-deoxyribosyl sugar moiety.

200. The oligomeric compound of any of embodiments 50-61 or 67-69, wherein the one modified sugar moiety of the central region is a 2'-O-methyl substituted ribosyl sugar moiety at position 2, 3, 4, 5, 6, 7, 8, or 9 of the central region.

201. The oligomeric compound of any of embodiments 50-61 or 67-69, wherein the one modified sugar moiety of the central region is a 2'-O-methyl substituted ribosyl sugar moiety at position 2, 3, 4, 8, or 9 of the central region.

202. The oligomeric compound of any of embodiments 50-61 or 67-69, wherein the one modified sugar moiety of the central region is a 2'-F substituted ribosyl sugar moiety at position 2, 3, or 4 of the central region.

203. The oligomeric compound of any of embodiments 50-61 or 67-69, wherein the one modified sugar moiety of the central region is a 2'-F substituted ribosyl sugar moiety at position 3 or 4 of the central region.

204. The oligomeric compound of any of embodiments 50-61 or 67-69, wherein the one modified sugar moiety of the central region is a 2'-MOE substituted ribosyl sugar moiety at position 2, 3, or 4 of the central region.

205. The oligomeric compound of any of embodiments 50-61 or 67-69, wherein the one modified sugar moiety of the central region is a 4'-methyl substituted 2'-deoxyribosyl sugar moiety at position 3 or 4 of the central region.

206. The oligomeric compound of any of embodiments 50-61 or 67-69, wherein the one modified sugar moiety of the central region is a 5'-(R)-methyl substituted 2'-deoxyribosyl sugar moiety at position 3 or 4 of the central region.

207. The oligomeric compound of any of embodiments 50-61 or 67-69, wherein the one modified sugar moiety of the central region is a 5'-(S)-methyl substituted 2'-deoxyribosyl sugar moiety at position 2, 3, or 4 of the central region.

208. The oligomeric compound of any of embodiments 50-61 or 67-69, wherein the one modified sugar moiety of the central region is a 5'-(R)-ethyl substituted 2'-deoxyribosyl sugar moiety at position 3 or 4 of the central region.
209. The oligomeric compound of any of embodiments 50-61 or 67-69, wherein the one modified sugar moiety of the central region is a 5'-(S)-ethyl substituted 2'-deoxyribosyl sugar moiety at position 3 or 4 of the central region.
210. The oligomeric compound of any of embodiments 50-61 or 67-69, wherein the one modified sugar moiety of the central region is a 5'-(R)-allyl substituted 2'-deoxyribosyl sugar moiety at position 3 or 4 of the central region.
211. The oligomeric compound of any of embodiments 50-61 or 67-69, wherein the one modified sugar moiety of the central region is a 5'-(S)-allyl substituted 2'-deoxyribosyl sugar moiety at position 3 or 4 of the central region.
212. The oligomeric compound of any of embodiments 50-61 or 67-69, wherein the one modified sugar moiety of the central region is a 5'-stereorandom allyl substituted 2'-deoxyribosyl sugar moiety at position 2, 3, or 4 of the central region.
213. The oligomeric compound of any of embodiments 50-61 or 67-69, wherein the one modified sugar moiety of the central region is a cEt ribosyl sugar moiety at position 2, 3, or 4 of the central region.
214. The oligomeric compound of any of embodiments 50-61 or 67-69, wherein the one modified sugar moiety of the central region is a cEt ribosyl sugar moiety at position 3 or 4 of the central region.
215. The oligomeric compound of any of embodiments 50-61 or 67-69, wherein the one modified sugar moiety of the central region is a LNA ribosyl sugar moiety at position 2, 3, or 4 of the central region.
216. The oligomeric compound of any of embodiments 50-61 or 67-69, wherein the one modified sugar moiety of the central region is a LNA ribosyl sugar moiety at position 3 or 4 of the central region.
217. The oligomeric compound of any of embodiments 50-61 or 67-69, wherein the one modified sugar moiety of the central region is a morpholino sugar moiety at position 1, 3, 4, or 6 of the central region.
218. The oligomeric compound of any of embodiments 50-61 or 67-69, wherein the one modified sugar moiety of the central region is a morpholino sugar moiety at position 1, 3, or 4 of the central region.
219. The oligomeric compound of any of embodiments 50-61 or 67-69, wherein the one modified sugar moiety of the central region is a modified, unsubstituted 2'-deoxyfuranosyl sugar moiety.
220. The oligomeric compound of any of embodiments 50-61 or 67-69, wherein the one modified sugar moiety of the central region is a modified, unsubstituted 2'-deoxyfuranosyl sugar moiety at position 1, 2, 3, 4, 5, 6, 7, 8, or 9 of the central region.
221. The oligomeric compound of any of embodiments 50-61 or 67-69, wherein the one modified sugar moiety of the central region is a modified, unsubstituted 2'-deoxyfuranosyl sugar moiety at position 1, 2, 3, 4, 5, or 9 of the central region.
222. The oligomeric compound of any of embodiments 50-61 or 67-69, wherein the one modified sugar moiety of the central region is an unsubstituted α-D-2'-deoxyribosyl sugar moiety.
223. The oligomeric compound of any of embodiments 50-61 or 67-69, wherein the one modified sugar moiety of the central region is an unsubstituted α-D-2'-deoxyribosyl sugar moiety at position 1, 2, 3, 4, 6, or 8 of the central region.
224. The oligomeric compound of any of embodiments 50-61 or 67-69, wherein the one modified sugar moiety of the central region is an unsubstituted α-D-2'-deoxyribosyl sugar moiety at position 1, 2, or 4 of the central region.
225. The oligomeric compound of any of embodiments 50-61 or 67-69, wherein the one modified sugar moiety of the central region is an unsubstituted α-L-2'-deoxyribosyl sugar moiety.
226. The oligomeric compound of any of embodiments 50-61 or 67-69, wherein the one modified sugar moiety of the central region is an unsubstituted α-L-2'-deoxyribosyl sugar moiety at position 3, 4, or 7 of the central region.
227. The oligomeric compound of any of embodiments 50-61 or 67-69, wherein the one modified sugar moiety of the central region is an unsubstituted β-L-2'-deoxyribosyl sugar moiety.
228. The oligomeric compound of any of embodiments 50-61 or 67-69, wherein the one modified sugar moiety of the central region is an unsubstituted β-L-2'-deoxyribosyl sugar moiety at position 1, 3, 4, 5, 6, 7, 8, or 9 of the central region.
229. The oligomeric compound of any of embodiments 50-61 or 67-69, wherein the one modified sugar moiety of the central region is an unsubstituted β-L-2'-deoxyribosyl sugar moiety at position 3, 4, 5, or 9 of the central region.
230. The oligomeric compound of any of embodiments 50-61 or 67-69, wherein the one modified sugar moiety of the central region is an unsubstituted β-D-2'-deoxyxylosyl sugar moiety.
231. The oligomeric compound of any of embodiments 53-55 or 60-230, wherein the one modified internucleoside linkage of the central region other than phosphorothioate is a phosphonate or phosphotriester internucleoside linkage.
232. The oligomeric compound of embodiment 231, wherein the one modified internucleoside linkage of the central region other than phosphorothioate is an alkyl phosphonate or alkoxy phosphonate internucleoside linkage.
233. The oligomeric compound of embodiment 232, wherein the one modified internucleoside linkage of the central region other than phosphorothioate is a methoxypropyl internucleoside linkage.
234. The oligomeric compound of embodiment 232, wherein the one modified internucleoside linkage of the central region other than phosphorothioate is a methyl phosphonate internucleoside linkage.
235. The oligomeric compound of embodiment 232, wherein the one modified internucleoside linkage of the central region other than phosphorothioate is an isopropyl phosphonate internucleoside linkage.
236. The oligomeric compound of embodiment 232, wherein the one modified internucleoside linkage of the central region other than phosphorothioate is an isobutyl phosphonate internucleoside linkage.
237. The oligomeric compound of embodiment 231, wherein the one modified internucleoside linkage of the central region other than phosphorothioate is a phosphonoacetate internucleoside linkage.
238. The oligomeric compound of embodiment 231, wherein the one modified internucleoside linkage of the central region other than phosphorothioate is an isopropyl phosphotriester internucleoside linkage.

239. The oligomeric compound of embodiment 231, wherein the one modified internucleoside linkage of the central region other than phosphorothioate is a tetrahydropyran phosphotriester internucleoside linkage.

240. The oligomeric compound of any of embodiments 53, 55, or 60-230, wherein the one modified internucleoside linkage of the central region other than phosphorothioate is a formacetal internucleoside linkage.

241. The oligomeric compound of any of embodiments 53, 55, or 60-230, wherein the one modified internucleoside linkage of the central region other than phosphorothioate is an acetamide internucleoside linkage.

242. The oligomeric compound of any of embodiments 53, 55, or 60-230, wherein the one modified internucleoside linkage of the central region other than phosphorothioate is a thioacetamide internucleoside linkage.

243. The oligomeric compound of any of embodiments 231-242, wherein the one modified internucleoside linakge of the central region other than phosphorothioate is between the nucleosides at positions 1 and 2 of the central region.

244. The oligomeric compound of any of embodiments 231-242, wherein the one modified internucleoside linakge of the central region other than phosphorothioate is between the nucleosides at positions 2 and 3 of the central region.

245. The oligomeric compound of any of embodiments 231-242, wherein the one modified internucleoside linakge of the central region other than phosphorothioate is between the nucleosides at positions 3 and 4 of the central region.

246. The oligomeric compound of any of embodiments 231-242, wherein the one modified internucleoside linakge of the central region other than phosphorothioate is between the nucleosides at positions 4 and 5 of the central region.

247. The oligomeric compound of any of embodiments 231-246, wherein the one modified internucleoside linkage of the central region other than phosphorothioate is directly linked to a nucleoside comprising a modified sugar moiety.

248. The oligomeric compound of any of embodiments 56-230, wherein the two neutral internucleoside linkages of the central region are independently selected from a phosphonate internucleoside linkage, phosphotriester internucleoside linkage, and a neutral internucleoside linkage that does not contain phosphorus.

249. The oligomeric compound of embodiment 248, wherein at least one of the modified internucleoside linkages of the central region other than phosphorothioate is an alkyl phosphonate or alkoxy phosphonate internucleoside linkage.

250. The oligomeric compound of embodiment 248, wherein at least one of the modified internucleoside linkages of the central region other than phosphorothioate is a methoxypropyl internucleoside linkage.

251. The oligomeric compound of embodiment 248, wherein at least one of the modified internucleoside linkages of the central region other than phosphorothioate is a methyl phosphonate internucleoside linkage.

252. The oligomeric compound of embodiment 248, wherein at least one of the modified internucleoside linkages of the central region other than phosphorothioate is an isopropyl phosphonate internucleoside linkage.

253. The oligomeric compound of embodiment 248, wherein at least one of the modified internucleoside linkages of the central region other than phosphorothioate is an isobutyl phosphonate internucleoside linkage.

254. The oligomeric compound of embodiment 248, wherein at least one of the modified internucleoside linkages of the central region other than phosphorothioate is a phosphonoacetate internucleoside linkage.

255. The oligomeric compound of embodiment 248, wherein at least one of the modified internucleoside linkages of the central region other than phosphorothioate is an isopropyl phosphotriester internucleoside linkage.

256. The oligomeric compound of embodiment 248, wherein at least one of the modified internucleoside linkages of the central region other than phosphorothioate is a tetrahydropyran phosphotriester internucleoside linkage.

257. The oligomeric compound of embodiment 248, wherein at least one of the modified internucleoside linkages of the central region other than phosphorothioate is a formacetal internucleoside linkage.

258. The oligomeric compound of embodiment 248, wherein at least one of the modified internucleoside linkages of the central region other than phosphorothioate is an acetamide internucleoside linkage.

259. The oligomeric compound of embodiment 248, wherein at least one of the modified internucleoside linkages of the central region other than phosphorothioate is a thioacetamide internucleoside linkage.

260. The oligomeric compound of any of embodiments 248-259, wherein the two modified internucleoside linkages other than phosphorothiaote of the central region are adjacent to each other.

261. The oligomeric compound of any of claims 248-260, wherein the two modified internucleoside linkages other than phosphorothioate of the central region are the same as one another.

262. The oligomeric compound of any of embodiments 248-261, wherein one of the modified internucleoside linakges of the central region other than phosphorothioate is between the nucleosides at positions 1 and 2 of the central region.

263. The oligomeric compound of any of embodiments 248-261, wherein one of the modified internucleoside linakges of the central region other than phosphorothioate is between the nucleosides at positions 2 and 3 of the central region.

264. The oligomeric compound of any of embodiments 248-261, wherein one of the modified internucleoside linakges of the central region other than phosphorothioate is between the nucleosides at positions 3 and 4 of the central region.

265. The oligomeric compound of any of embodiments 248-261, wherein one of the modified internucleoside linakges of the central region other than phosphorothioate is between the nucleosides at positions 4 and 5 of the central region.

266. The oligomeric compound of any of embodiments 248-261, wherein one of the modified internucleoside linakges of the central region other than phosphorothioate is directly linked to a nucleoside comprising a modified sugar moiety.

267. The oligomeric compound of any of embodiments 60-266, wherein the one modified nucleobase other than 5-methylcytosine of the central region is 2-thiothymine, 6-methyladenine, inosine, or pseudouracil.

268. The oligomeric compound of embodiment 267, wherein the one modified nucleobase other than 5-methylcytosine is at position 1, 2, 3, or 4 of the central region.

269. The oligomeric compound of embodiment 267, wherein the one modified nucleobase other than 5-methylcytosine is at position 2, 3, or 4 of the central region.

270. The oligomeric compound of embodiment 267, wherein the one modified nucleobase other than 5-methylcytosine is at position 1 of the central region.

271. The oligomeric compound of embodiment 267, wherein the one modified nucleobase other than 5-methylcytosine is at position 2 of the central region.

272. The oligomeric compound of embodiment 267, wherein the one modified nucleobase other than 5-methylcytosine is at position 3 of the central region.

273. The oligomeric compound of embodiment 267, wherein the one modified nucleobase other than 5-methylcytosine is at position 4 of the central region.

274. The oligomeric compound of any of embodiments 267 or 270, wherein the one modified nucleobase other than 5-methylcytosine is 2-thiothymine.

275. The oligomeric compound of any of embodiments 267 or 271, wherein the one modified nucleobase other than 5-methylcytosine is 6-methyladenine.

276. The oligomeric compound of any of embodiments 267 or 271, wherein the one modified nucleobase other than 5-methylcytosine is inosine.

277. The oligomeric compound of any of embodiments 267-273, wherein the one modified nucleobase other than 5-methylcytosine is pseudouracil.

278. The oligomeric compound of embodiment 277, wherein the nucleoside comprising the pseudouracil nucleobase comprises an unmodified ribosyl sugar moiety.

279. The oligomeric compound of any of embodiments 1-52, 60-230, or 267-278, wherein each internucleoside linkage of the central region is independently selected from among a phosphodiester or a phosphorothioate internucleoside linkage.

280. The oligomeric compound of embodiment 279, wherein each internucleoside of the central region is a phosphorothioate internucleoside linkage.

281. The oligomeric compound of any of embodiments 1-279, wherein the central region does not comprise any phosphodiester internucleoside linkages.

282. The oligomeric compound of any of embodiments 1-281, wherein each phosphorothioate internucleoside linkage of the oligomeric compound is strereorandom.

283. The oligomeric compound of any of embodiments 1-281, wherein at least one phosphorothioate internucleoside linkage of the oligomeric compound is in the Rp configuration.

284. The oligomeric compound of any of embodiments 1-281, wherein at least one phosphorothioate internucleoside linkage of the oligomeric compound is in the Sp configuration.

285. The oligomeric compound of any of embodiments 1-284, wherein the nucleobase sequence of the modified oligonucleotide is complementary to a target RNA.

286. The oligomeric compound of embodiment 285, wherein the nucleobase sequence of the modified oligonucleotide is at least 75% complementary to the target RNA.

287. The oligomeric compound of embodiment 285, wherein the nucleobase sequence of the modified oligonucleotide is at least 80% complementary to the target RNA.

288. The oligomeric compound of embodiment 285, wherein the nucleobase sequence of the modified oligonucleotide is at least 85% complementary to the target RNA.

289. The oligomeric compound of embodiment 285, wherein the nucleobase sequence of the modified oligonucleotide is at least 90% complementary to the target RNA.

290. The oligomeric compound of embodiment 285, wherein the nucleobase sequence of the modified oligonucleotide is at least 95% complementary to the target RNA.

291. The oligomeric compound of embodiment 285, wherein the nucleobase sequence of the modified oligonucleotide is 100% complementary to the target RNA.

292. The oligomeric compound of any of embodiments 285-291, wherein the target RNA is a target mRNA or a target pre-mRNA.

293. The oligomeric compound of embodiment 292, wherein the target mRNA or target pre-mRNA is not a mouse, rat, monkey, or human PTEN RNA.

294. The oligomeric compound of embodiment 292 or 293, wherein the target mRNA or target pre-mRNA is not a mouse, rat, monkey, or human SRB-1 RNA.

295. The oligomeric compound of any of embodiments 292-294, wherein the target mRNA or target pre-mRNA is not a mouse, rat, monkey, or human MYD88 RNA.

296. The oligomeric compound of any of embodiments 292-295, wherein the target mRNA or target pre-mRNA is not a mouse, rat, monkey, or human HTT RNA, is not a mouse, rat, monkey, or human SOD1 RNA, and is not a mouse, rat, monkey, or human alpha-synuclein RNA.

297. The oligomeric compound of any of embodiments 285-296, wherein the target RNA is a human RNA.

298. The oligomeric compound of any of embodiments 285-297, wherein the target RNA is expressed in the liver.

299. The oligomeric compound of any of embodiments 285-298, wherein the target RNA is a liver target.

300. The oligomeric compound of any of embodiments 285-297, wherein the target RNA is not expressed in the liver.

301. The oligomeric compound of any of embodiments 285-298 or 300, wherein the target RNA is not a liver target.

302. The oligomeric compound of any of embodiments 285-299, wherein modulation of the expression of the target RNA in the liver is associated with treating a disorder or condition.

303. The oligomeric compound of embodiment 302, wherein the disorder or condition is a liver disorder or condition.

304. The oligomeric compound of any of embodiments 285-303, wherein the target RNA is expressed in the central nervous system.

305. The oligomeric compound of any of embodiments 285-303, wherein the target RNA is not expressed in the central nervous system.

306. The oligomeric compound of any of embodiments 285-298, 300, 301, or 304, wherein the target RNA is a central nervous system target.

307. The oligomeric compound of any of embodiments 285-305, wherein the target RNA is not a central nervous system target.

308. The oligomeric compound of any of embodiments 285-298, 300-301, 304, or 306, wherein the target RNA is a MeCP2, DUX4, HDAC2, APP, Ataxin 1, Ataxin 2, Ataxin 3, Ataxin 6, Ataxin 7, C9ORF72, UBE3A, Prion, PMP22, Tau, LRRK2, LINGO2, GYS1, KCNT1, IRF8, Progranulin, or GFAP RNA.

309. The oligomeric compound of any of embodiments 285-297, 300-301, 304, or 306, wherein the target RNA is a HTT RNA.

310. The oligomeric compound of embodiment 308, wherein the target RNA is a MeCP2 RNA.

311. The oligomeric compound of embodiment 308, wherein the target RNA is a DUX4 RNA.

312. The oligomeric compound of embodiment 308, wherein the target RNA is a HDAC2 RNA.

313. The oligomeric compound of embodiment 308, wherein the target RNA is a Ataxin 1 RNA.

314. The oligomeric compound of embodiment 308, wherein the target RNA is a Ataxin 2 RNA.

315. The oligomeric compound of embodiment 308, wherein the target RNA is a Ataxin 3 RNA.

316. The oligomeric compound of embodiment 308, wherein the target RNA is a Ataxin 6 RNA.

317. The oligomeric compound of embodiment 308, wherein the target RNA is a Ataxin 7 RNA.

318. The oligomeric compound of embodiment 308, wherein the target RNA is a C9ORF72 RNA.

319. The oligomeric compound of embodiment 285-297, 300-301, 304, or 306, wherein the target RNA is an alpha-synuclein RNA.

320. The oligomeric compound of embodiment 308, wherein the target RNA is an UBE3A RNA.

321. The oligomeric compound of embodiment 285-297, 300-301, 304, or 306, wherein the target RNA is a SOD1 RNA.

322. The oligomeric compound of embodiment 308, wherein the target RNA is a Prion RNA.

323. The oligomeric compound of embodiment 308, wherein the target RNA is a PMP22 RNA.

324. The oligomeric compound of embodiment 308, wherein the target RNA is a Tau RNA.

325. The oligomeric compound of embodiment 308, wherein the target RNA is a LRRK2 RNA.

326. The oligomeric compound of embodiment 308, wherein the target RNA is an APP RNA.

327. The oligomeric compound of embodiment 308, wherein the target RNA is a LINGO2 RNA.

328. The oligomeric compound of embodiment 308, wherein the target RNA is a GYS1 RNA.

329. The oligomeric compound of embodiment 308, wherein the target RNA is a KCNT1 RNA.

330. The oligomeric compound of embodiment 308, wherein the target RNA is a IRF8 RNA.

331. The oligomeric compound of embodiment 308, wherein the target RNA is a Progranulin RNA.

332. The oligomeric compound of embodiment 308, wherein the target RNA is a GFAP RNA.

333. The oligomeric compound of any of embodiments 304, 306, or 308-332, wherein modulation of the expression of the target RNA in the central nervous system is associated with treating a disorder or condition.

334. The oligomeric compound of embodiment 333, wherein the disorder or condition is a neurological disorder or condition.

335. The oligomeric compound of embodiment 333 or 334, wherein the disorder or condition alters the function of sensory or motor neurons.

336. The oligomeric compound of any of embodiments 333-335, wherein the disorder or condition alters the function of sensory neurons.

337. The oligomeric compound of any of embodiments 333-336, wherein the disorder or condition alters the function of motor neurons.

338. The oligomeric compound of any of embodiments 333-337, wherein the disorder or condition alters the function of glial cells.

339. The oligomeric compound of embodiment 338, wherein the disorder or condition alters the function of astrocytes.

340. The oligomeric compound of embodiment 338, wherein the disorder or condition alters the function of oligodendrocytes.

341. The oligomeric compound of embodiment 338, wherein the disorder or condition alters the function of microglia.

342. The oligomeric compound of embodiment 338, wherein the disorder or condition alters the function of ependymal cells.

343. The oligomeric compound of any of embodiments 333-342, wherein the disorder or condition is Alzheimer's Disease, Amyotrophic Lateral Sclerosis, Parkinson's Disease, a Spinocerebellar ataxia, Angelman Syndrome, Alexander's Disease, Lafora Disease, Charcot-Marie Tooth Disease, Prion Disease, a dementia, neurodegeneration, MeCP2 Duplication Syndrome, encephalopathy, neuroinflammation, or multiple sclerosis.

344. The oligomeric compound of embodiment 343, wherein the disorder or condition is Alzheimer's Disease.

345. The oligomeric compound of embodiment 343, wherein the disorder or condition is Amyotrophic Lateral Sclerosis.

346. The oligomeric compound of embodiment 343, wherein the disorder or condition is Parkinson's Disease.

347. The oligomeric compound of embodiment 343, wherein the disorder or condition is a Spinocerebellar ataxia.

348. The oligomeric compound of embodiment 343, wherein the disorder or condition is Angelman Syndrome.

349. The oligomeric compound of embodiment 343, wherein the disorder or condition is Alexander's Disease.

350. The oligomeric compound of embodiment 343, wherein the disorder or condition is Lafora Disease.

351. The oligomeric compound of embodiment 343, wherein the disorder or condition is Charcot-Marie Tooth Disease.

352. The oligomeric compound of embodiment 343, wherein the disorder or condition is Prion Disease.

353. The oligomeric compound of embodiment 343, wherein the disorder or condition is a dementia.

354. The oligomeric compound of embodiment 343, wherein the disorder or condition is neurodegeneration.

355. The oligomeric compound of embodiment 343, wherein the disorder or condition is MeCP2 Duplication Syndrome.

356. The oligomeric compound of embodiment 343, wherein the disorder or condition is encephalopathy.

357. The oligomeric compound of embodiment 343, wherein the disorder or condition is neuroinflammation.

358. The oligomeric compound of embodiment 343, wherein the disorder or condition is multiple sclerosis.

359. The oligomeric compound of any of embodiments 1-358, wherein the parent oligomeric compound of the oligomeric compound of any of embodiments 1-358 is cytotoxic in vitro.

360. The oligomeric compound of embodiment 359, wherein the parent oligomeric compound is cytotoxic in a standard in vitro cytotoxicity assay.

361. The oligomeric compound of any of embodiments 1-360, wherein administration to a mouse of the parent oligomeric compound of the oligomeric compound of any of embodiments 1-360 is hepatotoxic to the mouse.

362. The oligomeric compound of embodiment 361, wherein the administration of the parent oligomeric compound to the mouse is systemic administration.

363. The oligomeric compound of embodiment 362, wherein the systemic administration is subcutaneous administration.

364. The oligomeric compound of any of embodiments 361-363, wherein the mouse is a CD-1 mouse.

365. The oligomeric compound of any of embodiments 361-363, wherein the mouse is a C57BL/6 mouse.

366. The oligomeric compound of any of embodiments 361-363, wherein the mouse is a BALB/c mouse.

367. The oligomeric compound of any of embodiments 361-366, wherein the plasma ALT level in the mouse is higher than 500 units per liter following the administration of the parent oligomeric compound.

368. The oligomeric compound of any of embodiments 361-366, wherein the plasma AST level in the mouse is higher than 500 units per liter following the administration of the parent oligomeric compound.

369. The oligomeric compound of any of embodiments 361-366, wherein the plasma ALT level in the mouse is higher than 1000 units per liter following the administration of the parent oligomeric compound.

370. The oligomeric compound of any of embodiments 361-366, wherein the plasma AST level in the mouse is higher than 1000 units per liter following the administration of the parent oligomeric compound.

371. The oligomeric compound of any of embodiments 361-370, wherein the hepatotoxicity is measured 24-48 hours following the administration of the parent oligomeric compound.

372. The oligomeric compound of any of embodiments 361-370, wherein the hepatotoxicity is measured 72 hours following the administration of the parent oligomeric compound.

373. The oligomeric compound of any of embodiments 361-370, wherein the hepatotoxicity is measured 3 days following the administration of the parent oligomeric compound.

374. The oligomeric compound of any of embodiments 361-370, wherein the hepatotoxicity is measured 5 days following the administration of the parent oligomeric compound.

375. The oligomeric compound of any of embodiments 361-370, wherein the hepatotoxicity is measured 7 days following the administration of the parent oligomeric compound.

376. The oligomeric compound of any of embodiments 361-370, wherein the hepatotoxicity is measured 10 days following the administration of the parent oligomeric compound.

377. The oligomeric compound of any of embodiments 361-370, wherein the hepatotoxicity is measured 14 days following the administration of the parent oligomeric compound.

378. The oligomeric compound of any of embodiments 361-377, wherein 1-10 mg/kg of the parent oligomeric compound is administered to the mouse.

379. The oligomeric compound of any of embodiments 361-377, wherein 10-25 mg/kg of the parent oligomeric compound is administered to the mouse.

380. The oligomeric compound of any of embodiments 361-377, wherein 25-50 mg/kg of the parent oligomeric compound is administered to the mouse.

381. The oligomeric compound of any of embodiments 361-377, wherein 50-100 mg/kg of the parent oligomeric compound is administered to the mouse.

382. The oligomeric compound of any of embodiments 361-377, wherein 100-150 mg/kg of the parent oligomeric compound is administered to the mouse.

383. The oligomeric compound of any of embodiments 361-363, 366-370, 372, or 382, wherein the mouse is a BALB/c mouse, wherein 150 mg/kg of the parent oligomeric compound is administered to the mouse, and wherein the plasma ALT level in the mouse is measured 72 hours following the administration of the parent oligomeric compound.

384. The oligomeric compound of any of embodiments 1-383, wherein administration of 50 mg/kg of the oligomeric compound of any of embodiments 1-383 to a mouse is not hepatotoxic to the mouse.

385. The oligomeric compound of embodiment 384, wherein plasma ALT level in the mouse is lower than 100 units per liter following the administration of the oligomeric compound of embodiment 384.

386. The oligomeric compound of embodiment 384 or 385, wherein plasma ALT level in the mouse is at least 10-fold lower than plasma ALT level in a mouse administered the parent oligomeric compound of the oligomeric compound of embodiment 384 or 385, wherein the administrations and plasma ALT measurements of both the oligomeric compound of embodiment 384 or 385 and the parent oligomeric compound are completed in the same way.

387. The oligomeric compound of embodiment 386, wherein the plasma ALT level in the mouse is at least 100-fold lower than the plasma ALT level in the mouse administered the parent oligomeric compound.

388. The oligomeric compound of embodiment 386, wherein the plasma ALT level in the mouse is at least 500-fold lower than the plasma ALT level in the mouse administered the parent oligomeric compound.

389. The oligomeric compound of any of embodiments 359-388, wherein the therapeutic index in a mouse of the oligomeric compound of any of embodiments 359-388 is increased relative to the therapeutic index of the parent oligomeric compound.

390. The oligomeric compound of embodiment 389, wherein the therapeutic index in a mouse of the oligomeric compound of embodiment 365 is at least two-fold greater than the therapeutic index of the parent oligomeric compound.

391. The oligomeric compound of any of embodiments 1-390, wherein an otherwise identical oligomeric compound lacking the at least one modified internucleoside linkage other than phosphorothioate and/or at least one modified nucleoside comprising a modified nucleobase other than 5-methylcytosine and/or a modified sugar moiety in the central region is hepatotoxic following administration to a mouse; and wherein the otherwise identical oligomeric compound has a central region consisting of phosphorothioate internucleoside linkages, unmodified 2'-β-D-deoxyribosyl sugar moieties, and nucleobases selected from thymine, uracil, adenine, guanine, cytosine, and 5-methylcytosine.

392. The oligomeric compound of embodiment 391, wherein the at least one modified internucleoside linkage other than phosphorothioate and/or at least one modified nucleoside comprising a modified nucleobase other than 5-methylcytosine and/or a modified sugar moiety in the central region is a 2'-O-methyl modified sugar moiety.

393. The oligomeric compound of embodiment 392, wherein the 2'-O-methyl modified sugar moiety is at position 2 of the central region.

394. The oligomeric compound of embodiment 392 or 393, wherein the otherwise identical oligomeric compound lacks a 2'-O-methyl modified sugar moiety, and wherein the otherwise identical oligomeric compound comprises an unmodified 2'-β-D-deoxyribosyl sugar moiety in place of the 2'-O-methyl modified sugar moiety.

395. The oligomeric compound of any of embodiments 391-394, wherein the nucleobase sequence of the otherwise identical oligomeric compound is 100% complementary to the target RNA.

396. The oligomeric compound of any of embodiments 391-395, wherein the otherwise identical oligomeric compound is a parent oligomeric compound of the oligomeric compound of any of embodiments 391-395.

397. The oligomeric compound of any of embodiments 285-396, wherein the oligomeric compound inhibits the target RNA with an IC50 lower than 100 nM in a standard in vitro activity assay.

398. The oligomeric compound of any of embodiments 285-397, wherein the parent oligomeric compound of the oligomeric compound of any of embodiments 285-397 inhibits the target RNA with an IC50 lower than 100 nM in a standard in vitro activity assay.

399. The oligomeric compound of any of embodiments 285-398, wherein the difference between the IC50 of the parent oligomeric compound measured in a standard in vitro activity assay and the IC50 of the oligomeric compound of any of embodiments 285-398 measured in a standard in vitro activity assay is less than 4-fold.

400. The oligomeric compound of any of embodiments 285-398, wherein the difference between the IC50 of the parent oligomeric compound measured in a standard in vitro activity assay and the IC50 of the oligomeric compound of any of embodiments 285-398 measured in a standard in vitro activity assay is less than 3-fold.

401. The oligomeric compound of any of embodiments 285-398, wherein the difference between the IC50 of the parent oligomeric compound measured in a standard in vitro activity assay and the IC50 of the oligomeric compound of any of embodiments 285-398 measured in a standard in vitro activity assay is less than 2-fold.

402. The oligomeric compound of any of embodiments 359-390 or 396-401, wherein each sugar moiety of the central region of the parent oligomeric compound is an unmodified 2'-β-D-deoxyribosyl sugar moiety, and wherein each internucleoside linkage of the central region of the parent oligomeric compound is a phosphorothioate internucleoside linkage.

403. The oligomeric compound of any of embodiments 359-390 or 396-402, wherein the nucleobase sequence of the parent oligomeric compound is 100% complementary to the target RNA.

404. The oligomeric compound of any of embodiments 1-403, wherein administration of 10-50 mg of the oligomeric compound to a human is not hepatotoxic to the human.

405. The oligomeric compound of any of embodiments 1-403, wherein administration of 50-100 mg of the oligomeric compound to a human is not hepatotoxic to the human.

406. The oligomeric compound of any of embodiments 1-403, wherein administration of 100-300 mg of the oligomeric compound to a human is not hepatotoxic to the human.

407. The oligomeric compound of any of embodiments 404-406, wherein the administration is systemic administration.

408. A composition comprising the oligomeric compound of any of embodiments 1-407 and a second oligomeric compound, wherein the second oligomeric compound is complementary to the oligomeric compound of any of embodiments 1-407.

409. The composition of embodiment 408, wherein the second oligomeric compound comprises at least 14 contiguous linked nucleosides that are at least 90% complementary to the oligomeric compound of any of embodiments 1-407.

410. The composition of embodiment 408, wherein the second oligomeric compound comprises at least 14 contiguous linked nucleosides that are 100% complementary to the oligomeric compound of any of embodiments 1-407.

411. A pharmaceutical composition comprising the oligomeric compound of any of embodiments 1-407 or the composition of any of embodiments 408-410, comprising a pharmaceutically acceptable carrier or diluent.

412. A method comprising administering the oligomeric compound or composition of any of embodiments 1-411 to a human subject.

413. A method of treating a disease or disorder comprising administering the oligomeric compound or composition of any of embodiments 1-411 to a human subject.

414. A method of modulating the amount or activity of a target RNA in a human subject comprising administering the oligomeric compound or composition of any of embodiments 1-411 to the human subject; and thereby modulating the amount or activity of the target RNA in the human subject.

415. A method of treating a disease or disorder in a human subject comprising administering the oligomeric compound or composition of any of embodiments 1-411 to the human subject having the disease or disorder; and thereby treating the disease or disorder in the human subject.

416. The method of embodiment 413 or 415, wherein the disease or disorder is a liver disease, and wherein the oligomeric compound modulates the amount or activity of a liver target RNA.

417. The method of embodiment 413 or 415, wherein the disease or disorder is a central nervous system disease, and wherein the oligomeric compound modulates the amount or activity of a central nervous system target RNA.

418. The method of any of embodiments 413 or 415-417, wherein the disease or disorder is a cancer, a neurodegenerative disease, a cardiovascular disease, an immunological disease, a hereditary disease, a repeat expansion disease, a muscle-wasting disease, or a metabolic disease.

419. The method of any of embodiments 412-418, wherein the plasma ALT level of the human subject after the administration is not more than three times higher than it was prior to the administration.

420. The method of any of embodiments 412-418, wherein the plasma ALT level of the human subject after the administration is not more than 150 units per liter.

421. The method of any of embodiments 412-416 or 418-420, wherein the human subject is susceptible to liver damage.

422. The method of any of embodiments 412-416 or 418-420, wherein the human subject is susceptible to liver degeneration.

423. The method of any of embodiments 412-416 or 418-420, wherein the human subject is susceptible to elevated apoptosis in the liver.

424. The method of any of embodiments 412-416 or 418-423, wherein the human subject has a liver disease.

425. The method of any of embodiments 412-424, comprising administering the parent oligomeric compound of the oligomeric compound of any of embodiments 1-407 to a mouse.

426. The method of any of embodiments 412-424, comprising contacting a cell with the parent oligomeric compound of the oligomeric compound of any of embodiments 1-407.

427. The method of embodiment 425 or 426, wherein each sugar moiety of the central region of the parent oligomeric compound is an unmodified 2'-β-D-deoxyribosyl sugar moiety, and wherein each internucleoside linkage of the central region of the parent oligomeric compound is a phosphorothioate internucleoside linkage.

428. A method of designing an oligomeric compound comprising starting with a parent oligomeric compound and changing the design of that compound in order to arrive at an oligomeric compound of any one of embodiments 1-407.

429. A method of designing an oligomeric compound comprising identifying a parent oligomeric compound and changing the design of that parent oligomeric compound to arrive at a second oligomeric compound, wherein the second oligomeric compound is an oligomeric compound of any one of embodiments 1-407.

430. A method of improving hepatotoxicity of an oligomeric compound comprising the steps of (i) identifying a parent oligomeric compound that has plasma ALT levels above 300 units per liter in a mouse, and (ii) providing an oligomeric compound according to any one of embodiments 1-407.

431. The method of embodiment 428, wherein the method designs an oligomeric compound with improved therapeutic index relative to the parent oligomeric compound.

432. The method of embodiment 428 or 431, wherein the method designs an oligomeric compound with lower hepatotoxicity relative to the parent oligomeric compound.

433. The method of embodiment 429, wherein the second oligomeric compound has an improved therapeutic index relative to the parent oligomeric compound.

434. The method of embodiment 429 or 433, wherein the second oligomeric compound has reduced hepatotoxicity in a mouse relative to the parent oligomeric compound.

435. The method of embodiment 430, wherein the oligomeric compound according to any one of embodiments 1-407 has reduced hepatotoxicity relative to the parent oligomeric compound.

436. A method comprising administering an oligomeric compound of any of embodiments 1-407 to a mouse and separately administering the parent oligomeric compound of the oligomeric compound of any of embodiments 1-407 to a second mouse, wherein the therapeutic index of the oligomeric compound of any of embodiments 1-407 is improved relative to the therapeutic index of the parent oligomeric compound.

437. The method of any of embodiments 412-436, wherein the level of p21 RNA is measured in the mouse, the cell, and/or the human subject.

438. A method comprising administering an oligomeric compound to a subject and measuring the level of p21 RNA in the subject.

439. A method comprising administering an oligomeric compound of any of embodiments 1-407 to a subject and measuring the level of p21 RNA in the subject.

440. The method of embodiment 438 or 439, wherein the subject is a mouse.

441. The method of embodiment 438 or 439, wherein the subject is a human.

442. The method of any of embodiments 437-441, wherein the p21 RNA level is measured within 24 hours of the administration.

443. The method of any of embodiments 437-441, wherein the p21 RNA level is measured 24-48 hours following the administration.

444. An oligomeric compound or composition of any one of embodiments 1-411, for use in medical therapy.

445. A method comprising contacting a cell with an oligomeric compound and detecting the cellular localization of p54nrb protein in the cell.

446. The method of embodiment 445, comprising determining the relative amount of p54nrb protein in the nucleolus relative to other cells contacted with different oligomeric compounds.

447. The method of embodiment 445 or 446, comprising determining the relative amount of p54nrb in the nucleolus relative to the amount of p54nrb in the rest of the cell.

448. The method of any of embodiments 445-447, wherein the cell is in a plate containing at least 96 wells.

449. The method of any of embodiments 445-448, wherein the detection of the cellular localization of p54nrb comprises contacting the cell with a p54nrb antibody.

450. A method of screening for a tolerable oligomeric compound comprising any of the methods of embodiments 445-449.

451. The method of any of embodiments 445-450, wherein the oligomeric compound is the oligomeric compound of any of embodiments 1-407.

452. An oligomeric compound comprising a modified oligonucleotide consisting of 12-23 linked nucleosides, wherein the modified oligonucleotide comprises a 5'-region, a central region, and a 3'-region wherein:

the 5'-region consists of 1-5 linked modified nucleosides;

the 3'-region consists of 1-5 linked modified nucleosides; and the central region consists of 7-11 linked nucleosides and has the formula:

$$(N_{d1})(N_x)(N_y)(N_z)(N_d)_q$$

wherein one of $N_x$, $N_y$, and $N_z$, is a safety enhancing nucleoside;

the other two of $N_x$, $N_y$, and $N_z$ are independently selected from an unmodified 2'-β-D-deoxyribosyl, a DNA isomer, and a DNA mimic;

$N_{d1}$ and each $N_d$ is independently selected from an unmodified 2'-β-D-deoxyribosyl, a DNA isomer, and a DNA mimic; and wherein q is 2-7.

453. The oligomeric compound of embodiment 1, wherein the safety enhancing nucleoside is $N_x$ or $N_y$.

454. The oligomeric compound of embodiment 1, wherein the safety enhancing nucleoside is N.

455. The oligomeric compound of embodiment 1, wherein the safety enhancing nucleoside is $N_y$.

456. The oligomeric compound of embodiment 1, wherein the safety enhancing nucleoside is $N_z$.

457. The oligomeric compound of any of embodiments 452-456, wherein the safety enhancing nucleoside has a sugar moiety selected from among a sugar surrogate, a bicyclic furanosyl sugar moiety, a non-bicyclic 2'-modified furanosyl sugar moiety, a non-bicyclic 4'-modified furanosyl sugar moiety, or a non-bicyclic 5'-modified furanosyl sugar moiety.

458. The oligomeric compound of any of embodiments 452-457, wherein the safety-enhancing nucleoside has a sugar moiety selected from among a morpholino, a 2'-O-methyl-2'-β-D-deoxyribosy sugar moiety, a cEt bicyclic sugar moiety, a LNA sugar moiety, an ENA sugar moiety, a 5'-methyl substituted 2'-deoxyribosyl sugar moiety, 5'-ethyl substituted 2'-deoxyribosyl sugar moiety, a 5'-allyl substituted 2'-deoxyribosyl sugar moiety and a 2'-β-L-deoxyxylosyl sugar moiety.

459. The oligomeric compound of any of embodiments 452-458, wherein the safety-enhancing nucleoside has a sugar moiety selected from among a 2'-O-methyl-modified sugar moiety and a 5'-modified sugar moiety.

460. The oligomeric compound of embodiment 459, wherein the safety-enhancing nucleoside has a 2'-O-methyl substituted ribosyl sugar moiety.

461. The oligomeric compound of any of embodiments 452-457, wherein the safety-enhancing nucleoside is a sugar surrogate.

462. The oligomeric compound of embodiment 461, wherein the sugar surrogate is selected from among a morpholino, a modified morpholino, and F-HNA.

463. The oligomeric compound of any of embodiments 452-462, wherein $N_{d1}$ is an unmodified 2'-β-D-deoxyribosyl sugar moiety.

464. The oligomeric compound of any of embodiments 452-462, wherein $N_{d1}$ is a DNA isomer.

465. The oligomeric compound of any of embodiments 452-462, wherein $N_{d1}$ is a DNA mimic.

466. The oligomeric compound of any of embodiments 452-465, wherein no more than 3 of the central region nucleosides comprise a sugar moiety other than 2'-β-D-deoxyribosyl.

467. The oligomeric compound of any of embodiments 452-466, wherein each DNA isomer has a sugar moiety independently selected from among 2'-β-D-deoxyxylosyl, 2'-α-L-deoxyribosyl, 2'-β-L-deoxyribosyl, 2'-α-D-deoxyxylosyl, 1, 2'-α-L-deoxyxylosyl, and 2'-β-L-deoxyxylosyl.

468. The oligomeric compound of any of embodiments 452-467, wherein each DNA mimic has a sugar moiety is independently selected from among 5'-methyl-2'-β-D-deoxyribosyl and 5'-ethyl-2'-β-D-deoxyribosyl.

469. The oligomeric compound of any of embodiments 452-463, wherein each nucleoside of the central region other than the safety-enhancing nucleoside has a 2'-β-D-deoxyribosyl sugar moiety.

470. The oligomeric compound of any of 452-469, wherein at least one internucleoside linkage is a phosphorothioate linkage.

471. The oligomeric compound of any of embodiments 452-470, wherein at least 4 internucleoside linkages are phosphorothioate linkages.

472. The oligomeric compound of any of embodiments 452-471, wherein at least one internucleoside linkage is a neutral internucleoside linkage.

473. The oligomeric compound of any of embodiments 452-472, wherein at least one neutral internucleoside linkage is a phosphonate internucleoside linkage.

474. The oligomeric compound of any of embodiments 452-474, wherein at least one neutral internucleoside linkage is a methoxypropyl internucleoside linkage.

475. The oligomeric compound of any of embodiments 452-475, wherein at least one internucleoside linkage of the central region selected from among: the internucleoside Nd1 to Nx, Nx to Ny, Ny to Nz, or Nz to the adjacent Nd is a neutral internucleoside linkage.

476. The oligomeric compound of embodiment 475, wherein the modified oligonucleotide comprises one neutral linkage and the other internucleoside linkages are each independently selected from phosphodiester and phosphorothioate.

477. The oligomeric compound of any of embodiments 542-454 or embodiments 457-476, wherein the safety enhancing nucleoside is $N_x$ and is a 2'O-methyl-substituted nucleoside.

478. The oligomeric compound of any of embodiments 2-453, 455, or embodiments 457-476, wherein the safety enhancing nucleoside is $N_y$ and is a 2'O-methyl-substituted nucleoside.

479. The oligomeric compound of any of embodiments 452-453, 455, or embodiments 457-476, wherein the safety enhancing nucleoside is $N_y$ and has a 5'-substituted 2'-deoxyribosyl sugar moiety.

480. The oligomeric compound of any of embodiments 452 or embodiments 457-476, wherein the safety enhancing nucleoside is $N_z$ and has a 5'-substituted 2'-deoxyribosyl sugar moiety.

481. The oligomeric compound of embodiments 479 or 480, wherein the 5'-substituted ribosyl sugar moiety is a 5'-methyl, 5'-ethyl, or 5'-allyl substituted 2'-deoxyribosyl sugar moiety.

482. The oligomeric compound of embodiments 477-481, wherein at least one nucleoside of the 5'-region comprises a bicyclic furanosyl sugar moiety.

483. The oligomeric compound of any of embodiments 477-482, wherein each nucleoside of the 5'-region comprises a bicyclic furanosyl sugar moiety.

484. The oligomeric compound of any of embodiments 482 or 483, wherein each bicyclic sugar moiety of the 5'-region is selected from among cEt, LNA, and ENA.

485. The oligomeric compound of any of embodiments 452-482 or 484, wherein at least one nucleoside of the 5'-region comprises a non-bicyclic sugar moiety.

486. The oligomeric compound of embodiment 485, wherein the non-bicyclic sugar moiety of the at least one nucleoside of the 5'-region is a 2'-substituted ribosyl sugar moiety.

487. The oligomeric compound of any of embodiments 485-487, wherein each non-bicyclic sugar moiety of the 5'-region has a 2'-substituent selected from among 2'-MOE, 2'-OMe, and 2'-NMA.

488. The oligomeric compound of any of embodiments 477-480, wherein the 5'-region comprises a 2'-MOE modified nucleoside and an LNA modified nucleoside.

489. The oligomeric compound of any of embodiments 477-480, wherein the 5'-region comprises a 2'-MOE modified nucleoside and a cEt modified nucleoside.

490. The oligomeric compound of embodiments 477-489, wherein at least one nucleoside of the 3'-region comprises a bicyclic furanosyl sugar moiety.

491. The oligomeric compound of any of embodiments 477-490, wherein each nucleoside of the 3'-region comprises a bicyclic furanosyl sugar moiety.

492. The oligomeric compound of any of embodiments 490 or 491, wherein each bicyclic sugar moiety of the 3'-region is selected from among cEt, LNA, and ENA.

493. The oligomeric compound of any of embodiments 490 or 492, wherein at least one nucleoside of the 3'-region comprises a non-bicyclic sugar moiety.
494. The oligomeric compound of embodiment 493, wherein the non-bicyclic sugar moiety of the at least one nucleoside of the 3'-region is a 2'-substituted ribosyl sugar moiety.
495. The oligomeric compound of any of embodiments 490 or 492-494, wherein each non-bicyclic sugar moiety of the 3'-region has a 2'-substituent selected from among 2'-MOE, 2'-OMe, and 2'-NMA.
496. The oligomeric compound of any of embodiments 477-490 or 492-495, wherein the 3'-region comprises a 2'-MOE modified nucleoside and an LNA modified nucleoside.
497. The oligomeric compound of any of embodiments 477-490 or 492-495, wherein the 3'-region comprises a 2'-MOE modified nucleoside and a cEt modified nucleoside.
498. The oligomeric compound of any of embodiments 477-480, wherein each nucleoside of the 5'-region comprises a bicyclic furanosyl sugar moiety and each nucleoside of the 3'-region comprises a non-bicyclic sugar moiety.
499. The oligomeric compound of any of embodiments 477-480, wherein each nucleoside of the 5'-region comprises an LNA sugar moiety and each nucleoside of the 3'-region comprises a 2'MOE sugar moiety.
500. The oligomeric compound of any of embodiments 477-480, wherein each nucleoside of the 5'-region comprises cEt sugar moiety and each nucleoside of the 3'-region comprises a 2'MOE sugar moiety.
501. The oligomeric compound of any of embodiments 452-500, wherein the modified oligonucleotide has a nucleobase sequence complementary to a target RNA; wherein the target RNA is a mRNA or pre-mRNA.
502. The oligomeric compound of embodiment 501, wherein the target RNA encodes a protein that is expressed in the liver.
503. The oligomeric compound of embodiment 502, wherein the target RNA encodes a protein that is expressed in the CNS.
504. The oligomeric compound of any of embodiments 452-503, wherein the oligomeric compound is not toxic.
505. The oligomeric compound of any of embodiment 452-504, wherein a comparator compound is toxic; wherein the comparator compound is identical to the oligomeric compound except that each nucleoside of the central region of the comparator compound is a nucleoside comprising 2'-β-D-deoxyribosyl sugar moiety.
506. The oligomeric compound of embodiment 505, wherein administering a dose of the oligomeric compound to an animal results in a circulating ALT level that is at least 3-fold lower than the ALT level that results from administering the same dose of the comparator compound to an animal for at least one matched dose.
507. The oligomeric compound of embodiment 505 or 506, wherein the lowest dose of the oligomeric compound that raises circulating ALT to over 300 units per liter is at least three-fold higher than the lowest dose of the comparator compound that raises circulating ALT to over 300 units per liter.
508. The oligomeric compound of any of embodiments 502-507, wherein the oligomeric compound is capable of reducing the target RNA in a cell.
509. The oligomeric compound of embodiment 508, wherein the oligomeric compound has RNA-reducing activity comparable to a comparator compound, wherein the comparator compound is identical to the oligomeric compound except that each nucleoside of the central region of the comparator compound is a nucleoside comprising 2'-β-D-deoxyribosyl sugar moiety.
510. The oligomeric compound of embodiment 509 having RNA-reducing activity that is no more than 2-fold worse than the RNA-reducing activity of the comparator compound.
511. An oligomeric compound comprising a modified oligonucleotide consisting of 12-23 linked nucleosides, wherein the modified oligonucleotide comprises a 5'-region, a central region, and a 3'-region wherein:
the 5'-region consists of 1-5 linked nucleosides; wherein at least one 5'-region nucleoside is modified;
the 3'-region consists of 1-5 linked nucleosides; wherein at least one 3'-region nucleoside is modified; and
the central region consists of 7-11 linked nucleosides, and has the formula:

$$(N_{d1})_{L1}(N_{d2})_{L2}(N_{d3})_{L3}(N_{d4})_{L4}(N_d)_q;$$

wherein $N_{d1}$, $N_{d2}$, $N_{d3}$, $N_{d4}$, and each $N_d$ are independently selected from among a nucleoside comprising an unmodified 2'-β-D-deoxyribosyl sugar moiety, a DNA isomer sugar moiety, or a DNA mimic sugar moiety;
wherein each L1, L2, L3, and L4 is an internucleoside linkage; and wherein at least one of L1, L2, L3, and L4 is a neutral internucleoside linkage.
512. The oligomeric compound of embodiment 511, wherein L1 is a neutral internucleoside linkage.
513. The oligomeric compound of embodiment 511, wherein L2 is a neutral internucleoside linkage.
514. The oligomeric compound of embodiment 511, wherein L3 is a neutral internucleoside linkage.
515. The oligomeric compound of any of embodiments 511-514, wherein the neutral linkage is a phosphonate internucleoside linkage.
516. The oligomeric compound of any of embodiments 511-515, wherein the neutral linkage is a methoxypropyl internucleoside linkage.
517. The oligomeric compound of any of embodiments 511-516, wherein each remaining internucleoside linkage is a phosphodiester or phosphorothioate internucleoside linkage.
518. A method comprising administering the oligomeric compound or composition of any of embodiments 452-517 to a human subject.
519. A method of treating a disease or disorder comprising administering the oligomeric compound or composition of any of embodiments 452-517 to a human subject.
520. A method of modulating the amount or activity of a target RNA in a human subject comprising administering the oligomeric compound or composition of any of embodiments 452-517 to the human subject; and thereby modulating the amount or activity of the target RNA in the human subject.
521. A method of treating a disease or disorder in a human subject comprising administering the oligomeric compound or composition of any of embodiments 452-517 to the human subject having the disease or disorder; and thereby treating the disease or disorder in the human subject.
522. The method of embodiment 520 or 521, wherein the disease or disorder is a liver disease, and wherein the oligomeric compound modulates the amount or activity of a liver target RNA.

523. The method of embodiment 520 or 521, wherein the disease or disorder is a central nervous system disease, and wherein the oligomeric compound modulates the amount or activity of a central nervous system target RNA.

524. The method of any of embodiments 519-523, wherein the disease or disorder is a cancer, a neurodegenerative disease, a cardiovascular disease, an immunological disease, a hereditary disease, a repeat expansion disease, a muscle-wasting disease, or a metabolic disease.

525. The method of any of embodiments 518-524, wherein the plasma ALT level of the human subject after the administration is not more than three times higher than it was prior to the administration.

526. The method of any of embodiments 518-525, wherein the plasma ALT level of the human subject after the administration is not more than 150 units per liter.

527. The method of any of embodiments 518-526, wherein the human subject is susceptible to liver damage.

528. The method of any of embodiments 518-527, wherein the human subject is susceptible to liver degeneration.

529. The method of any of embodiments 518-528, wherein the human subject is susceptible to elevated apoptosis in the liver.

530. The method of any of embodiments 518-529, wherein the human subject has a liver disease.

531. The method of any of embodiments 518-530, comprising administering the parent oligomeric compound of the oligomeric compound of any of embodiments 452-517 to a mouse.

532. The method of any of embodiments 518-531, comprising contacting a cell with the parent oligomeric compound of the oligomeric compound of any of embodiments 452-517.

533. The method of embodiment 518-532, wherein each sugar moiety of the central region of the parent oligomeric compound is an unmodified 2'-β-D-deoxyribosyl sugar moiety, and wherein each internucleoside linkage of the central region of the parent oligomeric compound is a phosphorothioate internucleoside linkage.

534. A method of designing an oligomeric compound comprising starting with a parent oligomeric compound and changing the design of that compound in order to arrive at an oligomeric compound of any one of embodiments 452-517.

535. A method of designing an oligomeric compound comprising identifying a parent oligomeric compound and changing the design of that parent oligomeric compound to arrive at a second oligomeric compound, wherein the second oligomeric compound is an oligomeric compound of any one of embodiments 452-517.

536. A method of improving hepatotoxicity of an oligomeric compound comprising the steps of (i) identifying a parent oligomeric compound that has plasma ALT levels above 300 units per liter in a mouse, and (ii) providing an oligomeric compound according to any one of embodiments 452-517.

537. The method of embodiment 536, wherein the method designs an oligomeric compound with improved therapeutic index relative to the parent oligomeric compound.

538. The method of embodiment 534-537, wherein the method designs an oligomeric compound with lower hepatotoxicity relative to the parent oligomeric compound.

539. The method of embodiment 535-538, wherein the second oligomeric compound has an improved therapeutic index relative to the parent oligomeric compound.

540. The method of embodiment 535-539, wherein the second oligomeric compound has reduced hepatotoxicity in a mouse relative to the parent oligomeric compound.

541. The method of embodiment 540, wherein the oligomeric compound according to any one of embodiments 452-517 has reduced hepatotoxicity relative to the parent oligomeric compound.

542. A method comprising administering an oligomeric compound of any of embodiments 452-517 to a mouse and separately administering the parent oligomeric compound of the oligomeric compound of any of embodiments 452-517 to a second mouse, wherein the therapeutic index of the oligomeric compound of any of embodiments 452-517 is improved relative to the therapeutic index of the parent oligomeric compound.

543. The method of any of embodiments 518-542, wherein the level of p21 RNA is measured in the mouse, the cell, and/or the human subject.

544. A method comprising administering an oligomeric compound of any of embodiments 452-517 to a subject and measuring the level of p21 RNA in the subject.

545. The method of embodiment 543 or 544, wherein the subject is a mouse.

546. The method of embodiment 543 or 544, wherein the subject is a human.

547. The method of any of embodiments 543-546, wherein the p21 RNA level is measured within 24 hours of the administration.

548. The method of any of embodiments 437-441, wherein the p21 RNA level is measured 24-48 hours following the administration.

549. An oligomeric compound or composition of any one of embodiments 452-517, for use in medical therapy.

550. The method of any of embodiments 445-449, wherein the oligomeric compound is the oligomeric compound of any of embodiments 452-517.

551. An oligomeric compound comprising a modified oligonucleotide consisting of 12-21 linked nucleosides, wherein the modified oligonucleotide has the formula A-B-C, wherein A is a 5'-region, B is a central region, and C is a 3'-region; wherein:

the 5'-region consists of 1-5 linked nucleosides, wherein at least one nucleoside of the 5'-region is a modified nucleoside comprising a modified sugar;

the 3'-region consists of 1-5 linked nucleosides wherein at least one nucleoside of the 3'-region is a modified nucleoside comprising a modified sugar; and the central region consists of 7-11 linked nucleosides, wherein the 5'-most portion of the central region has the following formula:

$$(N_{da})(N_x)(N_y)(N_z)(N_{db})$$

wherein one of $N_x$, $N_y$, and $N_z$, is a safety-enhancing nucleoside;

the other two of $N_x$, $N_y$, and $N_z$ are independently selected from a DNA nucleoside, a DNA isomer, a modified DNA isomer, and a DNA mimic; and $N_{da}$ and $N_{db}$ are each independently selected from a DNA nucleoside, a DNA isomer, a modified DNA isomer, and a DNA mimic.

552. The oligomeric compound of embodiment 551, wherein the 5'-region consists of one nucleoside.

553. The oligomeric compound of embodiment 551, wherein the 5'-region consists of 2-5 linked nucleosides.

554. The oligomeric compound of embodiment 551, wherein the 5'-region consists of 2-4 linked nucleosides.

555. The oligomeric compound of embodiment 551, wherein the 5'-region consists of 2 linked nucleosides.
556. The oligomeric compound of embodiment 551, wherein the 5'-region consists of 3 linked nucleosides.
557. The oligomeric compound of embodiment 551, wherein the 5'-region consists of 4 linked nucleosides.
558. The oligomeric compound of embodiment 551, wherein the 5'-region consists of 5 linked nucleosides.
559. The oligomeric compound of any of embodiments 551-558, wherein each nucleoside of the 5'-region is a modified nucleoside.
560. The oligomeric compound of any of embodiments 551-559, wherein each nucleoside of the 5'-region is a modified nucleoside comprising a modified sugar.
561. The oligomeric compound of any of embodiments 551-560, wherein each modified nucleoside of the 5'-region has the same modification.
562. The oligomeric compound of and of embodiments 551-560, wherein at least two nucleosides of the 5'-region are modified nucleosides having different modifications.
563. The oligomeric compound of any of embodiments 551-562, wherein each nucleoside of the 5'-region comprises a 2'-modified ribosyl sugar moiety.
564. The oligomeric compound of any of embodiments 551-563, wherein at least one nucleoside of the 5'-region comprises a bicyclic furanosyl sugar moiety.
565. The oligomeric compound of any of embodiments 551-564, wherein each nucleoside of the 5'-region comprises a bicyclic furanosyl sugar moiety.
566. The oligomeric compound of any of embodiments 551-565, wherein at least one nucleoside of the 5'-region comprises a non-bicyclic sugar moiety.
567. The oligomeric compound of embodiment 566, wherein the non-bicyclic sugar moiety of the at least one nucleoside of the 5'-region is a 2'-substituted ribosyl sugar moiety.
568. The oligomeric compound of any of embodiments 551-567, wherein each nucleoside of the 5'-region comprises a non-bicyclic sugar moiety.
569. The oligomeric compound of embodiment 568, wherein each nucleoside of the 5'-region comprises a 2'-substituted furanosyl sugar moiety.
570. The oligomeric compound of any of embodiments 551-569, wherein each nucleoside of the 5'-region comprises a 2'-modified furanosyl sugar moiety independently selected from a bicyclic sugar moiety and a non-bicyclic 2'-substituted ribosyl sugar moiety.
571. The oligomeric compound of any of embodiments 551-570, wherein each nucleoside of the 5'-region comprises a bicyclic sugar moiety.
572. The oligomeric compound of any of embodiments 551-571, wherein each nucleoside of the 5'-region comprises a non-bicyclic 2'-substituted ribosyl sugar moiety.
573. The oligomeric compound of any of embodiments 551-572, wherein each bicyclic sugar moiety of the 5'-region is selected from among cEt, LNA, and ENA.
574. The oligomeric compound of any of embodiments 551-573, wherein each bicyclic sugar moiety of the 5'-region is a cEt sugar moiety.
575. The oligomeric compound of any of embodiments 551-574, wherein each bicyclic sugar moiety of the 5'-region is an LNA sugar moiety.
576. The oligomeric compound of any of embodiments 551-575, wherein each non-bicyclic sugar moiety of the 5'-region has a 2'-substituent selected from among 2'-MOE, 2'-OMe, and 2'-NMA.
577. The oligomeric compound of any of embodiments 551-576, wherein none of the nucleosides of the 5'-region comprise a sugar moiety having a 2'-F substituent.
578. The oligomeric compound of any of embodiments 551-577, wherein none of the nucleosides of the 5'-region comprise a sugar moiety having a 2'-MOE substituent.
579. The oligomeric compound of any of embodiments 551-578, wherein none of the nucleosides of the 5'-region comprise a sugar moiety having a 2'-OMe substituent.
580. The oligomeric compound of any of embodiments 551-579, wherein none of the nucleosides of the 5'-region comprise a cEt sugar moiety.
581. The oligomeric compound of any of embodiments 551-580, wherein none of the nucleosides of the 5'-region comprise a LNA sugar moiety.
582. The oligomeric compound of any of embodiments 551-581, wherein each nucleobase of the 5'-region is independently selected from among thymine, uracil, guanine, cytosine, 5-methylcytosine, and adenine.
583. The oligomeric compound of any of embodiments 551-582, wherein each internucleoside linkage of the 5'-region is selected from among phosphodiester and phosphorothioate internucleoside linkages.
584. The oligomeric compound of any of embodiments 551-583, wherein the 3'-region consists of one nucleoside.
585. The oligomeric compound of any of embodiments 551-583, wherein the 3'-region consists of 2-5 linked nucleosides.
586. The oligomeric compound of any of embodiments 551-583, wherein the 3'-region consists of 2-4 linked nucleosides.
587. The oligomeric compound of any of embodiments 551-583, wherein the 3'-region consists of 2 linked nucleosides.
588. The oligomeric compound of any of embodiments 551-583, wherein the 3'-region consists of 3 linked nucleosides.
589. The oligomeric compound of any of embodiments 551-583, wherein the 3'-region consists of 4 linked nucleosides.
590. The oligomeric compound of any of embodiments 551-583, wherein the 3'-region consists of 5 linked nucleosides.
591. The oligomeric compound of any of embodiments 551-590, wherein each nucleoside of the 3'-region is a modified nucleoside.
592. The oligomeric compound of any of embodiments 551-591, wherein each nucleoside of the 3'-region is a modified nucleoside comprising a modified sugar moiety.
593. The oligomeric compound of any of embodiments 551-592, wherein each modified nucleoside of the 3'-region has the same modification.
594. The oligomeric compound of and of embodiments 551-592, wherein at least two nucleosides of the 3'-region are modified nucleosides having different modifications.
595. The oligomeric compound of any of embodiments 551-594, wherein each nucleoside of the 3'-region comprises a 2'-modified ribosyl sugar moiety.
596. The oligomeric compound of any of embodiments 551-595, wherein at least one nucleoside of the 3'-region comprises a bicyclic furanosyl sugar moiety.
597. The oligomeric compound of any of embodiments 551-596, wherein each nucleoside of the 3'-region comprises a bicyclic furanosyl sugar moiety.
598. The oligomeric compound of any of embodiments 551-597, wherein at least one nucleoside of the 3'-region comprises a non-bicyclic sugar moiety.

599. The oligomeric compound of embodiment 598, wherein the non-bicyclic sugar moiety of the at least one nucleoside of the 3'-region is a 2'-substituted ribosyl sugar moiety.
600. The oligomeric compound of any of embodiments 551-599, wherein each nucleoside of the 3'-region comprises a non-bicyclic sugar moiety.
601. The oligomeric compound of embodiment 600, wherein each nucleoside of the 3'-region comprises a 2'-substituted furanosyl sugar moiety.
602. The oligomeric compound of any of embodiments 551-601, wherein each nucleoside of the 3'-region comprises a 2'-modified furanosyl sugar moiety independently selected from a bicyclic sugar moiety and a non-bicyclic 2'-substituted ribosyl sugar moiety.
603. The oligomeric compound of any of embodiments 551-602, wherein each nucleoside of the 3'-region comprises a bicyclic sugar moiety.
604. The oligomeric compound of any of embodiments 551-602, wherein each nucleoside of the 3'-region comprises a non-bicyclic 2'-substituted ribosyl sugar moiety.
605. The oligomeric compound of any of embodiments 551-603, wherein each bicyclic sugar moiety of the 3'-region is selected from among cEt, LNA, and ENA.
606. The oligomeric compound of any of embodiments 551-605, wherein each bicyclic sugar moiety of the 3'-region is a cEt sugar moiety.
607. The oligomeric compound of any of embodiments 551-606, wherein each bicyclic sugar moiety of the 3'-region is an LNA sugar moiety.
608. The oligomeric compound of any of embodiments 551-607, wherein each non-bicyclic sugar moiety of the 3'-region has a 2'-substituent selected from among 2'-MOE, 2'-OMe, and 2'-NMA.
609. The oligomeric compound of any of embodiments 551-608, wherein none of the nucleosides of the 3'-region comprise a sugar moiety having a 2'-F substituent.
610. The oligomeric compound of any of embodiments 551-609, wherein none of the nucleosides of the 3'-region comprise a sugar moiety having a 2'-MOE substituent.
611. The oligomeric compound of any of embodiments 551-610, wherein none of the nucleosides of the 3'-region comprise a sugar moiety having a 2'-OMe substituent.
612. The oligomeric compound of any of embodiments 551-611, wherein none of the nucleosides of the 3'-region comprise a cEt sugar moiety.
613. The oligomeric compound of any of embodiments 551-612, wherein none of the nucleosides of the 3'-region comprise a LNA sugar moiety.
614. The oligomeric compound of any of embodiments 551-613, wherein each nucleobase of the 3'-region is independently selected from among thymine, uracil, guanine, cytosine, 5-methylcytosine, and adenine.
615. The oligomeric compound of any of embodiments 551-614, wherein each internucleoside linkage of the 3'-region is selected from among phosphodiester and phosphorothioate internucleoside linkages.
616. The oligomeric compound of any of embodiments 551-615, wherein the modified nucleosides of the 5'-region have the same modifications as the modifications of the modified nucleosides of the 3'-region.
617. The oligomeric compound of any of embodiments 551-615, wherein at least one modified nucleoside of the 5'-region and one modified nucleoside of the 3'-region comprise modifications that differ from one another.
618. The oligomeric compound of any of embodiments 551-617, wherein the 5'-region and the 3'-region together include at least one non-bicyclic 2'-substituted modified nucleoside and at least one bicyclic nucleoside.
619. The oligomeric compound of any of embodiment 618, where the bicyclic nucleoside is a cEt nucleoside.
620. The oligomeric compound of embodiment 618, where the bicyclic nucleoside is an LNA nucleoside.
621. The oligomeric compound of any of embodiments 618-620, wherein the non-bicyclic 2'-modified nucleoside is a 2'-MOE nucleoside.
622. The oligomeric compound of any of embodiments 618-620, wherein the non-bicyclic 2'-modified nucleoside is a 2'-OMe nucleoside.
623. The oligomeric compound of any of embodiments 618-622, wherein at least one nucleoside of the 5'-region or the 3'-region is an unmodified DNA nucleoside.
624. The oligomeric compound of any of embodiments 551-623, wherein the central region has the formula:

$$(N_{da})(N_x)(N_y)(N_z)(N_{db})(N_{dc})_q$$

wherein each $N_{dc}$ is independently selected from an unmodified DNA nucleoside, a DNA isomer, a 2'-modified DNA isomer, and a DNA mimic; and q is 2-6.
625. The oligomeric compound of any of embodiments 551-624, wherein the central region consists of 7 linked nucleosides.
626. The oligomeric compound of any of embodiments 551-624, wherein the central region consists of 8 linked nucleosides.
627. The oligomeric compound of any of embodiments 551-624, wherein the central region consists of 9 linked nucleosides.
628. The oligomeric compound of any of embodiments 551-624, wherein the central region consists of 10 linked nucleosides.
629. The oligomeric compound of any of embodiments 551-624, wherein the central region consists of 11 linked nucleosides.
630. The oligomeric compound of any of embodiments 551-629, wherein Nx is the safety-enhancing nucleoside.
631. The oligomeric compound of any of embodiments 551-629, wherein Ny is the safety-enhancing nucleoside.
632. The oligomeric compound of any of embodiments 551-629, wherein Nz is the safety-enhancing nucleoside.
633. The oligomeric compound of any of embodiments 551-632, wherein the safety enhancing nucleoside is a DNA isomer or a modified DNA isomer, or a modified nucleoside comprising either a sugar surrogate, a bicyclic furanosyl sugar moiety, or a non-bicyclic modified furanosyl sugar moiety.
634. The oligomeric compound of any of embodiments 551-33, wherein the safety enhancing nucleoside is a DNA isomer or a modified DNA isomer, or comprises either a sugar surrogate, a bicyclic furanosyl sugar moiety, a non-bicyclic, 2'-modified furanosyl sugar moiety, a non-bicyclic 3'-modified furanosyl sugar moiety, a non-bicyclic, 4'-modified furanosyl sugar moiety, or a non-bicyclic 5'-modified furanosyl sugar moiety.
635. The oligomeric compound of any of embodiments 551-634, wherein the safety enhancing nucleoside comprises a sugar surrogate selected from a morpholino, a modified morpholino, a modified cyclohexenyl, or a modified tetrahydropyran.
636. The oligomeric compound of any of embodiments 551-634, wherein the safety enhancing nucleoside comprises a sugar surrogate selected from a morpholino, a modified morpholino, CeNA, F-CeNA, HNA, OMe-HNA or F-HNA.

637. The oligomeric compound of any of embodiments 551-634, wherein the safety enhancing nucleoside is a DNA isomer comprising a sugar moiety selected from among 2'-β-D-deoxyxylosyl, 2'-α-L-deoxyribosyl, 2'-β-L-deoxyribosyl, 2'-α-D-deoxyxylosyl, 2'-α-D-deoxyribosyl, 2'-α-L-deoxyxylosyl, and 2'-β-L-deoxyxylosyl.

638. The oligomeric compound of any of embodiments 551-634, wherein the safety enhancing nucleoside is a DNA isomer comprising a sugar moiety selected from among 2'-β-D-deoxyxylosyl, 2'-α-L-deoxyribosyl, and 2'-β-L-deoxyribosyl.

639. The oligomeric compound of any of embodiments 551-634, wherein the safety enhancing nucleoside is a modified DNA isomer comprising a 2'-modified sugar moiety, wherein the sugar moiety has the conformation 2'-β-D-deoxyxylosyl, 2'-α-L-deoxyribosyl, 2'-β-L-deoxyribosyl, 2'-α-D-deoxyxylosyl, 1, 2'-α-L-deoxyxylosyl, and 2'-β-L-deoxyxylosyl and the 2' position is further substituted with a hydroxyl, a fluoro, or O—$C_1$-$C_{10}$ alkoxy substituent.

640. The oligomeric compound of any of embodiments 551-634, wherein the safety enhancing nucleoside is a modified DNA isomer comprising a 2'-modified sugar moiety, wherein the sugar moiety has the conformation 2'-β-D-deoxyxylosyl, 2'-α-L-deoxyribosyl, 2'-β-L-deoxyribosyl, 2'-α-D-deoxyxylosyl, 1, 2'-α-L-deoxyxylosyl, and 2'-β-L-deoxyxylosyl and the 2' position is further substituted with a hydroxyl, a fluoro, or OMe substituent.

641. The oligomeric compound of any of embodiments 551-634, wherein the safety enhancing nucleoside is a modified DNA isomer comprising a 2'-modified sugar moiety, wherein the sugar moiety has the conformation 2'-β-D-deoxyxylosyl, 2'-α-L-deoxyribosyl, 2'-β-L-deoxyribosyl, 2'-α-D-deoxyxylosyl, 1, 2'-α-L-deoxyxylosyl, and 2'-β-L-deoxyxylosyl and the 2' position is further substituted with a fluoro or OMe substituent.

642. The oligomeric compound of any of embodiments 551-634, wherein the safety enhancing nucleoside is a modified DNA isomer comprising a sugar moiety selected from among 2'-β-D-deoxyxylosyl, 2'-α-L-deoxyribosyl, and 2'-β-L-deoxyribosyl and the 2' position is further substituted with a hydroxyl, fluoro, or OMe substituent.

643. The oligomeric compound of any of embodiments 551-634, wherein the safety enhancing nucleoside is a modified nucleoside comprising a bicyclic furanosyl sugar moiety 644. The oligomeric compound of any of embodiments 551-634, wherein the safety enhancing nucleoside is selected from among cEt, LNA, α-L-LNA, and ENA.

645. The oligomeric compound of any of embodiments 551-634, wherein the safety enhancing nucleoside comprises a 2'-substituted furanosyl sugar moiety.

646. The oligomeric compound of embodiment 645, wherein the 2'-substituted furanosyl sugar moiety of the safety enhancing nucleoside has a 2' substituent selected from: halo, allyl, amino, azido, SH, CN, OCN, $CF_3$, $OCF_3$, O—$C_1$-$C_{10}$ alkoxy, O—$C_1$-$C_{10}$ substituted alkoxy, $C_1$-$C_{10}$ alkyl, $C_1$-$C_{10}$ substituted alkyl, S-alkyl, $N(R_m)$-alkyl, O-alkenyl, S-alkenyl, $N(R_m)$-alkenyl, O-alkynyl, S-alkynyl, $N(R_m)$-alkynyl, O-alkylenyl-O-alkyl, alkynyl, alkaryl, aralkyl, O-alkaryl, O-aralkyl, $O(CH_2)_2SCH_3$, $O(CH_2)_2ON(R_m)(R_n)$ or $OCH_2C({=}O){-}N(R_m)(R_n)$, where each $R_m$ and $R_n$ is, independently, H, an amino protecting group, or substituted or unsubstituted $C_1$-$C_{10}$ alkyl.

647. The oligomeric compound of embodiment 645, wherein the 2'-substituted furanosyl sugar moiety of the safety enhancing nucleoside has a 2' substituent selected from: halo, O—$C_1$-$C_{10}$ alkoxy, O—$C_1$-$C_{10}$ substituted alkoxy, $C_1$-$C_{10}$ alkyl, $C_1$-$C_{10}$ substituted alkyl, S-alkyl, $N(R_m)$-alkyl, $O(CH_2)_2ON(R_m)(R_n)$ or $OCH_2C({=}O){-}N(R_m)(R_n)$, where each $R_m$ and $R_n$ is, independently, H, an amino protecting group, or substituted or unsubstituted $C_1$-$C_{10}$ alkyl.

648. The oligomeric compound of embodiment 645, wherein the 2'-substituted furanosyl sugar moiety of the safety enhancing nucleoside has a 2' substituent selected from: fluoro, OMe, MOE, NMA.

649. The oligomeric compound of any of embodiments 551-648, wherein the safety enhancing nucleoside comprises a 2'-substituted furanosyl sugar moiety comprising a 2'-OMe or 2'-MOE.

650. The oligomeric compound of any of embodiments 551-649, wherein the safety enhancing nucleoside comprises a 2'-substituted furanosyl sugar moiety comprising a 2'-OMe.

651. The oligomeric compound of any of embodiments 551-650, wherein the safety enhancing nucleoside comprises a 2'-OMe modified 2'-β-D-deoxyribosyl sugar moiety.

652. The oligomeric compound of any of embodiments 551-634, wherein the safety enhancing nucleoside comprises a 3'-modified furanosyl sugar moiety having a 3' substituent selected from: halo, allyl, amino, azido, SH, CN, $CF_3$, $OCF_3$, $C_1$-$C_{10}$ alkyl, $C_1$-$C_{10}$ substituted alkyl, S-alkyl, $N(R_m)$-alkyl, $N(R_m)$-alkenyl, $N(R_m)$-alkynyl, O-alkylenyl-O-alkyl, alkynyl, alkaryl, or aralkyl.

653. The oligomeric compound of any of embodiments 551-634 or embodiment 652, wherein the safety enhancing nucleoside comprises a 3'-modified furanosyl sugar moiety having a 3' substituent selected from: $C_1$-$C_{10}$ alkyl, or $C_1$-$C_{10}$ substituted alkyl.

654. The oligomeric compound of any of embodiments 551-634 or 652-653, wherein the safety enhancing nucleoside comprises a 3'-methyl furanosyl sugar moiety.

655. The oligomeric compound of any of embodiments 551-634, wherein the safety enhancing nucleoside comprises a 4'-modified furanosyl sugar moiety having a 4' substituent selected from: halo, allyl, amino, azido, SH, CN, OCN, $CF_3$, $OCF_3$, O—$C_1$-$C_{10}$ alkoxy, O—$C_1$-$C_{10}$ substituted alkoxy, $C_1$-$C_{10}$ alkyl, $C_1$-$C_{10}$ substituted alkyl, S-alkyl, $N(R_m)$-alkyl, O-alkenyl, S-alkenyl, $N(R_m)$-alkenyl, O-alkynyl, S-alkynyl, $N(R_m)$-alkynyl, O-alkylenyl-O-alkyl, alkynyl, alkaryl, aralkyl, O-alkaryl, O-aralkyl, $O(CH_2)_2SCH_3$, $O(CH_2)_2ON(R_m)(R_n)$ or $OCH_2C({=}O){-}N(R_m)(R_n)$, where each $R_m$ and $R_n$ is, independently, H, an amino protecting group, or substituted or unsubstituted $C_1$-$C_{10}$ alkyl.

656. The oligomeric compound of any of embodiments 551-634 or 655, wherein the safety enhancing nucleoside comprises a 4'-modified furanosyl sugar moiety having a 4'-methyl.

657. The oligomeric compound of any of embodiments 551-634, wherein the safety enhancing nucleoside has the structure shown below, wherein R represents an optional 2' substituent group and Bx is a heterocyclic base moiety:

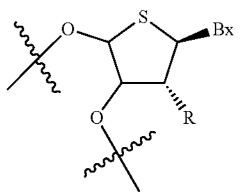

658. The oligomeric compound of embodiment 657, wherein in R is selected from among H, OH, OMe, F, or MOE.

659. The oligomeric compound of any of embodiments 551-634, wherein the safety enhancing nucleoside comprises a 5'-modified furanosyl sugar moiety having a 5' substituent selected from: halo, allyl, amino, azido, SH, CN, OCN, $CF_3$, $OCF_3$, O—$C_1$-$C_{10}$ alkoxy, O—$C_1$-$C_{10}$ substituted alkoxy, $C_1$-$C_{10}$ alkyl, $C_1$-$C_{10}$ substituted alkyl, S-alkyl, N($R_m$)-alkyl, O-alkenyl, S-alkenyl, N($R_m$)-alkenyl, O-alkynyl, S-alkynyl, N($R_m$)-alkynyl, O-alkylenyl-O-alkyl, alkynyl, alkaryl, aralkyl, O-alkaryl, O-aralkyl, $O(CH_2)_2SCH_3$, $O(CH_2)_2ON(R_m)(R_n)$ or $OCH_2C(=O)$—$N(R_m)(R_n)$, where each $R_m$ and $R_n$ is, independently, H, an amino protecting group, or substituted or unsubstituted $C_1$-$C_{10}$ alkyl.

660. The oligomeric compound of any of embodiments 551-634 or 659, wherein the safety enhancing nucleoside comprises a 5'-modified furanosyl sugar moiety with a 5' substituent selected from: 5'-methyl, 5'-ethyl or a 5'-allyl.

661. The oligomeric compound of any of embodiments 551-634 or 659-660, wherein the safety enhancing nucleoside comprises a 5'-modified furanosyl sugar moiety with a 5' substituent selected from: 5'-(R)-methyl- or 5'-(R)-ethyl.

662. The oligomeric compound of any of embodiments 551-634 or 659-661, wherein the safety enhancing nucleoside comprises a 5'-(R)-methyl-2'-β-D-deoxyribosyl sugar moiety.

663. The oligomeric compound of any of embodiments 551-634 or 659-662, wherein the safety enhancing nucleoside comprises a 5'-(R)-ethyl-2'-β-D-deoxyribosyl sugar moiety.

664. The oligomeric compound of any of embodiments 551-663, wherein the safety enhancing nucleoside does not comprise a 2'-F modified sugar moiety.

665. The oligomeric compound of any of embodiments 551-664, wherein the safety enhancing nucleoside does not comprise a cEt modified sugar moiety.

666. The oligomeric compound of any of embodiments 551-665, wherein the safety enhancing nucleoside does not comprise a 2'-MOE modified sugar moiety.

667. The oligomeric compound of any of embodiments 551-666, wherein the safety enhancing nucleoside comprises a hypoxanthine nucleobase.

668. The oligomeric compound of any of embodiments 551-667, wherein the safety enhancing nucleoside comprises a nucleobase selected from among A, T, G, C, $^m$C, and U.

669. The oligomeric compound of any of embodiments 551-668, wherein the safety enhancing nucleoside is a modified nucleoside other than cEt, MOE, LNA, or FANA.

670. The oligomeric compound of any of embodiments 551-669, wherein each Nd is independently selected from among a DNA nucleoside, a DNA isomer, a modified DNA isomer, and a DNA mimic.

671. The oligomeric compound of embodiment 670, wherein each DNA isomer comprises a sugar moiety selected from among 2'-β-D-deoxyxylosyl, 2'-α-L-deoxyribosyl, 2'-β-L-deoxyribosyl, 2'-α-D-deoxyxylosyl, 2'-α-D-deoxyribosyl, 2'-α-L-deoxyxylosyl, and 2'-β-L-deoxyxylosyl.

672. The oligomeric compound of embodiment 671, wherein each DNA isomer comprises a sugar moiety selected from among 2'-β-D-deoxyxylosyl, 2'-α-L-deoxyribosyl, and 2'-β-L-deoxyribosyl.

673. The oligomeric compound of embodiment 670, wherein each modified DNA isomer comprises a 2'-modified sugar moiety, wherein the sugar moiety has the conformation 2'-β-D-deoxyxylosyl, 2'-α-L-deoxyribosyl, 2'-β-L-deoxyribosyl, 2'-α-D-deoxyxylosyl, 1, 2'-α-L-deoxyxylosyl, and 2'-β-L-deoxyxylosyl and the 2' position is further substituted with a hydroxyl, a fluoro, or O—$C_1$-$C_{10}$ alkoxy substituent.

674. The oligomeric compound of embodiment 673, wherein each modified DNA isomer comprises a 2'-modified sugar moiety, wherein the sugar moiety has the conformation 2'-β-D-deoxyxylosyl, 2'-α-L-deoxyribosyl, 2'-β-L-deoxyribosyl, 2'-α-D-deoxyxylosyl, 1, 2'-α-L-deoxyxylosyl, and 2'-β-L-deoxyxylosyl and the 2' position is further substituted with a hydroxyl, a fluoro, or OMe substituent.

675. The oligomeric compound of embodiment 674, wherein each modified DNA isomer comprises a 2'-modified sugar moiety, wherein the sugar moiety has the conformation 2'-β-D-deoxyxylosyl, 2'-α-L-deoxyribosyl, 2'-β-L-deoxyribosyl, 2'-α-D-deoxyxylosyl, 1, 2'-α-L-deoxyxylosyl, and 2'-β-L-deoxyxylosyl and the 2' position is further substituted with a fluoro or OMe substituent.

676. The oligomeric compound of embodiment 675, wherein each modified DNA isomer comprises a 2'-modified sugar moiety, wherein the sugar moiety is selected from among 2'-β-D-deoxyxylosyl, 2'-α-L-deoxyribosyl, and 2'-β-L-deoxyribosyl and the 2' position is further substituted with a hydroxyl, fluoro, or OMe substituent.

677. The oligomeric compound of embodiment 670, wherein each DNA mimic comprises a structure represented by one of the formulas below:

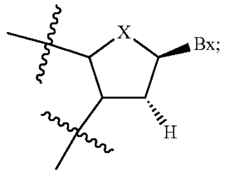

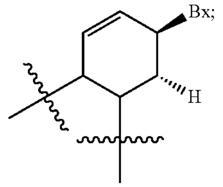

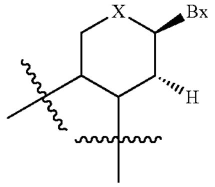

wherein X is O or S and Bx represents a heteorcylic base moiety.

678. The oligomeric compound of embodiment 670, wherein each DNA mimic comprises a structure represented by one of the formulas below:

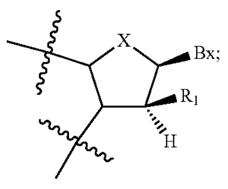

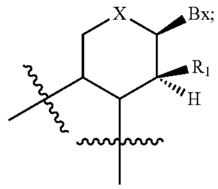

-continued

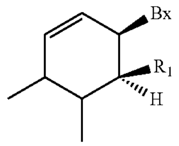

wherein X is O or S, Bx represents a heterocyclic base moiety, and R1 is selected from among H, OH, halo, allyl, amino, azido, SH, CN, OCN, $CF_3$, $OCF_3$, O—$C_1$-$C_{10}$ alkoxy, O—$C_1$-$C_{10}$ substituted alkoxy, $C_1$-$C_{10}$ alkyl, $C_1$-$C_{10}$ substituted alkyl, S-alkyl, N(Rm)-alkyl, O-alkenyl, S-alkenyl, N(Rm)-alkenyl, O-alkynyl, S-alkynyl, N($R_m$)-alkynyl, O-alkylenyl-O-alkyl, alkynyl, alkaryl, aralkyl, O-alkaryl, O-aralkyl, $O(CH_2)_2SCH_3$, $O(CH_2)_2ON(R_m)(R_n)$ or $OCH_2C(=O)—N(R_m)(R_n)$, where each $R_m$ and $R_n$ is, independently, H, an amino protecting group, or substituted or unsubstituted $C_1$-$C_{10}$ alkyl.

679. The oligomeric compound of embodiment 678, wherein R1 is H, OH, OMe, or F.

680. The oligomeric compound of embodiment 678, wherein R1 is not F.

681. The oligomeric compound of embodiment 670, wherein each DNA mimic comprises a structure represented by the formula below:

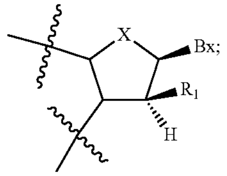

wherein X is O, Bx represents a heterocyclic base moiety, and R1 is H.

682. The oligomeric compound of embodiment 670, wherein DNA mimic has a sugar moiety selected from among: 5'-methyl-2'-β-D-deoxyribosyl, 5'-ethyl-2'-β-D-deoxyribosyl, and 5'-allyl-2'-β-D-deoxyribosyl.

683. The oligomeric compound of embodiment 670, wherein DNA mimic comprises a 2'-fluoro-β-D-arabinofuranosyl sugar moiety 684. The oligomeric compound of embodiment 670, wherein the DNA mimic does not comprise a 2'-fluoro-β-D-arabinofuranosyl sugar moiety.

685. The oligomeric compound of any of embodiments 551-684, wherein each Nd is a DNA nucleoside.

686. The oligomeric compound of any of embodiments 551-685, wherein the central region comprises no more than four nucleosides selected from among DNA isomers, modified DNA isomers, and DNA mimics.

687. The oligomeric compound of any of embodiments 551-685, wherein the central region comprises no more than three nucleosides selected from among DNA isomers, modified DNA isomers, and DNA mimics.

688. The oligomeric compound of any of embodiments 551-685, wherein the central region comprises no more than two nucleosides selected from among DNA isomers, modified DNA isomers, and DNA mimics.

689. The oligomeric compound of any of embodiments 551-685, wherein the central region comprises no more than one nucleoside selected from among DNA isomers, modified DNA isomers, and DNA mimics.

690. The oligomeric compound of any of embodiments 551-689, wherein the central region contains exactly one safety enhancing nucleoside and the remainder of nucleosides in the central region are DNA nucleosides.

691. The oligomeric compound of any of embodiments 551-690, wherein at least one internucleoside linkage of the central region selected from among: the internucleoside Nda to Nx, Nx to Ny, Ny to Nz, or Nz to the adjacent Ndb is a neutral internucleoside linkage.

692. The oligomeric compound of embodiments 691, wherein the neutral linkage is a phosphonate internucleoside linkage.

693. The oligomeric compound of embodiments 691, wherein the neutral linkage is a methoxypropyl internucleoside linkage.

694. The oligomeric compound of embodiments 691, wherein each remaining internucleoside linkage is a phosphodiester or phosphorothioate internucleoside linkage.

695. A chirally enriched population of modified oligonucleotides of any of embodiments 551-690, wherein the central region has at least one particular phorphorothioate internucleoside linkage having a particular stereochemical configuration.

696. The chirally enriched population of embodiment 695, wherein the central region has at least one phorphorothioate internucleoside linkage having the (Sp) configuration.

697. The chirally enriched population of embodiment 695, wherein central region has at least one phorphorothioate internucleoside linkage having the (Rp) configuration.

698. The chirally enriched population of embodiment 695, wherein the central region has a particular, independently selected stereochemical configuration at each phosphorothioate internucleoside linkage.

699. The chirally enriched population of embodiment 698, wherein the each phosphorothioate internucleoside linkage of the central region has the (Sp) configuration.

700. The chirally enriched population of embodiment 698, wherein the central region has one phosphorothioate internucleoside linkage having the (Rp) configuration and wherein each remaining central region phosphorothioate internucleoside linkage has the (Sp) configuration.

701. The chirally enriched population of embodiment 695, wherein the central region has an (Rp) phosphorothioate internucleoside linkage adjacent to an (Sp) phosphorothioate internucleoside linkage.

702. The chirally enriched population of embodiment 695, wherein the central region has an (Rp) phosphorothioate internucleoside linkage adjacent to a second (Rp) phosphorothioate internucleoside linkage.

703. The chirally enriched population of embodiment 695, wherein the central region has an (Rp) phosphorothioate internucleoside linkage adjacent to a second (Rp) phosphorothioate internucleoside linkage, and wherein each remaining central region phosphorothioate internucleoside linkage has the (Sp) configuration.

704. The chirally enriched population of any of embodiments 696, 697, 701, or 702 wherein each phosphorothioate internucleoside linkage that does not have the (Rp) or (Sp) configuration is stereorandom.

705. The oligomeric compound of any of embodiments 551-704 comprising a conjugate group.

706. The oligomeric compound of embodiment 705, wherein the conjugate group comprises a linking group attaching the remainder of the conjugate group to the modified oligonucleotide, wherein the linking group comprises 1-5 nucleosides.

707. The oligomeric compound of any of embodiments 1-705, wherein the oligomeric compound does not comprise additional nucleosides beyond those of the modified oligonucleotide.
708. The oligomeric compound of any of embodiments 551-707, wherein the nucleobase sequence of the modified oligonucleotide is complementary to a target RNA.
709. The oligomeric compound of embodiment 708, wherein the nucleobase sequence of the modified oligonucleotide is at least 85% complementary to the target RNA.
710. The oligomeric compound of embodiment 708, wherein the nucleobase sequence of the modified oligonucleotide is at least 90% complementary to the target RNA.
711. The oligomeric compound of embodiment 708, wherein the nucleobase sequence of the modified oligonucleotide is at least 95% complementary to the target RNA.
712. The oligomeric compound of embodiment 711, wherein the nucleobase sequence of the modified oligonucleotide is 100% complementary to the target RNA.
713. The oligomeric compound of any of embodiments 708-712, wherein the target RNA is a target mRNA or a target pre-mRNA.
714. The oligomeric compound of embodiment 713, wherein the target mRNA or target pre-mRNA is not a mouse, rat, monkey, or human PTEN RNA.
715. The oligomeric compound of embodiment 713 or 714, wherein the target mRNA or target pre-mRNA is not a mouse, rat, monkey, or human SRB-1 RNA.
716. The oligomeric compound of any of embodiments 713-715, wherein the target mRNA or target pre-mRNA is not a mouse, rat, monkey, or human MYD88 RNA.
717. The oligomeric compound of any of embodiments 713-716, wherein the target mRNA or target pre-mRNA is not a mouse, rat, monkey, or human HTT RNA, is not a mouse, rat, monkey, or human SOD1 RNA, and is not a mouse, rat, monkey, or human alpha-synuclein RNA.
718. The oligomeric compound of any of embodiments 708-717, wherein the target RNA is a human RNA.
719. The oligomeric compound of any of embodiments 708-718, wherein the target RNA is expressed in the liver.
720. The oligomeric compound of any of embodiments 708-719, wherein the target RNA is a liver target.
721. The oligomeric compound of any of embodiments 708-718, wherein the target RNA is not expressed in the liver.
722. The oligomeric compound of any of embodiments 708-718 or 721, wherein the target RNA is not a liver target.
723. The oligomeric compound of any of embodiments 708-722, wherein modulation of the expression of the target RNA in the liver is associated with treating a disorder or condition.
724. The oligomeric compound of embodiment 723, wherein the disorder or condition is a liver disorder or condition.
725. The oligomeric compound of any of embodiments 708-724, wherein the target RNA is expressed in the central nervous system.
726. The oligomeric compound of any of embodiments 708-724, wherein the target RNA is not expressed in the central nervous system.
727. The oligomeric compound of any of embodiments 708-725, wherein the target RNA is a central nervous system target.
728. The oligomeric compound of any of embodiments 708-726, wherein the target RNA is not a central nervous system target.
729. The oligomeric compound of any of embodiments 708-727, wherein the target RNA is a MeCP2, DUX4, HDAC2, APP, Ataxin 1, Ataxin 2, Ataxin 3, Ataxin 6, Ataxin 7, C9ORF72, UBE3A, Prion, PMP22, Tau, LRRK2, LINGO2, GYS1, KCNT1, IRF8, Progranulin, or GFAP RNA.
730. The oligomeric compound of any of embodiments 708-729, wherein the target RNA is a HTT RNA.
731. The oligomeric compound of embodiment 729, wherein the target RNA is a MeCP2 RNA.
732. The oligomeric compound of embodiment 729, wherein the target RNA is a DUX4 RNA.
733. The oligomeric compound of embodiment 729, wherein the target RNA is a HDAC2 RNA.
734. The oligomeric compound of embodiment 729, wherein the target RNA is a Ataxin 1 RNA.
735. The oligomeric compound of embodiment 729, wherein the target RNA is a Ataxin 2 RNA.
736. The oligomeric compound of embodiment 729, wherein the target RNA is a Ataxin 3 RNA.
737. The oligomeric compound of embodiment 729, wherein the target RNA is a Ataxin 6 RNA.
738. The oligomeric compound of embodiment 729, wherein the target RNA is a Ataxin 7 RNA.
739. The oligomeric compound of embodiment 729, wherein the target RNA is a C9ORF72 RNA.
740. The oligomeric compound of embodiment 708-727, wherein the target RNA is an alpha-synuclein RNA.
741. The oligomeric compound of embodiment 729, wherein the target RNA is an UBE3A RNA.
742. The oligomeric compound of any of embodiments 708-727, wherein the target RNA is a SOD1 RNA.
743. The oligomeric compound of any of embodiments 708-727, wherein the target RNA is a Prion RNA.
744. The oligomeric compound of any of embodiments 708-727, wherein the target RNA is a PMP22 RNA.
745. The oligomeric compound of any of embodiments 708-727, wherein the target RNA is a Tau RNA.
746. The oligomeric compound of any of embodiments 708-727, wherein the target RNA is a LRRK2 RNA.
747. The oligomeric compound of any of embodiments 708-727, wherein the target RNA is an APP RNA.
748. The oligomeric compound of any of embodiments 708-727, wherein the target RNA is a LINGO2 RNA.
749. The oligomeric compound of any of embodiments 708-727, wherein the target RNA is a GYS1 RNA.
750. The oligomeric compound of any of embodiments 708-727, wherein the target RNA is a KCNT1 RNA.
751. The oligomeric compound of any of embodiments 708-727, wherein the target RNA is a IRF8 RNA.
752. The oligomeric compound of any of embodiments 708-727, wherein the target RNA is a Progranulin RNA.
753. The oligomeric compound of any of embodiments 708-727, wherein the target RNA is a GFAP RNA.
754. The oligomeric compound of any of embodiments 725-753, wherein modulation of the expression of the target RNA in the central nervous system is associated with treating a disorder or condition.
755. The oligomeric compound of embodiment 754, wherein the disorder or condition is a neurological disorder or condition.
756. The oligomeric compound of embodiment 754-755, wherein the disorder or condition alters the function of sensory or motor neurons.

757. The oligomeric compound of any of embodiments 754-756, wherein the disorder or condition alters the function of sensory neurons.
758. The oligomeric compound of any of embodiments 754-757, wherein the disorder or condition alters the function of motor neurons.
759. The oligomeric compound of any of embodiments 754-758, wherein the disorder or condition alters the function of glial cells.
760. The oligomeric compound of any of embodiments 754-759, wherein the disorder or condition alters the function of astrocytes.
761. The oligomeric compound of any of embodiments 754-760, wherein the disorder or condition alters the function of oligodendrocytes.
762. The oligomeric compound of any of embodiments 754-761, wherein the disorder or condition alters the function of microglia.
763. The oligomeric compound of any of embodiments 754-762, wherein the disorder or condition alters the function of ependymal cells.
764. The oligomeric compound of any of embodiments 754-763, wherein the disorder or condition is Alzheimer's Disease, Amyotrophic Lateral Sclerosis, Parkinson's Disease, a Spinocerebellar ataxia, Angelman Syndrome, Alexander's Disease, Lafora Disease, Charcot-Marie Tooth Disease, Prion Disease, a dementia, neurodegeneration, MeCP2 Duplication Syndrome, encephalopathy, neuroinflammation, or multiple sclerosis.
765. The oligomeric compound of embodiment 764, wherein the disorder or condition is Alzheimer's Disease.
766. The oligomeric compound of embodiment 764, wherein the disorder or condition is Amyotrophic Lateral Sclerosis.
767. The oligomeric compound of embodiment 764, wherein the disorder or condition is Parkinson's Disease.
768. The oligomeric compound of embodiment 764, wherein the disorder or condition is a Spinocerebellar ataxia.
769. The oligomeric compound of embodiment 764, wherein the disorder or condition is Angelman Syndrome.
770. The oligomeric compound of embodiment 764, wherein the disorder or condition is Alexander's Disease.
771. The oligomeric compound of embodiment 764, wherein the disorder or condition is Lafora Disease.
772. The oligomeric compound of embodiment 764, wherein the disorder or condition is Charcot-Marie Tooth Disease.
773. The oligomeric compound of embodiment 764, wherein the disorder or condition is Prion Disease.
774. The oligomeric compound of embodiment 764, wherein the disorder or condition is a dementia.
775. The oligomeric compound of embodiment 764, wherein the disorder or condition is neurodegeneration.
776. The oligomeric compound of embodiment 764, wherein the disorder or condition is MeCP2 Duplication Syndrome.
777. The oligomeric compound of embodiment 764, wherein the disorder or condition is encephalopathy.
778. The oligomeric compound of embodiment 764, wherein the disorder or condition is neuroinflammation.
779. The oligomeric compound of embodiment 764, wherein the disorder or condition is multiple sclerosis.
780. The oligomeric compound of any of embodiments 551-779, wherein the parent oligomeric compound of the oligomeric compound of any of embodiments 551-779 is cytotoxic in vitro.
781. The oligomeric compound of embodiment 780, wherein the parent oligomeric compound is cytotoxic in a standard in vitro cytotoxicity assay.
782. The oligomeric compound of any of embodiments 551-781 wherein administration to a mouse of the parent oligomeric compound of the oligomeric compound of any of embodiments 551-781 is hepatotoxic to the mouse.
783. The oligomeric compound of embodiment 782, wherein the administration of the parent oligomeric compound to the mouse is systemic administration.
784. The oligomeric compound of embodiment 783, wherein the systemic administration is subcutaneous administration.
785. The oligomeric compound of any of embodiments 782-784, wherein the mouse is a CD-1 mouse.
786. The oligomeric compound of any of embodiments 782-784, wherein the mouse is a C57BL/6 mouse.
787. The oligomeric compound of any of embodiments 782-784, wherein the mouse is a BALB/c mouse.
788. The oligomeric compound of any of embodiments 782-784, wherein the plasma ALT level in the mouse is higher than 500 units per liter following the administration of the parent oligomeric compound.
789. The oligomeric compound of any of embodiments 782-788, wherein the plasma AST level in the mouse is higher than 500 units per liter following the administration of the parent oligomeric compound.
790. The oligomeric compound of any of embodiments 782-789, wherein the plasma ALT level in the mouse is higher than 1000 units per liter following the administration of the parent oligomeric compound.
791. The oligomeric compound of any of embodiments 782-790, wherein the plasma AST level in the mouse is higher than 1000 units per liter following the administration of the parent oligomeric compound.
792. The oligomeric compound of any of embodiments 782-791, wherein the hepatotoxicity is measured 24-48 hours following the administration of the parent oligomeric compound.
793. The oligomeric compound of any of embodiments 782-791, wherein the hepatotoxicity is measured 72 hours following the administration of the parent oligomeric compound.
794. The oligomeric compound of any of embodiments 782-791, wherein the hepatotoxicity is measured 3 days following the administration of the parent oligomeric compound.
795. The oligomeric compound of any of embodiments 782-791, wherein the hepatotoxicity is measured 5 days following the administration of the parent oligomeric compound.
796. The oligomeric compound of any of embodiments 782-791, wherein the hepatotoxicity is measured 7 days following the administration of the parent oligomeric compound.
797. The oligomeric compound of any of embodiments 782-791, wherein the hepatotoxicity is measured 10 days following the administration of the parent oligomeric compound.
798. The oligomeric compound of any of embodiments 782-791, wherein the hepatotoxicity is measured 14 days following the administration of the parent oligomeric compound.
799. The oligomeric compound of any of embodiments 782-791, wherein 1-10 mg/kg of the parent oligomeric compound is administered to the mouse.

800. The oligomeric compound of any of embodiments 782-791, wherein 10-25 mg/kg of the parent oligomeric compound is administered to the mouse.
801. The oligomeric compound of any of embodiments 782-791, wherein 25-50 mg/kg of the parent oligomeric compound is administered to the mouse.
802. The oligomeric compound of any of embodiments 782-791, wherein 50-100 mg/kg of the parent oligomeric compound is administered to the mouse.
803. The oligomeric compound of any of embodiments 782-791, wherein 100-150 mg/kg of the parent oligomeric compound is administered to the mouse.
804. The oligomeric compound of any of embodiments 782-791, wherein the mouse is a BALB/c mouse, wherein 150 mg/kg of the parent oligomeric compound is administered to the mouse, and wherein the plasma ALT level in the mouse is measured 72 hours following the administration of the parent oligomeric compound.
805. The oligomeric compound of any of embodiments 551-804, wherein administration of 50 mg/kg of the oligomeric compound of any of embodiments 551-804 to a mouse is not hepatotoxic to the mouse.
806. The oligomeric compound of embodiment 805, wherein plasma ALT level in the mouse is lower than 100 units per liter following the administration of the oligomeric compound of embodiment 805.
807. The oligomeric compound of embodiment 805 or 806, wherein plasma ALT level in the mouse is at least 10-fold lower than plasma ALT level in a mouse administered the parent oligomeric compound of the oligomeric compound of embodiment 384 or 385, wherein the administrations and plasma ALT measurements of both the oligomeric compound of embodiment 384 or 385 and the parent oligomeric compound are completed in the same way.
808. The oligomeric compound of embodiment 807, wherein the plasma ALT level in the mouse is at least 100-fold lower than the plasma ALT level in the mouse administered the parent oligomeric compound.
809. The oligomeric compound of embodiment 807, wherein the plasma ALT level in the mouse is at least 500-fold lower than the plasma ALT level in the mouse administered the parent oligomeric compound.
810. The oligomeric compound of any of embodiments 782-809, wherein the therapeutic index in a mouse of the oligomeric compound of any of embodiments 782-809 is increased relative to the therapeutic index of the parent oligomeric compound.
811. The oligomeric compound of embodiment 810, wherein the therapeutic index in a mouse of the oligomeric compound of embodiment 365 is at least two-fold greater than the therapeutic index of the parent oligomeric compound.
812. The oligomeric compound of any of embodiments 551-811, wherein an otherwise identical oligomeric compound lacking the at least one modified internucleoside linkage other than phosphorothioate and/or at least one modified nucleoside comprising a modified nucleobase other than 5-methylcytosine and/or a modified sugar moiety in the central region is hepatotoxic following administration to a mouse; and wherein the otherwise identical oligomeric compound has a central region consisting of phosphorothioate internucleoside linkages, unmodified 2'-β-D-deoxyribosyl sugar moieties, and nucleobases selected from thymine, uracil, adenine, guanine, cytosine, and 5-methylcytosine.
813. The oligomeric compound of embodiment 812, wherein the at least one modified internucleoside linkage other than phosphorothioate and/or at least one modified nucleoside comprising a modified nucleobase other than 5-methylcytosine and/or a modified sugar moiety in the central region is a 2'-O-methyl modified sugar moiety.
814. The oligomeric compound of embodiment 813, wherein the 2'-O-methyl modified sugar moiety is at position 2 of the central region.
815. The oligomeric compound of embodiment 812-814, wherein the otherwise identical oligomeric compound lacks a 2'-O-methyl modified sugar moiety, and wherein the otherwise identical oligomeric compound comprises an unmodified 2'-β-D-deoxyribosyl sugar moiety in place of the 2'-O-methyl modified sugar moiety.
816. The oligomeric compound of any of embodiments 812-815, wherein the nucleobase sequence of the otherwise identical oligomeric compound is 100% complementary to the target RNA.
817. The oligomeric compound of any of embodiments 812-816, wherein the otherwise identical oligomeric compound is a parent oligomeric compound of the oligomeric compound of any of embodiments 812-816.
818. The oligomeric compound of any of embodiments 708-817, wherein the oligomeric compound inhibits the target RNA with an IC50 lower than 100 nM in a standard in vitro activity assay.
819. The oligomeric compound of any of embodiments 708-818, wherein the parent oligomeric compound of the oligomeric compound of any of embodiments 708-818 inhibits the target RNA with an IC50 lower than 100 nM in a standard in vitro activity assay.
820. The oligomeric compound of any of embodiments 708-819, wherein the difference between the IC50 of the parent oligomeric compound measured in a standard in vitro activity assay and the IC50 of the oligomeric compound of any of embodiments 708-819 measured in a standard in vitro activity assay is less than 4-fold.
821. The oligomeric compound of any of embodiments 708-820, wherein the difference between the IC50 of the parent oligomeric compound measured in a standard in vitro activity assay and the IC50 of the oligomeric compound of any of embodiments 708-820 measured in a standard in vitro activity assay is less than 3-fold.
822. The oligomeric compound of any of embodiments 708-821, wherein the difference between the IC50 of the parent oligomeric compound measured in a standard in vitro activity assay and the IC50 of the oligomeric compound of any of embodiments 708-821 measured in a standard in vitro activity assay is less than 2-fold.
823. The oligomeric compound of any of embodiments 708-822, wherein each sugar moiety of the central region of the parent oligomeric compound is an unmodified 2'-β-D-deoxyribosyl sugar moiety, and wherein each internucleoside linkage of the central region of the parent oligomeric compound is a phosphorothioate internucleoside linkage.
824. The oligomeric compound of any of embodiments 708-823, wherein the nucleobase sequence of the parent oligomeric compound is 100% complementary to the target RNA.
825. The oligomeric compound of any of embodiments 551-824, wherein administration of 10-50 mg of the oligomeric compound to a human is not hepatotoxic to the human.
826. The oligomeric compound of any of embodiments 551-824, wherein administration of 50-100 mg of the oligomeric compound to a human is not hepatotoxic to the human.

827. The oligomeric compound of any of embodiments 551-824, wherein administration of 100-300 mg of the oligomeric compound to a human is not hepatotoxic to the human.

828. The oligomeric compound of any of embodiments 825-827, wherein the administration is systemic administration.

829. A composition comprising the oligomeric compound of any of embodiments 551-828 and a second oligomeric compound, wherein the second oligomeric compound is complementary to the oligomeric compound of any of embodiments 551-828.

830. The composition of embodiment 829, wherein the second oligomeric compound comprises at least 14 contiguous linked nucleosides that are at least 90% complementary to the oligomeric compound of any of embodiments 551-828.

831. The composition of embodiment 830, wherein the second oligomeric compound comprises at least 14 contiguous linked nucleosides that are 100% complementary to the oligomeric compound of any of embodiments 551-828.

832. A pharmaceutical composition comprising the oligomeric compound of any of embodiments 551-828 or the composition of any of embodiments 829-831, comprising a pharmaceutically acceptable carrier or diluent.

833. A method comprising administering the oligomeric compound or composition of any of embodiments 551-832 to a human subject.

834. A method of treating a disease or disorder comprising administering the oligomeric compound or composition of any of embodiments 551-832 to a human subject.

835. A method of modulating the amount or activity of a target RNA in a human subject comprising administering the oligomeric compound or composition of any of embodiments 551-832 to the human subject; and thereby modulating the amount or activity of the target RNA in the human subject.

836. A method of treating a disease or disorder in a human subject comprising administering the oligomeric compound or composition of any of embodiments 551-832 to the human subject having the disease or disorder; and thereby treating the disease or disorder in the human subject.

837. The method of embodiment 835-836, wherein the disease or disorder is a liver disease, and wherein the oligomeric compound modulates the amount or activity of a liver target RNA.

838. The method of embodiment 835-837, wherein the disease or disorder is a central nervous system disease, and wherein the oligomeric compound modulates the amount or activity of a central nervous system target RNA.

839. The method of any of embodiments 834-838, wherein the disease or disorder is a cancer, a neurodegenerative disease, a cardiovascular disease, an immunological disease, a hereditary disease, a repeat expansion disease, a muscle-wasting disease, or a metabolic disease.

840. The method of any of embodiments 834-839, wherein the plasma ALT level of the human subject after the administration is not more than three times higher than it was prior to the administration.

841. The method of any of embodiments 834-840, wherein the plasma ALT level of the human subject after the administration is not more than 150 units per liter.

842. The method of any of embodiments 834-841, wherein the human subject is susceptible to liver damage.

843. The method of any of embodiments 834-842, wherein the human subject is susceptible to liver degeneration.

844. The method of any of embodiments 834-843, wherein the human subject is susceptible to elevated apoptosis in the liver.

845. The method of any of embodiments 834-844, wherein the human subject has a liver disease.

846. The method of any of embodiments 834-841, comprising administering the parent oligomeric compound of the oligomeric compound of any of embodiments 551-832 to a mouse.

847. The method of any of embodiments 833-846, comprising contacting a cell with the parent oligomeric compound of the oligomeric compound of any of embodiments 551-832.

848. The method of embodiment 846-847, wherein each sugar moiety of the central region of the parent oligomeric compound is an unmodified 2'-β-D-deoxyribosyl sugar moiety, and wherein each internucleoside linkage of the central region of the parent oligomeric compound is a phosphorothioate internucleoside linkage.

849. A method of designing an oligomeric compound comprising starting with a parent oligomeric compound and changing the design of that compound in order to arrive at an oligomeric compound of any one of embodiments 551-833.

850. A method of designing an oligomeric compound comprising identifying a parent oligomeric compound and changing the design of that parent oligomeric compound to arrive at a second oligomeric compound, wherein the second oligomeric compound is an oligomeric compound of any one of embodiments 551-833.

851. A method of improving hepatotoxicity of an oligomeric compound comprising the steps of (i) identifying a parent oligomeric compound that has plasma ALT levels above 300 units per liter in a mouse, and (ii) providing an oligomeric compound according to any one of embodiments 551-833.

852. The method of embodiment 851, wherein the method designs an oligomeric compound with improved therapeutic index relative to the parent oligomeric compound.

853. The method of embodiment 851-852, wherein the method designs an oligomeric compound with lower hepatotoxicity relative to the parent oligomeric compound.

854. The method of embodiment 853, wherein the second oligomeric compound has an improved therapeutic index relative to the parent oligomeric compound.

855. The method of embodiment 851-852, wherein the second oligomeric compound has reduced hepatotoxicity in a mouse relative to the parent oligomeric compound.

856. The method of embodiment 855, wherein the oligomeric compound according to any one of embodiments 551-833 has reduced hepatotoxicity relative to the parent oligomeric compound.

857. A method comprising administering an oligomeric compound of any of embodiments 551-833 to a mouse and separately administering the parent oligomeric compound of the oligomeric compound of any of embodiments 551-833 to a second mouse, wherein the therapeutic index of the oligomeric compound of any of embodiments 551-833 is improved relative to the therapeutic index of the parent oligomeric compound.

858. The method of any of embodiments 833-857, wherein the level of p21 RNA is measured in the mouse, the cell, and/or the human subject.

859. A method comprising administering an oligomeric compound of any of embodiments 551-833 to a subject and measuring the level of p21 RNA in the subject.

860. The method of embodiment 858 or 859, wherein the subject is a mouse.

861. The method of embodiment 858 or 859, wherein the subject is a human.

862. The method of any of embodiments 858-861, wherein the p21 RNA level is measured within 24 hours of the administration.

863. The method of any of embodiments 858-862, wherein the p21 RNA level is measured 24-48 hours following the administration.

864. An oligomeric compound or composition of any one of embodiments 551-832, for use in medical therapy.

865. The oligomeric compound of any of embodiments 551-832, wherein the oligomeric compound is not toxic.

866. The oligomeric compound of any of embodiment 551-832, wherein a comparator compound is toxic; wherein the comparator compound is identical to the oligomeric compound except that each nucleoside of the central region of the comparator compound is a nucleoside comprising 2'-β-D-deoxyribyl sugar moiety.

867. The oligomeric compound of embodiment 866, wherein administering a dose of the oligomeric compound to an animal results in a circulating ALT level that is at least 3-fold lower than the ALT level that results from administering the same dose of the comparator compound to an animal for at least one matched dose.

868. The oligomeric compound of embodiment 866 or 867, wherein the lowest dose of the oligomeric compound that raises circulating ALT to over 300 units per liter is at least three-fold higher than the lowest dose of the comparator compound that raises circulating ALT to over 300 units per liter.

869. The oligomeric compound of any of embodiments 865-868, wherein the oligomeric compound is capable of reducing the target RNA in a cell.

870. The oligomeric compound of embodiment 869, wherein the oligomeric compound has RNA-reducing activity comparable to a comparator compound, wherein the comparator compound is identical to the oligomeric compound except that each nucleoside of the central region of the comparator compound is a nucleoside comprising 2'-β-D-deoxyribosyl sugar moiety.

871. The oligomeric compound of embodiment 870 having RNA-reducing activity that is no more than 2-fold worse than the RNA-reducing activity of the comparator compound.

872. A method of modulating the amount or activity of a target RNA in a human subject comprising administering the oligomeric compound or composition of any of embodiments 551-832 to the human subject; and thereby modulating the amount or activity of the target RNA in the human subject.

873. A method of treating a disease or disorder in a human subject comprising administering the oligomeric compound or composition of any of embodiments 551-832 to the human subject having the disease or disorder; and thereby treating the disease or disorder in the human subject.

874. The method of embodiment 872-873, wherein the disease or disorder is a liver disease, and wherein the oligomeric compound modulates the amount or activity of a liver target RNA.

875. The method of embodiment 872-873, wherein the disease or disorder is a central nervous system disease, and wherein the oligomeric compound modulates the amount or activity of a central nervous system target RNA.

876. The method of any of embodiments 872-874, wherein the disease or disorder is a cancer, a neurodegenerative disease, a cardiovascular disease, an immunological disease, a hereditary disease, a repeat expansion disease, a muscle-wasting disease, or a metabolic disease.

877. The method of any of embodiments 872-876, wherein the plasma ALT level of the human subject after the administration is not more than three times higher than it was prior to the administration.

878. The method of any of embodiments 872-877, wherein the plasma ALT level of the human subject after the administration is not more than 150 units per liter.

879. A method of treating a disease or disorder in a human subject comprising administering the oligomeric compound or composition of any of embodiments 1-410, 452-518, 551-828, or 864-871 to the human subject having the disease or disorder; and thereby treating the disease or disorder in the human subject.

880. The method of embodiment 879, wherein the disease or disorder is not a CNS disease or disorder.

881. The method of embodiment 879, wherein the disease or disorder is a disease or disorder of the muscle.

882. The method of embodiment 879, wherein the disease or disorder is a disease or disorder of the lung.

883. The method of embodiment 879, wherein the disease or disorder is a disease or disorder of the kidney.

884. The method of embodiment 879, wherein the disease or disorder is a disease or disorder of the eye.

885. The method of embodiment 879, wherein the disease or disorder is a disease or disorder of the pancreas.

886. A method of screening a library of oligomeric compounds for activity against a target RNA, wherein the library of oligomeric compounds comprises a plurality of oligomeric compounds of any of embodiments 1-410, 452-218, 551-831, or 864-871.

887. An oligomeric compound comprising a modified oligonucleotide consisting of 12-21 linked nucleosides, wherein the modified oligonucleotide has the formula A-B-C, wherein A is a 5'-region, B is a central region, and C is a 3'-region; wherein:

the 5'-region consists of 1-5 linked nucleosides, wherein at least one nucleoside of the 5'-region is a modified nucleoside comprising a modified sugar;

the 3'-region consists of 1-5 linked nucleosides wherein at least one nucleoside of the 3'-region is a modified nucleoside comprising a modified sugar; and the central region consists of 7-11 linked nucleosides, wherein the 5'-most portion of the central region has the following formula:

$$(N_{da})(N_x)(N_y)(N_z)(N_{db})$$

wherein one of $N_x$, $N_y$, and $N_z$, is a safety-enhancing nucleoside;

the other two of $N_x$, $N_y$, and $N_z$ are independently selected from a DNA nucleoside, a DNA isomer, a modified DNA isomer, and a DNA mimic; and $N_{da}$ and $N_{db}$ are each independently selected from a DNA nucleoside, a DNA isomer, a modified DNA isomer, and a DNA mimic.

888. The oligomeric compound of embodiment 887, wherein the 5'-region consists of one nucleoside.

889. The oligomeric compound of embodiment 887, wherein the 5'-region consists of 2-5 linked nucleosides.

890. The oligomeric compound of embodiment 887, wherein the 5'-region consists of 2-4 linked nucleosides.
891. The oligomeric compound of embodiment 887, wherein the 5'-region consists of 2 linked nucleosides.
892. The oligomeric compound of embodiment 887, wherein the 5'-region consists of 3 linked nucleosides.
893. The oligomeric compound of embodiment 887, wherein the 5'-region consists of 4 linked nucleosides.
894. The oligomeric compound of embodiment 887, wherein the 5'-region consists of 5 linked nucleosides.
895. The oligomeric compound of any of embodiments 887-894, wherein each nucleoside of the 5'-region is a modified nucleoside.
896. The oligomeric compound of any of embodiments 887-895, wherein each nucleoside of the 5'-region is a modified nucleoside comprising a modified sugar.
897. The oligomeric compound of any of embodiments 887-896, wherein each modified nucleoside of the 5'-region has the same modification.
898. The oligomeric compound of any of embodiments 887-896, wherein at least two nucleosides of the 5'-region are modified nucleosides having different modifications.
899. The oligomeric compound of any of embodiments 887-898, wherein each nucleoside of the 5'-region comprises a 2'-modified ribosyl sugar moiety.
900. The oligomeric compound of any of embodiments 887-899, wherein at least one nucleoside of the 5'-region comprises a bicyclic furanosyl sugar moiety.
901. The oligomeric compound of any of embodiments 887-900, wherein each nucleoside of the 5'-region comprises a bicyclic furanosyl sugar moiety.
902. The oligomeric compound of any of embodiments 887-900, wherein at least one nucleoside of the 5'-region comprises a non-bicyclic sugar moiety.
903. The oligomeric compound of embodiment 902, wherein the non-bicyclic sugar moiety of the at least one nucleoside of the 5'-region is a 2'-substituted ribosyl sugar moiety.
904. The oligomeric compound of any of embodiments 887-889 or 902-903, wherein each nucleoside of the 5'-region comprises a non-bicyclic sugar moiety.
905. The oligomeric compound of embodiment 904, wherein each nucleoside of the 5'-region comprises a 2'-substituted furanosyl sugar moiety.
906. The oligomeric compound of any of embodiments 887-905, wherein each nucleoside of the 5'-region comprises a 2'-modified furanosyl sugar moiety independently selected from a bicyclic sugar moiety and a non-bicyclic 2'-substituted ribosyl sugar moiety.
907. The oligomeric compound of any of embodiments 887-901 or 906, wherein each nucleoside of the 5'-region comprises a bicyclic sugar moiety.
908. The oligomeric compound of any of embodiments 887-889 or 902-906, wherein each nucleoside of the 5'-region comprises a non-bicyclic 2'-substituted ribosyl sugar moiety.
909. The oligomeric compound of any of embodiments 887-903 or 906-907, wherein each bicyclic sugar moiety of the 5'-region is selected from among cEt, LNA, and ENA.
910. The oligomeric compound of any of embodiments 887-903 or 906-909, wherein each bicyclic sugar moiety of the 5'-region is a cEt sugar moiety.
911. The oligomeric compound of any of embodiments 887-903, or 906-907 or 909 wherein each bicyclic sugar moiety of the 5'-region is an LNA sugar moiety.
912. The oligomeric compound of any of embodiments 887-900, 902-906, or 908-911, wherein each non-bicyclic sugar moiety of the 5'-region has a 2'-substituent selected from among 2'-MOE, 2'-OMe, and 2'-NMA.
913. The oligomeric compound of any of embodiments 887-912, wherein none of the nucleosides of the 5'-region comprise a sugar moiety having a 2'-F substituent.
914. The oligomeric compound of any of embodiments 887-913, wherein none of the nucleosides of the 5'-region comprise a sugar moiety having a 2'-MOE substituent.
915. The oligomeric compound of any of embodiments 887-914, wherein none of the nucleosides of the 5'-region comprise a sugar moiety having a 2'-OMe substituent.
916. The oligomeric compound of any of embodiments 887-915, wherein none of the nucleosides of the 5'-region comprise a cEt sugar moiety.
917. The oligomeric compound of any of embodiments 887-916, wherein none of the nucleosides of the 5'-region comprise a LNA sugar moiety.
918. The oligomeric compound of any of embodiments 887-917, wherein each nucleobase of the 5'-region is independently selected from among thymine, uracil, guanine, cytosine, 5-methylcytosine, and adenine.
919. The oligomeric compound of any of embodiments 887-918, wherein each internucleoside linkage of the 5'-region is independently selected from among phosphodiester and phosphorothioate internucleoside linkages.
920. The oligomeric compound of any of embodiments 887-919, wherein the 3'-region consists of one nucleoside.
921. The oligomeric compound of any of embodiments 887-919, wherein the 3'-region consists of 2-5 linked nucleosides.
922. The oligomeric compound of any of embodiments 887-919, wherein the 3'-region consists of 2-4 linked nucleosides.
923. The oligomeric compound of any of embodiments 887-919, wherein the 3'-region consists of 2 linked nucleosides.
924. The oligomeric compound of any of embodiments 887-919, wherein the 3'-region consists of 3 linked nucleosides.
925. The oligomeric compound of any of embodiments 887-919, wherein the 3'-region consists of 4 linked nucleosides.
926. The oligomeric compound of any of embodiments 887-919, wherein the 3'-region consists of 5 linked nucleosides.
927. The oligomeric compound of any of embodiments 887-926, wherein each nucleoside of the 3'-region is a modified nucleoside.
928. The oligomeric compound of any of embodiments 887-927, wherein each nucleoside of the 3'-region is a modified nucleoside comprising a modified sugar moiety.
929. The oligomeric compound of any of embodiments 887-928, wherein each modified nucleoside of the 3'-region has the same modification.
930. The oligomeric compound of and of embodiments 887-928, wherein at least two nucleosides of the 3'-region are modified nucleosides having different modifications.
931. The oligomeric compound of any of embodiments 887-930, wherein each nucleoside of the 3'-region comprises a 2'-modified ribosyl sugar moiety.
932. The oligomeric compound of any of embodiments 887-931, wherein at least one nucleoside of the 3'-region comprises a bicyclic furanosyl sugar moiety.

933. The oligomeric compound of any of embodiments 887-932, wherein each nucleoside of the 3'-region comprises a bicyclic furanosyl sugar moiety.
934. The oligomeric compound of any of embodiments 887-933, wherein at least one nucleoside of the 3'-region comprises a non-bicyclic sugar moiety.
935. The oligomeric compound of embodiment 934, wherein the non-bicyclic sugar moiety of the at least one nucleoside of the 3'-region is a 2'-substituted ribosyl sugar moiety.
936. The oligomeric compound of any of embodiments 887-935, wherein each nucleoside of the 3'-region comprises a non-bicyclic sugar moiety.
937. The oligomeric compound of embodiment 936, wherein each nucleoside of the 3'-region comprises a 2'-substituted furanosyl sugar moiety.
938. The oligomeric compound of any of embodiments 887-937, wherein each nucleoside of the 3'-region comprises a 2'-modified furanosyl sugar moiety independently selected from a bicyclic sugar moiety and a non-bicyclic 2'-substituted ribosyl sugar moiety.
939. The oligomeric compound of any of embodiments 887-935, or 938 wherein each nucleoside of the 3'-region comprises a bicyclic sugar moiety.
940. The oligomeric compound of any of embodiments 887-932 or 934-938, wherein each nucleoside of the 3'-region comprises a non-bicyclic 2'-substituted ribosyl sugar moiety.
941. The oligomeric compound of any of embodiments 887-935 or 938-939, wherein each bicyclic sugar moiety of the 3'-region is selected from among cEt, LNA, and ENA.
942. The oligomeric compound of any of embodiments 887-935, 938-939, or 941, wherein each bicyclic sugar moiety of the 3'-region is a cEt sugar moiety.
943. The oligomeric compound of any of embodiments 887-935, 938-939, or 941, wherein each bicyclic sugar moiety of the 3'-region is an LNA sugar moiety.
944. The oligomeric compound of any of embodiments 887-932, 934-938 or 940, wherein each non-bicyclic sugar moiety of the 3'-region has a 2'-substituent selected from among 2'-MOE, 2'-OMe, and 2'-NMA.
945. The oligomeric compound of any of embodiments 887-944, wherein none of the nucleosides of the 3'-region comprise a sugar moiety having a 2'-F substituent.
946. The oligomeric compound of any of embodiments 887-945, wherein none of the nucleosides of the 3'-region comprise a sugar moiety having a 2'-MOE substituent.
947. The oligomeric compound of any of embodiments 887-946, wherein none of the nucleosides of the 3'-region comprise a sugar moiety having a 2'-OMe substituent.
948. The oligomeric compound of any of embodiments 887-947, wherein none of the nucleosides of the 3'-region comprise a cEt sugar moiety.
949. The oligomeric compound of any of embodiments 887-948, wherein none of the nucleosides of the 3'-region comprise a LNA sugar moiety.
950. The oligomeric compound of any of embodiments 887-949, wherein each nucleobase of the 3'-region is independently selected from among thymine, uracil, guanine, cytosine, 5-methylcytosine, and adenine.
951. The oligomeric compound of any of embodiments 887-950, wherein each internucleoside linkage of the 3'-region is independently selected from among phosphodiester and phosphorothioate internucleoside linkages.
952. The oligomeric compound of any of embodiments 887-951, wherein the modified nucleosides of the 5'-region have the same modifications as the modifications of the modified nucleosides of the 3'-region.
953. The oligomeric compound of any of embodiments 887-951, wherein at least one modified nucleoside of the 5'-region and one modified nucleoside of the 3'-region comprise modifications that differ from one another.
954. The oligomeric compound of any of embodiments 887-898, 900, 902-903, 906, 909-932, 934-935, 938, 941-953, wherein the 5'-region and the 3'-region together include at least one non-bicyclic 2'-substituted modified nucleoside and at least one bicyclic nucleoside.
955. The oligomeric compound of embodiment 954, where the bicyclic nucleoside is a cEt nucleoside.
956. The oligomeric compound of embodiment 954, where the bicyclic nucleoside is an LNA nucleoside.
957. The oligomeric compound of any of embodiments 954-956, wherein the non-bicyclic 2'-modified nucleoside is a 2'-MOE nucleoside.
958. The oligomeric compound of any of embodiments 954-956, wherein the non-bicyclic 2'-modified nucleoside is a 2'-OMe nucleoside.
959. The oligomeric compound of any of embodiments 954-958, wherein at least one nucleoside of the 5'-region or the 3'-region is an unmodified DNA nucleoside.
960. The oligomeric compound of any of embodiments 887-959, wherein the central region has the formula:

$$(N_{da})(N_x)(N_y)(N_z)(N_{db})(N_{dc})_q$$

wherein each $N_{dc}$ is independently selected from an unmodified DNA nucleoside, a DNA isomer, a modified DNA isomer, and a DNA mimic; and q is 2-6.
961. The oligomeric compound of any of embodiments 887-960, wherein the central region consists of 7 linked nucleosides.
962. The oligomeric compound of any of embodiments 887-960, wherein the central region consists of 8 linked nucleosides.
963. The oligomeric compound of any of embodiments 887-960, wherein the central region consists of 9 linked nucleosides.
964. The oligomeric compound of any of embodiments 887-960, wherein the central region consists of 10 linked nucleosides.
965. The oligomeric compound of any of embodiments 887-960, wherein the central region consists of 11 linked nucleosides.
966. The oligomeric compound of any of embodiments 887-965, wherein Nx is the safety-enhancing nucleoside.
967. The oligomeric compound of any of embodiments 887-965, wherein Ny is the safety-enhancing nucleoside.
968. The oligomeric compound of any of embodiments 887-965, wherein Nz is the safety-enhancing nucleoside.
969. The oligomeric compound of any of embodiments 887-968, wherein the safety enhancing nucleoside is a DNA isomer or a modified DNA isomer, or a modified nucleoside comprising either a sugar surrogate, a bicyclic furanosyl sugar moiety, or a non-bicyclic modified furanosyl sugar moiety.
970. The oligomeric compound of any of embodiments 887-969, wherein the safety enhancing nucleoside is a DNA isomer or a modified DNA isomer, or comprises either a sugar surrogate, a bicyclic furanosyl sugar moiety, a non-bicyclic, 2'-modified furanosyl sugar moiety, a non-bicyclic 3'-modified furanosyl sugar moiety, a nonbicyclic, 4'-modified furanosyl sugar moiety, or a non-bicyclic 5'-modified furanosyl sugar moiety.

971. The oligomeric compound of any of embodiments 887-970, wherein the safety enhancing nucleoside comprises a sugar surrogate selected from a morpholino, a modified morpholino, a modified cyclohexenyl, or a modified tetrahydropyran.

972. The oligomeric compound of any of embodiments 887-970, wherein the safety enhancing nucleoside comprises a sugar surrogate selected from a morpholino, a modified morpholino, CeNA, F-CeNA, HNA, OMe-HNA or F-HNA.

973. The oligomeric compound of any of embodiments 887-970, wherein the safety enhancing nucleoside is a DNA isomer comprising a sugar moiety selected from among 2'-β-D-deoxyxylosyl, 2'-α-L-deoxyribosyl, 2'-β-L-deoxyribosyl, 2'-α-D-deoxyxylosyl, 2'-α-D-deoxyribosyl, 2'-α-L-deoxyxylosyl, and 2'-β-L-deoxyxylosyl.

974. The oligomeric compound of any of embodiments 887-970 or 973, wherein the safety enhancing nucleoside is a DNA isomer comprising a sugar moiety selected from among 2'-β-D-deoxyxylosyl, 2'-α-L-deoxyribosyl, and 2'-β-L-deoxyribosyl.

975. The oligomeric compound of any of embodiments 887-970, wherein the safety enhancing nucleoside is a modified DNA isomer comprising a 2'-modified sugar moiety, wherein the sugar moiety has the conformation 2'-β-D-deoxyxylosyl, 2'-α-L-deoxyribosyl, 2'-β-L-deoxyribosyl, 2'-α-D-deoxyxylosyl, 1, 2'-α-L-deoxyxylosyl, and 2'-β-L-deoxyxylosyl and the 2' position is further substituted with a hydroxyl, a fluoro, or O—$C_1$-$C_{10}$ alkoxy substituent.

976. The oligomeric compound of any of embodiments 887-970 or 975, wherein the safety enhancing nucleoside is a modified DNA isomer comprising a 2'-modified sugar moiety, wherein the sugar moiety has the conformation 2'-β-D-deoxyxylosyl, 2'-α-L-deoxyribosyl, 2'-β-L-deoxyribosyl, 2'-α-D-deoxyxylosyl, 1, 2'-α-L-deoxyxylosyl, and 2'-β-L-deoxyxylosyl and the 2' position is further substituted with a hydroxyl, a fluoro, or OMe substituent.

977. The oligomeric compound of any of embodiments 887-970 or 975-976, wherein the safety enhancing nucleoside is a modified DNA isomer comprising a 2'-modified sugar moiety, wherein the sugar moiety has the conformation 2'-β-D-deoxyxylosyl, 2'-α-L-deoxyribosyl, 2'-β-L-deoxyribosyl, 2'-α-D-deoxyxylosyl, 1, 2'-α-L-deoxyxylosyl, and 2'-β-L-deoxyxylosyl and the 2' position is further substituted with a fluoro or OMe substituent.

978. The oligomeric compound of any of embodiments 887-970 or 975-977, wherein the safety enhancing nucleoside is a modified DNA isomer comprising a sugar moiety selected from among 2'-β-D-deoxyxylosyl, 2'-α-L-deoxyribosyl, and 2'-β-L-deoxyribosyl and the 2' position is further substituted with a hydroxyl, fluoro, or OMe substituent.

979. The oligomeric compound of any of embodiments 887-970, wherein the safety enhancing nucleoside is a modified nucleoside comprising a bicyclic furanosyl sugar moiety.

980. The oligomeric compound of any of embodiments 887-970, wherein the safety enhancing nucleoside is selected from among cEt, LNA, α-L-LNA, and ENA.

981. The oligomeric compound of any of embodiments 887-970, wherein the safety enhancing nucleoside comprises a 2'-substituted furanosyl sugar moiety.

982. The oligomeric compound of embodiment 981, wherein the 2'-substituted furanosyl sugar moiety of the safety enhancing nucleoside has a 2' substituent selected from: halo, allyl, amino, azido, SH, CN, OCN, $CF_3$, $OCF_3$, O—$C_1$-$C_{10}$ alkoxy, O—$C_1$-$C_{10}$ substituted alkoxy, $C_1$-$C_{10}$ alkyl, $C_1$-$C_{10}$ substituted alkyl, S-alkyl, N($R_m$)-alkyl, O-alkenyl, S-alkenyl, N($R_m$)-alkenyl, O-alkynyl, S-alkynyl, N($R_m$)-alkynyl, O-alkylenyl-O-alkyl, alkynyl, alkaryl, aralkyl, O-alkaryl, O-aralkyl, $O(CH_2)_2SCH_3$, $O(CH_2)_2ON(R_m)(R_n)$ or $OCH_2C(=O)—N(R_m)(R_n)$, where each $R_m$ and $R_n$ is, independently, H, an amino protecting group, or substituted or unsubstituted $C_1$-$C_{10}$ alkyl.

983. The oligomeric compound of embodiment 981, wherein the 2'-substituted furanosyl sugar moiety of the safety enhancing nucleoside has a 2' substituent selected from: halo, O—$C_1$-$C_{10}$ alkoxy, O—$C_1$-$C_{10}$ substituted alkoxy, $C_1$-$C_{10}$ alkyl, $C_1$-$C_{10}$ substituted alkyl, S-alkyl, N($R_m$)-alkyl, $O(CH_2)_2ON(R_m)(R_n)$ or $OCH_2C(=O)—N(R_m)(R_n)$, where each $R_m$ and $R_n$ is, independently, H, an amino protecting group, or substituted or unsubstituted $C_1$-$C_{10}$ alkyl.

984. The oligomeric compound of embodiment 981, wherein the 2'-substituted furanosyl sugar moiety of the safety enhancing nucleoside has a 2' substituent selected from: fluoro, OMe, MOE, NMA.

985. The oligomeric compound of any of embodiments 887-978 or 981-984, wherein the safety enhancing nucleoside comprises a 2'-substituted furanosyl sugar moiety comprising a 2'-OMe or 2'-MOE.

986. The oligomeric compound of any of embodiments 887-978 or 981-986, wherein the safety enhancing nucleoside comprises a 2'-substituted furanosyl sugar moiety comprising a 2'-OMe.

987. The oligomeric compound of any of embodiments 887-978 or 981-986, wherein the safety enhancing nucleoside comprises a 2'-OMe modified 2'-β-D-deoxyribosyl sugar moiety.

988. The oligomeric compound of any of embodiments 887-970, wherein the safety enhancing nucleoside comprises a 3'-modified furanosyl sugar moiety having a 3' substituent selected from: halo, allyl, amino, azido, SH, CN, $CF_3$, $OCF_3$, $C_1$-$C_{10}$ alkyl, $C_1$-$C_{10}$ substituted alkyl, S-alkyl, N($R_m$)-alkyl, N($R_m$)-alkenyl, N($R_m$)-alkynyl, O-alkylenyl-O-alkyl, alkynyl, alkaryl, or aralkyl.

989. The oligomeric compound of any of embodiments 887-970 or embodiment 988, wherein the safety enhancing nucleoside comprises a 3'-modified furanosyl sugar moiety having a 3' substituent selected from: $C_1$-$C_{10}$ alkyl, or $C_1$-$C_{10}$ substituted alkyl.

990. The oligomeric compound of any of embodiments 887-970 or 988-989, wherein the safety enhancing nucleoside comprises a 3'-methyl furanosyl sugar moiety.

991. The oligomeric compound of any of embodiments 887-970, wherein the safety enhancing nucleoside comprises a 4'-modified furanosyl sugar moiety having a 4' substituent selected from: halo, allyl, amino, azido, SH, CN, OCN, $CF_3$, $OCF_3$, O—$C_1$-$C_{10}$ alkoxy, O—$C_1$-$C_{10}$ substituted alkoxy, $C_1$-$C_{10}$ alkyl, $C_1$-$C_{10}$ substituted alkyl, S-alkyl, N($R_m$)-alkyl, O-alkenyl, S-alkenyl, N($R_m$)-alkenyl, O-alkynyl, S-alkynyl, N($R_m$)-alkynyl, O-alkylenyl-O-alkyl, alkynyl, alkaryl, aralkyl, O-alkaryl, O-aralkyl, $O(CH_2)_2SCH_3$, $O(CH_2)_2ON(R_m)(R_n)$ or $OCH_2C(=O)—N(R_m)(R_n)$, where each $R_m$ and $R_n$ is, independently, H, an amino protecting group, or substituted or unsubstituted $C_1$-$C_{10}$ alkyl.

992. The oligomeric compound of any of embodiments 887-970 or 991, wherein the safety enhancing nucleoside comprises a 4'-modified furanosyl sugar moiety having a 4'-methyl.

993. The oligomeric compound of any of embodiments 887-970, wherein the safety enhancing nucleoside has the structure shown below, wherein R represents an optional 2' substituent group and Bx is a heterocyclic base moiety:

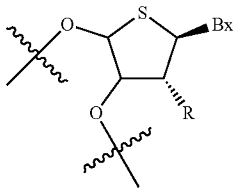

994. The oligomeric compound of embodiment 993, wherein in R is selected from among H, OH, OMe, F, or MOE.

995. The oligomeric compound of any of embodiments 887-970, wherein the safety enhancing nucleoside comprises a 5'-modified furanosyl sugar moiety having a 5' substituent selected from: halo, allyl, amino, azido, SH, CN, OCN, $CF_3$, $OCF_3$, O—$C_1$-$C_{10}$ alkoxy, O—$C_1$-$C_{10}$ substituted alkoxy, $C_1$-$C_{10}$ alkyl, $C_1$-$C_{10}$ substituted alkyl, S-alkyl, N($R_m$)-alkyl, O-alkenyl, S-alkenyl, N($R_m$)-alkenyl, O-alkynyl, S-alkynyl, N($R_m$)-alkynyl, O-alkylenyl-O-alkyl, alkynyl, alkaryl, aralkyl, O-alkaryl, O-aralkyl, $O(CH_2)_2SCH_3$, $O(CH_2)_2ON(R_m)(R_n)$ or $OCH_2C(=O)$—$N(R_m)(R_n)$, where each $R_m$ and $R_n$ is, independently, H, an amino protecting group, or substituted or unsubstituted $C_1$-$C_{10}$ alkyl.

996. The oligomeric compound of any of embodiments 887-970 or 995, wherein the safety enhancing nucleoside comprises a 5'-modified furanosyl sugar moiety with a 5' substituent selected from: 5'-methyl, 5'-ethyl or a 5'-allyl.

997. The oligomeric compound of any of embodiments 887-970 or 995-996, wherein the safety enhancing nucleoside comprises a 5'-modified furanosyl sugar moiety with a 5' substituent selected from: 5'-(R)-methyl- or 5'-(R)-ethyl.

998. The oligomeric compound of any of embodiments 887-970 or 995-997, wherein the safety enhancing nucleoside comprises a 5'-(R)-methyl-2'-β-D-deoxyribosyl sugar moiety.

999. The oligomeric compound of any of embodiments 887-970 or 995-998, wherein the safety enhancing nucleoside comprises a 5'-(R)-ethyl-2'-β-D-deoxyribosyl sugar moiety.

1000. The oligomeric compound of any of embodiments 887-999, wherein the safety enhancing nucleoside does not comprise a 2'-F modified sugar moiety.

1001. The oligomeric compound of any of embodiments 887-1000, wherein the safety enhancing nucleoside does not comprise a cEt modified sugar moiety.

1002. The oligomeric compound of any of embodiments 887-1001, wherein the safety enhancing nucleoside does not comprise a 2'-MOE modified sugar moiety.

1003. The oligomeric compound of any of embodiments 887-1002, wherein the safety enhancing nucleoside comprises a hypoxanthine nucleobase.

1004. The oligomeric compound of any of embodiments 887-1003, wherein the safety enhancing nucleoside comprises a nucleobase selected from among thymine, uracil, guanine, cytosine, 5-methylcytosine, and adenine.

1005. The oligomeric compound of any of embodiments 887-1004, wherein the safety enhancing nucleoside is a modified nucleoside other than cEt, MOE, LNA, or FANA.

1006. The oligomeric compound of any of embodiments 887-1005, wherein each Nd is independently selected from among a DNA nucleoside, a DNA isomer, a 2'-modified DNA isomer, and a DNA mimic.

1007. The oligomeric compound of embodiment 1006, wherein each DNA isomer comprises a sugar moiety selected from among 2'-β-D-deoxyxylosyl, 2'-α-L-deoxyribosyl, 2'-β-L-deoxyribosyl, 2'-α-D-deoxyxylosyl, 2'-α-D-deoxyribosyl, 2'-α-L-deoxyxylosyl, and 2'-β-L-deoxyxylosyl.

1008. The oligomeric compound of embodiment 1007, wherein each DNA isomer comprises a sugar moiety selected from among 2'-β-D-deoxyxylosyl, 2'-α-L-deoxyribosyl, and 2'-β-L-deoxyribosyl.

1009. The oligomeric compound of embodiment 1006, wherein each modified DNA isomer comprises a 2'-modified sugar moiety, wherein the sugar moiety has the conformation 2'-β-D-deoxyxylosyl, 2'-α-L-deoxyribosyl, 2'-β-L-deoxyribosyl, 2'-α-D-deoxyxylosyl, 1, 2'-α-L-deoxyxylosyl, and 2'-β-L-deoxyxylosyl and the 2' position is further substituted with a hydroxyl, a fluoro, or O—$C_1$-$C_{10}$ alkoxy substituent.

1010. The oligomeric compound of embodiment 1009, wherein each modified DNA isomer comprises a 2'-modified sugar moiety, wherein the sugar moiety has the conformation 2'-β-D-deoxyxylosyl, 2'-α-L-deoxyribosyl, 2'-β-L-deoxyribosyl, 2'-α-D-deoxyxylosyl, 1, 2'-α-L-deoxyxylosyl, and 2'-β-L-deoxyxylosyl and the 2' position is further substituted with a hydroxyl, a fluoro, or OMe substituent.

1011. The oligomeric compound of embodiment 1010, wherein each modified DNA isomer comprises a 2'-modified sugar moiety, wherein the sugar moiety has the conformation 2'-β-D-deoxyxylosyl, 2'-α-L-deoxyribosyl, 2'-β-L-deoxyribosyl, 2'-α-D-deoxyxylosyl, 1, 2'-α-L-deoxyxylosyl, and 2'-β-L-deoxyxylosyl and the 2' position is further substituted with a fluoro or OMe substituent.

1012. The oligomeric compound of embodiment 1011, wherein each modified DNA isomer comprises a 2'-modified sugar moiety, wherein the sugar moiety is selected from among 2'-β-D-deoxyxylosyl, 2'-α-L-deoxyribosyl, and 2'-β-L-deoxyribosyl and the 2' position is further substituted with a hydroxyl, fluoro, or OMe substituent.

1013. The oligomeric compound of embodiment 1006, wherein each DNA mimic comprises a structure represented by one of the formulas below:

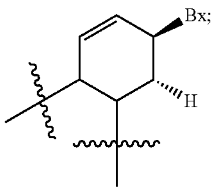

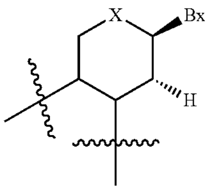

wherein X is O or S and Bx represents a heteorcylic base moiety.

1014. The oligomeric compound of embodiment 1006, wherein each DNA mimic comprises a structure represented by one of the formulas below:

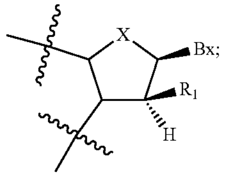
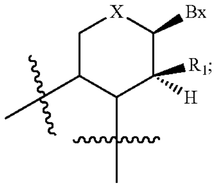
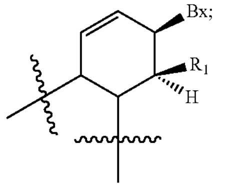

wherein X is O or S;

Bx represents a heterocyclic base moiety; and $R_1$ is selected from among H, OH, halo, allyl, amino, azido, SH, CN, OCN, $CF_3$, $OCF_3$, O—$C_1$-$C_{10}$ alkoxy, O—$C_1$-$C_{10}$ substituted alkoxy, $C_1$-$C_{10}$ alkyl, $C_1$-$C_{10}$ substituted alkyl, S-alkyl, N($R_m$)-alkyl, O-alkenyl, S-alkenyl, N($R_m$)-alkenyl, O-alkynyl, S-alkynyl, N($R_m$)-alkynyl, O-alkylenyl-O-alkyl, alkynyl, alkaryl, aralkyl, O-alkaryl, O-aralkyl, $O(CH_2)_2SCH_3$, $O(CH_2)_2ON(R_m)(R_n)$ or $OCH_2C(=O)—N(R_m)(R_n)$, where each $R_m$ and $R_n$ is, independently, H, an amino protecting group, or substituted or unsubstituted $C_1$-$C_{10}$ alkyl;

wherein if the DNA mimic comprises the structure:

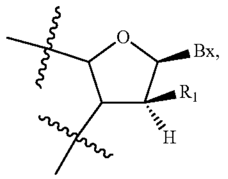

$R_1$ is other than H.

1015. The oligomeric compound of embodiment 1014, wherein $R_1$ is H, OH, OMe, or F.

1016. The oligomeric compound of embodiment 1014, wherein R1 is not F.

1017. The oligomeric compound of embodiment 1006, wherein each DNA mimic comprises a structure represented by the formula below:

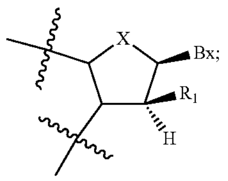

wherein X is S, Bx represents a heterocyclic base moiety, and R1 is H.

1018. The oligomeric compound of embodiment 1006, wherein the DNA mimic has a sugar moiety selected from among: 5'-methyl-2'-β-D-deoxyribosyl, 5'-ethyl-2'-β-D-deoxyribosyl, and 5'-allyl-2'-β-D-deoxyribosyl.

1019. The oligomeric compound of embodiment 1006, wherein the DNA mimic comprises a 2'-fluoro-β-D-arabinofuranosyl sugar moiety.

1020. The oligomeric compound of embodiment 1006, wherein the DNA mimic does not comprise a 2'-fluoro-β-D-arabinofuranosyl sugar moiety.

1021. The oligomeric compound of any of embodiments 887-1020, wherein each Na is a DNA nucleoside.

1022. The oligomeric compound of any of embodiments 887-1021, wherein the central region comprises no more than four nucleosides selected from among DNA isomers, modified DNA isomers, and DNA mimics.

1023. The oligomeric compound of any of embodiments 887-1021, wherein the central region comprises no more than three nucleosides selected from among DNA isomers, modified DNA isomers, and DNA mimics.

1024. The oligomeric compound of any of embodiments 887-1021, wherein the central region comprises no more than two nucleosides selected from among DNA isomers, modified DNA isomers, and DNA mimics.

1025. The oligomeric compound of any of embodiments 887-1021, wherein the central region comprises no more than one nucleoside selected from among DNA isomers, modified DNA isomers, and DNA mimics.

1026. The oligomeric compound of any of embodiments 887-1025, wherein the central region contains exactly one safety enhancing nucleoside and the remainder of nucleosides in the central region are DNA nucleosides.

1027. The oligomeric compound of any of embodiments 887-1026, wherein at least one internucleoside linkage of the central region selected from among: the internucleoside Nda to Nx, Nx to Ny, Ny to Nz, or Nz to the adjacent Ndb is a neutral internucleoside linkage.

1028. The oligomeric compound of embodiments 1027, wherein the neutral linkage is a phosphonate internucleoside linkage.

1029. The oligomeric compound of embodiments 1027, wherein the neutral linkage is a methoxypropyl internucleoside linkage.

1030. The oligomeric compound of embodiments 1027, wherein each remaining internucleoside linkage is a phosphodiester or phosphorothioate internucleoside linkage.

1031. A chirally enriched population of modified oligonucleotides of any of embodiments 887-1026, wherein the central region has at least one particular phorphorothioate internucleoside linkage having a particular stereochemical configuration.

1032. The chirally enriched population of embodiment 1031, wherein the central region has at least one phorphorothioate internucleoside linkage having the (Sp) configuration.

1033. The chirally enriched population of embodiment 1031, wherein central region has at least one phorphorothioate internucleoside linkage having the (Rp) configuration.

1034. The chirally enriched population of embodiment 1031, wherein the central region has a particular, independently selected stereochemical configuration at each phosphorothioate internucleoside linkage.

1035. The chirally enriched population of embodiment 1034, wherein the each phosphorothioate internucleoside linkage of the central region has the (Sp) configuration.

1036. The chirally enriched population of embodiment 1034, wherein the central region has one phosphorothioate internucleoside linkage having the (Rp) configuration and wherein each remaining central region phosphorothioate internucleoside linkage has the (Sp) configuration.

1037. The chirally enriched population of embodiment 1031, wherein the central region has an (Rp) phosphorothioate internucleoside linkage adjacent to an (Sp) phosphorothioate internucleoside linkage.

1038. The chirally enriched population of embodiment 1031, wherein the central region has an (Rp) phosphorothioate internucleoside linkage adjacent to a second (Rp) phosphorothioate internucleoside linkage.

1039. The chirally enriched population of embodiment 1031, wherein the central region has an (Rp) phosphorothioate internucleoside linkage adjacent to a second (Rp) phosphorothioate internucleoside linkage, and wherein each remaining central region phosphorothioate internucleoside linkage has the (Sp) configuration.

1040. The chirally enriched population of any of embodiments 1032, 1033, 1037, or 1038 wherein each phosphorothioate internucleoside linkage that does not have the (Rp) or (Sp) configuration is stereorandom.

1041. The oligomeric compound of any of embodiments 887-1040 comprising a conjugate group.

1042. The oligomeric compound of embodiment 1041, wherein the conjugate group comprises a linking group attaching the remainder of the conjugate group to the modified oligonucleotide, wherein the linking group comprises 1-5 nucleosides.

1043. The oligomeric compound of any of embodiments 887-1041, wherein the oligomeric compound does not comprise additional nucleosides beyond those of the modified oligonucleotide.

1044. The oligomeric compound of any of embodiments 887-1043, wherein the nucleobase sequence of the modified oligonucleotide is complementary to a target RNA.

1045. The oligomeric compound of embodiment 1044, wherein the nucleobase sequence of the modified oligonucleotide is at least 85% complementary to the target RNA.

1046. The oligomeric compound of embodiment 1044, wherein the nucleobase sequence of the modified oligonucleotide is at least 90% complementary to the target RNA.

1047. The oligomeric compound of embodiment 1044, wherein the nucleobase sequence of the modified oligonucleotide is at least 95% complementary to the target RNA.

1048. The oligomeric compound of embodiment 1047, wherein the nucleobase sequence of the modified oligonucleotide is 100% complementary to the target RNA.

1049. The oligomeric compound of any of embodiments 1044-1048, wherein the target RNA is a target mRNA or a target pre-mRNA.

1050. The oligomeric compound of embodiment 1049, wherein the target mRNA or target pre-mRNA is not a mouse, rat, monkey, or human PTEN RNA.

1051. The oligomeric compound of embodiment 1049 or 1050, wherein the target mRNA or target pre-mRNA is not a mouse, rat, monkey, or human SRB-1 RNA.

1052. The oligomeric compound of any of embodiments 1049-1051, wherein the target mRNA or target pre-mRNA is not a mouse, rat, monkey, or human MYD88 RNA.

1053. The oligomeric compound of any of embodiments 1049-1052, wherein the target mRNA or target pre-mRNA is not a mouse, rat, monkey, or human HTT RNA, is not a mouse, rat, monkey, or human SOD1 RNA, and is not a mouse, rat, monkey, or human alpha-synuclein RNA.

1054. The oligomeric compound of any of embodiments 1044-1053, wherein the target RNA is a human RNA.

1055. The oligomeric compound of any of embodiments 1044-1054, wherein the target RNA is expressed in the liver.

1056. The oligomeric compound of any of embodiments 1044-1055, wherein the target RNA is a liver target.

1057. The oligomeric compound of any of embodiments 1044-1054, wherein the target RNA is not expressed in the liver.

1058. The oligomeric compound of any of embodiments 1044-1054 or 1057, wherein the target RNA is not a liver target.

1059. The oligomeric compound of any of embodiments 1044-1056, wherein modulation of the expression of the target RNA in the liver is associated with treating a disorder or condition.

1060. The oligomeric compound of embodiment 1059, wherein the disorder or condition is a liver disorder or condition.

1061. The oligomeric compound of any of embodiments 1044-1060, wherein the target RNA is expressed in the central nervous system.

1062. The oligomeric compound of any of embodiments 1044-1060, wherein the target RNA is not expressed in the central nervous system.

1063. The oligomeric compound of any of embodiments 1044-1061, wherein the target RNA is a central nervous system target.

1064. The oligomeric compound of any of embodiments 1044-1062, wherein the target RNA is not a central nervous system target.

1065. The oligomeric compound of any of embodiments 1044-1064, wherein the target RNA is expressed in white fat cells.

1066. The oligomeric compound of any of embodiments 1044-1064, wherein the target RNA is expressed in brown fat cells.

1067. The oligomeric compound of any of embodiments 1044-1064, wherein the target RNA is expressed in adipocytes.

1068. The oligomeric compound of any of embodiments 1044-1064, wherein the target RNA is expressed in macrophages.

1069. The oligomeric compound of any of embodiments 1044-1064, wherein the target RNA is expressed in cancer cells.

1070. The oligomeric compound of any of embodiments 1044-1064, wherein the target RNA is expressed in tumor cells.

1071. The oligomeric compound of any of embodiments 1044-1064, wherein the target RNA is expressed in smooth muscle cells.

1072. The oligomeric compound of any of embodiments 1044-1064, wherein the target RNA is expressed in lymphocytes.

1073. The oligomeric compound of any of embodiments 1044-1064, wherein the target RNA is expressed in pulmonary cells.

1074. The oligomeric compound of any of embodiments 1044-1064, wherein the target RNA is expressed in heart muscle cells.

1075. The oligomeric compound of any of embodiments 1044-1064, wherein the target RNA is expressed in cardiomyocytes.

1076. The oligomeric compound of any of embodiments 1044-1064, wherein the target RNA is expressed in endothelial cells.

1077. The oligomeric compound of any of embodiments 1044-1064, wherein the target RNA is expressed in fibroblasts.

1078. The oligomeric compound of any of embodiments 1044-1064, wherein the target RNA is expressed in glial cells.

1079. The oligomeric compound of any of embodiments 1044-1064, wherein the target RNA is expressed in Schwann cells.

1080. The oligomeric compound of any of embodiments 1044-1064, wherein the target RNA is expressed in pancreatic cells.

1081. The oligomeric compound of any of embodiments 1044-1064, wherein the target RNA is expressed in kidney cells.

1082. The oligomeric compound of any of embodiments 1044-1064, wherein the target RNA is expressed in beta cells.

1083. The oligomeric compound of any of embodiments 1044-1064, wherein the target RNA is expressed in non-parenchymal cells.

1084. The oligomeric compound of any of embodiments 1044-1064, wherein the target RNA is expressed in hepatocytes.

1085. The oligomeric compound of any of embodiments 1044-1064, wherein the target RNA is expressed in oligodendrocytes.

1086. The oligomeric compound of any of embodiments 1044-1064, wherein the target RNA is expressed in astrocytes.

1087. The oligomeric compound of any of embodiments 1044-1064, wherein the target RNA is expressed in microglia.

1088. The oligomeric compound of any of embodiments 1044-1064, wherein the target RNA is expressed in ependymal cells.

1089. The oligomeric compound of any of embodiments 1044-1064, wherein the target RNA is expressed in sensory neurons.

1090. The oligomeric compound of any of embodiments 1044-1064, wherein the target RNA is expressed in motor neurons.

1091. The oligomeric compound of any of embodiments 1044-1064, wherein the target RNA is expressed in skeletal muscle.

1092. The oligomeric compound of any of embodiments 1044-1064, wherein the target RNA is expressed in cardiac muscle.

1093. The oligomeric compound of any of embodiments 1044-1064, wherein the target RNA is expressed in smooth muscle.

1094. The oligomeric compound of any of embodiments 1044-1064, wherein the target RNA is expressed in adipose tissue.

1095. The oligomeric compound of any of embodiments 1044-1064, wherein the target RNA is expressed in white adipose tissue.

1096. The oligomeric compound of any of embodiments 1044-1064, wherein the target RNA is expressed in the spleen.

1097. The oligomeric compound of any of embodiments 1044-1064, wherein the target RNA is expressed in the bone.

1098. The oligomeric compound of any of embodiments 1044-1064, wherein the target RNA is expressed in the bone marrow.

1099. The oligomeric compound of any of embodiments 1044-1064, wherein the target RNA is expressed in the intestine.

1100. The oligomeric compound of any of embodiments 1044-1064, wherein the target RNA is expressed in the adrenal glands.

1101. The oligomeric compound of any of embodiments 1044-1064, wherein the target RNA is expressed in the testes.

1102. The oligomeric compound of any of embodiments 1044-1064, wherein the target RNA is expressed in the ovaries.

1103. The oligomeric compound of any of embodiments 1044-1064, wherein the target RNA is expressed in the pancreas.

1104. The oligomeric compound of any of embodiments 1044-1064, wherein the target RNA is expressed in the pituitary gland.

1105. The oligomeric compound of any of embodiments 1044-1064, wherein the target RNA is expressed in the prostate gland.

1106. The oligomeric compound of any of embodiments 1044-1064, wherein the target RNA is expressed in the skin.

1107. The oligomeric compound of any of embodiments 1044-1064, wherein the target RNA is expressed in the epidermis.

1108. The oligomeric compound of any of embodiments 1044-1064, wherein the target RNA is expressed in the uterus.

1109. The oligomeric compound of any of embodiments 1044-1064, wherein the target RNA is expressed in the bladder.

1110. The oligomeric compound of any of embodiments 1044-1064, wherein the target RNA is expressed in the brain.

1111. The oligomeric compound of any of embodiments 1044-1064, wherein the target RNA is expressed in the glomerulus.

1112. The oligomeric compound of any of embodiments 1044-1064, wherein the target RNA is expressed in the distal tubular epithelium.

1113. The oligomeric compound of any of embodiments 1044-1064, wherein the target RNA is expressed in breast tissue.

1114. The oligomeric compound of any of embodiments 1044-1064, wherein the target RNA is expressed in the lung.

1115. The oligomeric compound of any of embodiments 1044-1064, wherein the target RNA is expressed in the heart.

1116. The oligomeric compound of any of embodiments 1044-1064, wherein the target RNA is expressed in the kidney.

1117. The oligomeric compound of any of embodiments 1044-1064, wherein the target RNA is expressed in the ganglion.

1118. The oligomeric compound of any of embodiments 1044-1064, wherein the target RNA is expressed in the frontal cortex.

1119. The oligomeric compound of any of embodiments 1044-1064, wherein the target RNA is expressed in the spinal cord.

1120. The oligomeric compound of any of embodiments 1044-1064, wherein the target RNA is expressed in the trigeminal ganglion.

1121. The oligomeric compound of any of embodiments 1044-1064, wherein the target RNA is expressed in the sciatic nerve.

1122. The oligomeric compound of any of embodiments 1044-1064, wherein the target RNA is expressed in the dorsal root ganglion.

1123. The oligomeric compound of any of embodiments 1044-1064, wherein the target RNA is expressed in the epidymal fat.

1124. The oligomeric compound of any of embodiments 1044-1064, wherein the target RNA is expressed in the diaphragm.

1125. The oligomeric compound of any of embodiments 1044-1064, wherein the target RNA is expressed in the colon.

1126. The oligomeric compound of any of embodiments 1044-1064, wherein the target RNA is a white fat cell target.

1127. The oligomeric compound of any of embodiments 1044-1064, wherein the target RNA is a brown fat cell target.

1128. The oligomeric compound of any of embodiments 1044-1064, wherein the target RNA is an adipocyte target.

1129. The oligomeric compound of any of embodiments 1044-1064, wherein the target RNA is a macrophage target.

1130. The oligomeric compound of any of embodiments 1044-1064, wherein the target RNA is a cancer cell target.

1131. The oligomeric compound of any of embodiments 1044-1064, wherein the target RNA is a tumor cell target.

1132. The oligomeric compound of any of embodiments 158-178, wherein the target RNA is a smooth muscle cell target.

1133. The oligomeric compound of any of embodiments 1044-1064, wherein the target RNA is a lymphocyte target.

1134. The oligomeric compound of any of embodiments 1044-1064, wherein the target RNA is a pulmonary cell target.

1135. The oligomeric compound of any of embodiments 1044-1064, wherein the target RNA is a heart muscle cell target.

1136. The oligomeric compound of any of embodiments 1044-1064, wherein the target RNA is a cardiomyocyte target.

1137. The oligomeric compound of any of embodiments 1044-1064, wherein the target RNA is a endothelial cell target.

1138. The oligomeric compound of any of embodiments 1044-1064, wherein the target RNA is a fibroblast target.

1139. The oligomeric compound of any of embodiments 1044-1064, wherein the target RNA is a glial cell target.

1140. The oligomeric compound of any of embodiments 1044-1064, wherein the target RNA is a Schwann cell target.

1141. The oligomeric compound of any of embodiments 1044-1064, wherein the target RNA is a pancreatic cell target.

1142. The oligomeric compound of any of embodiments 1044-1064, wherein the target RNA is a kidney cell target.

1143. The oligomeric compound of any of embodiments 1044-1064, wherein the target RNA is a beta cell target.

1144. The oligomeric compound of any of embodiments 1044-1064, wherein the target RNA is a non-parenchymal cell target.

1145. The oligomeric compound of any of embodiments 1044-1064, wherein the target RNA is a hepatocyte target.

1146. The oligomeric compound of any of embodiments 1044-1064, wherein the target RNA a oligodendrocyte target.

1147. The oligomeric compound of any of embodiments 1044-1064, wherein the target RNA is a astrocyte target.

1148. The oligomeric compound of any of embodiments 1044-1064, wherein the target RNA is a microglia target.

1149. The oligomeric compound of any of embodiments 1044-1064, wherein the target RNA is a ependymal cell target.

1150. The oligomeric compound of any of embodiments 1044-1064, wherein the target RNA is a sensory neuron target.

1151. The oligomeric compound of any of embodiments 1044-1064, wherein the target RNA is a motor neuron target.

1152. The oligomeric compound of any of embodiments 1044-1064, wherein the target RNA is a skeletal muscle target.

1153. The oligomeric compound of any of embodiments 1044-1064, wherein the target RNA is a cardiac muscle target.

1154. The oligomeric compound of any of embodiments 1044-1064, wherein the target RNA is a smooth muscle target.

1155. The oligomeric compound of any of embodiments 1044-1064, wherein the target RNA is a adipose tissue target.

1156. The oligomeric compound of any of embodiments 1044-1064, wherein the target RNA is a white adipose tissue target.

1157. The oligomeric compound of any of embodiments 1044-1064, wherein the target RNA is a spleen target.

1158. The oligomeric compound of any of embodiments 1044-1064, wherein the target RNA is a bone target.

1159. The oligomeric compound of any of embodiments 1044-1064, wherein the target RNA is a bone marrow target.

1160. The oligomeric compound of any of embodiments 1044-1064, wherein the target RNA is an intestinal target.

1161. The oligomeric compound of any of embodiments 1044-1064, wherein the target RNA is an adrenal gland target.

1162. The oligomeric compound of any of embodiments 1044-1064, wherein the target RNA is a testicular target.

1163. The oligomeric compound of any of embodiments 1044-1064, wherein the target RNA is an ovarian target.

1164. The oligomeric compound of any of embodiments 1044-1064, wherein the target RNA is a pancreatic target.

1165. The oligomeric compound of any of embodiments 1044-1064, wherein the target RNA is a pituitary gland target.

1166. The oligomeric compound of any of embodiments 1044-1064, wherein the target RNA is a prostate gland target.

1167. The oligomeric compound of any of embodiments 1044-1064, wherein the target RNA is a skin target.

1168. The oligomeric compound of any of embodiments 1044-1064, wherein the target RNA is an epidermal target.

1169. The oligomeric compound of any of embodiments 1044-1064, wherein the target RNA is a uterine target.

1170. The oligomeric compound of any of embodiments 1044-1064, wherein the target RNA is a bladder target.

1171. The oligomeric compound of any of embodiments 1044-1064, wherein the target RNA is a brain target.

1172. The oligomeric compound of any of embodiments 1044-1064, wherein the target RNA is a glomerulus target.

1173. The oligomeric compound of any of embodiments 1044-1064, wherein the target RNA is a distal tubular epithelium target.

1174. The oligomeric compound of any of embodiments 1044-1064, wherein the target RNA is a breast tissue target.

1175. The oligomeric compound of any of embodiments 1044-1064, wherein the target RNA is a lung target.

1176. The oligomeric compound of any of embodiments 1044-1064, wherein the target RNA is a heart target.

1177. The oligomeric compound of any of embodiments 1044-1064, wherein the target RNA is a kidney target.

1178. The oligomeric compound of any of embodiments 1044-1064, wherein the target RNA is a ganglion target.

1179. The oligomeric compound of any of embodiments 1044-1064, wherein the target RNA is a frontal cortex target.

1180. The oligomeric compound of any of embodiments 1044-1064, wherein the target RNA is a spinal cord target.

1181. The oligomeric compound of any of embodiments 1044-1064, wherein the target RNA is a trigeminal ganglion target.

1182. The oligomeric compound of any of embodiments 1044-1064, wherein the target RNA is a sciatic nerve target.

1183. The oligomeric compound of any of embodiments 1044-1064, wherein the target RNA is a dorsal root ganglion target.

1184. The oligomeric compound of any of embodiments 1044-1064, wherein the target RNA is a epidymal fat target.

1185. The oligomeric compound of any of embodiments 1044-1064, wherein the target RNA is a diaphragm target.

1186. The oligomeric compound of any of embodiments 1044-1064, wherein the target RNA is a colon target.

1187. The oligomeric compound of any of embodiments 1044-1186, wherein the target RNA is a MeCP2, DUX4, HDAC2, APP, Ataxin 1, Ataxin 2, Ataxin 3, Ataxin 6, Ataxin 7, C9ORF72, UBE3A, Prion, PMP22, Tau, LRRK2, LINGO2, GYS1, KCNT1, IRF8, Progranulin, or GFAP RNA.

1188. The oligomeric compound of any of embodiments 1044-1186, wherein the target RNA is a HTT RNA.

1189. The oligomeric compound of embodiment 1187, wherein the target RNA is a MeCP2 RNA.

1190. The oligomeric compound of embodiment 1187, wherein the target RNA is a DUX4 RNA.

1191. The oligomeric compound of embodiment 1187, wherein the target RNA is a HDAC2 RNA.

1192. The oligomeric compound of embodiment 1187, wherein the target RNA is a Ataxin 1 RNA.

1193. The oligomeric compound of embodiment 1187, wherein the target RNA is a Ataxin 2 RNA.

1194. The oligomeric compound of embodiment 1187, wherein the target RNA is a Ataxin 3 RNA.

1195. The oligomeric compound of embodiment 1187, wherein the target RNA is a Ataxin 6 RNA.

1196. The oligomeric compound of embodiment 1187, wherein the target RNA is a Ataxin 7 RNA.

1197. The oligomeric compound of embodiment 1187, wherein the target RNA is a C9ORF72 RNA.

1198. The oligomeric compound of embodiment 1044-1186, wherein the target RNA is an alpha-synuclein RNA.

1199. The oligomeric compound of embodiment 1187, wherein the target RNA is an UBE3A RNA.

1200. The oligomeric compound of any of embodiments 1044-1186, wherein the target RNA is a SOD1 RNA.

1201. The oligomeric compound of embodiment 1187, wherein the target RNA is a Prion RNA.

1202. The oligomeric compound of embodiment 1187, wherein the target RNA is a PMP22 RNA.

1203. The oligomeric compound of any of embodiments 1044-1187, wherein the target RNA is a Tau RNA.

1204. The oligomeric compound of embodiment 1187, wherein the target RNA is a LRRK2 RNA.

1205. The oligomeric compound of embodiment 1187, wherein the target RNA is an APP RNA.

1206. The oligomeric compound of 1187, wherein the target RNA is a LINGO2 RNA.

1207. The oligomeric compound of any of embodiments 1187, wherein the target RNA is a GYS1 RNA.

1208. The oligomeric compound of any of embodiments 1187, wherein the target RNA is a KCNT1 RNA.

1209. The oligomeric compound of any of embodiments 1187, wherein the target RNA is a IRF8 RNA.

1210. The oligomeric compound of any of embodiments 1187, wherein the target RNA is a Progranulin RNA.

1211. The oligomeric compound of any of embodiments 1187, wherein the target RNA is a GFAP RNA.

1212. The oligomeric compound of any of embodiments 1044-1211, wherein modulation of the expression of the target RNA is associated with treating a disorder or condition.

1213. The oligomeric compound of any of embodiments 1212, wherein the disorder or condition is Alzheimer's Disease, Amyotrophic Lateral Sclerosis, Parkinson's Disease, a Spinocerebellar ataxia, Angelman Syndrome, Alexander's Disease, Lafora Disease, Charcot-Marie Tooth Disease, Prion Disease, a dementia, neurodegeneration, MeCP2 Duplication Syndrome, encephalopathy, neuroinflammation, or multiple sclerosis.

1214. The oligomeric compound of embodiment 1212, wherein the disorder or condition is Alzheimer's Disease.

1215. The oligomeric compound of embodiment 1212, wherein the disorder or condition is Amyotrophic Lateral Sclerosis.

1216. The oligomeric compound of embodiment 1212, wherein the disorder or condition is Parkinson's Disease.

1217. The oligomeric compound of embodiment 1212, wherein the disorder or condition is a Spinocerebellar ataxia.

1218. The oligomeric compound of embodiment 1212, wherein the disorder or condition is Angelman Syndrome.

1219. The oligomeric compound of embodiment 1212, wherein the disorder or condition is Alexander's Disease.

1220. The oligomeric compound of embodiment 1212, wherein the disorder or condition is Lafora Disease.

1221. The oligomeric compound of embodiment 1212, wherein the disorder or condition is Charcot-Marie Tooth Disease.

1222. The oligomeric compound of embodiment 1212, wherein the disorder or condition is Prion Disease.

1223. The oligomeric compound of embodiment 1212, wherein the disorder or condition is a dementia.

1224. The oligomeric compound of embodiment 1212, wherein the disorder or condition is neurodegeneration.

1225. The oligomeric compound of embodiment 1212, wherein the disorder or condition is MeCP2 Duplication Syndrome.

1226. The oligomeric compound of embodiment 1212, wherein the disorder or condition is encephalopathy.

1227. The oligomeric compound of embodiment 1212, wherein the disorder or condition is neuroinflammation.

1228. The oligomeric compound of embodiment 1212, wherein the disorder or condition is multiple sclerosis.

1229. The oligomeric compound of any of embodiments 887-1228, wherein the parent oligomeric compound of the oligomeric compound of any of embodiments 887-1228 is cytotoxic in vitro.

1230. The oligomeric compound of embodiment 1228, wherein the parent oligomeric compound is cytotoxic in a standard in vitro cytotoxicity assay.

1231. The oligomeric compound of any of embodiments 887-1229 wherein administration to a mouse of the parent oligomeric compound of the oligomeric compound of any of embodiments 887-1229 is hepatotoxic to the mouse.

1232. The oligomeric compound of embodiment 1230, wherein the administration of the parent oligomeric compound to the mouse is systemic administration.

1233. The oligomeric compound of embodiment 1230, wherein the systemic administration is subcutaneous administration.

1234. The oligomeric compound of any of embodiments 1230-1232, wherein the mouse is a CD-1 mouse.

1235. The oligomeric compound of any of embodiments 1230-1232, wherein the mouse is a C57BL/6 mouse.

1236. The oligomeric compound of any of embodiments 1230-1232, wherein the mouse is a BALB/c mouse.

1237. The oligomeric compound of any of embodiments 1230-1236, wherein the plasma ALT level in the mouse is higher than 500 units per liter following the administration of the parent oligomeric compound.

1238. The oligomeric compound of any of embodiments 1230-1237, wherein the plasma AST level in the mouse is higher than 500 units per liter following the administration of the parent oligomeric compound.

1239. The oligomeric compound of any of embodiments 1230-1238, wherein the plasma ALT level in the mouse is higher than 1000 units per liter following the administration of the parent oligomeric compound.

1240. The oligomeric compound of any of embodiments 1230-1239, wherein the plasma AST level in the mouse is higher than 1000 units per liter following the administration of the parent oligomeric compound.

1241. The oligomeric compound of any of embodiments 1230-1240, wherein the hepatotoxicity is measured 24-48 hours following the administration of the parent oligomeric compound.

1242. The oligomeric compound of any of embodiments 1230-1241, wherein the hepatotoxicity is measured 72 hours following the administration of the parent oligomeric compound.

1243. The oligomeric compound of any of embodiments 1230-1241, wherein the hepatotoxicity is measured 3 days following the administration of the parent oligomeric compound.

1244. The oligomeric compound of any of embodiments 1230-1241, wherein the hepatotoxicity is measured 5 days following the administration of the parent oligomeric compound.

1245. The oligomeric compound of any of embodiments 1230-1241, wherein the hepatotoxicity is measured 7 days following the administration of the parent oligomeric compound.

1246. The oligomeric compound of any of embodiments 1230-1241, wherein the hepatotoxicity is measured 10 days following the administration of the parent oligomeric compound.

1247. The oligomeric compound of any of embodiments 1230-1241, wherein the hepatotoxicity is measured 14 days following the administration of the parent oligomeric compound.

1248. The oligomeric compound of any of embodiments 1230-1241, wherein 1-10 mg/kg of the parent oligomeric compound is administered to the mouse.

1249. The oligomeric compound of any of embodiments 1230-1241, wherein 10-25 mg/kg of the parent oligomeric compound is administered to the mouse.

1250. The oligomeric compound of any of embodiments 1230-1241, wherein 25-50 mg/kg of the parent oligomeric compound is administered to the mouse.

1251. The oligomeric compound of any of embodiments 1230-1241, wherein 50-100 mg/kg of the parent oligomeric compound is administered to the mouse.

1252. The oligomeric compound of any of embodiments 1230-1241, wherein 100-150 mg/kg of the parent oligomeric compound is administered to the mouse.

1253. The oligomeric compound of any of embodiments 1230-1241, wherein the mouse is a BALB/c mouse, wherein 150 mg/kg of the parent oligomeric compound is administered to the mouse, and wherein the plasma ALT level in the mouse is measured 72 hours following the administration of the parent oligomeric compound.

1254. The oligomeric compound of any of embodiments 887-1253, wherein administration of 50 mg/kg of the oligomeric compound of any of embodiments 887-1253 to a mouse is not hepatotoxic to the mouse.

1255. The oligomeric compound of embodiment 1254, wherein plasma ALT level in the mouse is lower than 100 units per liter following the administration of the oligomeric compound of embodiment 1254.

1256. The oligomeric compound of embodiment 1254 or 1255, wherein plasma ALT level in the mouse is at least 10-fold lower than plasma ALT level in a mouse administered the parent oligomeric compound of the oligomeric compound of embodiment 1254 or 1255, wherein the administrations and plasma ALT measurements of both the oligomeric compound of embodiment 1254 or 1255 and the parent oligomeric compound are completed in the same way.

1257. The oligomeric compound of embodiment 1256, wherein the plasma ALT level in the mouse is at least 100-fold lower than the plasma ALT level in the mouse administered the parent oligomeric compound.

1258. The oligomeric compound of embodiment 1256, wherein the plasma ALT level in the mouse is at least 500-fold lower than the plasma ALT level in the mouse administered the parent oligomeric compound.

1259. The oligomeric compound of any of embodiments 1230-1258, wherein the therapeutic index in a mouse of the oligomeric compound of any of embodiments 1230-1258 is increased relative to the therapeutic index of the parent oligomeric compound.

1260. The oligomeric compound of embodiment 1259, wherein the therapeutic index in a mouse of the oligomeric compound of embodiment 1259 is at least two-fold greater than the therapeutic index of the parent oligomeric compound.

1261. The oligomeric compound of any of embodiments 887-1229, wherein an otherwise identical oligomeric compound lacking the at least one modified internucleoside linkage other than phosphorothioate and/or at least one modified nucleoside comprising a modified nucleobase other than 5-methylcytosine and/or a modified sugar moiety in the central region is hepatotoxic following administration to a mouse;

and wherein the otherwise identical oligomeric compound has a central region consisting of phosphorothioate internucleoside linkages, unmodified 2'-β-D-deoxyribosyl sugar moieties, and nucleobases selected from thymine, uracil, adenine, guanine, cytosine, and 5-methylcytosine.

1262. The oligomeric compound of embodiment 1261, wherein the at least one modified internucleoside linkage other than phosphorothioate and/or at least one modified nucleoside comprising a modified nucleobase other than 5-methylcytosine and/or a modified sugar moiety in the central region is a 2'4)-methyl modified sugar moiety.

1263. The oligomeric compound of embodiment 1262, wherein the 2'-O-methyl modified sugar moiety is at position 2 of the central region.

1264. The oligomeric compound of embodiment 1261-1263, wherein the otherwise identical oligomeric compound lacks a 2'-O-methyl modified sugar moiety, and wherein the otherwise identical oligomeric compound comprises an unmodified 2'-β-D-deoxyribosyl sugar moiety in place of the 2'-O-methyl modified sugar moiety.

1265. The oligomeric compound of any of embodiments 1261-1264, wherein the nucleobase sequence of the otherwise identical oligomeric compound is 100% complementary to the target RNA.

1266. The oligomeric compound of any of embodiments 1261-1265, wherein the otherwise identical oligomeric compound is a parent oligomeric compound of the oligomeric compound of any of embodiments 1202-1206.

1267. The oligomeric compound of any of embodiments 1044-1266, wherein the oligomeric compound inhibits the target RNA with an $IC_{50}$ lower than 100 nM in a standard in vitro activity assay.

1268. The oligomeric compound of any of embodiments 1044-1266, wherein the parent oligomeric compound of the oligomeric compound of any of embodiments 1044-1266 inhibits the target RNA with an $IC_{50}$ lower than 100 nM in a standard in vitro activity assay.

1269. The oligomeric compound of any of embodiments 1044-1268, wherein the difference between the $IC_{50}$ of the parent oligomeric compound measured in a standard in vitro activity assay and the $IC_{50}$ of the oligomeric compound of any of embodiments 1044-1268 measured in a standard in vitro activity assay is less than 4-fold.

1270. The oligomeric compound of any of embodiments 1044-1268, wherein the difference between the $IC_{50}$ of the parent oligomeric compound measured in a standard in vitro activity assay and the $IC_{50}$ of the oligomeric compound of any of embodiments 1044-1268 measured in a standard in vitro activity assay is less than 3-fold.

1271. The oligomeric compound of any of embodiments 1044-1268, wherein the difference between the $IC_{50}$ of the parent oligomeric compound measured in a standard in vitro activity assay and the $IC_{50}$ of the oligomeric compound of any of embodiments 1044-1268 measured in a standard in vitro activity assay is less than 2-fold.

1272. The oligomeric compound of any of embodiments 1044-1271, wherein each sugar moiety of the central region of the parent oligomeric compound is an unmodified 2'-β-D-deoxyribosyl sugar moiety, and wherein each internucleoside linkage of the central region of the parent oligomeric compound is a phosphorothioate internucleoside linkage.

1273. The oligomeric compound of any of embodiments 1044-1272, wherein the nucleobase sequence of the parent oligomeric compound is 100% complementary to the target RNA.

1274. The oligomeric compound of any of embodiments 887-1273, wherein administration of 10-50 mg of the oligomeric compound to a human is not hepatotoxic to the human.

1275. The oligomeric compound of any of embodiments 887-1273, wherein administration of 50-100 mg of the oligomeric compound to a human is not hepatotoxic to the human.

1276. The oligomeric compound of any of embodiments 887-1273, wherein administration of 100-300 mg of the oligomeric compound to a human is not hepatotoxic to the human.

1277. The oligomeric compound of any of embodiments 1274-1276, wherein the administration is systemic administration.

1278. A composition comprising the oligomeric compound of any of embodiments 887-1277, and a second oligomeric compound, wherein the second oligomeric compound is complementary to the oligomeric compound of any of embodiments 887-1277.

1279. The composition of embodiment 1278, wherein the second oligomeric compound comprises at least 14 contiguous linked nucleosides that are at least 90% complementary to the oligomeric compound of any of embodiments 887-1277.

1280. The composition of embodiment 1278, wherein the second oligomeric compound comprises at least 14 contiguous linked nucleosides that are 100% complementary to the oligomeric compound of any of embodiments 887-1277.

1281. A pharmaceutical composition comprising the oligomeric compound of any of embodiments 887-1277 or the composition of any of embodiments 1278-1280, comprising a pharmaceutically acceptable carrier or diluent.

1282. A method comprising administering the oligomeric compound or composition of any of embodiments 887-1281 to a human subject.

1283. A method of treating a disease or disorder comprising administering the oligomeric compound or composition of any of embodiments 887-1281 to a human subject.

1284. A method of modulating the amount or activity of a target RNA in a human subject comprising administering the oligomeric compound or composition of any of embodiments 887-1281 to the human subject; and thereby modulating the amount or activity of the target RNA in the human subject.

1285. A method of treating a disease or disorder in a human subject comprising administering the oligomeric compound or composition of any of embodiments 887-1281 to the human subject having the disease or disorder; and thereby treating the disease or disorder in the human subject.

1286. The method of embodiment 1284 or 1285, wherein the disease or disorder is a liver disease, and wherein the oligomeric compound modulates the amount or activity of a liver target RNA.

1287. The method of embodiment 1284 or 1285, wherein the disease or disorder is a central nervous system disease, and wherein the oligomeric compound modulates the amount or activity of a central nervous system target RNA.

1288. The method of any of embodiments 1284-1287, wherein the disease or disorder is a cancer, a neurodegenerative disease, a cardiovascular disease, an immunological disease, a hereditary disease, a repeat expansion disease, a muscle-wasting disease, or a metabolic disease.

1289. The method of embodiment 1284 or 1285, wherein the oligomeric compound modulates the amount or activity of a white fat cell target.

1290. The method of embodiment 1284 or 1285, wherein the oligomeric compound modulates the amount or activity of a brown fat cell target.

1291. The method of embodiment 1284 or 1285, wherein the oligomeric compound modulates the amount or activity of an adipocyte target.

1292. The method of embodiment 1284 or 1285, wherein the oligomeric compound modulates the amount or activity of a macrophage target.

1293. The method of embodiment 1284 or 1285, wherein the oligomeric compound modulates the amount or activity of a cancer cell target.

1294. The method of embodiment 1284 or 1285, wherein the oligomeric compound modulates the amount or activity of a tumor cell target.

1295. The method of embodiment 1284 or 1285, wherein the oligomeric compound modulates the amount or activity of a smooth muscle cell target.

1296. The method of embodiment 1284 or 1285, wherein the oligomeric compound modulates the amount or activity of a lymphocyte target.

1297. The method of embodiment 1284 or 1285, wherein the oligomeric compound modulates the amount or activity of a pulmonary cell target.

1298. The method of embodiment 1284 or 1285, wherein the oligomeric compound modulates the amount or activity of a heart muscle cell target.

1299. The method of embodiment 1284 or 1285, wherein the oligomeric compound modulates the amount or activity of a cardiomyocyte target.

1300. The method of embodiment 1284 or 1285, wherein the oligomeric compound modulates the amount or activity of a endothelial cell target.

1301. The method of embodiment 1284 or 1285, wherein the oligomeric compound modulates the amount or activity of a fibroblast target.

1302. The method of embodiment 1284 or 1285, wherein the oligomeric compound modulates the amount or activity of a glial cell target.

1303. The method of embodiment 1284 or 1285, wherein the oligomeric compound modulates the amount or activity of a Schwann cell target.

1304. The method of embodiment 1284 or 1285, wherein the oligomeric compound modulates the amount or activity of a pancreatic cell target.

1305. The method of embodiment 1284 or 1285, wherein the oligomeric compound modulates the amount or activity of a kidney cell target.

1306. The method of embodiment 1284 or 1285, wherein the oligomeric compound modulates the amount or activity of a beta cell target.

1307. The method of embodiment 1284 or 1285, wherein the oligomeric compound modulates the amount or activity of a non-parenchymal cell target.

1308. The method of embodiment 1284 or 1285, wherein the oligomeric compound modulates the amount or activity of a hepatocyte target.

1309. The method of embodiment 1284 or 1285, wherein the oligomeric compound modulates the amount or activity of a oligodendrocyte target.

1310. The method of embodiment 1284 or 1285, wherein the oligomeric compound modulates the amount or activity of a astrocyte target.

1311. The method of embodiment 1284 or 1285, wherein the oligomeric compound modulates the amount or activity of a microglia target.

1312. The method of embodiment 1284 or 1285, wherein the oligomeric compound modulates the amount or activity of a ependymal cell target.

1313. The method of embodiment 1284 or 1285, wherein the oligomeric compound modulates the amount or activity of a sensory neuron target.

1314. The method of embodiment 1284 or 1285, wherein the oligomeric compound modulates the amount or activity of a motor neuron target.

1315. The method of embodiment 1284 or 1285, wherein the oligomeric compound modulates the amount or activity of a skeletal muscle target.

1316. The method of embodiment 1284 or 1285, wherein the oligomeric compound modulates the amount or activity of a cardiac muscle target.

1317. The method of embodiment 1284 or 1285, wherein the oligomeric compound modulates the amount or activity of a smooth muscle target.

1318. The method of embodiment 1284 or 1285, wherein the oligomeric compound modulates the amount or activity of a adipose tissue target.

1319. The method of embodiment 1284 or 1285, wherein the oligomeric compound modulates the amount or activity of a white adipose tissue target.

1320. The method of embodiment 1284 or 1285, wherein the oligomeric compound modulates the amount or activity of a spleen target.

1321. The method of embodiment 1284 or 1285, wherein the oligomeric compound modulates the amount or activity of a bone target.

1322. The method of embodiment 1284 or 1285, wherein the oligomeric compound modulates the amount or activity of a bone marrow target.

1323. The method of embodiment 1284 or 1285, wherein the oligomeric compound modulates the amount or activity of an intestinal target.

1324. The method of embodiment 1284 or 1285, wherein the oligomeric compound modulates the amount or activity of an adrenal gland target.

1325. The method of embodiment 1284 or 1285, wherein the oligomeric compound modulates the amount or activity of a testicular target.

1326. The method of embodiment 1284 or 1285, wherein the oligomeric compound modulates the amount or activity of an ovarian target.

1327. The method of embodiment 1284 or 1285, wherein the oligomeric compound modulates the amount or activity of a pancreatic target.

1328. The method of embodiment 1284 or 1285, wherein the oligomeric compound modulates the amount or activity of a pituitary gland target.

1329. The method of embodiment 1284 or 1285, wherein the oligomeric compound modulates the amount or activity of a prostate gland target.

1330. The method of embodiment 1284 or 1285, wherein the oligomeric compound modulates the amount or activity of a skin target.

1331. The method of embodiment 1284 or 1285, wherein the oligomeric compound modulates the amount or activity of an epidermal target.

1332. The method of embodiment 1284 or 1285, wherein the oligomeric compound modulates the amount or activity of a uterine target.

1333. The method of embodiment 1284 or 1285, wherein the oligomeric compound modulates the amount or activity of a bladder target.

1334. The method of embodiment 1284 or 1285, wherein the oligomeric compound modulates the amount or activity of a brain target.

1335. The method of embodiment 1284 or 1285, wherein the oligomeric compound modulates the amount or activity of a glomerulus target.

1336. The method of embodiment 1284 or 1285, wherein the oligomeric compound modulates the amount or activity of a distal tubular epithelium target.

1337. The method of embodiment 1284 or 1285, wherein the oligomeric compound modulates the amount or activity of a breast tissue target.

1338. The method of embodiment 1284 or 1285, wherein the oligomeric compound modulates the amount or activity of a lung target.

1339. The method of embodiment 1284 or 1285, wherein the oligomeric compound modulates the amount or activity of a heart target.

1340. The method of embodiment 1284 or 1285, wherein the oligomeric compound modulates the amount or activity of a kidney target.

1341. The method of embodiment 1284 or 1285, wherein the oligomeric compound modulates the amount or activity of a ganglion target.

1342. The method of embodiment 1284 or 1285, wherein the oligomeric compound modulates the amount or activity of a frontal cortex target.

1343. The method of embodiment 1284 or 1285, wherein the oligomeric compound modulates the amount or activity of a spinal cord target.

1344. The method of embodiment 1284 or 1285, wherein the oligomeric compound modulates the amount or activity of a trigeminal ganglion target.

1345. The method of embodiment 1284 or 1285, wherein the oligomeric compound modulates the amount or activity of a sciatic nerve target.

1346. The method of embodiment 1284 or 1285, wherein the oligomeric compound modulates the amount or activity of a dorsal root ganglion target.

1347. The method of embodiment 1284 or 1285, wherein the oligomeric compound modulates the amount or activity of a epidymal fat target.

1348. The method of embodiment 1284 or 1285, wherein the oligomeric compound modulates the amount or activity of a diaphragm target.

1349. The method of embodiment 1284 or 1285, wherein the oligomeric compound modulates the amount or activity of a colon target.

1350. The method of any of embodiments 1282-1349, wherein the plasma ALT level of the human subject after the administration is not more than three times higher than it was prior to the administration.

1351. The method of any of embodiments 1282-1350, wherein the plasma ALT level of the human subject after the administration is not more than 150 units per liter.

1352. The method of any of embodiments 1282-1351, wherein the human subject is susceptible to liver damage.

1353. The method of any of embodiments 1282-1352, wherein the human subject is susceptible to liver degeneration.

1354. The method of any of embodiments 1282-1353, wherein the human subject is susceptible to elevated apoptosis in the liver.

1355. The method of any of embodiments 1282-1354, wherein the human subject has a liver disease.

1356. The method of any of embodiments 1282-1355, wherein the human subject has kidney disease.

1357. The method of any of embodiments 1282-1356, wherein the human subject is susceptible to kidney damage.

1358. The method of any of embodiments 1282-1357, wherein the human subject has heart disease.

1359. The method of any of embodiments 1282-1358, wherein the human subject is susceptible to heart damage.

1360. The method of any of embodiments 1282-1359, wherein the human subject has pancreatitis.

1361. The method of any of embodiments 1282-1360, wherein the human subject is susceptible to pancreatic damage.

1362. The method of any of embodiments 1282-1361, wherein the human subject has a neurological disease.

1363. The method of any of embodiments 1282-1362, wherein the human subject is susceptible to neurological damage.

1364. The method of any of embodiments 1282-1363, comprising administering the parent oligomeric compound of the oligomeric compound of any of embodiments 887-1281 to a mouse.

1365. The method of any of embodiments 1282-1363, comprising contacting a cell with the parent oligomeric compound of the oligomeric compound of any of embodiments 887-1281.

1366. The method of embodiment 1364 or 1365, wherein each sugar moiety of the central region of the parent oligomeric compound is an unmodified 2'-β-D-deoxyribosyl sugar moiety, and wherein each internucleoside linkage of the central region of the parent oligomeric compound is a phosphorothioate internucleoside linkage.

1367. A method of designing an oligomeric compound comprising starting with a parent oligomeric compound and changing the design of that compound in order to arrive at an oligomeric compound of any one of embodiments 887-1281.

1368. A method of designing an oligomeric compound comprising identifying a parent oligomeric compound and changing the design of that parent oligomeric compound to arrive at a second oligomeric compound, wherein the second oligomeric compound is an oligomeric compound of any one of embodiments 887-1281.

1369. A method of improving hepatotoxicity of an oligomeric compound comprising the steps of (i) identifying a parent oligomeric compound that has plasma ALT levels above 300 units per liter in a mouse, and (ii) providing an oligomeric compound according to any one of embodiments 887-1281.

1370. The method of embodiment 1368 or 1369, wherein the method designs an oligomeric compound with improved therapeutic index relative to the parent oligomeric compound.

1371. The method of embodiment 1368 or 1369, wherein the method designs an oligomeric compound with lower hepatotoxicity relative to the parent oligomeric compound.

1372. The method of embodiment 1368, wherein the second oligomeric compound has an improved therapeutic index relative to the parent oligomeric compound.

1373. The method of embodiment 1368 or 1369, wherein the second oligomeric compound has reduced hepatotoxicity in a mouse relative to the parent oligomeric compound.

1374. The method of embodiment 1368, wherein the oligomeric compound according to any one of embodiments 887-1281 has reduced hepatotoxicity relative to the parent oligomeric compound.

1375. A method comprising administering an oligomeric compound of any of embodiments 887-1281 to a mouse and separately administering the parent oligomeric compound of the oligomeric compound of any of embodiments 887-1281 to a second mouse, wherein the therapeutic index of the oligomeric compound of any of embodiments 887-1281 is improved relative to the therapeutic index of the parent oligomeric compound.

1376. The method of any of embodiments 1282-1375, wherein the level of p21 RNA is measured in the mouse, the cell, and/or the human subject.

1377. A method comprising administering an oligomeric compound of any of embodiments 887-1281 to a subject and measuring the level of p21 RNA in the subject.

1378. The method of embodiment 1377, wherein the subject is a mouse.

1379. The method of embodiment 1377, wherein the subject is a human.

1380. The method of any of embodiments 1377-1379, wherein the p21 RNA level is measured within 24 hours of the administration.

1381. The method of any of embodiments 1377-1380, wherein the p21 RNA level is measured 24-48 hours following the administration.

1382. An oligomeric compound or composition of any one of embodiments 887-1281, for use in medical therapy.

1383. The oligomeric compound of any of embodiments 887-1281, wherein the oligomeric compound is not toxic.

1384. The oligomeric compound of any of embodiment 887-1281, wherein a comparator compound is toxic; wherein the comparator compound is identical to the oligomeric compound except that each nucleoside of the central region of the comparator compound is a nucleoside comprising 2'-β-D-deoxyribosyl sugar moiety.

1385. The oligomeric compound of embodiment 1384, wherein administering a dose of the oligomeric compound to an animal results in a circulating ALT level that is at least 3-fold lower than the ALT level that results from administering the same dose of the comparator compound to an animal for at least one matched dose.

1386. The oligomeric compound of embodiment 1384 or 1385, wherein the lowest dose of the oligomeric compound that raises circulating ALT to over 300 units per liter is at least three-fold higher than the lowest dose of the comparator compound that raises circulating ALT to over 300 units per liter.

1387. The oligomeric compound of any of embodiments 1384-1386, wherein the oligomeric compound is capable of reducing the target RNA in a cell.

1388. The oligomeric compound of embodiment 1387, wherein the oligomeric compound has RNA-reducing activity comparable to a comparator compound, wherein the comparator compound is identical to the oligomeric compound except that each nucleoside of the central region of the comparator compound is a nucleoside comprising 2'-β-D-deoxyribosyl sugar moiety.

1389. The oligomeric compound of embodiment 1388 having RNA-reducing activity that is no more than 2-fold worse than the RNA-reducing activity of the comparator compound.

1390. A method of modulating the amount or activity of a target RNA in a human subject comprising administering the oligomeric compound or composition of any of embodiments 887-1281 to the human subject; and thereby modulating the amount or activity of the target RNA in the human subject.

1391. A method of treating a disease or disorder in a human subject comprising administering the oligomeric compound or composition of any of embodiments 887-1281 to the human subject having the disease or disorder; and thereby treating the disease or disorder in the human subject.

1392. The method of embodiment 1390 or 1391, wherein the disease or disorder is a liver disease, and wherein the oligomeric compound modulates the amount or activity of a liver target RNA.

1393. The method of embodiment 1390 or 1391, wherein the disease or disorder is a central nervous system disease, and wherein the oligomeric compound modulates the amount or activity of a central nervous system target RNA.

1394. The method of any of embodiments 1390-1393, wherein the disease or disorder is a cancer, a neurodegenerative disease, a cardiovascular disease, an immunological disease, a hereditary disease, a repeat expansion disease, a muscle-wasting disease, or a metabolic disease.

1395. The method of any of embodiments 1390-1394, wherein the plasma ALT level of the human subject after the administration is not more than three times higher than it was prior to the administration.

1396. The method of any of embodiments 1390-1395, wherein the plasma ALT level of the human subject after the administration is not more than 150 units per liter.

1397. A method of treating a disease or disorder in a human subject comprising administering the oligomeric compound or composition of any of embodiments 887-1281 to the human subject having the disease or disorder; and thereby treating the disease or disorder in the human subject.

1398. The method of embodiment 1397, wherein the disease or disorder is not a CNS disease or disorder.

1399. The method of embodiment 1397, wherein the disease or disorder is a disease or disorder of the white fat cells.

1400. The method of embodiment 1397, wherein the disease or disorder is a disease or disorder of the brown fat cells.

1401. The method of embodiment 1397, wherein the disease or disorder is a disease or disorder of the adipocytes.

1402. The method of embodiment 1397, wherein the disease or disorder is a disease or disorder of the macrophages.

1403. The method of embodiment 1397, wherein the disease or disorder is a disease or disorder of the cancer cells.

1404. The method of embodiment 1397, wherein the disease or disorder is a disease or disorder of the tumor cells.

1405. The method of embodiment 1397, wherein the disease or disorder is a disease or disorder of the smooth muscle cells.

1406. The method of embodiment 1397, wherein the disease or disorder is a disease or disorder of the lymphocytes.

1407. The method of embodiment 1397, wherein the disease or disorder is a disease or disorder of the pulmonary cells.

1408. The method of embodiment 1397, wherein the disease or disorder is a disease or disorder of the heart muscle cells.

1409. The method of embodiment 1397, wherein the disease or disorder is a disease or disorder of the cardiomyocytes.

1410. The method of embodiment 1397, wherein the disease or disorder is a disease or disorder of the endothelial cells.

1411. The method of embodiment 1397, wherein the disease or disorder is a disease or disorder of the fibroblasts.

1412. The method of embodiment 1397, wherein the disease or disorder is a disease or disorder of the glial cells.

1413. The method of embodiment 1397, wherein the disease or disorder is a disease or disorder of the Schwann cells.

1414. The method of embodiment 1397, wherein the disease or disorder is a disease or disorder of the pancreatic cells.

1415. The method of embodiment 1397, wherein the disease or disorder is a disease or disorder of the kidney cells.

1416. The method of embodiment 1397, wherein the disease or disorder is a disease or disorder of the beta cells.

1417. The method of embodiment 1397, wherein the disease or disorder is a disease or disorder of the non-parenchymal cells.

1418. The method of embodiment 1397, wherein the disease or disorder is a disease or disorder of the hepatocytes.

1419. The method of embodiment 1397, wherein the disease or disorder is a disease or disorder of the oligodendrocytes.

1420. The method of embodiment 1397, wherein the disease or disorder is a disease or disorder of the astrocytes.

1421. The method of embodiment 1397, wherein the disease or disorder is a disease or disorder of the microglia.

1422. The method of embodiment 1397, wherein the disease or disorder is a disease or disorder of the ependymal cells.

1423. The method of embodiment 1397, wherein the disease or disorder is a disease or disorder of the sensory neurons.

1424. The method of embodiment 1397, wherein the disease or disorder is a disease or disorder of the motor neurons.

1425. The method of embodiment 1397, wherein the disease or disorder is a disease or disorder of the skeletal muscle.

1426. The method of embodiment 1397, wherein the disease or disorder is a disease or disorder of the cardiac muscle.

1427. The method of embodiment 1397, wherein the disease or disorder is a disease or disorder of the smooth muscle.

1428. The method of embodiment 1397, wherein the disease or disorder is a disease or disorder of the adipose tissue.

1429. The method of embodiment 1397, wherein the disease or disorder is a disease or disorder of the white adipose tissue.

1430. The method of embodiment 1397, wherein the disease or disorder is a disease or disorder of the spleen.

1431. The method of embodiment 1397, wherein the disease or disorder is a disease or disorder of the bone.

1432. The method of embodiment 1397, wherein the disease or disorder is a disease or disorder of the bone marrow.

1433. The method of embodiment 1397, wherein the disease or disorder is a disease or disorder of the intestine.

1434. The method of embodiment 1397, wherein the disease or disorder is a disease or disorder of the adrenal glands.

1435. The method of embodiment 1397, wherein the disease or disorder is a disease or disorder of the testes.

1436. The method of embodiment 1397, wherein the disease or disorder is a disease or disorder of the ovaries.

1437. The method of embodiment 1397, wherein the disease or disorder is a disease or disorder of the pancreas.

1438. The method of embodiment 1397, wherein the disease or disorder is a disease or disorder of the pituitary gland.

1439. The method of embodiment 1397, wherein the disease or disorder is a disease or disorder of the prostate gland.

1440. The method of embodiment 1397, wherein the disease or disorder is a disease or disorder of the skin.

1441. The method of embodiment 1397, wherein the disease or disorder is a disease or disorder of the epidermis.

1442. The method of embodiment 1397, wherein the disease or disorder is a disease or disorder of the uterus.

1443. The method of embodiment 1397, wherein the disease or disorder is a disease or disorder of the bladder.

1444. The method of embodiment 1397, wherein the disease or disorder is a disease or disorder of the brain.

1445. The method of embodiment 1397, wherein the disease or disorder is a disease or disorder of the glomerulus.

1446. The method of embodiment 1397, wherein the disease or disorder is a disease or disorder of the distal tubular epithelium.

1447. The method of embodiment 1397, wherein the disease or disorder is a disease or disorder of the breast tissue.

1448. The method of embodiment 1397, wherein the disease or disorder is a disease or disorder of the lung.

1449. The method of embodiment 1397, wherein the disease or disorder is a disease or disorder of the heart.

1450. The method of embodiment 1397, wherein the disease or disorder is a disease or disorder of the kidney.

1451. The method of embodiment 1397, wherein the disease or disorder is a disease or disorder of the ganglion.

1452. The method of embodiment 1397, wherein the disease or disorder is a disease or disorder of the frontal cortex.

1453. The method of embodiment 1397, wherein the disease or disorder is a disease or disorder of the spinal cord.

1454. The method of embodiment 1397, wherein the disease or disorder is a disease or disorder of the trigeminal ganglion.

1455. The method of embodiment 1397, wherein the disease or disorder is a disease or disorder of the sciatic nerve.

1456. The method of embodiment 1397, wherein the disease or disorder is a disease or disorder of the dorsal root ganglion.

1457. The method of embodiment 1397, wherein the disease or disorder is a disease or disorder of the epidymal fat.

1458. The method of embodiment 1397, wherein the disease or disorder is a disease or disorder of the diaphragm.

1459. The method of embodiment 1397, wherein the disease or disorder is a disease or disorder of the colon.

1460. A method of screening a library of oligomeric compounds for activity against a target RNA, wherein the library of oligomeric compounds comprises a plurality of oligomeric compounds of any of embodiments 887-1281.

1461. An oligomeric compound comprising a modified oligonucleotide consisting of 12-21 linked nucleosides, wherein the modified oligonucleotide has the formula A-B-C, wherein A is a 5'-region, B is a central region, and C is a 3'-region; wherein:

the 5'-region consists of 1-5 linked nucleosides, wherein at least one nucleoside of the 5'-region is a modified nucleoside comprising a modified sugar;

the 3'-region consists of 1-5 linked nucleosides wherein at least one nucleoside of the 3'-region is a modified nucleoside comprising a modified sugar; and the central region consists of 7-11 linked nucleosides, wherein the 5'-most portion of the central region has the following formula:

$$(N_{da})(N_x)(N_y)(N_z)(N_{db})$$

wherein one of $N_x$, $N_y$, and $N_z$, is a safety-enhancing nucleoside;

the other two of $N_x$, $N_y$, and $N_z$ are independently selected from an unmodified 2'-β-D-deoxyribosyl sugar moiety, a DNA isomer, a modified DNA isomer, and a DNA mimic; and $N_{da}$ and $N_{db}$ are each independently selected from an unmodified 2'-β-D-deoxyribosyl sugar moiety, a DNA isomer, a modified DNA isomer, and a DNA mimic.

1462. The oligomeric compound of embodiment 1461, wherein the 5'-region consists of one nucleoside.

1463. The oligomeric compound of embodiment 1461, wherein the 5'-region consists of 2-5 linked nucleosides.

1464. The oligomeric compound of embodiment 1461, wherein the 5'-region consists of 2-4 linked nucleosides.

1465. The oligomeric compound of embodiment 1461, wherein the 5'-region consists of 2 linked nucleosides.

1466. The oligomeric compound of embodiment 1461, wherein the 5'-region consists of 3 linked nucleosides.

1467. The oligomeric compound of embodiment 1461, wherein the 5'-region consists of 4 linked nucleosides.

1468. The oligomeric compound of embodiment 1461, wherein the 5'-region consists of 5 linked nucleosides.

1469. The oligomeric compound of any of embodiments 1461-1468, wherein each nucleoside of the 5'-region is a modified nucleoside.

1470. The oligomeric compound of any of embodiments 1461-1469, wherein each nucleoside of the 5'-region is a modified nucleoside comprising a modified sugar.

1471. The oligomeric compound of any of embodiments 1461-1470, wherein each modified nucleoside of the 5'-region has the same modification.

1472. The oligomeric compound of and of embodiments 1461-1470, wherein at least two nucleosides of the 5'-region are modified nucleosides having different modifications.

1473. The oligomeric compound of any of embodiments 1461-1472, wherein each nucleoside of the 5'-region comprises a 2'-modified ribosyl sugar moiety.

1474. The oligomeric compound of any of embodiments 1461-1473, wherein at least one nucleoside of the 5'-region comprises a bicyclic furanosyl sugar moiety.

1475. The oligomeric compound of any of embodiments 1461-1474, wherein each nucleoside of the 5'-region comprises a bicyclic furanosyl sugar moiety.

1476. The oligomeric compound of any of embodiments 1461-1474, wherein at least one nucleoside of the 5'-region comprises a non-bicyclic sugar moiety.

1477. The oligomeric compound of embodiment 1476, wherein the non-bicyclic sugar moiety of the at least one nucleoside of the 5'-region is a 2'-substituted ribosyl sugar moiety.

1478. The oligomeric compound of any of embodiments 1461-1474 or 1476-1477, wherein each nucleoside of the 5'-region comprises a non-bicyclic sugar moiety.

1479. The oligomeric compound of embodiment 1478, wherein each nucleoside of the 5'-region comprises a 2'-substituted furanosyl sugar moiety.

1480. The oligomeric compound of any of embodiments 1461-1474 or 1476-1477, wherein each nucleoside of the 5'-region comprises a 2'-modified furanosyl sugar moiety independently selected from a bicyclic sugar moiety and a non-bicyclic 2'-substituted ribosyl sugar moiety.

1481. The oligomeric compound of any of embodiments 1461-1477 or 1480, wherein each nucleoside of the 5'-region comprises a bicyclic sugar moiety.

1482. The oligomeric compound of any of embodiments 1461-1474 or 1476-1480, wherein each nucleoside of the 5'-region comprises a non-bicyclic 2'-substituted ribosyl sugar moiety.

1483. The oligomeric compound of any of embodiments 1461-1477 or 1480-1481, wherein each bicyclic sugar moiety of the 5'-region is selected from among cEt, LNA, and ENA.

1484. The oligomeric compound of any of embodiments 1461-1477 or 1480-1481, wherein each bicyclic sugar moiety of the 5'-region is a cEt sugar moiety.

1485. The oligomeric compound of any of embodiments 1461-1477 or 1480-1481, wherein each bicyclic sugar moiety of the 5'-region is an LNA sugar moiety.

1486. The oligomeric compound of any of embodiments 1461-1474, 1476-1480, or 1482-1485, wherein each non-bicyclic sugar moiety of the 5'-region has a 2'-substituent selected from among 2'-MOE, 2'-OMe, and 2'-NMA.

1487. The oligomeric compound of any of embodiments 1461-1486, wherein none of the nucleosides of the 5'-region comprise a sugar moiety having a 2'-F substituent.

1488. The oligomeric compound of any of embodiments 1461-1487, wherein none of the nucleosides of the 5'-region comprise a sugar moiety having a 2'-MOE substituent.

1489. The oligomeric compound of any of embodiments 1461-1488, wherein none of the nucleosides of the 5'-region comprise a sugar moiety having a 2'-OMe substituent.

1490. The oligomeric compound of any of embodiments 1461-1489, wherein none of the nucleosides of the 5'-region comprise a cEt sugar moiety.

1491. The oligomeric compound of any of embodiments 1461-1490, wherein none of the nucleosides of the 5'-region comprise a LNA sugar moiety.

1492. The oligomeric compound of any of embodiments 1461-1491, wherein each nucleobase of the 5'-region is independently selected from among thymine, uracil, guanine, cytosine, 5-methylcytosine, and adenine.

1493. The oligomeric compound of any of embodiments 1461-1492, wherein each internucleoside linkage of the 5'-region is independently selected from among phosphodiester and phosphorothioate internucleoside linkages.

1494. The oligomeric compound of any of embodiments 1461-1493, wherein the 3'-region consists of one nucleoside.

1495. The oligomeric compound of any of embodiments 1461-1493, wherein the 3'-region consists of 2-5 linked nucleosides.

1496. The oligomeric compound of any of embodiments 1461-1493, wherein the 3'-region consists of 2-4 linked nucleosides.

1497. The oligomeric compound of any of embodiments 1461-1493, wherein the 3'-region consists of 2 linked nucleosides.

1498. The oligomeric compound of any of embodiments 1461-1493, wherein the 3'-region consists of 3 linked nucleosides.

1499. The oligomeric compound of any of embodiments 1461-1493, wherein the 3'-region consists of 4 linked nucleosides.

1500. The oligomeric compound of any of embodiments 1461-1493, wherein the 3'-region consists of 5 linked nucleosides.

1501. The oligomeric compound of any of embodiments 1461-1500, wherein each nucleoside of the 3'-region is a modified nucleoside.

1502. The oligomeric compound of any of embodiments 1461-1501, wherein each nucleoside of the 3'-region is a modified nucleoside comprising a modified sugar moiety.

1503. The oligomeric compound of any of embodiments 1461-1502, wherein each modified nucleoside of the 3'-region has the same modification.

1504. The oligomeric compound of and of embodiments 1461-1502, wherein at least two nucleosides of the 3'-region are modified nucleosides having different modifications.

1505. The oligomeric compound of any of embodiments 1461-1504, wherein each nucleoside of the 3'-region comprises a 2'-modified ribosyl sugar moiety.

1506. The oligomeric compound of any of embodiments 1461-1505, wherein at least one nucleoside of the 3'-region comprises a bicyclic furanosyl sugar moiety.

1507. The oligomeric compound of any of embodiments 1461-1506, wherein each nucleoside of the 3'-region comprises a bicyclic furanosyl sugar moiety.

1508. The oligomeric compound of any of embodiments 1461-1506, wherein at least one nucleoside of the 3'-region comprises a non-bicyclic sugar moiety.

1509. The oligomeric compound of embodiment 1508, wherein the non-bicyclic sugar moiety of the at least one nucleoside of the 3'-region is a 2'-substituted ribosyl sugar moiety.

1510. The oligomeric compound of any of embodiments 1461-1509, wherein each nucleoside of the 3'-region comprises a non-bicyclic sugar moiety.

1511. The oligomeric compound of embodiment 1510, wherein each nucleoside of the 3'-region comprises a 2'-substituted furanosyl sugar moiety.

1512. The oligomeric compound of any of embodiments 1461-1511, wherein each nucleoside of the 3'-region comprises a 2'-modified furanosyl sugar moiety independently selected from a bicyclic sugar moiety and a non-bicyclic 2'-substituted ribosyl sugar moiety.

1513. The oligomeric compound of any of embodiments 1461-1512, wherein each nucleoside of the 3'-region comprises a bicyclic sugar moiety.

1514. The oligomeric compound of any of embodiments 1461-1512, wherein each nucleoside of the 3'-region comprises a non-bicyclic 2'-substituted ribosyl sugar moiety.

1515. The oligomeric compound of any of embodiments 1461-1509 or 1512-1513, wherein each bicyclic sugar moiety of the 3'-region is selected from among cEt, LNA, and ENA.

1516. The oligomeric compound of any of embodiments 1461-1509, 1512-1513, or 1515, wherein each bicyclic sugar moiety of the 3'-region is a cEt sugar moiety.

1517. The oligomeric compound of any of embodiments 1461-1509, 1512-1513, or 1515, wherein each bicyclic sugar moiety of the 3'-region is an LNA sugar moiety.

1518. The oligomeric compound of any of embodiments 1461-1506, 1508-1512 or 1514, wherein each non-bicyclic sugar moiety of the 3'-region has a 2'-substituent selected from among 2'-MOE, 2'-OMe, and 2'-NMA.

1519. The oligomeric compound of any of embodiments 1461-1518, wherein none of the nucleosides of the 3'-region comprise a sugar moiety having a 2'-F substituent.

1520. The oligomeric compound of any of embodiments 1461-1519, wherein none of the nucleosides of the 3'-region comprise a sugar moiety having a 2'-MOE substituent.

1521. The oligomeric compound of any of embodiments 1461-1520, wherein none of the nucleosides of the 3'-region comprise a sugar moiety having a 2'-OMe substituent.

1522. The oligomeric compound of any of embodiments 1461-1521, wherein none of the nucleosides of the 3'-region comprise a cEt sugar moiety.

1523. The oligomeric compound of any of embodiments 1461-1522, wherein none of the nucleosides of the 3'-region comprise a LNA sugar moiety.

1524. The oligomeric compound of any of embodiments 1461-1523, wherein each nucleobase of the 3'-region is independently selected from among thymine, uracil, guanine, cytosine, 5-methylcytosine, and adenine.

1525. The oligomeric compound of any of embodiments 1461-1524, wherein each internucleoside linkage of the 3'-region is independently selected from among phosphodiester and phosphorothioate internucleoside linkages.

1526. The oligomeric compound of any of embodiments 1461-1525, wherein the modified nucleosides of the 5'-region have the same modifications as the modifications of the modified nucleosides of the 3'-region.

1527. The oligomeric compound of any of embodiments 1461-1525, wherein at least one modified nucleoside of the 5'-region and one modified nucleoside of the 3'-region comprise modifications that differ from one another.

1528. The oligomeric compound of any of embodiments 1461-1474, 1476-1477, 1480, 1483-1506, 1508-1509, 1512, 1515-1527, wherein the 5'-region and the 3'-region together include at least one non-bicyclic 2'-substituted modified nucleoside and at least one bicyclic nucleoside.

1529. The oligomeric compound of any of embodiment 1528, where the bicyclic nucleoside is a cEt nucleoside.

1530. The oligomeric compound of embodiment 1528, where the bicyclic nucleoside is an LNA nucleoside.

1531. The oligomeric compound of any of embodiments 1528-1530, wherein the non-bicyclic 2'-modified nucleoside is a 2'-MOE nucleoside.

1532. The oligomeric compound of any of embodiments 1528-1530, wherein the non-bicyclic 2'-modified nucleoside is a 2'-OMe nucleoside.

1533. The oligomeric compound of any of embodiments 1528-1532, wherein at least one nucleoside of the 5'-region or the 3'-region is an unmodified 2'-β-D-deoxyribosyl sugar moiety.

1534. The oligomeric compound of any of embodiments 1461-1533, wherein the central region has the formula:

$$(N_{da})(N_x)(N_y)(N_z)(N_{db})(N_{dc})_q$$

wherein each $N_{dc}$ is independently selected from an unmodified 2'-β-D-deoxyribosyl sugar moiety, a DNA isomer, a modified DNA isomer, and a DNA mimic; and q is 2-6.

1535. The oligomeric compound of any of embodiments 1461-1534, wherein the central region consists of 7 linked nucleosides.

1536. The oligomeric compound of any of embodiments 1461-1534, wherein the central region consists of 8 linked nucleosides.

1537. The oligomeric compound of any of embodiments 1461-1534, wherein the central region consists of 9 linked nucleosides.

1538. The oligomeric compound of any of embodiments 1461-1534, wherein the central region consists of 10 linked nucleosides.

1539. The oligomeric compound of any of embodiments 1461-1534, wherein the central region consists of 11 linked nucleosides.

1540. The oligomeric compound of any of embodiments 1461-1539, wherein Nx is the safety-enhancing nucleoside.

1541. The oligomeric compound of any of embodiments 1461-1539, wherein Ny is the safety-enhancing nucleoside.

1542. The oligomeric compound of any of embodiments 1461-1539, wherein Nz is the safety-enhancing nucleoside.

1543. The oligomeric compound of any of embodiments 1461-1542, wherein the safety enhancing nucleoside is a DNA isomer or a modified DNA isomer, or a modified nucleoside comprising either a sugar surrogate, a bicyclic furanosyl sugar moiety, or a non-bicyclic modified furanosyl sugar moiety.

1544. The oligomeric compound of any of embodiments 1461-1543, wherein the safety enhancing nucleoside is a DNA isomer or a modified DNA isomer, or comprises either a sugar surrogate, a bicyclic furanosyl sugar moiety, a non-bicyclic, 2'-modified furanosyl sugar moiety, a non-bicyclic 3'-modified furanosyl sugar moiety, a non-bicyclic, 4'-modified furanosyl sugar moiety, or a non-bicyclic 5'-modified furanosyl sugar moiety.

1545. The oligomeric compound of any of embodiments 1461-1544, wherein the safety enhancing nucleoside comprises a sugar surrogate selected from a morpholino, a modified morpholino, a modified cyclohexenyl, or a modified tetrahydropyran.

1546. The oligomeric compound of any of embodiments 1461-1544, wherein the safety enhancing nucleoside comprises a sugar surrogate selected from a morpholino, a modified morpholino, 2'-fluoroarabinose, 2'-fluororibose, CeNA, F-CeNA, HNA, OMe-HNA or F-HNA.

1547. The oligomeric compound of any of embodiments 1461-1544, wherein the safety enhancing nucleoside is a DNA isomer comprising a sugar moiety selected from among 2'-β-D-deoxyxylosyl, 2'-α-L-deoxyribosyl, 2'-β-L-deoxyribosyl, 2'-α-D-deoxyxylosyl, 2'-α-D-deoxyribosyl, 2'-α-L-deoxyxylosyl, and 2'-β-L-deoxyxylosyl.

1548. The oligomeric compound of any of embodiments 1461-1544 or 1547, wherein the safety enhancing nucleoside is a DNA isomer comprising a sugar moiety selected from among 2'-β-D-deoxyxylosyl, 2'-α-L-deoxyribosyl, and 2'-β-L-deoxyribosyl.

1549. The oligomeric compound of any of embodiments 1461-1544, wherein the safety enhancing nucleoside is a modified DNA isomer comprising a 2'-modified sugar moiety, wherein the sugar moiety has the conformation 2'-β-D-deoxyxylosyl, 2'-α-L-deoxyribosyl, 2'-β-L-deoxyribosyl, 2'-α-D-deoxyxylosyl, 1, 2'-α-L-deoxyxylosyl, and 2'-β-L-deoxyxylosyl and the 2' position is further substituted with a hydroxyl, a fluoro, or O—$C_1$-$C_{10}$ alkoxy substituent.

1550. The oligomeric compound of any of embodiments 1461-1544 or 1549, wherein the safety enhancing nucleoside is a modified DNA isomer comprising a 2'-modified sugar moiety, wherein the sugar moiety has the conformation 2'-β-D-deoxyxylosyl, 2'-α-L-deoxyribosyl, 2'-β-L-deoxyribosyl, 2'-α-D-deoxyxylosyl, 1, 2'-α-L-deoxyxylosyl, and 2'-β-L-deoxyxylosyl and the 2' position is further substituted with a hydroxyl, a fluoro, or OMe substituent.

1551. The oligomeric compound of any of embodiments 1461-1544 or 1549-1550, wherein the safety enhancing nucleoside is a modified DNA isomer comprising a 2'-modified sugar moiety, wherein the sugar moiety has the conformation 2'-β-D-deoxyxylosyl, 2'-α-L-deoxyribosyl, 2'-β-L-deoxyribosyl, 2'-α-D-deoxyxylosyl, 1, 2'-α-L-deoxyxylosyl, and 2'-β-L-deoxyxylosyl and the 2' position is further substituted with a fluoro or OMe substituent.

1552. The oligomeric compound of any of embodiments 1461-1544 or 1549-1551, wherein the safety enhancing nucleoside is a modified DNA isomer comprising a sugar moiety selected from among 2'-β-D-deoxyxylosyl, 2'-α-L-deoxyribosyl, and 2'-β-L-deoxyribosyl and the 2' position is further substituted with a hydroxyl, fluoro, or OMe substituent.

1553. The oligomeric compound of any of embodiments 1461-1544, wherein the safety enhancing nucleoside is a modified nucleoside comprising a bicyclic furanosyl sugar moiety.

1554. The oligomeric compound of any of embodiments 1461-1544, wherein the safety enhancing nucleoside is selected from among cEt, LNA, α-L-LNA, and ENA.

1555. The oligomeric compound of any of embodiments 1461-1544, wherein the safety enhancing nucleoside comprises a 2'-substituted furanosyl sugar moiety.

1556. The oligomeric compound of embodiment 1555, wherein the 2'-substituted furanosyl sugar moiety of the safety enhancing nucleoside has a 2' substituent selected from: halo, allyl, amino, azido, SH, CN, OCN, $CF_3$, $OCF_3$, O—$C_1$-$C_{10}$ alkoxy, O—$C_1$-$C_{10}$ substituted alkoxy, $C_1$-$C_{10}$ alkyl, $C_1$-$C_{10}$ substituted alkyl, S-alkyl, N($R_m$)-alkyl, O-alkenyl, S-alkenyl, N($R_m$)-alkenyl, O-alkynyl, S-alkynyl, N($R_m$)-alkynyl, O-alkylenyl-O-alkyl, alkynyl, alkaryl, aralkyl, O-alkaryl, O-aralkyl, $O(CH_2)_2SCH_3$, $O(CH_2)_2ON(R_m)(R_n)$ or $OCH_2C(=O)—N(R_m)(R_n)$, where each $R_m$ and $R_n$ is, independently, H, an amino protecting group, or substituted or unsubstituted $C_1$-$C_{10}$ alkyl.

1557. The oligomeric compound of embodiment 1555, wherein the 2'-substituted furanosyl sugar moiety of the safety enhancing nucleoside has a 2' substituent selected from: halo, O—$C_1$-$C_{10}$ alkoxy, O—$C_1$-$C_{10}$ substituted alkoxy, $C_1$-$C_{10}$ alkyl, $C_1$-$C_{10}$ substituted alkyl, S-alkyl, N($R_m$)-alkyl, $O(CH_2)_2ON(R_m)(R_n)$ or $OCH_2C(=O)—N(R_m)(R_n)$, where each $R_m$ and $R_n$ is, independently, H, an amino protecting group, or substituted or unsubstituted $C_1$-$C_{10}$ alkyl.

1558. The oligomeric compound of embodiment 1555, wherein the 2'-substituted furanosyl sugar moiety of the safety enhancing nucleoside has a 2' substituent selected from: fluoro, OMe, MOE, NMA.

1559. The oligomeric compound of any of embodiments 1461-1558, wherein the safety enhancing nucleoside comprises a 2'-substituted furanosyl sugar moiety comprising a 2'-OMe or 2'-MOE.

1560. The oligomeric compound of any of embodiments 1461-1559, wherein the safety enhancing nucleoside comprises a 2'-substituted furanosyl sugar moiety comprising a 2'-OMe.

1561. The oligomeric compound of any of embodiments 1461-1560, wherein the safety enhancing nucleoside comprises a 2'-OMe modified 2'-β-D-deoxyribosyl sugar moiety.

1562. The oligomeric compound of any of embodiments 1461-1544, wherein the safety enhancing nucleoside comprises a 3'-modified furanosyl sugar moiety having a 3' substituent selected from: halo, allyl, amino, azido, SH, CN, $CF_3$, $OCF_3$, $C_1$-$C_{10}$ alkyl, $C_1$-$C_{10}$ substituted alkyl, S-alkyl, N($R_m$)-alkyl, N($R_m$)-alkenyl, N($R_m$)-alkynyl, O-alkylenyl-O-alkyl, alkynyl, alkaryl, or aralkyl.

1563. The oligomeric compound of any of embodiments 1461-1544 or embodiment 1562, wherein the safety enhancing nucleoside comprises a 3'-modified furanosyl sugar moiety having a 3' substituent selected from: $C_1$-$C_{10}$ alkyl, or $C_1$-$C_{10}$ substituted alkyl.

1564. The oligomeric compound of any of embodiments 1461-1544 or 1562-1563, wherein the safety enhancing nucleoside comprises a 3'-methyl furanosyl sugar moiety.

1565. The oligomeric compound of any of embodiments 1461-1544, wherein the safety enhancing nucleoside comprises a 4'-modified furanosyl sugar moiety having a 4' substituent selected from: halo, allyl, amino, azido, SH, CN, OCN, $CF_3$, $OCF_3$, O—$C_1$-$C_{10}$ alkoxy, O—$C_1$-$C_{10}$ substituted alkoxy, $C_1$-$C_{10}$ alkyl, $C_1$-$C_{10}$ substituted alkyl, S-alkyl, N($R_m$)-alkyl, O-alkenyl, S-alkenyl, N($R_m$)-alkenyl, O-alkynyl, S-alkynyl, N($R_m$)-alkynyl, O-alkylenyl-O-alkyl, alkynyl, alkaryl, aralkyl, O-alkaryl, O-aralkyl, $O(CH_2)_2SCH_3$, $O(CH_2)_2ON(R_m)(R_n)$ or $OCH_2C(=O)$—$N(R_m)(R_n)$, where each $R_m$ and $R_n$ is, independently, H, an amino protecting group, or substituted or unsubstituted $C_1$-$C_{10}$ alkyl.

1566. The oligomeric compound of any of embodiments 1461-1544 or 1565, wherein the safety enhancing nucleoside comprises a 4'-modified furanosyl sugar moiety having a 4'-methyl.

1567. The oligomeric compound of any of embodiments 1461-1544, wherein the safety enhancing nucleoside has the structure shown below, wherein R represents an optional 2' substituent group and Bx is a heterocyclic base moiety:

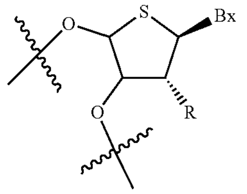

1568. The oligomeric compound of embodiment 1567, wherein in R is selected from among H, OH, OMe, F, or MOE.

1569. The oligomeric compound of any of embodiments 1461-1544, wherein the safety enhancing nucleoside comprises a 5'-modified furanosyl sugar moiety having a 5' substituent selected from: halo, allyl, amino, azido, SH, CN, OCN, $CF_3$, $OCF_3$, O—$C_1$-$C_{10}$ alkoxy, O—$C_1$-$C_{10}$ substituted alkoxy, $C_1$-$C_{10}$ alkyl, $C_1$-$C_{10}$ substituted alkyl, S-alkyl, N($R_m$)-alkyl, O-alkenyl, S-alkenyl, N($R_m$)-alkenyl, O-alkynyl, S-alkynyl, N($R_m$)-alkynyl, O-alkylenyl-O-alkyl, alkynyl, alkaryl, aralkyl, O-alkaryl, O-aralkyl, $O(CH_2)_2SCH_3$, $O(CH_2)_2ON(R_m)(R_n)$ or $OCH_2C(=O)$—$N(R_m)(R_n)$, where each $R_m$ and $R_n$ is, independently, H, an amino protecting group, or substituted or unsubstituted $C_1$-$C_{10}$ alkyl.

1570. The oligomeric compound of any of embodiments 1461-1544 or 1569, wherein the safety enhancing nucleoside comprises a 5'-modified furanosyl sugar moiety with a 5' substituent selected from: 5'-methyl, 5'-ethyl or a 5'-allyl.

1571. The oligomeric compound of any of embodiments 1461-1544 or 1569-1570, wherein the safety enhancing nucleoside comprises a 5'-modified furanosyl sugar moiety with a 5' substituent selected from: 5'-(R)-methyl- or 5'-(R)-ethyl.

1572. The oligomeric compound of any of embodiments 1461-1544 or 1569-1571, wherein the safety enhancing nucleoside comprises a 5'-(R)-methyl-2'-β-D-deoxyribosyl sugar moiety.

1573. The oligomeric compound of any of embodiments 1461-154 or 1569-1572, wherein the safety enhancing nucleoside comprises a 5'-(R)-ethyl-2'-β-D-deoxyribosyl sugar moiety.

1574. The oligomeric compound of any of embodiments 1461-1573, wherein the safety enhancing nucleoside does not comprise a 2'-F modified sugar moiety.

1575. The oligomeric compound of any of embodiments 1461-1574, wherein the safety enhancing nucleoside does not comprise a cEt modified sugar moiety.

1576. The oligomeric compound of any of embodiments 1461-1575, wherein the safety enhancing nucleoside does not comprise a 2'-MOE modified sugar moiety.

1577. The oligomeric compound of any of embodiments 1461-1576, wherein the safety enhancing nucleoside comprises a hypoxanthine nucleobase.

1578. The oligomeric compound of any of embodiments 1461-1577, wherein the safety enhancing nucleoside comprises a nucleobase selected from among thymine, uracil, guanine, cytosine, 5-methylcytosine, and adenine.

1579. The oligomeric compound of any of embodiments 1461-1578, wherein the safety enhancing nucleoside is a modified nucleoside other than cEt, MOE, LNA, or FANA.

1580. The oligomeric compound of any of embodiments 1461-1579, wherein each Nd is independently selected from among an unmodified 2'-β-D-deoxyribosyl sugar moiety, a DNA isomer, a 2'-modified DNA isomer, and a DNA mimic.

1581. The oligomeric compound of embodiment 1580, wherein each DNA isomer comprises a sugar moiety selected from among 2'-β-D-deoxyxylosyl, 2'-α-L-deoxyribosyl, 2'-β-L-deoxyribosyl, 2'-α-D-deoxyxylosyl, 2'-α-D-deoxyribosyl, 2'-α-L-deoxyxylosyl, and 2'-β-L-deoxyxylosyl.

1582. The oligomeric compound of embodiment 1581, wherein each DNA isomer comprises a sugar moiety selected from among 2'-β-D-deoxyxylosyl, 2'-α-L-deoxyribosyl, and 2'-β-L-deoxyribosyl.

1583. The oligomeric compound of embodiment 1580, wherein each modified DNA isomer comprises a 2'-modified sugar moiety, wherein the sugar moiety has the conformation 2'-β-D-deoxyxylosyl, 2'-α-L-deoxyribosyl, 2'-β-L-deoxyribosyl, 2'-α-D-deoxyxylosyl, 1, 2'-α-L-deoxyxylosyl, and 2'-β-L-deoxyxylosyl and the 2' position is further substituted with a hydroxyl, a fluoro, or O—$C_1$-$C_{10}$ alkoxy substituent.

1584. The oligomeric compound of embodiment 1583, wherein each modified DNA isomer comprises a 2'-modified sugar moiety, wherein the sugar moiety has the conformation 2'-β-D-deoxyxylosyl, 2'-α-L-deoxyribosyl, 2'-β-L-deoxyribosyl, 2'-α-D-deoxyxylosyl, 1, 2'-α-L-deoxyxylosyl, and 2'-β-L-deoxyxylosyl and the 2' position is further substituted with a hydroxyl, a fluoro, or OMe substituent.

1585. The oligomeric compound of embodiment 1584, wherein each modified DNA isomer comprises a 2'-modified sugar moiety, wherein the sugar moiety has the conformation 2'-β-D-deoxyxylosyl, 2'-α-L-deoxyribosyl, 2'-β-L-deoxyribosyl, 2'-α-D-deoxyxylosyl, 1, 2'-α-L-deoxyxylosyl, and 2'-β-L-deoxyxylosyl and the 2' position is further substituted with a fluoro or OMe substituent.

1586. The oligomeric compound of embodiment 1585, wherein each modified DNA isomer comprises a 2'-modified sugar moiety, wherein the sugar moiety is selected from among 2'-β-D-deoxyxylosyl, 2'-α-L-deoxyribosyl, and 2'-β-L-deoxyribosyl and the 2' position is further substituted with a hydroxyl, fluoro, or OMe substituent.

1587. The oligomeric compound of embodiment 1580, wherein each DNA mimic comprises a structure represented by one of the formulas below:

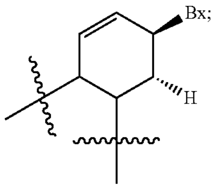

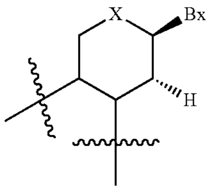

wherein X is O or S and Bx represents a heteorcylic base moiety.

1588. The oligomeric compound of embodiment 1580, wherein each DNA mimic comprises a structure represented by one of the formulas below:

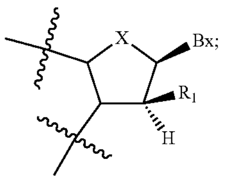

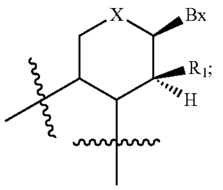

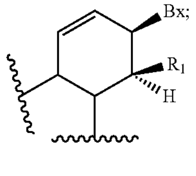

wherein X is O or S;

Bx represents a heterocyclic base moiety; and $R_1$ is selected from among H, OH, halo, allyl, amino, azido, SH, CN, OCN, $CF_3$, $OCF_3$, O—$C_1$-$C_{10}$ alkoxy, O—$C_1$-$C_{10}$ substituted alkoxy, $C_1$-$C_{10}$ alkyl, $C_1$-$C_{10}$ substituted alkyl, S-alkyl, N($R_m$)-alkyl, O-alkenyl, S-alkenyl, N($R_m$)-alkenyl, O-alkynyl, S-alkynyl, N($R_m$)-alkynyl, O-alkylenyl-O-alkyl, alkynyl, alkaryl, aralkyl, O-alkaryl, O-aralkyl, $O(CH_2)_2SCH_3$, $O(CH_2)_2ON(R_m)(R_n)$ or $OCH_2C(=O)—N(R_m)(R_n)$, where each $R_m$ and $R_n$ is, independently, H, an amino protecting group, or substituted or unsubstituted $C_1$-$C_{10}$ alkyl;

wherein if the DNA mimic comprises the structure:

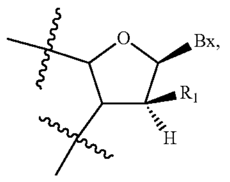

$R_1$ is other than H.

1589. The oligomeric compound of embodiment 1588, wherein R1 is H, OH, OMe, or F.

1590. The oligomeric compound of embodiment 1588, wherein R1 is not F.

1591. The oligomeric compound of embodiment 1580, wherein each DNA mimic comprises a structure represented by the formula below:

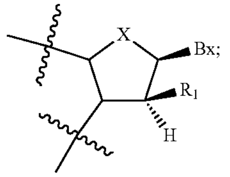

wherein X is S, Bx represents a heterocyclic base moiety, and R1 is H.

1592. The oligomeric compound of embodiment 1580, wherein the DNA mimic has a sugar moiety selected from among: 5'-methyl-2'-β-D-deoxyribosyl, 5'-ethyl-2'-β-D-deoxyribosyl, and 5'-allyl-2'-β-D-deoxyribosyl.

1593. The oligomeric compound of embodiment 1580, wherein the DNA mimic comprises a 2'-fluoro-β-D-arabinofuranosyl sugar moiety.

1594. The oligomeric compound of embodiment 1580, wherein the DNA mimic does not comprise a 2'-fluoro-β-D-arabinofuranosyl sugar moiety.

1595. The oligomeric compound of any of embodiments 1461-1594, wherein each $N_d$ is an unmodified 2'-β-D-deoxyribosyl sugar moiety.

1596. The oligomeric compound of any of embodiments 1461-1595, wherein the central region comprises no more than four nucleosides selected from among DNA isomers, modified DNA isomers, and DNA mimics.

1597. The oligomeric compound of any of embodiments 1461-1595, wherein the central region comprises no more than three nucleosides selected from among DNA isomers, modified DNA isomers, and DNA mimics.

1598. The oligomeric compound of any of embodiments 1461-1595, wherein the central region comprises no more than two nucleosides selected from among DNA isomers, modified DNA isomers, and DNA mimics.

1599. The oligomeric compound of any of embodiments 1461-1595, wherein the central region comprises no more than one nucleoside selected from among DNA isomers, modified DNA isomers, and DNA mimics.

1600. The oligomeric compound of any of embodiments 1461-1599, wherein the central region contains exactly one safety enhancing nucleoside and the remainder of nucleosides in the central region are unmodified 2'-β-D-deoxyribosyl sugar moieties.

1601. The oligomeric compound of any of embodiments 1461-1600, wherein at least one internucleoside linkage of the central region selected from among: the internucleoside Nda to Nx, Nx to Ny, Ny to Nz, or Nz to the adjacent Ndb is a neutral internucleoside linkage.

1602. The oligomeric compound of embodiment 1601, wherein the neutral linkage is a phosphonate internucleoside linkage.

1603. The oligomeric compound of embodiment 1601, wherein the neutral linkage is a methoxypropyl internucleoside linkage.

1604. The oligomeric compound of embodiment 1601, wherein each remaining internucleoside linkage is a phosphodiester or phosphorothioate internucleoside linkage.

1605. The oligomeric compound of any of embodiments 1461-1600, wherein at least one internucleoside linkage of the central region is a 2'-5' internucleoside linkage.

1606. The oligomeric compound of any of embodiments 1461-1600, wherein exactly one internucleoside linkage of the central region is a 2'-5' internucleoside linkage.

1607. The oligomeric compound of any of embodiments 1461-1600, wherein at least one internucleoside linkage of the central region selected from among: the internucleoside Nda to Nx, Nx to Ny, Ny to Nz, or Nz to the adjacent Ndb is a a 2'-5' internucleoside linkage.

1608. A chirally enriched population of modified oligonucleotides of any of embodiments 1461-1607, wherein the central region has at least one particular phorphorothioate internucleoside linkage having a particular stereochemical configuration.

1609. The chirally enriched population of embodiment 1608, wherein the central region has at least one phorphorothioate internucleoside linkage having the (Sp) configuration.

1610. The chirally enriched population of embodiment 1608, wherein central region has at least one phorphorothioate internucleoside linkage having the (Rp) configuration.

1611. The chirally enriched population of embodiment 1608, wherein the central region has a particular, independently selected stereochemical configuration at each phosphorothioate internucleoside linkage.

1612. The chirally enriched population of embodiment 1608, wherein the each phosphorothioate internucleoside linkage of the central region has the (Sp) configuration.

1613. The chirally enriched population of embodiment 1608, wherein the central region has one phosphorothioate internucleoside linkage having the (Rp) configuration and wherein each remaining central region phosphorothioate internucleoside linkage has the (Sp) configuration.

1614. The chirally enriched population of embodiment 1608, wherein the central region has an (Rp) phosphorothioate internucleoside linkage adjacent to an (Sp) phosphorothioate internucleoside linkage.

1615. The chirally enriched population of embodiment 1608, wherein the central region has an (Rp) phosphorothioate internucleoside linkage adjacent to a second (Rp) phosphorothioate internucleoside linkage.

1616. The chirally enriched population of embodiment 1608, wherein the central region has an (Rp) phosphorothioate internucleoside linkage adjacent to a second (Rp) phosphorothioate internucleoside linkage, and wherein each remaining central region phosphorothioate internucleoside linkage has the (Sp) configuration.

1617. The chirally enriched population of any of embodiments 1609, 1610, 1614, or 1615 wherein each phosphorothioate internucleoside linkage that does not have the (Rp) or (Sp) configuration is stereorandom.

1618. The oligomeric compound of any of embodiments 1461-1617 comprising a conjugate group.

1619. The oligomeric compound of embodiment 1618, wherein the conjugate group comprises a linking group attaching the remainder of the conjugate group to the modified oligonucleotide, wherein the linking group comprises 1-5 nucleosides.

1620. The oligomeric compound of any of embodiments 1461-1618, wherein the oligomeric compound does not comprise additional nucleosides beyond those of the modified oligonucleotide.

1621. The oligomeric compound of any of embodiments 1461-1620, wherein the nucleobase sequence of the modified oligonucleotide is complementary to a target RNA.

1622. The oligomeric compound of embodiment 1621, wherein the nucleobase sequence of the modified oligonucleotide is at least 85% complementary to the target RNA.

1623. The oligomeric compound of embodiment 1621, wherein the nucleobase sequence of the modified oligonucleotide is at least 90% complementary to the target RNA.

1624. The oligomeric compound of embodiment 1621, wherein the nucleobase sequence of the modified oligonucleotide is at least 95% complementary to the target RNA.

1625. The oligomeric compound of embodiment 1621, wherein the nucleobase sequence of the modified oligonucleotide is 100% complementary to the target RNA.

1626. The oligomeric compound of any of embodiments 1621-1625, wherein the target RNA is a target mRNA or a target pre-mRNA.

1627. The oligomeric compound of embodiment 1626, wherein the target mRNA or target pre-mRNA is not a mouse, rat, monkey, or human PTEN RNA.

1628. The oligomeric compound of embodiment 1626 or 1627, wherein the target mRNA or target pre-mRNA is not a mouse, rat, monkey, or human SRB-1 RNA.

1629. The oligomeric compound of any of embodiments 1626-1628, wherein the target mRNA or target pre-mRNA is not a mouse, rat, monkey, or human MYD88 RNA.

1630. The oligomeric compound of any of embodiments 1626-1629, wherein the target mRNA or target pre-mRNA is not a mouse, rat, monkey, or human HTT RNA, is not a mouse, rat, monkey, or human SOD1 RNA, and is not a mouse, rat, monkey, or human alpha-synuclein RNA.

1631. The oligomeric compound of any of embodiments 1621-1630, wherein the target RNA is a human RNA.

1632. The oligomeric compound of any of embodiments 1621-1631, wherein the target RNA is expressed in the liver.

1633. The oligomeric compound of any of embodiments 1621-1632, wherein the target RNA is a liver target.

1634. The oligomeric compound of any of embodiments 1621-1631, wherein the target RNA is not expressed in the liver.

1635. The oligomeric compound of any of embodiments 1621-1631 or 1634, wherein the target RNA is not a liver target.

1636. The oligomeric compound of any of embodiments 1621-1635, wherein modulation of the expression of the target RNA in the liver is associated with treating a disorder or condition.

1637. The oligomeric compound of embodiment 1636, wherein the disorder or condition is a liver disorder or condition.

1638. The oligomeric compound of any of embodiments 1621-1637, wherein the target RNA is expressed in the central nervous system.

1639. The oligomeric compound of any of embodiments 1621-1637, wherein the target RNA is not expressed in the central nervous system.

1640. The oligomeric compound of any of embodiments 1621-1638, wherein the target RNA is a central nervous system target.

1641. The oligomeric compound of any of embodiments 1621-1639, wherein the target RNA is not a central nervous system target.

1642. The oligomeric compound of any of embodiments 1621-1641, wherein the target RNA is expressed in white fat cells.

1643. The oligomeric compound of any of embodiments 1621-1641, wherein the target RNA is expressed in brown fat cells.

1644. The oligomeric compound of any of embodiments 1621-1641, wherein the target RNA is expressed in adipocytes.

1645. The oligomeric compound of any of embodiments 1621-1641, wherein the target RNA is expressed in macrophages.

1646. The oligomeric compound of any of embodiments 1621-1641, wherein the target RNA is expressed in cancer cells.

1647. The oligomeric compound of any of embodiments 1621-1641, wherein the target RNA is expressed in tumor cells.

1648. The oligomeric compound of any of embodiments 1621-1641, wherein the target RNA is expressed in smooth muscle cells.

1649. The oligomeric compound of any of embodiments 1621-1641, wherein the target RNA is expressed in lymphocytes.

1650. The oligomeric compound of any of embodiments 1621-1641, wherein the target RNA is expressed in pulmonary cells.

1651. The oligomeric compound of any of embodiments 1621-1641, wherein the target RNA is expressed in heart muscle cells.

1652. The oligomeric compound of any of embodiments 1621-1641, wherein the target RNA is expressed in cardiomyocytes.

1653. The oligomeric compound of any of embodiments 1621-1641, wherein the target RNA is expressed in endothelial cells.

1654. The oligomeric compound of any of embodiments 1621-1641, wherein the target RNA is expressed in fibroblasts.

1655. The oligomeric compound of any of embodiments 1621-1641, wherein the target RNA is expressed in glial cells.

1656. The oligomeric compound of any of embodiments 1621-1641, wherein the target RNA is expressed in Schwann cells.

1657. The oligomeric compound of any of embodiments 1621-1641, wherein the target RNA is expressed in pancreatic cells.

1658. The oligomeric compound of any of embodiments 1621-1641, wherein the target RNA is expressed in kidney cells.

1659. The oligomeric compound of any of embodiments 1621-1641, wherein the target RNA is expressed in beta cells.

1660. The oligomeric compound of any of embodiments 1621-1641, wherein the target RNA is expressed in non-parenchymal cells.

1661. The oligomeric compound of any of embodiments 1621-1641, wherein the target RNA is expressed in hepatocytes.

1662. The oligomeric compound of any of embodiments 1621-1641, wherein the target RNA is expressed in oligodendrocytes.

1663. The oligomeric compound of any of embodiments 1621-1641, wherein the target RNA is expressed in astrocytes.

1664. The oligomeric compound of any of embodiments 1621-1641, wherein the target RNA is expressed in microglia.

1665. The oligomeric compound of any of embodiments 1621-1641, wherein the target RNA is expressed in ependymal cells.

1666. The oligomeric compound of any of embodiments 1621-1641, wherein the target RNA is expressed in sensory neurons.

1667. The oligomeric compound of any of embodiments 1621-1641, wherein the target RNA is expressed in motor neurons.

1668. The oligomeric compound of any of embodiments 1621-1641, wherein the target RNA is expressed in skeletal muscle.

1669. The oligomeric compound of any of embodiments 1621-1641, wherein the target RNA is expressed in cardiac muscle.

1670. The oligomeric compound of any of embodiments 1621-1641, wherein the target RNA is expressed in smooth muscle.

1671. The oligomeric compound of any of embodiments 1621-1641, wherein the target RNA is expressed in adipose tissue.

1672. The oligomeric compound of any of embodiments 1621-1641, wherein the target RNA is expressed in white adipose tissue.

1673. The oligomeric compound of any of embodiments 1621-1641, wherein the target RNA is expressed in the spleen.

1674. The oligomeric compound of any of embodiments 1621-1641, wherein the target RNA is expressed in the bone.

1675. The oligomeric compound of any of embodiments 1621-1641, wherein the target RNA is expressed in the bone marrow.

1676. The oligomeric compound of any of embodiments 1621-1641, wherein the target RNA is expressed in the intestine.

1677. The oligomeric compound of any of embodiments 1621-1641, wherein the target RNA is expressed in the adrenal glands.

1678. The oligomeric compound of any of embodiments 1621-1641, wherein the target RNA is expressed in the testes.

1679. The oligomeric compound of any of embodiments 1621-1641, wherein the target RNA is expressed in the ovaries.

1680. The oligomeric compound of any of embodiments 1621-1641, wherein the target RNA is expressed in the pancreas.

1681. The oligomeric compound of any of embodiments 1621-1641, wherein the target RNA is expressed in the pituitary gland.

1682. The oligomeric compound of any of embodiments 1621-1641, wherein the target RNA is expressed in the prostate gland.

1683. The oligomeric compound of any of embodiments 1621-1641, wherein the target RNA is expressed in the skin.

1684. The oligomeric compound of any of embodiments 1621-1641, wherein the target RNA is expressed in the epidermis.

1685. The oligomeric compound of any of embodiments 1621-1641, wherein the target RNA is expressed in the uterus.

1686. The oligomeric compound of any of embodiments 1621-1641, wherein the target RNA is expressed in the bladder.

1687. The oligomeric compound of any of embodiments 1621-1641, wherein the target RNA is expressed in the brain.

1688. The oligomeric compound of any of embodiments 1621-1641, wherein the target RNA is expressed in the glomerulus.

1689. The oligomeric compound of any of embodiments 1621-1641, wherein the target RNA is expressed in the distal tubular epithelium.

1690. The oligomeric compound of any of embodiments 1621-1641, wherein the target RNA is expressed in breast tissue.

1691. The oligomeric compound of any of embodiments 1621-1641, wherein the target RNA is expressed in the lung.

1692. The oligomeric compound of any of embodiments 1621-1641, wherein the target RNA is expressed in the heart.

1693. The oligomeric compound of any of embodiments 1621-1641, wherein the target RNA is expressed in the kidney.

1694. The oligomeric compound of any of embodiments 1621-1641, wherein the target RNA is expressed in the ganglion.

1695. The oligomeric compound of any of embodiments 1621-1641, wherein the target RNA is expressed in the frontal cortex.

1696. The oligomeric compound of any of embodiments 1621-1641, wherein the target RNA is expressed in the spinal cord.

1697. The oligomeric compound of any of embodiments 1621-1641, wherein the target RNA is expressed in the trigeminal ganglion.

1698. The oligomeric compound of any of embodiments 1621-1641, wherein the target RNA is expressed in the sciatic nerve.

1699. The oligomeric compound of any of embodiments 1621-1641, wherein the target RNA is expressed in the dorsal root ganglion.

1700. The oligomeric compound of any of embodiments 1621-1641, wherein the target RNA is expressed in the epidymal fat.

1701. The oligomeric compound of any of embodiments 1621-1641, wherein the target RNA is expressed in the diaphragm.

1702. The oligomeric compound of any of embodiments 1621-1641, wherein the target RNA is expressed in the colon.

1703. The oligomeric compound of any of embodiments 1621-1641, wherein the target RNA is a white fat cell target.

1704. The oligomeric compound of any of embodiments 1621-1641, wherein the target RNA is a brown fat cell target.

1705. The oligomeric compound of any of embodiments 1621-1641, wherein the target RNA is an adipocyte target.

1706. The oligomeric compound of any of embodiments 1621-1641, wherein the target RNA is a macrophage target.

1707. The oligomeric compound of any of embodiments 1621-1641, wherein the target RNA is a cancer cell target.

1708. The oligomeric compound of any of embodiments 1621-1641, wherein the target RNA is a tumor cell target.

1709. The oligomeric compound of any of embodiments 1621-1641, wherein the target RNA is a smooth muscle cell target.

1710. The oligomeric compound of any of embodiments 1621-1641, wherein the target RNA is a lymphocyte target.

1711. The oligomeric compound of any of embodiments 1621-1641, wherein the target RNA is a pulmonary cell target.

1712. The oligomeric compound of any of embodiments 1621-1641, wherein the target RNA is a heart muscle cell target.

1713. The oligomeric compound of any of embodiments 1621-1641, wherein the target RNA is a cardiomyocyte target.

1714. The oligomeric compound of any of embodiments 1621-1641, wherein the target RNA is a endothelial cell target.

1715. The oligomeric compound of any of embodiments 1621-1641, wherein the target RNA is a fibroblast target.

1716. The oligomeric compound of any of embodiments 1621-1641, wherein the target RNA is a glial cell target.

1717. The oligomeric compound of any of embodiments 1621-1641, wherein the target RNA is a Schwann cell target.

1718. The oligomeric compound of any of embodiments 1621-1641, wherein the target RNA is a pancreatic cell target.

1719. The oligomeric compound of any of embodiments 1621-1641, wherein the target RNA is a kidney cell target.

1720. The oligomeric compound of any of embodiments 1621-1641, wherein the target RNA is a beta cell target.

1721. The oligomeric compound of any of embodiments 1621-1641, wherein the target RNA is a non-parenchymal cell target.

1722. The oligomeric compound of any of embodiments 1621-1641, wherein the target RNA is a hepatocyte target.

1723. The oligomeric compound of any of embodiments 1621-1641, wherein the target RNA a oligodendrocyte target.

1724. The oligomeric compound of any of embodiments 1621-1641, wherein the target RNA is a astrocyte target.

1725. The oligomeric compound of any of embodiments 1621-1641, wherein the target RNA is a microglia target.

1726. The oligomeric compound of any of embodiments 1621-1641, wherein the target RNA is a ependymal cell target.

1727. The oligomeric compound of any of embodiments 1621-1641, wherein the target RNA is a sensory neuron target.

1728. The oligomeric compound of any of embodiments 1621-1641, wherein the target RNA is a motor neuron target.

1729. The oligomeric compound of any of embodiments 1621-1641, wherein the target RNA is a skeletal muscle target.

1730. The oligomeric compound of any of embodiments 1621-1641, wherein the target RNA is a cardiac muscle target.

1731. The oligomeric compound of any of embodiments 1621-1641, wherein the target RNA is a smooth muscle target.

1732. The oligomeric compound of any of embodiments 1621-1641, wherein the target RNA is a adipose tissue target.

1733. The oligomeric compound of any of embodiments 1621-1641, wherein the target RNA is a white adipose tissue target.

1734. The oligomeric compound of any of embodiments 1621-1641, wherein the target RNA is a spleen target.

1735. The oligomeric compound of any of embodiments 1621-1641, wherein the target RNA is a bone target.

1736. The oligomeric compound of any of embodiments 1621-1641, wherein the target RNA is a bone marrow target.

1737. The oligomeric compound of any of embodiments 1621-1641, wherein the target RNA is an intestinal target.

1738. The oligomeric compound of any of embodiments 1621-1641, wherein the target RNA is an adrenal gland target.

1739. The oligomeric compound of any of embodiments 1621-1641, wherein the target RNA is a testicular target.

1740. The oligomeric compound of any of embodiments 1621-1641, wherein the target RNA is an ovarian target.

1741. The oligomeric compound of any of embodiments 1621-1641, wherein the target RNA is a pancreatic target.

1742. The oligomeric compound of any of embodiments 1621-1641, wherein the target RNA is a pituitary gland target.

1743. The oligomeric compound of any of embodiments 1621-1641, wherein the target RNA is a prostate gland target.

1744. The oligomeric compound of any of embodiments 1621-1641, wherein the target RNA is a skin target.

1745. The oligomeric compound of any of embodiments 1621-1641, wherein the target RNA is an epidermal target.

1746. The oligomeric compound of any of embodiments 1621-1641, wherein the target RNA is a uterine target.

1747. The oligomeric compound of any of embodiments 1621-1641, wherein the target RNA is a bladder target.

1748. The oligomeric compound of any of embodiments 1621-1641, wherein the target RNA is a brain target.

1749. The oligomeric compound of any of embodiments 1621-1641, wherein the target RNA is a glomerulus target.

1750. The oligomeric compound of any of embodiments 1621-1641, wherein the target RNA is a distal tubular epithelium target.

1751. The oligomeric compound of any of embodiments 1621-1641, wherein the target RNA is a breast tissue target.

1752. The oligomeric compound of any of embodiments 1621-1641, wherein the target RNA is a lung target.

1753. The oligomeric compound of any of embodiments 1621-1641, wherein the target RNA is a heart target.

1754. The oligomeric compound of any of embodiments 1621-1641, wherein the target RNA is a kidney target.

1755. The oligomeric compound of any of embodiments 1621-1641, wherein the target RNA is a ganglion target.

1756. The oligomeric compound of any of embodiments 1621-1641, wherein the target RNA is a frontal cortex target.

1757. The oligomeric compound of any of embodiments 1621-1641, wherein the target RNA is a spinal cord target.

1758. The oligomeric compound of any of embodiments 1621-1641, wherein the target RNA is a trigeminal ganglion target.

1759. The oligomeric compound of any of embodiments 1621-1641, wherein the target RNA is a sciatic nerve target.

1760. The oligomeric compound of any of embodiments 1621-1641, wherein the target RNA is a dorsal root ganglion target.

1761. The oligomeric compound of any of embodiments 1621-1641, wherein the target RNA is a epidymal fat target.

1762. The oligomeric compound of any of embodiments 1621-1641, wherein the target RNA is a diaphragm target.

1763. The oligomeric compound of any of embodiments 1621-1641, wherein the target RNA is a colon target.

1764. The oligomeric compound of any of embodiments 1621-1763, wherein the target RNA is a MeCP2, DUX4, HDAC2, APP, Ataxin 1, Ataxin 2, Ataxin 3, Ataxin 6, Ataxin 7, C9ORF72, UBE3A, Prion, PMP22, Tau, LRRK2, LINGO2, GYS1, KCNT1, IRF8, Progranulin, or GFAP RNA.

1765. The oligomeric compound of any of embodiments 1621-1763, wherein the target RNA is a HTT RNA.

1766. The oligomeric compound of embodiment 1764, wherein the target RNA is a MeCP2 RNA.

1767. The oligomeric compound of embodiment 1764, wherein the target RNA is a DUX4 RNA.

1768. The oligomeric compound of embodiment 1764, wherein the target RNA is a HDAC2 RNA.

1769. The oligomeric compound of embodiment 1764, wherein the target RNA is a Ataxin 1 RNA.

1770. The oligomeric compound of embodiment 1764, wherein the target RNA is a Ataxin 2 RNA.

1771. The oligomeric compound of embodiment 1764, wherein the target RNA is a Ataxin 3 RNA.

1772. The oligomeric compound of embodiment 1764, wherein the target RNA is a Ataxin 6 RNA.

1773. The oligomeric compound of embodiment 1764, wherein the target RNA is a Ataxin 7 RNA.

1774. The oligomeric compound of embodiment 1764, wherein the target RNA is a C9ORF72 RNA.

1775. The oligomeric compound of embodiment 1621-1763, wherein the target RNA is an alpha-synuclein RNA.

1776. The oligomeric compound of embodiment 1764, wherein the target RNA is an UBE3A RNA.

1777. The oligomeric compound of any of embodiments 1621-1763, wherein the target RNA is a SOD1 RNA.

1778. The oligomeric compound of embodiment 1764, wherein the target RNA is a Prion RNA.

1779. The oligomeric compound of embodiment 1764, wherein the target RNA is a PMP22 RNA.

1780. The oligomeric compound of any of embodiments 1621-1764, wherein the target RNA is a Tau RNA.

1781. The oligomeric compound of embodiment 1764, wherein the target RNA is a LRRK2 RNA.

1782. The oligomeric compound of embodiment 1764, wherein the target RNA is an APP RNA.

1783. The oligomeric compound of 1764, wherein the target RNA is a LINGO2 RNA.

1784. The oligomeric compound of any of embodiments 1764, wherein the target RNA is a GYS1 RNA.

1785. The oligomeric compound of any of embodiments 1764, wherein the target RNA is a KCNT1 RNA.

1786. The oligomeric compound of any of embodiments 1764, wherein the target RNA is a IRF8 RNA.

1787. The oligomeric compound of any of embodiments 1764, wherein the target RNA is a Progranulin RNA.

1788. The oligomeric compound of any of embodiments 1764, wherein the target RNA is a GFAP RNA.

1789. The oligomeric compound of any of embodiments 1621-1788, wherein modulation of the expression of the target RNA is associated with treating a disorder or condition.

1790. The oligomeric compound of embodiment 1789, wherein the disorder or condition is Alzheimer's Disease, Amyotrophic Lateral Sclerosis, Parkinson's Disease, a Spinocerebellar ataxia, Angelman Syndrome, Alexander's Disease, Lafora Disease, Charcot-Marie Tooth Disease, Prion Disease, a dementia, neurodegeneration, MeCP2 Duplication Syndrome, encephalopathy, neuroinflammation, or multiple sclerosis.

1791. The oligomeric compound of embodiment 1790, wherein the disorder or condition is Alzheimer's Disease.

1792. The oligomeric compound of embodiment 1790, wherein the disorder or condition is Amyotrophic Lateral Sclerosis.

1793. The oligomeric compound of embodiment 1790, wherein the disorder or condition is Parkinson's Disease.

1794. The oligomeric compound of embodiment 1790 wherein the disorder or condition is a Spinocerebellar ataxia.

1795. The oligomeric compound of embodiment 1790 wherein the disorder or condition is Angelman Syndrome.

1796. The oligomeric compound of embodiment 1790, wherein the disorder or condition is Alexander's Disease.

1797. The oligomeric compound of embodiment 1790, wherein the disorder or condition is Lafora Disease.

1798. The oligomeric compound of embodiment 1790, wherein the disorder or condition is Charcot-Marie Tooth Disease.

1799. The oligomeric compound of embodiment 1790, wherein the disorder or condition is Prion Disease.

1800. The oligomeric compound of embodiment 1790, wherein the disorder or condition is a dementia.

1801. The oligomeric compound of embodiment 1790, wherein the disorder or condition is neurodegeneration.

1802. The oligomeric compound of embodiment 1790, wherein the disorder or condition is MeCP2 Duplication Syndrome.

1803. The oligomeric compound of embodiment 1790, wherein the disorder or condition is encephalopathy.

1804. The oligomeric compound of embodiment 1790, wherein the disorder or condition is neuroinflammation.

1805. The oligomeric compound of embodiment 1790, wherein the disorder or condition is multiple sclerosis.

1806. The oligomeric compound of any of embodiments 1461-1805, wherein the parent oligomeric compound of the oligomeric compound of any of embodiments 1461-1805 is cytotoxic in vitro.

1807. The oligomeric compound of embodiment 1806, wherein the parent oligomeric compound is cytotoxic in a standard in vitro cytotoxicity assay.

1808. The oligomeric compound of any of embodiments 1461-1805 wherein administration to a mouse of the parent oligomeric compound of the oligomeric compound of any of embodiments 1461-1805 is hepatotoxic to the mouse.

1809. The oligomeric compound of embodiment 1808, wherein the administration of the parent oligomeric compound to the mouse is systemic administration.

1810. The oligomeric compound of embodiment 1809, wherein the systemic administration is subcutaneous administration.

1811. The oligomeric compound of any of embodiments 1808-1810, wherein the mouse is a CD-1 mouse.

1812. The oligomeric compound of any of embodiments 1808-1810, wherein the mouse is a C57BL/6 mouse.

1813. The oligomeric compound of any of embodiments 1808-1810, wherein the mouse is a BALB/c mouse.

1814. The oligomeric compound of any of embodiments 1807-1813, wherein the plasma ALT level in the mouse is higher than 500 units per liter following the administration of the parent oligomeric compound.

1815. The oligomeric compound of any of embodiments 1807-1814, wherein the plasma AST level in the mouse is higher than 500 units per liter following the administration of the parent oligomeric compound.

1816. The oligomeric compound of any of embodiments 1807-1815, wherein the plasma ALT level in the mouse is higher than 1000 units per liter following the administration of the parent oligomeric compound.

1817. The oligomeric compound of any of embodiments 1807-1816, wherein the plasma AST level in the mouse is higher than 1000 units per liter following the administration of the parent oligomeric compound.

1818. The oligomeric compound of any of embodiments 1807-1817, wherein the hepatotoxicity is measured 24-48 hours following the administration of the parent oligomeric compound.

1819. The oligomeric compound of any of embodiments 1807-1817, wherein the hepatotoxicity is measured 72 hours following the administration of the parent oligomeric compound.

1820. The oligomeric compound of any of embodiments 1807-1817, wherein the hepatotoxicity is measured 3 days following the administration of the parent oligomeric compound.

1821. The oligomeric compound of any of embodiments 1807-1817, wherein the hepatotoxicity is measured 5 days following the administration of the parent oligomeric compound.

1822. The oligomeric compound of any of embodiments 1807-1817, wherein the hepatotoxicity is measured 7 days following the administration of the parent oligomeric compound.

1823. The oligomeric compound of any of embodiments 1807-1817, wherein the hepatotoxicity is measured 10 days following the administration of the parent oligomeric compound.

1824. The oligomeric compound of any of embodiments 1807-1817, wherein the hepatotoxicity is measured 14 days following the administration of the parent oligomeric compound.

1825. The oligomeric compound of any of embodiments 1807-1817, wherein 1-10 mg/kg of the parent oligomeric compound is administered to the mouse.

1826. The oligomeric compound of any of embodiments 1807-1817, wherein 10-25 mg/kg of the parent oligomeric compound is administered to the mouse.

1827. The oligomeric compound of any of embodiments 1807-1817, wherein 25-50 mg/kg of the parent oligomeric compound is administered to the mouse.

1828. The oligomeric compound of any of embodiments 1807-1817, wherein 50-100 mg/kg of the parent oligomeric compound is administered to the mouse.

1829. The oligomeric compound of any of embodiments 1807-1817, wherein 100-150 mg/kg of the parent oligomeric compound is administered to the mouse.

1830. The oligomeric compound of any of embodiments 1807-1817, wherein the mouse is a BALB/c mouse, wherein 150 mg/kg of the parent oligomeric compound is administered to the mouse, and wherein the plasma ALT level in the mouse is measured 72 hours following the administration of the parent oligomeric compound.

1831. The oligomeric compound of any of embodiments 1461-1830, wherein administration of 50 mg/kg of the oligomeric compound of any of embodiments 1461-1830 to a mouse is not hepatotoxic to the mouse.

1832. The oligomeric compound of embodiment 1831, wherein plasma ALT level in the mouse is lower than 100 units per liter following the administration of the oligomeric compound of embodiment 1831.

1833. The oligomeric compound of embodiment 1831 or 1832, wherein plasma ALT level in the mouse is at least 10-fold lower than plasma ALT level in a mouse administered the parent oligomeric compound of the oligomeric compound of embodiment 1831 or 1832, wherein the administrations and plasma ALT measurements of both the oligomeric compound of embodiment 1831 or 1832 and the parent oligomeric compound are completed in the same way.

1834. The oligomeric compound of embodiment 1833, wherein the plasma ALT level in the mouse is at least 100-fold lower than the plasma ALT level in the mouse administered the parent oligomeric compound.

1835. The oligomeric compound of embodiment 1833, wherein the plasma ALT level in the mouse is at least 500-fold lower than the plasma ALT level in the mouse administered the parent oligomeric compound.

1836. The oligomeric compound of any of embodiments 1807-1835, wherein the therapeutic index in a mouse of the oligomeric compound of any of embodiments 1807-1835 is increased relative to the therapeutic index of the parent oligomeric compound.

1837. The oligomeric compound of embodiment 1836, wherein the therapeutic index in a mouse of the oligomeric compound of embodiment 1836 is at least two-fold greater than the therapeutic index of the parent oligomeric compound.

1838. The oligomeric compound of any of embodiments 1461-1805, wherein an otherwise identical oligomeric compound lacking the at least one modified internucleoside linkage other than phosphorothioate and/or at least one modified nucleoside comprising a modified nucleobase other than 5-methylcytosine and/or a modified sugar moiety in the central region is hepatotoxic following administration to a mouse;

and wherein the otherwise identical oligomeric compound has a central region consisting of phosphorothioate internucleoside linkages, unmodified 2'-β-D-deoxyribosyl sugar moieties, and nucleobases selected from thymine, uracil, adenine, guanine, cytosine, and 5-methylcytosine.

1839. The oligomeric compound of embodiment 1838, wherein the at least one modified internucleoside linkage other than phosphorothioate and/or at least one modified nucleoside comprising a modified nucleobase other than 5-methylcytosine and/or a modified sugar moiety in the central region is a 2'-O-methyl modified sugar moiety.

1840. The oligomeric compound of embodiment 1839, wherein the 2'-O-methyl modified sugar moiety is at position 2 of the central region.

1841. The oligomeric compound of embodiment 1838-1840, wherein the otherwise identical oligomeric compound lacks a 2'-O-methyl modified sugar moiety, and wherein the otherwise identical oligomeric compound comprises an unmodified 2'-β-D-deoxyribosyl sugar moiety in place of the 2'-O-methyl modified sugar moiety.

1842. The oligomeric compound of any of embodiments 1838-1841, wherein the nucleobase sequence of the otherwise identical oligomeric compound is 100% complementary to the target RNA.

1843. The oligomeric compound of any of embodiments 1838-1842, wherein the otherwise identical oligomeric compound is a parent oligomeric compound of the oligomeric compound of any of embodiments 1838-1842.

1844. The oligomeric compound of any of embodiments 1621-1843, wherein the oligomeric compound inhibits the target RNA with an $IC_{50}$ lower than 100 nM in a standard in vitro activity assay.

1845. The oligomeric compound of any of embodiments 1621-1843, wherein the parent oligomeric compound of the oligomeric compound of any of embodiments 1621-1843 inhibits the target RNA with an $IC_{50}$ lower than 100 nM in a standard in vitro activity assay.

1846. The oligomeric compound of any of embodiments 1621-1845, wherein the difference between the $IC_{50}$ of the parent oligomeric compound measured in a standard in vitro activity assay and the $IC_{50}$ of the oligomeric compound of any of embodiments 1621-1845 measured in a standard in vitro activity assay is less than 4-fold.

1847. The oligomeric compound of any of embodiments 1621-1845, wherein the difference between the $IC_{50}$ of the parent oligomeric compound measured in a standard in vitro activity assay and the $IC_{50}$ of the oligomeric compound of any of embodiments 1621-1845 measured in a standard in vitro activity assay is less than 3-fold.

1848. The oligomeric compound of any of embodiments 1621-1845, wherein the difference between the $IC_{50}$ of the parent oligomeric compound measured in a standard in vitro activity assay and the $IC_{50}$ of the oligomeric compound of any of embodiments 1621-1845 measured in a standard in vitro activity assay is less than 2-fold.

1849. The oligomeric compound of any of embodiments 1621-1848, wherein each sugar moiety of the central region of the parent oligomeric compound is an unmodified 2'-β-D-deoxyribosyl sugar moiety, and wherein each internucleoside linkage of the central region of the parent oligomeric compound is a phosphorothioate internucleoside linkage.

1850. The oligomeric compound of any of embodiments 1621-1849, wherein the nucleobase sequence of the parent oligomeric compound is 100% complementary to the target RNA.

1851. The oligomeric compound of any of embodiments 1461-1850, wherein administration of 10-50 mg of the oligomeric compound to a human is not hepatotoxic to the human.

1852. The oligomeric compound of any of embodiments 1461-1850, wherein administration of 50-100 mg of the oligomeric compound to a human is not hepatotoxic to the human.

1853. The oligomeric compound of any of embodiments 1461-1850, wherein administration of 100-300 mg of the oligomeric compound to a human is not hepatotoxic to the human.

1854. The oligomeric compound of any of embodiments 1851-1853, wherein the administration is systemic administration.

1855. A composition comprising the oligomeric compound of any of embodiments 1461-1854, and a second oligomeric compound, wherein the second oligomeric compound is complementary to the oligomeric compound of any of embodiments 1461-1854.

1856. The composition of embodiment 1855, wherein the second oligomeric compound comprises at least 14 contiguous linked nucleosides that are at least 90% complementary to the oligomeric compound of any of embodiments 1851-1853.

1857. The composition of embodiment 1855, wherein the second oligomeric compound comprises at least 14 contiguous linked nucleosides that are 100% complementary to the oligomeric compound of any of embodiments 1461-1854.

1858. A pharmaceutical composition comprising the oligomeric compound of any of embodiments 1461-1854 or the composition of any of embodiments 1855-1857, comprising a pharmaceutically acceptable carrier or diluent.

1859. A method comprising administering the oligomeric compound or composition of any of embodiments 1461-1858 to a human subject.

1860. A method of treating a disease or disorder comprising administering the oligomeric compound or composition of any of embodiments 1461-1858 to a human subject.

1861. A method of modulating the amount or activity of a target RNA in a human subject comprising administering the oligomeric compound or composition of any of embodiments 1461-1858 to the human subject; and thereby modulating the amount or activity of the target RNA in the human subject.

1862. A method of treating a disease or disorder in a human subject comprising administering the oligomeric compound or composition of any of embodiments 1461-1858 to the human subject having the disease or disorder; and thereby treating the disease or disorder in the human subject.

1863. The method of embodiment 1861 or 1862, wherein the disease or disorder is a liver disease, and wherein the oligomeric compound modulates the amount or activity of a liver target RNA.

1864. The method of embodiment 1861 or 1862, wherein the disease or disorder is a central nervous system disease, and wherein the oligomeric compound modulates the amount or activity of a central nervous system target RNA.

1865. The method of any of embodiments 1861-1864, wherein the disease or disorder is a cancer, a neurodegenerative disease, a cardiovascular disease, an immunological disease, a hereditary disease, a repeat expansion disease, a muscle-wasting disease, or a metabolic disease.

1866. The method of embodiment 1861 or 1862, wherein the oligomeric compound modulates the amount or activity of a white fat cell target.

1867. The method of embodiment 1861 or 1862, wherein the oligomeric compound modulates the amount or activity of a brown fat cell target.

1868. The method of embodiment 1861 or 1862, wherein the oligomeric compound modulates the amount or activity of an adipocyte target.

1869. The method of embodiment 1861 or 1862, wherein the oligomeric compound modulates the amount or activity of a macrophage target.

1870. The method of embodiment 1861 or 1862, wherein the oligomeric compound modulates the amount or activity of a cancer cell target.

1871. The method of embodiment 1861 or 1862, wherein the oligomeric compound modulates the amount or activity of a tumor cell target.

1872. The method of embodiment 1861 or 1862, wherein the oligomeric compound modulates the amount or activity of a smooth muscle cell target.

1873. The method of embodiment 1861 or 1862, wherein the oligomeric compound modulates the amount or activity of a lymphocyte target.

1874. The method of embodiment 1861 or 1862, wherein the oligomeric compound modulates the amount or activity of a pulmonary cell target.

1875. The method of embodiment 1861 or 1862, wherein the oligomeric compound modulates the amount or activity of a heart muscle cell target.

1876. The method of embodiment 1861 or 1862, wherein the oligomeric compound modulates the amount or activity of a cardiomyocyte target.

1877. The method of embodiment 1861 or 1862, wherein the oligomeric compound modulates the amount or activity of a endothelial cell target.

1878. The method of embodiment 1861 or 1862, wherein the oligomeric compound modulates the amount or activity of a fibroblast target.

1879. The method of embodiment 1861 or 1862, wherein the oligomeric compound modulates the amount or activity of a glial cell target.

1880. The method of embodiment 1861 or 1862, wherein the oligomeric compound modulates the amount or activity of a Schwann cell target.

1881. The method of embodiment 1861 or 1862, wherein the oligomeric compound modulates the amount or activity of a pancreatic cell target.

1882. The method of embodiment 1861 or 1862, wherein the oligomeric compound modulates the amount or activity of a kidney cell target.

1883. The method of embodiment 1861 or 1862, wherein the oligomeric compound modulates the amount or activity of a beta cell target.

1884. The method of embodiment 1861 or 1862, wherein the oligomeric compound modulates the amount or activity of a non-parenchymal cell target.

1885. The method of embodiment 1861 or 1862, wherein the oligomeric compound modulates the amount or activity of a hepatocyte target.

1886. The method of embodiment 1861 or 1862, wherein the oligomeric compound modulates the amount or activity of a oligodendrocyte target.

1887. The method of embodiment 1861 or 1862, wherein the oligomeric compound modulates the amount or activity of a astrocyte target.

1888. The method of embodiment 1861 or 1862, wherein the oligomeric compound modulates the amount or activity of a microglia target.

1889. The method of embodiment 1861 or 1862, wherein the oligomeric compound modulates the amount or activity of a ependymal cell target.

1890. The method of embodiment 1861 or 1862, wherein the oligomeric compound modulates the amount or activity of a sensory neuron target.

1891. The method of embodiment 1861 or 1862, wherein the oligomeric compound modulates the amount or activity of a motor neuron target.

1892. The method of embodiment 1861 or 1862, wherein the oligomeric compound modulates the amount or activity of a skeletal muscle target.

1893. The method of embodiment 1861 or 1862, wherein the oligomeric compound modulates the amount or activity of a cardiac muscle target.

1894. The method of embodiment 1861 or 1862, wherein the oligomeric compound modulates the amount or activity of a smooth muscle target.

1895. The method of embodiment 1861 or 1862, wherein the oligomeric compound modulates the amount or activity of a adipose tissue target.

1896. The method of embodiment 1861 or 1862, wherein the oligomeric compound modulates the amount or activity of a white adipose tissue target.

1897. The method of embodiment 1861 or 1862, wherein the oligomeric compound modulates the amount or activity of a spleen target.

1898. The method of embodiment 1861 or 1862, wherein the oligomeric compound modulates the amount or activity of a bone target.

1899. The method of embodiment 1861 or 1862, wherein the oligomeric compound modulates the amount or activity of a bone marrow target.

1900. The method of embodiment 1861 or 1862, wherein the oligomeric compound modulates the amount or activity of an intestinal target.

1901. The method of embodiment 1861 or 1862, wherein the oligomeric compound modulates the amount or activity of an adrenal gland target.

1902. The method of embodiment 1861 or 1862, wherein the oligomeric compound modulates the amount or activity of a testicular target.

1903. The method of embodiment 1861 or 1862, wherein the oligomeric compound modulates the amount or activity of an ovarian target.

1904. The method of embodiment 1861 or 1862, wherein the oligomeric compound modulates the amount or activity of a pancreatic target.

1905. The method of embodiment 1861 or 1862, wherein the oligomeric compound modulates the amount or activity of a pituitary gland target.

1906. The method of embodiment 1861 or 1862, wherein the oligomeric compound modulates the amount or activity of a prostate gland target.

1907. The method of embodiment 1861 or 1862, wherein the oligomeric compound modulates the amount or activity of a skin target.

1908. The method of embodiment 1861 or 1862, wherein the oligomeric compound modulates the amount or activity of an epidermal target.

1909. The method of embodiment 1861 or 1862, wherein the oligomeric compound modulates the amount or activity of a uterine target.

1910. The method of embodiment 1861 or 1862, wherein the oligomeric compound modulates the amount or activity of a bladder target.

1911. The method of embodiment 1861 or 1862, wherein the oligomeric compound modulates the amount or activity of a brain target.

1912. The method of embodiment 1861 or 1862, wherein the oligomeric compound modulates the amount or activity of a glomerulus target.

1913. The method of embodiment 1861 or 1862, wherein the oligomeric compound modulates the amount or activity of a distal tubular epithelium target.

1914. The method of embodiment 1861 or 1862, wherein the oligomeric compound modulates the amount or activity of a breast tissue target.

1915. The method of embodiment 1861 or 1862, wherein the oligomeric compound modulates the amount or activity of a lung target.

1916. The method of embodiment 1861 or 1862, wherein the oligomeric compound modulates the amount or activity of a heart target.

1917. The method of embodiment 1861 or 1862, wherein the oligomeric compound modulates the amount or activity of a kidney target.

1918. The method of embodiment 1861 or 1862, wherein the oligomeric compound modulates the amount or activity of a ganglion target.

1919. The method of embodiment 1861 or 1862, wherein the oligomeric compound modulates the amount or activity of a frontal cortex target.

1920. The method of embodiment 1861 or 1862, wherein the oligomeric compound modulates the amount or activity of a spinal cord target.

1921. The method of embodiment 1861 or 1862, wherein the oligomeric compound modulates the amount or activity of a trigeminal ganglion target.

1922. The method of embodiment 1861 or 1862, wherein the oligomeric compound modulates the amount or activity of a sciatic nerve target.

1923. The method of embodiment 1861 or 1862, wherein the oligomeric compound modulates the amount or activity of a dorsal root ganglion target.

1924. The method of embodiment 1861 or 1862, wherein the oligomeric compound modulates the amount or activity of a epidymal fat target.

1925. The method of embodiment 1861 or 1862, wherein the oligomeric compound modulates the amount or activity of a diaphragm target.

1926. The method of embodiment 1861 or 1862, wherein the oligomeric compound modulates the amount or activity of a colon target.

1927. The method of any of embodiments 1802-1926, wherein the plasma ALT level of the human subject after the administration is not more than three times higher than it was prior to the administration.

1928. The method of any of embodiments 1802-1926, wherein the plasma ALT level of the human subject after the administration is not more than 150 units per liter.

1929. The method of any of embodiments 1802-1928, wherein the human subject is susceptible to liver damage.

1930. The method of any of embodiments 1802-1928, wherein the human subject is susceptible to liver degeneration.

1931. The method of any of embodiments 1802-1930, wherein the human subject is susceptible to elevated apoptosis in the liver.

1932. The method of any of embodiments 1802-1931, wherein the human subject has a liver disease.

1933. The method of any of embodiments 1802-1932, wherein the human subject has kidney disease.

1934. The method of any of embodiments 1802-1933, wherein the human subject is susceptible to kidney damage.

1935. The method of any of embodiments 1802-1934, wherein the human subject has heart disease.

1936. The method of any of embodiments 1802-1935, wherein the human subject is susceptible to heart damage.

1937. The method of any of embodiments 1802-1936, wherein the human subject has pancreatitis.

1938. The method of any of embodiments 1802-1937, wherein the human subject is susceptible to pancreatic damage.

1939. The method of any of embodiments 1802-1938, wherein the human subject has a neurological disease.

1940. The method of any of embodiments 1802-1939, wherein the human subject is susceptible to neurological damage.

1941. The method of any of embodiments 1859-1940, comprising administering the parent oligomeric compound of the oligomeric compound of any of embodiments 1461-1858 to a mouse.

1942. The method of any of embodiments 1859-1940, comprising contacting a cell with the parent oligomeric compound of the oligomeric compound of any of embodiments 1461-1858.

1943. The method of embodiment 1941 or 1942, wherein each sugar moiety of the central region of the parent oligomeric compound is an unmodified 2'-β-D-deoxyribosyl sugar moiety, and wherein each internucleoside linkage of the central region of the parent oligomeric compound is a phosphorothioate internucleoside linkage.

1944. A method of designing an oligomeric compound comprising starting with a parent oligomeric compound and changing the design of that compound in order to arrive at an oligomeric compound of any one of embodiments 1461-1858.

1945. A method of designing an oligomeric compound comprising identifying a parent oligomeric compound and changing the design of that parent oligomeric compound to arrive at a second oligomeric compound, wherein the second oligomeric compound is an oligomeric compound of any one of embodiments 1461-1858.

1946. A method of improving hepatotoxicity of an oligomeric compound comprising the steps of (i) identifying a parent oligomeric compound that has plasma ALT levels above 300 units per liter in a mouse, and (ii) providing an oligomeric compound according to any one of embodiments 1461-1858.

1947. The method of embodiment 1945 or 1946, wherein the method designs an oligomeric compound with improved therapeutic index relative to the parent oligomeric compound.

1948. The method of embodiment 1945 or 1946, wherein the method designs an oligomeric compound with lower hepatotoxicity relative to the parent oligomeric compound.

1949. The method of embodiment 1945, wherein the second oligomeric compound has an improved therapeutic index relative to the parent oligomeric compound.

1950. The method of embodiment 1945 or 1946, wherein the second oligomeric compound has reduced hepatotoxicity in a mouse relative to the parent oligomeric compound.

1951. The method of embodiment 1945, wherein the oligomeric compound according to any one of embodiments 1461-1858 has reduced hepatotoxicity relative to the parent oligomeric compound.

1952. A method comprising administering an oligomeric compound of any of embodiments 1461-1858 to a mouse and separately administering the parent oligomeric compound of the oligomeric compound of any of embodiments 1461-1858 to a second mouse, wherein the therapeutic index of the oligomeric compound of any of embodiments 1461-1858 is improved relative to the therapeutic index of the parent oligomeric compound.

1953. The method of any of embodiments 1859-1952, wherein the level of p21 RNA is measured in the mouse, the cell, and/or the human subject.

1954. A method comprising administering an oligomeric compound of any of embodiments 1461-1858 to a subject and measuring the level of p21 RNA in the subject.

1955. The method of embodiment 1954, wherein the subject is a mouse.

1956. The method of embodiment 1954, wherein the subject is a human.

1957. The method of any of embodiments 1954-1956, wherein the p21 RNA level is measured within 24 hours of the administration.

1958. The method of any of embodiments 1954-1956, wherein the p21 RNA level is measured 24-48 hours following the administration.

1959. An oligomeric compound or composition of any one of embodiments 1461-1858, for use in medical therapy.

1960. The oligomeric compound of any of embodiments 1461-1858, wherein the oligomeric compound is not toxic.

1961. The oligomeric compound of any of embodiment 1461-1858, wherein a comparator compound is toxic; wherein the comparator compound is identical to the oligomeric compound except that each nucleoside of the central region of the comparator compound is a nucleoside comprising 2'-β-D-deoxyribosyl sugar moiety.

1962. The oligomeric compound of embodiment 1961, wherein administering a dose of the oligomeric compound to an animal results in a circulating ALT level that is at least 3-fold lower than the ALT level that results from administering the same dose of the comparator compound to an animal for at least one matched dose.

1963. The oligomeric compound of embodiment 1961 or 1962, wherein the lowest dose of the oligomeric compound that raises circulating ALT to over 300 units per liter is at least three-fold higher than the lowest dose of the comparator compound that raises circulating ALT to over 300 units per liter.

1964. The oligomeric compound of any of embodiments 1961-1963, wherein the oligomeric compound is capable of reducing the target RNA in a cell.

1965. The oligomeric compound of embodiment 1964, wherein the oligomeric compound has RNA-reducing activity comparable to a comparator compound, wherein the comparator compound is identical to the oligomeric compound except that each nucleoside of the central region of the comparator compound is a nucleoside comprising 2'-β-D-deoxyribosyl sugar moiety.

1966. The oligomeric compound of embodiment 1965 having RNA-reducing activity that is no more than 2-fold worse than the RNA-reducing activity of the comparator compound.

1967. A method of modulating the amount or activity of a target RNA in a human subject comprising administering the oligomeric compound or composition of any of embodiments 1461-1858 to the human subject; and thereby modulating the amount or activity of the target RNA in the human subject.

1968. A method of treating a disease or disorder in a human subject comprising administering the oligomeric compound or composition of any of embodiments 1461-1858 to the human subject having the disease or disorder; and thereby treating the disease or disorder in the human subject.

1969. The method of embodiment 1967 or 1968, wherein the disease or disorder is a liver disease, and wherein the oligomeric compound modulates the amount or activity of a liver target RNA.

1970. The method of embodiment 1967 or 1968, wherein the disease or disorder is a central nervous system disease, and wherein the oligomeric compound modulates the amount or activity of a central nervous system target RNA.

1971. The method of any of embodiments 1967-1970, wherein the disease or disorder is a cancer, a neurodegenerative disease, a cardiovascular disease, an immunological disease, a hereditary disease, a repeat expansion disease, a muscle-wasting disease, or a metabolic disease.

1972. The method of any of embodiments 1967-1971, wherein the plasma ALT level of the human subject after the administration is not more than three times higher than it was prior to the administration.

1973. The method of any of embodiments 1967-1972, wherein the plasma ALT level of the human subject after the administration is not more than 150 units per liter.

1974. A method of treating a disease or disorder in a human subject comprising administering the oligomeric compound or composition of any of embodiments 1461-1858 to the human subject having the disease or disorder; and thereby treating the disease or disorder in the human subject.

1975. The method of embodiment 1974, wherein the disease or disorder is not a CNS disease or disorder.

1976. The method of embodiment 1974, wherein the disease or disorder is a disease or disorder of the white fat cells.

1977. The method of embodiment 1974, wherein the disease or disorder is a disease or disorder of the brown fat cells.

1978. The method of embodiment 1974, wherein the disease or disorder is a disease or disorder of the adipocytes.

1979. The method of embodiment 1974, wherein the disease or disorder is a disease or disorder of the macrophages.

1980. The method of embodiment 1974, wherein the disease or disorder is a disease or disorder of the cancer cells.

1981. The method of embodiment 1974, wherein the disease or disorder is a disease or disorder of the tumor cells.

1982. The method of embodiment 1974, wherein the disease or disorder is a disease or disorder of the smooth muscle cells.

1983. The method of embodiment 1974, wherein the disease or disorder is a disease or disorder of the lymphocytes.

1984. The method of embodiment 1974, wherein the disease or disorder is a disease or disorder of the pulmonary cells.

1985. The method of embodiment 1974, wherein the disease or disorder is a disease or disorder of the heart muscle cells.

1986. The method of embodiment 1974, wherein the disease or disorder is a disease or disorder of the cardiomyocytes.

1987. The method of embodiment 1974, wherein the disease or disorder is a disease or disorder of the endothelial cells.

1988. The method of embodiment 1974, wherein the disease or disorder is a disease or disorder of the fibroblasts.

1989. The method of embodiment 1974, wherein the disease or disorder is a disease or disorder of the glial cells.

1990. The method of embodiment 1974, wherein the disease or disorder is a disease or disorder of the Schwann cells.

1991. The method of embodiment 1974, wherein the disease or disorder is a disease or disorder of the pancreatic cells.

1992. The method of embodiment 1974, wherein the disease or disorder is a disease or disorder of the kidney cells.

1993. The method of embodiment 1974, wherein the disease or disorder is a disease or disorder of the beta cells.

1994. The method of embodiment 1974, wherein the disease or disorder is a disease or disorder of the non-parenchymal cells.

1995. The method of embodiment 1974, wherein the disease or disorder is a disease or disorder of the hepatocytes.

1996. The method of embodiment 1974, wherein the disease or disorder is a disease or disorder of the oligodendrocytes.

1997. The method of embodiment 1974, wherein the disease or disorder is a disease or disorder of the astrocytes.

1998. The method of embodiment 1974, wherein the disease or disorder is a disease or disorder of the microglia.

1999. The method of embodiment 1974, wherein the disease or disorder is a disease or disorder of the ependymal cells.

2000. The method of embodiment 1974, wherein the disease or disorder is a disease or disorder of the sensory neurons.

2001. The method of embodiment 1974, wherein the disease or disorder is a disease or disorder of the motor neurons.

2002. The method of embodiment 1974, wherein the disease or disorder is a disease or disorder of the skeletal muscle.

2003. The method of embodiment 1974, wherein the disease or disorder is a disease or disorder of the cardiac muscle.

2004. The method of embodiment 1974, wherein the disease or disorder is a disease or disorder of the smooth muscle.

2005. The method of embodiment 1974, wherein the disease or disorder is a disease or disorder of the adipose tissue.

2006. The method of embodiment 1974, wherein the disease or disorder is a disease or disorder of the white adipose tissue.

2007. The method of embodiment 1974, wherein the disease or disorder is a disease or disorder of the spleen.

2008. The method of embodiment 1974, wherein the disease or disorder is a disease or disorder of the bone.

2009. The method of embodiment 1974, wherein the disease or disorder is a disease or disorder of the bone marrow.

2010. The method of embodiment 1974, wherein the disease or disorder is a disease or disorder of the intestine.

2011. The method of embodiment 1974, wherein the disease or disorder is a disease or disorder of the adrenal glands.

2012. The method of embodiment 1974, wherein the disease or disorder is a disease or disorder of the testes.

2013. The method of embodiment 1974, wherein the disease or disorder is a disease or disorder of the ovaries.

2014. The method of embodiment 1974, wherein the disease or disorder is a disease or disorder of the pancreas.

2015. The method of embodiment 1974, wherein the disease or disorder is a disease or disorder of the pituitary gland.

2016. The method of embodiment 1974, wherein the disease or disorder is a disease or disorder of the prostate gland.

2017. The method of embodiment 1974, wherein the disease or disorder is a disease or disorder of the skin.

2018. The method of embodiment 1974, wherein the disease or disorder is a disease or disorder of the epidermis.

2019. The method of embodiment 1974, wherein the disease or disorder is a disease or disorder of the uterus.

2020. The method of embodiment 1974, wherein the disease or disorder is a disease or disorder of the bladder.

2021. The method of embodiment 1974, wherein the disease or disorder is a disease or disorder of the brain.

2022. The method of embodiment 1974, wherein the disease or disorder is a disease or disorder of the glomerulus.

2023. The method of embodiment 1974, wherein the disease or disorder is a disease or disorder of the distal tubular epithelium.

2024. The method of embodiment 1974, wherein the disease or disorder is a disease or disorder of the breast tissue.

2025. The method of embodiment 1974, wherein the disease or disorder is a disease or disorder of the lung.
2026. The method of embodiment 1974, wherein the disease or disorder is a disease or disorder of the heart.
2027. The method of embodiment 1974, wherein the disease or disorder is a disease or disorder of the kidney.
2028. The method of embodiment 1974, wherein the disease or disorder is a disease or disorder of the ganglion.
2029. The method of embodiment 1974, wherein the disease or disorder is a disease or disorder of the frontal cortex.
2030. The method of embodiment 1974, wherein the disease or disorder is a disease or disorder of the spinal cord.
2031. The method of embodiment 1974, wherein the disease or disorder is a disease or disorder of the trigeminal ganglion.
2032. The method of embodiment 1974, wherein the disease or disorder is a disease or disorder of the sciatic nerve.
2033. The method of embodiment 1974, wherein the disease or disorder is a disease or disorder of the dorsal root ganglion.
2034. The method of embodiment 1974, wherein the disease or disorder is a disease or disorder of the epidymal fat.
2035. The method of embodiment 1974, wherein the disease or disorder is a disease or disorder of the diaphragm.
2036. The method of embodiment 1974, wherein the disease or disorder is a disease or disorder of the colon.
2037. A method of screening a library of oligomeric compounds for activity against a target RNA, wherein the library of oligomeric compounds comprises a plurality of oligomeric compounds of any of embodiments 1461-1858.

Certain Compounds

In certain embodiments, compounds described herein are oligomeric compounds comprising or consisting of oligonucleotides consisting of linked nucleosides. Oligonucleotides may be unmodified oligonucleotides or may be modified oligonucleotides. Modified oligonucleotides comprise at least one modification relative to an unmodified oligonucleotide (i.e., comprise at least one modified nucleoside (comprising a modified sugar moiety and/or a modified nucleobase) and/or at least one modified internucleoside linkage).

I. MODIFICATIONS

A. Modified Nucleosides

Modified nucleosides comprise a modified sugar moiety, a modified nucleobase, or both a modified sugar moiety and a modified nucleobase.

1. Certain Modified Sugar Moieties

In certain embodiments, sugar moieties are non-bicyclic, modified furanosyl sugar moieties. In certain embodiments, modified sugar moieties are bicyclic or tricyclic furanosyl sugar moieties. In certain embodiments, modified sugar moieties are sugar surrogates. Such sugar surrogates may comprise one or more substitutions corresponding to those of other types of modified sugar moieties.

In certain embodiments, modified sugar moieties are non-bicyclic modified furanosyl sugar moieties comprising one or more acyclic substituent, including but not limited to substituents at the 2', 3', 4', and/or 5' positions. In certain embodiments, the furanosyl sugar moiety is a ribosyl sugar moiety. In certain embodiments, the furanosyl sugar moiety is a β-D-ribofuranosyl sugar moiety. In certain embodiments one or more acyclic substituent of non-bicyclic modified sugar moieties is branched. Examples of 2'-substituent groups suitable for non-bicyclic modified sugar moieties include but are not limited to: 2'-F, 2'-$OCH_3$ ("2'-OMe" or "2'-O-methyl"), and 2'-$O(CH_2)_2OCH_3$ ("2'-MOE"). In certain embodiments, 2'-substituent groups are selected from among: halo, allyl, amino, azido, SH, CN, OCN, $CF_3$, $OCF_3$, O—$C_1$-$C_{10}$ alkoxy, O—$C_1$-$C_{10}$ substituted alkoxy, $C_1$-$C_{10}$ alkyl, $C_1$-$C_{10}$ substituted alkyl, S-alkyl, $N(R_m)$-alkyl, O-alkenyl, S-alkenyl, $N(R_m)$-alkenyl, O-alkynyl, S-alkynyl, $N(R_m)$-alkynyl, O-alkylenyl-O-alkyl, alkynyl, alkaryl, aralkyl, O-alkaryl, O-aralkyl, $O(CH_2)_2SCH_3$, $O(CH_2)_2ON(R_m)(R_n)$ or $OCH_2C(=O)—N(R_m)(R_n)$, where each $R_m$ and $R_n$ is, independently, H, an amino protecting group, or substituted or unsubstituted $C_1$-$C_{10}$ alkyl, and the 2'-substituent groups described in Cook et al., U.S. Pat. No. 6,531,584; Cook et al., U.S. Pat. No. 5,859,221; and Cook et al., U.S. Pat. No. 6,005,087. Certain embodiments of these 2'-substituent groups can be further substituted with one or more substituent groups independently selected from among: hydroxyl, amino, alkoxy, carboxy, benzyl, phenyl, nitro ($NO_2$), thiol, thioalkoxy, thioalkyl, halogen, alkyl, aryl, alkenyl and alkynyl. Examples of 3'-substituent groups include 3'-methyl (see Frier, et al., The ups and downs of nucleic acid duplex stability: structure-stability studies on chemically-modified DNA:RNA duplexes. Nucleic Acids Res., 25, 4429-4443, 1997.) Examples of 4'-substituent groups suitable for non-bicyclic modified sugar moieties include but are not limited to alkoxy (e.g., methoxy), alkyl, and those described in Manoharan et al., WO 2015/106128. Examples of 5'-substituent groups suitable for non-bicyclic modified sugar moieties include but are not limited to: 5'-methyl (R or S), 5'-allyl, 5'-ethyl, 5'-vinyl, and 5'-methoxy. In certain embodiments, non-bicyclic modified sugars comprise more than one non-bridging sugar substituent, for example, 2'-F-5'-methyl sugar moieties and the modified sugar moieties and modified nucleosides described in Migawa et al., WO 2008/101157 and Rajeev et al., US2013/0203836. 2',4'-difluoro modified sugar moieties have been described in Martinez-Montero, et al., Rigid 2',4'-difluororibonucleosides: synthesis, conformational analysis, and incorporation into nascent RNA by HCV polymerase. *J. Org. Chem.,* 2014, 79:5627-5635. Modified sugar moieties comprising a 2'-modification (OMe or F) and a 4'-modification (OMe or F) have also been described in Malek-Adamian, et al., *J. Org. Chem,* 2018, 83: 9839-9849.

In certain embodiments, a 2'-substituted nucleoside or non-bicyclic 2'-modified nucleoside comprises a sugar moiety comprising a non-bridging 2'-substituent group selected from: F, $NH_2$, $N_3$, $OCF_3$, $OCH_3$, $O(CH_2)_3NH_2$, $CH_2CH=CH_2$, $OCH_2CH=CH_2$, $OCH_2CH_2OCH_3$, $O(CH_2)_2SCH_3$, $O(CH_2)_2ON(R_m)(R_n)$, $O(CH_2)_2O(CH_2)_2N(CH_3)_2$, and N-substituted acetamide ($OCH_2C(=O)—N(R_m)(R_n)$), where each $R_m$ and $R_n$ is, independently, H, an amino protecting group, or substituted or unsubstituted $C_1$-$C_{10}$ alkyl.

In certain embodiments, a 2'-substituted nucleoside or non-bicyclic 2'-modified nucleoside comprises a sugar moiety comprising a non-bridging 2'-substituent group selected from: F, $OCF_3$, $OCH_3$, $OCH_2CH_2OCH_3$, $O(CH_2)_2SCH_3$, $O(CH_2)_2ON(CH_3)_2$, $O(CH_2)_2O(CH_2)_2N(CH_3)_2$, and $OCH_2C(=O)—N(H)CH_3$ ("NMA").

In certain embodiments, a 2'-substituted nucleoside or non-bicyclic 2'-modified nucleoside comprises a sugar moiety comprising a non-bridging 2'-substituent group selected from: F, $OCH_3$, and $OCH_2CH_2OCH_3$.

In certain embodiments, the 4' O of 2'-deoxyribose can be substituted with a S to generate 4'-thio DNA (see Takahashi, et al., *Nucleic Acids Research* 2009, 37: 1353-1362). This modification can be combined with other modifications detailed herein. In certain such embodiments, the sugar moiety is further modified at the 2' position. In certain embodiments the sugar moiety comprises a 2'-fluoro. A thymidine with this sugar moiety has been described in Watts, et al., *J. Org. Chem.* 2006, 71(3): 921-925 (4'-S-fluoro5-methylarauridine or FAMU).

Certain modified sugar moieties comprise a bridging sugar substituent that forms a second ring resulting in a bicyclic sugar moiety. In certain such embodiments, the bicyclic sugar moiety comprises a bridge between the 4' and the 2' furanose ring atoms. In certain such embodiments, the furanose ring is a ribose ring. Examples of sugar moieties comprising such 4' to 2' bridging sugar substituents include but are not limited to bicyclic sugars comprising: 4'-$CH_2$-2', 4'-$(CH_2)_2$-2', 4'-$(CH_2)_3$-2', 4'-$CH_2$—O-2' ("LNA"), 4'-$CH_2$—S-2', 4'-$(CH_2)_2$—O-2' ("ENA"), 4'-$CH(CH_3)$—O-2' (referred to as "constrained ethyl" or "cEt" when in the S configuration), 4'-$CH_2$—O—$CH_2$-2', 4'-$CH_2$—N(R)-2', 4'-$CH(CH_2OCH_3)$—O-2' ("constrained MOE" or "cMOE") and analogs thereof (see, e.g., Seth et al., U.S. Pat. No. 7,399,845, Bhat et al., U.S. Pat. No. 7,569,686, Swayze et al., U.S. Pat. No. 7,741,457, and Swayze et al., U.S. Pat. No. 8,022,193), 4'-$C(CH_3)(CH_3)$—O-2' and analogs thereof (see, e.g., Seth et al., U.S. Pat. No. 8,278,283), 4'-$CH_2$—N$(OCH_3)$-2' and analogs thereof (see, e.g., Prakash et al., U.S. Pat. No. 8,278,425), 4'-$CH_2$—O—$N(CH_3)$-2' (see, e.g., Allerson et al., U.S. Pat. No. 7,696,345 and Allerson et al., U.S. Pat. No. 8,124,745), 4'-$CH_2$—$C(H)(CH_3)$-2' (see, e.g., Zhou, et al., *J. Org. Chem.,* 2009, 74, 118-134), 4'-$CH_2$—$C(=CH_2)$-2' and analogs thereof (see e.g., Seth et al., U.S. Pat. No. 8,278,426), 4'-$C(R_aR_b)$—N(R)—O-2', 4'-C$(R_aR_b)$—O—N(R)-2', 4'-$CH_2$—O—N(R)-2', and 4'-$CH_2$—N(R)—O-2', wherein each R, $R_a$, and $R_b$ is, independently, H, a protecting group, or $C_1$-$C_{12}$ alkyl (see, e.g. Imanishi et al., U.S. Pat. No. 7,427,672), 4'-C(=O)—$N(CH_3)_2$-2', 4'-C(=O)—$N(R)_2$-2', 4'-C(=S)—$N(R)_2$-2' and analogs thereof (see, e.g., Obika et al., WO2011052436A1, Yusuke, WO2017018360A1).

In certain embodiments, such 4' to 2' bridges independently comprise from 1 to 4 linked groups independently selected from: —$[C(R_a)(R_b)]_n$—, —$[C(R_a)(R_b)]_n$—O—, —$C(R_n)$=$C(R_b)$—, —$C(R_a)$=N—, —$C(=NR_a)$—, —C(=O)—, —C(=S)—, —O—, —$Si(R_a)_2$—, —$S(=O)_x$—, and —$N(R_a)$—;

wherein:

x is 0, 1, or 2;

n is 1, 2, 3, or 4;

each $R_a$ and $R_b$ is, independently, H, a protecting group, hydroxyl, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, heterocycle radical, substituted heterocycle radical, heteroaryl, substituted heteroaryl, $C_5$-$C_7$ alicyclic radical, substituted $C_5$-$C_7$ alicyclic radical, halogen, $OJ_1$, $NJ_1J_2$, $SJ_1$, $N_3$, $COOJ_1$, acyl (C(=O)—H), substituted acyl, CN, sulfonyl ($S(=O)_2$-$J_1$), or sulfoxyl (S(=O)-$J_1$); and each $J_1$ and $J_2$ is, independently, H, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, acyl (C(=O)—H), substituted acyl, a heterocycle radical, a substituted heterocycle radical, $C_1$-$C_{12}$ aminoalkyl, substituted $C_1$-$C_{12}$ aminoalkyl, or a protecting group.

Additional bicyclic sugar moieties are known in the art, see, for example: Freier et al., *Nucleic Acids Research,* 1997, 25(22), 4429-4443, Albaek et al., *J. Org. Chem.,* 2006, 71, 7731-7740, Singh et al., *Chem. Commun.,* 1998, 4, 455-456; Koshkin et al., *Tetrahedron,* 1998, 54, 3607-3630; Kumar et al., *Bioorg. Med. Chem. Lett.,* 1998, 8, 2219-2222; Singh et al., *J. Org. Chem.,* 1998, 63, 10035-10039; Srivastava et al., *J. Am. Chem. Soc.,* 2017, 129, 8362-8379; Elayadi et al., Christiansen, et al., *J. Am. Chem. Soc.* 1998, 120, 5458-5463; Wengel et a., U.S. Pat. No. 7,053,207; Imanishi et al., U.S. Pat. No. 6,268,490; Imanishi et al. U.S. Pat. No. 6,770,748; Imanishi et al., U.S. RE44,779; Wengel et al., U.S. Pat. No. 6,794,499; Wengel et al., U.S. Pat. No. 6,670,461; Wengel et al., U.S. Pat. No. 7,034,133; Wengel et al., U.S. Pat. No. 8,080,644; Wengel et al., U.S. Pat. No. 8,034,909; Wengel et al., U.S. Pat. No. 8,153,365; Wengel et al., U.S. Pat. No. 7,572,582; and Ramasamy et al., U.S. Pat. No. 6,525,191; Torsten et al., WO 2004/106356; Wengel et al., WO 1999/014226; Seth et al., WO 2007/134181; Seth et al., U.S. Pat. No. 7,547,684; Seth et al., U.S. Pat. No. 7,666,854; Seth et al., U.S. Pat. No. 8,088,746; Seth et al., U.S. Pat. No. 7,750,131; Seth et al., U.S. Pat. No. 8,030,467; Seth et al., U.S. Pat. No. 8,268,980; Seth et al., U.S. Pat. No. 8,546,556; Seth et al., U.S. Pat. No. 8,530,640; Migawa et al., U.S. Pat. No. 9,012,421; Seth et al., U.S. Pat. No. 8,501,805; and U.S. Patent Publication Nos. Allerson et al., US2008/0039618 and Migawa et al., US2015/0191727.

In certain embodiments, bicyclic sugar moieties and nucleosides incorporating such bicyclic sugar moieties are further defined by isomeric configuration. For example, an LNA nucleoside (described herein) may be in the α-L configuration or in the β-D configuration.

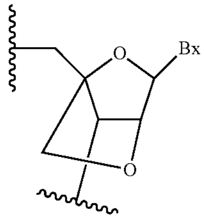

LNA (β-D-configuration)
bridge = 4'-$CH_2$-O-2'

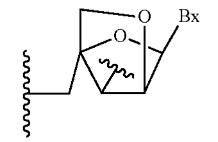

α-*L*-LNA (α-*L*-configuration)
bridge = 4'-$CH_2$-O-2'

α-L-methyleneoxy (4'-$CH_2$—O-2') or α-L-LNA bicyclic nucleosides have been incorporated into antisense oligonucleotides that showed antisense activity (Frieden et al., *Nucleic Acids Research,* 2003, 21, 6365-6372). Herein, general descriptions of bicyclic nucleosides include both isomeric configurations. When the positions of specific bicyclic nucleosides (e.g., LNA) are identified in exemplified embodiments herein, they are in the β-D configuration, unless otherwise specified.

In certain embodiments, modified sugar moieties comprise one or more non-bridging sugar substituent and one or more bridging sugar substituent (e.g., 5'-substituted and 4'-2' bridged sugars).

Nucleosides comprising modified furanosyl sugar moieties and modified furanosyl sugar moieties may be referred to by the position(s) of the substitution(s) on the sugar moiety of the nucleoside. The term "modified" following a position of the furanosyl ring, such as "2'-modified", indicates that the sugar moiety comprises the indicated modification at the 2' position and may comprise additional modifications and/or substituents. A 4'-2' bridged sugar moiety is 2'-modified and 4'-modified, or, alternatively, "2', 4'-modified". The term "substituted" following a position of the furanosyl ring, such as "2'-substituted" or "2'-4'-substituted", indicates that is the only position(s) having a substituent other than those found in unmodified sugar moieties in oligonucleotides. Accordingly, the following sugar moieties are represented by the following formulas.

In the context of a nucleoside and/or an oligonucleotide, a non-bicyclic, modified furanosyl sugar moiety is represented by formula I:

I

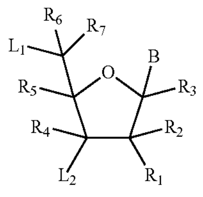

wherein B is a nucleobase; and L1 and L2 are each, independently, an internucleoside linkage, a terminal group, a conjugate group, or a hydroxyl group. Among the R groups, at least one of $R_{3-7}$ is not H and/or at least one of $R_1$ and $R_2$ is not H or OH. In a 2'-modified furanosyl sugar moiety, at least one of $R_1$ and $R_2$ is not H or OH and each of $R_{3-7}$ is independently selected from H or a substituent other than H. In a 4'-modified furanosyl sugar moiety, $R_5$ is not H and each of $R_{1-4, 6, 7}$ are independently selected from H and a substituent other than H; and so on for each position of the furanosyl ring. The stereochemistry is not defined unless otherwise noted.

In the context of a nucleoside and/or an oligonucleotide, a non-bicyclic, modified, substituted fuarnosyl sugar moiety is represented by formula I, wherein B is a nucleobase; and $L_1$ and $L_2$ are each, independently, an internucleoside linkage, a terminal group, a conjugate group, or a hydroxyl group. Among the R groups, either one (and no more than one) of $R_{3-7}$ is a substituent other than H or one of $R_1$ or $R_2$ is a substituent other than H or OH. The stereochemistry is not defined unless otherwise noted. Examples of non-bicyclic, modified, substituted furanosyl sugar moieties include 2'-substituted ribosyl, 4'-substituted ribosyl, and 5'-substituted ribosyl sugar moieties, as well as substituted 2'-deoxyfuranosyl sugar moieties, such as 4'-substituted 2'-deoxyribosyl and 5'-substituted 2'-deoxyribosyl sugar moieties.

In the context of a nucleoside and/or an oligonucleotide, a 2'-substituted ribosyl sugar moiety is represented by formula II:

II

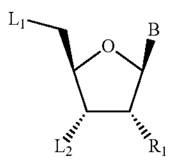

wherein B is a nucleobase; and $L_1$ and $L_2$ are each, independently, an internucleoside linkage, a terminal group, a conjugate group, or a hydroxyl group. $R_1$ is a substituent other than H or OH. The stereochemistry is defined as shown.

In the context of a nucleoside and/or an oligonucleotide, a 4'-substituted ribosyl sugar moiety is represented by formula III:

III

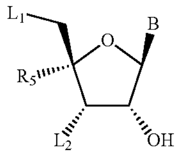

wherein B is a nucleobase; and $L_1$ and $L_2$ are each, independently, an internucleoside linkage, a terminal group, a conjugate group, or a hydroxyl group. $R_5$ is a substituent other than H. The stereochemistry is defined as shown.

In the context of a nucleoside and/or an oligonucleotide, a 5'-substituted ribosyl sugar moiety is represented by formula IV:

IV

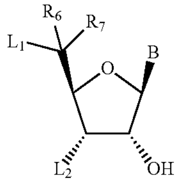

wherein B is a nucleobase; and $L_1$ and $L_2$ are each, independently, an internucleoside linkage, a terminal group, a conjugate group, or a hydroxyl group. $R_6$ or $R_7$ is a substituent other than H. The stereochemistry is defined as shown.

In the context of a nucleoside and/or an oligonucleotide, a 2'-deoxyfuranosyl sugar moiety is represented by formula V:

V

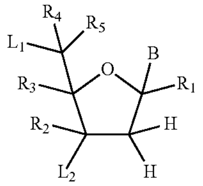

wherein B is a nucleobase; and $L_1$ and $L_2$ are each, independently, an internucleoside linkage, a terminal group, a conjugate group, or a hydroxyl group. Each of $R_{1-5}$ are independently selected from H and a non-H substituent. If all of $R_{1-5}$ are each H, the sugar moiety is an unsubstituted 2'-deoxyfuranosyl sugar moiety. The stereochemistry is not defined unless otherwise noted.

In the context of a nucleoside and/or an oligonucleotide, a 4'-substituted 2'-deoxyribosyl sugar moiety is represented by formula VI:

VI

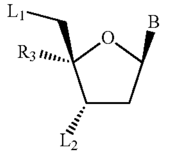

wherein B is a nucleobase; and $L_1$ and $L_2$ are each, independently, an internucleoside linkage, a terminal group, a conjugate group, or a hydroxyl group. $R_3$ is a substituent other than H. The stereochemistry is defined as shown.

In the context of a nucleoside and/or an oligonucleotide, a 5'-substituted 2'-deoxyribosyl sugar moiety is represented by formula VII:

VII

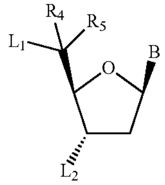

wherein B is a nucleobase; and $L_1$ and $L_2$ are each, independently, an internucleoside linkage, a terminal group, a conjugate group, or a hydroxyl group. $R_4$ or $R_5$ is a substituent other than H. The stereochemistry is defined as shown.

Unsubstituted 2'-deoxyfuranosyl sugar moieties may be unmodified (β-D-2'-deoxyribosyl) or modified. Examples of modified, unsubstituted 2'-deoxyfuranosyl sugar moieties include β-L-2'-deoxyribosyl, α-L-2'-deoxyribosyl, α-D-2'-deoxyribosyl, and β-D-xylosyl sugar moieties. For example, in the context of a nucleoside and/or an oligonucleotide, a β-L-2'-deoxyribosyl sugar moiety is represented by formula VIII:

VIII

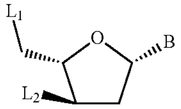

wherein B is a nucleobase; and $L_1$ and $L_2$ are each, independently, an internucleoside linkage, a terminal group, a conjugate group, or a hydroxyl group. The stereochemistry is defined as shown. Synthesis of α-L-ribosyl nucleotides and β-D-xylosyl nucleotides has been described by Gaubert, et al., *Tetehedron* 2006, 62: 2278-2294. Additional isomers of DNA and RNA nucleosides are described by Vester, et. al., "Chemically modified oligonucleotides with efficient RNase H response," Bioorg. Med. Chem. Letters, 2008, 18: 2296-2300.

In certain embodiments, modified sugar moieties are sugar surrogates. In certain such embodiments, the oxygen atom of the sugar moiety is replaced, e.g., with a sulfur, carbon or nitrogen atom. In certain such embodiments, such modified sugar moieties also comprise bridging and/or non-bridging substituents as described herein. For example, certain sugar surrogates comprise a 4'-sulfur atom and a substitution at the 2'-position (see, e.g., Bhat et al., U.S. Pat. No. 7,875,733 and Bhat et al., U.S. Pat. No. 7,939,677) and/or the 5' position.

In certain embodiments, sugar surrogates comprise rings having other than 5 atoms. For example, in certain embodiments, a sugar surrogate comprises a six-membered tetrahydropyran ("THP"). Such tetrahydropyrans may be further modified or substituted. Nucleosides comprising such modified tetrahydropyrans include but are not limited to hexitol nucleic acid ("HNA"), altritol nucleic acid ("ANA"), mannitol nucleic acid ("MNA") (see, e.g., Leumann, C J. *Bioorg. & Med. Chem.* 2002, 10, 841-854), fluoro HNA ("F-HNA", see e.g. Swayze et al., U.S. Pat. No. 8,088,904; Swayze et al., U.S. Pat. No. 8,440,803; Swayze et al., U.S. Pat. No. 8,796,437; and Swayze et al., U.S. Pat. No. 9,005,906; F-HNA can also be referred to as a F-THP or 3'-fluoro tetrahydropyran), F-CeNA, and 3'-ara-HNA, having the formulas below, where $L_1$ and $L_2$ are each, independently, an internucleoside linkage linking the modified THP nucleoside to the remainder of an oligonucleotide or one of $L_1$ and $L_2$ is an internucleoside linkage linking the modified THP nucleoside to the remainder of an oligonucleotide and the other of $L_1$ and $L_2$ is H, a hydroxyl protecting group, a linked conjugate group, or a 5' or 3'-terminal group.

HNA

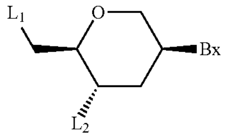

F-HNA

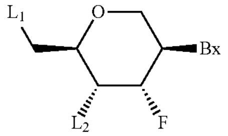

F-CeNA

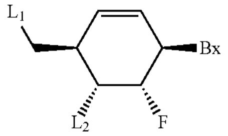

3'-ara-F-HNA

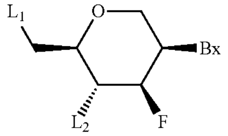

Additional sugar surrogates comprise THP compounds having the formula:

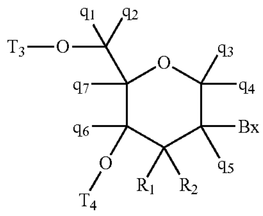

wherein, independently, for each of said modified THP nucleoside:

Bx is a nucleobase moiety;

$T_3$ and $T_4$ are each, independently, an internucleoside linkage linking the modified THP nucleoside to the remainder of an oligonucleotide or one of $T_3$ and $T_4$ is an internucleoside linkage linking the modified THP nucleoside to the remainder of an oligonucleotide and the other of $T_3$ and $T_4$ is H, a hydroxyl protecting group, a linked conjugate group, or a 5' or 3'-terminal group;

$q_1$, $q_2$, $q_3$, $q_4$, $q_5$, $q_6$ and $q_7$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, or substituted $C_2$-$C_6$ alkynyl; and each of $R_1$ and $R_2$ is independently selected from among: hydrogen, halogen, substituted or unsubstituted alkoxy, $NJ_1J_2$, $SJ_1$, $N_3$, $OC(=X)J_1$, $OC(=X)NJ_1J_2$, $NJ_3C(=X)NJ_1J_2$, and CN, wherein X is O, S or $NJ_1$, and each $J_1$, $J_2$, and $J_3$ is, independently, H or $C_1$-$C_6$ alkyl.

In certain embodiments, modified THP nucleosides are provided wherein $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and $q_7$ is other than H. In certain embodiments, at least one of $q_1$, $q_2$, $q_3$, $q_4$, $q_5$, $q_6$ and $q_7$ is methyl. In certain embodiments, modified THP nucleosides are provided wherein one of $R_1$ and $R_2$ is F. In certain embodiments, $R_1$ is F and $R_2$ is H, in certain embodiments, $R_1$ is methoxy and $R_2$ is H, and in certain embodiments, $R_1$ is methoxyethoxy and $R_2$ is H.

In certain embodiments, sugar surrogates comprise rings having no heteroatoms. For example, nucleosides comprising bicyclo [3.1.0]-hexane have been described (see, e.g., Marquez, et al., *J. Med. Chem.* 1996, 39:3739-3749).

In certain embodiments, sugar surrogates comprise rings having more than 5 atoms and more than one heteroatom. For example, nucleosides comprising morpholino sugar moieties and their use in oligonucleotides have been reported (see, e.g., Braasch et al., Biochemistry, 2002, 41, 4503-4510 and Summerton et al., U.S. Pat. No. 5,698,685; Summerton et al., U.S. Pat. No. 5,166,315; Summerton et al., U.S. Pat. No. 5,185,444; and Summerton et al., U.S. Pat. No. 5,034,506). As used here, the term “morpholino” means a sugar surrogate comprising the following structure:

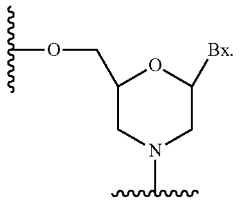

In certain embodiments, morpholinos may be modified, for example by adding or altering various substituent groups from the above morpholino structure. Such sugar surrogates are referred to herein as “modified morpholinos.” In certain embodiments, morpholino residues replace a full nucleotide, including the internucleoside linkage, and have the structures shown below, wherein Bx is a heterocyclic base moiety.

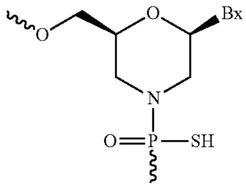

morpholino PS

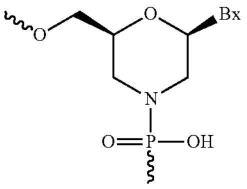

morpholino PO

In certain embodiments, sugar surrogates comprise acyclic moieties. Examples of nucleosides and oligonucleotides comprising such acyclic sugar surrogates include but are not limited to: peptide nucleic acid (“PNA”), acyclic butyl nucleic acid (see, e.g., Kumar et al., *Org. Biomol. Chem.*, 2013, 11, 5853-5865), glycol nucleic acid (“GNA”, see Schlegel, et al., *J. Am. Chem. Soc.* 2017, 139:8537-8546) and nucleosides and oligonucleotides described in Manoharan et al., WO2011/133876.

Many other bicyclic and tricyclic sugar and sugar surrogate ring systems are known in the art that can be used in modified nucleosides. Certain such ring systems are described in Hanessian, et al., *J. Org. Chem.*, 2013, 78: 9051-9063 and include bcDNA and tcDNA. Modifications to bcDNA and tcDNA, such as 6'-fluoro, have also been described (Dogovic and Leumann, *J. Org. Chem.*, 2014, 79: 1271-1279).

In certain embodiments, modified nucleosides are DNA mimics. “DNA mimic” means a nucleoside other than a DNA nucleoside wherein the nucleobase is directly linked to a carbon atom of a ring bound to a second carbon atom within the ring, wherein the second carbon atom comprises a bond to at least one hydrogen atom, wherein the nucleobase and at least one hydrogen atom are trans to one another relative to the bond between the two carbon atoms.

In certain embodiments, a DNA mimic comprises a structure represented by the formula below:

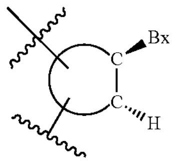

Wherein Bx represents a heterocyclic base moiety.

In certain embodiments, a DNA mimic comprises a structure represented by one of the formulas below:

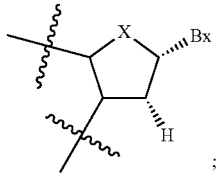

;

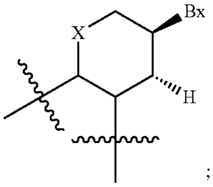

;

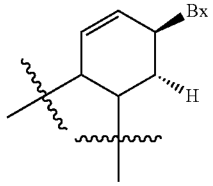

wherein X is O or S and Bx represents a heterocyclic base moiety.

In certain embodiments, a DNA mimic is a sugar surrogate. In certain embodiments, a DNA mimic is a cycohexenyl or hexitol nucleic acid. In certain embodiments, a DNA mimic is described in FIG. 1 of Vester, et. al., “Chemically modified oligonucleotides with efficient RNase H response,” *Bioorg. Med. Chem. Letters*, 2008, 18: 2296-2300, incorporated by reference herein. In certain embodiments, a DNA mimic nucleoside has a formula selected from:

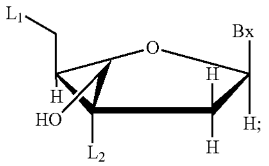
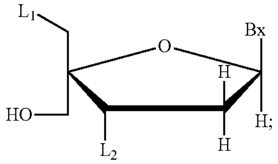
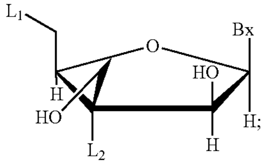
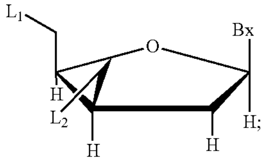
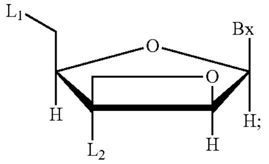
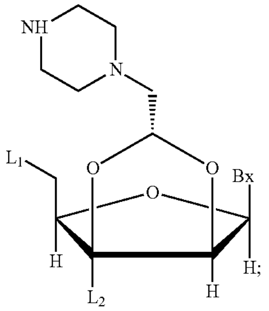

wherein Bx is a heterocyclic base moiety, and $L_1$ and $L_2$ are each, independently, an internucleoside linkage linking the modified THP nucleoside to the remainder of an oligonucleotide or one of $L_1$ and $L_2$ is an internucleoside linkage linking the modified nucleoside to the remainder of an oligonucleotide and the other of $L_1$ and $L_2$ is H, a hydroxyl protecting group, a linked conjugate group, or a 5' or 3'-terminal group. In certain embodiments, a DNA mimic is α,β-constrained nucleic acid (CAN), 2',4'-carbocyclic-LNA, or 2',4'-carbocyclic-ENA. In certain embodiments, a DNA mimic has a sugar moiety selected from among: 4'-C-hydroxymethyl-2'-deoxyribosyl, 3'-C-hydroxymethyl-2'-deoxyribosyl, 3'-C-hydroxymethyl-arabinosyl, 3'-C-2'-O-arabinosyl, 3'-C-methylene-extended-xyolosyl, 3'-C-2'-O-piperazino-arabinosyl. In certain embodiments, a DNA mimic has a sugar moiety selected from among: 2'-methylribosyl, 2'-S-methylribosyl, 2'-aminoribosyl, 2'-$NH(CH_2)$-ribosyl, 2'-$NH(CH_2)_2$-ribosyl, 2'-$CH_2$—F-ribosyl, 2'-$CHF_2$-ribosyl, 2'-$CF_3$-ribosyl, 2'=$CF_2$ ribosyl, 2'-ethylribosyl, 2'-alkenylribosyl, 2'-alkynylribosyl, 2'-O-4'-C-methyleneribosyl, 2'-cyanoarabinosyl, 2'-chloroarabinosyl, 2'-fluoroarabinosyl, 2'-bromoarabinosyl, 2'-azidoarabinosyl, 2'-methoxyarabinosyl, and 2'-arabinosyl. In certain embodiments, a DNA mimic has a sugar moiety selected from 4'-methyl-modified deoxyfuranosyl, 4'-F-deoxyfuranosyl, 4'-OMe-deoxyfuranosyl. In certain embodiments, a DNA mimic has a sugar moiety selected from among: 5'-methyl-2'-β-D-deoxyribosyl, 5'-ethyl-2'-β-D-deoxyribosyl, 5'-allyl-2'-β-D-deoxyribosyl, 2'-fluoro-β-D-arabinofuranosyl. In certain embodiments, DNA mimics are listed on page 32-33 of PCT/US00/267929 as B-form nucleotides, incorporated by reference herein in its entirety.

2. Modified Nucleobases

In certain embodiments, modified nucleobases are selected from: 5-substituted pyrimidines, 6-azapyrimidines, alkyl or alkynyl substituted pyrimidines, alkyl substituted purines, and N-2, N-6 and 0-6 substituted purines. In certain embodiments, modified nucleobases are selected from: 2-aminopropyladenine, 5-hydroxymethyl cytosine, xanthine, hypoxanthine, 2-aminoadenine, 6-N-methylguanine, 6-N-methyladenine, 2-propyladenine, 2-thiouracil, 2-thiothymine and 2-thiocytosine, 5-propynyl ($—C≡C—CH_3$) uracil, 5-propynylcytosine, 6-azouracil, 6-azocytosine, 6-azothymine, 5-ribosyluracil (pseudouracil), 4-thiouracil, 8-halo, 8-amino, 8-thiol, 8-thioalkyl, 8-hydroxyl, 8-aza and other 8-substituted purines, 5-halo, particularly 5-bromo, 5-trifluoromethyl, 5-halouracil, and 5-halocytosine, 7-methylguanine, 7-methyladenine, 2-F-adenine, 2-aminoadenine, 7-deazaguanine, 7-deazaadenine, 3-deazaguanine, 3-deazaadenine, 6-N-benzoyladenine, 2-N-isobutyrylguanine, 4-N-benzoylcytosine, 4-N-benzoyluracil, 5-methyl 4-N-benzoylcytosine, 5-methyl 4-N-benzoyluracil, universal bases, hydrophobic bases, promiscuous bases, size-expanded bases, and fluorinated bases. Further modified nucleobases include tricyclic pyrimidines, such as 1,3-diazaphenoxazine-2-one, 1,3-diazaphenothiazine-2-one and 9-(2-aminoethoxy)-1,3-diazaphenoxazine-2-one (G-clamp). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in Merigan et al., U.S. Pat. No. 3,687,808, those disclosed in *The Concise Encyclopedia Of Polymer Science And Engineering, Kroschwitz*, J. I., Ed., John Wiley & Sons, 1990, 858-859; Englisch et al., *Angewandte Chemie*, International Edition, 1991, 30, 613; Sanghvi, Y. S., Chapter 15, *Antisense Research and Applications*, Crooke, S. T. and Lebleu, B., Eds., CRC Press, 1993, 273-288; and those disclosed in Chapters 6 and 15, *Antisense Drug Technology*, Crooke S. T., Ed., CRC Press, 2008, 163-166 and 442-443. In certain embodiments, modified nucleosides comprise double-headed nucleosides having two nucleobases. Such compounds are described in detail in Sorinaset al., *J. Org. Chem,* 2014 79: 8020-8030.

Publications that teach the preparation of certain of the above noted modified nucleobases as well as other modified nucleobases include without limitation, Manoharan et al., US2003/0158403; Manoharan et al., US2003/0175906; Dinh et al., U.S. Pat. No. 4,845,205; Spielvogel et al., U.S. Pat. No. 5,130,302; Rogers et al., U.S. Pat. No. 5,134,066; Bischofberger et al., U.S. Pat. No. 5,175,273; Urdea et al., U.S. Pat. No. 5,367,066; Benner et al., U.S. Pat. No. 5,432,272; Matteucci et al., U.S. Pat. No. 5,434,257; Gmeiner et al., U.S. Pat. No. 5,457,187; Cook et al., U.S. Pat. No. 5,459,255; Froehler et al., U.S. Pat. No. 5,484,908; Matteucci et al., U.S. Pat. No. 5,502,177; Hawkins et al., U.S. Pat. No. 5,525,711; Haralambidis et al., U.S. Pat. No. 5,552,540; Cook et al., U.S. Pat. No. 5,587,469; Froehler et al., U.S. Pat. No. 5,594,121; Switzer et al., U.S. Pat. No.

5,596,091; Cook et al., U.S. Pat. No. 5,614,617; Froehler et al., U.S. Pat. No. 5,645,985; Cook et al., U.S. Pat. No. 5,681,941; Cook et al., U.S. Pat. No. 5,811,534; Cook et al., U.S. Pat. No. 5,750,692; Cook et al., U.S. Pat. No. 5,948,903; Cook et al., U.S. Pat. No. 5,587,470; Cook et al., U.S. Pat. No. 5,457,191; Matteucci et al., U.S. Pat. No. 5,763,588; Froehler et al., U.S. Pat. No. 5,830,653; Cook et al., U.S. Pat. No. 5,808,027; Cook et al., U.S. Pat. No. 6,166,199; and Matteucci et al., U.S. Pat. No. 6,005,096.

In certain embodiments, compounds comprise or consist of a modified oligonucleotide complementary to an target nucleic acid comprising one or more modified nucleobases. In certain embodiments, the modified nucleobase is 5-methylcytosine. In certain embodiments, each cytosine is a 5-methylcytosine.

B. Modified Internucleoside Linkages

In certain embodiments, compounds described herein having one or more modified internucleoside linkages are selected over compounds having only phosphodiester internucleoside linkages because of desirable properties such as, for example, enhanced cellular uptake, enhanced affinity for target nucleic acids, and increased stability in the presence of nucleases.

In certain embodiments, compounds comprise or consist of a modified oligonucleotide complementary to a target nucleic acid comprising one or more modified internucleoside linkages. In certain embodiments, the modified internucleoside linkages are phosphorothioate linkages. In certain embodiments, each internucleoside linkage of an antisense compound is a phosphorothioate internucleoside linkage.

In certain embodiments, nucleosides of modified oligonucleotides may be linked together using any internucleoside linkage. The two main classes of internucleoside linkages are defined by the presence or absence of a phosphorus atom. Representative phosphorus-containing internucleoside linkages include unmodified phosphodiester internucleoside linkages, modified phosphotriesters such as THP phosphotriester and isopropyl phosphotriester, phosphonates such as methylphosphonate, isopropyl phosphonate, isobutyl phosphonate, and phosphonoacetate, phosphoramidates, phosphorothioate, and phosphorodithioate ("HS—P=S"). Representative non-phosphorus containing internucleoside linkages include but are not limited to methylenemethylimino ($—CH_2—N(CH_3)—O—CH_2—$), thiodiester, thionocarbamate (—O—C(=O)(NH)—S—); siloxane ($—O—SiH_2—O—$); formacetal, thioacetamido (TANA), alt-thioformacetal, glycine amide, and N,N'-dimethylhydrazine ($—CH_2—N(CH_3)—N(CH_3)—$). Modified internucleoside linkages, compared to naturally occurring phosphate linkages, can be used to alter, typically increase, nuclease resistance of the oligonucleotide. Methods of preparation of phosphorous-containing and non-phosphorous-containing internucleoside linkages are well known to those skilled in the art.

Representative internucleoside linkages having a chiral center include but are not limited to alkylphosphonates and phosphorothioates. Modified oligonucleotides comprising internucleoside linkages having a chiral center can be prepared as populations of modified oligonucleotides comprising stereorandom internucleoside linkages, or as populations of modified oligonucleotides comprising phosphorothioate linkages in particular stereochemical configurations. In certain embodiments, populations of modified oligonucleotides comprise phosphorothioate internucleoside linkages wherein all of the phosphorothioate internucleoside linkages are stereorandom. Such modified oligonucleotides can be generated using synthetic methods that result in random selection of the stereochemical configuration of each phosphorothioate linkage. All phosphorothioate linkages described herein are stereorandom unless otherwise specified. Nonetheless, as is well understood by those of skill in the art, each individual phosphorothioate of each individual oligonucleotide molecule has a defined stereoconfiguration. In certain embodiments, populations of modified oligonucleotides are enriched for modified oligonucleotides comprising one or more particular phosphorothioate internucleoside linkages in a particular, independently selected stereochemical configuration. In certain embodiments, the particular configuration of the particular phosphorothioate linkage is present in at least 65% of the molecules in the population. In certain embodiments, the particular configuration of the particular phosphorothioate linkage is present in at least 70% of the molecules in the population. In certain embodiments, the particular configuration of the particular phosphorothioate linkage is present in at least 80% of the molecules in the population. In certain embodiments, the particular configuration of the particular phosphorothioate linkage is present in at least 90% of the molecules in the population. In certain embodiments, the particular configuration of the particular phosphorothioate linkage is present in at least 99% of the molecules in the population. Such chirally enriched populations of modified oligonucleotides can be generated using synthetic methods known in the art, e.g., methods described in Oka et al., *JACS* 125, 8307 (2003), Wan et al. *Nuc. Acid. Res.* 42, 13456 (2014), and WO 2017/015555. In certain embodiments, a population of modified oligonucleotides is enriched for modified oligonucleotides having at least one indicated phosphorothioate in the (Sp) configuration. In certain embodiments, a population of modified oligonucleotides is enriched for modified oligonucleotides having at least one phosphorothioate in the (Rp) configuration. In certain embodiments, modified oligonucleotides comprising (Rp) and/or (Sp) phosphorothioates comprise one or more of the following formulas, respectively, wherein "B" indicates a nucleobase:

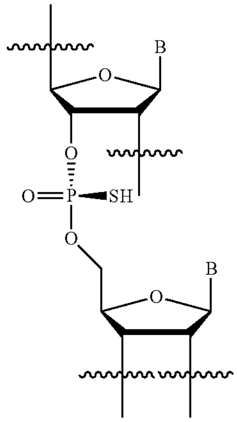

($R_p$)

-continued ($S_p$)

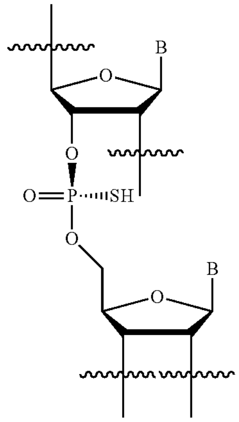

Unless otherwise indicated, chiral internucleoside linkages of modified oligonucleotides described herein can be stereorandom or in a particular stereochemical configuration.

Neutral internucleoside linkages include, without limitation, phosphotriesters, phosphonates, MMI (3'-$CH_2$—N($CH_3$)—O-5'), amide-3 (3'-$CH_2$—C(═O)—N(H)-5'), amide-4 (3'-$CH_2$—N(H)—C(═O)-5'), formacetal (3'-O—$CH_2$—O-5), methoxypropyl, and thioformacetal (3'-S—$CH_2$—O-5'). Further neutral internucleoside linkages include nonionic linkages comprising siloxane (dialkylsiloxane), carboxylate ester, carboxamide, sulfide, sulfonate ester and amides (See for example: Carbohydrate Modifications in Antisense Research; Y. S. Sanghvi and P. D. Cook, Eds., ACS Symposium Series 580; Chapters 3 and 4, 40-65). Further neutral internucleoside linkages include nonionic linkages comprising mixed N, O, S and $CH_2$ component parts.

In certain embodiments, nucleic acids can be linked 2' to 5' rather than the standard 3' to 5' linkage. Such a linkage is illustrated below.

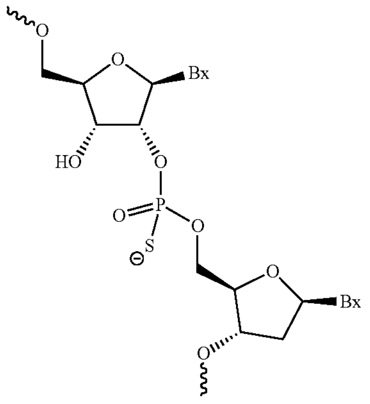

In the context of a nucleoside and/or an oligonucleotide, a non-bicyclic, 2'-linked modified furanosyl sugar moiety is represented by formula IX:

IX

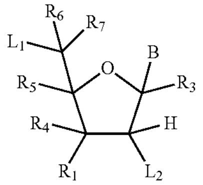

wherein B is a nucleobase; L1 is an internucleoside linkage, a terminal group, a conjugate group, or a hydroxyl group and L2 is an internucleoside linkage. The stereochemistry is not defined unless otherwise noted.

In certain embodiments, nucleosides can be linked by vinicinal 2', 3'-phosphodiester bonds. In certain such embodiments, the nucleosides are threofuranosyl nucleosides (TNA; see Bala, et al., *J Org. Chem.* 2017, 82:5910-5916). A TNA linkage is shown below.

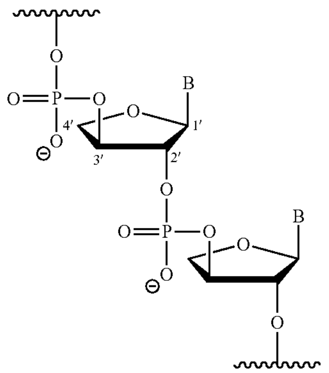

threose nucleic acid
(TNA)

Additional modified linkages include α,β-D-CNA type linkages and related comformationally-constrained linkages, shown below. Synthesis of such molecules has been described previously (see Dupouy, et al. *Angew, Chem. Int. Ed. Engl.,* 2014, 45: 3623-3627; Borsting, et al. *Tetahedron,* 2004, 60:10955-10966; Ostergaard, et al., *ACS Chem. Biol.* 2014, 9: 1975-1979; Dupouy, et al., *Eur. J. Org. Chem.,* 2008, 1285-1294; Martinez, et al., *PLoS One,* 2011, 6:e25510; Dupouy, of al., *Eur. J Org. Chem.,* 2007, 5256-5264; Boissonnet, et al., *New J Chem.,* 2011, 35: 1528-1533.)

($R_{C5'}$, $R_P$)

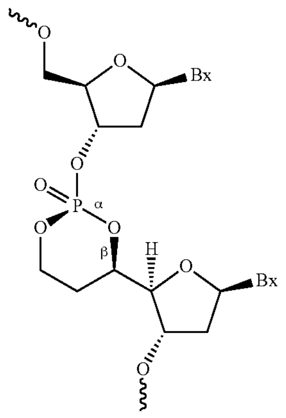

α,β-D-CNA

-continued ($S_{C5'}$, $R_P$)

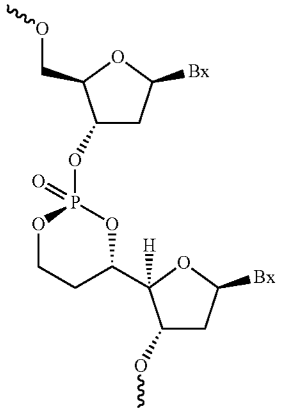

α,β-D-CNA

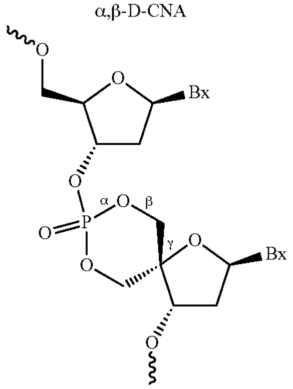

α,β,γ-D-CNA

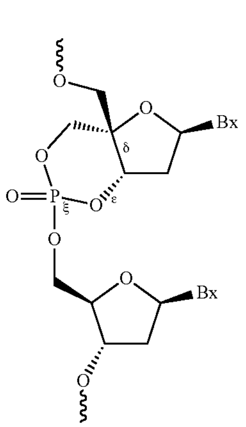

δ,ε,ξ-D-CNA

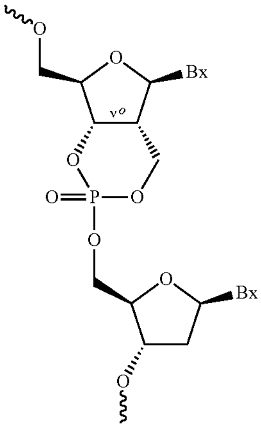

$\nu^o$,ε,ξ-D-CNA

II. CERTAIN MOTIFS

In certain embodiments, oligomeric compounds described herein comprise or consist of oligonucleotides. Oligonucleotides can have a motif, e.g. a pattern of unmodified and/or modified sugar moieties, nucleobases, and/or internucleoside linkages. In certain embodiments, modified oligonucleotides comprise one or more modified nucleoside comprising a modified sugar. In certain embodiments, modified oligonucleotides comprise one or more modified nucleosides comprising a modified nucleobase. In certain embodiments, modified oligonucleotides comprise one or more modified internucleoside linkage. In such embodiments, the modified, unmodified, and differently modified sugar moieties, nucleobases, and/or internucleoside linkages of a modified oligonucleotide define a pattern or motif. In certain embodiments, the patterns or motifs of sugar moieties, nucleobases, and internucleoside linkages are each independent of one another. Thus, a modified oligonucleotide may be described by its sugar motif, nucleobase motif and/or internucleoside linkage motif (as used herein, nucleobase motif describes the modifications to the nucleobases independent of the sequence of nucleobases).

A. Certain Sugar Motifs

In certain embodiments, oligomeric compounds described herein comprise or consist of oligonucleotides. In certain embodiments, oligonucleotides comprise one or more type of modified sugar and/or unmodified sugar moiety arranged along the oligonucleotide or region thereof in a defined pattern or sugar motif. In certain instances, such sugar motifs include but are not limited to any of the sugar modifications discussed herein.

In certain embodiments, a modified oligonucleotide comprises or consists of a gapmer. The sugar motif of a gapmer defines the regions of the gapmer: 5'-region, central region, and 3'-region. The positions of the nucleosides within each region are counted beginning at the 5'-end of each region. Each region of a gapmer is connected by an internucleoside linkage, as are the nucleosides within each region. Each nucleoside of the 5'-region and each nucleoside of the 3'-region comprise a 2'-modified furanosyl sugar moiety. The nucleoside at the first position (position 1) of the central region and the nucleoside at the last position of the central region are adjacent to the 5'-region and 3'-region, respectively, and each comprise a sugar moiety independently selected from a 2'-deoxyfuranosyl sugar moiety or a sugar surrogate. Unlike the nucleosides at the first and last positions of the central region, the nucleosides at the other positions within the central region may comprise a 2'-modified furanosyl sugar moiety. In certain embodiments, the 2'-modified furanosyl sugar moiety in the 5' and 3'-regions is a 4'-2'-bicyclic sugar moiety. In certain embodiments, the 2'-modified furanosyl sugar moiety in the 5' and 3' regions is a cEt. In certain embodiments, the 2'-modified furanosyl sugar moiety is a 2'-MOE furanosyl sugar moiety. In certain embodiments, each nucleoside within the gap supports RNase H cleavage. In certain embodiments, a plurality of nucleosides within the gap support RNase H cleavage. In certain embodiments, the nucleoside at the first and last positions of the central region adjacent to the 5' and 3' regions are DNA nucleosides.

Herein, the lengths (number of nucleosides) of the three regions of a gapmer may be provided using the notation [# of nucleosides in the 5'-wing]-[# of nucleosides in the gap]-[# of nucleosides in the 3'-wing]. Thus, a 3-10-3 gapmer consists of 3 linked nucleosides in each wing and 10 linked nucleosides in the gap. Where such nomenclature is followed by a specific modification, that modification is the modification of each sugar moiety of each wing and the gap nucleosides comprise 2'-β-D-deoxyribosyl sugar moieties. Thus, a 5-10-5 MOE gapmer consists of 5 linked nucleosides comprising 2'-MOE-β-D-ribofuranosyl sugar moieties in the 5'-wing, 10 linked nucleosides comprising a 2'-β-D-deoxyribosyl sugar moiety in the gap, and 5 linked nucleosides comprising 2'-MOE-β-D-ribofuranosyl sugar moieties in the 3'-wing. A 3-10-3 cEt gapmer consists of 3 linked nucleosides comprising a cEt in the 5'-wing, 10 linked nucleosides comprising a 2'-β-D-deoxyribosyl sugar moiety in the gap, and 3 linked nucleosides comprising a cEt in the 3'-wing.

In certain embodiments, modified oligonucleotides are 5-10-5 MOE gapmers. In certain embodiments, modified oligonucleotides are 3-10-3 BNA gapmers. In certain embodiments, modified oligonucleotides are 3-10-3 cEt gapmers. In certain embodiments, modified oligonucleotides are 3-10-3 LNA gapmers.

The sugar motif of a 3-10-3 cEt gapmer may also be denoted by the notation kkk-d(10)-kkk, wherein each "k" represents a cEt and each "d" represents a 2'-β-D-deoxyribosyl sugar moiety. This sugar motif is independent of the nucleobase sequence, the internucleoside linkage motif, and any nucleobase modifications. A 5-10-5 MOE gapmer may be denoted by the notation eeeee-d(10)-eeeee or e(5)-d(10)-e(5), wherein each "e" represents a 2'-MOE-β-D-ribofuranosyl sugar moiety, and each "d" represents a 2'-β-D-deoxyribosyl sugar moiety.

B. Certain Nucleobase Motifs

In certain embodiments, oligomeric compounds described herein comprise or consist of oligonucleotides. In certain embodiments, oligonucleotides comprise modified and/or unmodified nucleobases arranged along the oligonucleotide or region thereof in a defined pattern or motif. In certain embodiments, each nucleobase is modified. In certain embodiments, none of the nucleobases are modified. In certain embodiments, each purine or each pyrimidine is modified. In certain embodiments, each adenine is modified. In certain embodiments, each guanine is modified. In certain embodiments, each thymine is modified. In certain embodiments, each uracil is modified. In certain embodiments, each cytosine is modified. In certain embodiments, some or all of the cytosine nucleobases in a modified oligonucleotide are 5-methylcytosines.

In certain embodiments, modified oligonucleotides comprise a block of modified nucleobases. In certain such embodiments, the block is at the 3'-end of the oligonucleotide. In certain embodiments the block is within 3 nucleosides of the 3'-end of the oligonucleotide. In certain embodiments, the block is at the 5'-end of the oligonucleotide. In certain embodiments the block is within 3 nucleosides of the 5'-end of the oligonucleotide.

In certain embodiments, one nucleoside comprising a modified nucleobase is in the central region of a modified oligonucleotide. In certain such embodiments, the sugar moiety of said nucleoside is a 2'-β-D-deoxyribosyl moiety. In certain such embodiments, the modified nucleobase is selected from: 5-methyl cytosine, 2-thiopyrimidine, 2-thiothymine, 6-methyladenine, inosine, pseudouracil, or 5-propynepyrimidine.

C. Certain Internucleoside Linkage Motifs

In certain embodiments, oligomeric compounds described herein comprise or consist of oligonucleotides. In certain embodiments, oligonucleotides comprise modified and/or unmodified internucleoside linkages arranged along the oligonucleotide or region thereof in a defined pattern or motif. In certain embodiments, each internucleoside linkage is a phosphodiester internucleoside linkage (P═O). In certain embodiments, each internucleoside linkage of a modified oligonucleotide is a phosphorothioate internucleoside linkage (P═S). In certain embodiments, each internucleoside linkage of a modified oligonucleotide is independently selected from a phosphorothioate internucleoside linkage and phosphodiester internucleoside linkage. In certain embodiments, each phosphorothioate internucleoside linkage is independently selected from a stereorandom phosphorothioate, a (Sp) phosphorothioate, and a (Rp) phosphorothioate. In certain embodiments, the internucleoside linkages within the central region of a modified oligonucleotide are all modified. In certain such embodiments, some or all of the internucleoside linkages in the 5'-region and 3'-region are unmodified phosphate linkages. In certain embodiments, the terminal internucleoside linkages are modified. In certain embodiments, the internucleoside linkage motif comprises at least one phosphodiester internucleoside linkage in at least one of the 5'-region and the 3'-region, wherein the at least one phosphodiester linkage is not a terminal internucleoside linkage, and the remaining internucleoside linkages are phosphorothioate internucleoside linkages. In certain such embodiments, all of the phosphorothioate linkages are stereorandom. In certain embodiments, all of the phosphorothioate linkages in the 5'-region and 3'-region are (Sp) phosphorothioates, and the central region comprises at least one Sp, Sp, Rp motif. In certain embodiments, populations of modified oligonucleotides are enriched for modified oligonucleotides comprising such internucleoside linkage motifs.

In certain embodiments, oligonucleotides comprise a region having an alternating internucleoside linkage motif. In certain embodiments, oligonucleotides comprise a region of uniformly modified internucleoside linkages. In certain such embodiments, the internucleoside linkages are phosphorothioate internucleoside linkages. In certain embodiments, all of the internucleoside linkages of the oligonucleotide are phosphorothioate internucleoside linkages. In certain embodiments, each internucleoside linkage of the oligonucleotide is selected from phosphodiester or phosphate and phosphorothioate. In certain embodiments, each internucleoside linkage of the oligonucleotide is selected from phosphodiester or phosphate and phosphorothioate and at least one internucleoside linkage is phosphorothioate.

In certain embodiments, the oligonucleotide comprises at least 6 phosphorothioate internucleoside linkages. In certain embodiments, the oligonucleotide comprises at least 8 phosphorothioate internucleoside linkages. In certain embodiments, the oligonucleotide comprises at least 10 phosphorothioate internucleoside linkages. In certain embodiments, the oligonucleotide comprises at least one block of at least 6 consecutive phosphorothioate internucleoside linkages. In certain embodiments, the oligonucleotide comprises at least one block of at least 8 consecutive phosphorothioate internucleoside linkages. In certain embodiments, the oligonucleotide comprises at least one block of at least 10 consecutive phosphorothioate internucleoside linkages. In certain embodiments, the oligonucleotide comprises at least block of at least one 12 consecutive phosphorothioate internucleoside linkages. In certain such embodiments, at least one such block is located at the 3' end of the oligonucleotide. In certain such embodiments, at least one such block is located within 3 nucleosides of the 3' end of the oligonucleotide.

In certain embodiments, oligonucleotides comprise one or more methylphosphonate linkages. In certain embodiments, modified oligonucleotides comprise a linkage motif comprising all phosphorothioate linkages except for one or two methylphosphonate linkages. In certain embodiments, one methylphosphonate linkage is in the central region of an oligonucleotide.

In certain embodiments, it is desirable to arrange the number of phosphorothioate internucleoside linkages and phosphodiester internucleoside linkages to maintain nuclease resistance. In certain embodiments, it is desirable to arrange the number and position of phosphorothioate internucleoside linkages and the number and position of phosphodiester internucleoside linkages to maintain nuclease resistance. In certain embodiments, the number of phosphorothioate internucleoside linkages may be decreased and the number of phosphodiester internucleoside linkages may be increased. In certain embodiments, the number of phosphorothioate internucleoside linkages may be decreased and the number of phosphodiester internucleoside linkages may be increased while still maintaining nuclease resistance. In certain embodiments it is desirable to decrease the number of phosphorothioate internucleoside linkages while retaining nuclease resistance. In certain embodiments it is desirable to increase the number of phosphodiester internucleoside linkages while retaining nuclease resistance.

III. CERTAIN MODIFIED OLIGONUCLEOTIDES

In certain embodiments, oligomeric compounds described herein comprise or consist of modified oligonucleotides. In certain embodiments, the above modifications (sugar, nucleobase, internucleoside linkage) are incorporated into a modified oligonucleotide. In certain embodiments, modified oligonucleotides are characterized by their modifications, motifs, and overall lengths. In certain embodiments, such parameters are each independent of one another. Thus, unless otherwise indicated, each internucleoside linkage of a modified oligonucleotide may be modified or unmodified and may or may not follow the modification pattern of the sugar moieties. Likewise, such modified oligonucleotides may comprise one or more modified nucleobase independent of the pattern of the sugar modifications. Furthermore, in certain instances, a modified oligonucleotide is described by an overall length or range and by lengths or length ranges of two or more regions (e.g., a region of nucleosides having specified sugar modifications), in such circumstances it may be possible to select numbers for each range that result in an oligonucleotide having an overall length falling outside the specified range. In such circumstances, both elements must be satisfied. For example, in certain embodiments, a modified oligonucleotide consists of 15-20 linked nucleosides and has a sugar motif consisting of three regions or segments, A, B, and C, wherein region or segment A consists of 2-6 linked nucleosides having a specified sugar moiety, region or segment B consists of 6-10 linked nucleosides having a specified sugar moiety, and region or segment C consists of 2-6 linked nucleosides having a specified sugar moiety. Such embodiments do not include modified oligonucleotides where A and C each consist of 6 linked nucleosides and B consists of 10 linked nucleosides (even though those numbers of nucleosides are permitted within the requirements for A, B, and C) because the overall length of such oligonucleotide is 22, which exceeds the upper limit of 20 for the overall length of the modified oligonucleotide. Unless otherwise indicated, all modifications are independent of nucleobase sequence except that the modified nucleobase 5-methylcytosine is necessarily a “C” in an oligonucleotide sequence. In certain embodiments, when a DNA nucleoside or DNA-like nucleoside that comprises a T in a DNA sequence is replaced with a RNA-like nucleoside, including a nucleoside comprising a 2'-OMe modified sugar moiety, the nucleobase T is replaced with the nucleobase U. Each of these compounds has an identical target RNA.

In certain embodiments, oligonucleotides consist of X to Y linked nucleosides, where X represents the fewest number of nucleosides in the range and Y represents the largest number nucleosides in the range. In certain such embodiments, X and Y are each independently selected from 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50; provided that $X \leq Y$. For example, in certain embodiments, oligonucleotides consist of 12 to 13, 12 to 14, 12 to 15, 12 to 16, 12 to 17, 12 to 18, 12 to 19, 12 to 20, 12 to 21, 12 to 22, 12 to 23, 12 to 24, 12 to 25, 12 to 26, 12 to 27, 12 to 28, 12 to 29, 12 to 30, 13 to 14, 13 to 15, 13 to 16, 13 to 17, 13 to 18, 13 to 19, 13 to 20, 13 to 21, 13 to 22, 13 to 23, 13 to 24, 13 to 25, 13 to 26, 13 to 27, 13 to 28, 13 to 29, 13 to 30, 14 to 15, 14 to 16, 14 to 17, 14 to 18, 14 to 19, 14 to 20, 14 to 21, 14 to 22, 14 to 23, 14 to 24, 14 to 25, 14 to 26, 14 to 27, 14 to 28, 14 to 29, 14 to 30, 15 to 16, 15 to 17, 15 to 18, 15 to 19, 15 to 20, 15 to 21, 15 to 22, 15 to 23, 15 to 24, 15 to 25, 15 to 26, 15 to 27, 15 to 28, 15 to 29, 15 to 30, 16 to 17, 16 to 18, 16 to 19, 16 to 20, 16 to 21, 16 to 22, 16 to 23, 16 to 24, 16 to 25, 16 to 26, 16 to 27, 16 to 28, 16 to 29, 16 to 30, 17 to 18, 17 to 19, 17 to 20, 17 to 21, 17 to 22, 17 to 23, 17 to 24, 17 to 25, 17 to 26, 17 to 27, 17 to 28, 17 to 29, 17 to 30, 18 to 19, 18 to 20, 18 to 21, 18 to 22, 18 to 23, 18 to 24, 18 to 25, 18 to 26, 18 to 27, 18 to 28, 18 to 29, 18 to 30, 19 to 20, 19 to 21, 19 to 22, 19 to 23, 19 to 24, 19 to 25, 19 to 26, 19 to 29, 19 to 28, 19 to 29, 19 to 30, 20 to 21, 20 to 22, 20 to 23, 20 to 24, 20 to 25, 20 to 26, 20 to 27, 20 to 28, 20 to 29, 20 to 30, 21 to 22, 21 to 23, 21 to 24, 21 to 25, 21 to 26, 21 to 27, 21 to 28, 21 to 29, 21 to 30, 22 to 23, 22 to 24, 22 to 25, 22 to 26, 22 to 27, 22 to 28, 22 to 29, 22 to 30, 23 to 24, 23 to 25, 23 to 26, 23 to 27, 23 to 28, 23 to 29, 23 to 30, 24 to 25, 24 to 26, 24 to 27, 24 to 28, 24 to 29, 24 to 30, 25 to 26, 25 to 27, 25 to 28, 25 to 29, 25 to 30, 26 to 27, 26 to 28, 26 to 29, 26 to 30, 27 to 28, 27 to 29, 27 to 30, 28 to 29, 28 to 30, or 29 to 30 linked nucleosides.

In certain embodiments oligonucleotides have a nucleobase sequence that is complementary to a second oligonucleotide or an identified reference nucleic acid, such as a target nucleic acid. In certain embodiments, a region of an oligonucleotide has a nucleobase sequence that is complementary to a second oligonucleotide or an identified reference nucleic acid, such as a target nucleic acid. In certain embodiments, the nucleobase sequence of a region or entire length of an oligonucleotide is at least 70%, at least 80%, at least 90%, at least 95%, or 100% complementary to the second oligonucleotide or nucleic acid, such as a target nucleic acid.

IV. CERTAIN CONJUGATED COMPOUNDS

In certain embodiments, the oligomeric compounds described herein comprise or consist of an oligonucleotide (modified or unmodified) and optionally one or more conjugate groups and/or terminal groups. Conjugate groups consist of one or more conjugate moiety and a conjugate linker that links the conjugate moiety to the oligonucleotide. Conjugate groups may be attached to either or both ends of an oligonucleotide and/or at any internal position. In certain embodiments, conjugate groups are attached to the 2'-position of a nucleoside of a modified oligonucleotide. In certain embodiments, conjugate groups that are attached to either or both ends of an oligonucleotide are terminal groups. In certain such embodiments, conjugate groups or terminal groups are attached at the 3' and/or 5'-end of oligonucleotides. In certain such embodiments, conjugate groups (or terminal groups) are attached at the 3'-end of oligonucleotides. In certain embodiments, conjugate groups are attached near the 3'-end of oligonucleotides. In certain embodiments, conjugate groups (or terminal groups) are attached at the 5'-end of oligonucleotides. In certain embodiments, conjugate groups are attached near the 5'-end of oligonucleotides.

Examples of terminal groups include but are not limited to conjugate groups, capping groups, phosphate moieties, protecting groups, modified or unmodified nucleosides, and two or more nucleosides that are independently modified or unmodified.

A. Certain Conjugate Groups

In certain embodiments, oligonucleotides are covalently attached to one or more conjugate groups. In certain embodiments, conjugate groups modify one or more properties of the attached oligonucleotide, including but not limited to pharmacodynamics, pharmacokinetics, stability, binding, absorption, tissue distribution, cellular distribution, cellular uptake, charge and clearance. In certain embodiments, conjugate groups impart a new property on the attached oligonucleotide, e.g., fluorophores or reporter groups that enable detection of the oligonucleotide.

Certain conjugate groups and conjugate moieties have been described previously, for example: cholesterol moiety (Letsinger et al., *Proc. Natl. Acad. Sci. USA,* 1989, 86, 6553-6556), cholic acid (Manoharan et al., *Bioorg. Med. Chem. Lett.,* 1994, 4, 1053-1060), a thioether, e.g., hexyl-S-tritylthiol (Manoharan et al., *Ann. N.Y. Acad. Sci.,* 1992, 660, 306-309; Manoharan et al., *Bioorg. Med. Chem. Lett.,* 1993, 3, 2765-2770), a thiocholesterol (Oberhauser et al., *Nucl. Acids Res.,* 1992, 20, 533-538), an aliphatic chain, e.g., do-decan-diol or undecyl residues (Saison-Behmoaras et al., *EMBO* 1, 1991, 10, 1111-1118; Kabanov et al., *FEBS Lett.,* 1990, 259, 327-330; Svinarchuk et al., *Biochimie,* 1993, 75, 49-54), a phospholipid, e.g., di-hexadecyl-rac-glycerol or triethyl-ammonium 1,2-di-O-hexadecyl-rac-glycero-3-H-phosphonate (Manoharan et al., *Tetrahedron Lett.,* 1995, 36, 3651-3654; Shea et al., *Nucl. Acids Res.,* 1990, 18, 3777-3783), a polyamine or a polyethylene glycol chain (Manoharan et al., *Nucleosides & Nucleotides,* 1995, 14, 969-973), or adamantane acetic, a palmityl moiety (Mishra et al., *Biochim. Biophys. Acta,* 1995, 1264, 229-237), an octadecylamine or hexylamino-carbonyl-oxycholesterol moiety (Crooke et al., *J. Pharmacol. Exp. Ther.,* 1996, i, 923-937), a tocopherol group (Nishina et al., *Molecular Therapy Nucleic Acids,* 2015, 4, e220; doi:10.1038/mtna.2014.72 and Nishina et al., *Molecular Therapy,* 2008, 16, 734-740), or a GalNAc cluster (e.g., WO2014/179620).

1. Conjugate Moieties

Conjugate moieties include, without limitation, intercalators, reporter molecules, polyamines, polyamides, peptides, carbohydrates (e.g., GalNAc), vitamin moieties, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins, fluorophores, and dyes.

In certain embodiments, a conjugate moiety comprises an active drug substance, for example, aspirin, warfarin, phenylbutazone, ibuprofen, suprofen, fen-bufen, ketoprofen, (S)-(+)-pranoprofen, carprofen, dansylsarcosine, 2,3,5-triiodobenzoic acid, fingolimod, flufenamic acid, folinic acid, a benzothiadiazide, chlorothiazide, a diazepine, indomethicin, a barbiturate, a cephalosporin, a sulfa drug, an antidiabetic, an antibacterial or an antibiotic.

2. Conjugate Linkers

Conjugate moieties are attached to oligonucleotides through conjugate linkers. In certain oligomeric compounds, a conjugate linker is a single chemical bond (i.e. conjugate moiety is attached to an oligonucleotide via a conjugate linker through a single bond). In certain embodiments, the conjugate linker comprises a chain structure, such as a hydrocarbyl chain, or an oligomer of repeating units such as ethylene glycol, nucleosides, or amino acid units.

In certain embodiments, a conjugate linker comprises one or more groups selected from alkyl, amino, oxo, amide, disulfide, polyethylene glycol, ether, thioether, and hydroxylamino. In certain such embodiments, the conjugate linker comprises groups selected from alkyl, amino, oxo, amide and ether groups. In certain embodiments, the conjugate linker comprises groups selected from alkyl and amide groups. In certain embodiments, the conjugate linker comprises groups selected from alkyl and ether groups. In certain embodiments, the conjugate linker comprises at least one phosphorus moiety. In certain embodiments, the conjugate linker comprises at least one phosphate group. In certain embodiments, the conjugate linker includes at least one neutral linking group.

In certain embodiments, conjugate linkers, including the conjugate linkers described above, are bifunctional linking moieties, e.g., those known in the art to be useful for attaching conjugate groups to oligomeric compounds, such as the oligonucleotides provided herein. In general, a bifunctional linking moiety comprises at least two functional groups. One of the functional groups is selected to bind to a particular site on an oligomeric compound and the other is selected to bind to a conjugate group. Examples of functional groups used in a bifunctional linking moiety include but are not limited to electrophiles for reacting with nucleophilic groups and nucleophiles for reacting with electrophilic groups. In certain embodiments, bifunctional linking moieties comprise one or more groups selected from amino, hydroxyl, carboxylic acid, thiol, alkyl, alkenyl, and alkynyl.

Examples of conjugate linkers include but are not limited to pyrrolidine, 8-amino-3,6-dioxaoctanoic acid (ADO), succinimidyl 4-(N-maleimidomethyl) cyclohexane-1-carboxylate (SMCC) and 6-aminohexanoic acid (AHEX or AHA). Other conjugate linkers include but are not limited to substituted or unsubstituted $C_1$-$C_{10}$ alkyl, substituted or unsubstituted $C_2$-$C_{10}$ alkenyl or substituted or unsubstituted $C_2$-$C_{10}$ alkynyl, wherein a nonlimiting list of preferred substituent groups includes hydroxyl, amino, alkoxy, carboxy, benzyl, phenyl, nitro, thiol, thioalkoxy, halogen, alkyl, aryl, alkenyl and alkynyl.

In certain embodiments, conjugate linkers comprise 1-10 linker-nucleosides. In certain embodiments, such linker-nucleosides are modified nucleosides. In certain embodiments such linker-nucleosides comprise a modified sugar moiety. In certain embodiments, linker-nucleosides are unmodified. In certain embodiments, linker-nucleosides comprise an optionally protected heterocyclic base selected from a purine, substituted purine, pyrimidine or substituted pyrimidine. In certain embodiments, a cleavable moiety is a nucleoside selected from uracil, thymine, cytosine, 4-N-benzoylcytosine, 5-methylcytosine, 4-N-benzoyl-5-methylcytosine, adenine, 6-N-benzoyladenine, guanine and 2-N-isobutyrylguanine. It is typically desirable for linker-nucleosides to be cleaved from the oligomeric compound after it reaches a target tissue. Accordingly, linker-nucleosides are typically linked to one another and to the remainder of the oligomeric compound through cleavable bonds. In certain embodiments, such cleavable bonds are phosphodiester bonds.

Herein, linker-nucleosides are not considered to be part of the oligonucleotide. Accordingly, in embodiments in which an oligomeric compound comprises an oligonucleotide consisting of a specified number or range of linked nucleosides and/or a specified percent complementarity to a reference nucleic acid and the oligomeric compound also comprises a conjugate group comprising a conjugate linker comprising linker-nucleosides, those linker-nucleosides are not counted toward the length of the oligonucleotide and are not used in determining the percent complementarity of the oligonucleotide for the reference nucleic acid. For example, an oligomeric compound may comprise (1) a modified oligonucleotide consisting of 8-30 nucleosides and (2) a conjugate group comprising 1-10 linker-nucleosides that are contiguous with the nucleosides of the modified oligonucleotide. The total number of contiguous linked nucleosides in such a compound is more than 30. Alternatively, an oligomeric compound may comprise a modified oligonucleotide consisting of 8-30 nucleosides and no conjugate group. The total number of contiguous linked nucleosides in such a compound is no more than 30. Unless otherwise indicated conjugate linkers comprise no more than 10 linker-nucleosides. In certain embodiments, conjugate linkers comprise no more than 5 linker-nucleosides. In certain embodiments, conjugate linkers comprise no more than 3 linker-nucleosides. In certain embodiments, conjugate linkers comprise no more than 2 linker-nucleosides. In certain embodiments, conjugate linkers comprise no more than 1 linker-nucleoside.

In certain embodiments, it is desirable for a conjugate group to be cleaved from the oligonucleotide. For example, in certain circumstances oligomeric compounds comprising a particular conjugate moiety are better taken up by a particular cell type, but once the compound has been taken up, it is desirable that the conjugate group be cleaved to release the unconjugated oligonucleotide. Thus, certain conjugate may comprise one or more cleavable moieties, typically within the conjugate linker. In certain embodiments, a cleavable moiety is a cleavable bond. In certain embodiments, a cleavable moiety is a group of atoms comprising at least one cleavable bond. In certain embodiments, a cleavable moiety comprises a group of atoms having one, two, three, four, or more than four cleavable bonds. In certain embodiments, a cleavable moiety is selectively cleaved inside a cell or subcellular compartment, such as a lysosome. In certain embodiments, a cleavable moiety is selectively cleaved by endogenous enzymes, such as nucleases.

In certain embodiments, a cleavable bond is selected from among: an amide, an ester, an ether, one or both esters of a phosphodiester, a phosphate ester, a carbamate, or a disulfide. In certain embodiments, a cleavable bond is one or both of the esters of a phosphodiester. In certain embodiments, a cleavable moiety comprises a phosphate or phosphodiester. In certain embodiments, the cleavable moiety is a phosphate or phosphodiester linkage between an oligonucleotide and a conjugate moiety or conjugate group.

In certain embodiments, a cleavable moiety comprises or consists of one or more linker-nucleosides. In certain such embodiments, one or more linker-nucleosides are linked to one another and/or to the remainder of the oligomeric compound through cleavable bonds. In certain embodiments, such cleavable bonds are unmodified phosphodiester bonds. In certain embodiments, a cleavable moiety is a nucleoside comprising a 2'-deoxyfuranosyl that is attached to either the 3' or 5'-terminal nucleoside of an oligonucleotide by a phosphodiester internucleoside linkage and covalently attached to the remainder of the conjugate linker or conjugate moiety by a phosphodiester or phosphorothioate linkage. In certain such embodiments, the cleavable moiety is a nucleoside comprising a 2'-β-D-deoxyribosyl sugar moiety. In certain such embodiments, the cleavable moiety is 2'-deoxyadenosine.

3. Certain Cell-Targeting Conjugate Moieties

In certain embodiments, a conjugate group comprises a cell-targeting conjugate moiety. In certain embodiments, a conjugate group has the general formula:

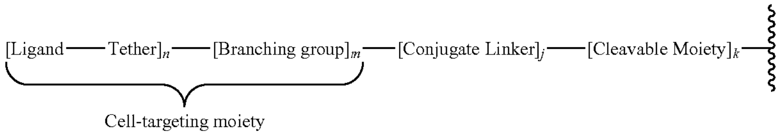

wherein n is from 1 to about 3, m is 0 when n is 1, m is 1 when n is 2 or greater, j is 1 or 0, and k is 1 or O.

In certain embodiments, n is 1, j is 1 and k is 0. In certain embodiments, n is 1, j is 0 and k is 1. In certain embodiments, n is 1, j is 1 and k is 1. In certain embodiments, n is 2, j is 1 and k is 0. In certain embodiments, n is 2, j is 0 and k is 1. In certain embodiments, n is 2, j is 1 and k is 1. In certain embodiments, n is 3, j is 1 and k is 0. In certain embodiments, n is 3, j is 0 and k is 1. In certain embodiments, n is 3, j is 1 and k is 1.

In certain embodiments, conjugate groups comprise cell-targeting moieties that have at least one tethered ligand. In certain embodiments, cell-targeting moieties comprise two tethered ligands covalently attached to a branching group. In certain embodiments, cell-targeting moieties comprise three tethered ligands covalently attached to a branching group.

In certain embodiments, the cell-targeting moiety comprises a branching group comprising one or more groups selected from alkyl, amino, oxo, amide, disulfide, polyethylene glycol, ether, thioether and hydroxylamino groups. In certain embodiments, the branching group comprises a branched aliphatic group comprising groups selected from alkyl, amino, oxo, amide, disulfide, polyethylene glycol, ether, thioether and hydroxylamino groups. In certain such embodiments, the branched aliphatic group comprises groups selected from alkyl, amino, oxo, amide and ether groups. In certain such embodiments, the branched aliphatic group comprises groups selected from alkyl, amino and ether groups. In certain such embodiments, the branched aliphatic group comprises groups selected from alkyl and ether groups. In certain embodiments, the branching group comprises a mono or polycyclic ring system.

In certain embodiments, each tether of a cell-targeting moiety comprises one or more groups selected from alkyl, substituted alkyl, ether, thioether, disulfide, amino, oxo, amide, phosphodiester, and polyethylene glycol, in any combination. In certain embodiments, each tether is a linear aliphatic group comprising one or more groups selected from alkyl, ether, thioether, disulfide, amino, oxo, amide, and polyethylene glycol, in any combination. In certain embodiments, each tether is a linear aliphatic group comprising one or more groups selected from alkyl, phosphodiester, ether, amino, oxo, and amide, in any combination. In certain embodiments, each tether is a linear aliphatic group comprising one or more groups selected from alkyl, ether, amino, oxo, and amid, in any combination. In certain embodiments, each tether is a linear aliphatic group comprising one or more groups selected from alkyl, amino, and oxo, in any combination. In certain embodiments, each tether is a linear aliphatic group comprising one or more groups selected from alkyl and oxo, in any combination. In certain embodiments, each tether is a linear aliphatic group comprising one or more groups selected from alkyl and phosphodiester, in any combination. In certain embodiments, each tether comprises at least one phosphorus linking group or neutral linking group. In certain embodiments, each tether comprises a chain from about 6 to about 20 atoms in length. In certain embodiments, each tether comprises a chain from about 10 to about 18 atoms in length. In certain embodiments, each tether comprises about 10 atoms in chain length.

In certain embodiments, each ligand of a cell-targeting moiety has an affinity for at least one type of receptor on a target cell. In certain embodiments, each ligand has an affinity for at least one type of receptor on the surface of a mammalian lung cell.

In certain embodiments, each ligand of a cell-targeting moiety is a carbohydrate, carbohydrate derivative, modified carbohydrate, polysaccharide, modified polysaccharide, or polysaccharide derivative. In certain such embodiments, the conjugate group comprises a carbohydrate cluster (see, e.g., Maier et al., "Synthesis of Antisense Oligonucleotides Conjugated to a Multivalent Carbohydrate Cluster for Cellular Targeting," *Bioconjugate Chemistry,* 2003, 14, 18-29, or Rensen et al., "Design and Synthesis of Novel N-Acetylgalactosamine-Terminated Glycolipids for Targeting of Lipoproteins to the Hepatic Asiaglycoprotein Receptor," *J Med. Chem.* 2004, 47, 5798-5808, which are incorporated herein by reference in their entirety). In certain such embodiments, each ligand is an amino sugar or a thio sugar. For example, amino sugars may be selected from any number of compounds known in the art, such as sialic acid, α-D-galactosamine, β-muramic acid, 2-deoxy-2-methylamino-L-glucopyranose, 4,6-dideoxy-4-formamido-2,3-di-O-methyl-D-mannopyranose, 2-deoxy-2-sulfoamino-D-glucopyranose and N-sulfo-D-glucosamine, and N-glycoloyl-α-neuraminic acid. For example, thio sugars may be selected from 5-Thio-β-D-glucopyranose, methyl 2,3,4-tri-O-acetyl-1-thio-6-O-trityl-α-D-glucopyranoside, 4-thio-β-D-galactopyranose, and ethyl 3,4,6,7-tetra-O-acetyl-2-deoxy-1,5-dithio-α-D-gluco-heptopyranoside.

In certain embodiments, oligomeric compounds described herein comprise a conjugate group found in any of the following references: Lee, *Carbohydr Res,* 1978, 67, 509-514; Connolly et al., *J Biol Chem,* 1982, 257, 939-945; Pavia et al., *Int J Pep Protein Res,* 1983, 22, 539-548; Lee et al., *Biochem,* 1984, 23, 4255-4261; Lee et al., *Glycoconjugate J,* 1987, 4, 317-328; Toyokuni et al., *Tetrahedron Lett,* 1990, 31, 2673-2676; Biessen et al., *J Med Chem,* 1995, 38, 1538-1546; Valentijn et al., *Tetrahedron,* 1997, 53, 759-770; Kim et al., *Tetrahedron Lett,* 1997, 38, 3487-3490; Lee et al., *Bioconjug Chem,* 1997, 8, 762-765; Kato et al., *Glycobiol,* 2001, 11, 821-829; Rensen et al., *J Biol Chem,* 2001, 276, 37577-37584; Lee et al., *Methods Enzymol,* 2003, 362, 38-43; Westerlind et al., *Glycoconj J,* 2004, 21, 227-241; Lee et al., *Bioorg Med Chem Lett,* 2006, 16(19), 5132-5135; Maierhofer et al., *Bioorg Med Chem,* 2007, 15, 7661-7676; Khorev et al., *Bioorg Med Chem,* 2008, 16, 5216-5231; Lee et al., *Bioorg Med Chem,* 2011, 19, 2494-2500; Kornilova et al., *Analyt Biochem,* 2012, 425, 43-46; Pujol et al., *Angew Chemie Int Ed Engl,* 2012, 51, 7445-7448; Biessen et al., *J Med Chem,* 1995, 38, 1846-1852; Sliedregt et al., *J Med Chem,* 1999, 42, 609-618; Rensen et al., *J Med Chem,* 2004, 47, 5798-5808; Rensen et al., *Arterioscler Thromb Vasc Biol,* 2006, 26, 169-175; van Rossenberg et al., *Gene Ther,* 2004, 11, 457-464; Sato et al., *J Am Chem Soc,* 2004, 126, 14013-14022; Lee et al., *J Org Chem,* 2012, 77, 7564-7571; Biessen et al., *FASEB J,* 2000, 14, 1784-1792; Rajur et al., *Bioconjug Chem,* 1997, 8, 935-940; Duff et al., *Methods Enzymol,* 2000, 313, 297-321; Maier et al., *Bioconjug Chem,* 2003, 14, 18-29; Jayaprakash et al., *Org Lett,* 2010, 12, 5410-5413; Manoharan, Antisense *Nucleic Acid Drug Dev,* 2002, 12, 103-128; Merwin et al., *Bioconjug Chem,* 1994, 5, 612-620; Tomiya et al., *Bioorg Med Chem,* 2013, 21, 5275-5281; International applications WO1998/013381; WO2011/038356; WO1997/046098; WO2008/098788; WO2004/101619; WO2012/037254; WO2011/120053; WO2011/100131; WO2011/163121; WO2012/177947; WO2013/033230; WO2013/075035; WO2012/083185; WO2012/083046; WO2009/082607; WO2009/134487; WO2010/144740; WO2010/148013; WO1997/020563; WO2010/088537; WO2002/043771; WO2010/129709; WO2012/068187; WO2009/126933; WO2004/024757; WO2010/054406; WO2012/089352; WO2012/089602; WO2013/166121; WO2013/165816; U.S. Pat. Nos. 4,751,219; 8,552,163; 6,908,903; 7,262,177; 5,994,517; 6,300,319; 8,106,022; 7,491,805; 7,491,805; 7,582,744; 8,137,695; 6,383,812; 6,525,031; 6,660,720; 7,723,509; 8,541,548; 8,344,125; 8,313,772; 8,349,308; 8,450,467; 8,501,930; 8,158,601; 7,262,177; 6,906,182; 6,620,916; 8,435,491; 8,404,862; 7,851,615; Published U.S. Patent Application Publications US2011/0097264; US2011/0097265; US2013/0004427; US2005/0164235; US2006/0148740; US2008/0281044; US2010/0240730; US2003/0119724; US2006/0183886; US2008/0206869; US2011/0269814; US2009/0286973; US2011/0207799; US2012/0136042; US2012/0165393; US2008/0281041; US2009/0203135; US2012/0035115; US2012/0095075; US2012/0101148; US2012/0128760; US2012/0157509; US2012/0230938; US2013/0109817; US2013/0121954; US2013/0178512; US2013/0236968; US2011/0123520; US2003/0077829; US2008/0108801; and US2009/0203132.

Compositions and Methods for Formulating Pharmaceutical Compositions

Oligomeric compounds described herein may be admixed with pharmaceutically acceptable active or inert substances for the preparation of pharmaceutical compositions. Compositions and methods for the formulation of pharmaceutical compositions are dependent upon a number of criteria, including, but not limited to, route of administration, extent of disease, or dose to be administered.

Certain embodiments provide pharmaceutical compositions comprising one or more oligomeric compounds or a salt thereof. In certain embodiments, the oligomeric compounds comprise or consist of a modified oligonucleotide. In certain such embodiments, the pharmaceutical composition comprises a suitable pharmaceutically acceptable diluent or carrier. In certain embodiments, a pharmaceutical composition comprises a sterile saline solution and one or more oligomeric compound. In certain embodiments, such pharmaceutical composition consists of a sterile saline solution and one or more oligomeric compound. In certain embodiments, the sterile saline is pharmaceutical grade saline. In certain embodiments, a pharmaceutical composition comprises one or more oligomeric compound and sterile water. In certain embodiments, a pharmaceutical composition consists of one oligomeric compound and sterile water. In certain embodiments, the sterile water is pharmaceutical grade water. In certain embodiments, a pharmaceutical composition comprises or consists of one or more oligomeric compound and phosphate-buffered saline (PBS). In certain embodiments, a pharmaceutical composition consists of one or more oligomeric compound and sterile PBS. In certain embodiments, the sterile PBS is pharmaceutical grade PBS. Compositions and methods for the formulation of pharmaceutical compositions are dependent upon a number of criteria, including, but not limited to, route of administration, extent of disease, or dose to be administered.

An oligomeric compound described herein complementary to a target nucleic acid can be utilized in pharmaceutical compositions by combining the oligomeric compound with a suitable pharmaceutically acceptable diluent or carrier and/or additional components such that the pharmaceutical composition is suitable for injection. In certain embodiments, a pharmaceutically acceptable diluent is phosphate buffered saline. Accordingly, in one embodiment, employed in the methods described herein is a pharmaceutical composition comprising an oligomeric compound complementary to a target nucleic acid and a pharmaceutically acceptable diluent. In certain embodiments, the pharmaceutically acceptable diluent is phosphate buffered saline. In certain embodiments, the oligomeric compound comprises or consists of a modified oligonucleotide provided herein.

Pharmaceutical compositions comprising oligomeric compounds provided herein encompass any pharmaceutically acceptable salts, esters, or salts of such esters, or any other oligonucleotide which, upon administration to an animal, including a human, is capable of providing (directly or indirectly) the biologically active metabolite or residue thereof. In certain embodiments, the oligomeric compound comprises or consists of a modified oligonucleotide. Accordingly, for example, the disclosure is also drawn to pharmaceutically acceptable salts of compounds, prodrugs, pharmaceutically acceptable salts of such prodrugs, and other bioequivalents. Suitable pharmaceutically acceptable salts include, but are not limited to, sodium and potassium salts.

Certain Mechanisms

In certain embodiments, oligomeric compounds described herein comprise or consist of modified oligonucleotides. In certain such embodiments, the oligomeric compounds described herein are capable of hybridizing to a target nucleic acid, resulting in at least one antisense activity. In certain embodiments, compounds described herein selectively affect one or more target nucleic acid. Such compounds comprise a nucleobase sequence that hybridizes to one or more target nucleic acid, resulting in one or more desired antisense activity and does not hybridize to one or more non-target nucleic acid or does not hybridize to one or more non-target nucleic acid in such a way that results in a significant undesired antisense activity.

In certain antisense activities, hybridization of a compound described herein to a target nucleic acid results in recruitment of a protein that cleaves the target nucleic acid. For example, certain compounds described herein result in RNase H mediated cleavage of the target nucleic acid. RNase H is a cellular endonuclease that cleaves the RNA strand of an RNA:DNA duplex. The DNA in such an RNA:DNA duplex need not be unmodified DNA. In certain embodiments, compounds described herein are sufficiently "DNA-like" to elicit RNase H activity. Nucleosides that are sufficiently "DNA-like" to elicit RNase H activity are referred to as DNA mimics herein. Further, in certain embodiments, one or more non-DNA-like nucleoside in in the RNA:DNA duplex is tolerated.

In certain antisense activities, compounds described herein or a portion of the compound is loaded into an RNA-induced silencing complex (RISC), ultimately resulting in cleavage of the target nucleic acid. For example, certain compounds described herein result in cleavage of the target nucleic acid by Argonaute. Compounds that are loaded into RISC are RNAi compounds. RNAi compounds may be double-stranded (siRNA) or single-stranded (ssRNA).

Antisense activities may be observed directly or indirectly. In certain embodiments, observation or detection of an antisense activity involves observation or detection of a change in an amount of a target nucleic acid or protein encoded by such target nucleic acid, a change in the ratio of splice variants of a nucleic acid or protein, and/or a phenotypic change in a cell or animal.

Certain Toxicities

For a compound to be a viable therapeutic agent, it must be safe at therapeutically relevant doses. It has become clear that toxicity of oligonucleotides can arise from one or more of several mechanisms. For example, some oligonucleotides hybridize an unintended RNA (or "off-target RNA") resulting in reduction of the off-target RNA and the protein encoded by that off-target RNA. Such unintended protein reduction may have toxic consequences. The data disclosed herein demonstrate that toxicity can result from oligonucleotides binding certain proteins and subsequent sub-cellular localization of the oligonucleotide/protein complex. Other mechanisms of toxicity may also contribute. Of course, for an oligonucleotide to be a suitable drug for use in therapy, all of the forms or mechanisms of toxicity must be acceptably low.

Since toxicity can result from multiple mechanisms, the observed toxicity for a particular compound will typically be the most toxic mechanism or the mechanism that results in toxicity at the lowest dose for that particular compound (the "limiting toxicity"). Changes to a compound that reduce the limiting toxicity will result in a compound having an observable improvement in toxic profile. Changes that reduce a form of toxicity that is not the limiting toxicity may not result in an observable improvement in toxicity, because the improvement may be masked by the limiting toxicity. In such instances, the improvement to a non-limiting toxicity can nonetheless have value. For example, the limiting toxicity might be controlled through additional changes to the compound or through changes in dose or dose frequency or through use of a separate therapy that mitigates the limiting toxicity; at that point, a previously masked toxicity would become limiting. Alternatively, in certain circumstances, the limiting toxicity might be less relevant (for example, if the drug is intended for delivery to specific tissues not affected by the limiting toxicity or if the compound is for the treatment of severe or life-threatening indications where a certain degree of the limiting toxicity may be acceptable). In such instances, improvements to a non-limiting toxicity can have significant benefit. Further, the various forms and mechanisms of toxicity may have a cumulative effect, particularly over time. Accordingly, the beneficial effects of improvements to a particular mechanism of toxicity might be masked at an early time point where another mechanism is the limiting toxicity, but over time such masked toxicity may contribute or even predominate the overall safety profile.

In certain embodiments, oligomeric compounds of the invention have improved toxicity profiles compared to standard gapmer compounds having a gap comprising only nucleosides having 2'-β-D-deoxyribosyl sugar moieties and the same nucleobase sequence. It should be noted that some standard gapmers are suitable therapeutic agents. Toxicity is driven in part by nucleobase sequence (oligonucleotides having identical chemical modification patterns but different sequences can have vastly different safety profiles). When one attempts to modulate a particular target RNA, one might find an antisense oligonucleotide that has an acceptable safety profile at therapeutic doses. On other occasions, however, the most active/potent oligonucleotides have unacceptable toxicity. In such instances, it is desirable to modify such compounds to reduce their toxicity, ideally with no loss or only modest loss in activity/potency. In certain embodiments, modification motifs described herein reduce toxicity with little or no loss in activity/potency.

Without limitation to any particular mechanism, it is believed that certain modification motifs described herein may reduce interactions between an oligomeric compound and certain proteins. In certain embodiments, such interactions result in the limiting toxicity and so disruption of these interactions results in observable improvements in the toxicity profile. In certain embodiments, the motifs described herein may alter off-target cleavage. In certain embodiments, the disclosed motifs improve toxicity through an undefined mechanism. In certain embodiments, the motifs may improve toxicity through multiple mechanisms, including, but not limited to those described here.

Disclosed herein for comparison are certain gapmer oligonucleotides that are notably more toxic than other gapmers. These toxic gapmer oligonucleotides cause rapid delocalization of paraspeckle proteins, including p54nrb, to nucleoli, possibly due to the binding of these toxic oligonucleotides to the p54nrb protein and/or other paraspeckle proteins. Certain such toxic oligonucleotides have both more global protein binding than their nontoxic (or less toxic) counterparts and have higher binding affinities (i.e., lower Kd values) for key paraspeckle proteins, including p54nrb and RNase H1. Certain such toxic oligonucleotides, but not nontoxic (or less toxic) oligonucleotides, cause the paraspeckle proteins PSF, PSPC1, and FUS to localize to the nucleoli as well, as observed across a number of mouse and human cell types. In certain instances, the nucleolar delocalization of paraspeckle proteins is mediated by RNase H1. Importantly, in some instances, nontoxic (or less toxic) modified oligonucleotides with the same chemical modification pattern (gapmer motif) and a different sequence do not cause the delocalization of p54nrb to nucleoli. This early event leads to nucleolar stress, p53 activation, and apoptotic cell death, both in vitro across a number of mammalian cell types and in vivo in mice. These results were consistent for gapmers with toxic sequences and containing several different commonly-used chemical modifications of modified oligonucleotides, including LNA, cEt, and 2'-MOE.

In certain embodiments, the instant invention is directed towards modified oligonucleotides having chemical modifications that can alleviate the observed toxicity. In certain embodiments, such toxicity is related to protein binding and the resulting nucleolar mislocalization of proteins, such as paraspeckle proteins described above. In certain embodiments, the incorporation of a safety-enhancing nucleoside at position 2, 3 or 4 of the central region (or "gap") of the modified oligonucleotide can reduce both global protein binding and the associated toxicity. In certain embodiments, the safety-enhancing nucleoside is a nucleoside comprising a 2'-OMe β-D-deoxyribosyl sugar moiety at position 2 of the central region. Incorporation of a nucleoside comprising a 2'-OMe-β-D-deoxyribosyl sugar moiety at position 2 of the central region in a toxic 3-10-3, 3-10-4, 4-10-3 cEt gapmer, a 3-10-3 LNA gapmer, a 5-10-5 MOE gapmer, or several cEt/MOE mixed wing gapmers reduced cellular toxicity and apoptosis in vitro and hepatoxicity in vivo across a wide variety of sequences, while having only a modest effect, if any, on antisense activity. In certain embodiments, incorporation of a nucleoside comprising a 2'-OMe-β-D-deoxyribosyl sugar moiety at position 2 of the central region also reduced delayed neurotoxicity, suggesting a common mechanism for delayed neurotoxicity and hepatoxicity. In certain embodiments, the safety-enhancing nucleoside is a nucleoside comprising a 5'-alkyl or 5'-allyl modified β-D-deoxyribosyl sugar moiety at position 3 or position 4 of the central region. In certain instances, incorporation of a nucleoside comprising a 5'-alkyl β-D-deoxyribosyl sugar moiety at position 3 or position 4 of the central region of a 3-10-3 cEt gapmer reduces cellular toxicity and apoptosis in vitro and hepatoxicity in vivo across a variety of sequences, while having a modest effect, if any, on antisense activity. In certain embodiments, the incorporation of a safety-enhancing internucleoside linkage between the nucleosides at positions 2-3 or positions 3-4 of the central region can reduce toxicity. In certain embodiments, one or more of a safety-enhancing linkages linking the nucleosides from positions 2-4 of the central region is a neutral linkage. In certain embodiments, one or more of a safety-enhancing linkages linking the nucleosides from positions 2-4 of the central region is a 2'-5' internucleoside linkage. The instant invention extends to any chemical modification introduced at positions 2, 3 or 4 of the central region, including modifications to nucleosides and to internucleoside linkages. In certain embodiments, such modification reduces in vitro toxicity (compared to the modified oligonucleotide lacking the safety enhancing nucleoside at positions 2, 3 or 4 of the central region or lacking the safety enhancing internucleoside linkage between positions 2-3 or 3-4 of the central region) as measured by the caspase 3/7 assay and/or in vivo hepatotoxicity, as measured by ALT or AST, and/or in vivo neurotoxicity, as measured by an FOB score or accumulation of markers of glial inflammation, Aifl and GFAP.

In certain embodiments, introducing chemical modifications at positions 2, 3 or 4 of the central region can significantly reduce toxicity with only a modest loss in potency, if any. This leads to an improvement in therapeutic index for a given target sequence. In certain cases, such improvements in therapeutic index are large enough to allow further drug development based on a compound targeted to a previously-toxic (but potent) sequence.

Target Nucleic Acids, Target Regions and Nucleotide Sequences

In certain embodiments, compounds described herein comprise or consist of an oligonucleotide comprising a region that is complementary to a target nucleic acid. In certain embodiments, the target nucleic acid is an endogenous RNA molecule. In certain embodiments, the target nucleic acid encodes a protein. In certain such embodiments, the target nucleic acid is selected from: an mRNA and a pre-mRNA, including intronic, exonic and untranslated regions. In certain embodiments, the target RNA is an mRNA. In certain embodiments, the target nucleic acid is a pre-mRNA. In certain embodiments, a pre-mRNA and corresponding mRNA are both target nucleic acids of a single compound. In certain such embodiments, the target region is entirely within an intron of a target pre-mRNA. In certain embodiments, the target region spans an intron/exon junction. In certain embodiments, the target region is at least 50% within an intron.

Certain Compounds Having Central Region Modifications

In certain embodiments, the oligomeric compounds herein comprise a gapmer comprising one or more an altered nucleotides in the central region of the gapmer. Each of such oligomeric compounds has a corresponding parent oligomeric compound that is identical to the first oligomeric compound except that is lacking the one or more altered nucleotides in the central region of the gapmer. Examples of such parent oligomeric compounds and their corresponding identical oligomeric compounds lacking the altered nucleotide are found in Tables 1 and 2 of Example 1 as well as throughout the Examples section. In Example 1, 558807 is the parent oligonucleotide. In certain embodiments, the central region of a parent oligomeric compound comprises only phosphodiester and/or phosphorothioate internucleoside linkages, unmodified nucleobases and/or 5-methylcytosine, and unmodified, 2'β-D-deoxyribosyl sugar moieties.

In certain embodiments, the present disclosure provides oligomeric compounds that comprise a gapmer comprising one or more altered nucleotides in the central region of the gapmer that have an increased therapeutic index an/or increased tolerability compared to the corresponding parent oligomeric compounds. In certain such embodiments, the modification or modifications of the central region of the oligomeric compounds with increased therapeutic index and/or increased tolerability are particularly useful in providing oligomeric compounds having reduced toxicity without significantly altering the potency. The modifications in the central region described herein can be at any position in the central region, and examples of embodiments comprising modifications at such positions are disclosed in the numbered embodiments and Examples. In certain embodiments, the altered nucleotide is an altered nucleoside attached to a phosphorothioate or phosphodiester internucleoside linkage. In a preferred embodiment, the altered nucleotide is at positions 1-4 of the central region of the modified oligonucleotide. In another preferred embodiment, the altered nucleotide comprises a nucleoside comprising a 2'-modified sugar moiety at position 2 of the central region of the modified oligonucleotide. In another preferred embodiment, the altered nucleotide comprises a nucleoside comprising a 5'-modified sugar moiety at positions 3 or 4 of the central region of the modified oligonucleotide. In another preferred embodiment, the altered nucleotide comprises a neutral internucleoside linkage between positions 2-3 or positions 3-4 of the central region of the modified oligonucleotide.

Certain compounds described herein (e.g., modified oligonucleotides) have one or more asymmetric center and thus give rise to enantiomers, diastereomers, and other stereoisomeric configurations that may be defined, in terms of absolute stereochemistry, as (R) or (S), as a or 13 such as for sugar anomers, or as (D) or (L), such as for amino acids, etc. Compounds provided herein that are drawn or described as having certain stereoisomeric configurations include only the indicated compounds. Compounds provided herein that are drawn or described with undefined stereochemistry include all such possible isomers, including their stereorandom and optically pure forms. All tautomeric forms of the compounds provided herein are included unless otherwise indicated.

The compounds described herein include variations in which one or more atoms are replaced with a non-radioactive isotope or radioactive isotope of the indicated element. For example, compounds herein that comprise hydrogen atoms encompass all possible deuterium substitutions for each of the $^{1}H$ hydrogen atoms. Isotopic substitutions encompassed by the compounds herein include but are not limited to: $^{2}H$ or $^{3}H$ in place of $^{1}H$, $^{13}C$ or $^{14}C$ in place of $^{12}C$, $^{15}N$ in place of $^{14}N$, $^{17}O$ or $^{18}O$ in place of $^{16}O$, and $^{33}S$, $^{34}S$, $^{35}S$, or $^{36}S$ in place of $^{32}S$. In certain embodiments, non-radioactive isotopic substitutions may impart new properties on the oligomeric compound that are beneficial for use as a therapeutic or research tool. In certain embodiments, radioactive isotopic substitutions may make the compound suitable for research or diagnostic purposes such as imaging.

EXAMPLES

Non-Limiting Disclosure and Incorporation by Reference

Although the sequence listing accompanying this filing identifies each sequence as either "RNA" or "DNA" as required, in reality, those sequences may be modified with any combination of chemical modifications. One of skill in the art will readily appreciate that such designation as "RNA" or "DNA" to describe modified oligonucleotides is, in certain instances, arbitrary. For example, an oligonucleotide comprising a nucleoside comprising a 2'-OH sugar moiety and a thymine nucleobase could be described as a DNA having an RNA sugar, or as an RNA having a DNA nucleobase.

Accordingly, nucleic acid sequences provided herein, including, but not limited to those in the sequence listing, are intended to encompass nucleic acids containing any combination of unmodified or modified RNA and/or DNA, including, but not limited to such nucleic acids having modified nucleobases. By way of further example and without limitation, an oligonucleotide having the nucleobase sequence "ATCGATCG" encompasses any oligonucleotides having such nucleobase sequence, whether modified or unmodified, including, but not limited to, such compounds comprising RNA bases, such as those having sequence "AUCGAUCG" and those having some DNA bases and some RNA bases such as "AUCGATCG" and compounds having other modified nucleobases, such as "AT$^{m}$CGAUCG," wherein $^{m}$C indicates a cytosine base comprising a methyl group at the 5-position. In certain cases, compounds comprising a uridine nucleobase and a 2'-OMe sugar moiety are compared to compounds comprising a thymidine nucoebase with a 2'-β-D-deoxyribosyl sugar moiety at the same position. While these compounds have different SEQ ID NO: they are not considered distinct sequences, and they have identical target RNA. In certain cases, compounds comprising a cytosine nucleobase and a 2'-OMe sugar moiety are compared to compounds comprising a 5-methylcytosine nucleobase and a 2'-β-D-deoxyribosyl sugar moiety at the same position.

In the Examples below, modified oligonucleotides are represented by a chemistry notation, always shown in the 5'-to-3' direction, of the format $B_{sl}B_{sl}{}^{m}B_{s}$, where "B" or "$^{m}$B" represents the nucleobase, with a superscript "m" before "B" representing a 5-methyl modification, the subscript in position "s" represents the sugar moiety, and the subscript in position "l" represents the 5'-to-3' internucleoside linkage. While certain compounds, compositions and methods described herein have been described with specificity in accordance with certain embodiments, the following examples serve only to illustrate the compounds described herein and are not intended to limit the same. Each of the references recited in the present application is incorporated herein by reference in its entirety.

Example 1 Effect of Position-Specific 2'-Modifications on In Vitro Activity and In Vivo Liver Toxicity of Modified Oligonucleotides Complementary to CXCL12

Modified oligonucleotides were synthesized with kkk-x-d(9)-kkk, kkk-d-x-d(8)-kkk, kkk-dd-x-d(7)-kkk or kkk-d(3)- x-d(6)-kkk sugar motifs, respectively, where "x" represents a sugar moiety having the modification indicated in the table below, "k" represents a cEt, and "d" represents an unmodified, 2'-β-D-deoxyribosyl sugar moiety. These modified oligonucleotides were compared to the otherwise identical modified oligonucleotide lacking an altered nucleotide in the central region, a 3-10-3 cEt gapmer, having three cEt nucleosides in each of the 5' and 3' regions and 10 DNA nucleosides in the central region. Each internucleoside linkage is a phosphorothioate. The compounds in the table below are 100% complementary to mouse CXCL12, GENBANK NT_039353.7 truncated from 69/430,515 to 69/445,350 (SEQ ID NO: 1), at position 6877 to 6892.

TABLE 1

Modified oligonucleotides complementary to CXCL12

| Compound ID | position of altered nucleotide in central region | sugar modification of altered nucleotide | Chemistry Notation (5'-3') | SEQ ID NO |
|---|---|---|---|---|
| 558807 | n/a | n/a | $G_{ks}{}^{m}C_{ks}A_{ks}T_{ds}G_{ds}T_{ds}T_{ds}{}^{m}C_{ds}T_{ds}{}^{m}C_{ds}A_{ds}{}^{m}C_{ds}A_{ds}T_{ks}T_{ks}A_{k}$ | 18 |
| 936049 | 1 | 2'-OMe | $G_{ks}{}^{m}C_{ks}A_{ks}U_{ms}G_{ds}T_{ds}T_{ds}{}^{m}C_{ds}T_{ds}{}^{m}C_{ds}A_{ds}{}^{m}C_{ds}A_{ds}T_{ks}T_{ks}A_{k}$ | 19 |
| 828910 | 1 | 2'-MOE | $G_{ks}{}^{m}C_{ks}A_{ks}T_{es}G_{ds}T_{ds}T_{ds}{}^{m}C_{ds}T_{ds}{}^{m}C_{ds}A_{ds}{}^{m}C_{ds}A_{ds}T_{ks}T_{ks}A_{k}$ | 18 |
| 936050 | 1 | cEt | $G_{ks}{}^{m}C_{ks}A_{ks}T_{ks}G_{ds}T_{ds}T_{ds}{}^{m}C_{ds}T_{ds}{}^{m}C_{ds}A_{ds}{}^{m}C_{ds}A_{ds}T_{ks}T_{ks}A_{k}$ | 18 |
| 936054 | 1 | 2'-FANA | $G_{ks}{}^{m}C_{ks}A_{ks}U_{(FANA)s}G_{ds}T_{ds}T_{ds}{}^{m}C_{ds}T_{ds}{}^{m}C_{ds}A_{ds}{}^{m}C_{ds}A_{ds}T_{ks}T_{ks}A_{k}$ | 19 |
| 936048 | 1 | 2'-ribo-F | $G_{ks}{}^{m}C_{ks}A_{ks}U_{fs}G_{ds}T_{ds}T_{ds}{}^{m}C_{ds}T_{ds}{}^{m}C_{ds}A_{ds}{}^{m}C_{ds}A_{ds}T_{ks}T_{ks}A_{k}$ | 19 |
| 936053 | 2 | 2'-OMe | $G_{ks}{}^{m}C_{ks}A_{ks}T_{ds}G_{ms}T_{ds}T_{ds}{}^{m}C_{ds}T_{ds}{}^{m}C_{ds}A_{ds}{}^{m}C_{ds}A_{ds}T_{ks}T_{ks}A_{k}$ | 18 |
| 828911 | 2 | 2'-MOE | $G_{ks}{}^{m}C_{ks}A_{ks}T_{ds}G_{es}T_{ds}T_{ds}{}^{m}C_{ds}T_{ds}{}^{m}C_{ds}A_{ds}{}^{m}C_{ds}A_{ds}T_{ks}T_{ks}A_{k}$ | 18 |
| 1070041 | 2 | cEt | $G_{ks}{}^{m}C_{ks}A_{ks}T_{ds}G_{ks}T_{ds}T_{ds}{}^{m}C_{ds}T_{ds}{}^{m}C_{ds}A_{ds}{}^{m}C_{ds}A_{ds}T_{ks}T_{ds}A_{k}$ | 18 |
| 1061314 | 2 | 2'-OH (RNA) | $G_{ks}{}^{m}C_{ks}A_{ks}T_{ds}G_{rs}T_{ds}T_{ds}{}^{m}C_{ds}T_{ds}{}^{m}C_{ds}A_{ds}{}^{m}C_{ds}A_{ds}T_{ks}T_{ks}A_{k}$ | 18 |
| 936051 | 2 | 2'-FANA | $G_{ks}{}^{m}C_{ks}A_{ks}T_{ds}G_{(FANA)s}T_{ds}T_{ds}{}^{m}C_{ds}T_{ds}{}^{m}C_{ds}A_{ds}{}^{m}C_{ds}A_{ds}T_{ks}T_{ks}A_{k}$ | 18 |
| 936052 | 2 | 2'-ribo-F | $G_{ks}{}^{m}C_{ks}A_{ks}T_{ds}G_{fs}T_{ds}T_{ds}{}^{m}C_{ds}T_{ds}{}^{m}C_{ds}A_{ds}{}^{m}C_{ds}A_{ds}T_{ks}T_{ks}A_{k}$ | 18 |
| 892826 | 3 | 2'-OMe | $G_{ks}{}^{m}C_{ks}A_{ks}T_{ds}G_{ds}U_{ms}T_{ds}{}^{m}C_{ds}T_{ds}{}^{m}C_{ds}A_{ds}{}^{m}C_{ds}A_{ds}T_{ks}T_{ks}A_{k}$ | 20 |
| 828912 | 3 | 2'-MOE | $G_{ks}{}^{m}C_{ks}A_{ks}T_{ds}G_{ds}T_{es}T_{ds}{}^{m}C_{ds}T_{ds}{}^{m}C_{ds}A_{ds}{}^{m}C_{ds}A_{ds}T_{ks}T_{ks}A_{k}$ | 18 |
| 892816 | 3 | cEt | $G_{ks}{}^{m}C_{ks}A_{ks}T_{ds}G_{ds}T_{ks}T_{ds}{}^{m}C_{ds}T_{ds}{}^{m}C_{ds}A_{ds}{}^{m}C_{ds}A_{ds}T_{ks}T_{ks}A_{k}$ | 18 |
| 895596 | 3 | 2'-FANA | $G_{ks}{}^{m}C_{ks}A_{ks}T_{ds}G_{ds}U_{(FANA)s}T_{ds}{}^{m}C_{ds}T_{ds}{}^{m}C_{ds}A_{ds}{}^{m}C_{ds}A_{ds}T_{ks}T_{ks}A_{k}$ | 20 |
| 892821 | 3 | 2'-ribo-F | $G_{ks}{}^{m}C_{ks}A_{ks}T_{ds}G_{ds}U_{fs}T_{ds}{}^{m}C_{ds}T_{ds}{}^{m}C_{ds}A_{ds}{}^{m}C_{ds}A_{ds}T_{ks}T_{ks}A_{k}$ | 20 |
| 892819 | 4 | 2'-OMe | $G_{ks}{}^{m}C_{ks}A_{ks}T_{ds}G_{ds}T_{ds}U_{ms}{}^{m}C_{ds}T_{ds}{}^{m}C_{ds}A_{ds}{}^{m}C_{ds}A_{ds}T_{ks}T_{ks}A_{k}$ | 21 |
| 828913 | 4 | 2'-MOE | $G_{ks}{}^{m}C_{ks}A_{ks}T_{ds}G_{ds}T_{ds}T_{es}{}^{m}C_{ds}T_{ds}{}^{m}C_{ds}A_{ds}{}^{m}C_{ds}A_{ds}T_{ks}T_{ks}A_{k}$ | 18 |
| 892817 | 4 | cEt | $G_{ks}{}^{m}C_{ks}A_{ks}T_{ds}G_{ds}T_{ds}T_{ds}{}^{m}C_{ds}T_{ds}{}^{m}C_{ds}A_{ds}{}^{m}C_{ds}A_{ds}T_{ks}T_{ds}A_{k}$ | 18 |
| 895595 | 4 | 2'-FANA | $G_{ks}{}^{m}C_{ks}A_{ks}T_{ds}G_{ds}T_{ds}U_{(FANA)s}{}^{m}C_{ds}T_{ds}{}^{m}C_{ds}A_{ds}{}^{m}C_{ds}A_{ds}T_{ks}T_{ks}A_{k}$ | 21 |
| 892822 | 4 | 2'-ribo-F | $G_{ks}{}^{m}C_{ks}A_{ks}T_{ds}G_{ds}T_{ds}U_{fs}{}^{m}C_{ds}T_{ds}{}^{m}C_{ds}A_{ds}{}^{m}C_{ds}A_{ds}T_{ks}T_{ks}A_{k}$ | 21 |

A subscript "d" indicates an unmodified, 2'-β-D-deoxyribosyl sugar moiety. A subscript "e" indicates a 2'-MOE-β-D-ribofuranosyl sugar moiety. A subscript "m" indicates a 2'-O-methyl-β-D-ribofuranosyl sugar moiety. A subscript "k" indicates a cEt. A subscript "s" indicates a phosphorothioate internucleoside linkage. A subscript "f" indicates a 2'-F-β-D-2'-deoxyribosyl sugar moiety. A subscript "(FANA)" indicates a 2'-F-β-D-arabinofuranosyl modified sugar moiety. A superscript "m" before a C indicates 5-methyl Cytosine.

For in vitro activity studies, approximately 20,000 mouse 3T3-L1 cells were electroporated with 0, 27 nM, 82 nM, 247 nM, 740 nM, 2,220 nM, 6,660 nM or 20,000 nM antisense oligonucleotide. mRNA was harvested and analyzed by RT-qPCR. CXCL12 mRNA was detected with primer probe set RTS2605 (forward sequence CCAGAGCCAACGTCAAGCAT, SEQ ID NO: 9; reverse sequence: CAGCCGTGCAACAATCTGAA, SEQ ID NO: 10; probe sequence: TGAAAATCCTCAACACTCCAAACTGTGCC, SEQ ID NO: 11) and RAPTOR mRNA was detected with primer probe set RTS3420 (forward sequence GCCCTCAGAAAGCTCTGGAA, SEQ ID NO: 12; reverse sequence: TAGGGTCGAGGCTCTGCTTGT, SEQ ID NO: 13; probe sequence: CCATCGGTGCAAACCTACAGAAGCAGTATG, SEQ ID NO: 14). RAPTOR is a sentinel gene that can be indicative of toxicity, as described in US 20160160280, hereby incorporated by reference.

For acute in vivo toxicity studies, three BALB/C mice per group were administered 150 mg/kg modified oligonucleotide by subcutaneous injection and sacrificed 72 hours later. Three mice were administered an injection of saline as a control. Plasma levels of ALT were measured using an automated clinical chemistry analyzer. Increased ALT is indicative of acute liver toxicity.

TABLE 2

Activity and toxicity of modified oligonucleotides complementary CXCL12

| Compound ID | position of altered nucleotide in central region | sugar modification of altered nucleotide | in vitro CXCL12 $IC_{50}$ (μM) | in vitro RAPTOR $IC_{50}$ (μM) | ALT @ 150 mg/kg (IU/L) |
|---|---|---|---|---|---|
| PBS | n/a | n/a | n/a | n/a | 23 |
| 558807 | n/a | n/a | 0.2 | 1.26 | n.d.** |
| 936049 | 1 | 2'-OMe | 0.17 | 4.8 | 8622 |
| 828910 | 1 | 2'-MOE | 0.12 | 7.2 | 2175 |
| 936050 | 1 | cEt | 0.15 | 6.5 | 912 |
| 936054 | 1 | 2'-FANA | 0.12 | 9.9 | 5755 |
| 936048 | 1 | 2'-ribo-F | 0.15 | 1.9 | death |
| 936053 | 2 | 2'-OMe | 0.17 | >>10 | 46 |
| 828911 | 2 | 2'-MOE | 0.42 | >>10 | 27 |
| 1070041 | 2 | cEt | 0.52 | n.d. | 96 |
| 1061314 | 2 | 2'-OH (RNA) | n.d. | n.d. | 26 |
| 936051 | 2 | 2'-FANA | 0.12 | 2.34 | death |
| 936052 | 2 | 2'-ribo-F | 0.19 | 13.5 | 1110 |
| 892826 | 3 | 2'-OMe | 0.21 | 7.1 | 10463 |
| 828912 | 3 | 2'-MOE | 0.28 | 10 | 701 |
| 892816 | 3 | cEt | 0.17 | 11 | 278 |
| 895596 | 3 | 2'-FANA | 0.12 | 7.4 | 17369 |
| 892821 | 3 | 2'-ribo-F | 0.18 | 4.5 | 6333 |

TABLE 2-continued

Activity and toxicity of modified oligonucleotides complementary CXCL12

| Compound ID | position of altered nucleotide in central region | sugar modification of altered nucleotide | in vitro CXCL12 $IC_{50}$ (μM) | in vitro RAPTOR $IC_{50}$ (μM) | ALT @ 150 mg/kg (IU/L) |
|---|---|---|---|---|---|
| 892819 | 4 | 2'-OMe | 0.18 | >10 | 565 |
| 828913 | 4 | 2'-MOE | 0.22 | 10 | 2474 |
| 892817 | 4 | cEt | 0.23 | 9 | 5264 |
| 895595 | 4 | 2'-FANA | 0.08 | 8.8 | 22082 |
| 892822 | 4 | 2'-ribo-F | 0.04 | 4.85 | 4020 |

**558807 treatment at 16.7 mg/kg leads to an ALT of 586 IU/L in this experiment; mice that are treated with 558807 at 150 mg/kg typically experience death before 72 hours post-treatment.

For the in vitro study reported in the tables below, 3T3-L1 cells were electroporated with 27 nM, 80 nM, 250 nM, 740 nM, 2, 222 nM, 6,667 nM, or 20,000 nM of modified oligonucleotide and levels of P21 and Gadd45a were measured by RT-qPCR. Levels of Gadd45a were analyzed using primer probe set Mm00432802 ml (ThermoFisher). Levels of P21 were analyzed using primer probe set Mm04207341_ml (ThermoFisher).

TABLE 2b in vitro P21 Expression in 3T3-L1 cells

| Compound ID | 27 nM | 80 nM | 250 nM | 740 nM | 2,222 nM | 6,667 nM | 20,000 nM |
|---|---|---|---|---|---|---|---|
| | Expression level of P21 mRNA (% Control) | | | | | | |
| 558807 | 110 | 98 | 69 | 99 | 117 | 228 | 488 |
| 936049 | 63 | 116 | 96 | 93 | 121 | 151 | 199 |
| 936053 | 151 | 144 | 158 | 160 | 152 | 143 | 155 |
| 892826 | 140 | 104 | 104 | 128 | 138 | 181 | 177 |

TABLE 2c in vitro Gadd45a Expression in 3T3-L1 cells

| Compound ID | 27 nM | 80 nM | 250 nM | 740 nM | 2,222 nM | 6,667 nM | 20,000 nM |
|---|---|---|---|---|---|---|---|
| | Expression level of Gadd45a mRNA (% Control) | | | | | | |
| 558807 | 115 | 120 | 111 | 136 | 155 | 237 | 298 |
| 936049 | 101 | 124 | 131 | 158 | 172 | 212 | 276 |
| 936053 | 144 | 227 | 175 | 203 | 197 | 201 | 193 |
| 892826 | 132 | 114 | 134 | 152 | 147 | 163 | 158 |

For the in vitro study reported in the tables below, b.END cells were electroporated with 27 nM, 80 nM, 250 nM, 740 nM, 2, 222 nM, 6,667 nM, or 20,000 nM of modified oligonucleotide and levels of P21 were measured by RT-qPCR using primer probe set Mm04207341_ml (ThermoFisher).

TABLE 2d in vitro P21 Expression in b.END cells

| Compound ID | 27 nM | 80 nM | 250 nM | 740 nM | 2,222 nM | 6,667 nM | 20,000 nM |
|---|---|---|---|---|---|---|---|
| | Expression level of P21 mRNA (% Control) | | | | | | |
| 558807 | 138 | 117 | 93 | 73 | 107 | 160 | 226 |
| 936053 | 108 | 112 | 96 | 90 | 111 | 101 | 118 |
| 892826 | 112 | 112 | 114 | 107 | 117 | 116 | 137 |
| 1061314 | 126 | 128 | 103 | 115 | 128 | 122 | 112 |

TABLE 2d-continued in vitro P21 Expression in b.END cells

| Compound ID | 27 nM | 80 nM | 250 nM | 740 nM | 2,222 nM | 6,667 nM | 20,000 nM |
|---|---|---|---|---|---|---|---|
| | Expression level of P21 mRNA (% Control) | | | | | | |
| 936051 | 114 | 113 | 109 | 118 | 117 | 123 | 178 |
| 936052 | 109 | 116 | 102 | 100 | 112 | 119 | 138 |
| 828911 | 115 | 108 | 120 | 113 | 114 | 115 | 122 |
| 1070041 | 101 | 100 | 109 | 104 | 104 | 120 | 132 |

TABLE 2e in vitro Gadd45a Expression in b.END cells

| Compound ID | 27 nM | 80 nM | 250 nM | 740 nM | 2,222 nM | 6,667 nM | 20,000 nM |
|---|---|---|---|---|---|---|---|
| | Expression level of P21 mRNA (% Control) | | | | | | |
| 558807 | 558807 | 86 | 132 | 93 | 101 | 178 | 220 |
| 936053 | 936053 | 111 | n.d. | 148 | 150 | 200 | 215 |
| 892826 | 892826 | 134 | 177 | 160 | 170 | 177 | 162 |
| 1061314 | 1061314 | 135 | 149 | 150 | 197 | 199 | 184 |
| 936051 | 136 | 132 | 152 | 185 | 199 | 193 | 258 |
| 936052 | 125 | 160 | 146 | 173 | 210 | 201 | 228 |
| 828911 | 121 | 154 | 158 | 193 | 190 | 189 | 249 |
| 1070041 | 118 | 139 | 163 | 194 | 225 | 301 | 313 |

For the in vivo activity and toxicity study in the table below, 2 or 3 BALB/C mice per group were administered modified oligonucleotide at 1.8 mg/kg, 5.5 mg/kg, or 16.7 mg/kg by subcutaneous injection and sacrificed after 72 hours.

TABLE 2f in vivo Activity and Toxicity

| Compound ID | position of altered nucleotide in central region | sugar modification of altered nucleotide | in vivo CXCL12 ED50 (mg/kg) | ALT @5.5 mg/kg (IU/L) | ALT @ 16.7 mg/kg (IU/L) |
|---|---|---|---|---|---|
| PBS | n/a | n/a | n/a | 30 (@0 mg/kg) | |
| 558807 | n/a | n/a | 1.6 | 40 | 1721 |
| 936051 | 2 | 2'-FANA | 0.15 | 44 | 4285 |
| 936053 | 2 | 2'-OMe | 5.5 | 27 | 25 |
| 828911 | 2 | 2'-MOE | 14 | 36 | 25 |
| 936052 | 2 | 2'-ribo-F | 2.9 | 26 | 29 |

For in vivo activity and toxicity study in the table below, 3 BALB/C mice per group were administered modified oligonucleotide by subcutaneous injection and sacrificed after 72 hours. Compound 558807 was dosed at 1.8, 5.5, or 16.7 mg/kg, compounds 828911, 936052 and 936053 were dosed at 1.8, 5.5, 16.7 and 50 mg/kg, and compounds 1061315 and 1070041 were dosed at 1.8, 5.5, 16.7, 50 or 150 mg/kg. Tissue were collected and mRNA was isolated and levels of CXCL12 were measured by RT-qPCR with primer probe set RTS2605 as described above. Levels of Gadd45a were analyzed using primer probe set Mm00432802_ml (ThermoFisher). Levels of P21 were analyzed using primer probe set Mm04207341_ml (ThermoFisher). Levels of Tnfrsf10b were analyzed using primer probe set Mm00457866_ml (ThermoFisher). Expression levels were normalized with Ribogreen® and are presented relative to levels in mice treated with PBS.

TABLE 2g

In Vivo Activity and Toxicity of modified oligonucleotides complementary to CXCL12

| Compound ID | position of altered nucleotide in central region | sugar modification of altered nucleotide | in vivo CXCL12 ED50 (mg/kg) | ALT @50 mg/kg (IU/L) | ALT @ 150 mg/kg (IU/L) |
|---|---|---|---|---|---|
| PBS | n/a | n/a | n/a | 28 (@0 mg/kg) | |
| 558807 | n/a | n/a | 2.7 | n.d.** | |
| 936053 | 2 | 2'-OMe | 4.9 | 23 | n.d. |
| 828911 | 2 | 2'-MOE | 14 | 27 | n.d. |
| 1070041 | 2 | cEt | 29 | 25 | 78 |
| 1061314 | 2 | 2'-OH (RNA) | 78 | 21 | 24 |
| 936052 | 2 | 2'-ribo-F | 4.2 | 39 | n.d. |

**558807 treatment at 16.7 mg/kg leads to an ALT of 586 IU/L; mice that are treated with 558807 at 150 mg/kg typically experience death before 72 hours post-treatment.

TABLE 2h

In Vivo Dose-response of Gadd45a mRNA upon treatment with modified oligonucleotides complementary to CXCL12

| Compound ID | 1.8 mg/kg | 5.5 mg/kg | 16.7 mg/kg | 50 mg/kg | 150 mg/kg |
|---|---|---|---|---|---|
| | Expression level of Gadd45a mRNA (% Control) | | | | |
| 558807 | 100 | 172 | 856 | n/a | n/a |
| 936053 | 61 | 99 | 91 | 92 | n/a |
| 828911 | 80 | 100 | 96 | 100 | n/a |
| 1070041 | 128 | 225 | 139 | 177 | 169 |
| 1061314 | 112 | 84 | 89 | 105 | 180 |
| 936052 | 84 | 80 | 134 | 126 | n/a |

TABLE 2i

In Vivo Dose-response of Tnfrsf10b mRNA upon treatment with modified oligonucleotides complementary to CXCL12

| Compound ID | 1.8 mg/kg | 5.5 mg/kg | 16.7 mg/kg | 50 mg/kg | 150 mg/kg |
|---|---|---|---|---|---|
| | Expression level of Tnfrsf10b mRNA (% Control) | | | | |
| 558807 | 102 | 267 | 790 | n/a | n/a |
| 936053 | 106 | 111 | 130 | 100 | n/a |
| 828911 | 120 | 116 | 95 | 102 | n/a |
| 1070041 | 106 | 139 | 252 | 483 | 1021 |
| 1061314 | 79 | 66 | 81 | 136 | 220 |
| 936052 | 82 | 101 | 183 | 138 | n/a |

TABLE 2j

In Vivo Dose-response of P21 mRNA upon treatment with modified oligonucleotides complementary to CXCL12

| Compound ID | 1.8 mg/kg | 5.5 mg/kg | 16.7 mg/kg | 50 mg/kg | 150 mg/kg |
|---|---|---|---|---|---|
| | Expression level of P21 mRNA (% Control) | | | | |
| 558807 | 100 | 61 | 609 | n/a | n/a |
| 936053 | 104 | 94 | 104 | 89 | n/a |
| 828911 | 90 | 145 | 52 | 92 | n/a |
| 1070041 | 28 | 93 | 83 | 132 | 264 |
| 1061314 | 45 | 59 | 30 | 34 | 178 |
| 936052 | 70 | 71 | 51 | 101 | n/a |

For the in vivo activity study in the tables below, 3 BALB/C mice per group were administered 3.37, 11, 33, or 100 mg/kg doses of modified oligonucleotide, as indicated in the table below, by subcutaneous injection and sacrificed 72 hours later. Liver mRNA was isolated an analyzed by RT-PCR as described in above. Expression levels were normalized with Ribogreen® and are expressed relative to PBS-treated control mice.

TABLE 2k

Activity and toxicity of modified oligonucleotides complementary to CXCL12

| Compound ID | position of altered nucleotide central region | sugar modification of altered nucleotide | ALT (IU/L) at 100 mg/kg | ALT (IU/L) at 33 mg/kg |
|---|---|---|---|---|
| 558807 | n/a | n/a | death | 3740 |
| 936049 | 1 | 2'-OMe | 3060 | 612 |
| 936053 | 2 | 2'-OMe | 42 | 21 |
| 892826 | 3 | 2'-OMe | 1127 | 2281 |

TABLE 2l

In Vivo Dose-response of CXCL12 mRNA upon treatment with modified oligonucleotides complementary to CXCL12

| Compound ID | 3.37 mg/kg | 11 mg/kg | 33 mg/kg | 100 mg/kg |
|---|---|---|---|---|
| | Expression level of CXCL12 mRNA (% Control) | | | |
| 558807 | 95 | 29 | 12 | n.d. |
| 936049 | 102 | 50 | 22 | 14 |
| 936053 | 100 | 70 | 40 | 31 |
| 892826 | 100 | 49 | 16 | 10 |

TABLE 2m

In Vivo Dose-response of P21 mRNA upon treatment with modified oligonucleotides complementary to CXCL12

| Compound ID | 3.37 mg/kg | 11 mg/kg | 33 mg/kg | 100 mg/kg |
|---|---|---|---|---|
| | Expression level of P21 mRNA (% Control) | | | |
| 558807 | 194 | 186 | 32700 | n.d. |
| 936049 | 126 | 127 | 3156 | 21746 |
| 936053 | 100 | 49 | 89 | 185 |
| 892826 | 60 | 60 | 2401 | 12981 |

Example 2 Effect of Position-Specific 5'-Modifications on In Vitro Activity and In Vivo Liver Toxicity of Modified Oligonucleotides Complementary CXCL12

Modified oligonucleotides containing 5'-methyl, 5'-allyl, and 5'-ethyl modifications at various positions were synthesized. Procedures for the synthesis of 5'-methyl and 5'-allyl analogs are detailed in WO2013022967. Procedures for the synthesis of 5'-ethyl analogs are detailed herein below in Example 39. These modified oligonucleotides were compared to the otherwise identical modified oligonucleotide lacking a modified nucleoside in the central region, a 3-10-3 cEt modified oligonucleotide, containing three cEt nucleosides in each of the 5' and 3' regions and 10 unmodified DNA nucleobases in the central region. The compounds in the table below are 100% complementary to mouse CXCL12, GENBANK NT_039353.7 truncated from 69/430,515 to 69/445,350 (SEQ ID NO: 1), at position 6877 to 6892.

TABLE 3

Modified oligonucleotides complementary to CXCL12

| Compound ID | position of altered nucleotide in central region | sugar modification of altered nucleotide | Chemistry Notation (5'-3') | SEQ ID NO |
|---|---|---|---|---|
| 558807 | n/a | n/a | $G_{ks}{}^{m}C_{ks}A_{ks}T_{ds}G_{ds}T_{ds}T_{ds}{}^{m}C_{ds}T_{ds}{}^{m}C_{ds}A_{ds}{}^{m}C_{ds}A_{ds}T_{ks}T_{ks}A_{k}$ | 18 |
| 1123320 | 2 | 5'-(S)-Me | $G_{ks}{}^{m}C_{ks}A_{ks}T_{ds}G_{[(S)\text{-}\mu]s}T_{ds}T_{ds}{}^{m}C_{ds}T_{ds}{}^{m}C_{ds}A_{ds}{}^{m}C_{ds}A_{ds}T_{ks}T_{ks}A_{k}$ | 18 |
| 1123322 | 2 | 5'-(R)-Me | $G_{ks}{}^{m}C_{ks}A_{ks}T_{ds}G_{[(R)\text{-}\mu]s}T_{ds}T_{ds}{}^{m}C_{ds}T_{ds}{}^{m}C_{ds}A_{ds}{}^{m}C_{ds}A_{ds}T_{ks}T_{ks}A_{k}$ | 18 |
| 1123479 | 2 | 5'-(R,S)-allyl | $G_{ks}{}^{m}C_{ks}A_{ks}T_{ds}G_{[\gamma]s}T_{ds}T_{ds}{}^{m}C_{ds}T_{ds}{}^{m}C_{ds}A_{ds}{}^{m}C_{ds}A_{ds}T_{ks}T_{ks}A_{k}$ | 18 |
| 942943 | 3 | 5'-(R)-Me | $G_{ks}{}^{m}C_{ks}A_{ks}T_{ds}G_{ds}T_{[(R)\text{-}\mu]s}T_{ds}{}^{m}C_{ds}T_{ds}{}^{m}C_{ds}A_{ds}{}^{m}C_{ds}A_{ds}T_{ks}T_{ks}A_{k}$ | 18 |
| 957908 | 3 | 5'-(S)-Me | $G_{ks}{}^{m}C_{ks}A_{ks}T_{ds}G_{ds}T_{[(S)\text{-}\mu]s}C_{ds}A_{ds}{}^{m}C_{ds}A_{ds}T_{ks}T_{ks}A_{k}$ | 18 |
| 957910 | 3 | 5'-(R)-allyl | $G_{ks}{}^{m}C_{ks}A_{ks}T_{ds}G_{ds}T_{[(R)\text{-}\gamma]s}T_{ds}{}^{m}C_{ds}T_{ds}{}^{m}C_{ds}A_{ds}{}^{m}C_{ds}A_{ds}T_{ks}T_{ks}A_{k}$ | 18 |
| 957912 | 3 | 5'-(S)-allyl | $G_{ks}{}^{m}C_{ks}A_{ks}T_{ds}G_{ds}T_{[(S)\text{-}\gamma]s}T_{ds}{}^{m}C_{ds}T_{ds}{}^{m}C_{ds}A_{ds}{}^{m}C_{ds}A_{ds}T_{ks}T_{ks}A_{k}$ | 18 |
| 1175787 | 3 | 5'-(R-Et | $G_{ks}{}^{m}C_{ks}A_{ks}T_{ds}G_{ds}T_{[(R)\text{-}\varepsilon]s}T_{ds}{}^{m}C_{ds}T_{ds}{}^{m}C_{ds}A_{ds}{}^{m}C_{ds}A_{ds}T_{ks}T_{ks}A_{k}$ | 18 |
| 1175785 | 3 | 5'-(S)-Et | $G_{ks}{}^{m}C_{ks}A_{ks}T_{ds}G_{ds}T_{[(S)\text{-}\varepsilon]s}T_{ds}{}^{m}C_{ds}T_{ds}{}^{m}C_{ds}A_{ds}{}^{m}C_{ds}A_{ds}T_{ks}T_{ks}A_{k}$ | 18 |
| 942944 | 4 | 5'-(R)-Me | $G_{ks}{}^{m}C_{ks}A_{ks}T_{ds}G_{ds}T_{ds}T_{[(R)\text{-}\mu]s}C_{ds}T_{ds}{}^{m}C_{ds}A_{ds}{}^{m}C_{ds}A_{ds}T_{ks}T_{ks}A_{k}$ | 18 |
| 957909 | 4 | 5'-(S)-Me | $G_{ks}{}^{m}C_{ks}A_{ks}T_{ds}G_{ds}T_{ds}T_{[(S)\text{-}\mu]s}C_{ds}T_{ds}{}^{m}C_{ds}A_{ds}{}^{m}C_{ds}A_{ds}T_{ks}T_{ks}A_{k}$ | 18 |
| 957911 | 4 | 5'-(R)-allyl | $G_{ks}{}^{m}C_{ks}A_{ks}T_{ds}G_{ds}T_{ds}T_{[(R)\text{-}\gamma]s}{}^{m}C_{ds}T_{ds}{}^{m}C_{ds}A_{ds}{}^{m}C_{ds}A_{ds}T_{ks}T_{ks}A_{k}$ | 18 |
| 957913 | 4 | 5'-(S)-allyl | $G_{ks}{}^{m}C_{ks}A_{ks}T_{ds}G_{ds}T_{ds}T_{[(S)\text{-}\gamma]s}{}^{m}C_{ds}T_{ds}{}^{m}C_{ds}A_{ds}{}^{m}C_{ds}A_{ds}T_{ks}T_{ks}A_{k}$ | 18 |
| 1175786 | 4 | 5'-(R)-Et | $G_{ks}{}^{m}C_{ks}A_{ks}T_{ds}G_{ds}T_{ds}T_{[(R)\text{-}\varepsilon]s}{}^{m}C_{ds}T_{ds}{}^{m}C_{ds}A_{ds}{}^{m}C_{ds}A_{ds}T_{ks}T_{ks}A_{k}$ | 18 |
| 1175782 | 4 | 5'-(S)-Et | $G_{ks}{}^{m}C_{ks}A_{ks}T_{ds}G_{ds}T_{ds}T_{[(S)\text{-}\varepsilon]s}{}^{m}C_{ds}T_{ds}{}^{m}C_{ds}A_{ds}{}^{m}C_{ds}A_{ds}T_{ks}T_{ks}A_{k}$ | 18 |

A subscript "d" indicates an unmodified, 2'-β-D-deoxyribosyl sugar moiety. A subscript "k" indicates a cEt. A subscript "s" indicates a phosphorothioate internucleoside linkage. A subscript "[μ]" indicates a 5'-(R,S)-Me-β-D-2'-deoxyribosyl sugar moiety. A subscript "[(R)-μ]" indicates a 5'-(R)-Me-β-D-2'-deoxyribosyl sugar moiety. A subscript "[(S)-μ]" indicates a 5'-(S)-Me-β-D-2'-deoxyribosyl sugar moiety. A subscript "[γ]" indicates a 5'-(R,S)-allyl-β-D-2'-deoxyribosyl sugar moiety. A subscript "[(R)-γ]" indicates a 5'-(R)-allyl-β-D-2'-deoxyribosyl sugar moiety. A subscript "[(S)-γ]" indicates a 5'-(S)-allyl-β-D-2'-deoxyribosyl sugar moiety. A subscript "[ε]" indicates a 5'-(R,S)-ethyl-β-D-2'-deoxyribosyl sugar moiety. A subscript "[(R)-ε]" indicates a 5'-(R)-ethyl-β-D-2'-deoxyribosyl sugar moiety. A subscript "[(S)-ε]" indicates a 5'-(S)-ethyl-β-D-2'-deoxyribosyl sugar moiety.

Experimental Procedures & Results

In vitro activity and in vivo activity and toxicity experiments were performed essentially as described in Example 1. For in vivo toxicity studies, a single BALB/C mouse per modified oligonucleotide was administered 150 mg/kg modified oligonucleotide by subcutaneous injection and sacrificed 72 hours later. For the in vivo activity study in the table below, 2 BALB/C mice per group were administered 1.8 mg/kg, 5.5 mg/kg, 16.7 mg/kg, 50 mg/kg dose of modified oligonucleotide subcutaneously and sacrificed after 72 hours. For 558807, only 1.8 mg/kg, 5.5 mg/kg, and 16.7 mg/kg doses were tested for dose response, due to acute toxicity of higher doses. Tissues were collected and liver mRNA was isolated and levels of CXCL12 were measured by RT-qPCR with primer probe set RTS2605 as described above.

TABLE 4

Activity and toxicity of modified oligonucleotides complementary CXCL12

| Compound ID | position of altered nucleotide in central region | sugar modification of altered nucleotide | In vitro IC50 CXCL12 (μM) | Raptor IC50 (tox marker) | in vivo ED50 (mg/kg) | ALT (at 150 mg/kg) |
|---|---|---|---|---|---|---|
| 558807 | n/a | Parent | 0.11 | 1.3 | 2.9 | n.d.** |
| 942943 | 3 | 5'-(R)—Me | 0.118 | 23 | 2.8 | 2466 |
| 942944 | 4 | 5'-(R)—Me | 0.169 | 22 | 3 | 233 |
| 957908 | 3 | 5'-(S)—Me | 0.193 | 33 | 3.7 | 52 |
| 957909 | 4 | 5'-(S)—Me | 0.159 | 4 | 2.2 | 1267 |
| 957910 | 3 | 5'-(R)-allyl | 0.239 | >>20 | 3.6 | 32 |
| 957911 | 4 | 5'-(R)-allyl | 0.269 | >>20 | 6.4 | 30 |
| 957912 | 3 | 5'-(S)-allyl | 0.234 | >>20 | 5.1 | 30 |
| 957913 | 4 | 5'-(S)-allyl | 0.263 | >>20 | 5.7 | 32 |

**Not tested in this experiment; mice that are treated with 558807 at 150 mg/kg typically experience death before 72 hours post-treatment.

For the in vivo activity and toxicity study reported in the table below, 2 BALB/C mice per group were administered 5 mg/kg or 150 mg/kg modified oligonucleotide subcutaneously and sacrificed 72 hours later. Plasma levels of ALT were measured and liver mRNA was analyzed for target reduction as in example 1 above.

TABLE 5

Activity and toxicity of modified oligonucleotides complementary CXCL12

| Compound ID | position of altered nucleotide in central region | sugar modification of altered nucleotide | CXCL12 mRNA (% control) 5 mg/kg | CXCL12 mRNA (% control) 150 mg/kg | ALT 5 mg/kg (IU/L) | ALT 150 mg/kg (IU/L) |
|---|---|---|---|---|---|---|
| 558807 | n/a | n/a | n.d. | n.d. | n.d. | n.d.** |
| 942943 | 3 | 5'-(R)—Me | 28 | 3 | 27 | 4407 |
| 957910 | 3 | 5'-(R)-allyl | 53 | 7 | 24 | 38 |
| 1175787 | 3 | 5'- (R)—Et | 57 | 6 | 27 | 39 |
| 1175785 | 3 | 5'-(S)—Et | 46 | 8 | 25 | 45 |
| 957909 | 4 | 5'-(S)—Me | 30 | 7 | 22 | 7133 |
| 957913 | 4 | 5'-(S)-allyl | 59 | 10 | 30 | 37 |
| 1175786 | 4 | 5'-(R)—Et | 44 | 35 | 24 | 44 |
| 1175782 | 4 | 5'-(S)—Et | 52 | 7 | 26 | 131 |

**Not tested in this experiment; mice that are treated with 558807 at 150 mg/kg typically experience death before 72 hours post-treatment.

For the results in the tables below, in vivo activity and toxicity experiments were performed essentially as described in Example 1. For in vivo toxicity studies, two BALB/C mice per group was administered 50 or 150 mg/kg modified oligonucleotide by subcutaneous injection and sacrificed 72 hours later. One animal was administered an injection of saline as a control. Plasma levels of ALT were measured using an automated clinical chemistry analyzer.

For the in vivo activity study in the tables below, 2 BALB/C mice per group were administered 1.8 mg/kg, 5.5 mg/kg, 16.7 mg/kg, 50 mg/kg, or 150 mg/kg doses of modified oligonucleotide, as indicated in the table below, by subcutaneous injection and sacrificed 72 hours later. For 558807, only 1.8 mg/kg, 5.5 mg/kg, and 16.7 mg/kg doses were tested for dose response, due to acute toxicity of higher doses. Liver mRNA was isolated an analyzed by RT-PCR as described in Example 1 above. Expression levels were normalized with Ribogreen® and are expressed relative to PBS-treated control mice.

TABLE 6

Activity and toxicity of modified oligonucleotides complementary CXCL12

| Compound ID | position of altered nucleotide in central region | sugar modification of altered nucleotide | in vivo $ED_{50}$ (mg/kg) | ALT (IU/L) at 150 mg/kg | ALT (IU/L) at 50 mg/kg |
|---|---|---|---|---|---|
| 558807 | n/a | n/a | 1.7* | n.d.** | n.d.** |
| 1123320 | 2 | 5'-(R)-Me | 2.8 | 7448 | 3987 |
| 1123322 | 2 | 5'-(S)-Me | 2.1 | 5181 | 1912 |
| 1123479 | 2 | 5'-(R,S)-allyl | 6.1 | 2562 | 56 |

*Compound 558807 was only dosed at 1.8, 5.5, and 16.7 mg/kg

**Not tested in this experiment; mice that are treated with 558807 150 mg/kg typically experience death within 72 hours post-treatment.

TABLE 6b

In Vivo Dose-response of Gadd45a mRNA upon treatment with modified oligonucleotides complementary to CXCL12

| Compound ID | 1.8 mg/kg | 5.5 mg/kg | 16.7 mg/kg | 50 mg/kg | 150 mg/kg |
|---|---|---|---|---|---|
| | Expression level of Gadd45a mRNA (% Control) | | | | |
| 558807 | 83 | 143 | 188 | n/a | n/a |
| 1123320 | 68 | 80 | 114 | 387 | 683 |

TABLE 6b-continued

In Vivo Dose-response of Gadd45a mRNA upon treatment with modified oligonucleotides complementary to CXCL12

| Compound ID | 1.8 mg/kg | 5.5 mg/kg | 16.7 mg/kg | 50 mg/kg | 150 mg/kg |
|---|---|---|---|---|---|
| | Expression level of Gadd45a mRNA (% Control) | | | | |
| 1123322 | 105 | 61 | 169 | 141 | 575 |
| 1123479 | 88 | 70 | 75 | 273 | 141 |

TABLE 6c

In Vivo Dose-response of Tnfrsf10b mRNA upon treatment with modified oligonucleotides complementary to CXCL12

| Compound ID | 1.8 mg/kg | 5.5 mg/kg | 16.7 mg/kg | 50 mg/kg | 150 mg/kg |
|---|---|---|---|---|---|
| | Expression level of Tnfrsf10b mRNA (% Control) | | | | |
| 558807 | 115 | 119 | 195 | n/a | n/a |
| 1123320 | 78 | 115 | 77 | 1,802 | 6,928 |
| 1123322 | 95 | 75 | 231 | 1,036 | 8,281 |
| 1123479 | 174 | 132 | 125 | 303 | 1,423 |

TABLE 6d

In Vivo Dose-response of P21 mRNA upon treatment with modified oligonucleotides complementary to CXCL12

| Compound ID | 1.8 mg/kg | 5.5 mg/kg | 16.7 mg/kg | 50 mg/kg | 150 mg/kg |
|---|---|---|---|---|---|
| | Expression level of P21 mRNA (% Control) | | | | |
| 558807 | 144 | 123 | 1212 | n/a | n/a |
| 1123320 | 109 | 224 | 114 | 17,332 | 51,431 |
| 1123322 | 218 | 92 | 303 | 10,383 | 75,226 |
| 1123479 | 271 | 209 | 295 | 838 | 12,248 |

TABLE 7

Activity and toxicity of modified oligonucleotides complementary CXCL12

| Compound ID | position of altered nucleotide in central region | sugar modification of altered nucleotide | in vivo $EC_{50}$ (mg/kg) | ALT (IU/L) at 150 mg/kg | ALT (IU/L) at 50 mg/kg |
|---|---|---|---|---|---|
| 936053 | 2 | 2'-OMe | 4.9 | 49 | 23 |
| 1175782 | 4 | 5'-(S)-Et | 3.7 | 153 | 37 |

TABLE 7-continued

| Activity and toxicity of modified oligonucleotides complementary CXCL12 | | | | | |
|---|---|---|---|---|---|
| Compound ID | position of altered nucleotide in central region | sugar modification of altered nucleotide | in vivo $EC_{50}$ (mg/kg) | ALT (IU/L) at 150 mg/kg | ALT (IU/L) at 50 mg/kg |
| 1175785 | 3 | 5'-(S)-Et | 6.6 | 34 | 24 |
| 1175786 | 4 | 5'-(R)-Et | 3.5 | 33 | 26 |
| 1175787 | 3 | 5'-(R)-Et | 5.8 | 39 | 28 |

Example 3 Effect of Position-Specific 2'-Modifications on In Vitro Activity and In Vivo Liver Toxicity of Modified Oligonucleotides Complementary to Factor XI Modified oligonucleotides were synthesized as indicated in the table below, comprising an altered nucleotide at positions 1-3 of the central region. These modified oligonucleotides were compared to the otherwise identical modified oligonucleotide lacking an altered nucleotide in the central region, a 3-10-3 cEt gapmer, containing three cEt nucleosides in each of the 5' and 3' regions and 10 unmodified DNA nucleosides in the central region. Each internucleoside linkage is a phosphorothioate internucleoside linkage. The compounds in the table below are 100% complementary to the complement of mouse Factor XI, GENBANK NT_039460.6 truncated from 6086000 to 6111000 (SEQ ID NO: 2), at position 11699 to 11714.

TABLE 8

| Modified oligonucleotides complementary to Factor XI | | | | |
|---|---|---|---|---|
| Compound ID | position of altered nucleotide in central region | sugar modification of altered nucleotide | Chemistry Notation (5'-3') | SEQ ID NO |
| 464917 | n/a | n/a | $G_{ks}T_{ks}{}^{m}C_{ks}T_{ds}G_{ds}T_{ds}G_{ds}{}^{m}C_{ds}A_{ds}T_{ds}{}^{m}C_{ds}T_{ds}{}^{m}C_{ds}T_{ks}{}^{m}C_{ks}{}^{m}C_{k}$ | 22 |
| 982033 | 1 | 2'-OMe | $G_{ks}T_{ks}{}^{m}C_{ks}U_{ms}G_{ds}T_{ds}G_{ds}{}^{m}C_{ds}A_{ds}T_{ds}{}^{m}C_{ds}T_{ds}{}^{m}C_{ds}T_{ks}{}^{m}C_{ks}{}^{m}C_{k}$ | 143 |
| 982034 | 2 | 2'-OMe | $G_{ks}T_{ks}{}^{m}C_{ks}T_{ds}G_{ms}T_{ds}G_{ds}{}^{m}C_{ds}A_{ds}T_{ds}{}^{m}C_{ds}T_{ds}{}^{m}C_{ds}T_{ks}{}^{m}C_{ks}{}^{m}C_{k}$ | 22 |
| 985292 | 2 | 2'-MOE | $G_{ks}T_{ks}{}^{m}C_{ks}T_{ds}G_{es}T_{ds}G_{ds}{}^{m}C_{ds}A_{ds}T_{ds}{}^{m}C_{ds}T_{ds}{}^{m}C_{ds}T_{ks}{}^{m}C_{ks}{}^{m}C_{k}$ | 22 |
| 985293 | 2 | cEt | $G_{ks}T_{ks}{}^{m}C_{ks}T_{ds}G_{ks}T_{ds}G_{ds}{}^{m}C_{ds}A_{ds}T_{ds}{}^{m}C_{ds}T_{ds}{}^{m}C_{ds}T_{ks}{}^{m}C_{ks}{}^{m}C_{k}$ | 22 |
| 1011274 | 2 | 2'-FANA | $G_{ks}T_{ks}{}^{m}C_{ks}T_{ds}G_{(FANA)s}T_{ds}G_{ds}{}^{m}C_{ds}A_{ds}T_{ds}{}^{m}C_{ds}T_{ds}{}^{m}C_{ds}T_{ks}{}^{m}C_{ks}{}^{m}C_{k}$ | 22 |
| 604581 | 2 | 2'-ribo-F | $G_{ks}T_{ks}{}^{m}C_{ks}T_{ds}G_{fs}T_{ds}G_{ds}{}^{m}C_{ds}A_{ds}T_{ds}{}^{m}C_{ds}T_{ds}{}^{m}C_{ds}T_{ks}{}^{m}C_{ks}{}^{m}C_{k}$ | 22 |
| 982035 | 3 | 2'-OMe | $G_{ks}T_{ks}{}^{m}C_{ks}T_{ds}G_{ds}U_{ms}G_{ds}{}^{m}C_{ds}A_{ds}T_{ds}{}^{m}C_{ds}T_{ds}{}^{m}C_{ds}T_{ks}{}^{m}C_{ks}{}^{m}C_{k}$ | 23 |
| 985294 | 3 | 2'-MOE | $G_{ks}T_{ks}{}^{m}C_{ks}T_{ds}G_{ds}T_{es}G_{ds}{}^{m}C_{ds}A_{ds}T_{ds}{}^{m}C_{ds}T_{ds}{}^{m}C_{ds}T_{ks}{}^{m}C_{ks}{}^{m}C_{k}$ | 22 |
| 985295 | 3 | cEt | $G_{ks}T_{ks}{}^{m}C_{ks}T_{ds}G_{ds}T_{ks}G_{ds}{}^{m}C_{ds}A_{ds}T_{ds}{}^{m}C_{ds}T_{ds}{}^{m}C_{ds}T_{ks}{}^{m}C_{ks}{}^{m}C_{k}$ | 22 |
| 1011276 | 3 | 2'-FANA | $G_{ks}T_{ks}{}^{m}C_{ks}T_{ds}G_{ds}U_{(FANA)s}G_{ds}{}^{m}C_{ds}A_{ds}T_{ds}{}^{m}C_{ds}T_{ds}{}^{m}C_{ds}T_{ks}{}^{m}C_{ks}{}^{m}C_{k}$ | 23 |
| 605933 | 3 | 2'-ribo-F | $G_{ks}T_{ks}{}^{m}C_{ks}T_{ds}G_{ds}U_{fs}G_{ds}{}^{m}C_{ds}A_{ds}T_{ds}{}^{m}C_{ds}T_{ds}{}^{m}C_{ds}T_{ks}{}^{m}C_{ks}{}^{m}C_{k}$ | 23 |

A subscript "d" indicates an unmodified, 2'-β-D-deoxyribosyl sugar moiety. A subscript "e" indicates a 2'-MOE-β-D-ribofuranosyl sugar moiety. A subscript "m" indicates a 2'-O-methyl-β-D-ribofuranosyl sugar moiety. A subscript "k" indicates a cEt. A subscript "s" indicates a phosphorothioate internucleoside linkage. A subscript "f" indicates a 2'-F-β-D-2'-deoxyribosyl sugar moiety. A subscript "(FANA)" indicates a 2'-F-β-D-arabinofuranosyl modified sugar moiety. A superscript "m" before a C indicates 5-methyl Cytosine.

Experimental Procedures & Results

For in vitro toxicity studies, 3T3-L1 cells were electroporated with 27, 80, 250, 740, 2, 222, 6,667, or 20,000 nM of modified oligonucleotide and levels of Raptor were measured by RT-qPCR as in Example 1. For in vivo toxicity studies, two BALB/C mice per group were administered 100 mg/kg modified oligonucleotide by subcutaneous injection and sacrificed 72 hours later. One animal was administered an injection of saline as a control. Plasma levels of ALT were measured using an automated clinical chemistry analyzer. Increased ALT is indicative of acute liver toxicity.

TABLE 8b

| Toxicity of modified oligonucleotides complementary Factor XI | | | | |
|---|---|---|---|---|
| Compound ID | position of altered nucleotide in central region | sugar modification of altered nucleotide | Raptor IC50 (μM) | ALT at 100 mg/kg (IU/L) |
| 464917 | n/a | n/a | 1.6 | 18751 * |
| 982034 | 2 | 2'-OMe | >20 | 1363 |
| 985292 | 2 | 2'-MOE | 15.5 | 2406 |
| 985293 | 2 | cEt | 9.3 | 15141 |
| 1011274 | 2 | 2'-FANA | 2.3 | death |
| 604581 | 2 | 2'-ribo-F | 6 | 14957 |
| 982035 | 3 | 2'-OMe | 1.8 | 6411 |
| 985294 | 3 | 2'-MOE | 6.2 | 2836 |
| 985295 | 3 | cEt | 5.2 | 3669 |
| 1011276 | 3 | 2'-FANA | >20 | death |
| 605933 | 3 | 2'-ribo-F | 4.6 | 18570 |

* ALT for 464917 is for a 50 mg/kg dose

For the in vitro study reported in the tables below, 3T3-L1 cells were electroporated with 27, 80, 250, 740, 2, 222, 6,667, or 20,000 nM of modified oligonucleotide and levels of P21 and Gadd45a were measured by RT-qPCR. Levels of Gadd45a were analyzed using primer probe set Mm00432802 ml (ThermoFisher). Levels of P21 were analyzed using primer probe set Mm04207341_ml (ThermoFisher).

TABLE 8c

| in vitro P21 Expression in 3T3-L1 cells | | | | | | | |
|---|---|---|---|---|---|---|---|
| Compound ID | 27 nM | 80 nM | 250 nM | 740 nM | 2,222 nM | 6,667 nM | 20,000 nM |
| | Expression level of P21 mRNA (% Control) | | | | | | |
| 464917 | 108 | 124 | 122 | 169 | 228 | 478 | 749 |
| 982033 | 119 | 120 | 128 | 128 | 218 | 498 | 895 |

TABLE 8c-continued

| in vitro P21 Expression in 3T3-L1 cells | | | | | | | |
|---|---|---|---|---|---|---|---|
| Compound | 27 nM | 80 nM | 250 nM | 740 nM | 2,222 nM | 6,667 nM | 20,000 nM |
| ID | Expression level of P21 mRNA (% Control) | | | | | | |
| 982034 | 115 | 121 | 110 | 102 | 136 | 266 | 840 |
| 982035 | 162 | 157 | 175 | 206 | 466 | 768 | 661 |

TABLE 8d

| in vitro Gadd45a Expression in 3T3-L1 cells | | | | | | | |
|---|---|---|---|---|---|---|---|
| Compound | 27 nM | 80 nM | 250 nM | 740 nM | 2,222 nM | 6,667 nM | 20,000 nM |
| ID | Expression level of Gadd45a mRNA (% Control) | | | | | | |
| 464917 | 130 | 150 | 115 | 179 | 321 | 632 | 633 |
| 982033 | 120 | 117 | 126 | 203 | 331 | 767 | 798 |
| 982034 | 89 | 111 | 103 | 102 | 173 | 678 | 800 |
| 982035 | 161 | 120 | 140 | 181 | 557 | 779 | 497 |

For the in vitro study reported in the tables below, b.END cells were electroporated with 27, 80, 250, 740, 2, 222, 6,667, or 20,000 nM of modified oligonucleotide and levels of P21 and Gadd45a were measured by RT-qPCR. Levels of Gadd45a were analyzed using primer probe set Mm00432802 ml (ThermoFisher). Levels of P21 were analyzed using primer probe set Mm04207341_ml (ThermoFisher).

TABLE 8e

| in vitro P21 Expression in b.END cells | | | | | | | |
|---|---|---|---|---|---|---|---|
| Compound | 27 nM | 80 nM | 250 nM | 740 nM | 2,222 nM | 6,667 nM | 20,000 nM |
| ID | Expression level of P21 mRNA (% Control) | | | | | | |
| 464917 | 111 | 115 | 124 | 120 | 139 | 192 | 446 |
| 982033 | 105 | 102 | 107 | 110 | 125 | 171 | 414 |
| 982034 | 106 | 102 | 109 | 112 | 120 | 132 | 208 |
| 982035 | 102 | 97 | 111 | 115 | 129 | 168 | 392 |

TABLE 8f

| in vitro Gadd45a Expression in b.END cells | | | | | | | |
|---|---|---|---|---|---|---|---|
| Compound | 27 nM | 80 nM | 250 nM | 740 nM | 2,222 nM | 6,667 nM | 20,000 nM |
| ID | Expression level of Gadd45a mRNA (% Control) | | | | | | |
| 464917 | 101 | 83 | 85 | 87 | 129 | 236 | 380 |
| 982033 | 89 | 76 | 101 | 91 | 177 | 347 | 731 |
| 982034 | 58 | 73 | 86 | 88 | 115 | 202 | 373 |
| 982035 | 68 | 72 | 81 | 103 | 166 | 298 | 620 |

For the in vivo activity study in the tables below, 3 BALB/C mice per group were administered 3.37, 11, 33, or 100 mg/kg doses of modified oligonucleotide, as indicated in the table below, by subcutaneous injection and sacrificed 72 hours later. Liver mRNA was isolated an analyzed by RT-PCR as described in Example 1 above. Expression levels were normalized with Ribogreen® and are expressed relative to PBS-treated control mice.

TABLE 8g

| Activity and toxicity of modified oligonucleotides complementary FXI | | | | |
|---|---|---|---|---|
| Compound ID | position of altered nucleotide in central region | sugar modification of altered nucleotide | ALT (IU/L) at 100 mg/kg | ALT (IU/L) at 33 mg/kg |
| 464917 | n/a | n/a | 11816 | 11682 |
| 982033 | 1 | OMe | 26992 | 3951 |
| 982034 | 2 | OMe | 7954 | 920 |
| 982035 | 3 | OMe | 28994 | 3848 |

TABLE 8h

| In Vivo Dose-response of FXI mRNA upon treatment with modified oligonucleotides complementary to FXI | | | | |
|---|---|---|---|---|
| | 3.37 mg/kg | 11 mg/kg | 33 mg/kg | 100 mg/kg |
| Compound ID | Expression level of FXI mRNA (% Control) | | | |
| 464917 | 47 | 12 | 8.0 | 1.8 |
| 982033 | 53 | 18 | 10 | 5.5 |
| 982034 | 53 | 24 | 9.9 | 3.5 |
| 982035 | 36 | 20 | 11 | 5.3 |

TABLE 8i

| In Vivo Dose-response of P21 mRNA upon treatment with modified oligonucleotides complementary to FXI | | | | |
|---|---|---|---|---|
| | 3.37 mg/kg | 11 mg/kg | 33 mg/kg | 100 mg/kg |
| Compound ID | Expression level of P21 mRNA (% Control) | | | |
| 464917 | 230 | 4143 | 4678 | 5289 |
| 982033 | 122 | 1106 | 2926 | 5653 |
| 982034 | 93 | 297 | 1694 | 4294 |
| 982035 | 418 | 1283 | 4759 | 6960 |

Example 4 Effect of Position-Specific 2' and 5'-Modifications on In Vivo Activity and Liver Toxicity of Modified Oligonucleotides Complementary to Factor XI Modified oligonucleotides were synthesized with 2' or 5' modifications as indicated in the table below. These modified oligonucleotides were compared to the otherwise identical modified oligonucleotide lacking a modified nucleoside in the central region, a 3-10-3 cEt modified oligonucleotide, containing three cEt nucleosides in each of the 5' and 3' regions and 10 unmodified DNA nucleobases in the central region. The compounds in the table below are 100% complementary to mouse Factor XI, the complement of GENBANK NT_039460.6 truncated from 6086000 to 6111000 (SEQ ID NO: 2), at position 11699 to 11714.

TABLE 9

| Modified oligonucleotides complementary to Factor XI | | | | |
|---|---|---|---|---|
| Compound ID | position of altered nucleotide in central region | sugar modification of altered nucleotide | Chemistry Notation (5'-3') | SEQ ID NO |
| 464917 | n/a | n/a | $G_{ks}T_{ks}{}^{m}C_{ks}T_{ds}G_{ds}T_{ds}G_{ds}{}^{m}C_{ds}A_{ds}T_{ds}{}^{m}C_{ds}T_{ds}{}^{m}C_{ds}T_{ks}{}^{m}C_{ks}{}^{m}C_{k}$ | 22 |
| 443919 | n/a | n/a | $G_{es}T_{es}{}^{m}C_{es}T_{ds}G_{ds}T_{ds}G_{ds}{}^{m}C_{ds}A_{ds}T_{ds}{}^{m}C_{ds}T_{ds}{}^{m}C_{ds}T_{es}{}^{m}C_{es}{}^{m}C_{e}$ | 22 |
| 465977 | n/a | n/a | $G_{ks}T_{ks}{}^{m}C_{ks}T_{ds}G_{ds}T_{ds}G_{ds}{}^{m}C_{ds}A_{ds}T_{ds}{}^{m}C_{ds}T_{ds}{}^{m}C_{ds}T_{es}{}^{m}C_{es}{}^{m}C_{e}$ | 22 |
| 483706 | n/a | n/a | $G_{es}T_{es}{}^{m}C_{es}T_{ds}G_{ds}T_{ds}G_{ds}{}^{m}C_{ds}A_{ds}T_{ds}{}^{m}C_{ds}T_{ds}{}^{m}C_{ds}T_{ks}{}^{m}C_{ks}{}^{m}C_{k}$ | 22 |
| 1183062 | 2 | 5'-(R)-Me | $G_{ks}T_{ks}{}^{m}C_{ks}T_{ds}G_{[(R)\text{-}\mu]s}T_{ds}G_{ds}{}^{m}C_{ds}A_{ds}T_{ds}{}^{m}C_{ds}T_{ds}{}^{m}C_{ds}T_{ks}{}^{m}C_{ks}{}^{m}C_{k}$ | 22 |
| 1183059 | 2 | 5'-(S)-Me | $G_{ks}T_{ks}{}^{m}C_{ks}T_{ds}G_{[(S)\text{-}\mu]s}T_{ds}G_{ds}{}^{m}C_{ds}A_{ds}T_{ds}{}^{m}C_{ds}T_{ds}{}^{m}C_{ds}T_{ks}{}^{m}C_{ks}{}^{m}C_{k}$ | 22 |
| 1183065 | 2 | 5'-(R)-allyl | $G_{ks}T_{ks}{}^{m}C_{ks}T_{ds}G_{[(R)\text{-}\gamma]s}T_{ds}G_{ds}{}^{m}C_{ds}A_{ds}T_{ds}{}^{m}C_{ds}T_{ds}{}^{m}C_{ds}T_{ks}{}^{m}C_{ks}{}^{m}C_{k}$ | 22 |
| 1183063 | 3 | 5'-(R)-Me | $G_{ks}T_{ks}{}^{m}C_{ks}T_{ds}G_{ds}T_{[(R)\text{-}\mu]s}G_{ds}{}^{m}C_{ds}A_{ds}T_{ds}{}^{m}C_{ds}T_{ds}{}^{m}C_{ds}T_{ks}{}^{m}C_{ks}{}^{m}C_{k}$ | 22 |
| 1183060 | 3 | 5'-(S)-Me | $G_{ks}T_{ks}{}^{m}C_{ks}T_{ds}G_{ds}T_{[(S)\text{-}\mu]s}G_{ds}{}^{m}C_{ds}A_{ds}T_{ds}{}^{m}C_{ds}T_{ds}{}^{m}C_{ds}T_{ks}{}^{m}C_{ks}{}^{m}C_{k}$ | 22 |
| 1183066 | 3 | 5'-(R)-allyl | $G_{ks}T_{ks}{}^{m}C_{ks}T_{ds}G_{ds}T_{[(R)\text{-}\gamma]s}G_{ds}{}^{m}C_{ds}A_{ds}T_{ds}{}^{m}C_{ds}T_{ds}{}^{m}C_{ds}T_{ks}{}^{m}C_{ks}{}^{m}C_{k}$ | 22 |
| 1183064 | 4 | 5'-(R)-Me | $G_{ks}T_{ks}{}^{m}C_{ks}T_{ds}G_{ds}T_{ds}G_{[(R)\text{-}\mu]s}{}^{m}C_{ds}A_{ds}T_{ds}{}^{m}C_{ds}T_{ds}{}^{m}C_{ds}T_{ks}{}^{m}C_{ks}{}^{m}C_{k}$ | 22 |
| 1183061 | 4 | 5'-(S)-Me | $G_{ks}T_{ks}{}^{m}C_{ks}T_{ds}G_{ds}T_{ds}G_{[(S)\text{-}\mu]s}{}^{m}C_{ds}A_{ds}T_{ds}{}^{m}C_{ds}T_{ds}{}^{m}C_{ds}T_{ks}{}^{m}C_{ks}{}^{m}C_{k}$ | 22 |
| 1183067 | 4 | 5'-(R)-allyl | $G_{ks}T_{ks}{}^{m}C_{ks}T_{ds}G_{ds}T_{ds}G_{[(R)\text{-}\gamma]s}{}^{m}C_{ds}A_{ds}T_{ds}{}^{m}C_{ds}T_{ds}{}^{m}C_{ds}T_{ks}{}^{m}C_{ks}{}^{m}C_{k}$ | 22 |

A subscript "d" indicates an unmodified, 2'-β-D-deoxyribosyl sugar moiety. A subscript "k" indicates a cEt. A subscript "s" indicates a phosphorothioate internucleoside linkage. A subscript "[μ]" indicates a 5'-(R,S)-Me-β-D-2'-deoxyribosyl sugar moiety. A subscript "[(R)-μ]" indicates a 5'-(R)-Me-β-D-2'-deoxyribosyl sugar moiety. A subscript "[(S)-μ]" indicates a 5'-(S)-Me-β-D-2'-deoxyribosyl sugar moiety. A subscript "[γ]" indicates a 5'-(R,S)-allyl-β-D-2'-deoxyribosyl sugar moiety. A subscript "[(R)-γ]" indicates a 5'-(R)-allyl-β-D-2'-deoxyribosyl sugar moiety. A subscript "[(S)-γ]" indicates a 5'-(S)-allyl-β-D-2'-deoxyribosyl sugar moiety. A subscript "[ε]" indicates a 5'-(R,S)-ethyl-β-D-2'-deoxyribosyl sugar moiety. A subscript "[(R)-ε]" indicates a 5'-(R)-ethyl-β-D-2'-deoxyribosyl sugar moiety. A subscript "[(S)-ε]" indicates a 5'-(S)-ethyl-β-D-2'-deoxyribosyl sugar moiety.

Experimental Procedures & Results

For the in vivo activity and toxicity study below, two BALB/C mice per group were administered 33 or 100 mg/kg modified oligonucleotide by subcutaneous injection and sacrificed 72 hours later. Expression levels of FXI were measured by RT-qPCR using primer probe set RTS2898 (forward sequence: ACATGACAGGCGCGATCTCT, SEQ ID NO: 78; reverse sequence: TCTAGGTTCACGTACACATCTTTGC, SEQ ID NO: 79; probe sequence: TTCCTTCAAGCAATGCCCTCAGCAAT, SEQ ID NO: 80). Plasma levels of ALT were measured using an automated clinical chemistry analyzer. Increased ALT is indicative of acute liver toxicity.

TABLE 10

| Toxicity and activity of modified oligonucleotides complementary Factor XI | | | | | | |
|---|---|---|---|---|---|---|
| Compound ID | position of altered nucleotide in central region | sugar modification of altered nucleotide | FXI mRNA (% control) 33 mg/kg | FXI mRNA (% control) 100 mg/kg | ALT (IU/L) at 33 mg/kg | ALT (IU/L) at 100 mg/kg |
| 464917 | n/a | n/a | 11 | 0.9 | 7511 | 31066* |
| 443919 | n/a | n/a | 27 | 7.9 | 24 | 57 |
| 465977 | n/a | n/a | 5.6 | n.d. | 11575 | death |
| 483706 | n/a | n/a | 20.3 | 4.9 | 52 | 732 |
| 1183062 | 2 | 5'-(R)—Me | 5.7 | n.d. | 12083 | death |
| 1183059 | 2 | 5'-(S)—Me | 4.0 | 2.4 | 662 | 7894 |
| 1183065 | 2 | 5'-(R)-allyl | 5.2 | 1.5 | 4707 | 24000 |
| 1183063 | 3 | 5'-(R)—Me | 4.9 | 2.0 | 2458 | 14891 |
| 1183060 | 3 | 5'-(S)—Me | 8.2 | 2.1 | 8710 | 23995 |
| 1183066 | 3 | 5'-(R)-allyl | 5.1 | 2.0 | 524 | 6473 |
| 1183064 | 4 | 5'-(R)—Me | 4.0 | 1.5 | 4357 | 11342 |
| 1183061 | 4 | 5'-(S)—Me | 4.1 | 2.3 | 1891 | 20557 |
| 1183067 | 4 | 5'-(R)-allyl | 11 | 3.6 | 184 | 2536 |

*One of two mice died

For the in vitro study reported in the tables below, 3T3-L1 cells were electroporated with 27 nM, 80 nM, 250 nM, 740 nM, 2, 222 nM, 6,667 nM, or 20,000 nM of modified oligonucleotide and levels of P21 and Gadd45a were measured by RT-qPCR as described in Example 1 above. Caspase-3 and caspase-7 activation was measured using the Caspase-Glo® 3/7 Assay System (G8090, Promega). Levels of caspase activation correlate with apoptotic cell death.

TABLE 10b

| in vitro P21 Expression in 3T3-L1 cells | | | | | | | |
|---|---|---|---|---|---|---|---|
| Compound ID | 27 nM | 80 nM | 250 nM | 740 nM | 2,222 nM | 6,667 nM | 20,000 nM |
| | Expression level of P21 mRNA (% Control) | | | | | | |
| 464917 | 100 | 100 | 116 | 139 | 216 | 496 | 1232 |
| 443919 | 122 | 116 | 99 | 86 | 114 | 105 | 184 |

TABLE 10b-continued

| in vitro P21 Expression in 3T3-L1 cells | | | | | | | |
|---|---|---|---|---|---|---|---|
| Compound ID | 27 nM | 80 nM | 250 nM | 740 nM | 2,222 nM | 6,667 nM | 20,000 nM |
| | Expression level of P21 mRNA (% Control) | | | | | | |
| 465977 | 104 | 117 | 103 | 106 | 139 | 220 | 578 |
| 483706 | 105 | 92 | 116 | 125 | 135 | 165 | 376 |

TABLE 10c

| in vitro Gadd45a Expression in 3T3-L1 cells | | | | | | | |
|---|---|---|---|---|---|---|---|
| Compound ID | 27 nM | 80 nM | 250 nM | 740 nM | 2,222 nM | 6,667 nM | 20,000 nM |
| | Expression level of Gadd45a mRNA (% Control) | | | | | | |
| 464917 | 89 | 93 | 106 | 113 | 157 | 324 | 599 |
| 443919 | 163 | 166 | 147 | 129 | 145 | 126 | 178 |
| 465977 | 101 | 110 | 119 | 100 | 135 | 150 | 334 |
| 483706 | 89 | 133 | 185 | 194 | 197 | 217 | 459 |

TABLE 10d

| in vitro Caspase Activation in 3T3-L1 cells | | | | | | | |
|---|---|---|---|---|---|---|---|
| Compound ID | 27 nM | 80 nM | 250 nM | 740 nM | 2,222 nM | 6,667 nM | 20,000 nM |
| | Caspase Activation | | | | | | |
| 464917 | 4388 | 4428 | 4656 | 6208 | 20274 | 48106 | 82324 |
| 443919 | 4200 | 4802 | 4986 | 4605 | 4714 | 4552 | 9385 |
| 465977 | 4017 | 4133 | 4253 | 4465 | 6983 | 34156 | 61008 |
| 483706 | 4155 | 4595 | 4020 | 4476 | 4585 | 6565 | 16766 |

For the in vivo study in the table below, three BALB/C mice per group were administered 11 or 33 mg/kg of modified oligonucleotide and sacrificed after 72 hours.

TABLE 10e

| in vivo Activity and toxicity of modified oligonucleotides complementary FXI | | | | | | |
|---|---|---|---|---|---|---|
| Compound ID | 2' sugar modification of nucleosides in 5' region | 2' sugar modification of nucleosides in 3' region | P21 mRNA @ 33 mg/kg (% control) | Tnfrsf10b mRNA @ 33 mg/kg (% control) | FXI mRNA @ 33 mg/kg (% control) | ALT@33 mg/kg |
| 464917 | kkk | kkk | 24040 | 108884 | 1.4 | 18316 |
| 443919 | kkk | eee | 109 | 110 | 16 | 68 |
| 465977 | eee | kkk | n.d. | n.d. | n.d. | death |
| 483706 | eee | eee | 1195 | 733 | 2.7 | 1424 |

Example 5 Effect of Position-Specific 2'-Modifications on In Vitro Activity and In Vivo Liver Toxicity of Modified Oligonucleotides Complementary to PTEN Modified oligonucleotides were synthesized with 2' modifications as indicated in the table below. These modified oligonucleotides were compared to the otherwise identical modified oligonucleotide lacking a modified nucleoside in the central region, a 3-10-3 cEt modified oligonucleotide, containing three cEt nucleosides in each of the 5' and 3' regions and 10 unmodified DNA nucleobases in the central region. The compounds in the table below are 100% complementary to mouse PTEN, GENBANK NC_000085.6, truncated from 32755001 to 32829000 (SEQ ID NO: 3), at position 2635 to 2650.

TABLE 11

| Modified oligonucleotides complementary to PTEN | | | | |
|---|---|---|---|---|
| Compound ID | position of altered nucleotide in central region | sugar modification of altered nucleotide | Chemistry Notation (5'-3') | SEQ ID NO |
| 482050 | n/a | n/a | $A_{ks}T_{ks}{}^{m}C_{ks}A_{ds}T_{ds}G_{ds}G_{ds}{}^{m}C_{ds}T_{ds}G_{ds}{}^{m}C_{ds}A_{ds}G_{ds}{}^{m}C_{ks}T_{ks}T_{k}$ | 24 |
| 982036 | 1 | 2'-OMe | $A_{ks}T_{ks}{}^{m}C_{ks}A_{ms}T_{ds}G_{ds}G_{ds}{}^{m}C_{ds}T_{ds}G_{ds}{}^{m}C_{ds}A_{ds}G_{ds}{}^{m}C_{ks}T_{ks}T_{k}$ | 24 |
| 982037 | 2 | 2'-OMe | $A_{ks}T_{ks}{}^{m}C_{ks}A_{ds}U_{ms}G_{ds}G_{ds}{}^{m}C_{ds}T_{ds}G_{ds}{}^{m}C_{ds}A_{ds}G_{ds}{}^{m}C_{ks}T_{ks}T_{k}$ | 25 |
| 985297 | 2 | 2'-MOE | $A_{ks}T_{ks}{}^{m}C_{ks}A_{ds}T_{es}G_{ds}G_{ds}{}^{m}C_{ds}T_{ds}G_{ds}{}^{m}C_{ds}A_{ds}G_{ds}{}^{m}C_{ks}T_{ks}T_{k}$ | 24 |
| 985298 | 2 | cEt | $A_{ks}T_{ks}{}^{m}C_{ks}A_{ds}T_{ks}G_{ds}G_{ds}{}^{m}C_{ds}T_{ds}G_{ds}{}^{m}C_{ds}A_{ds}G_{ds}{}^{m}C_{ks}T_{ks}T_{k}$ | 24 |
| 1011277 | 2 | 2'-FANA | $A_{ks}T_{ks}{}^{m}C_{ks}A_{ds}U_{(FANA)s}G_{ds}G_{ds}{}^{m}C_{ds}T_{ds}G_{ds}{}^{m}C_{ds}A_{ds}G_{ds}{}^{m}C_{ks}T_{ks}T_{k}$ | 25 |
| 985296 | 2 | 2'-ribo-F | $A_{ks}T_{ks}{}^{m}C_{ks}A_{ds}U_{fs}G_{ds}G_{ds}{}^{m}C_{ds}T_{ds}G_{ds}{}^{m}C_{ds}A_{ds}G_{ds}{}^{m}C_{ks}T_{ks}T_{k}$ | 25 |
| 982038 | 3 | 2'-OMe | $A_{ks}T_{ks}{}^{m}C_{ks}A_{ds}T_{ds}G_{ms}G_{ds}{}^{m}C_{ds}T_{ds}G_{ds}{}^{m}C_{ds}A_{ds}G_{ds}{}^{m}C_{ks}T_{ks}T_{k}$ | 24 |
| 985301 | 3 | 2'-MOE | $A_{ks}T_{ks}{}^{m}C_{ks}A_{ds}T_{ds}G_{es}G_{ds}{}^{m}C_{ds}T_{ds}G_{ds}{}^{m}C_{ds}A_{ds}G_{ds}{}^{m}C_{ks}T_{ks}T_{k}$ | 24 |
| 985302 | 3 | cEt | $A_{ks}T_{ks}{}^{m}C_{ks}A_{ds}T_{ds}G_{ks}G_{ds}{}^{m}C_{ds}T_{ds}G_{ds}{}^{m}C_{ds}A_{ds}G_{ds}{}^{m}C_{ks}T_{ks}T_{k}$ | 24 |
| 1011278 | 3 | 2'-FANA | $A_{ks}T_{ks}{}^{m}C_{ks}A_{ds}T_{ds}G_{(FANA)s}G_{ds}{}^{m}C_{ds}T_{ds}G_{ds}{}^{m}C_{ds}A_{ds}G_{ds}{}^{m}C_{ks}T_{ks}T_{k}$ | 24 |
| 985300 | 3 | 2'-ribo-F | $A_{ks}T_{ks}{}^{m}C_{ks}A_{ds}T_{ds}G_{fs}G_{ds}{}^{m}C_{ds}T_{ds}G_{ds}{}^{m}C_{ds}A_{ds}G_{ds}{}^{m}C_{ks}T_{ks}T_{k}$ | 24 |

A subscript "d" indicates an unmodified, 2'-β-D-deoxyribosyl sugar moiety. A subscript "e" indicates a 2'-MOE-β-D-ribofuranosyl sugar moiety. A subscript "m" indicates a 2'-O-methyl-β-D-ribofuranosyl sugar moiety. A subscript "k" indicates a cEt. A subscript "s" indicates a phosphorothioate internucleoside linkage. A subscript "f" indicates a 2'-F-β-D-2'-deoxyribosyl sugar moiety. A subscript "(FANA)" indicates a 2'-F-β-D-arabinofuranosyl modified sugar moiety. A superscript "m" before a C indicates 5-methyl Cytosine.

For in vitro activity studies, 3T3-L1 cells were plated and transfected with 16, 80, 400, 2,000, and 10,000 nM modified oligonucleotide by electroporation. mRNA was harvested and analyzed by RT-qPCR. PTEN mRNA was detected and RAPTOR mRNA was detected.

For in vivo toxicity studies, 2-4 BALB/C mice per group were administered 200 mg/kg modified oligonucleotide by subcutaneous injection and sacrificed 72 hours later. One animal was administered an injection of saline as a control. Plasma levels of ALT were measured using an automated clinical chemistry analyzer. Increased ALT is indicative of acute liver toxicity.

TABLE 12

Activity and toxicity of modified oligonucleotides complementary PTEN

| Compound ID | position of altered nucleotide in central region | sugar modification of altered nucleotide | PTEN $IC_{50}$ (μM) | RAPTOR $IC_{50}$ (μM) | ALT @ 200 mg/kg (IU/L) |
|---|---|---|---|---|---|
| 482050 | n/a | n/a | 3.9 | 2.4 | 2458 |
| 982037 | 2 | 2'-OMe | 2.7 | 10 | 133 |
| 985297 | 2 | 2'-MOE | 3 | 9.4 | 242 |
| 985298 | 2 | cEt | 1.4 | 2.1 | 890 |
| 1011277 | 2 | 2'-FANA | 3.1 | 3.5 | 1488 |
| 985296 | 2 | 2'-ribo-F | 2.2 | 6 | 1884 |
| 982038 | 3 | 2'-OMe | 1.8 | 3.7 | 327 |
| 985301 | 3 | 2'-MOE | 1.5 | 5 | 261 |
| 985302 | 3 | cEt | 2 | 3.3 | 87 |
| 1011278 | 3 | 2'-FANA | 1.7 | 1.1 | 14073 |
| 985300 | 3 | 2'-ribo-F | 2.2 | 6 | 107 |

For the in vitro study reported in the tables below, 3T3-L1 cells were transfected with 27, 80, 250, 740, 2, 222, 6,667, or 20,000 nM of modified oligonucleotide by electroporation and levels of P21 and Gadd45a were measured by RT-qPCR as described in example 1.

TABLE 12b in vitro P21 Expression

| Compound ID | 27 nM | 80 nM | 250 nM | 740 nM | 2,222 nM | 6,667 nM | 20,000 nM |
|---|---|---|---|---|---|---|---|
| | Expression level of P21 mRNA (% Control) | | | | | | |
| 482050 | 111 | 107 | 113 | 124 | 113 | 130 | 157 |
| 982036 | 92 | 95 | 93 | 95 | 91 | 110 | 162 |
| 982037 | 112 | 108 | 99 | 105 | 112 | 120 | 113 |
| 982038 | 108 | 105 | 111 | 111 | 114 | 99 | 108 |

TABLE 12c in vitro Gadd45a Expression

| Compound ID | 27 nM | 80 nM | 250 nM | 740 nM | 2,222 nM | 6,667 nM | 20,000 nM |
|---|---|---|---|---|---|---|---|
| | Expression level of Gadd45a mRNA (% Control) | | | | | | |
| 482050 | 65 | 64 | 70 | 67 | 79 | 176 | 276 |
| 982036 | 81 | 62 | 62 | 71 | 113 | 189 | 467 |
| 982037 | 107 | 90 | 79 | 75 | 79 | 100 | 165 |
| 982038 | 110 | 112 | 104 | 131 | 118 | 129 | 266 |

Example 6 Effect of Position-Specific 2'-Modifications on In Vitro Activity and In Vivo Liver Toxicity of Modified Oligonucleotides Complementary to SOD1

Modified oligonucleotides were synthesized with 2' modifications as indicated in the table below. These modified oligonucleotides were compared to the otherwise identical modified oligonucleotide lacking a modified nucleoside in the central region, a 3-10-3 cEt modified oligonucleotide, containing three cEt nucleosides in each of the 5' and 3' regions and 10 unmodified DNA nucleobases in the central region. The compounds in the table below are 100% complementary to mouse SOD1, GENBANK NT_039625.7 truncated from 24924000 to 24933000 (SEQ ID NO: 4), at position 5685 to 5880.

TABLE 13

Modified oligonucleotides complementary to SOD1

| Compound ID | position of altered nucleotide in central region | sugar modification of altered nucleotide | Chemistry Notation (5'-3') | SEQ ID NO |
|---|---|---|---|---|
| 508031 | n/a | n/a | $T_{ks}G_{ks}A_{ks}G_{ds}G_{ds}T_{ds}{}^{m}C_{ds}{}^{m}C_{ds}T_{ds}G_{ds}{}^{m}C_{ds}A_{ds}{}^{m}C_{ds}T_{ks}G_{ks}G_{k}$ | 26 |
| 508034 | n/a | n/a | $T_{ks}G_{ks}A_{ks}G_{ds}G_{ds}T_{ds}{}^{m}C_{ds}{}^{m}C_{ds}T_{ds}G_{ds}{}^{m}C_{ds}A_{ds}{}^{m}C_{ds}T_{es}G_{es}G_{e}$ | 26 |
| 508037 | n/a | n/a | $T_{es}G_{es}A_{es}G_{ds}G_{ds}T_{ds}{}^{m}C_{ds}{}^{m}C_{ds}T_{ds}G_{ds}{}^{m}C_{ds}A_{ds}{}^{m}C_{ds}T_{ks}G_{ks}G_{k}$ | 26 |
| 529933 | n/a | n/a | $T_{es}G_{es}A_{es}G_{ds}G_{ds}T_{ds}{}^{m}C_{ds}{}^{m}C_{ds}T_{ds}G_{ds}{}^{m}C_{ds}A_{ds}{}^{m}C_{ds}T_{es}G_{es}G_{e}$ | 26 |
| 895154 | 1 | 2'-OMe | $T_{ks}G_{ks}A_{ks}G_{ms}G_{ds}T_{ds}{}^{m}C_{ds}{}^{m}C_{ds}T_{ds}G_{ds}{}^{m}C_{ds}A_{ds}{}^{m}C_{ds}T_{ks}G_{ks}G_{k}$ | 26 |
| 895155 | 2 | 2'-OMe | $T_{ks}G_{ks}A_{ks}G_{ds}G_{ms}T_{ds}{}^{m}C_{ds}{}^{m}C_{ds}T_{ds}G_{ds}{}^{m}C_{ds}A_{ds}{}^{m}C_{ds}T_{ks}G_{ks}G_{k}$ | 26 |
| 985305 | 2 | 2'-MOE | $T_{ks}G_{ks}A_{ks}G_{ds}G_{es}T_{ds}{}^{m}C_{ds}{}^{m}C_{ds}T_{ds}G_{ds}{}^{m}C_{ds}A_{ds}{}^{m}C_{ds}T_{ks}G_{ks}G_{k}$ | 26 |
| 985306 | 2 | cEt | $T_{ks}G_{ks}A_{ks}G_{ds}G_{ks}T_{ds}{}^{m}C_{ds}{}^{m}C_{ds}T_{ds}G_{ds}{}^{m}C_{ds}A_{ds}{}^{m}C_{ds}T_{ks}G_{ks}G_{k}$ | 26 |
| 1011279 | 2 | 2'-FANA | $T_{ks}G_{ks}A_{ks}G_{ds}G_{(FANA)s}T_{ds}{}^{m}C_{ds}{}^{m}C_{ds}T_{ds}G_{ds}{}^{m}C_{ds}A_{ds}{}^{m}C_{ds}T_{ks}G_{ks}G_{k}$ | 26 |
| 985304 | 2 | 2'-ribo-F | $T_{ks}G_{ks}A_{ks}G_{ds}G_{fs}T_{ds}{}^{m}C_{ds}{}^{m}C_{ds}T_{ds}G_{ds}{}^{m}C_{ds}A_{ds}{}^{m}C_{ds}T_{ks}G_{ks}G_{k}$ | 26 |
| 895156 | 3 | 2'-OMe | $T_{ks}G_{ks}A_{ks}G_{ds}G_{ds}U_{ms}{}^{m}C_{ds}{}^{m}C_{ds}T_{ds}G_{ds}{}^{m}C_{ds}A_{ds}{}^{m}C_{ds}T_{ks}G_{ks}G_{k}$ | 27 |
| 985309 | 3 | 2'-MOE | $T_{ks}G_{ks}A_{ks}G_{ds}G_{ds}T_{es}{}^{m}C_{ds}{}^{m}C_{ds}T_{ds}G_{ds}{}^{m}C_{ds}A_{ds}{}^{m}C_{ds}T_{ks}G_{ks}G_{k}$ | 26 |
| 985310 | 3 | cEt | $T_{ks}G_{ks}A_{ks}G_{ds}G_{ds}T_{ks}{}^{m}C_{ds}{}^{m}C_{ds}T_{ds}G_{ds}{}^{m}C_{ds}A_{ds}{}^{m}C_{ds}T_{ks}G_{ks}G_{k}$ | 26 |
| 1011280 | 3 | 2'-FANA | $T_{ks}G_{ks}A_{ks}G_{ds}G_{ds}U_{(FANA)s}{}^{m}C_{ds}{}^{m}C_{ds}T_{ds}G_{ds}{}^{m}C_{ds}A_{ds}{}^{m}C_{ds}T_{ks}G_{ks}G_{k}$ | 27 |
| 985308 | 3 | 2'-ribo-F | $T_{ks}G_{ks}A_{ks}G_{ds}G_{ds}U_{fs}{}^{m}C_{ds}{}^{m}C_{ds}T_{ds}G_{ds}{}^{m}C_{ds}A_{ds}{}^{m}C_{ds}T_{ks}G_{ks}G_{k}$ | 27 |

A subscript "d" indicates an unmodified, 2'-β-D-deoxyribosyl sugar moiety. A subscript "e" indicates a 2'-MOE-β-D-ribofuranosyl sugar moiety. A subscript "m" indicates a 2'-O-methyl-β-D-ribofuranosyl sugar moiety. A subscript "k" indicates a cEt. A subscript "s" indicates a phosphorothioate internucleoside linkage. A subscript "f" indicates a 2'-F-β-D-2'-deoxyribosyl sugar moiety. A subscript "(FANA)" indicates a 2'-F-β-D-arabinofuranosyl modified sugar moiety. A superscript "m" before a C indicates 5-methyl Cytosine.

For in vitro activity studies, 3T3-L1 cells were plated at 20,000 cells/well and transfected with 16, 80, 400, 2,000, and 10,000 nM modified oligonucleotide by electroporation. mRNA was harvested and analyzed by RT-qPCR. SOD1 mRNA was detected using primer probe set RTS3025 (forward sequence: TTTTTTGCGCGGTCCTTTC (SEQ ID NO: 119); reverse sequence: GAGGGACCAGAGAGAGCAAGAC (SEQ ID NO: 120); probe sequence: CGCCTTCCGTCCGTCGGCT (SEQ ID NO:121)) and RAPTOR mRNA was detected as in Example 1 above.

For the in vivo toxicity study in the table below, two BALB/C mice per modified oligonucleotide were administered 150 mg/kg modified oligonucleotide by subcutaneous injection and sacrificed 72 hours later. One animal was administered an injection of saline as a control. Plasma levels of ALT were measured using an automated clinical chemistry analyzer. Increased ALT is indicative of acute liver toxicity.

TABLE 14

Activity and toxicity of modified oligonucleotides complementary SOD1

| Compound ID | position of altered nucleotide in central region | sugar modification of altered nucleotide | SOD1 $IC_{50}$ (μM) | RAPTOR $IC_{50}$ (μM) | ALT @ 150 mg/kg (IU/L) |
|---|---|---|---|---|---|
| 508031 | n/a | n/a | 0.03 | 0.46 | 21934 |
| 895155 | 2 | 2'-OMe | 0.04 | 1 | 112 |
| 985305 | 2 | 2'-MOE | 0.21 | n/a | 63 |
| 985306 | 2 | cEt | 1.61 | 10.2 | 826 |
| 1011279 | 2 | 2'-FANA | 0.28 | 1 | death |
| 985304 | 2 | 2'-ribo-F | 0.04 | 0.8 | 182 |
| 895156 | 3 | 2'-OMe | 0.48 | 4.5 | 1371 |
| 985309 | 3 | 2'-MOE | 0.61 | 6 | 1629 |
| 985310 | 3 | cEt | 1.46 | 11.9 | 178 |
| 1011280 | 3 | 2'-FANA | 0.6 | 4 | death |
| 985308 | 3 | 2'-ribo-F | 0.24 | 0.92 | 887 |

For in vitro activity studies, 3T3-L1 cells were plated at 20,000 cells/well and transfected with 30 nM, 80 nM, 250 nM, 740 nM, 2,222 nM, 6,667 nM, or 20,000 nM modified oligonucleotide by electroporation. P21 and Gadd45a mRNA were analyzed as in Example 1 above and caspase activation was measured as in Example 4 above. Results were normalized with Ribogreen® and are presented relative to the average of untreated control cells.

TABLE 14b in vitro P21 Expression

| Compound ID | 30 nM | 80 nM | 250 nM | 740 nM | 2,222 nM | 6,667 nM | 20,000 nM |
|---|---|---|---|---|---|---|---|
| | Expression level of P21 mRNA (% Control) | | | | | | |
| 508031 | 104 | 96 | 104 | 91 | 99 | 180 | 366 |
| 895154 | 94 | 117 | 85 | 93 | 105 | 159 | 181 |

TABLE 14b-continued in vitro P21 Expression

| Compound ID | 30 nM | 80 nM | 250 nM | 740 nM | 2,222 nM | 6,667 nM | 20,000 nM |
|---|---|---|---|---|---|---|---|
| | Expression level of P21 mRNA (% Control) | | | | | | |
| 895155 | 98 | 110 | 92 | 88 | 88 | 101 | 137 |
| 895156 | 95 | 104 | 74 | 97 | 125 | 139 | 283 |

TABLE 14c in vitro Gadd45a Expression

| Compound ID | 30 nM | 80 nM | 250 nM | 740 nM | 2,222 nM | 6,667 nM | 20,000 nM |
|---|---|---|---|---|---|---|---|
| | Expression level of Gadd45a mRNA (% Control) | | | | | | |
| 508031 | 103 | 99 | 113 | 103 | 139 | 564 | 844 |
| 895154 | 110 | 125 | 114 | 106 | 130 | 297 | 669 |
| 895155 | 129 | 139 | 120 | 126 | 122 | 145 | 340 |
| 895156 | 122 | 132 | 94 | 125 | 223 | 490 | 856 |

TABLE 14d in vitro Caspase Activation in 3T3-L1 cells

| Compound ID | 27 nM | 80 nM | 250 nM | 740 nM | 2,222 nM | 6,667 nM | 20,000 nM |
|---|---|---|---|---|---|---|---|
| | Caspase Activation | | | | | | |
| 508031 | 10871 | 11667 | 12107 | 14458 | 46619 | 101512 | 177873 |
| 895154 | 11681 | 11503 | 11656 | 11422 | 17167 | 70398 | 124774 |
| 895155 | 11669 | 11005 | 11479 | 11156 | 12487 | 20199 | 77630 |
| 895156 | 11980 | 10646 | 10616 | 11178 | 24226 | 72844 | 153302 |

For the in vivo toxicity study in the table below, three BALB/C mice per modified oligonucleotide were administered 100 mg/kg modified oligonucleotide by subcutaneous injection and sacrificed 72 hours later. One animal was administered an injection of saline as a control. Plasma levels of ALT and AST were measured using an automated clinical chemistry analyzer. Increased ALT and AST are indicative of acute liver toxicity.

For the in vivo study in the table below, three BALB/C mice per group were administered 33 or 100 mg/kg of modified oligonucleotide and sacrificed after 24 hours.

TABLE 15

Activity and toxicity of modified oligonucleotides complementary SOD1

| Compound ID | position of altered nucleotide in central region | sugar modification of altered nucleotide | P21 mRNA @ 100 mg/kg (% control) | Tnfrsf10b mRNA @ 100 mg/kg (% control) | Gadd45a mRNA @ 100 mg/kg (% control) | SOD1 mRNA @ 100 mg/kg (% control) |
|---|---|---|---|---|---|---|
| 508031 | n/a | n/a | 823 | 399 | 321 | 36 |
| 895154 | 1 | 2'-OMe | 125 | 176 | 345 | 56 |
| 895155 | 2 | 2'-OMe | 67 | 147 | 365 | 75 |
| 895156 | 3 | 2'-OMe | 538 | 351 | 525 | 51 |

For the in vivo study in the table below, three BALB/C mice per group were administered 33 or 100 mg/kg of modified oligonucleotide and sacrificed after 72 hours.

TABLE 15b

Activity and toxicity of modified oligonucleotides complementary SOD1

| Compound ID | position of altered nucleotide in central region | sugar modification of altered nucleotide | P21 mRNA @ 100 mg/kg (% control) | Tnfrsf10b mRNA @ 100 mg/kg (% control) | Gadd45a mRNA @ 100 mg/kg (% control) | SOD1 mRNA @ 100 mg/kg (% control) | ALT @ 100 mg/kg (IU/L) |
|---|---|---|---|---|---|---|---|
| 508031 | n/a | n/a | 6007 | 9032 | 392 | 13 | 16,317 |
| 895154 | 1 | 2'-OMe | 561 | 1042 | 129 | 19 | 206 |
| 895155 | 2 | 2'-OMe | 165 | 233 | 18 | 26 | 41 |
| 895156 | 3 | 2'-OMe | 3218 | 8189 | 190 | 9.6 | 1,242 |

TABLE 15c

Activity and toxicity of modified oligonucleotides complementary to SOD1

| Compound ID | 2' sugar modification in 5' region | 2' sugar modification in 3' region | P21 mRNA @ 100 mg/kg (% control) | Tnfrsf10b mRNA @ 100 mg/kg (% control) | SOD1 mRNA @ 100 mg/kg (% control) | ALT @ 100 mg/kg (IU/L) |
|---|---|---|---|---|---|---|
| 508031 | kkk | kkk | 3478 | 4593 | 9 | 14526 |
| 508034 | kkk | eee | 11365 | 7288 | 3 | 22396* |
| 508037 | eee | kkk | 130 | 225 | 17 | 20 |
| 529933 | eee | eee | 90 | 142 | 18 | 11 |

*2/3 animals were found dead

For the in vitro study reported in the tables below, 3T3-L1 cells were electroporated with 27 nM, 80 nM, 250 nM, 740 nM, 2, 222 nM, 6,667 nM, or 20,000 nM of modified oligonucleotide and levels of P21 and Gadd45a were measured by RT-qPCR as described in Example 1 above. Caspase-3 and caspase-7 activation was measured using the Caspase-Glo® 3/7 Assay System (G8090, Promega). Levels of caspase activation correlate with apoptotic cell death.

TABLE 15d in vitro Caspase Activation in 3T3-L1 cells

| Compound ID | 27 nM | 80 nM | 250 nM | 740 nM | 2,222 nM | 6,667 nM | 20,000 nM |
|---|---|---|---|---|---|---|---|
| | Caspase Activation | | | | | | |
| 508031 | 5969 | 6550 | 5986 | 8376 | 22499 | 56695 | 91450 |
| 508034 | 5652 | 5258 | 6555 | 7590 | 17098 | 49473 | 73813 |
| 508037 | 4027 | 4000 | 4222 | 4104 | 4208 | 3899 | 7869 |
| 529933 | 5904 | 5393 | 5595 | 5677 | 4772 | 4914 | 11918 |

TABLE 15e in vitro P21 mRNA in 3T3-L1 cells

| Compound ID | 27 nM | 80 nM | 250 nM | 740 nM | 2,222 nM | 6,667 nM | 20,000 nM |
|---|---|---|---|---|---|---|---|
| | Expression level of P21 mRNA (% Control) | | | | | | |
| 508031 | 132 | 116 | 119 | 108 | 121 | 185 | 692 |
| 508034 | 119 | 115 | 120 | 117 | 125 | 174 | 344 |
| 508037 | 120 | 119 | 121 | 121 | 117 | 122 | 149 |
| 529933 | 106 | 110 | 101 | 120 | 108 | 108 | 100 |

TABLE 15f in vitro Gadd45a mRNA in 3T3-L1 cells

| Compound ID | 27 nM | 80 nM | 250 nM | 740 nM | 2,222 nM | 6,667 nM | 20,000 nM |
|---|---|---|---|---|---|---|---|
| | Expression level of Gadd45a mRNA (% Control) | | | | | | |
| 508031 | 202 | 132 | 198 | 137 | 215 | 570 | 1046 |
| 508034 | 132 | 132 | 167 | 161 | 185 | 475 | 842 |
| 508037 | 175 | 164 | 181 | 175 | 195 | 215 | 416 |
| 529933 | 136 | 136 | 148 | 167 | 169 | 130 | 155 |

For the in vivo dose-response study in the table below, three BALB/C mice per group were administered 3.7, 11.1, 33, or 100 mg/kg 508031 or 3.7, 11.1, 33, 100, or 300 mg/kg 895155 by subcutaneous injection and sacrificed. Levels of Gadd45a, P21, and Tnfrsf1b mRNA were measured by RT-PCR as described in Example 1.

TABLE 15g

Activity and toxicity of modified oligonucleotides complementary to SOD1

| Compound ID | position of altered nucleotide in central region | sugar modification of altered nucleotide | $ED_{50}$ (mg/kg) |
|---|---|---|---|
| 508031 | n/a | n/a | 13.12 |
| 895155 | 2 | 2'-OMe | 38.8 |

TABLE 15h

In Vivo Dose-response of Tnfrsf10b mRNA upon treatment with modified oligonucleotides complementary to SOD1

| Compound ID | 3.7 mg/kg | 11.1 mg/kg | 33 mg/kg | 100 mg/kg | 300 mg/kg |
|---|---|---|---|---|---|
| | Expression level of Tnfrsf10b mRNA (% Control) | | | | |
| 508031 | 99 | 276 | 3443 | 6446 | n/a |
| 895155 | 81 | 105 | 115 | 193 | 2215 |

TABLE 15i

In Vivo Dose-response of P21 mRNA upon treatment with modified oligonucleotides complementary to SOD1

| Compound ID | 3.7 mg/kg | 11.1 mg/kg | 33 mg/kg | 100 mg/kg | 300 mg/kg |
|---|---|---|---|---|---|
| | Expression level of P21 mRNA (% Control) | | | | |
| 508031 | 163 | 222 | 1867 | 3788 | n/a |
| 895155 | 162 | 167 | 167 | 199 | 1467 |

Example 7 Effect of Position-Specific 2'-Modifications on In Vitro Activity and In Vivo Liver Toxicity of Modified Oligonucleotides Complementary to SRB1

Modified oligonucleotides were synthesized with 2' modifications as indicated in the table below. These modified oligonucleotides were compared to the otherwise identical modified oligonucleotide lacking a modified nucleoside in the central region, a 3-10-3 cEt modified oligonucleotide, containing three cEt nucleosides in each of the 5' and 3' regions and 10 unmodified DNA nucleosides in the central region. Each internucleoside linkage is a phosphorothioate. The compounds in the table below are 100% complementary to the complement of mouse SRB1, GENBANK NT_039313.7 truncated from 566000 to 632000 (SEQ ID NO: 5), at position 64840 to 64855.

TABLE 16

Modified oligonucleotides complementary to SRB1

| Compound ID | position of altered nucleotide in central region | sugar modification of altered nucleotide | Chemistry Notation (5'-3') | SEQ ID NO |
|---|---|---|---|---|
| 449093 | n/a | n/a | $T_{ks}T_{ks}{}^{m}C_{ks}A_{ds}G_{ds}T_{ds}{}^{m}C_{ds}A_{ds}T_{ds}G_{ds}A_{ds}{}^{m}C_{ds}T_{ds}T_{ks}{}^{m}C_{ks}{}^{m}C_{k}$ | 28 |
| 982030 | 1 | 2'-OMe | $T_{ks}T_{ks}{}^{m}C_{ks}A_{ms}G_{ds}T_{ds}{}^{m}C_{ds}A_{ds}T_{ds}G_{ds}A_{ds}{}^{m}C_{ds}T_{ds}T_{ks}{}^{m}C_{ks}{}^{m}C_{k}$ | 28 |
| 982031 | 2 | 2'-OMe | $T_{ks}T_{ks}{}^{m}C_{ks}A_{ds}G_{ms}T_{ds}{}^{m}C_{ds}A_{ds}T_{ds}G_{ds}A_{ds}{}^{m}C_{ds}T_{ds}T_{ks}{}^{m}C_{ks}{}^{m}C_{k}$ | 28 |
| 1042573 | 2 | 2'-MOE | $T_{ks}T_{ks}{}^{m}C_{ks}A_{ds}G_{es}T_{ds}{}^{m}C_{ds}A_{ds}T_{ds}G_{ds}A_{ds}{}^{m}C_{ds}T_{ds}T_{ks}{}^{m}C_{ks}{}^{m}C_{k}$ | 28 |
| 1042574 | 2 | cEt | $T_{ks}T_{ks}{}^{m}C_{ks}A_{ds}G_{ks}T_{ds}{}^{m}C_{ds}A_{ds}T_{ds}G_{ds}A_{ds}{}^{m}C_{ds}T_{ds}T_{ks}{}^{m}C_{ks}{}^{m}C_{k}$ | 28 |
| 1042575 | 2 | 2'-FANA | $T_{ks}T_{ks}{}^{m}C_{ks}A_{ds}G_{(FANA)s}T_{ds}{}^{m}C_{ds}A_{ds}T_{ds}G_{ds}A_{ds}{}^{m}C_{ds}T_{ds}T_{ds}{}^{m}C_{ks}{}^{m}C_{k}$ | 28 |
| 1042572 | 2 | 2'-ribo-F | $T_{ks}T_{ks}{}^{m}C_{ks}A_{ds}G_{fs}T_{ds}{}^{m}C_{ds}A_{ds}T_{ds}G_{ds}A_{ds}{}^{m}C_{ds}T_{ds}T_{ks}{}^{m}C_{ks}{}^{m}C_{k}$ | 28 |
| 982032 | 3 | 2'-OMe | $T_{ks}T_{ks}{}^{m}C_{ks}A_{ds}G_{ds}U_{ms}{}^{m}C_{ds}A_{ds}T_{ds}G_{ds}A_{ds}{}^{m}C_{ds}T_{ds}T_{ks}{}^{m}C_{ks}{}^{m}C_{k}$ | 29 |
| 1042577 | 3 | 2'-MOE | $T_{ks}T_{ks}{}^{m}C_{ks}A_{ds}G_{ds}T_{es}{}^{m}C_{ds}A_{ds}T_{ds}G_{ds}A_{ds}{}^{m}C_{ds}T_{ds}T_{ks}{}^{m}C_{ks}{}^{m}C_{k}$ | 28 |
| 1042578 | 3 | cEt | $T_{ks}T_{ks}{}^{m}C_{ks}A_{ds}G_{ds}T_{ks}{}^{m}C_{ds}A_{ds}T_{ds}G_{ds}A_{ds}{}^{m}C_{ds}T_{ds}T_{ks}{}^{m}C_{ks}{}^{m}C_{k}$ | 28 |
| 1042580 | 3 | 2'-FANA | $T_{ks}T_{ks}{}^{m}C_{ks}A_{ds}G_{ds}U_{(FANA)s}{}^{m}C_{ds}A_{ds}T_{ds}G_{ds}A_{ds}{}^{m}C_{ds}T_{ds}T_{ds}{}^{m}C_{ks}{}^{m}C_{k}$ | 29 |
| 1042576 | 3 | 2'-ribo-F | $T_{ks}T_{ks}{}^{m}C_{ks}A_{ds}G_{ds}U_{fs}{}^{m}C_{ds}A_{ds}T_{ds}G_{ds}A_{ds}{}^{m}C_{ds}T_{ds}T_{ks}{}^{m}C_{ks}{}^{m}C_{k}$ | 29 |

A subscript "d" indicates an unmodified, 2'-β-D-deoxyribosyl sugar moiety. A subscript "e" indicates a 2'-MOE-β-D-ribofuranosyl sugar moiety. A subscript "m" indicates a 2'-O-methyl-β-D-ribofuranosyl sugar moiety. A subscript "k" indicates a cEt. A subscript "s" indicates a phosphorothioate internucleoside linkage. A subscript "f" indicates a 2'-F-β-D-2'-deoxyribosyl sugar moiety. A subscript "(FANA)" indicates a 2'-F-β-D-arabinofuranosyl modified sugar moiety. A superscript "m" before a C indicates 5-methyl Cytosine.

For in vivo toxicity studies, two BALB/C mice per modified oligonucleotide was administered 150 mg/kg modified oligonucleotide by subcutaneous injection and sacrificed 72 hours later. One animal was administered an injection of saline as a control. Plasma levels of ALT were measured using an automated clinical chemistry analyzer. Increased ALT is indicative of acute liver toxicity.

TABLE 17

Toxicity of modified oligonucleotides complementary SRB1

| Compound ID | position of altered nucleotide in central region | sugar modification of altered nucleotide | ALT @ 150 mg/kg (IU/L) |
|---|---|---|---|
| 449093 | n/a | n/a | 2009 |
| 982031 | 2 | 2'-OMe | 2168 |

TABLE 17-continued

Toxicity of modified oligonucleotides complementary SRB1

| Compound ID | position of altered nucleotide in central region | sugar modification of altered nucleotide | ALT @ 150 mg/kg (IU/L) |
|---|---|---|---|
| 1042573 | 2 | 2'-MOE | 3368 |
| 1042574 | 2 | cEt | 1972 |
| 1042575 | 2 | 2'-FANA | 16335 |
| 1042572 | 2 | 2'-ribo-F | 3563 |
| 982032 | 3 | 2'-OMe | 1630 |
| 1042577 | 3 | 2'-MOE | 2965 |
| 1042578 | 3 | cEt | 3650 |

TABLE 17-continued

Toxicity of modified oligonucleotides complementary SRB1

| Compound ID | position of altered nucleotide in central region | sugar modification of altered nucleotide | ALT @ 150 mg/kg (IU/L) |
|---|---|---|---|
| 1042580 | 3 | 2'-FANA | 6622 |
| 1042576 | 3 | 2'-ribo-F | 3521 |

For the in vitro study reported in the tables below, 3T3-L1 cells were transfected with 27, 80, 250, 740, 2, 222, 6,667, or 20,000 nM of modified oligonucleotide by electroporation and levels of P21 and Gadd45a were measured by RT-qPCR as described in example 1.

TABLE 17b in vitro P21 Expression

| Compound ID | 27 nM | 80 nM | 250 nM | 740 nM | 2,222 nM | 6,667 nM | 20,000 nM |
|---|---|---|---|---|---|---|---|
| | Expression level of P21 mRNA (% Control) | | | | | | |
| 449093 | 99 | 107 | 101 | 104 | 175 | 212 | 255 |
| 982030 | 102 | 100 | 108 | 125 | 172 | 215 | 288 |

TABLE 17b-continued in vitro P21 Expression

| Compound ID | 27 nM | 80 nM | 250 nM | 740 nM | 2,222 nM | 6,667 nM | 20,000 nM |
|---|---|---|---|---|---|---|---|
| | Expression level of P21 mRNA (% Control) | | | | | | |
| 982031 | 115 | 116 | 114 | 137 | 174 | 204 | 330 |
| 982032 | 107 | 97 | 106 | 112 | 134 | 183 | 224 |

TABLE 17c in vitro Gadd45a Expression

| Compound ID | 27 nM | 80 nM | 250 nM | 740 nM | 2,222 nM | 6,667 nM | 20,000 nM |
|---|---|---|---|---|---|---|---|
| | Expression level of Gadd45a mRNA (% Control) | | | | | | |
| 449093 | 124 | 105 | 120 | 105 | 122 | 215 | 350 |
| 982030 | 105 | 103 | 107 | 104 | 126 | 249 | 551 |
| 982031 | 88 | 79 | 86 | 80 | 95 | 182 | 447 |
| 982032 | 82 | 69 | 73 | 76 | 89 | 172 | 366 |

Example 8 Effect of Inosine Substitution on In Vitro Activity and In Vivo Liver Toxicity of Modified Oligonucleotides Complementary to CXCL12 and Factor XI

TABLE 18

Modified oligonucleotides

| Compound ID | position of altered nucleotide in central region | nucleobase of altered nucleotide | Chemistry Notation (5'-3') | SEQ ID NO |
|---|---|---|---|---|
| 1061955 | 2 | Inosine | $Gk_{s}{}^{m}C_{ks}A_{ks}T_{ds}I_{ds}T_{ds}T_{ds}{}^{m}C_{ds}T_{ds}{}^{m}C_{ds}A_{ds}{}^{m}C_{ds}A_{ds}T_{ks}T_{ks}A_{k}$ | 30 |
| 1154233 | 2 | Inosine | $G_{ks}T_{ks}{}^{m}C_{ks}T_{ds}I_{ds}T_{ds}G_{ds}{}^{m}C_{ds}A_{ds}T_{ds}{}^{m}C_{ds}T_{ds}{}^{m}C_{ds}T_{ks}{}^{m}C_{ks}{}^{m}C_{k}$ | 40 |

A subscript "d" indicates a nucleoside comprising an unmodified, 2'-β-D-deoxyribosyl sugar moiety. A subscript "k" indicates a cEt. A subscript "s" indicates a phosphorothioate internucleoside linkage. A superscript "m" before C indicates 5-methyl Cytosine. I indicates inosine.

For in vitro activity studies, 3T3-L1 cells were plated at 20,000 cells/well and transfected with 27 nM, 80 nM, 250 nM, 740 nM, 2,222 nM, 6,667 nM, or 20,000 nM modified oligonucleotide by electroporation. mRNA was harvested and analyzed by RT-qPCR. CXCL12 mRNA and P21 mRNA were analyzed as in example 1.

Caspase-3 and caspase-7 activation was measured using the Caspase-Glo® 3/7 Assay System (G8090, Promega). Levels of caspase activation correlate with apoptotic cell death. Results are presented relative to the caspase activation in control cells not treated with modified oligonucleotide.

For the in vivo activity and toxicity study in the table below, two BALB/C mice per group were administered 16.7, 50, or 150 mg/kg modified oligonucleotide by subcutaneous injection and sacrificed 72 hours later. One animal was administered an injection of saline as a control. Plasma levels of ALT were measured using an automated clinical chemistry analyzer. Increased ALT is indicative of acute liver toxicity.

TABLE 19

Effect of Inosine on activity and toxicity

| Compound ID | position of altered nucleotide in central region | nucleobase of altered nucleotide | CXCL12 $IC_{50}$ (μM) | in vivo CXCL12 $ED_{50}$ (mg/kg) | ALT @ 16.7 mg/kg (IU/L) | ALT @ 50 mg/kg (IU/L) | ALT @ 150 mg/kg (IU/L) |
|---|---|---|---|---|---|---|---|
| 558807* | n/a | n/a | 0.2 | 1.7 | 209 | death | death |
| 1061955 | 2 | Inosine | 0.3 | 4.2 | 20.5 | 26 | 86 |

*Data presented above in Example 4

TABLE 19b in vitro P21 Expression

| Compound ID | 27 nM | 80 nM | 250 nM | 740 nM | 2,222 nM | 6,667 nM | 20,000 nM |
|---|---|---|---|---|---|---|---|
| | Expression level of P21 mRNA (% Control) | | | | | | |
| 558807 | 102 | 104 | 105 | 101 | 133 | 191 | 301 |
| 1061955 | 117 | 116 | 106 | 104 | 104 | 121 | 149 |

TABLE 19c in vitro Caspase Activation

| Compound ID | 27 nM | 80 nM | 250 nM | 740 nM | 2,222 nM | 6,667 nM | 20,000 nM |
|---|---|---|---|---|---|---|---|
| | Relative Caspase Activation (% Control) | | | | | | |
| 558807 | 135 | 110 | 131 | 115 | 147 | 476 | 462 |
| 1061955 | 75 | 81 | 134 | 120 | 121 | 162 | 170 |

For the study in the tables below, two BALB/C mice per group were administered 1.8 mg/kg, 5.5 mg/kg, 16.7 mg/kg, 50 mg/kg, or 150 mg/kg modified oligonucleotide by subcutaneous injection and sacrificed after 72 hours. 558807 was administered at 1.8 mg/kg, 5.5 mg/kg, 16.7 mg/kg due to acute toxicity at higher doses. Expression levels of Gadd45a, Tnfrsf10b, and P21 mRNA were measured as described in Example 1. Data for 558807 was also presented in Example 2, Tables 6b-6d.

TABLE 19d

| In Vivo Dose-response of Gadd45a mRNA upon treatment with modified oligonucleotides complementary to CXCL12 | | | | | |
|---|---|---|---|---|---|
| Compound ID | 1.8 mg/kg | 5.5 mg/kg | 16.7 mg/kg | 50 mg/kg | 150 mg/kg |
| | Expression level of Gadd45a mRNA (% Control) | | | | |
| 558807 | 122 | 211 | 278 | n/a | n/a |
| 1061955 | 109 | 86 | 93 | 84 | 123 |

TABLE 19e

| In Vivo Dose-response of Tnfrsf10b mRNA upon treatment with modified oligonucleotides complementary to CXCL12 | | | | | |
|---|---|---|---|---|---|
| Compound ID | 1.8 mg/kg | 5.5 mg/kg | 16.7 mg/kg | 50 mg/kg | 150 mg/kg |
| | Expression level of Tnfrsf10b mRNA (% Control) | | | | |
| 558807 | 160 | 166 | 271 | n/a | n/a |
| 1061955 | 158 | 77 | 126 | 134 | 192 |

TABLE 19f

| In Vivo Dose-response of P21 mRNA upon treatment with modified oligonucleotides complementary to CXCL12 | | | | | |
|---|---|---|---|---|---|
| Compound ID | 1.8 mg/kg | 5.5 mg/kg | 16.7 mg/kg | 50 mg/kg | 150 mg/kg |
| | Expression level of P21 mRNA (% Control) | | | | |
| 558807 | 173 | 148 | 1456 | n/a | n/a |
| 1061955 | 36 | 8.6 | 16 | 33 | 72 |

For the in vivo activity and toxicity study in the table below, two BALB/C mice per group were administered 33 or 100 mg/kg modified oligonucleotide by subcutaneous injection and sacrificed 72 hours later. Four mice were administered an injection of saline as a control. FXI mRNA expression was measured by RT-qPCR as described in Example 3. Plasma levels of ALT were measured using an automated clinical chemistry analyzer. Increased ALT is indicative of acute liver toxicity.

TABLE 19g

| Effect of Inosine on activity and toxicity | | | | | | |
|---|---|---|---|---|---|---|
| Compound ID | position of altered nucleotide in central region | nucleobase of altered nucleotide | FXI mRNA @ 33 mg/kg (% control) | FXI mRNA @ 100 mg/kg (% control) | ALT @ 33 mg/kg (IU/L) | ALT @ 100 mg/kg (IU/L) |
| 464917* | n/a | n/a | 10.9 | 0.9 | 7511 | 31066 |
| 1154233 | 2 | Inosine | 5.0 | 1.2 | 315 | 4553 |

*Data presented above in Example 4

Example 9 Effect of Position-Specific Nucleobase Substitutions on In Vitro Activity and In Vivo Liver Toxicity of Modified Oligonucleotides Complementary to CXCL12

Modified oligonucleotides containing nucleobase modifications at various positions were synthesized. These modified oligonucleotides were compared to the otherwise identical modified oligonucleotide lacking a modified nucleoside in the central region, a 3-10-3 cEt modified oligonucleotide, containing three cEt nucleosides in each of the 5' and 3' regions and 10 unmodified DNA nucleobases in the central region. The compounds in the table below are 100% complementary to mouse CXCL12, GENBANK NT_039353.7 truncated from 69/430,515 to 69/445,350 (SEQ ID NO: 1), at position 6877 to 6892.

Nucleobase Modifications:

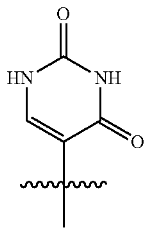

pseudouridine

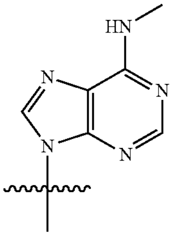

6-MeA

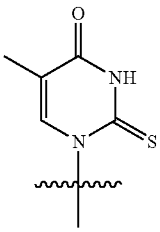

2-ThioT

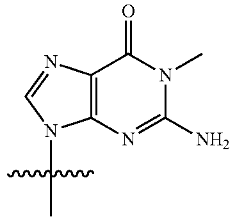

1-MeG

TABLE 20

| Modified oligonucleotides | | | | |
|---|---|---|---|---|
| Compound ID | position of altered nucleotide in central region | nucleobase of altered nucleotide | Chemistry Notation (5'-3') | SEQ ID NO |
| 1076587 | 2 | 6-MeA, 2'-OH | $G_{ks}{}^{m}C_{ks}A_{ks}T_{ds}{}^{m6}A_{rs}T_{ds}T_{ds}{}^{m}C_{ds}T_{ds}{}^{m}C_{ds}A_{ds}{}^{m}C_{ds}A_{ds}T_{ks}T_{ks}A_{k}$ | 31 |
| 1076588 | 3 | 6-MeA, 2'-OH | $G_{ks}{}^{m}C_{ks}A_{ks}T_{ds}G_{ds}{}^{m6}A_{rs}T_{ds}{}^{m}C_{ds}T_{ds}{}^{m}C_{ds}A_{ds}{}^{m}C_{ds}A_{ds}T_{ks}T_{ks}A_{k}$ | 32 |
| 1069852 | 2 | pseudouridine, 2'-OH | $G_{ks}{}^{m}C_{ks}A_{ks}T_{ds}\Psi_{rs}T_{ds}T_{ds}{}^{m}C_{ds}T_{ds}{}^{m}C_{ds}A_{ds}{}^{m}C_{ds}A_{ds}T_{ks}T_{ks}A_{k}$ | 33 |
| 1061328 | 3 | pseudouridine, 2'-OH | $G_{ks}{}^{m}C_{ks}A_{ks}T_{ds}G_{ds}\Psi_{rs}T_{ds}{}^{m}C_{ds}T_{ds}{}^{m}C_{ds}A_{ds}{}^{m}C_{ds}A_{ds}T_{ks}T_{ks}A_{k}$ | 34 |
| 1016673 | 1 | pseudouridine, 2'-H | $G_{ks}{}^{m}C_{ks}A_{ks}\Psi_{ds}G_{ds}T_{ds}T_{ds}{}^{m}C_{ds}T_{ds}{}^{m}C_{ds}A_{ds}{}^{m}C_{ds}A_{ds}T_{ks}T_{ks}A_{k}$ | 35 |
| 1004684 | 3 | pseudouridine, 2'-H | $G_{ks}{}^{m}C_{ks}A_{ks}T_{ds}T_{ds}\Psi_{ds}T_{ds}{}^{m}C_{ds}T_{ds}{}^{m}C_{ds}A_{ds}{}^{m}C_{ds}A_{ds}T_{ks}T_{ks}A_{k}$ | 36 |
| 1004685 | 4 | pseudouridine, 2'-H | $G_{ks}{}^{m}C_{ks}A_{ks}T_{ds}G_{ds}T_{ds}\Psi_{ds}{}^{m}C_{ds}T_{ds}{}^{m}C_{ds}A_{ds}{}^{m}C_{ds}A_{ds}T_{ks}T_{ks}A_{k}$ | 37 |
| 1016674 | 6 | pseudouridine, 2'-H | $G_{ks}{}^{m}C_{ks}A_{ks}T_{ds}G_{ds}T_{ds}{}^{m}C_{ds}T_{ds}\Psi_{ds}{}^{m}C_{ds}A_{ds}{}^{m}C_{ds}A_{ds}T_{ks}T_{ks}A_{k}$ | 38 |
| 863089 | 1 | 2-thioT | $G_{ks}{}^{m}C_{ks}A_{ks}{}^{s}T_{ds}G_{ds}T_{ds}T_{ds}{}^{m}C_{ds}T_{ds}{}^{m}C_{ds}A_{ds}{}^{m}C_{ds}A_{ds}T_{ks}T_{ks}A_{k}$ | 18 |
| 863090 | 3 | 2-thioT | $G_{ks}{}^{m}C_{ks}A_{ks}T_{ds}G_{ds}{}^{s}T_{ds}T_{ds}{}^{m}C_{ds}T_{ds}{}^{m}C_{ds}A_{ds}{}^{m}C_{ds}A_{ds}T_{ks}T_{ks}A_{k}$ | 18 |
| 863091 | 4 | 2-thioT | $G_{ks}{}^{m}C_{ks}A_{ks}T_{ds}G_{ds}T_{ds}{}^{s}T_{ds}{}^{m}C_{ds}T_{ds}{}^{m}C_{ds}A_{ds}{}^{m}C_{ds}A_{ds}T_{ks}T_{ks}A_{k}$ | 18 |
| 863092 | 6 | 2-thioT | $G_{ks}{}^{m}C_{ks}A_{ks}T_{ds}G_{ds}T_{ds}T_{ds}{}^{m}C_{ds}{}^{s}T_{ds}{}^{m}C_{ds}A_{ds}{}^{m}C_{ds}A_{ds}T_{ks}T_{ks}A_{k}$ | 18 |
| 1061964 | 2 | 1-MeG, 2'-OH | $G_{ks}{}^{m}C_{ks}A_{ks}T_{ds}{}^{m1}G_{rs}T_{ds}T_{ds}{}^{m}C_{ds}T_{ds}{}^{m}C_{ds}A_{ds}{}^{m}C_{ds}A_{ds}T_{ks}T_{ks}A_{k}$ | 18 |

A subscript "d" indicates an unmodified, 2'-β-D-deoxyribosyl sugar moiety. A subscript "r" indicates a unmodified, β-D-ribofuranosyl sugar moiety. A subscript "k" indicates a cEt. A subscript "s" indicates a phosphorothioate internucleoside linkage. A superscript "m" before C indicates 5-methyl Cytosine. A subscript "s" indicates a phosphorothioate internucleoside linkage. A superscript "m" before a nucleobase indicator indicates that the nucleobase has a 5-methyl group, such as methyl Cytosine, methyl Adenosine, or methyl Guanosine. A superscript "m6" before a A indicates 6-methyl Adenosine Ψ represents the nucleobase pseudouridine. ST represents the nucleobase 2-thiothymidine.

For in vitro activity studies, 3T3-L1 cells were plated at 20,000 cells/well and transfected with 10 nM, 30 nM, 250 nM, 740 nM, 2,220 nM, 6, 667 nM, or 20,000 nM modified oligonucleotide by electroporation. mRNA was harvested and analyzed by RT-qPCR. CXCL12 and RAPTOR mRNA was analyzed as in Example 1. The in vitro caspase assay was performed as described in Example 4.

For the in vivo toxicity study in the table below, two BALB/C mice per modified oligonucleotide were administered 50 or 150 mg/kg modified oligonucleotide by subcutaneous injection and sacrificed 72 hours later. One animal was administered an injection of saline as a control. Plasma levels of ALT were measured using an automated clinical chemistry analyzer. Increased ALT is indicative of acute liver toxicity.

TABLE 21

| Effect of modified nucleobases on activity and toxicity | | | | | | |
|---|---|---|---|---|---|---|
| Compound ID | position of altered nucleotide in central region | nucleobase of altered nucleotide | CXCL12 $IC_{50}$ (nM) | RAPTOR $IC_{50}$ (nM) | ALT @ 50 mg/kg (IU/L) | ALT @ 150 mg/kg (IU/L) |
| 558807 | n/a | n/a | 47 | 800 | 6303 | death |
| 1076587 | 2 | 6-MeA | 300 | 18 | n.d. | n.d. |
| 1076588 | 3 | 6-MeA | 1400 | 13 | n.d. | n.d. |
| 1016673 | 1 | pseudouridine, 2'-H | 156 | 3600 | n.d. | n.d. |
| 1004684 | 2 | pseudouridine, 2'-H | 105 | 2600 | n.d. | n.d. |
| 1004685 | 3 | pseudouridine, 2'-H | 157 | 4100 | n.d. | n.d. |
| 1016674 | 4 | pseudouridine, 2'-H | 142 | 3800 | n.d. | n.d. |
| 863089 | 1 | 2-thioT | 48 | 8800 | 390 | 3620 |
| 863090 | 3 | 2-thioT | 130 | 1400 | death | death |
| 863091 | 4 | 2-thioT | 155 | 1700 | 6237 | death |
| 863092 | 6 | 2-thioT | 110 | 1900 | 14514.5 | death |
| 1061964 | 2 | 1-MeG | 5200 | 8600 | n.d. | n.d. |

TABLE 21b

| in vitro Caspase Activation | | | | | | | |
|---|---|---|---|---|---|---|---|
| Compound ID | 27 nM | 80 nM | 250 nM | 740 nM | 2222 nM | 6667 nM | 20,000 nM |
| | Relative Caspase Activation (% Control) | | | | | | |
| 558807 | 100 | 100 | 100 | 97 | 110 | 202 | 298 |
| 1076587 | 90 | 86 | 80 | 82 | 81 | 77 | 94 |
| 1076588 | 91 | 91 | 96 | 91 | 96 | 97 | 114 |
| 1069852 | 97 | 87 | 105 | 100 | 89 | 79 | 85 |
| 1061328 | 92 | 95 | 96 | 98 | 102 | 153 | 199 |

TABLE 21c

| in vitro Caspase Activation | | | | | | | |
|---|---|---|---|---|---|---|---|
| Compound ID | 27 nM | 80 nM | 250 nM | 740 nM | 2,222 nM | 6,667 nM | 20,000 nM |
| | Relative Caspase Activation (% Control) | | | | | | |
| 558807 | 135 | 110 | 131 | 115 | 147 | 476 | 462 |
| 1061964 | 107 | 142 | 140 | 149 | 135 | 123 | 125 |

TABLE 21d

| in vitro P21 Expression | | | | | | | |
|---|---|---|---|---|---|---|---|
| Compound ID | 27 nM | 80 nM | 250 nM | 740 nM | 2,222 nM | 6,667 nM | 20,000 nM |
| | Expression level of P21 mRNA (% Control) | | | | | | |
| 558807 | 102 | 104 | 105 | 101 | 133 | 191 | 301 |
| 1061964 | 121 | 110 | 115 | 90 | 107 | 102 | 90 |

For in vivo activity and toxicity study in the table below, 2 BALB/C mice per group were administered modified oligonucleotide by subcutaneous injection and sacrificed after 72 hours. Compounds were dosed at 0.6, 1.8, 5.5, 16.7, 50 or 150 mg/kg. Tissue were collected and mRNA was isolated and levels of CXCL12 were measured by RT-qPCR with primer probe set RTS2605 as described above. Levels of Gadd45a were analyzed using primer probe set Mm00432802_ml (ThermoFisher). Levels of P21 were analyzed using primer probe set Mm04207341_ml (ThermoFisher). Levels of Tnfrsf10b were analyzed using primer probe set Mm00457866_ml (ThermoFisher). Expression levels were normalized with Ribogreen® and are presented relative to levels in mice treated with PBS.

TABLE 21e

| In Vivo of modified oligonucleotides complementary to CXCL12 containing 2-Thio-T | | | | |
|---|---|---|---|---|
| Compound ID | 2-Thio-T position in central region | ALT @ 16.7 mg/kg (IU/L) | ALT @ 50 mg/kg (IU/L) | ALT @ 150 mg/kg (IU/L) |
| PBS | n/a | 27 (@ 0 mg/kg) | | |
| 558807 | n/a | 2002 | 6303 | death |
| 863089 | 1 | 60 | 390 | 3620 |
| 863090 | 3 | 4929 | death | death |
| 863091 | 4 | 1894 | 6237 | death |
| 863092 | 6 | 1073 | 14515 | death |

TABLE 21f

| In Vivo Activity of modified oligonucleotides complementary to CXCL12 containing 2-Thio-T | | | | | | |
|---|---|---|---|---|---|---|
| Compound ID | 0.6 mg/kg | 1.8 mg/kg | 5.5 mg/kg | 16.7 mg/kg | 50 mg/kg | 150 mg/kg |
| | Expression level of CXCL12 mRNA (% Control) | | | | | |
| 558807 | 65 | 34 | 14 | 4 | 7 | n.d. |
| 863089 | 72 | 51 | 33 | 16 | 14 | 8 |
| 863090 | 58 | 31 | 11 | 11 | 0 | 0 |
| 863091 | 66 | 28 | 24 | 12 | 12 | 0 |
| 863092 | 59 | 42 | 20 | 5 | 6 | 0 |

Example 10 Effect of Position-Specific Morpholinos on In Vitro Activity and In Vivo Liver Toxicity of Modified Oligonucleotides Complementary to CXCL12

Modified oligonucleotides containing morpholinos at various positions were synthesized. These modified oligonucleotides were compared to the otherwise identical modified oligonucleotide lacking a modified nucleoside in the central region, a 3-10-3 cEt modified oligonucleotide, containing three cEt nucleosides in each of the 5' and 3' regions and 10 unmodified DNA nucleobases in the central region. The compounds in the table below are 100% complementary to mouse CXCL12, GENBANK NT_039353.7 truncated from 69/430,515 to 69/445,350 (SEQ ID NO: 1), at position 6877 to 6892. Morpholino residues replace a full nucleotide, including the internucleoside linkage, and have the structures shown below.

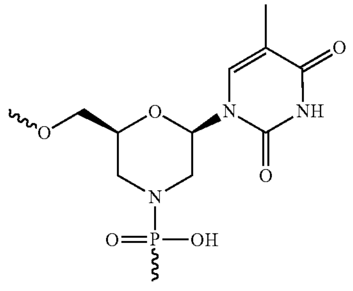

T morpholino PO

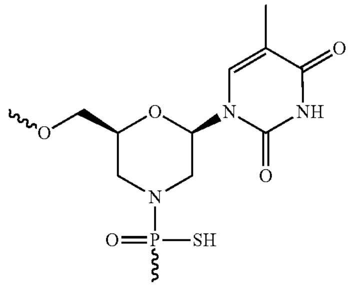

T morpholino PS

TABLE 22

| Modified oligonucleotides | | | | |
|---|---|---|---|---|
| Compound ID | morpholino position in central region | morpholino type | Chemistry Notation (5'-3') | SEQ ID NO |
| 1044689 | 1 | T-PO | $G_{ks}{}^{m}C_{ks}A_{ks}(MP^{T}{}_{o})G_{ds}T_{ds}T_{ds}{}^{m}C_{ds}T_{ds}{}^{m}C_{ds}A_{ds}{}^{m}C_{ds}A_{ds}T_{ks}T_{ks}A_{k}$ | 18 |
| 1044690 | 3 | T-PO | $G_{ks}{}^{m}C_{ks}A_{ks}T_{ds}G_{ds}(MP^{T}{}_{o})T_{ds}{}^{m}C_{ds}T_{ds}{}^{m}C_{ds}A_{ds}{}^{m}C_{ds}A_{ds}T_{ks}T_{ks}A_{k}$ | 18 |
| 1044691 | 4 | T-PO | $G_{ks}{}^{m}C_{ks}A_{ks}T_{ds}G_{ds}T_{ds}(MP^{T}{}_{o}){}^{m}C_{ds}T_{ds}{}^{m}C_{ds}A_{ds}{}^{m}C_{ds}A_{ds}T_{ks}T_{ks}A_{k}$ | 18 |
| 1044692 | 6 | T-PO | $G_{ks}{}^{m}C_{ks}A_{ks}T_{ds}G_{ds}T_{ds}T_{ds}{}^{m}C_{ds}(MP^{T}{}_{o}){}^{m}C_{ds}A_{ds}{}^{m}C_{ds}A_{ds}T_{ks}T_{ks}A_{k}$ | 18 |
| 1048416 | 1 | T-PS | $G_{ks}{}^{m}C_{ks}A_{ks}(MP^{T}{}_{s})G_{ds}T_{ds}T_{ds}{}^{m}C_{ds}T_{ds}{}^{m}C_{ds}A_{ds}{}^{m}C_{ds}A_{ds}T_{ks}T_{ks}A_{k}$ | 18 |
| 1048417 | 3 | T-PS | $G_{ks}{}^{m}C_{ks}A_{ks}T_{ds}G_{ds}(MP^{T}{}_{s})T_{ds}{}^{m}C_{ds}T_{ds}{}^{m}C_{ds}A_{ds}{}^{m}C_{ds}A_{ds}T_{ks}T_{ks}A_{k}$ | 18 |
| 1048418 | 4 | T-PS | $G_{ks}{}^{m}C_{ks}A_{ks}T_{ds}G_{ds}T_{ds}(MP^{T}{}_{s}){}^{m}C_{ds}T_{ds}{}^{m}C_{ds}A_{ds}{}^{m}C_{ds}A_{ds}T_{ks}T_{ks}A_{k}$ | 18 |
| 1048419 | 6 | T-PS | $G_{ks}{}^{m}C_{ks}A_{ks}T_{ds}G_{ds}T_{ds}T_{ds}{}^{m}C_{ds}(MP^{T}{}_{s}){}^{m}C_{ds}A_{ds}{}^{m}C_{ds}A_{ds}T_{ks}T_{ks}A_{k}$ | 18 |

A subscript "d" indicates a nucleoside comprising an unmodified, 2'-β-D-deoxyribosyl sugar moiety. A subscript "r" indicates a nucleoside comprising an unmodified, β-D-ribofuranosyl sugar moiety. A subscript "k" indicates a cEt. A subscript "s" indicates a phosphorothioate internucleoside linkage. A superscript "m" before C indicates 5-methyl Cytosine. A $(MP^{T}{}_{o})$ represents a phosphate thymidine morpholino, while $(MP^{T}{}_{S})$ represents a phosphorothioate thymidine morpholino.

TABLE 22

| Effect of morpholinos on in vitro activity and toxicity | | | | |
|---|---|---|---|---|
| Compound ID | morpholino position in central region | morpholino type | CXCL12 $IC_{50}$ (nM) | RAPTOR $IC_{50}$ (nM) |
| 558807 | n/a | n/a | 47 | 800 |
| 1044689 | 1 | T-PO | 405 | >20000 |
| 1044690 | 3 | T-PO | 182 | 4100 |
| 1044691 | 4 | T-PO | 128 | 4400 |
| 1044692 | 6 | T-PO | 145 | 1900 |
| 1048416 | 1 | T-PS | 333 | >20000 |
| 1048417 | 3 | T-PS | 159 | 3300 |
| 1048418 | 4 | T-PS | 134 | 5200 |
| 1048419 | 6 | T-PS | 119 | 1100 |

Example 11 Effect of Position-Specific MOP on In Vitro Activity and In Vivo Toxicity of Modified Oligonucleotides Complementary CXCL12, Factor XI, PTEN, and SOD-1

Modified oligonucleotides were synthesized with MOP neutral backbone linkages at specific positions in place of phosphorothioate linkages. These modified oligonucleotides were compared to the otherwise identical modified oligonucleotide lacking the altered nucleotide in the central region, a 3-10-3 cEt modified oligonucleotide, containing three cEt nucleosides in each of the 5' and 3' regions and 10 unmodified DNA nucleosides in the central region, and phosphorothioate linkages throughout. The compounds in the table below are 100% complementary to mouse CXCL12, Factor XI, PTEN, or SOD-1, with sequences described above.

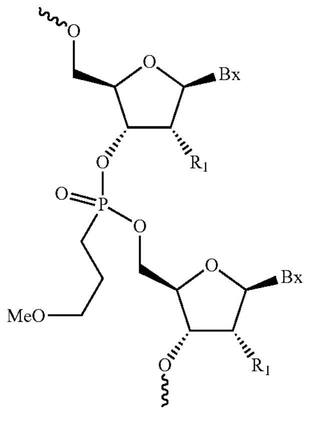

MOP
(alkyl phosphonate)

TABLE 23

| Modified oligonucleotides containing MOP linkages | | | | |
|---|---|---|---|---|
| Compound ID | MOP position in central region | Target | Chemistry Notation (5'-3') | SEQ ID NO |
| 766676 | 1 | CXCL12 | $G_{ks}{}^{m}C_{ks}A_{ks}T_{dx}G_{ds}T_{ds}T_{ds}{}^{m}C_{ds}T_{ds}{}^{m}C_{ds}A_{ds}{}^{m}C_{ds}A_{ds}T_{ks}T_{ks}A_{k}$ | 18 |
| 766677 | 2 | CXCL12 | $G_{ks}{}^{m}C_{ks}A_{ks}T_{ds}G_{dx}T_{ds}T_{ds}{}^{m}C_{ds}T_{ds}{}^{m}C_{ds}A_{ds}{}^{m}C_{ds}A_{ds}T_{ks}T_{ks}A_{k}$ | 18 |
| 766678 | 3 | CXCL12 | $G_{ks}{}^{m}C_{ks}A_{ks}T_{ds}G_{ds}T_{dx}T_{ds}{}^{m}C_{ds}T_{ds}{}^{m}C_{ds}A_{ds}{}^{m}C_{ds}A_{ds}T_{ks}T_{ks}A_{k}$ | 18 |
| 766679 | 4 | CXCL12 | $G_{ks}{}^{m}C_{ks}A_{ks}T_{ds}G_{ds}T_{ds}T_{dx}{}^{m}C_{ds}T_{ds}{}^{m}C_{ds}A_{ds}{}^{m}C_{ds}A_{ds}T_{ks}T_{ks}A_{k}$ | 18 |
| 766680 | 5 | CXCL12 | $G_{ks}{}^{m}C_{ks}A_{ks}T_{ds}G_{ds}T_{ds}T_{ds}{}^{m}C_{dx}T_{ds}{}^{m}C_{ds}A_{ds}{}^{m}C_{ds}A_{ds}T_{ks}T_{ks}A_{k}$ | 18 |
| 766681 | 6 | CXCL12 | $G_{ks}{}^{m}C_{ks}A_{ks}T_{ds}G_{ds}T_{ds}T_{ds}{}^{m}C_{ds}T_{ds}{}^{m}C_{ds}A_{ds}{}^{m}C_{ds}A_{ds}T_{ks}T_{ks}A_{k}$ | 18 |
| 766682 | 7 | CXCL12 | $G_{ks}{}^{m}C_{ks}A_{ks}T_{ds}G_{ds}T_{ds}T_{ds}{}^{m}C_{ds}T_{ds}{}^{m}C_{dx}A_{ds}{}^{m}C_{ds}A_{ds}T_{ks}T_{ks}A_{k}$ | 18 |
| 766683 | 8 | CXCL12 | $G_{ks}{}^{m}C_{ks}A_{ks}T_{ds}G_{ds}T_{ds}T_{ds}{}^{m}C_{ds}T_{ds}{}^{m}C_{ds}A_{dx}{}^{m}C_{ds}A_{ds}T_{ks}T_{ks}A_{k}$ | 18 |
| 766684 | 9 | CXCL12 | $G_{ks}{}^{m}C_{ks}A_{ks}T_{ds}G_{ds}T_{ds}T_{ds}{}^{m}C_{ds}T_{ds}{}^{m}C_{ds}A_{ds}{}^{m}C_{dx}A_{ds}T_{ks}T_{ks}A_{k}$ | 18 |
| 766685 | 10 | CXCL12 | $G_{ks}{}^{m}C_{ks}A_{ks}T_{ds}G_{ds}T_{ds}T_{ds}{}^{m}C_{ds}T_{ds}{}^{m}C_{ds}A_{ds}{}^{m}C_{ds}A_{dx}T_{ks}T_{ks}A_{k}$ | 18 |

TABLE 23-continued

Modified oligonucleotides containing MOP linkages

| Compound ID | MOP position in central region | Target | Chemistry Notation (5'-3') | SEQ ID NO |
|---|---|---|---|---|
| 965605 | 2 | FactorXI | $G_{ks}T_{ks}{}^{m}C_{ks}T_{ds}G_{dx}T_{ds}G_{ds}{}^{m}C_{ds}A_{ds}T_{ds}{}^{m}C_{ds}T_{ds}{}^{m}C_{ds}T_{ks}{}^{m}C_{ks}{}^{m}C_{k}$ | 22 |
| 965606 | 3 | FactorXI | $G_{ks}T_{ks}{}^{m}C_{ks}T_{ds}G_{ds}T_{dx}G_{ds}{}^{m}C_{ds}A_{ds}T_{ds}{}^{m}C_{ds}T_{ds}{}^{m}C_{ds}T_{ks}{}^{m}C_{ks}{}^{m}C_{k}$ | 22 |
| 985299 | 2 | PTEN | $A_{ks}T_{ks}{}^{m}C_{ks}A_{ds}T_{dx}G_{ds}G_{ds}{}^{m}C_{ds}T_{ds}G_{ds}{}^{m}C_{ds}A_{ds}G_{dsm}C_{ks}T_{ks}T_{k}$ | 24 |
| 985303 | 3 | PTEN | $A_{ks}T_{ks}{}^{m}C_{ks}A_{ds}T_{ds}G_{dx}G_{ds}{}^{m}C_{ds}T_{ds}G_{ds}{}^{m}C_{ds}A_{ds}G_{ds}{}^{m}C_{ks}T_{ks}T_{k}$ | 24 |
| 985307 | 2 | SOD1 | $T_{ks}G_{ks}A_{ks}G_{ds}G_{dx}T_{ds}{}^{m}C_{ds}{}^{m}C_{ds}T_{ds}G_{ds}{}^{m}C_{ds}A_{ds}{}^{m}C_{ds}T_{ks}G_{ks}G_{k}$ | 26 |
| 985311 | 3 | SOD1 | $T_{ks}G_{ks}A_{ks}G_{ds}G_{ds}T_{dx}{}^{m}C_{ds}{}^{m}C_{ds}T_{ds}G_{ds}{}^{m}C_{ds}A_{ds}{}^{m}C_{ds}T_{ks}G_{ks}G_{k}$ | 26 |

A subscript "d" indicates an unmodified, 2'-β-D-deoxyribosyl sugar moiety. A subscript "k" indicates a cEt. A subscript "s" indicates a phosphorothioate internucleoside linkage. A superscript "m" before a C indicates 5-methyl Cytosine. A subscript "x" indicates a MOP or methoxypropyl internucleoside linkage. The position of the internucleoside linkage is designated as the position of the nucleoside that is on the 5' end of the linkage.

For in vitro activity studies for compounds complementary to CXCL12, b.END cells were plated at 20,000 cells/well and transfected with 0, 27 nM, 82 nM, 247 nM, 740 nM, 2,220 nM, 6,660 nM or 20,000 nM antisense oligonucleotide by electroporation. mRNA was harvested and analyzed by RT-qPCR. CXCL12 and raptor mRNA was analyzed as in previous examples.

For in vitro activity studies for compounds complementary to Factor XI, PTEN or SOD1, 3T3-L1 cells were plated at 20,000 cells/well and transfected with 0, 27 nM, 82 nM, 247 nM, 740 nM, 2,220 nM, 6,660 nM or 20,000 nM antisense oligonucleotide by electroporation. mRNA was harvested and analyzed by RT-qPCR. Complementary mRNA and raptor mRNA was analyzed as in previous examples.

For the in vivo toxicity study in the table below, one or two BALB/C mice per modified oligonucleotide were administered modified oligonucleotide by subcutaneous injection and sacrificed 72 hours later. One animal was administered an injection of saline as a control. Plasma levels of ALT were measured using an automated clinical chemistry analyzer. Increased ALT is indicative of acute liver toxicity.

For the in vivo activity study in the table below, two to four BALB/C mice per dosing group were administered modified oligonucleotide by subcutaneous injection and sacrificed 24 hours later. Mice were administered 1.9 mg/kg, 5.6 mg/kg, 16.7 mg/kg, 50 mg/k or 150 mg/kg of compound 558807 or 766676-766685. Mice were administered 6.25 mg/kg, 12.5 mg/kg, 25 mg/kg, 50 mg/kg, or 100 mg/kg modified oligonucleotide for compounds 965605 and 965606. Mice were administered 6.25 mg/kg, 12.5 mg/kg, 25 mg/kg, or 100 mg/kg modified oligonucleotide for 464917. Mice were administered 6.25 mg/kg, 12.5 mg/kg, 25 mg/kg, or 150 mg/kg modified oligonucleotide for 482050. Mice were administered 6.25 mg/kg, 12.5 mg/kg, 25 mg/kg, 50 mg/kg or 150 mg/kg modified oligonucleotide for 985299 and 985303. Mice were administered 12.5 mg/kg, 25 mg/kg, 50 mg/kg or 150 mg/kg modified oligonucleotide for 508031, 985307, and 985311. Two animals were administered an injection of saline as a control.

TABLE 24

Effect of MOP backbone modifications on activity and toxicity

| Compound ID | MOP position in central region | Complementary mRNA | Complementary mRNA $IC_{50}$ (μM) | RAPTOR $IC_{50}$ (μM) | in vivo Complementary mRNA $ED_{50}$ (mg/kg) | ALT @ Max dose* (IU/L) |
|---|---|---|---|---|---|---|
| PBS | n/a | n/a | n/a | n/a | n/a | 23 |
| 558807 | n/a | CXCL12 | 0.095 | 1.26 | 2.9 | death |
| 766676 | 1 | CXCL12 | 0.100 | 5.8 | 4.5 | 7764 |
| 766677 | 2 | CXCL12 | 0.110 | >>10 | 6.8 | 46 |
| 766678 | 3 | CXCL12 | 0.115 | >>10 | 6.2 | 44 |
| 766679 | 4 | CXCL12 | 0.080 | 7.2 | 5.7 | 4481 |
| 766680 | 5 | CXCL12 | 0.085 | 3.5 | 5.1 | 9139 |
| 766681 | 6 | CXCL12 | 0.080 | 3.0 | 3.6 | 17846 |
| 766682 | 7 | CXCL12 | 0.090 | 3.8 | 4.4 | 12510 |
| 766683 | 8 | CXCL12 | 0.070 | 2.2 | 4.3 | death |
| 766684 | 9 | CXCL12 | 0.090 | 2.2 | 3.1 | death |
| 766685 | 10 | CXCL12 | 0.090 | 2.0 | 2.1 | death |
| 464917 | n/a | Factor XI | n.d. | 1.6 | 6.9 | 33848 |
| 965605 | 2 | Factor XI | n.d. | 3.7 | 10.2 | 3464 |
| 965606 | 3 | Factor XI | n.d. | 7.7 | 12.3 | 1160 |
| 482050 | n/a | PTEN | 3.9 | 2.4 | 67 | 2458 |
| 985299 | 2 | PTEN | 1.1 | 4 | 120 | 767 |
| 985303 | 3 | PTEN | 1.7 | 3.7 | 194 | 43 |
| 508031 | n/a | SOD1 | 0.03 | 0.46 | 63 | 21934 |

TABLE 24-continued

Effect of MOP backbone modifications on activity and toxicity

| Compound ID | MOP position in central region | Complementary mRNA | Complementary mRNA $IC_{50}$ (μM) | RAPTOR $IC_{50}$ (μM) | in vivo Complementary mRNA $ED_{50}$ (mg/kg) | ALT @ Max dose* (IU/L) |
|---|---|---|---|---|---|---|
| 985307 | 2 | SOD1 | 0.17 | 3.6 | 157 | 57 |
| 985311 | 3 | SOD1 | 0.78 | 5.1 | 173 | 71 |

*ALT at 150 mg/kg for CXCL12 oligonucleotides, 100 mg/kg for Factor XI oligonucleotides, 200 mg/kg for PTEN oligonucleotides 985299 and 985303, 100 mg/kg for PTEN oligonucleotide 482050 and 150 mg/kg for SOD1 oligonucleotides 985307 and 985311, and 100 mg/kg for SOD1 oligonucleotide 508031.
**Value represents the average of two independent experiments Relative caspase activation in 3T3-L1 cells was determined as described in Example 4.

For the in vitro study reported in the tables below, b.END cells were electroporated with 27 nM, 80 nM, 250 nM, 740 nM, 2, 222 nM, 6,667 nM, or 20,000 nM of modified oligonucleotide and levels of P21 were measured by RT-qPCR using primer probe set Mm04207341_ml (ThermoFisher).

Selected modified nucleotides described in above were tested for their effect on HeLa cells by microscopy. HeLa cells were transfected by lipofectamine 2000 with 200 nM of modified oligonucleotide for 2 hrs and then cellular protein p54nrb was stained by mP54 antibody (Santa Cruz Biotech, sc-376865) and DAPI was used to stain for the nucleus of cells. The number of cells with nucleolar p54nrb and the total number of cells in the images were counted.

TABLE 24a

Effect of MOP backbone modifications on activity and toxicity

| Compound ID | MOP position in central region | Complementary mRNA | Caspase (% mock) | in vitro p21 mRNA (% saline) | % nucleolar p54nrb |
|---|---|---|---|---|---|
| 558807 | n/a | CXCL12 | 313 | 243 | 82 |
| 766676 | 1 | CXCL12 | 243 | 187 | 32 |
| 766677 | 2 | CXCL12 | 121 | 179 | 25 |
| 766678 | 3 | CXCL12 | 136 | 180 | 32 |
| 766679 | 4 | CXCL12 | 240 | 195 | 39 |
| 766680 | 5 | CXCL12 | 351 | 263 | 86 |
| 766681 | 6 | CXCL12 | 315 | 309 | 79 |
| 766682 | 7 | CXCL12 | 345 | 236 | 71 |
| 766683 | 8 | CXCL12 | 257 | 260 | 91 |
| 766684 | 9 | CXCL12 | 314 | 247 | 88 |
| 766685 | 10 | CXCL12 | 308 | 291 | 90 |

For the in vivo toxicity study in the table below, two BALB/C mice per dosing group were administered modified oligonucleotide by subcutaneous injection and sacrificed 72 hours later. Mice were administered 10 mg/kg, 33 mg/kg, or 100 mg/kg modified oligonucleotide for compounds 464917, 965605, and 965606 and 10 mg/kg, 100 mg/kg, or 200 mg/kg for 482050, 985299, and 985303. Two animals were administered an injection of saline as a control. Plasma levels of ALT were measured using an automated clinical chemistry analyzer. Increased ALT is indicative of acute liver toxicity. Therapeutic index was calculated as the ratio of maximum non-toxic dose (MNTD)/$ED_{50}$, where $ED_{50}$ was determined via the in vivo activity study reported in the table above.

TABLE 24b in vivo Toxicity improvement for modified oligonucleotides complementary to Factor XI

| Compound ID | ALT @ 10 mg/kg | ALT @ 33 mg/kg | ALT @ 100 mg/kg | TI (MNTD/ ED50) |
|---|---|---|---|---|
| 464917 | 239 | 8199 | 33848 | 1.4 |
| 965605 | 46 | 125 | 3464 | 3.2 |
| 965606 | 55 | 77 | 1160 | 2.7 |

TABLE 24c in vivo Toxicity improvement for modified oligonucleotides complementary to PTEN

| Compound ID | ALT @ 10 mg/kg | ALT @ 100 mg/kg | ALT @ 200 mg/kg | TI (MNTD/ ED50) |
|---|---|---|---|---|
| 482050 | 55 | 9496 | 5329 | 0.15 |
| 985299 | 45 | 164 | 767 | 0.8 |
| 985303 | 33 | 39 | 43 | 1.0 |

TABLE 24d in vivo Toxicity improvement for modified oligonucleotides complementary to SOD1

| Compound ID | ALT @ 50 mg/kg | ALT @ 150 mg/kg | TI (MNTD/ ED50) |
|---|---|---|---|
| 482050 | 2189 | n.d. | <0.8 |
| 985307 | n.d. | 57 | >1.0 |
| 985311 | n.d. | 71 | >0.9 |

Example 12 Effect of Position-Specific MOP in Combination with 2'-Modifications Modified oligonucleotides were synthesized with MOP neutral backbone linkages at specific positions in place of phosphorothioate linkages in combination with 2'-FANA or 2'-OMe modified sugar moieties. These modified oligonucleotides were compared to the otherwise identical modified oligonucleotide lacking a modified nucleoside in the central region, a 3-10-3 cEt modified oligonucleotide, containing three cEt nucleosides in each of the 5' and 3' regions and 10 unmodified DNA nucleosides in the central region, and phosphorothioate linkages throughout. The compounds in the table below are 100% complementary to mouse CXCL12 or SOD1, with sequences as described above.

3'-HPPO-GalNAc refers to the structure below, wherein the phosphate group is attached to the 3'-oxygen atom of the 3' nucleoside:

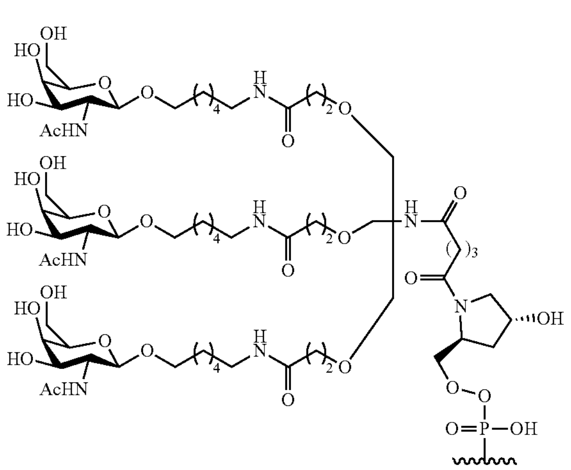

TABLE 25

Modified oligonucleotides containing MOP linkages and 2'-Modifications

| Compound ID | MOP position in central region | 2'-altered nucleotid eposition in central region | sugar modification of 2'-altered nucleotide | Target | Chemistry Notation (5'-3') | SEQ ID NO |
|---|---|---|---|---|---|---|
| 1061302 | 1 | 1 | 2'-OMe | CXCL12 | $G_{ks}{}^{m}C_{ks}A_{ks}T_{mx}G_{ds}T_{ds}T_{ds}{}^{m}C_{ds}T_{ds}{}^{m}C_{ds}A_{ds}{}^{m}C_{ds}A_{ds}T_{ks}T_{ks}A_{k}$ | 18 |
| 1061303 | 2 | 2 | 2'-OMe | CXCL12 | $G_{ks}{}^{m}C_{ks}A_{ks}T_{ds}G_{mx}T_{ds}T_{ds}{}^{m}C_{ds}T_{ds}{}^{m}C_{ds}A_{ds}{}^{m}C_{ds}A_{ds}T_{ks}T_{ks}A_{k}$ | 18 |
| 1061304 | 3 | 3 | 2'-OMe | CXCL12 | $G_{ks}{}^{m}C_{ks}A_{ks}T_{ds}G_{ds}T_{mx}T_{ds}{}^{m}C_{ds}T_{ds}{}^{m}C_{ds}A_{ds}{}^{m}C_{ds}A_{ds}T_{ks}T_{ks}A_{k}$ | 18 |
| 1061305 | 4 | 4 | 2'-OMe | CXCL12 | $G_{ks}{}^{m}C_{ks}A_{ks}T_{ds}G_{ds}T_{ds}T_{mx}{}^{m}C_{ds}T_{ds}{}^{m}C_{ds}A_{ds}{}^{m}C_{ds}A_{ds}T_{ks}T_{ks}A_{k}$ | 18 |
| 1061306 | 1 | 1 | 2'-OMe | SOD1 | $T_{ks}G_{ks}A_{ks}G_{mx}G_{ds}T_{ds}{}^{m}C_{ds}{}^{m}C_{ds}T_{ds}G_{ds}{}^{m}C_{ds}A_{ds}{}^{m}C_{ds}T_{ks}G_{ks}G_{k}$ | 26 |
| 1061307 | 2 | 2 | 2'-OMe | SOD1 | $T_{ks}G_{ks}A_{ks}G_{ds}G_{mx}T_{ds}{}^{m}C_{ds}{}^{m}C_{ds}T_{ds}G_{ds}{}^{m}C_{ds}A_{ds}{}^{m}C_{ds}T_{ks}G_{ks}G_{k}$ | 26 |
| 1061308 | 3 | 3 | 2'-OMe | SOD1 | $T_{ks}G_{ks}A_{ks}G_{ds}G_{ds}T_{mx}{}^{m}C_{ds}{}^{m}C_{ds}T_{ds}G_{ds}{}^{m}C_{ds}A_{ds}{}^{m}C_{ds}T_{ks}G_{ks}G_{k}$ | 26 |
| 955900 | 3 | 1 | 2'-FANA | CXCL12 | $G_{ks}{}^{m}C_{ks}A_{ks}U_{(FANA)s}G_{ds}T_{dx}T_{ds}{}^{m}C_{ds}T_{ds}{}^{m}C_{ds}A_{ds}{}^{m}C_{ds}A_{ds}T_{ks}T_{ks}A_{k}$ | 19 |
| 955901 | 3 | 2 | 2'-FANA | CXCL12 | $G_{ks}{}^{m}C_{ks}A_{ks}T_{ds}G_{(FANA)s}Td_{x}T_{ds}{}^{m}C_{ds}T_{ds}{}^{m}C_{ds}A_{ds}{}^{m}C_{ds}A_{ds}T_{ks}T_{ks}A_{k}$ | 18 |
| 955902 | 3 | 4 | 2'-FANA | CXCL12 | $G_{ks}{}^{m}C_{ks}A_{ks}T_{ds}G_{ds}T_{dx}U_{(FANA)s}{}^{m}C_{ds}T_{ds}{}^{m}C_{ds}A_{ds}{}^{m}C_{ds}A_{ds}T_{ks}T_{ks}A_{k}$ | 21 |
| 955903 | 3 | 5 | 2'-FANA | CXCL12 | $G_{ks}{}^{m}C_{ks}A_{ks}T_{ds}G_{ds}T_{dx}T_{ds}C_{(FANA)s}T_{ds}{}^{m}C_{ds}A_{ds}{}^{m}C_{ds}A_{ds}T_{ks}T_{ks}A_{k}$ | 18 |
| 955904 | 3 | 6 | 2'-FANA | CXCL12 | $G_{ks}{}^{m}C_{ks}A_{ks}T_{ds}G_{ds}T_{dx}T_{ds}{}^{m}C_{ds}U_{(FANA)s)}{}^{m}C_{ds}A_{ds}{}^{m}C_{ds}A_{ds}T_{ks}T_{ks}A_{k}$ | 39 |
| 955905 | 3 | 7 | 2'-FANA | CXCL12 | $G_{ks}{}^{m}C_{ks}A_{ks}T_{ds}G_{ds}T_{dx}T_{ds}{}^{m}C_{ds}T_{ds}{}^{m}C_{ds}T_{ds}C_{(FANA)s}A_{ds}{}^{m}C_{ds}A_{ds}T_{ks}T_{ks}A_{k}$ | 18 |
| 955906 | 3 | 8 | 2'-FANA | CXCL12 | $G_{ks}{}^{m}C_{ks}A_{ks}T_{ds}G_{ds}T_{dx}T_{ds}{}^{m}C_{ds}T_{ds}{}^{m}D_{ds}A_{(FANA)s}{}^{m}C_{ds}A_{ds}T_{ks}T_{ks}A_{k}$ | 18 |
| 955907 | 3 | 9 | 2'-FANA | CXCL12 | $G_{ks}{}^{m}C_{ks}A_{ks}T_{ds}G_{ds}T_{dx}T_{ds}{}^{m}C_{ds}T_{ds}{}^{m}C_{ds}A_{ds}C_{(FANA)s}A_{ds}T_{ks}T_{ks}A_{k}$ | 18 |
| 955908 | 3 | 10 | 2'-FANA | CXCL12 | $G_{ks}{}^{m}C_{ks}A_{ks}T_{ds}G_{ds}T_{dx}T_{ds}{}^{m}C_{ds}T_{ds}{}^{m}C_{ds}A_{ds}{}^{m}C_{ds}A_{(FANA)s}T_{ks}T_{ks}A_{k}$ | 18 |
| 855156 | n/a | n/a | n/a | CXCL12 | $G_{ks}{}^{m}C_{ks}A_{ks}T_{ds}G_{ds}T_{ds}T_{ds}{}^{m}C_{ds}T_{ds}{}^{m}C_{ds}A_{ds}{}^{m}C_{ds}A_{ds}T_{ks}T_{ks}A_{k}$-HPPO-GalNac | 18 |
| 855161 | 3 | n/a | n/a | CXCL12 | $G_{ks}{}^{m}C_{ks}A_{ks}T_{ds}G_{ds}T_{dx}T_{ds}{}^{m}C_{ds}T_{ds}{}^{m}C_{ds}A_{ds}{}^{m}C_{ds}A_{ds}T_{ks}T_{ks}A_{k}$-HPPO-GalNac | 18 |
| 855160 | 1,2 | n/a | n/a | CXCL12 | $G_{ks}{}^{m}C_{ks}A_{ks}T_{dx}G_{dx}T_{ds}T_{ds}{}^{m}C_{ds}T_{ds}{}^{m}C_{ds}A_{ds}{}^{m}C_{ds}A_{ds}T_{ks}T_{ks}A_{k}$-HPPO-GalNac | 18 |
| 895571 | n/a | 3 | 2'-MOE | CXCL12 | $G_{ks}{}^{m}C_{ks}A_{ks}T_{ds}G_{ds}T_{es}T_{ds}{}^{m}C_{ds}T_{ds}{}^{m}C_{ds}A_{ds}{}^{m}C_{ds}A_{ds}T_{ks}T_{ks}A_{k}$-HPPO-GalNac | 18 |

TABLE 25-continued

| Modified oligonucleotides containing MOP linkages and 2'-Modifications | | | | | | |
|---|---|---|---|---|---|---|
| Compound ID | MOP position in central region | 2'-altered nucleotid eposition in central region | sugar modification of 2'-altered nucleotide | Target | Chemistry Notation (5'-3') | SEQ ID NO |
| 978782 | 3 | 2 | 2'-FANA | CXCL12 | $G_{ks}{}^{m}C_{ks}A_{ks}T_{ds}G_{(FANA)s}T_{dx}$ $T_{ds}{}^{m}C_{ds}T_{ds}{}^{m}C_{ds}A_{ds}{}^{m}C_{ds}A_{ds}T_{ks}T_{ks}A_{k}$-HPPO-GalNac | 18<br>18 |
| 978783 | 3 | 4 | 2'-FANA | CXCL12 | $G_{ks}{}^{m}C_{ks}A_{ks}T_{ds}G_{ds}T_{dx}$ $U_{(FANA)s}{}^{m}C_{ds}T_{ds}{}^{m}C_{ds}A_{ds}{}^{m}C_{ds}A_{ds}T_{ks}T_{ks}A_{k}$-HPPO-GalNac | 21 |
| 978784 | 3 | 5 | 2'-FANA | CXCL12 | $G_{ks}{}^{m}C_{ks}A_{ks}T_{ds}G_{ds}T_{dx}$ $T_{ds}C_{(FANA)s}T_{ds}{}^{m}C_{ds}A_{ds}{}^{m}C_{ds}A_{ds}T_{ks}T_{ks}A_{k}$-HPPO-GalN | 18 |
| 978785 | 3 | 6 | 2'-FANA | CXCL12 | $G_{ks}{}^{m}C_{ks}A_{ks}T_{ds}G_{ds}T_{dx}$ $T_{ds}{}^{m}C_{ds}U_{(FANA)s}{}^{m}C_{ds}A_{ds}{}^{m}C_{ds}A_{ds}T_{ks}T_{ks}A_{k}$-HPPO-GalNac | 39 |
| 978786 | 3 | 10 | 2'-FANA | CXCL12 | $G_{ks}{}^{m}C_{ks}A_{ks}T_{ds}G_{ds}T_{dx}$ $T_{ds}{}^{m}C_{ds}T_{ds}{}^{m}C_{ds}A_{ds}{}^{m}C_{ds}A_{(FANA)s}T_{ks}T_{ks}A_{k}$-HPPO-GalNac | 18 |

A subscript "d" indicates an unmodified, 2'-β-D-deoxyribosyl sugar moiety. A subscript "e" indicates a 2'-MOE-β-D-ribofuranosyl sugar moiety. A subscript "m" indicates a 2'-O-methyl-β-D-ribofuranosyl sugar moiety. A subscript "k" indicates a cEt. A subscript "s" indicates a phosphorothioate internucleoside linkage. A subscript "f" indicates a 2'-F-β-D-2'-deoxyribosyl sugar moiety. A subscript "(FANA)" indicates a 2'-F-β-D-arabinofuranosyl modified sugar moiety. A superscript "m" before a C indicates 5-methyl Cytosine.

For in vitro activity studies, 3T3-L1 cells were plated at 20,000 cells/well and transfected with 0, 27 nM, 82 nM, 247 nM, 740 nM, 2,220 nM, 6,660 nM or 20,000 nM of modified oligonucleotide by electroporation. After X hours, mRNA was harvested and analyzed by RT-qPCR. Target and raptor mRNA was analyzed as previous examples.

TABLE 26

| Effect of MOP backbone modifications combined with ara-F modifications on in vitro activity and toxicity | | | | |
|---|---|---|---|---|
| Compound ID | MOP position in central region | FANA position in central region | Target $IC_{50}$ (nM) | RAPTOR $IC_{50}$ (nM) |
| 558807 | n/a | n/a | 34 | 1000 |
| 766678 | 3 | n/a | 67 | >20,000 |
| 955900 | 3 | 1 | 58 | >20,000 |
| 955901 | 3 | 2 | 43 | >20,000 |
| 955902 | 3 | 4 | 27 | >20,000 |
| 955903 | 3 | 5 | 27 | >20,000 |
| 955904 | 3 | 6 | 65 | >20,000 |
| 955905 | 3 | 7 | 93 | 16000 |
| 955906 | 3 | 8 | 99 | >20,000 |
| 955907 | 3 | 9 | 154 | >20,000 |
| 955908 | 3 | 10 | 171 | >20,000 |

For the in vivo toxicity study in the table below, three male BALB/C mice per modified oligonucleotide were administered 0.2, 0.6, 1.8 or 50 mg/kg modified oligonucleotide by subcutaneous injection and sacrificed 72 hours later. One animal was administered an injection of saline as a control. Plasma levels of ALT were measured using an automated clinical chemistry analyzer. Increased ALT is indicative of acute liver toxicity.

TABLE 27

| Effect of MOP backbone modifications combined with 2' modifications on in vivo activity and toxicity | | | | | |
|---|---|---|---|---|---|
| Compound ID | MOP position in central region | position of 2'-altered nucleotide in central region | sugar modification of 2'-altered nucleotide | in vivo CXCL12 $ED_{50}$ (mg/kg) | ALT @ 50 mg/kg |
| 855156 | n/a | n/a | n/a | 0.13 | 2938* |
| 855161 | 3 | n/a | n/a | 0.36 | 40 |
| 855160 | 2, 3 | n/a | n/a | 0.37 | 28 |
| 895571 | n/a | 3 | 2'-MOE | 0.43 | 319 |
| 978782 | 3 | 2 | 2'-FANA | 0.47 | 56 |
| 978783 | 3 | 4 | 2'-FANA | 0.43 | 39 |

*Value represents the ALT at 1.8 mg/kg

For the in vivo toxicity study in the table below, male BALB/C mice per modified oligonucleotide were administered 5, 50, or 150 mg/kg modified oligonucleotide by subcutaneous injection and sacrificed 72 hours later. One animal was administered an injection of saline as a control. Plasma levels of ALT were measured using an automated clinical chemistry analyzer. Increased ALT is indicative of acute liver toxicity. The caspase assay was performed in vitro as described in Example 8.

TABLE 28

Effect of MOP backbone modifications combined with 2'-OMe modified sugar moieties

| Compound ID | MOP position in central region | 2'-OMe position in central region | CXCL12 $IC_{50}$ (μM) | in vivo CXCL12 $ED_{50}$ (mg/kg) | ALT @ 50 mg/kg (IU/L) | ALT @ 150 mg/kg (IU/L) |
|---|---|---|---|---|---|---|
| 558807 | n/a | n/a | 0.18 | 2.88 | 8329 | death |
| 936053 | n/a | 2 | 0.17 | 1.75 | 75 | 40 |
| 1061302 | 1 | 1 | 0.09 | 0.39 | 101 | 2253 |
| 1061303 | 2 | 2 | 0.13 | 11 | 49 | 34 |
| 1061304 | 3 | 3 | 0.09 | 4.6 | 31 | 52 |
| 1061305 | 4 | 4 | 0.09 | 15.4 | 22 | 31 |

TABLE 28b in vitro Caspase Activation

| Compound ID | 27 nM | 80 nM | 250 nM | 740 nM | 2,222 nM | 6,667 nM | 20,000 nM |
|---|---|---|---|---|---|---|---|
| | Relative Caspase Activation (% Control) | | | | | | |
| 558807 | 98 | 106 | 112 | 139 | 288 | 587 | 1977 |
| 936053 | 106 | 111 | 113 | 91 | 98 | 107 | 153 |
| 1061302 | 98 | 90 | 106 | 111 | 149 | 456 | 1555 |
| 1061303 | 104 | 99 | 104 | 84 | 102 | 86 | 125 |
| 1061304 | 91 | 97 | 82 | 96 | 85 | 105 | 269 |
| 1061305 | 90 | 96 | 72 | 91 | 84 | 103 | 348 |

TABLE 28c

In Vivo Dose-response of Gadd45a mRNA upon treatment with modified oligonucleotides complementary to CXCL12

| Compound ID | 5.0 mg/kg | 50 mg/kg | 150 mg/kg |
|---|---|---|---|
| | Expression level of Gadd45a mRNA (% Control) | | |
| 558807 | 120 | 473 | n.d. |
| 936053 | 76 | 169 | 219 |
| 1061302 | 188 | 178 | 357 |
| 1061303 | 55 | 66 | 66 |
| 1061304 | 58 | 66 | 97 |
| 1061305 | 67 | 18 | 20 |

TABLE 28d

In Vivo Dose-response of Tnfrsf10b mRNA upon treatment with modified oligonucleotides complementary to CXCL12

| Compound ID | 5.0 mg/kg | 50 mg/kg | 150 mg/kg |
|---|---|---|---|
| | Expression level of Tnfrs10b mRNA (% Control) | | |
| 558807 | 137 | 8022 | n.d. |
| 936053 | 91 | 104 | 180 |
| 1061302 | 104 | 137 | 1217 |
| 1061303 | 90 | 92 | 110 |
| 1061304 | 70 | 75 | 149 |
| 1061305 | 79 | 60 | 50 |

TABLE 28e

In Vivo Dose-response of P21 mRNA upon treatment with modified oligonucleotides complementary to CXCL12

| Compound ID | 5.0 mg/kg | 50 mg/kg | 150 mg/kg |
|---|---|---|---|
| | Expression level of P21 mRNA (% Control) | | |
| 558807 | 84 | 58138 | n.d. |
| 936053 | 239 | 81 | 299 |
| 1061302 | 87 | 315 | 14680 |
| 1061303 | 293 | 495 | 480 |
| 1061304 | 182 | 400 | 353 |
| 1061305 | 353 | 321 | 223 |

Example 13 Effect of Position-Specific 2'-OMe on In Vitro Activity and Toxicity of Modified Oligonucleotides with a Variety of Sequences Modified oligonucleotides were synthesized as indicated in the table below. The compounds have the sugar motif kkk-d(10)-kkk or kkk-d-m-d(8)-kkk, where "k" represents a cEt, "d" represents an unmodified, 2'-β-D-deoxyribosyl sugar moiety, and "m" represents a 2'-OMe-β-D-ribofuranosyl sugar moiety. For sequences with a T at position 5 (from the 5' end) in the parent kkk-d(10)-kkk oligonucleotide, the kkk-d-m-d(8)-kkk contains a 2'-OMe modified U at this position. For sequences with a $^{m}$C at position 5 (from the 5' end) in the parent kkk-d(10)-kkk oligonucleotide, the kkk-d-m-d(8)-kkk contains a 2'-OMe modified C at this position, with no 5-Me group.

For the in vivo toxicity study in the table below, two male BALB/C mice per modified oligonucleotide were administered 150 mg/kg modified oligonucleotide by subcutaneous injection and sacrificed 72 hours later. One animal was administered an injection of saline as a control. Plasma levels of ALT was measured using an automated clinical chemistry analyzer. Increased ALT is indicative of acute liver toxicity.

For a subset of compounds, on-target activity was measured in the liver. RNA was isolated from the liver and measured by RT-qPCR using the primer probe sets described in Table 30 below. Results were normalized with Ribogreen® and are reported normalized to PBS-treated animals.

Levels of mRNA for Gadd45a, P21, and Tnfrsf10b were analyzed as in Example 1 for mice administered 150 mg/kg modified oligonucleotide. Results are normalized with Ribogreen® and presented relative to PBS-treated control animals.

The caspase assay was performed in vitro as described in Example 8.

TABLE 29

Targets and Sequences

| Parent Compound ID | Corresponding compound with 2'-OMe at position 2 of the central region | Complementary mRNA | Sequence | SEQ ID NO |
|---|---|---|---|---|
| 546006 | 1133071 | HDAC2 | GAGGATGGCAAGCACA | 41 |
| 549334 | | AR | CACCTGCGGGAAGCTC | 42 |
| | 1200896 | AR | CACCUGCGGGAAGCTC | 126 |
| 562920 | 1201379 | VWF | TGTGCCCCAGCCCATT | 43 |
| 572912 | 1200898 | PABPN1 | CTTCCACAGTATATCT | 44 |
| 576095 | 1200899 | EGLN2 | TACTGGTAGTGTTGCT | 45 |
| 597605 | 1200900 | HEGFL | TTGACACAAAGGGAGT | 46 |
| 601840 | 1201381 | MTDH | GAATCTCCTTTTCCAG | 47 |
| 640599 | 1201862 | EZH2 | TTTACACGCTTCCGCC | 48 |
| 694804 | | DNM2 | AGACTCTCGGTTCCGA | 49 |
| | 1202810 | | AGACUCTCGGTTCCGA | 127 |
| 738431 | 1200905 | Nestin | CTTTTCTATCAGTCTC | 51 |
| 739428 | | WWTR1/TNS | CTTCTTGATGTCTTTC | 52 |
| | 1201694 | | CTTCUTGATGTCTTTC | 129 |
| 747137 | 1200907 | FOXO1A | AAGTGTCACTAAAACC | 53 |
| 747149 | | FOXO1A | GGACTGAAATAGCAGA | 54 |
| | 1203759 | | GGACUGAAATAGCAGA | 130 |
| 747190 | | FOXO1A | AGGCTGGCCCCCACTG | 55 |
| | 1203759 | | AGGCUGGCCCCCACTG | 131 |

TABLE 29-continued

Targets and Sequences

| Parent Compound ID | Corresponding compound with 2'-OMe at position 2 of the central region | Complementary mRNA | Sequence | SEQ ID NO |
|---|---|---|---|---|
| 758252 | | CHOP/ | GGTTTTTGATTCTTCC | 56 |
| | 1203759 | DDIT3 | GGTTUTTGATTCTTCC | 132 |
| 797793 | 1201073 | DLL4 | GCATGCCGCCCCGTCC | 57 |
| 808013 | 1203761 | CYBB | TCTTCATACAATAGCA | 58 |
| 813942 | 1203762 | CDK9 | CGTTCAAATTCCGTCT | 59 |
| 832311 | 1201199 | PEMT | TCCGGCTGCGGCTCAG | 60 |

TABLE 30

Primer Probe Sets

| Transcript | PP Set Name | Primer | Sequence | SEQ ID NO: |
|---|---|---|---|---|
| HDAC2 | RTS3500 | Forward | TGATGGTGTTGAGGAAGCTTTTT | 15 |
| | | Reverse | TCCCTCAAGTCTCCTGTTCCA | 16 |
| | | Probe | ACAACAGATCGCGTGATGACCGTCTC | 17 |
| DNM2 | RTS36436 | Forward | AGAGGAGACCGAGCGAAT | 61 |
| | | Reverse | CATGGTTTGTGTTGATGTACGAC | 62 |
| | | Probe | CCTACATCAGGGAGCGAGAAGGGA | 63 |
| FOXO1A | RTS4973 | Forward | GTCAAGACTACAACACACAGC | 64 |
| | | Reverse | AAAACTATAAGGAGGGGTGAAGG | 65 |
| | | Probe | CTGAAGGACTTTTAAATGTAGCCTGCTCACTAA | 66 |
| PABPN1 | n/a | Forward | CCGGAGCTAGAAGCGATCAA | 70 |
| | | Reverse | CCTTTAGCTTCTCAGCCTCTTCCT | 71 |
| | | Probe | CTCGAGTCAGGGAGATG | 72 |

TABLE 31

Toxicity and Activity

| Compound ID | Position of 2'-altered nucleotide in central region | sugar modification of altered nucleotide | Gadd45a mRNA (% Control) | Tnfrsf10b mRNA (% Control) | P21 mRNA (% Control) | ALT @ 150 mg/kg | Relative Caspase Activation (% Control) @ 20 µM | Complementary mRNA* (% Control) |
|---|---|---|---|---|---|---|---|---|
| PBS | n/a | n/a | 100 | 100 | 111 | 28 @ 0 | n.d. | 100 |
| 546006 | n/a | n/a | 1885 | 4660 | 6556 | 131 | 291 | 38 |
| 1133071 | 2 | 2'-Ome | 1357 | 5569 | 6541 | 245 | 279 | 37 |
| 549334 | n/a | n/a | 187 | 225 | 182 | 30 | n.d. | n.d. |
| 1200896 | 2 | 2'-Ome | 165 | 126 | 130 | 28 | n.d. | n.d. |
| 562920 | n/a | n/a | 498 | 568 | 1336 | 109 | 473 | n.d. |
| 1201379 | 2 | 2'-Ome | 171 | 200 | 402 | 32 | 473 | n.d. |
| 572912 | n/a | n/a | 357 | 7503 | 5043 | 3883 | 205 | n.d. |
| 1200898 | 2 | 2'-Ome | 155 | 170 | 301 | 41 | 84 | n.d. |
| 576095 | n/a | n/a | 147 | 121 | 154 | 39 | n.d. | n.d. |
| 1200899 | 2 | 2'-Ome | 401 | 154 | 169 | 32 | n.d. | n.d. |
| 597605 | n/a | n/a | 353 | 1965 | 2263 | 488 | 328 | n.d. |
| 1200900 | 2 | 2'-Ome | 121 | 227 | 228 | 32 | 126 | n.d. |
| 601840 | n/a | n/a | 221 | 365 | 840 | 98 | 287 | n.d. |
| 1201381 | 2 | 2'-Ome | 103 | 123 | 72 | 24 | 274 | n.d. |
| 640599 | n/a | n/a | 111 | 286 | 376 | 26 | 184 | n.d. |

TABLE 31-continued

| Toxicity and Activity | | | | | | | | |
|---|---|---|---|---|---|---|---|---|
| Compound ID | Position of 2'-altered nucleotide in central region | sugar modification of altered nucleotide | Gadd45a mRNA (% Control) | Tnfrsf10b mRNA (% Control) | P21 mRNA (% Control) | ALT @ 150 mg/kg | Relative Caspase Activation (% Control) @ 20 μM | Complementary mRNA* (% Control) |
| 1201862 | 2 | 2'-Ome | 96 | 262 | 276 | 22 | 99 | n.d. |
| 694804 | n/a | n/a | 336 | 916 | 1297 | 1090 | 257 | 6 |
| 1202810 | 2 | 2'-Ome | 106 | 238 | 257 | 36 | 166 | 16 |
| 715415 | n/a | n/a | 186 | 1211 | 1249 | 420 | 137 | n.d. |
| 1203758 | 2 | 2'-Ome | 78 | 150 | 115 | 41 | 141 | n.d. |
| 738431 | n/a | n/a | 229 | 507 | 448 | 608 | 220 | n.d. |
| 1200905 | 2 | 2'-Ome | 141 | 193 | 197 | 69 | 181 | n.d. |
| 739428 | n/a | n/a | 234 | 1975 | 2107 | 533 | 269 | n.d. |
| 1201694 | 2 | 2'-Ome | 154 | 593 | 388 | 42 | 114 | n.d. |
| 747137 | n/a | n/a | 155 | 1379 | 1851 | 50 | 512 | 19 |
| 1200907 | 2 | 2'-Ome | 99 | 716 | 824 | 39 | 168 | 27 |
| 747149 | n/a | n/a | 454 | 5765 | 4892 | 606 | 166 | 9 |
| 1203759 | 2 | 2'-Ome | 105 | 119 | 211 | 33 | 109 | 22 |
| 747190 | n/a | n/a | 162 | 2856 | 4677 | 1315 | 393 | 2 |
| 1200961 | 2 | 2'-Ome | 129 | 237 | 345 | 71 | 305 | 7 |
| 758252 | n/a | n/a | 158 | 989 | 861 | 725 | 355 | n.d. |
| 1233760 | 2 | 2'-Ome | 94 | 106 | 182 | 47 | 187 | n.d. |
| 797793 | n/a | n/a | 190 | 1175 | 1181 | 1318 | 229 | n.d. |
| 1201073 | 2 | 2'-Ome | 184 | 230 | 201 | 78 | 125 | n.d. |
| 808013 | n/a | n/a | 126 | 2153 | 4617 | 169 | 437 | n.d. |
| 1203761 | 2 | 2'-Ome | 154 | 163 | 147 | 25 | 113 | n.d. |
| 813942 | n/a | n/a | 351 | 3758 | 4638 | 127 | 340 | n.d. |
| 1203762 | 2 | 2'-Ome | 103 | 89 | 257 | 28 | 88 | n.d. |
| 832311 | n/a | n/a | 305 | 1059 | 878 | 739 | 288 | n.d. |
| 1201199 | 2 | 2'-Ome | 294 | 720 | 597 | 208 | 256 | n.d. |

*Value represents the reduction of the mRNA that is complementary to the modified oligonucleotide as indicated in Table 29 above.

Example 14 Dose-Response of Position-Specific 2'-OMe on In Vitro and In Vivo Activity and Toxicity of Modified Oligonucleotides with a Variety of Sequences On target in vivo activity and toxicity was measured for a subset of compounds described in Example 13 above. Two male BALB/c mice per group were administered 1.85, 5.55, 16.67, 50, or 150 mg/kg modified oligonucleotide once via subcutaneous injection, as indicated in the tables below. Mice were sacrificed after 1 week and mRNA was isolated from the liver and measured by RT-qPCR using the primer probe sets described in Table 30 above. Levels of mRNA for Gadd45a, P21, and Tnfrsf10b were analyzed as in Example 1. Results were normalized with Ribogreen and are reported normalized to PBS-treated animals. Plasma levels of ALT was measured using an automated clinical chemistry analyzer. Increased ALT is indicative of acute liver toxicity. The therapeutic index is calculated as a ratio of the maximum non-toxic dose divided by the in vivo $ED_{50}$. The maximum non-toxic dose is the highest dose at which the ALT value remains less than 5× increased compared to PBS-treated mice, typically 150 IU/L.

TABLE 33

| in vivo dose response activity | | | | | | |
|---|---|---|---|---|---|---|
| | Target Expression (% Control) | | | | | |
| Compound Number | 1.9 mg/kg | 5.6 mg/kg | 16.7 mg/kg | 50 mg/kg | 150 mg/kg | ED50 (ng/g) |
| 546006 | 86.8 | 75.6 | 78.1 | 56.2 | 41.4 | 87.9 |
| 1133071 | 81.6 | 74.5 | 61.4 | 52.9 | 37.6 | 53.9 |
| 572912 | 80.7 | 58.2 | 34.6 | 26.2 | 21.7 | 10.0 |
| 1200898 | 84.8 | 80.2 | 67.4 | 42.4 | 16.3 | 31.5 |

TABLE 33-continued

| in vivo dose response activity | | | | | | |
|---|---|---|---|---|---|---|
| | Target Expression (% Control) | | | | | |
| Compound Number | 1.9 mg/kg | 5.6 mg/kg | 16.7 mg/kg | 50 mg/kg | 150 mg/kg | ED50 (ng/g) |
| 694804 | 62.8 | 38.2 | 15.3 | 7.8 | 7.6 | 3.2 |
| 1202810 | 71.0 | 46.7 | 33.2 | 21.0 | 10.1 | 5.8 |
| 747137 | 45.3 | 42.5 | 28.7 | 21.4 | 14.0 | 1.5 |
| 1200907 | 42.1 | 35.3 | 40.2 | 30.6 | 18.8 | 0.53 |
| 747149 | 72.8 | 42.2 | 23.6 | 14.6 | 7.3 | 6.0 |
| 1203759 | 52.9 | 40.6 | 24.4 | 21.5 | 18.3 | 2.1 |
| 715415 | 61.5 | 56.9 | 41.9 | 19.9 | 12.0 | 6.5 |
| 1203758 | 71.6 | 68.8 | 61.1 | 34.8 | 20.9 | 20.0 |

TABLE 34

| in vivo dose response toxicity (ALT) | | | | | |
|---|---|---|---|---|---|
| | ALT (IU/L) | | | | |
| Compound Number | 1.9 mg/kg | 5.6 mg/kg | 16.7 mg/kg | 50 mg/kg | 150 mg/kg |
| 546006 | 29 | 29 | 22 | 26 | 173 |
| 1133071 | 24 | 25 | 25 | 44 | 356 |
| 572912 | 23 | 27 | 112 | 730 | 4674 |
| 1200898 | 23 | 24 | 25 | 28 | 32 |
| 694804 | 29 | 24 | 24 | 143 | 2160 |
| 1202810 | 22 | 24 | 24 | 23 | 61 |
| 747137 | 24 | 22 | 24 | 25 | 86 |
| 1200907 | 23 | 21 | 21 | 31 | 32 |
| 747149 | 26 | 26 | 38 | 157 | 1867 |
| 1203759 | 25 | 21 | 23 | 27 | 27 |
| 715415 | 23 | 21 | 25 | 77 | 1384 |
| 1203758 | 25 | 23 | 23 | 23 | 54 |

TABLE 34b

In Vivo Dose-response of Gadd45a mRNA upon treatment with modified oligonucleotides complementary to HDAC2

| | 1.9 mg/kg | 5.6 mg/kg | 16.7 mg/kg | 50 mg/kg | 150 mg/kg |
|---|---|---|---|---|---|
| | Expression level of Gadd45a mRNA (% Control) | | | | |
| 546006 | 122 | 112 | 77 | 302 | 1070 |
| 1133071 | 94 | 134 | 154 | 396 | 873 |
| 572912 | 94 | 95 | 187 | 196 | 227 |
| 1200898 | 103 | 80 | 112 | 109 | 99 |
| 694804 | 126 | 106 | 161 | 163 | 459 |
| 1202810 | 115 | 93 | 91 | 188 | 169 |
| 747137 | 94 | 67 | 80 | 96 | 153 |
| 1200907 | 79 | 86 | 142 | 88 | 140 |
| 747149 | 123 | 172 | 146 | 283 | 575 |
| 1203759 | 100 | 147 | 102 | 172 | 154 |
| 715415 | 91 | 118 | 201 | 159 | 393 |
| 1203758 | 143 | 114 | 206 | 162 | 197 |

TABLE 34c

In Vivo Dose-response of Tnfrsf10b mRNA upon treatment with modified oligonucleotides

| Compound ID | 1.9 mg/kg | 5.6 mg/kg | 16.7 mg/kg | 50 mg/kg | 150 mg/kg |
|---|---|---|---|---|---|
| | Expression level of Tnfrsf10b mRNA (% Control) | | | | |
| 546006 | 87 | 78 | 161 | 248 | 4235 |
| 1133071 | 95 | 96 | 157 | 622 | 5166 |
| 572912 | 210 | 190 | 551 | 4070 | 5847 |
| 1200898 | 135 | 116 | 105 | 170 | 179 |
| 694804 | 81 | 98 | 116 | 284 | 1775 |
| 1202810 | 88 | 110 | 88 | 128 | 241 |
| 747137 | 56 | 74 | 115 | 273 | 1013 |
| 1200907 | 99 | 86 | 15 | 239 | 453 |
| 747149 | 73 | 70 | 116 | 636 | 6027 |
| 1203759 | 87 | 55 | 57 | 97 | 105 |
| 715415 | 62 | 57 | 111 | 259 | 999 |
| 1203758 | 67 | 72 | 64 | 79 | 126 |

TABLE 34d

In Vivo Dose-response of P21 mRNA upon treatment with modified oligonucleotides

| Compound ID | 1.9 mg/kg | 5.6 mg/kg | 16.7 mg/kg | 50 mg/kg | 150 mg/kg |
|---|---|---|---|---|---|
| | Expression level of P21 mRNA (% Control) | | | | |
| 546006 | 103 | 90 | 172 | 342 | 5193 |
| 1133071 | 97 | 68 | 197 | 773 | 6571 |
| 572912 | 224 | 228 | 762 | 2787 | 3182 |
| 1200898 | 98 | 106 | 70 | 164 | 172 |
| 694804 | 108 | 76 | 72 | 172 | 2212 |
| 1202810 | 91 | 125 | 245 | 51 | 162 |
| 747137 | 43 | 59 | 122 | 294 | 1220 |
| 1200907 | 108 | 97 | 110 | 383 | 708 |
| 747149 | 95 | 44 | 207 | 985 | 3869 |
| 1203759 | 61 | 30 | 47 | 71 | 95 |
| 715415 | 46 | 24 | 45 | 213 | 757 |
| 1203758 | 36 | 34 | 18 | 26 | 35 |

TABLE 34e

Therapeutic Index

| Compound ID | 2'-altered nucleotide position in central region | sugar modification of altered nucleotide | MNTD (mg/kg) | TI (MNTD/ $ED_{50}$) | Fold-TI improvement |
|---|---|---|---|---|---|
| 546006 | n/a | n/a | 50 | 0.6 | 1.5 |
| 1133071 | 2 | 2'-OMe | 50 | 0.9 | |
| 572912 | n/a | n/a | 16.7 | 2 | >2.4 |
| 1200898 | 2 | 2'-OMe | >150 | >4.8 | |
| 694804 | n/a | n/a | 50 | 16 | >1.6 |
| 1202810 | 2 | 2'-OMe | >150 | >26 | |
| 747137 | n/a | n/a | >150 | >99 | ~2.9 |
| 1200907 | 2 | 2'-OMe | >150 | >284 | |
| 747149 | n/a | n/a | 50 | 11 | >6.5 |
| 1203759 | 2 | 2'-OMe | >150 | >72 | |
| 715415 | n/a | n/a | 50 | 8 | n/a |
| 1203758 | 2 | 2'-OMe | >150 | >7.5 | |

Example 15 Effect of Modified Oligonucleotides on Nucleolar Localization of p54nrb Selected modified nucleotides described in above were tested for their effect on HeLa cells by microscopy. HeLa cells were transfected by lipofectamine 2000 with 200 nM of modified oligonucleotide for 2 hrs and then cellular protein p54nrb was stained by mP54 antibody (Santa Cruz Biotech, sc-376865) and DAPI was used to stain for the nucleus of cells. The number of cells with nucleolar p54nrb and the total number of cells in the images were counted. ALT data presented were previously described in Example 13 above.

TABLE 35

Nucleolar mislocalization of p54nrb and correlation with hepatoxicity

| Compound ID | 2'-altered nucleotide position in central region | sugar modification of altered nucleotide | % cells with mislocalization of p54nrb | ALT @ 150 mg/kg |
|---|---|---|---|---|
| 546006 | n/a | n/a | 56 | 131 |
| 1133071 | 2 | 2'-OMe | 67 | 245 |
| 572912 | n/a | n/a | 75 | 3883 |
| 1200898 | 2 | 2'-OMe | 3 | 41 |
| 758252 | n/a | n/a | 71 | 725 |
| 1233760 | 2 | 2'-OMe | 4 | 47 |

Example 16 Effect of Position-Specific 2'-OMe on In Vitro Activity and Toxicity of Modified Oligonucleotides with Various Sequences Modified oligonucleotides with the sugar motifs lll-d(10)-lll and lll-d-m-d(8)-lll were synthesized, where "l" indicates a β-D-locked nucleic acid (β-D-LNA), "d" represents a 2'-β-D-deoxyribosyl sugar moiety and "m" represents a 2'-OMe-β-D-ribofuranosyl sugar moiety. Each internucleoside linkage is a phosphorothioate internucleoside linkage. For sequences with a T at position 5 (from the 5' end) in the parent lll-d(10)-lll oligonucleotide, the lll-d-m-d(8)-lll contains a 2'-OMe modified U at this position. For sequences with a $^{m}$C at position 5 (from the 5' end) in the parent lll-d(10)-lll oligonucleotide, the lll-d-m-d(8)-lll contains a 2'-OMe modified C at this position lacking a 5-Me group.

TABLE 36

| Modified Oligonucleotides | | | | |
|---|---|---|---|---|
| lll-d(10)-lll compound ID | lll-d-m-d(8)-lll compound ID | Complementary mRNA | Sequence (5'-3') | SEQ ID NO |
| 1247569 | 1247570 | HDAC2 | GAGGATGGCAAGCACA | 41 |
| 1247571 | 1247572 | PABPN1 | CTTCCACAGTATATCT | 44 |
| 1247573 | | DNM2 | AGACTCTCGGTTCCGA | 49 |
| | 1247574 | | AGACUCTCGGTTCCGA | 127 |
| 1247575 | 1247576 | FOXO1A | AAGTGTCACTAAAACC | 53 |

TABLE 36-continued

| Modified Oligonucleotides | | | | |
|---|---|---|---|---|
| lll-d(10)-lll compound ID | lll-d-m-d(8)-lll compound ID | Complementary mRNA | Sequence (5'-3') | SEQ ID NO |
| 1247577 | 1247578 | FOXO1A | GGACTGAAATAGCAGA | 54 |
| | 1247578 | | GGACUGAAATAGCAGA | 130 |

In vivo toxicity and on target in vivo activity was measured for the compounds described above. Two male balb/c mice per group were administered 16.67 or 150 mg/kg modified oligonucleotide once via subcutaneous injection, as indicated in the tables below. Mice were sacrificed after 72 hours and mRNA was isolated from the liver and measured by RT-qPCR using the primer probe sets described in Table 30 above. Levels of mRNA for P21, and Tnfrsf10b were analyzed as in Example 1. Results were normalized with Ribogreen and are reported normalized to PBS-treated animals.

TABLE 37

| in vivo activity and toxicity | | | | | | | | |
|---|---|---|---|---|---|---|---|---|
| Compound | Complementary mRNA Expression (% Control) | | ALT (IU/L) | | P21 mRNA (% Control) | | Tnfrsf10b mRNA (% Control) | |
| Number | 16.7 mg/kg | 150 mg/kg | 16.7 mg/kg | 150 mg/kg | 16.7 mg/kg | 150 mg/kg | 16.7 mg/kg | 150 mg/kg |
| 1247569 | 70 | 35 | 37 | 2368 | 163 | 12778 | 158 | 7046 |
| 1247570 | 72 | 46 | 34 | 867 | 444 | 11860 | 320 | 6772 |
| 1247571 | 40 | 26 | 460 | 10838 | 3061 | 7588 | 2216 | 8133 |
| 1247572 | 54 | 16 | 26 | 330 | 90 | 928 | 124 | 679 |
| 1247573 | 7 | 19 | 59 | 20665 | 153 | 10379 | 157 | 4858 |
| 1247574 | 19 | 6 | 25 | 284 | 139 | 839 | 123 | 575 |
| 1247575 | 51 | 30 | 50 | 2404 | 390 | 11275 | 334 | 6365 |
| 1247576 | 57 | 27 | 25 | 85 | 142 | 1850 | 218 | 2033 |
| 1247577 | 52 | 25 | 34 | 2460 | 256 | 11736 | 193 | 14610 |
| 1247578 | 60 | 21 | 25 | 39 | 124 | 133 | 178 | 143 |
| 1247579 | 48 | 14 | 23 | 1696 | 95 | 3704 | 176 | 108 |
| 1247580 | 77 | 21 | 28 | 232 | 78 | 265 | 2850 | 307 |

Example 17 Effect of Position-Specific 2'-Modifications on In Vitro Activity and In Vivo Liver Toxicity of Modified Oligonucleotides Complementary to CPT1A Modified oligonucleotides were synthesized as indicated in the table below. These modified oligonucleotides were compared to the otherwise identical modified oligonucleotide lacking an altered nucleotide in the central region, a 5-10-5 MOE modified oligonucleotide, containing five nucleosides each comprising a 2'-MOE-β-D-ribofuranosyl sugar moiety in each of the 5' and 3' regions and 10 unmodified DNA nucleosides in the central region. Each internucleoside linkage is a phosphorothioate internucleoside linkage. The compounds in the table below are 100% complementary to mouse CPT1A, GENBANK NC 000085.6 truncated from 3319001 to 3389000 (SEQ ID NO: 6), at position 49870 to 49889. In certain instances, a modified oligonucleotide comprising a T at position 5 is compared to a modified oligonucleotide comprising a 2'-OMe U at position 5.

TABLE 38

| Modified oligonucleotides complementary to CPT1A | | | | |
|---|---|---|---|---|
| Compound ID | position of altered nucleotide in central region | sugar modification of altered nucleotide | Chemistry Notation | SEQ ID NO |
| 147420 | n/a | n/a | $A_{es}A_{es}T_{es}G_{es}T_{es}G_{ds}{}^{m}C_{ds}{}^{m}C_{ds}T_{ds}G_{ds}{}^{m}C_{ds}T_{ds}G_{ds}T_{ds}{}^{m}C_{ds}{}^{m}C_{es}T_{es}T_{es}G_{es}A_{e}$ | 73 |
| 994947 | n/a | OMe | $A_{es}A_{es}T_{es}G_{ms}T_{es}G_{ds}{}^{m}C_{ds}{}^{m}C_{ds}T_{ds}G_{ds}{}^{m}C_{ds}T_{ds}G_{ds}T_{ds}{}^{m}C_{ds}{}^{m}C_{es}T_{es}T_{es}G_{es}A_{e}$ | 73 |
| 994948 | n/a | OMe | $A_{es}A_{es}T_{es}G_{es}U_{ms}G_{ds}{}^{m}C_{ds}{}^{m}C_{ds}T_{ds}G_{ds}{}^{m}C_{ds}T_{ds}G_{ds}T_{ds}{}^{m}C_{ds}{}^{m}C_{es}T_{es}T_{es}G_{es}A_{e}$ | 74 |
| 994949 | 1 | OMe | $A_{es}A_{es}T_{es}G_{es}T_{es}G_{ms}{}^{m}C_{ds}{}^{m}C_{ds}T_{ds}G_{ds}{}^{m}C_{ds}T_{ds}G_{ds}T_{ds}{}^{m}C_{ds}{}^{m}C_{es}T_{es}T_{es}G_{es}A_{e}$ | 73 |
| 994950 | 2 | OMe | $A_{es}A_{es}T_{es}G_{es}T_{es}G_{ds}C_{ms}{}^{m}C_{ds}T_{ds}G_{ds}{}^{m}C_{ds}T_{ds}G_{ds}T_{ds}{}^{m}C_{ds}{}^{m}C_{es}T_{es}T_{es}G_{es}A_{e}$ | 73 |
| 994951 | 3 | OMe | $A_{es}A_{es}T_{es}G_{es}T_{es}G_{ds}{}^{m}C_{ds}C_{ms}T_{ds}G_{ds}{}^{m}C_{ds}T_{ds}G_{ds}T_{ds}{}^{m}C_{ds}{}^{m}C_{es}T_{es}T_{es}G_{es}A_{e}$ | 73 |

A subscript "d" indicates an unmodified, 2'-β-D-deoxyribosyl sugar moiety. A subscript "e" indicates a 2'-MOE-β-D-ribofuranosyl sugar moiety. A subscript "m" indicates a 2'-O-methyl-β-D-ribofuranosyl sugar moiety. A subscript "k" indicates a cEt. A subscript "s" indicates a phosphorothioate internucleoside linkage. A superscript "m" before a C indicates 5-methyl Cytosine. A subscript "x" indicates a MOP internucleoside linkage. A subscript "(FANA)" indicates a nucleoside comprising an ara 2'-F modified sugar moiety.

For the in vivo toxicity and activity study in the table below, BALB/C mice per modified oligonucleotide were administered 200 mg/kg modified oligonucleotide by subcutaneous injection and sacrificed 72 hours later. One animal was administered an injection of saline as a control. Plasma levels of ALT were measured using an automated clinical chemistry analyzer. Increased ALT is indicative of acute liver toxicity. Liver mRNA was harvested and analyzed by RT-qPCR. Cpt1a mRNA was detected using primer probe setRTS40014 (forward sequence: AGATCAATCGGACCCTAGACA, SEQ ID NO: 75; reverse sequence: CAGCACCTTCAGCGAGTA; SEQ ID NO: 76; probe sequence: AAGAGGACGCCACTCACGATGTTC, SEQ ID NO: 77) and P21 and Tnfrsf10b mRNA were detected as described in Example 1.

TABLE 39

| Activity and toxicity of modified oligonucleotides complementary CPT1A | | | | | | |
|---|---|---|---|---|---|---|
| Compound ID | position of altered nucleotide in central region | sugar modification of altered nucleotide | Cpt1a (% control) | P21 (% control) | Tnfrsf10b (% control) | ALT @ 200 mg/kg (IU/L) |
| 147420 | n/a | n/a | 6.42 | 6616 | 8796 | 15308 |
| 994947 | n/a | 2'-Ome | 6.49 | 6984 | 11499 | 18395 |
| 994948 | n/a | 2'-Ome | 8.99 | 7085 | 10520 | 10535 |
| 994949 | 1 | 2'-Ome | 5.90 | 6370 | 9595 | 12370 |
| 994950 | 2 | 2'-Ome | 12.19 | 2219 | 2146 | 52 |
| 994951 | 3 | 2'-Ome | 6.72 | 6275 | 10555 | 2991 |

For the in vivo activity study in the table below, three BALB/C mice per modified oligonucleotide were administered 2.5, 7.4, 22.2, 66.7, 200 mg/kg 147420 or 994950 by subcutaneous injection and sacrificed after 72 hours. Plasma levels of ALT were measured using an automated clinical chemistry analyzer. Increased ALT is indicative of acute liver toxicity. Cpt1a mRNA was detected using RT-qPCR as described above.

TABLE 40

| In Vivo Toxicity of modified oligonucleotides complementary CPT1A | | | | | |
|---|---|---|---|---|---|
| | ALT (IU/L) | | | | |
| Compound Number | 2.5 mg/kg | 7.4 mg/kg | 22.2 mg/kg | 66.7 mg/kg | 200 mg/kg |
| 147420 | 51 | 23 | 23 | 106 | 7794 |
| 994950 | 25 | 25 | 21 | 23 | 53 |

TABLE 41

| In Vivo Activity of modified oligonucleotides complementary CPT1A | | | | | |
|---|---|---|---|---|---|
| Compound | CPT1 mRNA (% Control) | | | | |
| Number | 2.5 mg/kg | 7.4 mg/kg | 22.2 mg/kg | 66.7 mg/kg | 200 mg/kg |
| 147420 | 115.9 | 93.1 | 78.2 | 33.7 | 4.6 |
| 994950 | 116.0 | 117.2 | 105.6 | 55.9 | 21.9 |

TABLE 42

| In Vivo Dose-response of Tnfrsf10b mRNA upon treatment with modified oligonucleotides | | | | | |
|---|---|---|---|---|---|
| Compound | Tnfrsf10b mRNA (% Control) | | | | |
| Number | 2.5 mg/kg | 7.4 mg/kg | 22.2 mg/kg | 66.7 mg/kg | 200 mg/kg |
| 147420 | 132 | 141 | 162 | 2341 | 8622 |
| 994950 | 119 | 133 | 125 | 153 | 1026 |

TABLE 43

| In Vivo Dose-response of P21 mRNA upon treatment with modified oligonucleotides | | | | | |
|---|---|---|---|---|---|
| | P21 mRNA (% Control) | | | | |
| Compound Number | 2.5 mg/kg | 7.4 mg/kg | 22.2 mg/kg | 66.7 mg/kg | 200 mg/kg |
| 147420 | 141 | 94 | 240 | 4305 | 15334 |
| 994950 | 105 | 89 | 103 | 208 | 2413 |

Example 18 Effect of 2'-OMe Modification in Modified Oligonucleotides Complementary to Factor XI Modified oligonucleotides were synthesized as indicated in the table below. The compounds have the sugar motif kkk-d(10)-kkk (“parent”) or kkk-d-m-d(8)-kkk, where “k” represents a cEt, “d” represents an unmodified, 2'-β-D-deoxyribosyl sugar moiety, and “m” represents a 2'-OMe-ribofuranosyl sugar moiety. For sequences with a T at position 5 (from the 5' end) in the parent kkk-d(10)-kkk oligonucleotide, the kkk-d-m-d(8)-kkk contains a 2'-OMe modified U at this position. For sequences with a $^{m}$C at position 5 (from the 5' end) in the kkk-d(10)-kkk oligonucleotide, the kkk-d-m-d(8)-kkk contains a 2'-OMe modified C at this position, lacking the 5-Me group. Each internucleoside linkage is a phosphorothioate internucleoside linkage.

For the in vitro activity study in the table below, primary mouse hepatocytes were isolated from male balb/c mice and transfected with 0.9, 2.7, 8.2, 24.7, 74.0, 222, 667, or 2,000 nM modified oligonucleotide. After 24 hrs, mRNA was harvested and analyzed for FXI and RAPTOR as described above.

For the in vivo toxicity study in the table below, two male BALB/C mice per modified oligonucleotide were administered 150 mg/kg modified oligonucleotide by subcutaneous injection and sacrificed 72 hours later. One animal was administered an injection of saline as a control. Plasma levels of ALT was measured using an automated clinical chemistry analyzer. Increased ALT is indicative of acute liver toxicity.

For a subset of compounds, on-target activity was measured in the liver. RNA was isolated from the liver and measured by RT-qPCR using the primer probe set RTS2898, described in Example 4 above. Results were normalized with Ribogreen® and are reported normalized to PBS-treated animals.

TABLE 44

| Sequences | | | |
|---|---|---|---|
| kkk-d(10)-kkk compound ID | kkk-d-m-d(8)-kkk compound ID | Sequence (5'-3') | SEQ ID NO |
| 464917 | 982034 | GTCTGTGCATCTCTCC | 22 |
| 464924 | | GTTATTGTGGTTGGCG | 81 |
| | 1133247 | GTTAUTGTGGTTGGCG | 133 |
| 465156 | | ATTCTGTGTGCACTGC | 82 |
| | 1133310 | ATTCUGTGTGCACTGC | 134 |
| 465162 | 1133316 | TCTTGTCTGACATTCT | 83 |
| 465163 | 1133317 | TTTTGTGTCTTCTGTA | 84 |
| 465172 | | CTGTTTGAGTTTTCTC | 85 |
| | 1133326 | CTGTUTGAGTTTTCTC | 135 |
| 465174 | 1133328 | CAAAGTGATACCAGTT | 86 |
| 465175 | | AATCTTCCAGGGCCAC | 87 |
| | 1133329 | AATCUTCCAGGGCCAC | 136 |
| 465176 | | TCATTTCTATGGAATA | 88 |
| | 1133330 | TCATUTCTATGGAATA | 137 |
| 465178 | 1133332 | GTCAGTATCCCAGTGT | 89 |
| 465179 | 1133333 | GGTTACAGTGGAAGAG | 90 |
| 465181 | 1133335 | TCTGGGTGTTCTTACG | 91 |
| 465186 | 1133340 | TTTCCTTGAGTAGTAG | 92 |
| 465187 | 1133341 | TCTCCTTGCTGTATTT | 93 |

TABLE 45

| Activity and Toxicity of Modified oligonucleotides complementary to Factor XI | | | | | | | | |
|---|---|---|---|---|---|---|---|---|
| Compound ID | altered nucleotide position in central region | sugar modification of altered nucleotide | in vitro FXI $IC_{50}$ (nM) | in vitro RAPTOR $IC_{50}$ (nM) | Relative Caspase Activation (% Control) @ 20 μM | p21 @ 150 mg/kg | FXI @ 10 mg/kg | ALT @ 150 mg/kg (IU/L) |
| 464917 | n/a | n/a | 101 | 44 | 700 | death | 25.4 | death |
| 982034 | 2 | 2'-OMe | 221 | 119 | 122 | 31922 | 40.8 | 13172 |
| 464924 | n/a | n/a | 115 | >2000 | 332 | 19340 | 8.6 | 5365 |
| 1133247 | 2 | 2'-OMe | 189 | >2000 | 190 | 753 | 12.1 | 33 |
| 465156 | n/a | n/a | 98 | 129 | 934 | 82279 | 14.4 | 24858 |
| 1133310 | 2 | 2'-OMe | 354 | 465 | 603 | 127 | 14.7 | 7034 |
| 465162 | n/a | n/a | 99 | >2000 | 758 | death | 15.1 | death |
| 1133316 | 2 | 2'-OMe | 144 | >2000 | 189 | 4660 | 34.2 | 60 |
| 465163 | n/a | n/a | 163 | >2000 | 115 | 34117 | 41.5 | 2347 |

TABLE 45-continued

Activity and Toxicity of Modified oligonucleotides complementary to Factor XI

| Compound ID | altered nucleotide position in central region | sugar modification of altered nucleotide | in vitro FXI $IC_{50}$ (nM) | in vitro RAPTOR $IC_{50}$ (nM) | Relative Caspase Activation (% Control) @ 20 μM | p21 @ 150 mg/kg | FXI @ 10 mg/kg | ALT @ 150 mg/kg (IU/L) |
|---|---|---|---|---|---|---|---|---|
| 1133317 | 2 | 2'-OMe | 272 | >2000 | 67 | 11844 | 79.4 | 478 |
| 465172 | n/a | n/a | 106 | >2000 | 429 | 512 | 57.6 | 23 |
| 1133326 | 2 | 2'-OMe | 176 | >2000 | 157 | 237 | 64.8 | 20 |
| 465174 | n/a | n/a | 69 | >2000 | 130 | 276 | 21.7 | 21 |
| 1133328 | 2 | 2'-OMe | 393 | >2000 | 113 | 167 | 33.8 | 23 |
| 465175 | n/a | n/a | 50 | 125 | 523 | 6957 | 37.8 | 1564 |
| 1133329 | 2 | 2'-OMe | 99 | 170 | 501 | 1564 | 59.8 | 60 |
| 465176 | n/a | n/a | 111 | >2000 | 219 | 344 | 98.6 | 27 |
| 1133330 | 2 | 2'-OMe | 89 | >2000 | 135 | 190 | 95.1 | 22 |
| 465178 | n/a | n/a | 11 | 115 | 364 | 900086 | 8.1 | 13168 |
| 1133332 | 2 | 2'-OMe | 24 | 1653 | 247 | 5982 | 27.0 | 75 |
| 465179 | n/a | n/a | 74 | >2000 | 188 | 4046 | 23.0 | 344 |
| 1133333 | 2 | 2'-OMe | 82 | >2000 | 102 | 122 | 62.4 | 23 |
| 465181 | n/a | n/a | 75 | 1571 | 487 | 17469 | 25.4 | 7087 |
| 1133335 | 2 | 2'-OMe | 56 | >2000 | 214 | 929 | 61.7 | 26 |
| 465186 | n/a | n/a | 75 | >2000 | 200 | 42551 | 17.3 | 3709 |
| 1133340 | 2 | 2'-OMe | 208 | >2000 | 125 | 513 | 42.8 | 34 |
| 465187 | n/a | n/a | 35 | 475 | 393 | 778834* | 10.4 | 11752* |
| 1133341 | 2 | 2'-OMe | 28 | >2000 | 167 | 1984 | 38.6 | 36 |

*1/2 animals were found dead

Example 19 Effect of 2'-OMe Incorporation on Toxicity of Modified Oligonucleotides Complementary to HDAC2

Modified oligonucleotides were synthesized as indicated in the table below. The compounds have the sugar motif kkk-d(10)-kkk ("parent") or kkk-d-m-d(8)-kkk, where "k" represents a cEt, "d" represents an unmodified, 2'-β-D-deoxyribosyl sugar moiety, and "m" represents a 2'-OMe-β-D-ribofuranosylsugar moiety. For sequences with a T at position 5 (from the 5' end) in the parent kkk-d(10)-kkk oligonucleotide, the kkk-d-m-d(8)-kkk contains a 2'-OMe modified U at this position. For sequences with a $^{m}$C at position 5 (from the 5' end) in the kkk-d(10)-kkk oligonucleotide, the kkk-d-m-d(8)-kkk contains a 2'-OMe modified C at this position, lacking the 5-Me group. Each internucleoside linkage is a phosphorothioate internucleoside linkage.

For the in vitro activity study in the table below, primary mouse hepatocytes were isolated from male balb/c mice and transfected with 0.9, 2.7, 8.2, 24.7, 74.0, 222, 667, or 2,000 nM modified oligonucleotide. After 24 hrs, mRNA was harvested and analyzed for HDAC2 and RAPTOR as described above. For the in vivo toxicity study in the table below, two male BALB/C mice per modified oligonucleotide were administered 10 or 150 mg/kg modified oligonucleotide by subcutaneous injection and sacrificed 72 hours later. One animal was administered an injection of saline as a control. Plasma levels of ALT was measured using an automated clinical chemistry analyzer. Increased ALT is indicative of acute liver toxicity.

For a subset of compounds, on-target activity was measured in the liver. RNA was isolated from the liver and measured by RT-qPCR using the primer probe set RTS3500 described above in Example 13. Results were normalized with Ribogreen® and are reported normalized to PBS-treated animals.

TABLE 46

Sequences

| kkk-d(10)-kkk compound ID | kkk-d-m-d(8)-kkk compound ID | Sequence (5'-3') | SEQ ID NO |
|---|---|---|---|
| 545984 | 1133060 | TTGCCAATATCACCAT | 94 |
| 545996 | | CAACUGAACCACCCGT | 95 |
| | 1133066 | CAACTGAACCACCCGT | 138 |
| 546004 | 1133070 | GCACAATATCATTAAC | 96 |
| 546009 | 1132933 | GACTCTCTGATGATAC | 97 |
| 546023 | 1132940 | CTATACCATCTCTCAT | 98 |
| 546024 | 1133080 | CATCATCTATACCATC | 99 |
| 546034 | 1133085 | ACACATTTAGCATGAC | 100 |
| 546045 | | ATTATATGGCAACTCA | 101 |
| | 1132951 | ATTAUATGGCAACTCA | 139 |
| 546049 | 1132953 | GACTAATATGCAGTTT | 102 |
| 546075 | 1132966 | GTCAAATTCAAGGGTT | 103 |
| 546095 | 1132976 | CATAAAGCATGGTGGA | 104 |
| 546108 | 1133122 | TAGTCTCTGTCAGTTA | 105 |
| 546109 | 1132983 | GTACCTATAGTCTCTG | 106 |
| 546110 | 1133123 | TCATGTACCTATAGTC | 107 |
| 546112 | 1133124 | TCTTAATTTCATGTAC | 108 |
| 546118 | 1133127 | ACCCTCAAGTCTCCTG | 109 |

TABLE 47

In vitro Activity and Toxicity of Modified oligonucleotides complementary to HDAC2

| Compound ID | altered nucleotide position in central region | sugar modification of altered nucleotide | in vitro HDAC 2 $IC_{50}$ (nM) | in vitro RAPTOR $IC_{50}$ (nM) | Relative Caspase Activation (% Control) @20 μM |
|---|---|---|---|---|---|
| 546009 | n/a | n/a | 44 | 773 | 632 |
| 1132933 | 2 | 2'-OMe | 89 | >2000 | 193 |
| 546023 | n/a | n/a | 79 | 1643 | 825 |
| 1132940 | 2 | 2'-OMe | 156 | >2000 | 980 |
| 546045 | n/a | n/a | 72 | 460 | 469 |
| 1132951 | 2 | 2'-OMe | 98 | >2000 | 326 |
| 546049 | n/a | n/a | 82 | >2000 | 127 |
| 1132953 | 2 | 2'-OMe | 144 | >2000 | 132 |
| 546075 | n/a | n/a | 81 | >2000 | 149 |
| 1132966 | 2 | 2'-OMe | 135 | >2000 | 143 |
| 546095 | n/a | n/a | 78 | >2000 | 126 |
| 1132976 | 2 | 2'-OMe | 128 | >2000 | 98 |
| 546109 | n/a | n/a | 30 | >2000 | 396 |
| 1132983 | 2 | 2'-OMe | 44 | >2000 | 117 |
| 545984 | n/a | n/a | 89 | 452 | 1235 |
| 1133060 | 2 | 2'-OMe | 126 | >2000 | 270 |
| 545996 | n/a | n/a | 297 | >2000 | 776 |
| 1133066 | 2 | 2'-OMe | 111 | >2000 | 327 |
| 546004 | n/a | n/a | 181 | >2000 | 124 |
| 1133070 | 2 | 2'-OMe | 164 | >2000 | 90 |
| 546024 | n/a | n/a | 85 | >2000 | 124 |
| 1133080 | 2 | 2'-OMe | 45 | >2000 | 123 |
| 546034 | n/a | n/a | 125 | >2000 | 107 |
| 1133085 | 2 | 2'-OMe | 125 | >2000 | 104 |
| 546108 | n/a | n/a | 21 | 144 | 1265 |
| 1133122 | 2 | 2'-OMe | 34 | >2000 | 176 |
| 546110 | n/a | n/a | 17 | >2000 | 82 |
| 1133123 | 2 | 2'-OMe | 30 | >2000 | 95 |
| 546112 | n/a | n/a | 178 | >2000 | 106 |
| 1133124 | 2 | 2'-OMe | 106 | >2000 | 98 |
| 546118 | n/a | n/a | 6 | 181 | 425 |
| 1133127 | 2 | 2'-OMe | 11 | >2000 | 158 |

TABLE 48

In vivo Activity and Toxicity of Modified oligonucleotides complementary to HDAC2

| Compound ID | HDAC 2 @ 10 mg/kg | HDAC2 @ 150 mg/kg | P21 mRNA @ 150 mg/kg | Tnfrsf10b @ 150 mg/kg | ALT @ 150 mg/kg (IU/L) |
|---|---|---|---|---|---|
| 546009 | 22 | 7.5 | 5739 | 7162 | 14907 |
| 1132933 | 40 | 7.5 | 98 | 176 | 31 |
| 546023 | 57 | 9.9 | 1586 | 754 | 820 |
| 1132940 | 61 | 12.7 | 1348 | 565 | 224 |
| 546045 | 68 | 17.2 | 5601 | 2362 | 1031 |
| 1132951 | 60 | 15.3 | 1726 | 970 | 183 |
| 546049 | 50 | 8.9 | 294 | 133 | 29 |
| 1132953 | 71 | 15.2 | 282 | 150 | 27 |
| 546075 | 71 | 16.2 | 282 | 232 | 21 |
| 1132966 | 61 | 27.7 | 741 | 621 | 86 |
| 546095 | 39 | 12.7 | 3303 | 2314 | 1063 |
| 1132976 | 50 | 15.3 | 685 | 512 | 94 |
| 546109 | 29 | 4.3 | 684 | 706 | 182 |
| 1132983 | 37 | 5.2 | 217 | 190 | 34 |
| 545984 | 31 | 4.9 | 14070 | 10327 | 37277 |
| 1133060 | 42 | 9.0 | 183 | 138 | 39 |
| 545996 | 56 | 14.7 | 613 | 458 | 433 |
| 1133066 | 60 | 24.2 | 215 | 156 | 28 |
| 546004 | 64 | 13.4 | 499 | 203 | 35 |
| 1133070 | 69 | 17.6 | 286 | 192 | 30 |
| 546024 | 34 | 6.2 | 381 | 169 | 25 |
| 1133080 | 41 | 8.1 | 452 | 201 | 26 |
| 546034 | 52 | 7.5 | 181 | 140 | 32 |
| 1133085 | 68 | 10.6 | 127 | 143 | 27 |
| 546108 | 3 | n.d. | n.d. | n.d. | death |
| 1133122 | 7 | 1.9 | 1524 | 1353 | 131 |
| 546110 | 15 | 6.2 | 23642 | 6298 | 5132 |
| 1133123 | 35 | 3.3 | 221 | 155 | 29 |
| 546112 | 52 | 14.3 | 817 | 350 | 34 |
| 1133124 | 59 | 13.9 | 822 | 571 | 29 |
| 546118 | 13 | 5.7 | 3853 | 3854 | 3894 |
| 1133127 | 15 | 4.8 | 470 | 473 | 139 |

For the FOB scores reported in the table below, mice per group were administered 100 μg modified oligonucleotide by intracerebroventricular (ICV) injection. At 3 hours and 2 weeks post-injection, mice were evaluated according to 7 different criteria. The criteria are (1) the mouse was bright, alert, and responsive; (2) the mouse was standing or hunched without stimuli; (3) the mouse showed any movement without stimuli; (4) the mouse demonstrated forward movement after it was lifted; (5) the mouse demonstrated any movement after it was lifted; (6) the mouse responded to tail pinching; (7) regular breathing. For each of the 7 criteria, a mouse was given a subscore of 0 if it met the criteria and 1 if it did not. After all 7 criteria were evaluated, the FOB scores were summed for each mouse and averaged within each treatment group. The results are presented in the table below.

Two weeks after injection of modified oligonucleotide, mice were sacrificed and levels of HDAC, p21 and Aifl were measured in the cortex and the spinal cord by RT-PCR as described above. Aifl is a marker for inflammation. Results are presented below relative to control animals.

TABLE 48b

In vivo Activity and Toxicity of Modified oligonucleotides complementary to HDAC2

| Compound ID | 3 hr FOB | 2 week FOB | HDAC mRNA Cortex | HDAC mRNA Spinal Cord | p21 mRNA Cortex | p21 mRNA Spinal Cord | Aifl mRNA Cortex | Aifl mRNA Spinal cord |
|---|---|---|---|---|---|---|---|---|
| 546009 | 5.5 | 5.5 | n.d. | n.d. | n.d. | n.d. | n.d. | n.d. |
| 1132933 | 3.5 | 0 | 45.3 | 45.3 | 148 | 227 | 96 | 129 |
| 546023 | 0 | 0 | 36.3 | 31.3 | 120 | 144 | 117 | 156 |
| 1132940 | 0 | 0 | 59.2 | 39.3 | 135 | 166 | 94 | 174 |
| 546045 | 4.5 | 0 | 43.4 | 39.2 | 136 | 284 | 113 | 161 |
| 1132951 | 3 | 0 | 61.4 | 42.6 | 128 | 200 | 86 | 121 |

TABLE 48b-continued

In vivo Activity and Toxicity of Modified oligonucleotides complementary to HDAC2

| Compound ID | 3 hr FOB | 2 week FOB | HDAC mRNA Cortex | HDAC mRNA Spinal Cord | p21 mRNA Cortex | p21 mRNA Spinal Cord | Aif1 mRNA Cortex | Aif1 mRNA Spinal cord |
|---|---|---|---|---|---|---|---|---|
| 546049 | 1 | 0 | 95.3 | 68.8 | 111 | 116 | 90 | 110 |
| 1132953 | 3 | 0 | 67.1 | 47.8 | 126 | 138 | 82 | 103 |
| 546075 | 7 | 7 | n.d. | n.d. | n.d. | n.d. | n.d. | n.d. |
| 1132966 | 2.5 | 0 | 39.9 | 40.9 | 129 | 174 | 116 | 130 |
| 546095 | 5.5 | 0 | 66.7 | 44.2 | 124 | 321 | 90 | 189 |
| 1132976 | 6 | 0 | 55 | 36 | 132 | 427 | 87 | 248 |
| 546109 | 7 | 7 | n.d. | n.d. | n.d. | n.d. | n.d. | n.d. |
| 1132983 | 7 | 7 | n.d. | n.d. | n.d. | n.d. | n.d. | n.d. |
| 545984 | 2.5 | 6.5 | n.d. | n.d. | n.d. | n.d. | n.d. | n.d. |
| 1133060 | 1 | 0 | 71.0 | 39.8 | 107 | 130 | 92 | 112 |
| 545996 | 3 | 0 | 59.1 | 48.9 | 122 | 220 | 104 | 171 |
| 1133066 | 7 | 7 | n.d. | n.d. | n.d. | n.d. | n.d. | n.d. |
| 546004 | 0 | 0 | 55.3 | 47.6 | 136 | 261 | 116 | 176 |
| 1133070 | 0 | 0 | 58.7 | 50.0 | 127 | 173 | 81 | 99 |
| 546024 | 6.5 | 0 | 20.2 | 20.5 | 134 | 211 | 115 | 140 |
| 1133080 | 1 | 0 | 34.6 | 18.4 | 109 | 139 | 88 | 112 |
| 546034 | 3 | 0 | 58.9 | 46.6 | 96 | 149 | 98 | 146 |
| 1133085 | 3 | 0 | 79.0 | 42.0 | 114 | 126 | 101 | 137 |
| 546108 | 2 | 6.5 | n.d. | n.d. | n.d. | n.d. | n.d. | n.d. |
| 1133122 | 3.5 | 1 | 25.4 | 17.7 | 97 | 166 | 120 | 178 |
| 546110 | 2.5 | 3 | 55.0 | 23.5 | 88 | 294 | 93 | 342 |
| 1133123 | 0 | 0 | 57.4 | 49.8 | 112 | 149 | 85 | 105 |
| 546112 | 3 | 0 | 68.5 | 46.6 | 108 | 119 | 97 | 420 |
| 1133124 | 1.5 | 0 | 70.8 | 52.8 | 122 | 107 | 157 | 873 |
| 546118 | 7 | 7 | n.d. | n.d. | n.d. | n.d. | n.d. | n.d. |
| 1133127 | 7 | 7 | n.d. | n.d. | n.d. | n.d. | n.d. | n.d. |

Example 20 Incorporation of 2'-OMe at Various Positions

Modified oligonucleotides were synthesized with kkk-m-d(9)-kkk, kkk-d-m-d(8)-kkk, kkk-dd-m-d(7)-kkk or kkk-d(3)-m-d(6)-kkk sugar motifs, respectively, where "m" represents a 2'-OMe-β-D-ribofuranosylsugar moiety, "k" represents a cEt, and "d" represents an unmodified, 2'-β-D-deoxyribosyl sugar moiety. In certain instances, 2'-OMeU replaces 2'-deoxyT. These modified oligonucleotides were compared to the otherwise identical modified oligonucleotide lacking an altered nucleotide in the central region, a 3-10-3 cEt modified oligonucleotide, containing three cEt nucleosides in each of the 5' and 3' regions and 10 unmodified DNA nucleosides in the central region. Each internucleoside linkage is a phosphorothioate internucleoside linkage. The compounds in the table below are 100% complementary to mouse CXCL12, GENBANK NT_039353.7 truncated from 69/430,515 to 69/445,350 (SEQ ID NO: 1), at position 6877 to 6892.

TABLE 49

Modified Oligonucleotides

| Compound ID | altered nucleotide position in central region | sugar moiety of altered nucleotide | Chemistry Notation | SEQ ID NO |
|---|---|---|---|---|
| 558807 | n/a | n/a | $G_{ks}{}^{m}C_{ks}A_{ks}T_{ds}G_{ds}T_{ds}T_{ds}{}^{m}C_{ds}T_{ds}{}^{m}C_{ds}A_{ds}{}^{m}C_{ds}A_{ds}T_{ks}T_{ks}A_{k}$ | 18 |
| 1061877 | 1 | 2'-OMe | $G_{ks}{}^{m}C_{ks}A_{ks}U_{ms}G_{ds}T_{ds}T_{ds}{}^{m}C_{ds}T_{ds}{}^{m}C_{ds}A_{ds}{}^{m}C_{ds}A_{ds}T_{ks}T_{ks}A_{k}$ | 19 |
| 936053 | 2 | 2'-OMe | $G_{ks}{}^{m}C_{ks}A_{ks}T_{ds}G_{ms}T_{ds}T_{ds}{}^{m}C_{ds}T_{ds}{}^{m}C_{ds}A_{ds}{}^{m}C_{ds}A_{ds}T_{ks}T_{ks}A_{k}$ | 18 |
| 1061879 | 3 | 2'-OMe | $G_{ks}{}^{m}C_{ks}A_{ks}T_{ds}G_{ds}U_{ms}T_{ds}{}^{m}C_{ds}T_{ds}{}^{m}C_{ds}A_{ds}{}^{m}C_{ds}A_{ds}T_{ks}T_{ks}A_{k}$ | 20 |
| 1061981 | 4 | 2'-OMe | $G_{ks}{}^{m}C_{ks}A_{ks}T_{ds}G_{ds}T_{ds}U_{ms}{}^{m}C_{ds}T_{ds}{}^{m}C_{ds}A_{ds}{}^{m}C_{ds}A_{ds}T_{ks}T_{ks}A_{k}$ | 21 |
| 1244110 | 5 | 2'-OMe | $G_{ks}{}^{m}C_{ks}A_{ks}T_{ds}G_{ds}T_{ds}T_{ds}C_{ms}T_{ds}{}^{m}C_{ds}A_{ds}{}^{m}C_{ds}A_{ds}T_{ks}T_{ks}A_{k}$ | 18 |
| 1244111 | 6 | 2'-OMe | $G_{ks}{}^{m}C_{ks}A_{ks}T_{ds}G_{ds}T_{ds}T_{ds}{}^{m}C_{ds}U_{ms}{}^{m}C_{ds}A_{ds}{}^{m}C_{ds}A_{ds}T_{ks}T_{ks}A_{k}$ | 39 |
| 1244112 | 7 | 2'-OMe | $G_{ks}{}^{m}C_{ks}A_{ks}T_{ds}G_{ds}T_{ds}T_{ds}{}^{m}C_{ds}T_{ds}C_{ms}A_{ds}{}^{m}C_{ds}A_{ds}T_{ks}T_{ks}A_{k}$ | 18 |
| 1244113 | 8 | 2'-OMe | $G_{ks}{}^{m}C_{ks}A_{ks}T_{ds}G_{ds}T_{ds}T_{ds}{}^{m}C_{ds}T_{ds}{}^{m}C_{ds}A_{ms}{}^{m}C_{ds}A_{ds}T_{ks}T_{ks}A_{k}$ | 18 |
| 1244114 | 9 | 2'-OMe | $G_{ks}{}^{m}C_{ks}A_{ks}T_{ds}G_{ds}T_{ds}T_{ds}{}^{m}C_{ds}T_{ds}{}^{m}C_{ds}A_{ds}C_{ms}A_{ds}T_{ks}T_{ks}A_{k}$ | 18 |
| 1244115 | 10 | 2'-OMe | $G_{ks}{}^{m}C_{ks}A_{ks}T_{ds}G_{ds}T_{ds}T_{ds}{}^{m}C_{ds}T_{ds}{}^{m}C_{ds}A_{ds}{}^{m}C_{ds}A_{ms}T_{ks}T_{ks}A_{k}$ | 18 |

A subscript "d" indicates an unmodified, 2'-β-D-deoxyribosyl sugar moiety. A subscript "m" indicates a 2'-O-methyl-β-D-ribofuranosyl sugar moiety. A subscript "k" indicates a cEt. A subscript "s" indicates a phosphorothioate internucleoside linkage. A superscript "m" before a C indicates 5-methyl Cytosine.

For the results in the tables below, in vitro activity and toxicity experiments were performed essentially as described in Example 1. For in vitro activity and toxicity studies, 3T3-L1 cells were transfected with 27 nM, 80 nM, 250 nM, 740 nM, 2, 222 nM, 6,667 nM, or 20,000 nM of modified oligonucleotide by electroporation and levels of p21 were measured by RT-qPCR as described in Example 1 above. The caspase assay was performed as described in Example 8 above in 3T3-L1 cells. Localization of p54nrb in HeLa cells was quantitated as described in Example 15.

TABLE 50

In vitro activity and toxicity of modified oligonucleotides complementary to CXCL12

| Compound ID | in vitro CXCL12 $IC_{50}$ (nM) | in vitro Caspase (% control) @ 20 μM | in vitro p21 (% control) @ 20 μM | % nucleolar p54nrb |
|---|---|---|---|---|
| 558807 | 47 | 641 | 307 | 92 |
| 1061877 | 13 | 519 | 266 | 43 |
| 936053 | 67 | 173 | 143 | 8 |
| 1061879 | 59 | 416 | 192 | 59 |
| 1061981 | 112 | 325 | 129 | 46 |
| 1244110 | 21 | 386 | 390 | 60 |
| 1244111 | 53 | 380 | 430 | 69 |
| 1244112 | 42 | 345 | 344 | 92 |
| 1244113 | 114 | 361 | 373 | 54 |
| 1244114 | 17 | 399 | 440 | 78 |
| 1244115 | 70 | 372 | 400 | 67 |

altered nucleotide in the central region, 558807, described in Table 1, Example 1 above. The compounds in Table 51 each comprise a 5' wing and a 3' wing each consisting of three linked cEt nucleosides and a central region comprising nucleosides each comprising 2'-β-D-deoxyribosyl sugar moieties aside from the altered nucleotide, as indicated. Each internucleoside linkage is a phosphodiester internucleoside linkage. The compounds in the table below are 100% complementary to mouse CXCL12, GENBANK NT_039353.7 truncated from 69/430,515 to 69/445,350 (SEQ ID NO: 1), at position 6877 to 6892.

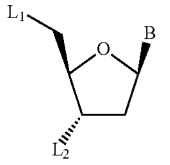

β-D-2'-DNA

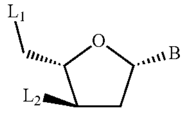

β-L-2'-DNA

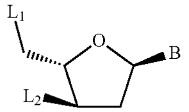

α-L-2'-DNA

B is any nucleobase and $L_1$ and $L_2$ are internucleoside linkages

TABLE 51 modified oligonucleotides with stereochemical modifications

| Compound ID | position of altered nucleotide in central region | stereochemical configuration of altered nucleotide | Chemistry Notation (5' to 3') | SEQ ID NO |
|---|---|---|---|---|
| 1215458 | 2 | β-L-DNA | $G_{ks}{}^{m}C_{ks}A_{ks}T_{ds}[_{\beta\text{-}L}G_{ds}]T_{ds}T_{ds}{}^{m}C_{ds}T_{ds}{}^{m}C_{ds}A_{ds}{}^{m}C_{ds}A_{ds}T_{ks}T_{ks}A_{k}$ | 18 |
| 1215459 | 3 | β-L-DNA | $G_{ks}{}^{m}C_{ks}A_{ks}T_{ds}G_{ds}[_{\beta\text{-}L}T_{ds}]T_{ds}{}^{m}C_{ds}T_{ds}{}^{m}C_{ds}A_{ds}{}^{m}C_{ds}A_{ds}T_{ks}T_{ks}A_{k}$ | 18 |
| 1215460 | 4 | β-L-DNA | $G_{ks}{}^{m}C_{ks}A_{ks}T_{ds}G_{ds}T_{ds}[_{\beta\text{-}L}T_{ds}]{}^{m}C_{ds}T_{ds}{}^{m}C_{ds}A_{ds}{}^{m}C_{ds}A_{ds}T_{ks}T_{ks}A_{k}$ | 18 |
| 1215461 | 3 | α-L-DNA | $G_{ks}{}^{m}C_{ks}A_{ks}T_{ds}G_{ds}[_{\alpha\text{-}L}T_{ds}]T_{ds}{}^{m}C_{ds}T_{ds}{}^{m}C_{ds}A_{ds}{}^{m}C_{ds}A_{ds}T_{ks}T_{ks}A_{k}$ | 18 |
| 1215462 | 4 | α-L-DNA | $G_{ks}{}^{m}C_{ks}A_{ks}T_{ds}G_{ds}T_{ds}[_{\alpha\text{-}L}T_{ds}]{}^{m}C_{ds}T_{ds}{}^{m}C_{ds}A_{ds}{}^{m}C_{ds}A_{ds}T_{ks}T_{ks}A_{k}$ | 18 |

Example 21 Stereochemical Isomers of Nucleosides

Modified oligonucleotides containing modified nucleotides with various stereochemical configurations at positions 1', 3', and 5' of the 2'-deoxyfuranosyl sugar were synthesized. Amidites for the synthesis of β-L-DNA-containing nucleotides are commercially available (ChemGenes) and the synthesis of both α-L and β-L dT phosphoramidites has been reported (Morvan, *Biochem and Biophys Research Comm,* 172(2): 537-543, 1990). The altered nucleotides were contained within the central region of the oligonucleotide.

These modified oligonucleotides were compared to the otherwise identical modified oligonucleotide lacking a an A subscript "d" indicates an unmodified, 2'-β-D-deoxyribosyl sugar moiety. A subscript "k" indicates a cEt. A subscript "s" indicates a phosphorothioate internucleoside linkage. $[_{\beta\text{-}L}B_{ds}]$ indicates a modified β-L-DNA nucleotide with a 2'-deoxyribosyl moiety, a phosphorothioate linkage, and base B. $[_{\alpha\text{-}L}\ B_{ds}]$ indicates a modified, α-L DNA nucleotide with a 2'-deoxyribosyl sugar moiety, a phosphorothioate linkage, and base B.

For the results in the tables below, in vitro activity and toxicity experiments were performed essentially as described in Example 1. For in vitro activity and toxicity studies, 3T3-L1 cells were transfected with 27 nM, 80 nM, 250 nM, 740 nM, 2, 222 nM, 6,667 nM, or 20,000 nM of modified oligonucleotide by electroporation and levels of P21 and Gadd45a and Tnfrsf10b were measured by RT-qPCR as described in Example 1 above. The caspase assay was performed as described in Example 8 above in 3T3-L1 cells.

For the in vivo activity study in the tables below, 2 BALB/C mice per group were administered 1.8 mg/kg, 5.5 mg/kg, 16.7 mg/kg, 50 mg/kg, or 150 mg/kg doses of modified oligonucleotide, as indicated in the table below, by subcutaneous injection and sacrificed 72 hours later. For 558807, only 1.8 mg/kg, 5.5 mg/kg, and 16.7 mg/kg doses were tested for dose response, due to acute toxicity of higher doses. Liver mRNA was isolated an analyzed by RT-PCR as described in Example 1 above. Expression levels were normalized with Ribogreen® and are expressed relative to PBS-treated control mice.

TABLE 52

Activity and toxicity of modified oligonucleotides complementary CXCL12

| Compound ID | in vitro CXCL12 $IC_{50}$ (μM) | in vitro RAPTOR $IC_{50}$ (μM) | in vivo CXCL12 $ED_{50}$ (mg/kg) | ALT @ 50 mg/kg (IU/L) | ALT @ 150 mg/kg (IU/L) |
|---|---|---|---|---|---|
| PBS | n/a | n/a | n/a | 25 @ 0 mg/kg | |
| 558807 | 0.10 | 1 | 2.9 | n.d.** | |
| 1215458 | 0.41 | >20 | 11 | 32 | 42 |
| 1215459 | 0.44 | >20 | 13 | 31 | 37 |
| 1215460 | 0.41 | >20 | 13 | 29 | 43 |
| 1215461 | 0.14 | 3 | 2.8 | 1725 | 6301 |
| 1215462 | 0.13 | 3 | 3.6 | 45 | 3652 |

**558807 treatment at 16.7 mg/kg leads to an ALT of 586 IU/L; mice that are treated with 558807 at 150 mg/kg typically experience death before 72 hours post-treatment.

TABLE 53 in vitro Caspase Activation

| Compound ID | 27 nM | 80 nM | 250 nM | 740 nM | 2,222 nM | 6,667 nM | 20,000 nM |
|---|---|---|---|---|---|---|---|
| | Relative Caspase Activation (% Control) | | | | | | |
| 558807 | 106 | 113 | 117 | 169 | 250 | 396 | 343 |
| 1215458 | 81 | 88 | 98 | 95 | 74 | 78 | 95 |
| 1215459 | 96 | 88 | 111 | 98 | 98 | 81 | 102 |
| 1215460 | 89 | 98 | 96 | 111 | 91 | 113 | 130 |
| 1215461 | 90 | 94 | 89 | 117 | 142 | 201 | 250 |
| 1215462 | 96 | 93 | 95 | 119 | 150 | 192 | 240 |

TABLE 53b in vitro P21 Expression

| Compound ID | 27 nM | 80 nM | 250 nM | 740 nM | 2,222 nM | 6,667 nM | 20,000 nM |
|---|---|---|---|---|---|---|---|
| | Expression level of P21 mRNA (% Control) | | | | | | |
| 558807 | 98 | 116 | 122 | 115 | 115 | 135 | 184 |
| 1215458 | 104 | 127 | 135 | 153 | 139 | 140 | 130 |
| 1215459 | 99 | 116 | 134 | 154 | 158 | 141 | 147 |
| 1215460 | 85 | 109 | 118 | 120 | 118 | 122 | 109 |

TABLE 53b-continued in vitro P21 Expression

| Compound ID | 27 nM | 80 nM | 250 nM | 740 nM | 2,222 nM | 6,667 nM | 20,000 nM |
|---|---|---|---|---|---|---|---|
| | Expression level of P21 mRNA (% Control) | | | | | | |
| 1215461 | 105 | 107 | 128 | 136 | 139 | 147 | 153 |
| 1215462 | 110 | 127 | 143 | 150 | 139 | 124 | 143 |

TABLE 53c in vitro Tnfrsf10b Expression

| Compound ID | 27 nM | 80 nM | 250 nM | 740 nM | 2,222 nM | 6,667 nM | 20,000 nM |
|---|---|---|---|---|---|---|---|
| | Expression level of Tnfrsf10b mRNA (% Control) | | | | | | |
| 558807 | 107 | 108 | 105 | 99 | 113 | 102 | 68 |
| 1215458 | 90 | 88 | 92 | 87 | 81 | 78 | 80 |
| 1215459 | 97 | 108 | 108 | 100 | 103 | 94 | 83 |
| 1215460 | 92 | 100 | 99 | 102 | 95 | 95 | 84 |
| 1215461 | 86 | 91 | 99 | 98 | 97 | 97 | 114 |
| 1215462 | 101 | 97 | 98 | 56 | 82 | 101 | 108 |

TABLE 53d in vitro Gadd45a Expression

| Compound ID | 27 nM | 80 nM | 250 nM | 740 nM | 2,222 nM | 6,667 nM | 20,000 nM |
|---|---|---|---|---|---|---|---|
| | Expression level of Gadd45a mRNA (% Control) | | | | | | |
| 558807 | 123 | 134 | 135 | 136 | 164 | 180 | 223 |
| 1215458 | 132 | 142 | 141 | 135 | 125 | 104 | 87 |
| 1215459 | 163 | 167 | 183 | 190 | 179 | 150 | 110 |
| 1215460 | 127 | 142 | 140 | 141 | 143 | 120 | 95 |
| 1215461 | 117 | 141 | 150 | 165 | 168 | 167 | 128 |
| 1215462 | 110 | 139 | 143 | 138 | 133 | 150 | 137 |

Example 22 Stereochemical Isomers of Nucleosides

Modified oligonucleotides containing β-L-DNA nucleotides (described in Example 21 above) at various positions were synthesized. These modified oligonucleotides were compared to compound 558807, described in Table 1, Example 1 above. Compound 558807 contains 5-methyl cytosine for all cytosine nucleosides, as do compounds 1215458-1215460 described in the table below. The compounds in Table 54 each comprise a 5' wing and a 3' wing each consisting of three linked cEt nucleosides and a central region comprising nucleosides each comprising 2'-β-D-deoxyribosyl sugar moieties aside from the altered nucleotide, as indicated. Each internucleoside linkage is a phosphodiester internucleoside linkage. Compounds 1244441-1244447 in the table below contain unmethylated cytosine in the central region of the compounds. The compounds in the table below are 100% complementary to mouse CXCL12, GENBANK NT_039353.7 truncated from 69/430,515 to 69/445,350 (SEQ ID NO: 1), at position 6877 to 6892.

TABLE 54

| modified oligonucleotides with stereochemical modifications | | | | |
|---|---|---|---|---|
| Compound ID | position of altered nucleotide in central region | stereo-chemical configuration of altered nucleotide | Chemistry Notation | SEQ ID NO |
| 1244441 | 1 | β-L-DNA | $G_{ks}{}^{m}C_{ks}A_{ks}[_{\beta\text{-}L}T_{ds}]G_{ds}T_{ds}T_{ds}C_{ds}T_{ds}C_{ds}A_{ds}C_{ds}A_{ds}T_{ks}T_{ks}A_{k}$ | 18 |
| 1215458 | 2 | β-L-DNA | $G_{ks}{}^{m}C_{ks}A_{ks}T_{ds}[_{\beta\text{-}L}G_{ds}]T_{ds}{}^{m}C_{ds}T_{ds}{}^{m}C_{ds}A_{ds}{}^{m}C_{ds}A_{ds}T_{ks}T_{ks}A_{k}$ | 18 |
| 1215459 | 3 | β-L-DNA | $G_{ks}{}^{m}C_{ks}A_{ks}T_{ds}G_{ds}[_{\beta\text{-}L}T_{ds}]T_{ds}{}^{m}C_{ds}T_{ds}{}^{m}C_{ds}A_{ds}{}^{m}C_{ds}A_{ds}T_{ks}T_{ks}A_{k}$ | 18 |
| 1215460 | 4 | β-L-DNA | $G_{ks}{}^{m}C_{ks}A_{ks}T_{ds}G_{ds}T_{ds}[_{\beta\text{-}L}T_{ds}]{}^{m}C_{ds}T_{ds}{}^{m}C_{ds}A_{ds}{}^{m}C_{ds}A_{ds}T_{ks}T_{ks}A_{k}$ | 18 |
| 1244442 | 5 | β-L-DNA | $G_{ks}{}^{m}C_{ks}A_{ks}T_{ds}G_{ds}T_{ds}T_{ds}[_{\beta\text{-}L}C_{ds}]T_{ds}C_{ds}A_{ds}C_{ds}A_{ds}T_{ks}T_{ks}A_{k}$ | 18 |
| 1244443 | 6 | β-L-DNA | $G_{ks}{}^{m}C_{ks}A_{ks}T_{ds}G_{ds}T_{ds}T_{ds}C_{ds}[_{\beta\text{-}L}T_{ds}]C_{ds}A_{ds}C_{ds}A_{ds}T_{ks}T_{ks}A_{k}$ | 18 |
| 1244444 | 7 | β-L-DNA | $G_{ks}{}^{m}C_{ks}A_{ks}T_{ds}G_{ds}T_{ds}T_{ds}C_{ds}T_{ds}[_{\beta\text{-}L}C_{ds}]A_{ds}C_{ds}A_{ds}T_{ks}T_{ks}A_{k}$ | 18 |
| 1244445 | 8 | β-L-DNA | $G_{ks}{}^{m}C_{ks}A_{ks}T_{ds}G_{ds}T_{ds}T_{ds}C_{ds}T_{ds}C_{ds}[_{\beta\text{-}L}A_{ds}]C_{ds}A_{ds}T_{ks}T_{ks}A_{k}$ | 18 |
| 1244446 | 9 | β-L-DNA | $G_{ks}{}^{m}C_{ks}A_{ks}T_{ds}G_{ds}T_{ds}T_{ds}C_{ds}T_{ds}C_{ds}A_{ds}[_{\beta\text{-}L}C_{ds}]A_{ds}T_{ks}T_{ks}A_{k}$ | 18 |
| 1244447 | 10 | β-L-DNA | $G_{ks}{}^{m}C_{ks}A_{ks}T_{ds}G_{ds}T_{ds}T_{ds}C_{ds}T_{ds}C_{ds}A_{ds}C_{ds}[_{\beta\text{-}L}A_{ds}]T_{ks}T_{ks}A_{k}$ | 18 |

A subscript "d" indicates a nucleoside comprising an n unmodified, 2'-β-D-deoxyribosyl sugar moiety. A subscript "k" indicates a cEt. A subscript "s" indicates a phosphorothioate internucleoside linkage. $[_{\beta\text{-}L}B_{ds}]$ indicates a modified β-L-DNA nucleotide with a 2'-deoxyribosyl sugar moiety, a phosphorothioate linkage, and base B.

For the results in the tables below, in vitro activity and toxicity experiments were performed essentially as described in Example 1. For in vitro activity and toxicity studies, 3T3-L1 cells were transfected with 27 nM, 80 nM, 250 nM, 740 nM, 2, 222 nM, 6,667 nM, or 20,000 nM of modified oligonucleotide by electroporation and levels of P21 and Gadd45a and Tnfrsf10b were measured by RT-qPCR as described in Example 1 above. The caspase assay was performed as described in Example 8 above in 3T3-L1 cells. Localization of p54nrb in HeLa cells was quantitated as described in Example 15.

TABLE 55

| In vitro activity and toxicity of modified oligonucleotides complementary to CXCL12 | | |
|---|---|---|
| Compound ID | in vitro CXCL12 $IC_{50}$ (nM) | in vitro Caspase (% control) @ 20 μM |
| 558807 | 0.029 | 321 |
| 1244441 | 0.471 | 108 |
| 1215458 | 0.200 | 104 |
| 1215459 | 0.191 | 111 |
| 1215460 | 0.130 | 133 |
| 1244442 | 0.134 | 185 |
| 1244443 | 0.083 | 279 |
| 1244444 | 0.109 | 213 |
| 1244445 | 0.198 | 249 |

TABLE 55-continued

| In vitro activity and toxicity of modified oligonucleotides complementary to CXCL12 | | |
|---|---|---|
| Compound ID | in vitro CXCL12 $IC_{50}$ (nM) | in vitro Caspase (% control) @ 20 μM |
| 1244446 | 0.127 | 243 |
| 1244447 | 0.080 | 333 |

Example 23 Stereochemical Isomers of Nucleosides

Modified oligonucleotides containing α-D-DNA nucleotides (see below) at various positions were synthesized. These modified oligonucleotides were compared to the otherwise identical modified oligonucleotide lacking an altered nucleotide in the central region. The compounds in Table 54 each comprise a 5' wing and a 3' wing each consisting of three linked cEt nucleosides and a central region comprising nucleosides each comprising 2'-β-D-deoxyribosyl sugar moieties aside from the altered nucleotide, as indicated. Each internucleoside linkage is a phosphodiester internucleoside linkage. The compounds in the table below are 100% complementary to mouse CXCL12, GENBANK NT_039353.7 truncated from 69/430,515 to 69/445, 350 (SEQ ID NO: 1), at position 6877 to 6892.

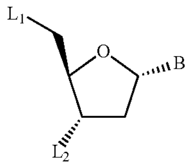

α-D-2'-DNA

TABLE 56

| modified oligonucleotides with stereochemical modifications | | | | |
|---|---|---|---|---|
| Compound ID | position of altered nucleotide in central region | stereo-chemical configuration of altered nucleotide | Chemistry Notation | SEQ ID NO |
| 1244458 | none | none | $G_{ks}{}^{m}C_{ks}A_{ks}T_{ds}G_{ds}T_{ds}T_{ds}C_{ds}T_{ds}C_{ds}A_{ds}C_{ds}A_{ds}T_{ks}T_{ks}A_{k}$ | 18 |
| 1244448 | 1 | α-D-DNA | $G_{ks}{}^{m}C_{ks}A_{ks}[_{\alpha\text{-}D}T_{ds}]G_{ds}T_{ds}T_{ds}C_{ds}T_{ds}C_{ds}A_{ds}C_{ds}A_{ds}T_{ks}T_{ks}A_{k}$ | 18 |
| 1244449 | 2 | α-D-DNA | $G_{ks}{}^{m}C_{ks}A_{ks}T_{ds}[_{\alpha\text{-}D}G_{ds}]T_{ds}T_{ds}C_{ds}T_{ds}C_{ds}A_{ds}C_{ds}A_{ds}T_{ks}T_{ks}A_{k}$ | 18 |
| 1244450 | 3 | α-D-DNA | $G_{ks}{}^{m}C_{ks}A_{ks}T_{ds}G_{ds}[_{\alpha\text{-}D}T_{ds}]T_{ds}C_{ds}T_{ds}C_{ds}A_{ds}C_{ds}A_{ds}T_{ks}T_{ks}A_{k}$ | 18 |
| 1244451 | 4 | α-D-DNA | $G_{ks}{}^{m}C_{ks}A_{ks}T_{ds}G_{ds}T_{ds}[_{\alpha\text{-}D}T_{ds}]C_{ds}T_{ds}C_{ds}A_{ds}C_{ds}A_{ds}T_{ks}T_{ks}A_{k}$ | 18 |
| 1244452 | 5 | α-D-DNA | $G_{ks}{}^{m}C_{ks}A_{ks}T_{ds}G_{ds}T_{ds}T_{ds}[_{\alpha\text{-}D}C_{ds}]T_{ds}C_{ds}A_{ds}C_{ds}A_{ds}T_{ks}T_{ks}A_{k}$ | 18 |
| 1244453 | 6 | α-D-DNA | $G_{ks}{}^{m}C_{ks}A_{ks}T_{ds}G_{ds}T_{ds}T_{ds}C_{ds}[_{\alpha\text{-}D}T_{ds}]C_{ds}A_{ds}C_{ds}A_{ds}T_{ks}T_{ks}A_{k}$ | 18 |
| 1244454 | 7 | α-D-DNA | $G_{ks}{}^{m}C_{ks}A_{ks}T_{ds}G_{ds}T_{ds}T_{ds}C_{ds}T_{ds}[_{\alpha\text{-}D}C_{ds}]A_{ds}C_{ds}A_{ds}T_{ks}T_{ks}A_{k}$ | 18 |
| 1244455 | 8 | α-D-DNA | $G_{ds}{}^{m}C_{ks}A_{ks}T_{ds}G_{ds}T_{ds}T_{ds}C_{ds}T_{ds}C_{ds}[_{\alpha\text{-}D}A_{ds}]C_{ds}A_{ds}T_{ks}T_{ks}A_{k}$ | 18 |
| 1244456 | 9 | α-D-DNA | $G_{ks}{}^{m}C_{ks}A_{ks}T_{ds}G_{ds}T_{ds}T_{ds}C_{ds}T_{ds}C_{ds}A_{ds}[_{\alpha\text{-}D}C_{ds}]A_{ds}T_{ks}T_{ks}A_{k}$ | 18 |
| 1244457 | 10 | α-D-DNA | $G_{ks}{}^{m}C_{ks}A_{ks}T_{ds}G_{ds}T_{ds}T_{ds}C_{ds}T_{ds}C_{ds}A_{ds}C_{ds}[_{\alpha\text{-}D}A_{ds}]T_{ks}T_{ks}A_{k}$ | 18 |

A subscript "d" indicates a nucleoside comprising an n unmodified, 2'-β-D-deoxyribosyl sugar moiety. A subscript "k" indicates a cEt. A subscript "s" indicates a phosphorothioate internucleoside linkage. $[_{\alpha\text{-}D}B_{ds}]$ indicates a modified, α-D-DNA nucleotide with a 2'-deoxyribosyl sugar moiety, a phosphorothioate linkage, and base B.

For the results in the tables below, in vitro activity and toxicity experiments were performed essentially as described in Example 1. For in vitro activity and toxicity studies, 3T3-L1 cells were transfected with 27 nM, 80 nM, 250 nM, 740 nM, 2, 222 nM, 6,667 nM, or 20,000 nM of modified oligonucleotide by electroporation and levels of p21 were measured by RT-qPCR as described in Example 1 above. The caspase assay was performed as described in Example 8 above in 3T3-L1 cells. Localization of p54nrb in HeLa cells was quantitated as described in Example 15.

TABLE 57

| In vitro activity and toxicity of modified oligonucleotides complementary CXCL12 | | | | |
|---|---|---|---|---|
| Compound ID | in vitro CXCL12 $IC_{50}$ (nM) | in vitro Caspase (% control) @ 20 μM | in vitro p21 (% control) @ 20 μM | % nucleolar p54nrb |
| 1244458 | 19 | 785 | 327 | 86 |
| 1244448 | 35 | 269 | 135 | 66 |
| 1244449 | 169 | 111 | 101 | 8 |
| 1244450 | 103 | 96 | 169 | 11 |
| 1244451 | 45 | 261 | 206 | 78 |
| 1244452 | 393 | 295 | 146 | 83 |
| 1244453 | 80 | 417 | 255 | 92 |
| 1244454 | 512 | 287 | 240 | 65 |
| 1244455 | 125 | 409 | 310 | 83 |
| 1244456 | 247 | 233 | 269 | 96 |
| 1244457 | 31 | 854 | 400 | 100 |

Example 24 4'-Methyl and Xylo DNA

Modified oligonucleotides containing an altered nucleotide with a 4'-methyl modified sugar moiety or a 2'-deoxy-β-D-xylofuranosyl (2'deoxy-β-D-XNA) sugar moiety at various positions were synthesized (see Table 58 below). Synthesis of oligonucleotides comprising 2'deoxy-β-D-XNA nucleosides has been described previously (Wang, et. al., *Biochemistry,* 56(29): 3725-3732, 2017). Synthesis of oligonucleotides comprising 4'-methyl modified nucleosides has been described previously (e.g., Detmer et. al., *European J. Org. Chem,* 1837-1846, 2003). The compounds in Table 58 each comprise a 5' wing and a 3' wing each consisting of three linked cEt nucleosides and a central region comprising nucleosides each comprising 2'43-D-deoxyribosyl sugar moieties aside from the altered nucleotide, as indicated. Each internucleoside linkage is a phosphodiester internucleoside linkage. These compounds were compared to a compound comprising a 2'-OMe modified sugar moiety at position 2 of the central region, 936053, described in Example 1 above. The compounds in the table below are 100% complementary to mouse CXCL12, GENBANK NT_039353.7 truncated from 69/430,515 to 69/445,350 (SEQ ID NO: 1), at position 6877 to 6892.

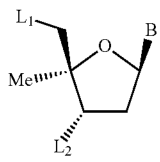

4'-methyl-β-D-2'-DNA

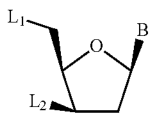

2'-deoxy-β-D-XNA

TABLE 58

| modified oligonucleotides with stereochemical modifications | | | | |
|---|---|---|---|---|
| Compound ID | position of altered nucleotide in central region | modification of altered nucleotide | Chemistry Notation | SEQ ID NO |
| 936053 | 2 | 2'-OMe | $G_{ks}{}^{m}C_{ks}A_{ks}T_{ds}G_{ms}T_{ds}T_{ds}{}^{m}C_{ds}T_{ds}{}^{m}C_{ds}A_{ds}{}^{m}C_{ds}A_{ds}T_{ks}T_{ks}A_{k}$ | 18 |
| 1244461 | 3 | 4'-Me | $G_{ks}{}^{m}C_{ks}A_{ks}T_{ds}G_{ds}T_{[4m]s}T_{ds}{}^{m}C_{ds}T_{ds}{}^{m}C_{ds}A_{ds}{}^{m}C_{ds}A_{ds}T_{ks}T_{ks}A_{k}$ | 18 |

TABLE 58-continued

| modified oligonucleotides with stereochemical modifications | | | | |
|---|---|---|---|---|
| Compound ID | position of altered nucleotide in central region | modification of altered nucleotide | Chemistry Notation | SEQ ID NO |
| 1244462 | 4 | 4'-Me | $G_{ks}{}^{m}C_{ks}A_{ks}T_{ds}G_{ds}T_{ds}T_{[4m]s}{}^{m}C_{ds}T_{ds}{}^{m}C_{ds}A_{ds}{}^{m}C_{ds}A_{ds}T_{ks}T_{ks}A_{k}$ | 18 |
| 1263776 | 3 | β-D-XNA | $G_{ks}{}^{m}C_{ks}A_{ks}T_{ds}G_{ds}[_{\beta\text{-}D}T_{xs}]T_{ds}{}^{m}C_{ds}T_{ds}{}^{m}C_{ds}A_{ds}{}^{m}C_{ds}A_{ds}T_{ks}T_{ks}A_{k}$ | 18 |
| 1263777 | 4 | β-D-XNA | $G_{ks}{}^{m}C_{ks}A_{ks}T_{ds}G_{ds}T_{ds}[_{\beta\text{-}D}T_{xs}]{}^{m}C_{ds}T_{ds}{}^{m}C_{ds}A_{ds}{}^{m}C_{ds}A_{ds}T_{ks}T_{ks}A_{k}$ | 18 |

A subscript "d" indicates an unmodified, 2'-β-D-deoxyribosyl sugar moiety. A subscript "k" indicates a cEt. A subscript "s" indicates a phosphorothioate internucleoside linkage. A superscript "m" indicates 5-methyl Cytosine. A subscript "[4m]" indicates a 4'-methyl-2'-β-D-deoxyribosyl sugar moiety. $[_{\beta\text{-}D}B_{xs}]$ indicates a modified, β-D-XNA (xylo) nucleotide with a 2'-deoxyxylosyl sugar moiety, a phosphorothioate linkage, and base B.

For in vivo activity and toxicity studies, 3 BALB/c mice per group were administered 10 or 150 mg/kg modified oligonucleotide by subcutaneous injection and sacrificed after 72 hours. Four animals were administered saline to serve as a control. RT-PCR was performed as described in Example 1 to determine mRNA levels of CXCL12, P21, Tnfrsf10b, and Gadd45a. Plasma levels of ALT was measured using an automated clinical chemistry analyzer. Increased ALT is indicative of acute liver toxicity.

TABLE 59

| In vivo activity and toxicity of modified oligonucleotides complementary to CXCL12 | | | | | | | |
|---|---|---|---|---|---|---|---|
| Compound ID | in vivo CXCL12 @ 10 mg/kg (% control) | in vivo CXCL12 @ 150 mg/kg (% control) | in vivo P21 @ 150 mg/kg (% control) | in vivo Tnfrsf10b @ 150 mg/kg (% control) | in vivo Gadd45a @ 150 mg/kg (% control) | in vivo ALT @ 10 mg/kg (IU/L) | in vivo ALT @ 150 mg/kg (IU/L) |
| PBS | 100 | 100 | 100 | 100 | 100 | 26 (@ 0 mg/kg) | |
| 936053 | 37 | 13 | 175 | 448 | 216 | 23 | 83 |
| 1244461 | 22 | 5 | 2994 | 4663 | 1124 | 31 | 5080 |
| 1244462 | 30 | 7* | 1038 | 717* | 407* | 28 | 1789* |
| 1263776 | 19 | 11 | 4846 | 10686 | 1032 | 27 | 9234 |
| 1263777 | 13 | n.d. | n.d. | n.d. | n.d. | 58 | death |

*Value represents the average of 2 samples.

Example 25 Microscopy

Selected modified nucleotides described in the Examples above were tested for their effect on HeLa cells by microscopy. HeLa cells were transfected by lipofectamine 2000 with 200 nM of modified oligonucleotide for 2 hrs and then cellular protein p54nrb was stained by mP54 antibody (Santa Cruz Biotech, sc-376865) and DAPI was used to stain for the nucleus of cells.

For experiments reported in the tables below, the number of cells with nucleolar p54nrb and the total number of cells in the images were counted and a percentage of cells with mislocalization of p54nrb was calculated. Where the same compound appears in multiple tables, these represent the results from independent experiments.

TABLE 60

| Nucleolar mislocalization of p54nrb | | | |
|---|---|---|---|
| Compound ID | Cells with nucleolar p54nrb | Total cells | % cells with mislocalization |
| Mock | 0 | 74 | 0 |
| 558807 | 45 | 51 | 88 |

TABLE 61

| Nucleolar mislocalization of p54nrb | | | |
|---|---|---|---|
| Compound ID | Sugar Motif | % cells with mislocalization | ALT @ 150 mg/kg (IU/L) |
| 464917 | kkk-d(10)-kkk | 75 | death |
| 982034 | kkk-d-m-(8)-kkk | <7 | 13,172 |
| 465175 | kkk-d(10)-kkk | 57 | 1,564 |
| 1133329 | kkk-d-m-(8)-kkk | 48 | 60 |
| 465181 | kkk-d(10)-kkk | 58 | 7,087 |

TABLE 61-continued

| Nucleolar mislocalization of p54nrb | | | |
|---|---|---|---|
| Compound ID | Sugar Motif | % cells with mislocalization | ALT @ 150 mg/kg (IU/L) |
| 1133335 | kkk-d-m-(8)-kkk | <1 | 26 |
| 545984 | kkk-d(10)-kkk | 98 | 37,277 |
| 1133060 | kkk-d-m-(8)-kkk | 0 | 39 |

For experiments reported in the tables below, selected images were qualitatively analyzed and assigned a score of (−), indicating that no p54nrb mislocalization to the nucleolus was observed, or a score of (+) indicating that mislocalization of p54nrb to the nucleolus was observed in some cells, or (++) indicating that p54nrb mislocalizization to the nucleolus was observed in most or all cells.

TABLE 62

| Nucleolar mislocalization of p54nrb and correlation with toxicity | | | |
|---|---|---|---|
| Compound ID | Complementary mRNA | Mislocalization of p54nrb | ALT @ max dose* |
| 558807 | CXCL12 | ++ | death |
| 936049 | CXCL12 | ++ | 8,622 |
| 936053 | CXCL12 | − | 46 |
| 892826 | CXCL12 | − | 10,463 |
| 766677 | CXCL12 | − | 23 |
| 828911 | CXCL12 | − | 27 |
| 936051 | CXCL12 | + | death |
| 936052 | CXCL12 | − | 1,110 |
| 1070041 | CXCL12 | + | 96 |
| 1061314 | CXCL12 | − | 26 |
| 1061302 | CXCL12 | + | 2,253 |
| 1061303 | CXCL12 | − | 34 |
| 1061304 | CXCL12 | − | 52 |
| 1061305 | CXCL12 | − | 31 |
| 1076587 | CXCL12 | − | n.d. |
| 1076588 | CXCL12 | + | n.d. |
| 1069852 | CXCL12 | − | n.d. |
| 1061328 | CXCL12 | + | n.d. |
| 1061955 | CXCL12 | − | 86 |
| 1061964 | CXCL12 | − | n.d. |
| 1244441 | CXCL12 | − | n.d. |
| 1215458 | CXCL12 | − | n.d. |
| 1215459 | CXCL12 | − | n.d. |
| 1215460 | CXCL12 | − | n.d. |
| 1244442 | CXCL12 | − | n.d. |
| 1244443 | CXCL12 | + | n.d. |
| 1244444 | CXCL12 | ++ | n.d. |
| 1244445 | CXCL12 | ++ | n.d. |
| 1244446 | CXCL12 | ++ | n.d. |
| 1244447 | CXCL12 | ++ | n.d. |
| 464917 | FXI | + | 18,316 |
| 465977 | FXI | + | death |
| 483706 | FXI | + | 1,424 |
| 443919 | FXI | − | 68 |
| 820685** | FXI | − | 59 |

TABLE 62-continued

| Nucleolar mislocalization of p54nrb and correlation with toxicity | | | |
|---|---|---|---|
| Compound ID | Complementary mRNA | Mislocalization of p54nrb | ALT @ max dose* |
| 508031 | SOD1 | ++ | 16,317 |
| 895154 | SOD1 | + | 206 |
| 895155 | SOD1 | − | 41 |
| 895156 | SOD1 | + | 1,242 |
| 508034 | SOD1 | + | 22,396 |
| 508037 | SOD1 | − | 20 |
| 529933 | SOD1 | − | 11 |

*Data presented in previous examples; maximum administered dose is 150 mg/kg for modified oligonucleotides complementary to CXCL12, 100 mg/kg for modified oligonucleotides complementary to SOD1, and 33 mg/kg for compounds complementary to FXI, except that the ALT for 820685 is at 100 mg/kg.

**820685 has the same sequence as 464917 and a sugar motif of kkk-m(10)-kkk.

Example 26 Nucleolar Mislocalization of p54nrb with Fluorescently-Labeled Modified Oligonucleotides Modified oligonucleotides described in the tables above were conjugated to Cy3 or FAM on the 3'-end via a phosphorothioate linker or on the 5'-end via a phosphorothioate linker to generate a compound comprising a conjugate group that comprises a fluorophore, resulting in a fluorescently labeled modified oligonucleotide. Fluorescently labeled modified oligonucleotides were incubated with HeLa cells at 200 nM for 2 hours and cells were imaged by fluorescent microscopy. Cellular protein p54nrb was stained by mP54 antibody (Santa Cruz Biotech, sc-376865) and DAPI was used to stain for the nucleus of cells. For experiments reported in the tables below, images were qualitatively analyzed and assigned a score of (−), indicating that no p54nrb mislocalization to the nucleolus was observed, or a score of (+) indicating that mislocalization of p54nrb to the nucleolus was observed in some cells, or (++) indicating that p54nrb mislocalization to the nucleolus was observed in most or all cells.

TABLE 63

| Fluorescently Labeled Modified Oligonucleotides | | | |
|---|---|---|---|
| Unlabelled compound ID | Fluorescently-labelled compound ID | Chemistry notation for Fluorescently-labelled compound | SEQ ID NO: |
| 558807 | 925819 | $G_{ks}{}^{m}C_{ks}A_{ks}T_{ds}G_{ds}T_{ds}T_{ds}{}^{m}C_{ds}T_{ds}{}^{m}C_{ds}A_{ds}{}^{m}C_{ds}A_{ds}T_{ks}T_{ks}A_{ks}$-Cy3 | 18 |
| 766676 | 925820 | $G_{ks}{}^{m}C_{ks}A_{ks}T_{dx}G_{ds}T_{ds}T_{ds}{}^{m}C_{ds}T_{ds}{}^{m}C_{ds}A_{ds}{}^{m}C_{ds}A_{ds}T_{ks}T_{ks}A_{ks}$-Cy3 | 18 |
| 766677 | 925821 | $G_{ks}{}^{m}C_{ks}A_{ks}T_{ds}G_{dx}T_{ds}T_{ds}{}^{m}C_{ds}T_{ds}{}^{m}C_{ds}A_{ds}{}^{m}C_{ds}A_{ds}T_{ks}T_{ks}A_{ks}$-Cy3 | 18 |
| 766678 | 925822 | $G_{ks}{}^{m}C_{ks}A_{ks}T_{ds}G_{ds}T_{dx}T_{ds}{}^{m}C_{ds}T_{ds}{}^{m}C_{ds}A_{ds}{}^{m}C_{ds}A_{ds}T_{ks}T_{ks}A_{ks}$-Cy3 | 18 |
| 766679 | 925826 | $G_{ks}{}^{m}C_{ks}A_{ks}T_{ds}G_{ds}T_{ds}T_{dx}{}^{m}C_{ds}T_{ds}{}^{m}C_{ds}A_{ds}{}^{m}C_{ds}A_{ds}T_{ks}T_{ks}A_{ks}$-Cy3 | 18 |
| 766684 | 925824 | $G_{ks}{}^{m}C_{ks}A_{ks}T_{ds}G_{ds}T_{ds}T_{ds}{}^{m}C_{ds}T_{ds}{}^{m}C_{ds}A_{ds}{}^{m}C_{dx}A_{ds}T_{ks}T_{ks}A_{ks}$-Cy3 | 18 |
| 936049 | 958339 | Cy3-$G_{ks}{}^{m}C_{ks}A_{ks}U_{ms}G_{ds}T_{ds}T_{ds}{}^{m}C_{ds}T_{ds}{}^{m}C_{ds}A_{ds}{}^{m}C_{ds}A_{ds}T_{ks}T_{ks}A_{k}$ | 19 |
| 936053 | 958340 | Cy3-$G_{ks}{}^{m}C_{ks}A_{ks}T_{ds}G_{ms}T_{ds}T_{ds}{}^{m}C_{ds}T_{ds}{}^{m}C_{ds}A_{ds}{}^{m}C_{ds}A_{ds}T_{ks}T_{ks}A_{k}$ | 18 |
| 892826 | 958341 | Cy3-$G_{ks}{}^{m}C_{ks}A_{ks}T_{ds}G_{ds}U_{ms}T_{ds}{}^{m}C_{ds}T_{ds}{}^{m}C_{ds}A_{ds}{}^{m}C_{ds}A_{ds}T_{ks}T_{ks}A_{k}$ | 20 |
| 558807 | 1189295 | FAM-$G_{ks}{}^{m}C_{ks}A_{ks}T_{ds}G_{ds}T_{ds}T_{ds}{}^{m}C_{ds}T_{ds}{}^{m}C_{ds}A_{ds}{}^{m}C_{ds}A_{ds}T_{ks}T_{ks}A_{ks}$ | 18 |
| 1061955 | 1189310 | FAM-$G_{ks}{}^{m}C_{ks}A_{ks}T_{ds}I_{ds}T_{ds}T_{ds}{}^{m}C_{ds}T_{ds}{}^{m}C_{ds}A_{ds}{}^{m}C_{ds}A_{ds}T_{ks}T_{ks}A_{ks}$ | 30 |
| 766677 | 1215929 | FAM-$G_{ks}{}^{m}C_{ks}A_{ks}T_{ds}G_{dx}T_{ds}T_{ds}{}^{m}C_{ds}T_{ds}{}^{m}C_{ds}A_{ds}{}^{m}C_{ds}A_{ds}T_{ks}T_{ks}A_{ks}$ | 18 |
| 936053 | 1189369 | FAM-$G_{ks}{}^{m}C_{ks}A_{ks}T_{ds}G_{ms}T_{ds}T_{ds}{}^{m}C_{ds}T_{ds}{}^{m}C_{ds}A_{ds}{}^{m}C_{ds}A_{ds}T_{ks}T_{ks}A_{k}$ | 18 |
| 942944 | 1215928 | FAM-$G_{ks}{}^{m}C_{ks}A_{ks}T_{ds}G_{ds}T_{ds}{}^{(R)\text{-}m}T_{ds}{}^{m}C_{ds}T_{ds}{}^{m}C_{ds}A_{ds}{}^{m}C_{ds}A_{ds}T_{ks}T_{ks}A_{k}$ | 18 |
| 464917 | 813223 | Cy3-$G_{ks}T_{ks}{}^{m}C_{ks}T_{ds}G_{ds}T_{ds}G_{ds}{}^{m}C_{ds}A_{ds}T_{ds}{}^{m}C_{ds}T_{ds}{}^{m}C_{ds}T_{ks}{}^{m}C_{ks}{}^{m}C_{k}$ | 22 |
| 508031 | 828939 | Cy3-$T_{ks}G_{ks}A_{ks}G_{ds}G_{ds}T_{ds}{}^{m}C_{ds}{}^{m}C_{ds}T_{ds}G_{ds}{}^{m}C_{ds}A_{ds}{}^{m}C_{ds}T_{ks}G_{ks}G_{k}$ | 26 |
| 482050 | 841864 | Cy3-$A_{ks}T_{ks}{}^{m}C_{ks}A_{ds}T_{ds}G_{ds}G_{ds}{}^{m}C_{ds}T_{ds}G_{ds}{}^{m}C_{ds}A_{ds}G_{ds}{}^{m}C_{ks}T_{ks}T_{k}$ | 24 |
| 449093 | 489982 | FAM-$T_{ks}T_{ks}{}^{m}C_{ks}A_{ds}G_{ds}T_{ds}{}^{m}C_{ds}A_{ds}T_{ds}G_{ds}A_{ds}{}^{m}C_{ds}T_{ds}T_{ks}{}^{m}C_{ks}{}^{m}C_{k}$ | 28 |
| 465178 | 869208 | Cy3-$G_{ks}T_{ks}{}^{m}C_{ks}A_{ds}G_{ds}T_{ds}A_{ds}T_{ds}{}^{m}C_{ds}{}^{m}C_{ds}{}^{m}C_{ds}A_{ds}G_{ds}T_{ks}G_{ks}T_{k}$ | 89 |
| 575013 | 869198 | Cy3-${}^{m}C_{ks}A_{ks}G_{ks}A_{ds}T_{ds}A_{ds}T_{ds}A_{ds}G_{ds}G_{ds}A_{ds}{}^{m}C_{ds}T_{ds}G_{ks}G_{ks}A_{k}$ | 110 |
| 549139 | 869199 | Cy3-$G_{ks}A_{ks}{}^{m}C_{ks}G_{ds}{}^{m}C_{ds}G_{ds}{}^{m}C_{ds}{}^{m}C_{ds}T_{ds}G_{ds}A_{ds}A_{ds}G_{ds}G_{ks}T_{ks}T_{k}$ | 111 |

TABLE 63-continued

| Fluorescently Labeled Modified Oligonucleotides | | | |
|---|---|---|---|
| Unlabelled compound ID | Fluorescently-labelled compound ID | Chemistry notation for Fluorescently-labelled compound | SEQ ID NO: |
| 508032 | 869200 | Cy3-$G_{ks}G_{ks}A_{ks}{}^{m}C_{ds}A_{ds}{}^{m}C_{ds}A_{ds}T_{ds}T_{ds}G_{ds}G_{ds}{}^{m}C_{ds}{}^{m}C_{ds}A_{ks}{}^{m}C_{ks}A_{k}$ | 112 |
| 464932 | 869201 | Cy3-$G_{ks}G_{ks}{}^{m}C_{ks}{}^{m}C_{ds}A_{ds}{}^{m}C_{ds}{}^{m}C_{ds}A_{ds}{}^{m}C_{ds}G_{ds}{}^{m}C_{ds}T_{ds}G_{ds}T_{ks}{}^{m}C_{ks}A_{k}$ | 113 |
| 465131 | 869202 | Cy3-$T_{ks}G_{ks}{}^{m}C_{ks}{}^{m}C_{ds}A_{ds}{}^{m}C_{ds}{}^{m}C_{ds}G_{ds}T_{ds}A_{ds}G_{ds}A_{ds}{}^{m}C_{ds}A_{ks}{}^{m}C_{ks}G_{k}$ | 114 |
| 147420 | 841863 | Cy3-$A_{es}A_{es}T_{es}G_{es}T_{es}G_{ds}{}^{m}C_{ds}{}^{m}C_{ds}T_{ds}G_{ds}{}^{m}C_{ds}T_{ds}G_{ds}T_{ds}{}^{m}C_{ds}{}^{m}C_{es}T_{es}T_{es}G_{es}A_{e}$ | 73 |

A subscript "d" indicates an unmodified, 2'-β-D-deoxyribosyl sugar moiety. A subscript "e" indicates a 2'-MOE-β-D-ribofuranosyl sugar moiety. A subscript "m" indicates a 2'-O-methyl-β-D-ribofuranosyl sugar moiety. A subscript "k" indicates a cEt. A subscript "s" indicates a phosphorothioate internucleoside linkage. A superscript "m" before a C indicates 5-methyl Cytosine. A subscript "x" indicates a MOP internucleoside linkage.

TABLE 64

| Nucleolar mislocalization of p54nrb | | | | |
|---|---|---|---|---|
| Unlabelled compound ID | Fluorescently-labelled Compound ID | Complementary mRNA | Mislocalization of p54nrb | ALT @ 150 mg/kg of unlabelled modified oligonucleotide |
| 558807 | 925819 | CXCL12 | ++ | death |
| 766676 | 925820 | CXCL12 | ++ | 5,475 |
| 766677 | 925821 | CXCL12 | − | 23 |
| 766678 | 925822 | CXCL12 | − | 67 |
| 766679 | 925823 | CXCL12 | + | 3,347 |
| 766684 | 925824 | CXCL12 | ++ | death |
| 936049 | 958339 | CXCL12 | ++ | 8,622 |
| 936053 | 958340 | CXCL12 | − | 46 |
| 892826 | 958341 | CXCL12 | + | 10,463 |
| 558807 | 1189295 | CXCL12 | ++ | death |
| 1061955 | 1189310 | CXCL12 | − | 86 |
| 766677 | 1215929 | CXCL12 | − | 23 |
| 936053 | 1189369 | CXCL12 | − | 46 |
| 942944 | 1215928 | CXCL12 | + | 233 |

TABLE 65

| Nucleolar mislocalization of p54nrb | | | | |
|---|---|---|---|---|
| Unlabelled compound ID | Fluorescently-labelled Compound ID | Complementary mRNA | Mislocalization of p54nrb | ALT @ 200 mg/kg of unlabelled modified oligonucleotide |
| 147420 | 841863 | CPT1A | ++ | 7,794 |

For in vivo maximum tolerated doses reported in the table below, 2-4 BALB/C mice per group were administered modified oligonucleotide at 3.7, 11, 33, 100, or 300 mg/kg by subcutaneous injection and sacrificed after 72 hours. Maximum tolerated dose is the highest dose at which ALT is below 5× that in PBS-treated control mice, or ~150 IU/L.

TABLE 67

| Nucleolar mislocalization of p54nrb | | | | |
|---|---|---|---|---|
| Unlabelled compound ID | Fluorescently-labelled compound ID | Complementary mRNA | Mislocalization of p54nrb, labelled modified oligonucleotide | Maximum tolerated dose unlabelled modified oligonucleotide (mg/kg, mouse) |
| 464917 | 813223 | FXI | + | 11 |
| 508031 | 828939 | SOD1 | ++ | 33 |
| 482050 | 841864 | PTEN | ++ | 33 |
| 449093 | 489982 | SRB1 | ++ | 33 |
| 465178 | 869208 | FXI | + | 100 |
| 575013 | 869198 | FXII | − | >300 |
| 549139 | 869199 | none | − | >300 |
| 508032 | 869200 | SOD1 | − | >300 |
| 464932 | 869201 | FXI | − | >300 |
| 465131 | 869202 | FXI | − | >300 |

TABLE 68

| Nucleolar mislocalization of p54nrb | | | | |
|---|---|---|---|---|
| Unlabelled compound ID | Fluorescently-labelled compound ID | Cells with nucleolar p54nrb | Total cells | % cells with p54nrb mislocalization |
| 558807 | 925819 | 57 | 74 | 77 |
| 936049 | 958339 | 51 | 72 | 71 |
| 936053 | 958340 | 6 | 65 | 9 |
| 892826 | 958341 | 30 | 53 | 57 |

Example 27 In Vivo and In Vitro Toxicity of LNA-Containing Modified Oligonucleotides Modified oligonucleotides in the table below have a 3-10-3 sugar motif with LNA nucleosides on the 5' and 3' ends and DNA nucleosides in the central region.

TABLE 69

| Modified Oligonucleotides | | |
|---|---|---|
| Compound ID | Chemistry notation | SEQ ID NO: |
| 569713 | $G_{ls}A_{ls}{}^{m}C_{ds}G_{ds}{}^{m}C_{ds}G_{ds}{}^{m}C_{ds}{}^{m}C_{ds}T_{ds}G_{ds}A_{ds}A_{ds}G_{ds}G_{ls}T_{ls}T_{l}$ | 111 |
| 569717 | $A_{ls}T_{ls}{}^{m}C_{ls}A_{ds}T_{ds}G_{ds}G_{ds}{}^{m}C_{ds}T_{ds}G_{ds}{}^{m}C_{ds}A_{ds}G_{ds}{}^{m}C_{ls}T_{ls}T_{l}$ | 24 |
| 569719 | $G_{ls}T_{ls}{}^{m}C_{ls}T_{ds}G_{ds}T_{ds}G_{ds}{}^{m}C_{ds}A_{ds}T_{ds}{}^{m}C_{ds}T_{ds}{}^{m}C_{ds}T_{ls}{}^{m}C_{ls}{}^{m}C_{l}$ | 22 |
| 569721 | $T_{ls}G_{ls}A_{ls}G_{ds}G_{ds}T_{ds}{}^{m}C_{ds}{}^{m}C_{ds}T_{ds}G_{ds}{}^{m}C_{ds}A_{ds}{}^{m}C_{ds}T_{ls}G_{ls}G_{l}$ | 26 |
| 814336 | $G_{ls}{}^{m}C_{ls}A_{ls}T_{ds}G_{ds}T_{ds}T_{ds}{}^{m}C_{ds}T_{ds}{}^{m}C_{ds}A_{ds}{}^{m}C_{ds}A_{ds}T_{ls}T_{ls}A_{l}$ | 18 |

A subscript "d" indicates an unmodified, 2'-β-D-deoxyribosyl sugar moiety. A subscript "1" indicates a β-D-LNA sugar moiety. A subscript "s" indicates a phosphorothioate internucleoside linkage. A superscript "m" before a C indicates 5-methyl Cytosine.

Modified nucleotides with 3-10-3 lll-d(10)-lll sugar motifs were tested for their effect on 3T3 cells by microscopy. 3T3 cells were transfected by lipofectamine 2000 with 200 nM of modified oligonucleotide for 2 hrs and then cellular protein p54nrb was stained by mP54 antibody (Santa Cruz Biotech, sc-376865) and DAPI was used to stain for the nucleus of cells. For experiments reported in the tables below, images were qualitatively analyzed and assigned a score of (−), indicating that no p54nrb mislocalization to the nucleolus was observed, or a scale of (+) indicating that mislocalization of p54nrb to the nucleolus was observed in some cells, or (++) indicating that p54nrb mislocalization to the nucleolus was observed in most or all cells. Modified nucleotides with 3-10-3 lll-d(10)-lll or kkk-d(10)-kkk sugar motifs were tested in vivo. For in vivo toxicity data, 2-4 BALB/C mice were administered modified oligonucleotide by subcutaneous injection at the doses indicated in the table below. Mice were sacrificed after 72 hours and mRNA was isolated and analyzed as described in Example 1 above. ALT values in plasma were obtained using a clinical chemistry analyzer.

TABLE 70

Modified oligonucleotide dosages administered to mice

| Compound ID | Dose 1 (mg/kg) | Dose 2 (mg/kg) (Maximum dose) |
|---|---|---|
| 549139 | 300 | n/a |
| 569713 | 300 | n/a |
| 482050 | 33 | 100 |
| 569717 | 33 | 100 |
| 464917 | 11 | 33 |
| 569719 | 11 | 33 |
| 508031 | 33 | 100 |
| 569721 | 33 | 100 |
| 558807 | 17 | 51 |
| 814336 | 17 | 51 |

TABLE 71

In vitro p54nrb localization and in vitro toxicity

| Compound ID | Complementary mRNA | Mislocalization of p54nrb | ALT @ maximum dose | P21 mRNA at maximum dose (% control) | Tnfrsf10b mRNA at maximum dose (% control) |
|---|---|---|---|---|---|
| 549139 | none | − | 35 | 306 | 252 |
| 569713 | none | − | 44 | 449 | 241 |
| 482050 | PTEN | n.d. | 6555 | 10,430 | 4,232 |
| 569717 | PTEN | n.d. | 270 | 17,295 | 9,568 |
| 464917 | FXI | ++ | 13,920 | 9,590 | 7,731 |
| 569719 | FXI | + | 14,449 | 13,020 | 6,569 |
| 508031 | SOD1 | ++ | 18,550 | 8,909 | 6,678 |
| 569721 | SOD1 | + | 33,246 | 12,193 | 9,169 |
| 558807 | CXCL12 | ++ | 9,510 | 11,904 | 6,831 |
| 814336 | CXCL12 | ++ | death* | n.d. | n.d. |

*At 17 mg/kg, ALT was 4725, P21 mRNA was 11,567, and Tnfrsf10b mRNA was 8,636.

For the in vitro study reported in the tables below, 3T3-L1 cells were electroporated with 27 nM, 80 nM, 250 nM, 740 nM, 2, 222 nM, 6,667 nM, or 20,000 nM of modified oligonucleotide and levels of P21 and Gadd45a were measured by RT-qPCR as described in Example 1 above. Caspase-3 and caspase-7 activation was measured using the Caspase-Glo® 3/7 Assay System (G8090, Promega). Levels of caspase activation correlate with apoptotic cell death.

TABLE 72 in vitro Caspase Activation

| Compound ID | 27 nM | 80 nM | 250 nM | 740 nM | 2,222 nM | 6,667 nM | 20,000 nM |
|---|---|---|---|---|---|---|---|
| | Caspase Activation | | | | | | |
| 549139 | 2693 | 2272 | 2536 | 2170 | 2664 | 2128 | 2406 |
| 569713 | 2219 | 1988 | 1996 | 1892 | 2099 | 2178 | 3202 |
| 464917 | 1988 | 2116 | 1907 | 2365 | 6580 | 13268 | 24228 |
| 569719 | 2080 | 2183 | 2610 | 4225 | 10773 | 14199 | 20524 |
| 508031 | 7082 | 6602 | 7123 | 8876 | 14962 | 20060 | 29955 |
| 569721 | 7905 | 7741 | 8508 | 10364 | 20715 | 24370 | 49476 |
| 558807 | 7272 | 7887 | 8672 | 12555 | 19397 | 25124 | 28133 |
| 814336 | 7308 | 7975 | 9150 | 12927 | 21327 | 26992 | 26794 |

TABLE 73 in vitro P21 Expression

| Compound ID | 27 nM | 80 nM | 250 nM | 740 nM | 2,222 nM | 6,667 nM | 20,000 nM |
|---|---|---|---|---|---|---|---|
| | Expression level of P21 mRNA (% Control) | | | | | | |
| 549139 | 108 | 104 | 93 | 97 | 97 | 88 | 99 |
| 569713 | 116 | 105 | 94 | 127 | 129 | 139 | 166 |
| 464917 | 129 | 132 | 145 | 149 | 275 | 595 | 1044 |
| 569719 | 120 | 118 | 144 | 160 | 332 | 731 | 922 |
| 508031 | 100 | 90 | 99 | 102 | 100 | 124 | 247 |
| 569721 | 116 | 104 | 123 | 119 | 148 | 123 | 470 |
| 558807 | 95 | 126 | 123 | 123 | 104 | 119 | 193 |
| 814336 | 86 | 100 | 96 | 85 | 119 | 170 | 254 |

TABLE 74 in vitro Gadd45a Expression

| Compound ID | 27 nM | 80 nM | 250 nM | 740 nM | 2,222 nM | 6,667 nM | 20,000 nM |
|---|---|---|---|---|---|---|---|
| | Expression level of Gadd45a mRNA (% Control) | | | | | | |
| 549139 | 113 | 125 | 105 | 83 | 72 | 61 | 35 |
| 569713 | 168 | 139 | 116 | 154 | 135 | 162 | 147 |
| 464917 | 153 | 170 | 187 | 210 | 376 | 906 | 933 |
| 569719 | 165 | 168 | 217 | 220 | 514 | 1223 | 1086 |
| 508031 | 106 | 115 | 111 | 112 | 114 | 211 | 345 |
| 569721 | 165 | 168 | 158 | 136 | 212 | 326 | 451 |
| 558807 | 200 | 198 | 222 | 216 | 200 | 235 | 263 |
| 814336 | 117 | 113 | 139 | 148 | 169 | 198 | 278 |

TABLE 75 in vitro Tnfrsf10b Expression

| Compound ID | 27 nM | 80 nM | 250 nM | 740 nM | 2,222 nM | 6,667 nM | 20,000 nM |
|---|---|---|---|---|---|---|---|
| | Expression level of Tnfrsf10b mRNA (% Control) | | | | | | |
| 549139 | 93 | 96 | 87 | 87 | 89 | 98 | 96 |
| 569713 | 116 | 111 | 79 | 119 | 115 | 128 | 114 |
| 464917 | 122 | 127 | 129 | 93 | 116 | 186 | 125 |
| 569719 | 105 | 107 | 117 | 88 | 119 | 151 | 36 |

Example 28 Total Protein Binding of Modified Oligonucleotides Complementary to SOD1

Modified oligonucleotides described in the examples above were evaluated for their total protein binding in HeLa nuclear lysate. Cellular proteins were captured with the biotin-conjugated modified oligonucleotide 791136, which has a 5'-biotin-TEG, the sugar motif kkk-d(10)-kkk and the same sequence as 464917, GTCTGTGCATCTCTCC (SEQ ID NO: 22) and eluted with increasing concentrations of 508031, 895154, 895155, and 895156, described in Example 6 above. Eluted proteins were run on an SDS-PAGE gel. Increased total protein binding is observed for compound 508031 and 895154 compared to compound 895155 and 895156.

Example 29 Total Protein Binding of Modified Oligonucleotides Complementary to FXI Modified oligonucleotides described in the examples above were evaluated for their total protein binding in HeLa nuclear lysate. Cellular proteins were captured with the biotin-conjugated modified oligonucleotide 791136, which has a 5'-biotin-TEG, the sugar motif kkk-d(10)-kkk and the same sequence as 464917, GTCTGTGCATCTCTCC (SEQ ID NO: 22) and eluted with increasing concentrations of 464917, 465977, 483706, and 820685, described in Examples 4 and 25 above. Eluted proteins were run on an SDS-PAGE gel. See FIG. 2A. Increased total protein binding is observed for compound 464917 and 465977 compared to compounds 483706 and 820685. A series of western blots was done to detect SSBP1, NCL1, PCNA, p54nrb, RNase H1, and PSF.

In an independent experiment, cellular proteins were captured with 791136 and eluted with increasing concentrations of 464917, 465178, 464392, and 465131. Increased total protein binding is observed for compound 464917 compared to 465178, 464932, and 465131.

Example 30 Total Protein Binding, Activity and Toxicity with MOP Linkages

Modified oligonucleotides were evaluated for their total protein binding in cells. Cellular proteins were captured with the biotin-conjugated modified oligonucleotide 592590, which has a 5'-biotin-TEG, the sugar motif kkk-d(10)-kkk and the sequence GCTAGCCTCTGGATTT (SEQ ID NO:115) and eluted with the modified oligonucleotides described in the table below. Eluted proteins were run on an SDS-PAGE gel and visualized. Decreased protein binding is observed for compounds with decreased toxicity compared to 558807, in particular for compounds 766654, 766655, and 766666.

TABLE 76

Modified oligonucleotides containing Two MOP linkages

| Compound ID | Linkage Mod position in central region | Target | Chemistry Notation | SEQ ID NO |
|---|---|---|---|---|
| 766653 | 1, 2 | CXCL12 | $G_{ks}{}^{m}C_{ks}A_{ks}T_{dx}G_{dx}T_{ds}T_{ds}{}^{m}C_{ds}T_{ds}{}^{m}C_{ds}A_{ds}{}^{m}C_{ds}A_{ds}T_{ks}T_{ks}A_{k}$ | 18 |
| 766654 | 2, 3 | CXCL12 | $G_{ks}{}^{m}C_{ks}A_{ks}T_{ds}G_{dx}T_{dx}T_{ds}{}^{m}C_{ds}T_{ds}{}^{m}C_{ds}A_{ds}{}^{m}C_{ds}A_{ds}T_{ks}T_{ks}A_{k}$ | 18 |
| 766655 | 3, 4 | CXCL12 | $G_{ks}{}^{m}C_{ks}A_{ks}T_{ds}G_{ds}T_{dx}T_{dx}{}^{m}C_{ds}T_{ds}{}^{m}C_{ds}A_{ds}{}^{m}C_{ds}A_{ds}T_{ks}T_{ks}A_{k}$ | 18 |
| 766656 | 4, 5 | CXCL12 | $G_{ks}{}^{m}C_{ks}A_{ks}T_{ds}G_{ds}T_{ds}T_{dx}{}^{m}C_{dx}T_{ds}{}^{m}C_{ds}A_{ds}{}^{m}C_{ds}A_{ds}T_{ks}T_{ks}A_{k}$ | 18 |
| 766657 | 5, 6 | CXCL12 | $G_{ks}{}^{m}C_{ks}A_{ks}T_{ds}G_{ds}T_{ds}T_{ds}{}^{m}C_{dx}T_{dx}{}^{m}C_{ds}A_{ds}{}^{m}C_{ds}A_{ds}T_{ks}T_{ks}A_{k}$ | 18 |
| 766658 | 6, 7 | CXCL12 | $G_{ks}{}^{m}C_{ks}A_{ks}T_{ds}G_{ds}T_{ds}T_{ds}{}^{m}C_{ds}T_{dx}{}^{m}C_{dx}A_{ds}{}^{m}C_{ds}A_{ds}T_{ks}T_{ks}A_{k}$ | 18 |
| 766659 | 7, 8 | CXCL12 | $G_{ks}{}^{m}C_{ks}A_{ks}T_{ds}G_{ds}T_{ds}T_{ds}{}^{m}C_{ds}T_{ds}{}^{m}C_{dx}A_{dx}{}^{m}C_{ds}A_{ds}T_{ks}T_{ks}A_{k}$ | 18 |
| 766665 | 8, 9 | CXCL12 | $G_{ks}{}^{m}C_{ks}A_{ks}T_{ds}G_{ds}T_{ds}T_{ds}{}^{m}C_{ds}T_{ds}{}^{m}C_{ds}A_{dx}{}^{m}C_{dx}A_{ds}T_{ks}T_{ks}A_{k}$ | 18 |
| 766664 | 9, 10 | CXCL12 | $G_{ks}{}^{m}C_{ks}A_{ks}T_{ds}G_{ds}T_{ds}T_{ds}{}^{m}C_{ds}T_{ds}{}^{m}C_{ds}A_{ds}{}^{m}C_{dx}A_{dx}T_{ks}T_{ks}A_{k}$ | 18 |

A subscript "d" indicates an unmodified, 2'-β-D-deoxyribosyl sugar moiety. A subscript "k" indicates a cEt. A subscript "s" indicates a phosphorothioate internucleoside linkage. A superscript "m" before a C indicates 5-methyl Cytosine. A subscript "x" indicates a MOP internucleoside linkage.

In vitro activity and in vivo activity and toxicity experiments were performed essentially as described in Example 1. For in vivo toxicity studies, a single BALB/C mouse per dose of modified oligonucleotide was administered 16.7 mg/kg, 50 mg/kg, or 150 mg/kg modified oligonucleotide by subcutaneous injection and sacrificed 72 hours later. ALT levels were measured using an automated clinical chemistry analyzer. For the in vivo activity study in the table below, 1 BALB/C mouse per group was administered 1.8 mg/kg, 5.5 mg/kg, 16.7 mg/kg, 50 mg/kg or 150 mg/kg modified oligonucleotide subcutaneously and sacrificed after 24 hours.

TABLE 77 in vivo Activity and Toxicity

| Compound ID | MOP linkage positions | in vivo CXCL12 ED50 (mg/kg) | ALT @ 50 mg/kg (IU/L) | ALT @ 150 mg/kg (IU/L) |
|---|---|---|---|---|
| PBS | n/a | n/a | 26 (@0 mg/kg) | |
| 558807 | n/a | 2.9 | 19,806 | death |
| 766653 | 1, 2 | 23.6 | 32 | 33 |
| 766654 | 2, 3 | 31.6 | 28 | 30 |
| 766655 | 3, 4 | 32.7 | 28 | 27 |
| 766656 | 4, 5 | 26.7 | 25 | 29 |
| 766657 | 5, 6 | 7.0 | 213 | 5,503 |
| 766658 | 6, 7 | 6.2 | 64 | 1,380 |
| 766659 | 7, 8 | 10.6 | 51 | 3,423 |
| 766665 | 8, 9 | 5.5 | 3,437 | 11,954 |
| 766664 | 9, 10 | 6.2 | 4,045 | death |

Example 31 Self-Structure of Modified Oligonucleotides Complementary to CXCL12

Tm was determined for self-structures of modified oligonucleotides described in the examples above. Compounds in the table below are complementary to CXCL12 and have sequences corresponding to SEQ ID NO: 18-21. Tm was also determined for duplexes of the modified oligonucleotides described in the examples above in complex with a RNA 20-mer with the sequence GAUAAUGUGAGAACAUGCCU (SEQ ID NO: 116).

TABLE 78

| Compound ID | linkage-altered nucleotide (position in central region) | Sugar-modification of altered nucleotide (position in central region) | Tm (° C.) Self structure | Tm (° C.) duplex |
|---|---|---|---|---|
| Tm of Modified Oligonucleotides complementary to CXCL12, Self-Structure and Duplex | | | | |
| 558807 | none | none | 48.6 | 65.1 |
| 1061955 | none | inosine (2) | 32.9 | 57.5 |
| 766676 | MOP(1) | none | 44.6 | 63.3 |
| 766677 | MOP(2) | none | 45.3 | 63.5 |
| 766678 | MOP(3) | none | 47.9 | 63.1 |
| 766679 | MOP(4) | none | 47.1 | 62.6 |
| 766680 | MOP(5) | none | n.d. | 63 |
| 766681 | MOP(6) | none | n.d. | 62.9 |
| 766682 | MOP(7) | none | n.d. | 63.8 |
| 766683 | MOP(8) | none | n.d. | 63.3 |
| 766684 | MOP(9) | none | n.d. | 64.1 |
| 766685 | MOP(10) | none | n.d. | 63.9 |
| 936053 | none | 2'-OMe (2) | 49.0 | 67.0 |
| 828911 | none | 2'-MOE (2) | 48.2 | 66.8 |
| 1070041 | none | cEt (2) | 52.7 | 69.5 |
| 936051 | none | 2'-FANA (2) | 46.1 | 64.8 |
| 936052 | none | 2'-ribo-F (2) | 47.2 | 66.0 |
| 1123320 | none | 5'-(R)-Me (2) | 49.4 | 65.5 |
| 1123322 | none | 5'-(S)-Me (2) | 43.0 | 62.0 |
| 942943 | none | 5'-(R)--Me (3) | 47.3 | 62.3 |
| 957908 | none | 5'-(S)-Me (3) | 45.1 | 65.1 |
| 942944 | none | 5'-(R)--Me (4) | 49.5 | 62.3 |
| 957909 | none | 5'-(S)-Me (4) | 46.2 | 66.3 |
| 957910 | none | 5'-(R)-allyl (3) | 44.4 | 62.1 |
| 957911 | none | 5'-(R)-allyl (4) | 47.3 | 62.4 |
| 957912 | none | 5'-(S)--allyl (3) | 41.7 | 64.0 |
| 957913 | none | 5'-(S)-allyl (4) | 47.1 | 64.6 |
| 1069852 | none | pseudoU (2) | 24.4 | 54.4 |
| 1061328 | none | pseudoU (3) | 44.6 | 55.3 |
| 1215458 | none | β-L-DNA (2) | n.d. | 58 |
| 1215459 | none | β-L-DNA (3) | 43 | 59 |
| 1215460 | none | β-L-DNA (4) | 45 | 62 |
| 1215461 | none | α-L-DNA (3) | 41 | 63 |
| 1215462 | none | α-L-DNA (4) | 49 | 65 |

TABLE 79

| Compound ID | Target | Tm (° C.) |
|---|---|---|
| Tm of Modified Oligonucleotide Self-Structure | | |
| 449093 | SRB1 | <40 |
| 464917 | FXI | <40 |
| 482050 | PTEN | 33.4 |
| 508031 | SOD-1 | 58.9 |

Example 32 2'-Modifications in 5' and 3'-Regions of Modified Oligonucleotides Modified oligonucleotides containing various sugar modification motifs were synthesized as indicated in the table below. The compounds in the table below are 100% complementary to mouse CXCL12, GENBANK NT_039353.7 truncated from 69/430,515 to 69/445,350 (SEQ ID NO: 1) at positions 6877 to 6892 (16-mers) or 6875 to 6894 (20-mers).

TABLE 80

| Compound ID | 2'-modified sugars on 5'-end | 2'-modified sugars on 3'-end | Chemistry Notation | SEQ ID NO |
|---|---|---|---|---|
| modified oligonucleotides with 2'-sugar modifications | | | | |
| 558807 | kkk | kkk | $G_{ks}{}^{m}C_{ks}A_{ks}T_{ds}G_{ds}T_{ds}T_{ds}{}^{m}C_{ds}T_{ds}{}^{m}C_{ds}A_{ds}{}^{m}C_{ds}A_{ds}T_{ks}T_{ks}A_{k}$ | 18 |
| 1035522 | kkk | eee | $G_{ks}{}^{m}C_{ks}A_{ks}T_{ds}G_{ds}T_{ds}T_{ds}{}^{m}C_{ds}T_{ds}{}^{m}C_{ds}A_{ds}{}^{m}C_{ds}A_{ds}T_{es}T_{es}A_{e}$ | 18 |
| 1035523 | eee | kkk | $G_{es}{}^{m}C_{es}A_{es}T_{ds}G_{ds}T_{ds}T_{ds}{}^{m}C_{ds}T_{ds}{}^{m}C_{ds}A_{ds}{}^{m}C_{ds}A_{ds}T_{ks}T_{ks}A_{k}$ | 18 |
| 985648 | eee | eee | $G_{es}{}^{m}C_{es}A_{es}T_{ds}G_{ds}T_{ds}T_{ds}{}^{m}C_{ds}T_{ds}{}^{m}C_{ds}A_{ds}{}^{m}C_{ds}A_{ds}T_{es}T_{es}A_{e}$ | 18 |
| 1069842 | kkeee | eeekk | $A_{ks}G_{ks}G_{es}{}^{m}C_{es}A_{es}T_{ds}G_{ds}T_{ds}T_{ds}{}^{m}C_{ds}T_{ds}{}^{m}C_{ds}A_{ds}{}^{m}C_{ds}A_{ds}T_{es}T_{es}A_{es}T_{ks}{}^{m}C_{k}$ | 117 |
| 1069843 | kkeee | kkkkk | $A_{ks}G_{ks}G_{es}{}^{m}C_{es}A_{es}T_{ds}G_{ds}T_{ds}T_{ds}{}^{m}C_{ds}T_{ds}{}^{m}C_{ds}A_{ds}{}^{m}C_{ds}A_{ds}T_{ks}T_{ks}A_{ks}T_{ks}{}^{m}C_{k}$ | 117 |
| 1069844 | kkkkk | eeekk | $A_{ks}G_{ks}G_{ks}{}^{m}C_{ks}A_{ks}T_{ds}G_{ds}T_{ds}T_{ds}{}^{m}C_{ds}T_{ds}{}^{m}C_{ds}A_{ds}{}^{m}C_{ds}A_{ds}T_{es}T_{es}A_{es}T_{ks}{}^{m}C_{k}$ | 117 |
| 386864 | eeeee | eeeee | $A_{es}G_{es}G_{es}{}^{m}C_{es}A_{es}T_{ds}G_{ds}T_{ds}T_{ds}{}^{m}C_{ds}T_{ds}{}^{m}C_{ds}A_{ds}{}^{m}C_{ds}A_{ds}T_{es}T_{es}A_{es}T_{es}{}^{m}C_{e}$ | 117 |
| 1069845 | kkkkk | kkkkk | $A_{ks}G_{ks}G_{ks}{}^{m}C_{ks}A_{ks}T_{ds}G_{ds}T_{ds}T_{ds}{}^{m}C_{ds}T_{ds}{}^{m}C_{ds}A_{ds}{}^{m}C_{ds}A_{ds}T_{ks}T_{ks}T_{ks}{}^{m}C_{k}$ | 117 |
| 1069846 | eekkkk | kkkkk | $A_{es}G_{es}G_{ks}{}^{m}C_{ks}A_{ks}T_{ds}G_{ds}T_{ds}T_{ds}{}^{m}C_{ds}T_{ds}{}^{m}C_{ds}A_{ds}{}^{m}C_{ds}A_{ds}T_{ks}T_{ks}A_{ks}T_{ks}{}^{m}C_{k}$ | 117 |
| 1069847 | kkkkk | kkkee | $A_{ks}G_{ks}G_{ks}{}^{m}C_{ks}A_{ss}T_{ds}G_{ds}T_{ds}T_{ds}{}^{m}C_{ds}T_{ds}{}^{m}C_{ds}A_{ds}{}^{m}C_{ds}A_{ds}T_{ks}T_{ks}A_{ks}T_{es}{}^{m}C_{e}$ | 117 |

A subscript "d" indicates an unmodified, 2'-β-D-deoxyribosyl sugar moiety. A subscript "k" indicates a cEt. A subscript "s" indicates a phosphorothioate internucleoside linkage. A superscript "m" before a C indicates 5-methyl Cytosine. A subscript "e" indicates a 2'-MOE-β-D-ribofuranosyl sugar moiety. A subscript "m" indicates a 2'-O-methyl-β-D-ribofuranosyl sugar moiety.

For the in vitro study reported in the tables below, 3T3-L1 cells were electroporated with 27 nM, 80 nM, 250 nM, 740 nM, 2, 222 nM, 6,667 nM, or 20,000 nM of modified oligonucleotide and levels of CXCL12 were measured by RT-qPCR as described in Example 1 above. Caspase activation was measured as described in Example 4 above. Results are presented relative to the caspase activation in control cells not treated with modified oligonucleotide. Mislocalization of p54nrb was analyzed as described in Example 15 above. For experiments reported in the tables below, selected images were qualitatively analyzed and assigned a score of (−), indicating that no p54nrb mislocalization to the nucleolus was observed, or a score of (+) indicating that mislocalization of p54nrb to the nucleolus was observed in some cells, or (++) indicating that p54nrb mislocalizization to the nucleolus was observed in most or all cells. Treatment of HeLa cells with certain modified oligonucleotides caused a filamentous appearance of p54nrb in cells. This is indicated by a "f" in the table below.

TABLE 81 in vitro Activity and Toxicity

| Compound ID | Caspase (% control) | CXCL12 IC$_{50}$ (nM) | p54nrb mislocalization |
|---|---|---|---|
| 558807 | 1135 | 30 | ++ |
| 1035522 | 1261 | 35 | +, f |
| 1035523 | 244 | 100 | +, f |
| 985648 | 207 | 200 | −, f |
| 1069842 | 353 | 350 | +, f |
| 1069843 | 670 | 100 | ++ |
| 1069844 | 748 | 350 | + |
| 386864 | 1104 | 200 | −, f |
| 1069845 | 213 | 350 | ++ |
| 1069846 | 963 | 100 | + |
| 1069847 | 923 | 250 | + |

Example 33 Effect of Treatment of b.END Cells with Modified Oligonucleotides

For the in vitro study reported in the tables below, b.END.3 cells were electroporated with 3.125, 6.25, 12.5, 25, or 50 nM of modified oligonucleotide 464917 (heptatotoxic) or 549148 (nontoxic). 549148 is a 3-10-3 cEt modified oligonucleotide with the sequence GGCTAC-TACGCCGTCA (SEQ ID NO: 118), which is not complementary to any known mouse gene. Expression levels of p21 and Gadd45a mRNA were measured after 0, 1, 2, 4, and 6 hours by RT-qPCR as described in Example 1.

TABLE 82

Relative mp21 mRNA dose response/time course in b.END cells

| Compound | Dose (nM) | % Control mp21 mRNA | | | |
|---|---|---|---|---|---|
| | | 1 hrs | 2 hrs | 4 hrs | 6 hrs |
| 464917 | 0 | 100 | 100 | 100 | 100 |
| 464917 | 3.125 | 102 | 134 | 147 | 174 |
| 464917 | 6.25 | 113 | 149 | 169 | 242 |
| 464917 | 12.50 | 107 | 141 | 199 | 250 |
| 464917 | 25.0 | 122 | 183 | 330 | 394 |
| 464917 | 50.0 | 113 | 210 | 399 | 427 |
| 549148 | 0 | 100 | 100 | 100 | 100 |
| 549148 | 3.125 | 111 | 42 | 140 | 107 |
| 549148 | 6.25 | 88 | 90 | 128 | 126 |
| 549148 | 12.50 | 120 | 86 | 119 | 109 |
| 549148 | 25.0 | 114 | 111 | 147 | 107 |
| 549148 | 50.0 | 111 | 94 | 126 | 119 |

TABLE 82a

Relative mGadd45a mRNA dose response/time course in b.END cells

| Compound | Dose (nM) | % Control mGadd45a mRNA | | | |
|---|---|---|---|---|---|
| | | 1 hrs | 2 hrs | 4 hrs | 6 hrs |
| 464917 | 0 | 100 | 100 | 100 | 100 |
| 464917 | 3.125 | 87 | 88 | 203 | 396 |
| 464917 | 6.25 | 81 | 154 | 259 | 565 |
| 464917 | 12.50 | 85 | 173 | 331 | 905 |
| 464917 | 25.0 | 102 | 247 | 715 | 1586 |
| 464917 | 50.0 | 132 | 420 | 1376 | 3339 |
| 549148 | 0 | 100 | 100 | 100 | 100 |
| 549148 | 3.125 | 85 | 31 | 106 | 109 |
| 549148 | 6.25 | 72 | 95 | 103 | 125 |
| 549148 | 12.50 | 85 | 87 | 106 | 127 |
| 549148 | 25.0 | 85 | 103 | 144 | 123 |
| 549148 | 50.0 | 97 | 107 | 131 | 198 |

Example 34 Nucleolar Delocalization of p54nrb in Various Cell Lines

Cells were plated at 20,000 cells/well and transfected with Lipofectamine 2,000 and 60 nM of modified oligonucleotide 791143, compound 464917 labeled on the 3'-end with Cy3. Cells were visualized 6 hours after transfection.

TABLE 83 p54nrb nucleolar mislocalization

| Compound ID | Cell line | p54nrb nucleolar mislocalization |
|---|---|---|
| 791143 | U2OS | + |
| 791143 | NIH3T3 | ++ |

Cells were plated at 20,000 cells/well and transfected by free uptake with modified oligonucleotide 791143 as indicated in the table below. Cells were visualized 5 hours after transfection.

TABLE 84 p54nrb nucleolar mislocalization

| Compound ID | Cell line | p54nrb nucleolar mislocalization |
|---|---|---|
| 791143 | MHT | + |
| 791143 | HeLa | ++ |

Cells were plated at 20,000 cells/well and transfected by NEON electroporation at 1400V, 20 ms, 2 pulses with 60 nM modified oligonucleotide 813223, compound 464917 labeled on the 5'-end with Cy3. Cells were visualized 5 hours after transfection.

TABLE 85 p54nrb nucleolar mislocalization

| Compound ID | Cell line | p54nrb nucleolar mislocalization |
|---|---|---|
| 813223 | HeLa | ++ |

Cells were transfected with 60 nM modified oligonucleotide 813223 or compound 813225. Compound 813225 is the control oligonucleotide 549148 described above labeled on the 5'-end with Cy3. Cells were visualized 4 hours after transfection.

TABLE 85b p54nrb nucleolar mislocalization

| Compound ID | Cell line | p54nrb nucleolar mislocalization |
|---|---|---|
| 813223 | b.END3 | ++ |
| 813225 | b.END3 | − |
| 813223 | NIH3T3 | + |
| 813223 | primary neuron | + |
| 813223 | primary hepatocyte | ++ |

Example 35 Effect of Depletion of RNaseH1 on Toxicity of Modified Oligonucleotides HeLa cells were plated at 150,000 cells/well and transfected with control siRNA targeting luciferase or siRNA targeted to RNaseH1 (s48357 or s48358 from ThermoFisher) at a final concentration of 3 nM using Lipofectamine RNAiMAX for 48 hours. Modified oligonucleotides 464917 and 549148 were added to the cells by free uptake. 549148 is a 3-10-3 cEt modified oligonucleotide with the sequence GGCTACTACGCCGTCA (SEQ ID NO: 118), which is not complementary to any known mouse gene. Confocal microscopy was used to visualize p54nrb localization as described in Example 15 above.

TABLE 86 in vitro p54nrb mislocalization

| Compound ID | siRNA | p54nrb nucleolar mislocalization |
|---|---|---|
| 464917 | mock | ++ |
| 464917 | RNaseH1a | − |
| 464917 | RNaseH1b | − |

TABLE 87 in vitro P21 Expression in HeLa cells

| Compound ID | siRNA | 0 nM | 3.125 nM | 6.25 nM | 12.5 nM | 25 nM | 50 nM |
|---|---|---|---|---|---|---|---|
| | | Expression level of P21 mRNA (% Control) | | | | | |
| 464917 | Luci | 90 | 134 | 141 | 143 | 171 | 201 |
| 464917 | H1 | 78 | 79 | 82 | 83 | 84 | 95 |
| 549148 | Luci | 100 | 119 | 105 | 84 | 94 | 82 |
| 549148 | H1 | 99 | 86 | 92 | 81 | 79 | 85 |

TABLE 88 in vitro Gadd45a Expression in HeLa cells

| Compound ID | siRNA | 0 nM | 3.125 nM | 6.25 nM | 12.5 nM | 25 nM | 50 nM |
|---|---|---|---|---|---|---|---|
| | | Expression level of P21 mRNA (% Control) | | | | | |
| 464917 | Luci | 73 | 119 | 126 | 179 | 270 | 463 |
| 464917 | H1 | 65 | 82 | 110 | 117 | 154 | 260 |
| 549148 | Luci | 100 | 89 | 107 | 102 | 97 | 83 |
| 549148 | H1 | 72 | 83 | 103 | 103 | 105 | 96 |

Example 36 Protein Binding of Modified Oligonucleotides

Modified oligonucleotides described in the examples above were evaluated for their protein binding in cells. Cellular proteins were captured with the biotin-conjugated modified oligonucleotide 791136, which has a 5'-biotin-TEG, the sugar motif kkk-d(10)-kkk, a full phosphorothioate backbone, and the same sequence as 464917, GTCTGTGCATCTCTCC (SEQ ID NO: 22). Proteins were eluted with increasing concentrations of 464917 or 549148. Eluted proteins were run on an SDS-PAGE gel and analyzed by western blot for p54nrb, FUS, RNaseH1, SSBP1, Ku70, PSPC1, SND1, FUBP, NCL1, and Ku80. Band intensities are represented in the table below: −, no band; +, faint band; ++, medium band; +++, intense band.

TABLE 89

Protein binding of modified oligonucleotides

| | Relative band intensity 464917 | | Relative band intensity 549148 | |
|---|---|---|---|---|
| Protein | 0.625 μM | 5 μM | 0.625 μM | 5 μM |
| p54nrb | − | +++ | − | + |
| FUS | − | ++ | − | − |
| RNaseH1 | − | ++ | − | + |
| SSBP1 | ++ | ++ | + | + |
| Ku70 | + | ++ | + | + |
| PSPC1 | − | + | − | + |
| SND1 | ++ | +++ | + | ++ |
| FUBP | + | ++ | + | + |
| NCL1 | + | ++ | + | + |
| Ku80 | + | ++ | ++ | ++ |

Total protein binding to 464917 and 549418 was tested using biotin-464917 or biotin-549148 to capture cellular proteins, which were then eluted with increasing concentrations of 464917 or 549148. The hepatotoxic compound 464917 shows increased global protein binding compared to 549148.

Example 37 In Vitro Activity and Toxicity of Modified Oligonucleotides Comprising Modified Internucleoside Linkages Modified oligonucleotides were designed based on the control oligonucleotide 558807, described in Example 1 herein and synthesized using standard procedures. Modified internucleoside linkages (1 or 2) were positioned at various positions within the central region of the oligonucleotides as illustrated below. The resulting modified oligonucleotides were tested for their ability to inhibit CXCL12 (Chemokine ligand 12) and Raptor expression levels. The potency of the modified oligonucleotides was evaluated and compared to the control oligonucleotide.

The modified oligonucleotides were tested in vitro in mouse b.END cells by electroporation. Cells at a density of 20,000 cells per well are transfected using electroporation with 0.027, 0.082, 0.25, 0.74, 2.22, 6.67 and 20 uM concentrations of each of the oligonucleotides listed below. After a treatment period of approximately 24 hours, RNA is isolated from the cells and mRNA levels are measured by quantitative real-time PCR and the CXCL12 mRNA and Raptor mRNA levels are adjusted according to total RNA content, as measured by RIBOGREEN®.

-continued

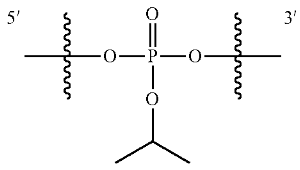

isopropylphosphotriester

TABLE 90

Modified Oligonucleotides

| Compound ID | Linkage-altered nucleotide position in central region | Linkage mod “x” | Chemistry Notation | SEQ ID NO |
|---|---|---|---|---|
| 558807 | n/a | n/a | $G_{ks}{}^{m}C_{ks}A_{ks}T_{ds}G_{ds}T_{ds}T_{ds}{}^{m}C_{ds}T_{ds}{}^{m}C_{ds}A_{ds}{}^{m}C_{ds}A_{ds}T_{ks}T_{ks}A_{k}$ | 18 |
| 857528 | 3 | THP phosphotriester | $G_{ks}{}^{m}C_{ks}A_{ks}T_{ds}G_{ds}T_{x}T_{ds}{}^{m}C_{ds}T_{ds}{}^{m}C_{ds}A_{ds}{}^{m}C_{ds}A_{ds}T_{ks}T_{ks}A_{k}$ | 18 |
| 857529 | 3 | isopropylphosphotriester | $G_{ks}{}^{m}C_{ks}A_{ks}T_{ds}G_{ds}T_{dx}T_{ds}{}^{m}C_{ds}T_{ds}{}^{m}C_{ds}A_{ds}{}^{m}C_{ds}A_{ds}T_{ks}T_{ks}A_{k}$ | 18 |
| 857530 | 3 | isobutylphosphonate | $G_{ks}{}^{m}C_{ks}A_{ks}T_{ds}G_{ds}T_{dx}T_{ds}{}^{m}C_{ds}T_{ds}{}^{m}C_{ds}A_{ds}{}^{m}C_{ds}A_{ds}T_{ks}T_{ks}A_{k}$ | 18 |
| 857505 | 3 | isopropylphosphonate | $G_{ks}{}^{m}C_{ks}A_{ks}T_{ds}G_{ds}T_{dx}T_{ds}{}^{m}C_{ds}T_{ds}{}^{m}C_{ds}A_{ds}{}^{m}C_{ds}A_{ds}T_{ks}T_{ks}A_{k}$ | 18 |
| 883401 | 3 | amide-3 | $G_{ks}{}^{m}C_{ks}A_{ks}T_{ds}G_{ds}T_{dx}T_{ds}{}^{m}C_{ds}T_{ds}{}^{m}C_{ds}A_{ds}{}^{m}C_{ds}A_{ds}T_{ks}T_{ks}A_{k}$ | 18 |
| 883521 | 3 | formacetal | $G_{ks}{}^{m}C_{ks}A_{ks}T_{ds}G_{ds}T_{dx}T_{ds}{}^{m}C_{ds}T_{ds}{}^{m}C_{ds}A_{ds}{}^{m}C_{ds}A_{ds}T_{ks}T_{ks}A_{k}$ | 18 |
| 857532 | 4 | THP phosphotriester | $G_{ks}{}^{m}C_{ks}A_{ks}T_{ds}G_{ds}T_{ds}T_{dx}{}^{m}C_{ds}T_{ds}{}^{m}C_{ds}A_{ds}{}^{m}C_{ds}A_{ds}T_{ks}T_{ks}A_{k}$ | 18 |
| 857533 | 4 | isopropylphosphotriester | $G_{ks}{}^{m}C_{ks}A_{ks}T_{ds}G_{ds}T_{ds}T_{dx}{}^{m}C_{ds}T_{ds}{}^{m}C_{ds}A_{ds}{}^{m}C_{ds}A_{ds}T_{ks}T_{ks}A_{k}$ | 18 |
| 857531 | 4 | isopropylphosphonate | $G_{ks}{}^{m}C_{ks}A_{ks}T_{ds}G_{ds}T_{ds}T_{dx}{}^{m}C_{ds}T_{ds}{}^{m}C_{ds}A_{ds}{}^{m}C_{ds}A_{ds}T_{ks}T_{ks}A_{k}$ | 18 |
| 857534 | 4 | isobutylphosphonate | $G_{ks}{}^{m}C_{ks}A_{ks}T_{ds}G_{ds}T_{ds}T_{dx}{}^{m}C_{ds}T_{ds}{}^{m}C_{ds}A_{ds}{}^{m}C_{ds}A_{ds}T_{ks}T_{ks}A_{k}$ | 18 |
| 857537 | 3, 4 | isopropylphosphonate | $G_{ks}{}^{m}C_{ks}A_{ks}T_{ds}G_{ds}T_{dx}T_{dx}{}^{m}C_{ds}T_{ds}{}^{m}C_{ds}A_{ds}{}^{m}C_{ds}A_{ds}T_{ks}T_{ks}A_{k}$ | 18 |
| 857540 | 3, 4 | isobutylphosphonate | $G_{ks}{}^{m}C_{ks}A_{ks}T_{ds}G_{ds}T_{dx}T_{dx}{}^{m}C_{ds}T_{ds}{}^{m}C_{ds}A_{ds}{}^{m}C_{ds}A_{ds}T_{ks}T_{ks}A_{k}$ | 18 |
| 857538 | 3, 4 | THP phosphotriester | $G_{ks}{}^{m}C_{ks}A_{ks}T_{ds}G_{ds}T_{dx}T_{dx}{}^{m}C_{ds}T_{ds}{}^{m}C_{ds}A_{ds}{}^{m}C_{ds}A_{ds}T_{ks}T_{ks}A_{k}$ | 18 |

A subscript “d” indicates a an unmodified, 2'-β-D-deoxyribosyl sugar moiety. A subscript “k” indicates a cEt. A subscript “s” indicates a phosphorothioate internucleoside linkage. A superscript “m” before a C indicates 5-methyl Cytosine. A subscript “x” indicates a modified internucleoside linkage as indicated in the “linkage mod x” column. These linkages are illustrated below.

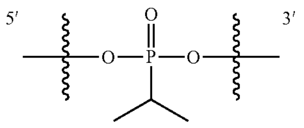

isopropylphosphonate

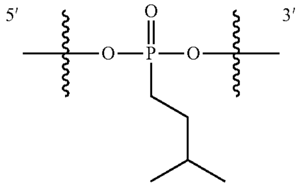

isobutylphosphonate

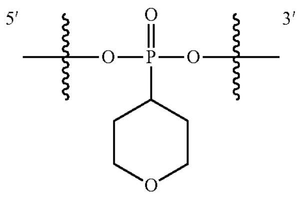

THP phosphotriester

-continued

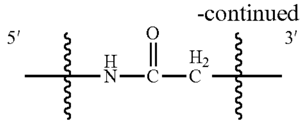

amide-3

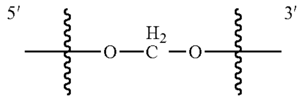

formacetal

The half maximal inhibitory concentration (IC50) of each oligonucleotide listed above was calculated by plotting the concentration of oligonucleotide versus the percent inhibition of CXCL12 mRNA or Raptor mRNA expression achieved at each concentration, and noting the concentration of oligonucleotide at which 50% inhibition of CXCL12 mRNA expression is achieved compared to the control. The results are presented in the table below.

TABLE 91

In vitro Activity and Toxicity

| Compound ID | $IC_{50}$ (μM) CXCL12 | Raptor % Control (4 μM) | Raptor IC50* (μM) |
|---|---|---|---|
| 558807 | 0.17 | 47 | 3.7 |
| 857505 | 0.15 | 82 | >4 |
| 857530 | 0.32 | 87 | >4 |
| 857528 | 0.23 | 110 | >4 |
| 857529 | 1.09 | 74 | >4 |
| 883401 | 30 | 65 | >4 |

TABLE 91-continued

| In vitro Activity and Toxicity | | | |
|---|---|---|---|
| Compound ID | $IC_{50}$ (μM) CXCL12 | Raptor % Control (4 μM) | Raptor IC50* (μM) |
| 883521 | 0.40 | 94 | >4 |
| 857531 | 0.27 | 99 | >4 |
| 857534 | 0.12 | 57 | >4 |
| 857532 | 0.16 | 69 | >4 |
| 857533 | 0.10 | 61 | >4 |
| 857537 | 1.4 | 82 | >4 |
| 857540 | 0.48 | 65 | >4 |

TABLE 91-continued

| In vitro Activity and Toxicity | | | |
|---|---|---|---|
| Compound ID | $IC_{50}$ (μM) CXCL12 | Raptor % Control (4 μM) | Raptor IC50* (μM) |
| 857538 | 0.33 | 110 | >4 |
| 857539 | 0.13 | 74 | >4 |

*IC50 values can only be calculated when less than the highest dose in the experiment, in this case, 4 μM Example 38

Modified oligonucleotides were designed based on 558807. Each modified oligonucleotide has a modified internucleoside linkage positioned between nucleosides 3 and 4 counting from the 5'-gap junction (not including the 3 cEt modified nucleosides in the 5'-wing) as illustrated below. Each of the modified oligonucleotides is conjugated with a HPPO-GalNAc conjugate group at the 3'-end as illustrated below. The oligonucleotides were evaluated for reduction in CXCL12 (Chemokine ligand 12) mRNA expression levels in vivo. The transaminase levels (ALT and AST) for each dose were also measured.

Six week old BALB/C mice (purchased from Charles River) were injected subcutaneously once at dosage 0.2, 0.6, 1.8 or 50 mg/kg with the modified oligonucleotides shown below or with saline control. For compound 855156, mice were injected with 0.21, 0.62, 1.85, or 5.56 mg/kg modified oligonucleotide. Each treatment group consisted of 3 animals. The mice were sacrificed 72 hours following administration, and organs and plasma were harvested for further analysis.

TABLE 92

| Modified Oligonucleotides | | | | |
|---|---|---|---|---|
| Compound ID | Linkage-altered nucleotide position in central region | Linkage mod "x" | Chemistry Notation | SEQ ID NO |
| 895566 | 3 | isopropylphosphonate | $G_{ks}{}^{m}C_{ks}A_{ks}T_{ds}G_{ds}T_{dx}T_{ds}{}^{m}C_{ds}T_{ds}{}^{m}C_{ds}A_{ds}{}^{m}C_{ds}A_{ds}T_{ks}T_{ks}A_{k}$-HPPO-GalNAc | 18 |
| 895567 | 3 | THP phosphotriester | $G_{ks}{}^{m}C_{ks}A_{ks}T_{ds}G_{ds}T_{dx}T_{ds}{}^{m}C_{ds}T_{ds}{}^{m}C_{ds}A_{ds}{}^{m}C_{ds}A_{ds}T_{ks}T_{ks}A_{k}$-HPPO-GalNAc | 18 |
| 895568 | 3 | isopropylphosphotriester | $G_{ks}{}^{m}C_{ks}A_{ks}T_{ds}G_{ds}T_{dx}T_{ds}{}^{m}C_{ds}T_{ds}{}^{m}C_{ds}A_{ds}{}^{m}C_{ds}A_{ds}T_{ks}T_{ks}A_{k}$-HPPO-GalNAc | 18 |
| 895569 | 3 | isobutylphosphonate | $G_{ks}{}^{m}C_{ks}A_{ks}T_{ds}G_{ds}T_{dx}T_{ds}{}^{m}C_{ds}T_{ds}{}^{m}C_{ds}A_{ds}{}^{m}C_{ds}A_{ds}T_{ks}T_{ks}A_{k}$-HPPO-GalNAc | 18 |
| 895570 | 3 | formacetal | $G_{ks}{}^{m}C_{ks}A_{ks}T_{ds}G_{ds}T_{dx}T_{ds}{}^{m}C_{ds}T_{ds}{}^{m}C_{ds}A_{ds}{}^{m}C_{ds}A_{ds}T_{ks}T_{ks}A_{k}$-HPPO-GalNAc | 18 |
| 913196 | 3 | amide-3 | $G_{ks}{}^{m}C_{ks}A_{ks}T_{ds}G_{ds}T_{dx}T_{ds}{}^{m}C_{ds}T_{ds}{}^{m}C_{ds}A_{ds}{}^{m}C_{ds}A_{ds}T_{ks}T_{ks}A_{k}$-HPPO-GalNAc | 18 |
| 920046 | 3 | TANA | $G_{ks}{}^{m}C_{ks}A_{ks}T_{ds}G_{ds}T_{dx}T_{ds}{}^{m}C_{ds}T_{ds}{}^{m}C_{ds}A_{ds}{}^{m}C_{ds}A_{ds}T_{ks}T_{ks}A_{k}$-HPPO-GalNAc | 18 |
| 951972 | 3 | (R)-MOP | $G_{ks}{}^{m}C_{ks}A_{ks}T_{ds}G_{ds}T_{dx}T_{ds}{}^{m}C_{ds}T_{ds}{}^{m}C_{ds}A_{ds}{}^{m}C_{ds}A_{ds}T_{ks}T_{ks}A_{k}$-HPPO-GalNAc | 18 |
| 951973 | 3 | (S)-MOP | $G_{ks}{}^{m}C_{ks}A_{ks}T_{ds}G_{ds}T_{dx}T_{ds}{}^{m}C_{ds}T_{ds}{}^{m}C_{ds}A_{ds}{}^{m}C_{ds}A_{ds}T_{ks}T_{ks}A_{k}$-HPPO-GalNAc | 18 |
| 974343 | 3 | alt-thioformacetal | $G_{ks}{}^{m}C_{ks}A_{ks}T_{ds}G_{ds}T_{dx}T_{ds}{}^{m}C_{ds}T_{ds}{}^{m}C_{ds}A_{ds}{}^{m}C_{ds}A_{ds}T_{ks}T_{ks}A_{k}$-HPPO-GalNAc | 18 |
| 974344 | 3 | glycine amide | $G_{ks}{}^{m}C_{ks}A_{ks}T_{ds}G_{ds}T_{dx}T_{ds}{}^{m}C_{ds}T_{ds}{}^{m}C_{ds}A_{ds}{}^{m}C_{ds}A_{ds}T_{ks}T_{ks}A_{k}$-HPPO-GalNAc | 18 |
| 1011295 | 3 | thioformacetal | $G_{ks}{}^{m}C_{ks}A_{ks}T_{ds}G_{ds}T_{dx}T_{ds}{}^{m}C_{ds}T_{ds}{}^{m}C_{ds}A_{ds}{}^{m}C_{ds}A_{ds}T_{ks}T_{ks}A_{k}$-HPPO-GalNAc | 18 |
| 1011296 | 3 | MMI | $G_{ks}{}^{m}C_{ks}A_{ks}T_{ds}G_{ds}T_{dx}T_{ds}{}^{m}C_{ds}T_{ds}{}^{m}C_{ds}A_{ds}{}^{m}C_{ds}A_{ds}T_{ks}T_{ks}A_{k}$-HPPO-GalNAc | 18 |

A subscript "d" indicates an unmodified, 2'-β-D-deoxyribosyl sugar moiety. A subscript "k" indicates a cEt. A subscript "s" indicates a phosphorothioate internucleoside linkage. A superscript "m" before a C indicates 5-methyl Cytosine. A subscript "x" indicates a modified internucleoside linkage as indicated in the "linkage mod x" column. These linkages are illustrated above and below.

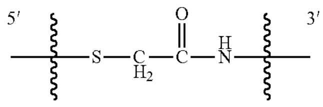

TANA

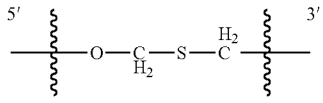

alt-thioformacetal

-continued

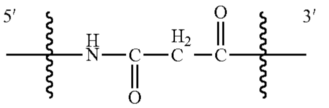

glycine amide

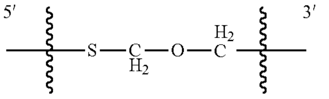

thioformacetal

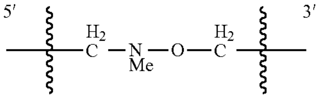

MMI

Each modified oligonucleotide in the study includes a 3'-HPPO-GalNAc conjugate group which is attached to the 3'-oxygen of the oligomeric compound. The 3'-HPPO-GalNAc conjugate group is illustrated below wherein the phosphate group is attached to the 3'-oxygen atom:

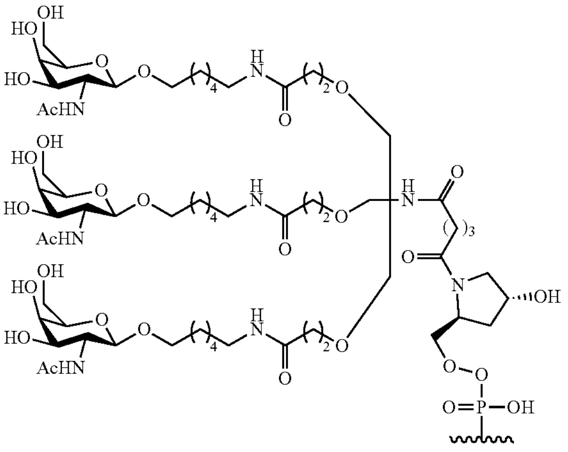

Liver tissues were homogenized and mRNA levels were quantitated using real-time PCR and normalized to RIBOGREEN as described herein. Plasma chemistry markers such as liver transaminase levels, alanine aminotranferase (ALT) in serum were measured relative to saline injected mice.

The $ED_{50}$ values were calculated by plotting the concentrations of oligonucleotides used versus the percent inhibition of CXCL12 mRNA expression achieved at each concentration, and noting the concentration of oligonucleotide at which 50% inhibition of CXCL12 mRNA expression was achieved compared to the control.

TABLE 93

In vivo Toxicity

| Compound ID | Linkage-altered nucleotideposition in Central region | Linkage Mod | ALT (at 50 mg/kg) |
|---|---|---|---|
| 855156* | n/a | n/a | 4298** |
| 855161 | 3 | MOP | 31 |
| 895566 | 3 | isopropylphosphonate | 24 |
| 895567 | 3 | THP phosphotriester | 25 |
| 895568 | 3 | isopropylphosphotriester | 38 |
| 895569 | 3 | isobutylphosphonate | 28 |
| 895570 | 3 | formacetal | 31 |
| 913196 | 3 | amide-3 | 29 |
| 920046 | 3 | TANA | 24 |
| 951972 | 3 | (R)-MOP | 47 |
| 951973 | 3 | (S)-MOP | 45 |
| 974343 | 3 | alt-thioacetal | 39 |
| 974344 | 3 | glycine amide | 30 |
| 1011295 | 3 | thioacetal | 38 |
| 1011296 | 3 | MMI | 56 |

*Described in Table 25 above

**Values determined in an independent experiment and shown for comparison; ALT value is at 5.56 mg/kg modified oligonucleotide TABLE 93b In Vivo CXCL12 mRNA levels

| Compound ID | 0.21 mg/kg | 0.62 mg/kg | 1.85 mg/kg | 5.56 mg/kg | 50 mg/kg |
|---|---|---|---|---|---|
| | Expression level of CXCL12 mRNA (% Control) | | | | |
| 855156* | 81 | 63 | 45 | 31 | n.d. |
| 895566 | 68 | 55 | 42 | n.d. | 22 |
| 895567 | 59 | 50 | 36 | n.d. | 18 |
| 895568 | 69 | 49 | 37 | n.d. | 17 |
| 895569 | 72 | 51 | 41 | n.d. | 18 |
| 895570 | 68 | 50 | 38 | n.d. | 17 |
| 913196 | 62 | 48 | 44 | n.d. | 19 |
| 920046 | 80 | 58 | 58 | n.d. | 25 |
| 855161 | 67 | 51 | 38 | 32 | 21 |
| 951972 | 77 | 61 | 39 | 29 | 20 |
| 951973 | 81 | 59 | 37 | 32 | 19 |
| 974343 | 86 | 56 | 37 | 27 | 16 |
| 974344 | 79 | 69 | 44 | 34 | 23 |
| 1011295 | 78 | 62 | 44 | 31 | 30 |
| 1011296 | 77 | 63 | 49 | 51 | 29 |

Example 39 Synthesis of 5'-(R)-Ethyl and 5'-(S)-Ethyl Phosphoramidites

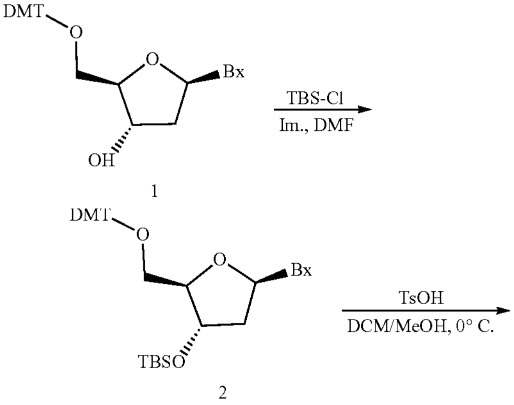

-continued

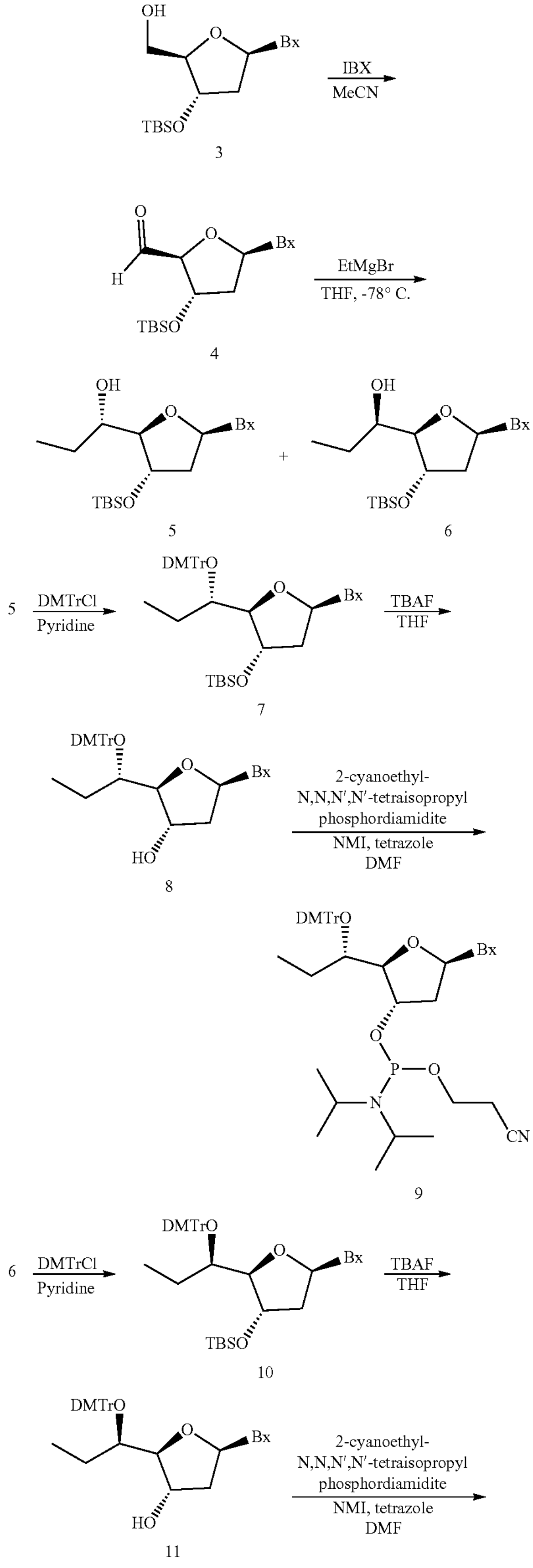

3, 4, 5, 6, 7, 8, 9, 10, 11

-continued

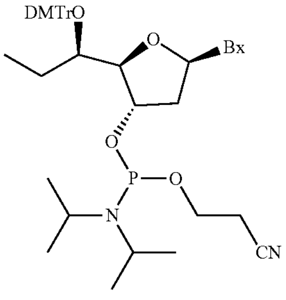

12

1 was synthesized by The National Institutes of Pharmaceutical R&D
Bx = N(Bz)-A, N(iBu)-G, N(Bz)MeC, T 5'-(R)-ethyl and 5'-(S)-ethyl phosphordiamidtes were prepared as per the scheme illustrated above.

Example 40 Time Course of Modified Oligonucleotides in HeLa Cells

HeLa cells were transfected with a modified oligonucleotide listed in the tables below. At 0, 0.5, 1, 2, 4, and 6 hours after transfection, cells were lysed and mRNA was isolated and analyzed by RT-qPCR. Primer probe set HTS3934 (forward sequence: TGGAGACTCTCAGGGTCGAAA, SEQ ID NO: 122; reverse sequence: GGCGTTTGGAGTGGTAGAAATC, SEQ ID NO: 123; probe sequence: CGGCGGCAGACCAGCATGAC, SEQ ID NO: 124) was used to detect human p21 mRNA, and primer probe set HS00169255_ml (ThermoFisher)) was used to detect human Gadd45a mRNA. Results are normalized to untreated cells.

TABLE 94

Relative hp21 mRNA timecourse in HeLa cells

| | % Control human p21 mRNA | | | | | |
|---|---|---|---|---|---|---|
| Compound | 0 hrs | 0.5 hrs | 1 hrs | 2 hrs | 4 hrs | 6 hrs |
| 464917 | 100 | 123 | 133 | 241 | 259 | 557 |
| 558807 | 97.8 | 113 | 135 | 187 | 253 | 528 |
| 549148 | 120 | 120 | 129 | 187 | 138 | 147 |
| 549139 | 102 | 125 | 124 | 143 | 133 | 213 |

TABLE 95

Relative hGadd45a mRNA timecourse in HeLa cells

| | % Control human Gadd45a mRNA | | | | | |
|---|---|---|---|---|---|---|
| Compound | 0 hrs | 0.5 hrs | 1 hrs | 2 hrs | 4 hrs | 6 hrs |
| 464917 | 100 | 157 | 281 | 375 | 632 | 746 |
| 558807 | 105 | 188 | 227 | 297 | 261 | 412 |
| 549148 | 106 | 156 | 200 | 231 | 156 | 180 |
| 549139 | 94 | 157 | 213 | 229 | 167 | 237 |

HeLa cells were transfected with various concentrations of modified oligonucleotide as indicated in the table below. At 0, 1, 2, 4, 6, and 8 hours after transfection, cells were lysed and mRNA was isolated and analyzed by RT-qPCR as described above.

TABLE 96

| Relative hp21 mRNA dose response/time course in HeLa cells | | | | | | | |
|---|---|---|---|---|---|---|---|
| | Dose | % Control human p21 mRNA | | | | | |
| Compound | (nM) | 0 hrs | 1 hrs | 2 hrs | 4 hrs | 6 hrs | 8 hrs |
| 464917 | 0 | 100 | 114 | 87 | 105 | 107 | 97 |
| 464917 | 3.125 | 100 | 109 | 76 | 111 | 179 | 126 |
| 464917 | 6.25 | 100 | 110 | 86 | 113 | 219 | 159 |
| 464917 | 12.50 | 100 | 112 | 86 | 126 | 287 | 239 |
| 464917 | 25.0 | 100 | 110 | 98 | 153 | 313 | 399 |
| 464917 | 50.0 | 100 | 96 | 94 | 165 | 392 | 490 |
| 464917 | 100.0 | 100 | 108 | 106 | 191 | 450 | 600 |
| 464917 | 200.0 | 100 | 99 | 100 | 230 | 510 | 660 |
| 549148 | 0 | 100 | 89 | 106 | 113 | 106 | 79 |
| 549148 | 3.125 | 100 | 105 | 100 | 117 | 126 | 96 |
| 549148 | 6.25 | 100 | 88 | 99 | 128 | 115 | 84 |
| 549148 | 12.50 | 100 | 95 | 108 | 107 | 115 | 107 |
| 549148 | 25.0 | 100 | 95 | 123 | 130 | 140 | 111 |
| 549148 | 50.0 | 100 | 101 | 111 | 122 | 131 | 114 |
| 549148 | 100.0 | 100 | 98 | 89 | 131 | 104 | 100 |
| 549148 | 200.0 | 100 | 93 | 95 | 163 | 102 | 99 |

TABLE 97

| Relative hGadd45a mRNA dose response/time course in HeLa cells | | | | | | | |
|---|---|---|---|---|---|---|---|
| | Dose | % Control human p21 mRNA | | | | | |
| Compound | (nM) | 0 hrs | 1 hrs | 2 hrs | 4 hrs | 6 hrs | 8 hrs |
| 464917 | 0 | 100 | 97 | 80 | 109 | 110 | 88 |
| 464917 | 3.125 | 100 | 117 | 95 | 156 | 208 | 170 |
| 464917 | 6.25 | 100 | 121 | 111 | 176 | 176 | 205 |
| 464917 | 12.50 | 100 | 139 | 126 | 165 | 271 | 261 |
| 464917 | 25.0 | 100 | 147 | 136 | 176 | 279 | 420 |
| 464917 | 50.0 | 100 | 130 | 171 | 203 | 368 | 700 |
| 464917 | 100.0 | 100 | 143 | 194 | 261 | 835 | 1234 |
| 464917 | 200.0 | 100 | 113 | 198 | 213 | 890 | 1111 |
| 549148 | 0 | 100 | 98 | 104 | 104 | 111 | 99 |
| 549148 | 3.125 | 100 | 124 | 133 | 120 | 132 | 133 |
| 549148 | 6.25 | 100 | 151 | 140 | 155 | 160 | 142 |
| 549148 | 12.50 | 100 | 159 | 159 | 131 | 120 | 144 |
| 549148 | 25.0 | 100 | 173 | 172 | 148 | 156 | 180 |
| 549148 | 50.0 | 100 | 155 | 170 | 164 | 104 | 164 |
| 549148 | 100.0 | 100 | 140 | 129 | 141 | 160 | 190 |
| 549148 | 200.0 | 100 | 121 | 115 | 128 | 107 | 185 |

Example 41 Time Course of Toxicity of Modified Oligonucleotide 464917 In Vivo The modified oligonucleotide 464917 was administered subcutaneously at 11, 33, or 100 mg/kg to 9 BALB/C mice per dosing group. Three mice from each group were sacrificed at 24 hours, three at 48 hours, and the last three at 72 hours after dosing. mRNA was isolated and analyzed as described in Example 1. ALT values in plasma were obtained using a clinical chemistry analyzer.

TABLE 98

| Time Course of Activity and Toxicity in mice | | | | | | | |
|---|---|---|---|---|---|---|---|
| Compound | Dose (mg/kg) | 24 hrs | 48 hrs | 72 hrs | 24 hrs | 48 hrs | 72 hrs |
| | | ALT | | | mFXI mRNA | | |
| 464917 | 0 | 44 | 58 | 29 | 100 | 100 | 100 |
| 464917 | 11 | 40 | 132 | 311* | 20 | 17 | 11* |
| 464917 | 33 | 98 | 2015 | 8072 | 2.7 | 2.6 | 5.7 |
| 464917 | 100 | 168 | 12261 | 26659* | 1.7 | 0.5 | 0.07** |

*Data represents a single mouse
**Data represents the average of two mice

TABLE 99

| Time Course of Toxicity in mice | | | | | | | |
|---|---|---|---|---|---|---|---|
| Compound | Dose (mg/kg) | 24 hrs | 48 hrs | 72 hrs | 24 hrs | 48 hrs | 72 hrs |
| | | mP21 mRNA | | | mTnfrsf10b mRNA | | |
| 464917 | 0 | 100 | 100 | 100 | 100 | 100 | 100 |
| 464917 | 11 | 518 | 607 | 2060* | 272 | 845 | 3401* |
| 464917 | 33 | 6451 | 1846 | 5221 | 2071 | 5333 | 7013 |
| 464917 | 100 | 163667 | 4067 | 4910** | 5451 | 12293 | 7402** |

*Data represents a single mouse
**Data represents the average of two mice

Example 42 Nucleolar Delocalization of p54nrb In Vivo

Compound 959265 is compound 464917 conjugated to a Cy3 on the 5'-end and HPPO-GalNAc on the 3'-end. Balb/c mice were administered 15 mg/kg of 959265 by subcutaneous injection. Hepatocytes were isolated and purified 40 hours after administration of modified oligonucleotide and plated on a confocal dish for 6-7 hours. After 6-7 hours, cells were fixed with formaldehyde and stained for p54nrb with immunofluorescent staining for p54nrb. Levels of FXI and p21 were detected by RT-qPCR as described above.

A single dose of 959265 at 15 mg/kg reduced FXI to 10.6% of control values. Levels of p21 mRNA were upregulated 1,046%. Isolated hepatocytes were observed to contain p54nrb that had been localized to the nucleolus or no detectable p54nrb.

Example 43 Nucleolar Delocalization of p54nrb In Vivo

Balb/c mice were administered 100 mg/kg of 464917 or 549148 by subcutaneous injection. Hepatocytes were isolated and purified 16 hours after administration of modified oligonucleotide and plated on a confocal dish for 1-2 hours. After 1-2 hours, cells were fixed with formaldehyde and stained for p54nrb with immunofluorescent staining for p54nrb.

Localization of p54nrb to the nucleolus of hepatocytes was observed for compound 464917 but not for compound 549148.

Example 44 In Vivo Activity and Toxicity of Compounds Containing a MOP Neutral Linkage Six week old BALB/C mice (purchased from Charles River) were injected subcutaneously once at dosage 0.2, 0.6, 1.8 5.4, or 50 mg/kg with the modified oligonucleotides shown below or with saline control. For compound 855156, mice were injected with 0.2, 0.6, 1.8, 5.4, or 15 mg/kg modified oligonucleotide. Each treatment group consisted of 3 animals. The mice were sacrificed 72 hours following administration, and organs and plasma were harvested for further analysis.

Liver tissues were homogenized and mRNA levels were quantitated using real-time PCR and normalized to RIBOGREEN as described herein. Plasma chemistry markers such as liver transaminase levels, alanine aminotranferase (ALT) in serum were measured relative to saline injected mice.

The $ED_{50}$ values were calculated by plotting the concentrations of oligonucleotides used versus the percent inhibition of CXCL12 mRNA expression achieved at each concentration, and noting the concentration of oligonucleotide at which 50% inhibition of CXCL12 mRNA expression was achieved compared to the control.

TABLE 100

Modified Oligonucleotides

| Compound ID | position of linkage-altered nucleotide in central region | Linkage mod | Chemistry Notation | SEQ ID NO |
|---|---|---|---|---|
| 869742 | n/a | n/a | $G_{ks}{}^{m}C_{ks}A_{ks}T_{ds}G_{ds}T_{ds}T_{ds}{}^{m}C_{ds}T_{ds}{}^{m}C_{ds}A_{ds}{}^{m}C_{ds}A_{ds}T_{ks}T_{ks}A_{ks}T_{k}$-HPPO-GalNAc | 125 |
| 898384 | 3 | MOP | $G_{ks}{}^{m}C_{ks}A_{ks}T_{ds}G_{ds}T_{dx}T_{ds}{}^{m}C_{ds}T_{ds}{}^{m}C_{ds}A_{ds}{}^{m}C_{ds}A_{ds}T_{ks}T_{ks}A_{ks}T_{k}$-HPPO-GalNAc | 125 |
| 898385 | 2, 3 | MOP | $G_{ks}{}^{m}C_{ks}A_{ks}T_{ds}G_{ds}T_{dx}T_{ds}{}^{m}C_{ds}T_{ds}{}^{m}C_{ds}A_{ds}{}^{m}C_{ds}A_{ds}T_{ks}T_{ks}A_{ks}T_{k}$-HPPO-GalNAc | 125 |

A subscript "d" indicates an unmodified, 2'-β-D-deoxyribosyl sugar moiety. A subscript "k" indicates a cEt. A subscript "s" indicates a phosphorothioate internucleoside linkage. A superscript "m" before a C indicates 5-methyl Cytosine. A subscript "x" indicates a MOP internucleoside linkage.

TABLE 101

In vivo Toxicity

| Compound ID | Linkage Mod position in Central region | Linkage Mod | ALT at 15 mg/kg | ALT at 50 mg/kg |
|---|---|---|---|---|
| 855156 | n/a | n/a | 9,639 | n/a |
| 869742 | n/a | n/a | 2,001 | n/a |
| 898384 | 3 | MOP | 30 | 32 |
| 898385 | 2, 3 | MOP | 32 | 30 |

TABLE 102

In Vivo CXCL12 mRNA levels

| Compound ID | 0.2 mg/kg | 0.6 mg/kg | 1.8 mg/kg | 5.4 mg/kg | 15 mg/kg | 50 mg/kg |
|---|---|---|---|---|---|---|
| | Expression level of CXCL12 mRNA (% Control) | | | | | |
| 855156 | 64 | 42 | 23 | 19 | 16 | n/a |
| 869742 | 87 | 58 | 32 | 23 | 18 | n/a |
| 898384 | 87 | 91 | 49 | 40 | 36 | 31 |
| 898385 | 91 | 90 | 64 | 64 | 55 | 41 |

Example 45

Modified oligonucleotides were tested for toxicity in vivo in Balb/c mice.

TABLE 103

Modified Oligonucleotides

| Compound ID | Chemistry notation | SEQ ID NO: |
|---|---|---|
| 575013 | ${}^{m}C_{ks}A_{ks}G_{ks}A_{ds}T_{ds}A_{ds}T_{ds}A_{ds}G_{ds}G_{ds}A_{ds}{}^{m}C_{ds}T_{ds}G_{ks}G_{ks}A_{k}$ | 110 |
| 465131 | $T_{ks}G_{ks}{}^{m}C_{ks}{}^{m}C_{ds}A_{ds}{}^{m}C_{ds}{}^{m}C_{ds}G_{ds}T_{ds}A_{ds}G_{ds}A_{ds}{}^{m}C_{ds}A_{ks}{}^{m}C_{ks}G_{k}$ | 114 |
| 549139 | $G_{ks}A_{ks}{}^{m}C_{ks}G_{ds}{}^{m}C_{ds}G_{ds}{}^{m}C_{ds}{}^{m}C_{ds}T_{ds}G_{ds}A_{ds}A_{ds}G_{ds}G_{ks}T_{ks}T_{k}$ | 111 |
| 464932 | $G_{ks}G_{ks}A_{ks}{}^{m}C_{ds}A_{ds}{}^{m}C_{ds}A_{ds}T_{ds}T_{ds}G_{ds}G_{ds}{}^{m}C_{ds}{}^{m}C_{ds}A_{ks}{}^{m}C_{ks}A_{k}$ | 112 |

A subscript "d" indicates an unmodified, 2'-β-D-deoxyribosyl sugar moiety. A subscript "k" indicates a cEt modified sugar moiety. A subscript "s" indicates a phosphorothioate internucleoside linkage. A superscript "m" before a C indicates 5-methyl Cytosine.

For in vivo toxicity studies, 3 BALB/c mice per group were administered the indicated dose of modified oligonucleotide by subcutaneous injection and sacrificed after 72 hours. Four animals were administered saline to serve as a control. RT-PCR was performed as described in Example 1 to determine mRNA levels of CXCL12, P21, Tnfrsf10b, and Gadd45a. Plasma levels of ALT were measured using an automated clinical chemistry analyzer. Increased ALT is indicative of acute liver toxicity.

For the in vitro toxicity study in the table below, the caspase assay was performed essentially as described in Example 8 in 3T3-L1 cells. The caspase assay was performed in HeLa cells by free uptake at 2 μM modified oligonucleotide and in b.END3 cells by free uptake at 50 μM modified oligonucleotide.

TABLE 104

In vivo and in vitro toxicity of modified oligonucleotides

| Compound ID | in vivo Dose (mg/kg) | ALT (IU/L) | in vivo P21 (% control) | in vivo Tnfrsf10b (% control) | in vitro caspase @20 μM, 3T3-L1 (% control) | in vitro caspase @2 μM, HeLa (% control) | in vitro caspase @50 μM, b.END (% control) |
|---|---|---|---|---|---|---|---|
| 575013 | 100 | 12 | 54 | 105 | 237 | 100 | 140 |
| 465131 | 100 | 21 | 111 | 164 | 114 | 119 | n.d. |
| 549139 | 100 | 24 | 118 | 135 | 125 | 111 | 113 |
| 549148 | 100 | 24 | 72 | 83 | 184 | 121 | 159 |
| 464932 | 100 | 5 | 150 | 180 | 280 | 113 | 187 |
| 449093 | 33 | 2324 | 42802 | 3835 | 2703 | 306 | 783 |
| | 100 | 9983 | 150994 | 3744 | | | |
| 482050 | 33 | 1470 | 7890 | 4725 | 1502 | 203 | 439 |
| | 100 | 6555 | 10430 | 4232 | | | |
| 508031 | 33 | 648 | 2980 | 2239 | 1082 | 255 | 357 |
| | 100 | 18550 | 8909 | 6678 | | | |
| 558807 | 17 | 1877 | 2763 | 1168 | 910 | 408 | 413 |
| | 51 | 9510 | 11904 | 6831 | | | |
| 464917 | 11 | 601 | 6098 | 3516 | 1724 | 219 | 552 |
| | 33 | 13920 | 9590 | 7731 | | | |

Example 46 Time Course of Toxicity and Activity of Modified Oligonucleotide 464932 or 464917 In Vivo The modified oligonucleotide 464932, described in Example 45 above, or 464917, described in Example 4 above, was administered subcutaneously at 33 mg/kg to BALB/C mice. Three mice from each dosing group were sacrificed at each indicated time point and mRNA was isolated and analyzed as described in Example 1. ALT values in plasma were obtained using a clinical chemistry analyzer and were normalized to saline-treated animals.

TABLE 105

Time Course of Activity and Toxicity in mice

| Treatment | Measurement | 8 hrs | 12 hrs | 16 hrs | 24 hrs | 48 hrs | 72 hrs |
|---|---|---|---|---|---|---|---|
| PBS | ALT | 20 | 41 | 40 | 40 | 44 | 41 |
| 464932 | ALT | 49 | 64 | 58 | 47 | 39 | 108 |
| | mFXI | 174 | 104 | 40 | 53 | 19 | 12 |
| | mP21 | 94 | 115 | 71 | 182 | 47 | 185 |
| | mTnfrsf10b | 133 | 101 | 112 | 108 | 117 | 140 |

TABLE 105-continued

Time Course of Activity and Toxicity in mice

| Treatment | Measurement | 8 hrs | 12 hrs | 16 hrs | 24 hrs | 48 hrs | 72 hrs |
|---|---|---|---|---|---|---|---|
| 464917 | ALT | 39 | 49 | 53 | 41 | 1903 | 13917 |
| | mFXI | 100 | 56 | 12 | 19 | 4 | 5 |
| | mP21 | 138 | 391 | 829 | 3751 | 1854 | 12716 |
| | mTnfrsf10b | 118 | 221 | 714 | 1250 | 6369 | 8781 |

Example 47 Time Course of Toxicity and Activity of Modified Oligonucleotide 558807 or 558765 In Vivo Modified oligonucleotide 558765 is a 3-10-3 cEt gapmer with a full phosphorothioate backbone and the sequence A$^m$CAT$^m$CTT$^m$CAGAT$^m$CATT (SEQ ID NO: 144). The modified oligonucleotide 558807 or 558765 was administered subcutaneously at 51 mg/kg to BALB/C mice. Three mice from each dosing group were sacrificed at each indicated time point and mRNA was isolated and analyzed as described in Example 1. ALT values in plasma were obtained using a clinical chemistry analyzer and were normalized to saline-treated animals.

TABLE 106

Time Course of Activity and Toxicity in mice

| Treatment | Measurement | 8 hrs | 12 hrs | 16 hrs | 24 hrs | 48 hrs | 72 hrs |
|---|---|---|---|---|---|---|---|
| PBS | ALT | 21 | 42 | 40 | 40 | 44 | 41 |
| 558765 | ALT | 34 | 53 | 46 | 92 | 33 | 36 |
| | mCXCL12 | 109 | 94 | 20 | 54 | 29 | 26 |
| | mP21 | 143 | 116 | 92 | 209 | 48 | 404 |
| | mTnfrsf10b | 106 | 70 | 118 | 98 | 154 | 215 |
| 558807 | ALT | 36 | 50 | 53 | 36 | 1888 | 7272 |
| | mCXCL12 | 43 | 18 | 5 | 10 | 3 | 3 |
| | mP21 | 136 | 142 | 86 | 580 | 1573 | 1642 |
| | mTnfrsf10b | 101 | 148 | 236 | 292 | 3375 | 7454 |

Example 48 Toxicity Improvement In Vivo with Incorporation 2'-OMe Modified-Nucleoside in the Central Region BALB/c mice were administered 1.8, 5.5, 16.7, or 50 mg/kg of 558807 or 1.8, 5.5, 16.7, 50, 100, 200, or 300 mg/kg of 936053 and sacrificed after 72 hours. Plasma levels of ALT were measured with a clinical chemistry analyzer and mRNA was isolated and analyzed as described in Example 1. Therapeutic index (TI) was calculated as the maximum non-toxic dose divided by the $ED_{50}$. Compound 936053 differs from compound 558807 only in the presence of a 2'-OMe group at position 5 from the 5' end of the compound, or position 2 of the central region.

TABLE 107

| in vivo dose response | | | | | | | | | |
|---|---|---|---|---|---|---|---|---|---|
| Compound ID | Dose (mg/kg) | ALT (IU/L) | in vivo P21 (% control) | in vivo Tnfrsf10b (% control) | in vivo Gadd45a (% control) | CXCL12 mRNA (% control) | ED50 (mg/kg) | MTND (mg/kg) | Therapeutic Index |
| 558807 | 1.8 | 24 | 118 | 120 | 147 | 67.5 | 2.75 | 5.5 | 2 |
| | 5.5 | 27 | 63 | 103 | 176 | 20.3 | | | |
| | 16.7 | 586 | 625 | 788 | 879 | 9.7 | | | |
| | 50 | death | n.d. | n.d. | n.d. | n.d. | | | |
| 936053 | 1.8 | 34 | 104 | 78 | 61 | 65.3 | 4.86 | 200 | 41 |
| | 5.5 | 26 | 94 | 137 | 99 | 47.4 | | | |
| | 16.7 | 23 | 104 | 110 | 91 | 32.7 | | | |
| | 50 | 23 | 89 | 122 | 90 | 14.4 | | | |
| | 100 | 42 | n.d. | n.d. | n.d. | n.d. | | | |
| | 200 | 109 | n.d. | n.d. | n.d. | n.d. | | | |
| | 300 | 231 | n.d. | n.d. | n.d. | n.d. | | | |

Example 49 Toxicity Improvement of Modified Oligonucleotides Targeted to FXI

BALB/c mice were administered 1.8, 5.5, 16.7, 50 or 150 mg/kg of modified oligonucleotide by subcutaneous injection. Each group contained 3 mice. A group of 4 mice was administered PBS as a control. Plasma levels of ALT were measured with a clinical chemistry analyzer and mRNA was isolated and analyzed as described in Example 1. Modified oligonucleotides are described in Example 18. Each pair of compounds, presented adjacent to each other in the table below, represents a compound with the motif kkk-d(10)-kkk (464xxx) and the same sequence with the motif kkk-d-m-d (8)-kkk (1133xxx). In instances where position 5 in the original sequence is a T, this nucleoside is a 2'-OMeU in the kkk-d-m-d(8)-kkk sequence.

TABLE 108

| in vivo dose response | | | | | | | |
|---|---|---|---|---|---|---|---|
| Compound ID | Dose (mg/kg) | ALT (IU/L) | in vivo P21 (% control) | FXI mRNA (% control) | ED50 (mg/kg) | MTND (mg/kg) | Therapeutic Index |
| 464924 | 1.8 | 27 | 136 | 59.7 | 2.4 | 16.7 | 7.0 |
| | 5.5 | 27 | 144 | 20.4 | | | |
| | 16.7 | 31 | 167 | 2.5 | | | |
| | 50 | 646 | 551 | 0.4 | | | |
| | 150 | 4509 | 1160 | 0.4 | | | |
| 1133247 | 1.8 | 32 | 130 | 75.0 | 3.4 | >150 | >44 |
| | 5.5 | 30 | 67 | 29.3 | | | |
| | 16.7 | 30 | 94 | 5.4 | | | |
| | 50 | 37 | 123 | 1.9 | | | |
| | 150 | 53 | 304 | 1.4 | | | |
| 465172 | 1.8 | 26 | 131 | 73.5 | 6.7 | >150 | >22 |
| | 5.5 | 22 | 102 | 57.8 | | | |
| | 16.7 | 23 | 99 | 28.8 | | | |
| | 50 | 25 | 102 | 13.8 | | | |
| | 150 | 33 | 177 | 6.2 | | | |
| 1133326 | 1.8 | 25 | 51 | 81.1 | 16.3 | >150 | >9 |
| | 5.5 | 25 | 64 | 81.8 | | | |
| | 16.7 | 24 | 55 | 49.0 | | | |
| | 50 | 24 | 78 | 21.1 | | | |
| | 150 | 22 | 90 | 11.8 | | | |

TABLE 108-continued

| in vivo dose response | | | | | | | |
|---|---|---|---|---|---|---|---|
| Compound ID | Dose (mg/kg) | ALT (IU/L) | in vivo P21 (% control) | FXI mRNA (% control) | ED50 (mg/kg) | MTND (mg/kg) | Therapeutic Index |
| 465174 | 1.8 | 25 | 192 | 67.5 | 4.2 | >150 | >36 |
| | 5.5 | 29 | 172 | 46.8 | | | |
| | 16.7 | 22 | 31 | 18.0 | | | |
| | 50 | 20 | 49 | 7.5 | | | |
| | 150 | 29 | 83 | 5.7 | | | |
| 1133328 | 1.8 | 21 | 40 | 74.8 | 4.8 | >150 | >32 |
| | 5.5 | 23 | 38 | 44.3 | | | |
| | 16.7 | 28 | 42 | 18.6 | | | |
| | 50 | 26 | 25 | 13.0 | | | |
| | 150 | 31 | 38 | 10.7 | | | |
| 465178 | 1.8 | 26 | 43 | 47.2 | 1.7 | 16.7 | 10 |
| | 5.5 | 35 | 119 | 18.4 | | | |
| | 16.7 | 73 | 627 | 4.3 | | | |
| | 50 | 1067 | 3509 | 0.7 | | | |
| | 150 | 11596 | 4849 | 0.4 | | | |
| 1133332 | 1.8 | 23 | 101 | 47.8 | 1.8 | 150 | 83 |
| | 5.5 | 35 | 42 | 30.7 | | | |
| | 16.7 | 33 | 136 | 13.1 | | | |
| | 50 | 41 | 600 | 3.7 | | | |
| | 150 | 117 | 1414 | 1.3 | | | |

Example 50 Toxicity Improvement of Modified Oligonucleotides Targeted to HDAC2

BALB/c mice were administered 1.8, 5.5, 16.7, 50 or 150 mg/kg of modified oligonucleotide by subcutaneous injection. Each group contained 3 mice. A group of 4 mice was administered PBS as a control. Plasma levels of ALT were measured with a clinical chemistry analyzer and mRNA was isolated and analyzed as described in Example 1. Modified oligonucleotides are described in Example 19. Each pair of compounds, presented adjacent to each other in the table below, represents a compound with the motif kkk-d(10)-kkk (546xxx) and the same sequence with the motif kkk-d-m-d (8)-kkk (1133xxx). In instances where position 5 in the original sequence is a T, this nucleoside is a 2'-OMeU in the kkk-d-m-d(8)-kkk sequence.

TABLE 109

| in vivo dose response | | | | | | |
|---|---|---|---|---|---|---|
| Compound ID | Dose (mg/kg) | ALT (IU/L) | HDAC2 mRNA (% control) | ED50 (mg/kg) | MTND (mg/kg) | Therapeutic Index |
| 546108 | 1.8 | 33 | 74 | 3.2 | 16.7 | 5.2 |
| | 5.5 | 47 | 26.2 | | | |
| | 16.7 | 168 | 3.8 | | | |
| | 50 | 1713 | 4.8 | | | |
| | 150 | 17844 | 4.5 | | | |
| 1133122 | 1.8 | 29 | 91.6 | 5.5 | >150 | >27 |
| | 5.5 | 25 | 48.3 | | | |
| | 16.7 | 2 | 11.0 | | | |
| | 50 | 43 | 1.1 | | | |
| | 150 | 78 | 1.1 | | | |
| 546110 | 1.8 | 25 | 72.9 | 6.4 | 16.7 | 2.6 |
| | 5.5 | 27 | 57.4 | | | |
| | 16.7 | 37 | 29.4 | | | |
| | 50 | 416 | 6.7 | | | |
| | 150 | 2817 | 6.0 | | | |
| 1133123 | 1.8 | 24 | 71.0 | 6.8 | >150 | >22 |
| | 5.5 | 80 | 49.6 | | | |
| | 16.7 | 25 | 47.8 | | | |
| | 50 | 25 | 8.0 | | | |
| | 150 | 28 | 3.0 | | | |
| 546118 | 1.8 | 30 | 69.9 | 23.8 | 16.7 | 0.7 |
| | 5.5 | 29 | 70.1 | | | |
| | 16.7 | 40 | 50.8 | | | |
| | 50 | 365 | 39.1 | | | |
| | 150 | 1681 | 36.0 | | | |
| 1133127 | 1.8 | 35 | 77.2 | 24.9 | >150 | >6 |
| | 5.5 | 25 | 60.6 | | | |
| | 16.7 | 26 | 57.1 | | | |
| | 50 | 25 | 39.9 | | | |
| | 150 | 33 | 34.4 | | | |

Example 51 Toxicity Improvement of Modified Oligonucleotides

Modified oligonucleotides were tested for toxicity in vivo in Balb/c mice. Compound 865060 has the motif kkk-d(10)-kkkk and compound 865061 has the motif kkkk-d(10)-kkk. Compounds 1269430 and 1269431 are otherwise identical compounds to 865060 and 865061, respectively, containing a 2'-OMe modified sugar moiety at the second position in the central region.

TABLE 110

| Modified Oligonucleotides | | |
|---|---|---|
| Compound ID | Chemistry notation | SEQ ID NO: |
| 865060 | $G_{ks}{}^{m}C_{ks}A_{ks}T_{ds}G_{ds}T_{ds}T_{ds}{}^{m}C_{ds}T_{ds}{}^{m}C_{ds}A_{ds}{}^{m}C_{ds}A_{ds}T_{ks}T_{ks}A_{ks}T_{k}$ | 125 |
| 865061 | $G_{ks}G_{ks}{}^{m}C_{ks}A_{ks}T_{ds}G_{ds}T_{ds}T_{ds}{}^{m}C_{ds}T_{ds}{}^{m}C_{ds}A_{ds}{}^{m}C_{ds}A_{ds}T_{ks}T_{ks}A_{k}$ | 141 |
| 1269430 | $G_{ks}{}^{m}C_{ks}A_{ks}T_{ds}G_{ms}T_{ds}T_{ds}{}^{m}C_{ds}T_{ds}{}^{m}C_{ds}A_{ds}{}^{m}C_{ds}A_{ds}T_{ks}T_{ks}A_{ks}T_{k}$ | 125 |
| 1269431 | $G_{ks}G_{ks}{}^{m}C_{ks}A_{ks}T_{ds}G_{ms}T_{ds}T_{ds}{}^{m}C_{ds}T_{ds}{}^{m}C_{ds}A_{ds}{}^{m}C_{ks}A_{ks}T_{ks}T_{ks}A_{k}$ | 141 |

A subscript "d" indicates an unmodified, 2'-β-D-deoxyribosyl sugar moiety. A subscript "k" indicates a cEt. A subscript "m" indicates a 2'-O-methyl-β-D-ribofuranosyl sugar moiety. A subscript "s" indicates a phosphorothioate internucleoside linkage. A superscript "m" before a C indicates 5-methyl Cytosine.

For in vivo toxicity studies, 3 BALB/c mice per group were administered the indicated dose of modified oligonucleotide by subcutaneous injection and sacrificed after 72 hours. Four animals were administered saline to serve as a control. RT-PCR was performed as described in Example 1 to determine mRNA levels of CXCL12, P21, Tnfrsf10b, and Gadd45a. Plasma levels of ALT was measured using an automated clinical chemistry analyzer. Increased ALT is indicative of acute liver toxicity.

For the in vitro toxicity study in the table below, the caspase assay was performed essentially as described in Example 8 in 3T3-L1 cells, the percent nucleolar p54nrb was visualized as described in Example 11, and the p21 mRNA levels were determined as described in Example 11.

Table 111

| In vivo and in vitro toxicity of modified oligonucleotides | | | | | | | |
|---|---|---|---|---|---|---|---|
| Compound ID | in vitro CXCL12 $IC_{50}$ (nM) | Relative Caspase Activation (% Control) @20 µM | in vitro p21 mRNA (% Control) @20 µM | in vitro % nucleolar p54nrb | in vivo p21 @150 mg/kg | in vivo Tnfrsf10*b* mRNA @ 150 mg/kg | ALT @ 150 mg/kg (IU/L) |
| 558807 | 183 | 432 | 285 | 82 | 7152* | 5504* | 9928* |
| 936053 | 259 | 114 | 114 | 0 | 166 | 204 | 12 |
| 865060 | 310 | 355 | 224 | 64 | 7604* | 9339* | 11058* |
| 1269430 | 308 | 110 | 127 | 0 | 209 | 350 | 10 |
| 865061 | 510 | 738 | 198 | 75 | 12531 | 6351 | 9014 |
| 1269431 | 849 | 116 | 134 | 0 | 376 | 661 | 52 |

*Value at 50 mg/kg dose; mice administered 150 mg/kg did not survive

Example 52 Long-Term Toxicity Improvement of Modified Oligonucleotides

Modified oligonucleotides were tested for toxicity in vivo in Balb/c mice. Mice were administered 50 mg/kg modified oligonucleotide once a week for six weeks and ALT was measured using an automated clinical chemistry analyzer. Compounds in the table below are described in Example 13. Each pair of compounds represents an oligonucleotide with the sugar motif kkk-d(10)-kkk (upper) and an oligonucleotide with the same sequence having the sugar motif kkk-d-m-d(8)-kkk (lower).

TABLE 112

| Long-term Toxicity | | | | | | |
|---|---|---|---|---|---|---|
| Compound | Week of Dosing | | | | | |
| ID | 1 | 2 | 3 | 4 | 5 | 6 |
| | ALT (IU/L) | | | | | |
| PBS | 35 | 65 | 27 | 45 | 55 | 23 |
| 572912 | 398 | 1036 | 2667 | 2787 | n.d. | n.d. |
| 1200898 | 36 | 53 | 70 | 112 | 187 | 513 |
| 797793 | 1210 | 972 | 1674 | 2703 | 3831 | 3635 |
| 1201073 | 99 | 143 | 165 | 178 | 217 | 330 |
| 576095 | 46 | 83 | 1017 | 1763 | 2886 | 4118 |
| 1200899 | 50 | 57 | 129 | 550 | 1225 | 1392 |

n.d. indicates that the mice were sacrificed prior to the measurement date.

Example 53

Modified oligonucleotides were designed based on 546118. Each of the modified oligonucleotides is conjugated with a THA-GalNAc conjugate group at the 3'-end. THA-GalNac refers to this structure:

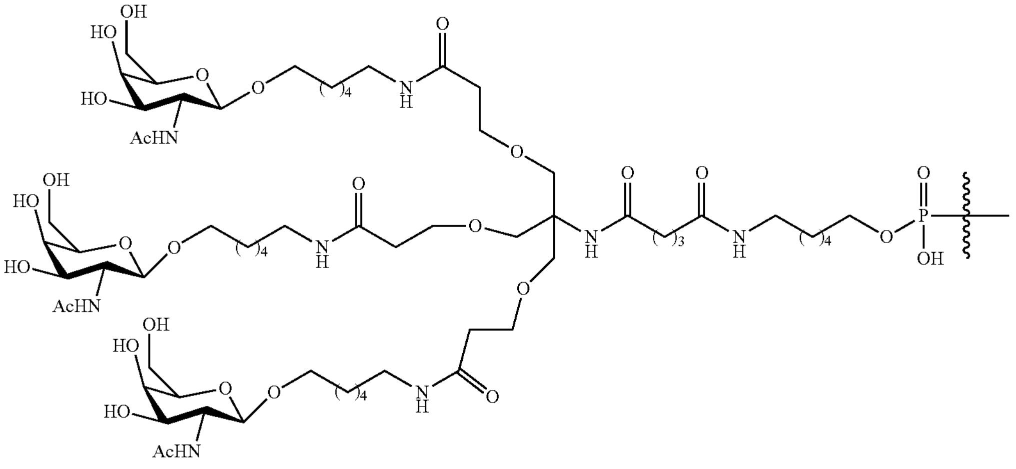

wherein the phosphate group is attached to the 3'-oxygen atom of the 3' nucleoside.

The oligonucleotides were evaluated for reduction in HDAC2 mRNA expression levels in vivo. P21 and Tnfrsf10b mRNA levels were also measured. The transaminase levels (ALT and AST) for each dose were also measured.

Six week old BALB/C mice (purchased from Charles River) were injected subcutaneously once at dosage 0.023, 0.067, 0.2, 0.6, 1.8, 5.4, 15, or 50 mg/kg with the modified oligonucleotides shown below or with saline control. Each treatment group consisted of 3 animals. The mice were sacrificed 72 hours following administration, and organs and plasma were harvested for further analysis.

TABLE 113

Modified Oligonucleotides

| Compound ID | position of altered nucleotide in central region | modification of altered nucleotide | Chemistry Notation | SEQ ID NO |
|---|---|---|---|---|
| 1270732 | N/A | N/A | $A_{ks}{}^{m}C_{ks}{}^{m}C_{ks}{}^{m}C_{ds}T_{ds}{}^{m}C_{ds}A_{ds}A_{ds}G_{ds}T_{ds}{}^{m}C_{ds}T_{ds}{}^{m}C_{ds}{}^{m}C_{ks}T_{ks}G_{k}$-THAGalNAc | 109 |
| 1270733 | 2 | 2'-OMe | $A_{ks}{}^{m}C_{ks}{}^{m}C_{ks}{}^{m}C_{ds}U_{ms}{}^{m}C_{ds}A_{ds}A_{ds}G_{ds}T_{ds}{}^{m}C_{ds}T_{ds}{}^{m}C_{ds}{}^{m}C_{ks}T_{ks}G_{k}$-THAGalNAc | 140 |
| 1270734 | 2 | MOP | $A_{ks}{}^{m}C_{ks}{}^{m}C_{ks}{}^{m}C_{ds}T_{dx}{}^{m}C_{ds}A_{ds}A_{ds}G_{ds}T_{ds}{}^{m}C_{ds}T_{ds}{}^{m}C_{ds}{}^{m}C_{ks}T_{ks}G_{k}$-THAGalNAc | 109 |

A subscript "d" indicates an unmodified, 2'-β-D-deoxyribosyl sugar moiety. A subscript "m" indicates a 2'-O-methyl-β-D-ribofuranosyl sugar moiety. A subscript "k" indicates a cEt. A subscript "s" indicates a phosphorothioate internucleoside linkage. A superscript "m" before a C indicates 5-methyl Cytosine. A subscript "x" indicates a MOP internucleoside linkage.

TABLE 114

In vivo Activity and Toxicity of Modified Oligonucleotides

| Compound ID | Dose (mg/kg) | ALT (IU/L) | P21 mRNA (% Control) | Tnfrsf10b mRNA (% Control) | HDAC2 ED50 (mg/kg) |
|---|---|---|---|---|---|
| 1270732 | 0.023 | 34 | 106 | n.d. | 0.060 |
| | 0.067 | 7 | 74 | n.d. | |
| | 0.2 | 15 | 113 | 80 | |
| | 0.6 | 13 | 112 | 76 | |
| | 1.8 | 33 | 537 | 118 | |
| | 5.4 | 122 | 688 | 271 | |
| | 15 | 1467 | 2606 | 1418 | |
| | 50 | 3429 | 5197 | 3064 | |

TABLE 114-continued

| In vivo Activity and Toxicity of Modified Oligonucleotides | | | | | |
|---|---|---|---|---|---|
| Compound ID | Dose (mg/kg) | ALT (IU/L) | P21 mRNA (% Control) | Tnfrsf10b mRNA (% Control) | HDAC2 ED50 (mg/kg) |
| 1270733 | 0.023 | 22 | 71 | n.d. | 0.066 |
| | 0.067 | 43 | 91 | n.d. | |
| | 0.2 | 18 | 89 | 80 | |
| | 0.6 | 20 | 103 | 104 | |
| | 1.8 | 17 | 81 | 81 | |
| | 5.4 | 23 | 154 | 81 | |
| | 15 | 11 | 172 | 110 | |
| | 50 | 22 | 988 | 353 | |
| 1270734 | 0.023 | 13 | 64 | n.d. | 0.084 |
| | 0.067 | 22 | 65 | n.d. | |
| | 0.2 | 31 | 158 | 93 | |
| | 0.6 | 7 | 230 | 149 | |
| | 1.8 | 12 | 64 | 93 | |
| | 5.4 | 20 | 169 | 110 | |
| | 15 | 318 | 1513 | 608 | |
| | 50 | 1650 | 2894 | 1368 | |

n.d. means a value was not determined.

Example 54

Modified oligonucleotides were designed based on 546110, described in Example 19 above. Each of the modified oligonucleotides is conjugated with a THA-GalNAc conjugate group at the 3'-end as described in Example 53 above. The oligonucleotides were evaluated for reduction in HDAC2 mRNA expression levels in vivo. P21 and Tnfrsf10b mRNA levels were also measured. The transaminase levels (ALT and AST) for each dose were also measured.

Six week old BALB/C mice (purchased from Charles River) were injected subcutaneously once at dosage 0.016, 0.08, 0.40, 2.0, or 50 mg/kg with the modified oligonucleotides shown below or with saline control. Each treatment group consisted of 3 animals. The mice were sacrificed 72 hours following administration, and organs and plasma were harvested for further analysis.

TABLE 115

| Modified Oligonucleotides | | | | |
|---|---|---|---|---|
| Compound ID | position of altered nucleotide in central region | modification of altered nucleotide | Chemistry Notation (5 to 3') | SEQ ID NO |
| 1270729 | n/a | n/a | $T_{ks}{}^{m}C_{ks}A_{ks}T_{ds}G_{ds}T_{ds}A_{ds}{}^{m}C_{ds}{}^{m}C_{ds}T_{ds}A_{ds}T_{ds}A_{ds}G_{ks}T_{ks}{}^{m}C_{k}$-THA-GalNAc | 107 |
| 1270733 | 2 | 2'-OMe | $T_{ks}{}^{m}C_{ks}A_{ks}T_{ds}GT_{ds}A_{ds}{}^{m}C_{ds}{}^{m}C_{ds}T_{ds}A_{ds}T_{ds}A_{ds}G_{ks}T_{ks}{}^{m}C_{k}$-THA-GalNAc | 107 |
| 1270734 | 2 | MOP | $T_{ks}{}^{m}C_{ks}A_{ks}T_{ds}G_{dx}T_{ds}A_{ds}{}^{m}C_{ds}{}^{m}C_{ds}T_{ds}A_{ds}T_{ds}A_{ds}G_{ks}T_{ks}{}^{m}C_{k}$-THA-GalNAc | 107 |

A subscript "d" indicates an unmodified, 2'-β-D-deoxyribosyl sugar moiety. A subscript "k" indicates a cEt. A subscript "m" indicates a 2'-O-methyl-β-D-ribofuranosyl sugar moiety. A subscript "s" indicates a phosphorothioate internucleoside linkage. A superscript "m" before a C indicates 5-methyl Cytosine. A subscript "x" indicates a MOP internucleoside linkage.

TABLE 116

| In vivo Activity and Toxicity of Modified Oligonucleotides | | | | | |
|---|---|---|---|---|---|
| Compound ID | Dose (mg/kg) | ALT (IU/L) | P21 mRNA (% Control) | Tnfrsf10b mRNA (% Control) | HDAC2 ED50 (mg/kg) |
| 1270729 | 0.016 | 6 | 69 | 123 | 0.76 |
| | 0.08 | 14 | 61 | 136 | |
| | 0.40 | 13 | 71 | 142 | |
| | 2.0 | 17 | 174 | 154 | |
| | 50 | 3655 | 7927 | 5297 | |
| 1270730 | 0.016 | 31 | 107 | 124 | 1.05 |
| | 0.08 | 10 | 144 | 132 | |
| | 0.40 | 17 | 65 | 99 | |
| | 2.0 | 9 | 88 | 123 | |
| | 50 | 11 | 110 | 164 | |
| 1270731 | 0.016 | 22 | 88 | 135 | 1.28 |
| | 0.08 | 13 | 86 | 101 | |
| | 0.40 | 20 | 135 | 138 | |
| | 2.0 | 13 | 66 | 137 | |
| | 50 | 6 | 76 | 164 | |

n.d. means a value was not determined.

Example 55

Modified oligonucleotides were designed based on 747149, described in Example 13 above. Each of the modified oligonucleotides is conjugated with a THA-GalNAc conjugate group at the 3'-end as described in Example 53 above. The oligonucleotides were evaluated for reduction in FBO1A mRNA expression levels in vivo. P21 and Tnfrsf10b mRNA levels were also measured. The transaminase levels (ALT and AST) for each dose were also measured.

Six week old BALB/C mice (purchased from Charles River) were injected subcutaneously once at dosage 0.025, 0.10, 0.40, 1.6, 6.4, or 50 mg/kg with the modified oligonucleotides shown below or with saline control. Each treatment group consisted of 3 animals. The mice were sacrificed 72 hours following administration, and organs and plasma were harvested for further analysis.

TABLE 117

| Modified Oligonucleotides | | | | |
|---|---|---|---|---|
| Compound ID | position of altered nucleotide in central region | modification of altered nucleotide modifi- | Chemistry Notation (5' to 3') | SEQ ID NO |
| 1270738 | N/A | N/A | $G_{ks}G_{ks}A_{ks}{}^{m}C_{ds}T_{ds}G_{ds}A_{ds}A_{ds}A_{ds}T_{ds}A_{ds}G_{ds}{}^{m}C_{ds}A_{ks}G_{ks}A_{k}$-THA-GalNAc | 54 |
| 1270739 | 2 | 2'-OMe | $G_{ks}G_{ks}A_{ks}{}^{m}C_{ds}U_{ms}G_{ds}A_{ds}A_{ds}A_{ds}T_{ds}A_{ds}G_{ds}{}^{m}C_{ds}A_{ks}G_{ks}A_{k}$-THA-GalNAc | 130 |
| 1270740 | 2 | MOP | $G_{ks}G_{ks}A_{ks}{}^{m}C_{ds}T_{dx}G_{ds}A_{ds}A_{ds}A_{ds}T_{ds}A_{ds}G_{ds}{}^{m}C_{ds}A_{ks}G_{ks}A_{k}$-THA-GalNAc | 54 |

A subscript "d" indicates an unmodified, 2'-β-D-deoxyribosyl sugar moiety. A subscript "k" indicates a cEt. A subscript "s" indicates a phosphorothioate internucleoside linkage. A superscript "m" before a C indicates 5-methyl Cytosine. A subscript "x" indicates a MOP internucleoside linkage. A subscript "m" indicates a 2'-O-methyl-β-D-ribofuranosyl sugar moiety.

TABLE 118

| In vivo Activity and Toxicity of Modified Oligonucleotides | | | | | |
|---|---|---|---|---|---|
| Compound ID | Dose (mg/kg) | ALT (IU/L) | P21 mRNA (% Control) | Tnfrsf10b mRNA (% Control) | FBO1A ED50 (mg/kg) |
| 1270738 | 0.025 | 29 | 49 | 114 | 1.23 |
| | 0.10 | 18 | 46 | 119 | |
| | 0.40 | 30 | 156 | 133 | |
| | 1.6 | 62 | 273 | 258 | |
| | 6.4 | 177 | 1020 | 1426 | |
| | 50 | 1467 | 4296 | 10211 | |
| 1270739 | 0.025 | 10 | 66 | 115 | 5.16 |
| | 0.10 | 14 | 54 | 120 | |
| | 0.40 | 9 | 39 | 93 | |
| | 1.6 | 16 | 34 | 98 | |
| | 6.4 | 12 | 88 | 116 | |
| | 50 | 26 | 163 | 115 | |

TABLE 118-continued

| In vivo Activity and Toxicity of Modified Oligonucleotides | | | | | |
|---|---|---|---|---|---|
| Compound ID | Dose (mg/kg) | ALT (IU/L) | P21 mRNA (% Control) | Tnfrsf10b mRNA (% Control) | FBO1A ED50 (mg/kg) |
| 1270740 | 0.025 | 25 | 59 | 94 | 3.33 |
| | 0.10 | 20 | 79 | 143 | |
| | 0.40 | 22 | 81 | 110 | |
| | 1.6 | 7 | 68 | 146 | |
| | 6.4 | 27 | 195 | 165 | |
| | 50 | 102 | 1378 | 439 | |

Example 56

Modified oligonucleotides were designed based on 464924, described in Example 18 above. Each of the modified oligonucleotides is conjugated with a THA-GalNAc conjugate group at the 3'-end as described in Example 53 above. The oligonucleotides were evaluated for reduction in FXI mRNA expression levels in vivo. P21 and Tnfrsf10b mRNA levels were also measured. The transaminase levels (ALT and AST) for each dose were also measured.

Six week old BALB/C mice (purchased from Charles River) were injected subcutaneously once at dosage 0.025, 0.10, 0.40, 1.6, 6.4, or 50 mg/kg with the modified oligonucleotides shown below or with saline control. Each treatment group consisted of 3 animals. The mice were sacrificed 72 hours following administration, and organs and plasma were harvested for further analysis.

TABLE 119

| Modified Oligonucleotides | | | | |
|---|---|---|---|---|
| Compound ID | position of altered nucleotide in central region | modification of altered nucleotide modifi- | Chemistry Notation (5' to 3') | SEQ ID NO |
| 1270735 | N/A | N/A | $G_{ks}T_{ks}T_{ks}A_{ds}T_{ds}T_{ds}G_{ds}T_{ds}G_{ds}G_{ds}T_{ds}T_{ds}G_{ds}G_{ks}{}^{m}C_{ks}G_{k}$-THA-GalNAc | 81 |
| 1270736 | 2 | 2'-OMe | $G_{ks}T_{ks}T_{ks}A_{ds}U_{ms}T_{ds}G_{ds}T_{ds}G_{ds}G_{ds}T_{ds}T_{ds}G_{ds}G_{ks}{}^{m}C_{ks}G_{k}$-THA-GalNAc | 133 |
| 1270737 | 2 | MOP | $G_{ks}T_{ks}T_{ks}A_{ds}T_{dx}T_{ds}G_{ds}T_{ds}G_{ds}G_{ds}T_{ds}T_{ds}G_{ds}G_{ks}{}^{m}C_{ks}G_{k}$-THA-GalNAc | 81 |

A subscript "d" indicates an unmodified, 2'-β-D-deoxyribosyl sugar moiety. A subscript "k" indicates a cEt. A subscript "m" indicates a 2'-O-methyl-β-D-ribofuranosyl sugar moiety. A subscript "s" indicates a phosphorothioate internucleoside linkage. A superscript "m" before a C indicates 5-methyl Cytosine. A subscript "x" indicates a MOP internucleoside linkage.

TABLE 120

In vivo Activity and Toxicity of Modified Oligonucleotides

| Compound ID | Dose (mg/kg) | ALT (IU/L) | P21 mRNA (% Control) | Tnfrsf10b mRNA (% Control) | FBO1A ED50 (mg/kg) |
|---|---|---|---|---|---|
| 1270735 | 0.025 | 9 | 86 | 93 | 0.86 |
| | 0.10 | 8 | 26 | 66 | |
| | 0.40 | 10 | 94 | 81 | |
| | 1.6 | 22 | 69 | 95 | |
| | 6.4 | 3 | 114 | 137 | |
| | 50 | 30 | 266 | 308 | |
| 1270736 | 0.025 | 17 | 95 | 70 | 0.81 |
| | 0.10 | 26 | 53 | 65 | |
| | 0.40 | 29 | 77 | 58 | |
| | 1.6 | 11 | 53 | 93 | |
| | 6.4 | 12 | 64 | 90 | |
| | 50 | 28 | 92 | 125 | |
| 1270740 | 0.025 | 17 | 63 | 77 | 1.47 |
| | 0.10 | 14 | 83 | 101 | |
| | 0.40 | 9 | 62 | 72 | |
| | 1.6 | 21 | 98 | 105 | |

TABLE 120-continued

In vivo Activity and Toxicity of Modified Oligonucleotides

| Compound ID | Dose (mg/kg) | ALT (IU/L) | P21 mRNA (% Control) | Tnfrsf10b mRNA (% Control) | FBO1A ED50 (mg/kg) |
|---|---|---|---|---|---|
| | 6.4 | 12 | 33 | 104 | |
| | 50 | 11 | 168 | 214 | |

Example 57 Introduction of 5'-Alkyl Modifications In Vivo

Modified oligonucleotides containing a 5'-alkyl modified nucleoside in the central region were synthesized.

The oligonucleotides were evaluated for reduction in target mRNA expression levels in vivo. The transaminase levels (ALT and AST) for each dose were measured.

For the in vitro toxicity study in the table below, the caspase assay was performed essentially as described in Example 8 in Hepa1-6 cells.

Fr the in vivo toxicity and activity study in the table below, six week old BALB/C mice (purchased from Charles River) were injected subcutaneously once at dosage 1.8, 5.5, 16.7, 50, or 150 mg/kg with the modified oligonucleotides shown below or with saline control. Each treatment group consisted of 3 animals. The mice were sacrificed 72 hours following administration, and organs and plasma were harvested for further analysis.

TABLE 121

Modified Oligonucleotides

| Compound ID | Chemistry notation | SEQ ID NO: |
|---|---|---|
| 546108 | $T_{ks}A_{ks}G_{ks}T_{ds}{}^{m}C_{ds}T_{ds}{}^{m}C_{ds}T_{ds}G_{ds}T_{ds}{}^{m}C_{ds}A_{ds}G_{ds}T_{ks}T_{ks}A_{k}$ | 105 |
| 1133122 | $T_{ks}A_{ks}G_{ks}T_{ds}C_{ms}T_{ds}{}^{m}C_{ds}T_{ds}G_{ds}T_{ds}{}^{m}C_{ds}A_{ds}G_{ds}T_{ks}T_{ks}A_{k}$ | 105 |
| 1280765 | $T_{ks}A_{ks}G_{ks}T_{ds}{}^{m}C_{dx}T_{ds}{}^{m}C_{ds}T_{ds}G_{ds}T_{ds}{}^{m}C_{ds}A_{ds}G_{ds}T_{ks}T_{ks}A_{k}$ | 105 |
| 1280766 | $T_{ks}A_{ks}G_{ks}T_{ds}{}^{m}C_{ds}T_{[(R)-\mu]s}{}^{m}C_{ds}T_{ds}G_{ds}T_{ds}{}^{m}C_{ds}A_{ds}G_{ds}T_{ks}T_{ks}A_{k}$ | 105 |
| 1280767 | $T_{ks}A_{ks}G_{ks}T_{ds}{}^{m}C_{ds}T_{ds}{}^{m}C_{[(R)-\mu]s}{}^{m}T_{ds}G_{ds}T_{ds}{}^{m}C_{ds}A_{ds}G_{ds}T_{ks}T_{ks}A_{k}$ | 105 |
| 1280768 | $T_{ks}A_{ks}G_{ks}T_{ds}{}^{m}C_{ds}T_{[(R)-\varepsilon]s}{}^{m}C_{ds}T_{ds}G_{ds}T_{ds}{}^{m}C_{ds}A_{ds}G_{ds}T_{ks}T_{ks}A_{k}$ | 105 |
| 1280769 | $T_{ks}A_{ks}G_{ks}T_{ds}{}^{m}C_{ds}T_{ds}{}^{m}C_{[(R)-\varepsilon]s}{}^{m}T_{ds}G_{ds}T_{ds}{}^{m}C_{ds}A_{ds}G_{ds}T_{ks}T_{ks}A_{k}$ | 105 |
| 694804 | $A_{ks}G_{ks}A_{ks}{}^{m}C_{ds}T_{ds}{}^{m}C_{ds}T_{ds}{}^{m}C_{ds}G_{ds}G_{ds}T_{ds}T_{ds}{}^{m}C_{ds}{}^{m}C_{ks}G_{ks}A_{k}$ | 49 |
| 1202810 | $A_{ks}G_{ks}A_{ks}{}^{m}C_{ds}U_{ms}{}^{m}C_{ds}T_{ds}{}^{m}C_{ds}G_{ds}G_{ds}T_{ds}T_{ds}{}^{m}C_{ds}{}^{m}C_{ks}G_{ks}A_{k}$ | 127 |
| 1280776 | $A_{ks}G_{ks}A_{ks}{}^{m}C_{ds}T_{dx}{}^{m}C_{ds}T_{ds}{}^{m}C_{ds}G_{ds}G_{ds}T_{ds}T_{ds}{}^{m}C_{ds}{}^{m}C_{ks}G_{ks}A_{k}$ | 49 |
| 1280785 | $A_{ks}G_{ks}A_{ks}{}^{m}C_{ds}T_{ds}{}^{m}C_{[(R)-\mu]s}T_{ds}{}^{m}C_{ds}G_{ds}G_{ds}T_{ds}T_{ds}{}^{m}C_{ds}{}^{m}C_{ks}G_{ks}A_{k}$ | 49 |
| 1280795 | $A_{ks}G_{ks}A_{ks}{}^{m}C_{ds}T_{ds}{}^{m}C_{ds}T_{[(R)-\mu]s}{}^{m}C_{ds}G_{ds}G_{ds}T_{ds}T_{ds}{}^{m}C_{ds}{}^{m}C_{ks}G_{ks}A_{k}$ | 49 |
| 1280804 | $A_{ks}G_{ks}A_{ks}{}^{m}C_{ds}T_{ds}{}^{m}C_{[(R)-\varepsilon]s}T_{ds}{}^{m}C_{ds}G_{ds}G_{ds}T_{ds}T_{ds}{}^{m}C_{ds}{}^{m}C_{ks}G_{ks}A_{k}$ | 49 |
| 1280810 | $A_{ks}G_{ks}A_{ks}{}^{m}C_{ds}T_{ds}{}^{m}C_{ds}T_{[(R)-\varepsilon]s}{}^{m}C_{ds}G_{ds}G_{ds}T_{ds}T_{ds}{}^{m}C_{ds}{}^{m}C_{ks}G_{ks}A_{k}$ | 49 |
| 465178 | $G_{ks}T_{ks}{}^{m}C_{ks}A_{ds}G_{ds}T_{ds}A_{ds}T_{ds}{}^{m}C_{ds}{}^{m}C_{ds}{}^{m}C_{ds}A_{ds}G_{ds}T_{ks}G_{ks}T_{k}$ | 89 |
| 1133332 | $G_{ks}T_{ks}{}^{m}C_{ks}A_{ds}G_{ms}T_{ds}A_{ds}T_{ds}{}^{m}C_{ds}{}^{m}C_{ds}{}^{m}C_{ds}A_{ds}G_{ds}T_{ks}G_{ks}T_{k}$ | 89 |
| 1280775 | $G_{ks}T_{ks}{}^{m}C_{ks}A_{ds}G_{dx}T_{ds}A_{ds}T_{ds}{}^{m}C_{ds}{}^{m}C_{ds}{}^{m}C_{ds}A_{ds}G_{ds}T_{ks}G_{ks}T_{k}$ | 89 |
| 1280784 | $G_{ks}T_{ks}{}^{m}C_{ks}A_{ds}G_{ds}T_{[(R)-\mu]s}A_{ds}T_{ds}{}^{m}C_{ds}{}^{m}C_{ds}{}^{m}C_{ds}A_{ds}G_{ds}T_{ks}G_{ks}T_{k}$ | 89 |
| 1280794 | $G_{ks}T_{ks}{}^{m}C_{ks}A_{ds}G_{ds}T_{ds}A_{[(R)-\mu]s}T_{ds}{}^{m}C_{ds}{}^{m}C_{ds}{}^{m}C_{ds}A_{ds}G_{ds}T_{ks}G_{ks}T_{k}$ | 89 |
| 1280803 | $G_{ks}T_{ks}{}^{m}C_{ks}A_{ds}G_{ds}T_{[(R)-\varepsilon]s}A_{ds}T_{ds}{}^{m}C_{ds}{}^{m}C_{ds}{}^{m}C_{ds}A_{ds}G_{ds}T_{ks}G_{ks}T_{k}$ | 89 |
| 1281809 | $G_{ks}T_{ks}{}^{m}C_{ks}A_{ds}G_{ds}T_{ds}A_{[(R)-\varepsilon]s}T_{ds}{}^{m}C_{ds}{}^{m}C_{ds}{}^{m}C_{ds}A_{ds}G_{ds}T_{ks}G_{ks}T_{k}$ | 89 |
| 546110 | $T_{ks}{}^{m}C_{ks}A_{ks}T_{ds}G_{ds}T_{ds}A_{ds}{}^{m}C_{ds}{}^{m}C_{ds}T_{ds}A_{ds}T_{ds}A_{ds}G_{ks}T_{ks}{}^{m}C_{k}$ | 107 |
| 1133201 | $T_{ks}{}^{m}C_{ks}A_{ks}T_{ds}G_{ms}T_{ds}A_{ds}{}^{m}C_{ds}{}^{m}C_{ds}T_{ds}A_{ds}T_{ds}A_{ds}G_{ks}T_{ks}{}^{m}C_{k}$ | 107 |
| 1280778 | $T_{ks}{}^{m}C_{ks}A_{ks}T_{ds}G_{dx}T_{ds}A_{ds}{}^{m}C_{ds}{}^{m}C_{ds}T_{ds}A_{ds}T_{ds}A_{ds}G_{ks}T_{ks}{}^{m}C_{k}$ | 107 |
| 1280779 | $T_{ks}{}^{m}C_{ks}A_{ks}T_{ds}G_{ds}T_{[(R)-\mu]s}A_{ds}{}^{m}C_{ds}{}^{m}C_{ds}T_{ds}A_{ds}T_{ds}A_{ds}G_{ks}T_{ks}{}^{m}C_{k}$ | 107 |
| 1280789 | $T_{ks}{}^{m}C_{ks}A_{ks}T_{ds}G_{ds}T_{ds}A_{[(R)-\mu]s}{}^{m}C_{ds}{}^{m}C_{ds}T_{ds}A_{ds}T_{ds}A_{ds}G_{ks}T_{ks}{}^{m}C_{k}$ | 107 |
| 1280798 | $T_{ks}{}^{m}C_{ks}A_{ks}T_{ds}G_{ds}T_{[(R)-\varepsilon]s}A_{ds}{}^{m}C_{ds}{}^{m}C_{ds}T_{ds}A_{ds}T_{ds}A_{ds}G_{ks}T_{ks}{}^{m}C_{k}$ | 107 |
| 1281804 | $T_{ks}{}^{m}C_{ks}A_{ks}T_{ds}G_{ds}T_{ds}A_{[(R)-\varepsilon]s}{}^{m}C_{ds}{}^{m}C_{ds}T_{ds}A_{ds}T_{ds}A_{ds}G_{ks}T_{ks}{}^{m}C_{k}$ | 107 |
| 464924 | $G_{ks}T_{ks}T_{ks}A_{ds}T_{ds}T_{ds}G_{ds}T_{ds}G_{ds}G_{ds}T_{ds}T_{ds}G_{ds}G_{ks}{}^{m}C_{ks}G_{k}$ | 81 |
| 1133247 | $G_{ks}T_{ks}T_{ks}A_{ds}U_{ms}T_{ds}G_{ds}T_{ds}G_{ds}G_{ds}T_{ds}T_{ds}G_{ds}G_{ks}{}^{m}C_{ks}G_{k}$ | 133 |
| 1280774 | $G_{ks}T_{ks}T_{ks}A_{ds}T_{dx}T_{ds}G_{ds}T_{ds}G_{ds}G_{ds}T_{ds}T_{ds}G_{ds}G_{ks}{}^{m}C_{ks}G_{k}$ | 81 |
| 1280783 | $G_{ks}T_{ks}T_{ks}A_{ds}T_{ds}T_{[(R)-\mu]s}G_{ds}T_{ds}G_{ds}G_{ds}T_{ds}T_{ds}G_{ds}G_{ks}{}^{m}C_{ks}G_{k}$ | 81 |
| 1280793 | $G_{ks}T_{ks}T_{ks}A_{ds}T_{ds}T_{ds}G_{[(R)-\mu]s}T_{ds}G_{ds}G_{ds}T_{ds}T_{ds}G_{ds}G_{ks}{}^{m}C_{ks}G_{k}$ | 81 |
| 747149 | $G_{ks}G_{ks}A_{ks}{}^{m}C_{ds}T_{ds}G_{ds}A_{ds}A_{ds}A_{ds}T_{ds}A_{ds}G_{ds}{}^{m}C_{ds}A_{ks}G_{ks}A_{k}$ | 54 |
| 1203759 | $G_{ks}G_{ks}A_{ks}{}^{m}C_{ds}U_{ms}G_{ds}A_{ds}A_{ds}A_{ds}T_{ds}A_{ds}G_{ds}{}^{m}C_{ds}A_{ks}G_{ks}A_{k}$ | 130 |

TABLE 121-continued

| Modified Oligonucleotides | | |
|---|---|---|
| Compound ID | Chemistry notation | SEQ ID NO: |
| 1280778 | $G_{ks}G_{ks}A_{ks}{}^{m}C_{ds}T_{dx}G_{ds}A_{ds}A_{ds}A_{ds}T_{ds}A_{ds}G_{ds}{}^{m}C_{ds}A_{ks}G_{ks}A_{k}$ | 54 |
| 1280787 | $G_{ks}G_{ks}A_{ks}{}^{m}C_{ds}T_{ds}G_{[(R)\text{-}\mu]s}A_{ds}A_{ds}A_{ds}T_{ds}A_{ds}G_{ds}{}^{m}C_{ds}A_{ks}G_{ks}A_{k}$ | 54 |
| 1280797 | $G_{ks}G_{ks}A_{ks}{}^{m}C_{ds}T_{ds}G_{ds}A_{[(R)\text{-}\mu]s}A_{ds}A_{ds}T_{ds}A_{ds}G_{ds}{}^{m}C_{ds}A_{ks}G_{ks}A_{k}$ | 54 |

A subscript "d" indicates an unmodified, 2'-β-D-deoxyribosyl sugar moiety. A subscript "k" indicates a cEt. A subscript "s" indicates a phosphorothioate internucleoside linkage. A subscript "[(R)-μ]" indicates a 5'-(R)-Me-β-D-2'-deoxyribosyl sugar moiety. A subscript "[(R)-ε]" indicates a 5'-(R)-ethyl-β-D-2'-deoxyribosyl sugar moiety.

TABLE 122

| Activity and Toxicity in vitro and in vivo | | | | | | |
|---|---|---|---|---|---|---|
| Compound ID | Target | position of altered nucleoside in central region | modification of altered nucleoside | in vivo Target $ED_{50}$ (mg/kg) | in vivo ALT @150 mg/kg | Relative Caspase Activation (% Control) @20 μM |
| 546108 | HDAC2 | N/A | N/A | n.d. | n.d. | 2436 |
| 1133122 | HDAC2 | 2 | 2'-OMe | 6.1 | 127 | 103 |
| 1280765 | HDAC2 | 2 | MOP | 7.7 | 29 | 157 |
| 1280766 | HDAC2 | 3 | 5'-(R)-Me | 4.5 | 61 | 158 |
| 1280767 | HDAC2 | 4 | 5'-(R)-Me | 5.9 | 79 | 122 |
| 1280768 | HDAC2 | 3 | 5'-(R)-Et | 8.6 | 39 | 70 |
| 1280769 | HDAC2 | 4 | 5'-(R)-Et | 9.6 | 55 | 90 |
| 694804 | DMN2 | N/A | N/A | n.d. | n.d. | 1443 |
| 1202810 | DMN2 | 2 | 2'-OMe | 14.7 | 50 | 70 |
| 1280776 | DMN2 | 2 | MOP | 8.6 | 24 | 214 |
| 1280785 | DMN2 | 3 | 5'-(R)-Me | 6.2 | 92 | 285 |
| 1280795 | DMN2 | 4 | 5'-(R)-Me | 7.3 | 27 | 113 |
| 1280804 | DMN2 | 3 | 5'-(R)-Et | 14.9 | 36 | 135 |
| 1280810 | DMN2 | 4 | 5'-(R)-Et | 16.2 | 26 | 211 |
| 465178 | FXI | N/A | N/A | n.d. | n.d. | 506 |
| 1133332 | FXI | 2 | 2'-OMe | 2.0 | 119 | 168 |
| 1280775 | FXI | 2 | MOP | 2.5 | 153 | 136 |
| 1280784 | FXI | 3 | 5'-(R)-Me | 1.7 | 260 | 145 |
| 1280794 | FXI | 4 | 5'-(R)-Me | 2.3 | 358 | 165 |
| 1280803 | FXI | 3 | 5'-(R)-Et | 4.9 | 122 | 104 |
| 1281809 | FXI | 4 | 5'-(R)-Et | 21.2 | 56 | 93 |
| 546110 | FXI | N/A | N/A | n.d. | n.d. | 404 |
| 1133201 | FXI | 2 | 2'-OMe | 10.6 | 127 | 96 |
| 1280778 | FXI | 2 | MOP | 26.6 | 29 | 105 |
| 1280779 | FXI | 3 | 5'-(R)-Me | 10.9 | 61 | 84 |
| 1280789 | FXI | 4 | 5'-(R)-Me | 11.7 | 79 | 74 |
| 1280798 | FXI | 3 | 5'-(R)-Et | 30.5 | 39 | 78 |
| 1281804 | FXI | 4 | 5'-(R)-Et | 31.5 | 55 | 80 |
| 464924 | FXI | N/A | N/A | n.d. | n.d. | n.d. |
| 1133247 | FXI | 2 | 2'-OMe | 4.6 | 51 | n.d. |
| 1280774 | FXI | 2 | MOP | 3.7 | 37 | n.d. |
| 1280783 | FXI | 3 | 5'-(R)-Me | 3.6 | 48 | n.d. |
| 1280793 | FXI | 4 | 5'-(R)-Me | 2.3 | 351 | n.d. |
| 747149 | FOXO1A | N/A | N/A | n.d. | n.d. | n.d. |
| 1203759 | FOXO1A | 2 | 2'-OMe | 24.9 | 30 | n.d. |
| 1280778 | FOXO1A | 2 | MOP | 8.5 | 35 | n.d. |
| 1280787 | FOXO1A | 3 | 5'-(R)-Me | 65.9 | 62 | n.d. |
| 1280797 | FOXO1A | 4 | 5'-(R)-Me | 20.4 | 22 | n.d. |

Example 58 Nucleosides with Chiral Phosphorothioate Linkages

Modified oligonucleotides containing chirally-controlled phosphorothioate linkages in the central region were synthesized. The compounds in the table below are 100% complementary to mouse CXCL12, GENBANK NT_039353.7 truncated from 69/430,515 to 69/445,350 (SEQ ID NO: 1), at position 6877 to 6892. Each compound has the kkk-d(10)-kkk sugar motif, wherein each "k" represents a 2'-constrained ethyl modified sugar moiety and each "d" represents a 2'-deoxy sugar moiety. Internucleoside linkages 1, 2, 3, 14, and 15 are stereorandom phosphorothioate linkages. Internucleoside linkages 4-13 have the stereochemistry indicated in the table below, wherein a subscript "s" indicates a stereorandom phosphorothioate internucleoside linkage, a subscript "r" indicates a phosphorothioate internucleoside linkage having the (Rp) configuration and a subscript "q" indicates a phosphorothioate internucleoside linkage having the (Sp) configuration.

-continued

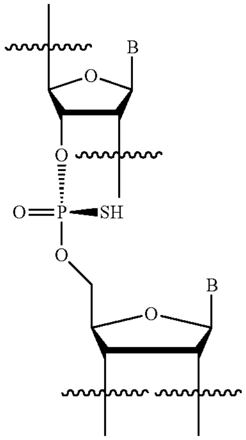

(Rp)

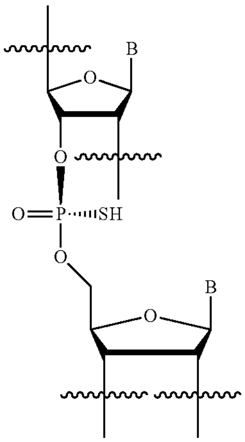

(Sp)

TABLE 123

| modified oligonucleotides with stereochemically-controlled phosphorothioate linkages | | |
|---|---|---|
| Compound ID | Chemistry Notation | SEQ ID NO |
| 558807 | $G_{ks}{}^{m}C_{ks}A_{ks}T_{ds}G_{ds}T_{ds}T_{ds}{}^{m}C_{ds}T_{ds}{}^{m}C_{ds}A_{ds}{}^{m}C_{ds}A_{ds}T_{ks}T_{ks}A_{k}$ | 18 |
| 1220041 | $G_{ks}{}^{m}C_{ks}A_{ks}T_{dq}G_{dq}T_{dq}T_{dq}{}^{m}C_{dq}T_{dq}{}^{m}C_{dq}A_{dq}{}^{m}C_{dq}A_{dq}T_{ks}T_{ks}A_{k}$ | 18 |
| 1220042 | $G_{ks}{}^{m}C_{ks}A_{ks}T_{dr}G_{dq}T_{dq}T_{dq}{}^{m}C_{dq}T_{dq}{}^{m}C_{dq}A_{dq}{}^{m}C_{dq}A_{dq}T_{ks}T_{ks}A_{k}$ | 18 |
| 1220043 | $G_{ks}{}^{m}C_{ks}A_{ks}T_{dq}G_{dq}T_{dq}T_{dq}{}^{m}C_{dq}T_{dq}{}^{m}C_{dq}A_{dq}{}^{m}C_{dq}A_{dq}T_{ks}T_{ks}A_{k}$ | 18 |
| 1220044 | $G_{ks}{}^{m}C_{ks}A_{ks}T_{dq}G_{dq}T_{dq}T_{dq}{}^{m}C_{dq}T_{dq}{}^{m}C_{dq}A_{dq}{}^{m}C_{dq}A_{dq}T_{ks}T_{ks}A_{k}$ | 18 |
| 1220045 | $G_{ks}{}^{m}C_{ks}A_{ks}T_{dq}G_{dq}T_{dq}T_{dr}{}^{m}C_{dq}T_{dq}{}^{m}C_{dq}A_{dq}{}^{m}C_{dq}A_{dq}T_{ks}T_{ks}A_{k}$ | 18 |
| 1220046 | $G_{ks}{}^{m}C_{ks}A_{ks}T_{dq}G_{dq}T_{dq}T_{dq}{}^{m}C_{dr}T_{dq}{}^{m}C_{dq}A_{dq}{}^{m}C_{dq}A_{dq}T_{ks}T_{ks}A_{k}$ | 18 |
| 1220051 | $G_{ks}{}^{m}C_{ks}A_{ks}T_{dq}G_{dq}T_{dq}T_{dq}{}^{m}C_{dq}T_{dr}{}^{m}C_{dq}A_{dq}{}^{m}C_{dq}A_{dq}T_{ks}T_{ks}A_{k}$ | 18 |
| 1220047 | $G_{ks}{}^{m}C_{ks}A_{ks}T_{dq}G_{dq}T_{dq}T_{dq}{}^{m}C_{dq}T_{dq}{}^{m}C_{dr}A_{dq}{}^{m}C_{dq}A_{dq}T_{ks}T_{ks}A_{k}$ | 18 |
| 1220048 | $G_{ks}{}^{m}C_{ks}A_{ks}T_{dq}G_{dq}T_{dq}T_{dq}{}^{m}C_{dq}T_{dq}{}^{m}C_{dq}A_{dr}{}^{m}C_{dq}A_{dq}T_{ks}T_{ks}A_{k}$ | 18 |
| 1220049 | $G_{ks}{}^{m}C_{ks}A_{ks}T_{dq}G_{dq}T_{dq}T_{dq}{}^{m}C_{dq}T_{dq}{}^{m}C_{dq}A_{dq}{}^{m}C_{dr}A_{dq}T_{ks}T_{ks}A_{k}$ | 18 |
| 1220050 | $G_{ks}{}^{m}C_{ks}A_{ks}T_{dq}G_{dq}T_{dq}T_{dq}{}^{m}C_{dq}T_{dq}{}^{m}C_{dq}A_{dq}{}^{m}C_{dq}A_{dr}T_{ks}T_{ks}A_{k}$ | 18 |
| 1237987 | $G_{ks}{}^{m}C_{ks}A_{ks}T_{dq}G_{dq}T_{dq}T_{dq}{}^{m}C_{dq}T_{dq}{}^{m}C_{dq}A_{dq}{}^{m}C_{dr}A_{dr}T_{ks}T_{ks}A_{k}$ | 18 |
| 1237988 | $G_{ks}{}^{m}C_{ks}A_{ks}T_{dq}G_{dq}T_{dq}T_{dq}{}^{m}C_{dq}T_{dq}{}^{m}C_{dr}A_{dr}{}^{m}C_{dq}A_{dq}T_{ks}T_{ks}A_{k}$ | 18 |
| 1237989 | $G_{ks}{}^{m}C_{ks}A_{ks}T_{dq}G_{dq}T_{dq}T_{dq}{}^{m}C_{dr}T_{dr}{}^{m}C_{dq}A_{dq}{}^{m}C_{dq}A_{dq}T_{ks}T_{ks}A_{k}$ | 18 |
| 1237990 | $G_{ks}{}^{m}C_{ks}A_{ks}T_{dq}G_{dq}T_{dr}T_{dr}{}^{m}C_{dq}T_{dq}{}^{m}C_{dq}A_{dq}{}^{m}C_{dq}A_{dq}T_{ks}T_{ks}A_{k}$ | 18 |
| 1237991 | $G_{ks}{}^{m}C_{ks}A_{ks}T_{dr}G_{dr}T_{dq}T_{dq}{}^{m}C_{dq}T_{dq}{}^{m}C_{dq}A_{dq}{}^{m}C_{dq}A_{dq}T_{ks}T_{ks}A_{k}$ | 18 |
| 1220052 | $G_{ks}{}^{m}C_{ks}A_{ks}T_{dr}G_{dr}T_{dr}T_{dr}{}^{m}C_{dr}T_{dr}{}^{m}C_{dr}A_{dr}{}^{m}C_{dr}A_{dr}T_{ks}T_{ks}A_{k}$ | 18 |
| 1220053 | $G_{ks}{}^{m}C_{ks}A_{ks}T_{dq}G_{dr}T_{dr}T_{dr}{}^{m}C_{dr}T_{dr}{}^{m}C_{dr}A_{dr}{}^{m}C_{dr}A_{dr}T_{ks}T_{ks}A_{k}$ | 18 |
| 1220054 | $G_{ks}{}^{m}C_{ks}A_{ks}T_{dr}G_{dq}T_{dr}T_{dr}{}^{m}C_{dr}T_{dr}{}^{m}C_{dr}A_{dr}{}^{m}C_{dr}A_{dr}T_{ks}T_{ks}A_{k}$ | 18 |
| 1220055 | $G_{ks}{}^{m}C_{ks}A_{ks}T_{dr}G_{dr}T_{dq}T_{dr}{}^{m}C_{dr}T_{dr}{}^{m}C_{dr}A_{dr}{}^{m}C_{dr}A_{dr}T_{ks}T_{ks}A_{k}$ | 18 |
| 1220056 | $G_{ks}{}^{m}C_{ks}A_{ks}T_{dr}G_{dr}T_{dr}T_{dq}{}^{m}C_{dr}T_{dr}{}^{m}C_{dr}A_{dr}{}^{m}C_{dr}A_{dr}T_{ks}T_{ks}A_{k}$ | 18 |
| 1220057 | $G_{ks}{}^{m}C_{ks}A_{ks}T_{dr}G_{dr}T_{dr}T_{dr}{}^{m}C_{dq}T_{dr}{}^{m}C_{dr}A_{dr}{}^{m}C_{dr}A_{dr}T_{ks}T_{ks}A_{k}$ | 18 |
| 1220058 | $G_{ks}{}^{m}C_{ks}A_{ks}T_{dr}G_{dr}T_{dr}T_{dr}{}^{m}C_{dr}T_{dq}{}^{m}C_{dr}A_{dr}{}^{m}C_{dr}A_{dr}T_{ks}T_{ks}A_{k}$ | 18 |
| 1220059 | $G_{ks}{}^{m}C_{ks}A_{ks}T_{dr}G_{dr}T_{dr}T_{dr}{}^{m}C_{dr}T_{dr}{}^{m}C_{dq}A_{dr}{}^{m}C_{dr}A_{dr}T_{ks}T_{ks}A_{k}$ | 18 |
| 1220060 | $G_{ks}{}^{m}C_{ks}A_{ks}T_{dr}G_{dr}T_{dr}T_{dr}{}^{m}C_{dr}T_{dr}{}^{m}C_{dr}A_{dq}{}^{m}C_{dr}A_{dr}T_{ks}T_{ks}A_{k}$ | 18 |
| 1220061 | $G_{ks}{}^{m}C_{ks}A_{ks}T_{dr}G_{dr}T_{dr}T_{dr}{}^{m}C_{dr}T_{dr}{}^{m}C_{dr}A_{dr}{}^{m}C_{dq}A_{dr}T_{ks}T_{ks}A_{k}$ | 18 |
| 1220062 | $G_{ks}{}^{m}C_{ks}A_{ks}T_{dr}G_{dr}T_{dr}T_{dr}{}^{m}C_{dr}T_{dr}{}^{m}C_{dr}A_{dr}{}^{m}C_{dr}A_{dq}T_{ks}T_{ks}A_{k}$ | 18 |
| 1220063 | $G_{ks}{}^{m}C_{ks}A_{ks}T_{dq}G_{dq}T_{dr}T_{dq}{}^{m}C_{dq}T_{dr}{}^{m}C_{dq}A_{dq}{}^{m}C_{dr}A_{dr}T_{ks}T_{ks}A_{k}$ | 18 |
| 1220064 | $G_{ks}{}^{m}C_{ks}A_{ks}T_{dr}G_{dr}T_{dq}T_{dr}{}^{m}C_{dr}T_{dq}{}^{m}C_{dr}A_{dr}{}^{m}C_{dq}A_{dq}T_{ks}T_{ks}A_{k}$ | 18 |

A subscript "d" an unmodified, 2'-β-D-deoxyribosyl sugar moiety. A subscript "k" indicates a cEt. A superscript "m" before a C indicates 5-methyl Cytosine. A subscript "s" indicates a stereorandom phosphorothioate internucleoside linkage, a subscript "r" indicates a phosphorothioate internucleoside linkage having the (Rp) configuration, and a subscript "q" indicates a phosphorothioate internucleoside linkage having the (Sp) configuration.

For in vitro activity studies, 3T3-L1 cells were plated at 20,000 cells/well and transfected with 27 nM, 80 nM, 250 nM, 740 nM, 2,222 nM, 6,667 nM, or 20,000 nMnM modified oligonucleotide by electroporation. mRNA was harvested and analyzed by RT-qPCR. CXCL12 mRNA was detected with primer probe set RTS 2605 (forward sequence CCAGAGCCAACGTCAAGCAT, SEQ ID NO: 9; reverse sequence: CAGCCGTGCAACAATCTGAA, SEQ ID NO: 10; probe sequence: TGAAAATCCTCAACACTCCAAACTGTGCC, SEQ ID NO: 11) and P21 mRNA was detected with primer probe set Mm04207341_ml (ThermoFisher).

Caspase-3 and caspase-7 activation was measured using the Caspase-Glo® 3/7 Assay System (G8090, Promega). Levels of caspase activation correlate with apoptotic cell death. Results are presented relative to the caspase activation in control cells not treated with modified oligonucleotide. Localization of p54nrb in HeLa cells was visualized with confocal microscopy. HeLa cells were transfected by lipofectamine 2000 with 200 nM of modified oligonucleotide for 2 hrs and then cellular protein p54nrb was stained by mP54 antibody (Santa Cruz Biotech, sc-376865) and DAPI was used to stain for the nucleus of cells. The number of cells with nucleolar p54nrb and the total number of cells in the images were counted. The self-structure Tm of each compound was determined.

TABLE 124

In vitro activity, toxicity, and Tm of modified oligonucleotides complementary to CXCL12

| Compound ID | in vitro CXCL12 $IC_{50}$ (nM) | in vitro Caspase (% control) @ 20 μM | P21 mRNA (% control) @ 20 μM | % nucleolar p54nrb | Tm (° C.) |
|---|---|---|---|---|---|
| 558807 | 39 | 1437 | 353 | 90 | 64.4 |
| 1220041 | 388 | 223 | 182 | 0 | 61.3 |
| 1220042 | 159 | 584 | 431 | 32 | 62.1 |
| 1220043 | 114 | 838 | 488 | 88 | 62 |
| 1220044 | 181 | 489 | 251 | 18 | 61.5 |
| 1220045 | 222 | 321 | 259 | 9.7 | 61.9 |
| 1220046 | 145 | 572 | 635 | 28 | 61.7 |
| 1220051 | 237 | 310 | 167 | 20 | 61.6 |
| 1220047 | 60 | 814 | 238 | 38 | 61.5 |
| 1220048 | 74 | 287 | 174 | 38 | 61.3 |
| 1220049 | 77 | 323 | 243 | 17 | 61.6 |
| 1220050 | 132 | 174 | 121 | 6.4 | 61.5 |
| 1237987 | 26 | 317 | 273 | 3.9 | 62.2 |
| 1237988 | 20 | 336 | 236 | 23 | 62.1 |

TABLE 124-continued

In vitro activity, toxicity, and Tm of modified oligonucleotides complementary to CXCL12

| Compound ID | in vitro CXCL12 $IC_{50}$ (nM) | in vitro Caspase (% control) @ 20 μM | P21 mRNA (% control) @ 20 μM | % nucleolar p54nrb | Tm (° C.) |
|---|---|---|---|---|---|
| 1237989 | 72 | 300 | 394 | 28 | 62.2 |
| 1237990 | 186 | 299 | 355 | 14 | 62.5 |
| 1237991 | 35 | 562 | 585 | 77 | 63 |

TABLE 125

In vitro activity, toxicity, and Tm of modified oligonucleotides complementary to CXCL12

| Compound ID | in vitro CXCL12 $IC_{50}$ (nM) | in vitro Caspase (% control) @ 20 μM | P21 mRNA (% control) @ 20 μM | % nucleolar p54nrb | Tm |
|---|---|---|---|---|---|
| 558807 | 95 | 647 | 235 | 93 | 64.4 |
| 1220052 | 63 | 484 | 272 | 98 | 67.4 |
| 1220053 | 99 | 621 | 261 | 95 | 66.2 |
| 1220054 | 197 | 495 | 192 | 96 | 66.8 |
| 1220055 | 51 | 606 | 370 | 100 | 66.9 |
| 1220056 | 103 | 569 | 369 | 97 | 67 |
| 1220057 | 104 | 593 | 330 | 92 | 67.1 |
| 1220058 | 125 | 578 | 273 | 100 | 67.3 |
| 1220059 | 109 | 525 | 351 | 62 | 66.7 |
| 1220060 | 61 | 553 | 328 | 100 | 67.3 |
| 1220061 | 84 | 409 | 329 | 100 | 67.1 |
| 1220062 | 123 | 550 | 394 | 100 | 67.1 |
| 1220063 | 111 | 138 | 128 | 12 | 63.1 |
| 1220064 | 53 | 160 | 218 | 100 | 65.3 |

Example 59 Nucleosides with Chiral Phosphorothioate Linkages and 3'-GalNAc

Modified oligonucleotides containing chirally-controlled phosphorothioate linkages in the central region and a 3'-THA-GalNAc were synthesized. The compounds in the table below are 100% complementary to mouse CXCL12, GENBANK NT_039353.7 truncated from 69/430,515 to 69/445,350 (SEQ ID NO: 1), at position 6877 to 6892. Each compound has the kkk-d(10)-kkk sugar motif, wherein each "k" represents a 2'-constrained ethyl modified sugar moiety and each "d" represents a 2'-deoxy sugar moiety. Internucleoside linkages 1, 2, 3, 14, and 15 are stereorandom phosphorothioate linkages. Internucleoside linkages 4-13 have the stereochemistry indicated in the table below, wherein a subscript "s" indicates a stereorandom phosphorothioate internucleoside linkage, a subscript "r" indicates a phosphorothioate internucleoside linkage having the (Rp) configuration and a subscript "q" indicates a phosphorothioate internucleoside linkage having the (Sp) configuration.

THA-GalNAc refers to this structure at the 3' end of the molecule:

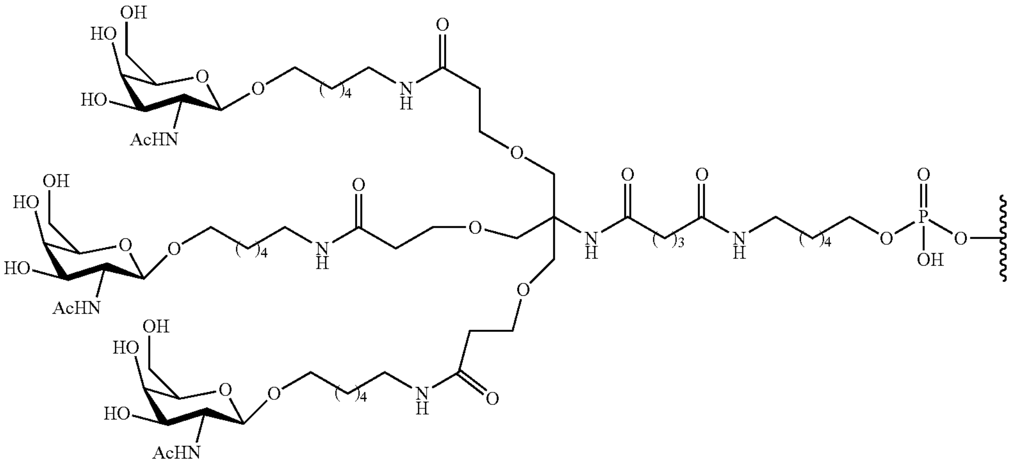

wherein the phosphate group is attached to the 3'-oxygen atom of the 3' nucleoside.

TABLE 126

| Compound ID | Chemistry Notation | SEQ ID NO |
|---|---|---|
| | Modified oligonucleotides | |
| 558807 | $G_{ks}{}^{m}C_{ks}A_{ks}T_{ds}G_{ds}T_{ds}T_{ds}{}^{m}C_{ds}T_{ds}{}^{m}C_{ds}A_{ds}{}^{m}C_{ds}A_{ds}T_{ks}T_{ks}A_{k}$ | 18 |
| 855156 | $G_{ks}{}^{m}C_{ks}A_{ks}T_{ds}G_{ds}T_{ds}T_{ds}{}^{m}C_{ds}T_{ds}{}^{m}C_{ds}A_{ds}{}^{m}C_{ds}A_{ds}T_{ks}T_{ks}A_{k}$-THA-GalNAc | 18 |
| 1220050 | $G_{ks}{}^{m}C_{ks}A_{ks}T_{dq}G_{dq}T_{dq}T_{dq}{}^{m}C_{dq}T_{dq}{}^{m}C_{dq}A_{dq}{}^{m}C_{dq}A_{dr}T_{ks}T_{ks}A_{k}$ | 18 |
| 1277251 | $G_{ks}{}^{m}C_{ks}A_{ks}T_{dq}G_{dq}T_{dq}T_{dq}{}^{m}C_{dq}T_{dq}{}^{m}C_{dq}A_{dq}{}^{m}C_{dq}A_{dr}T_{ks}T_{ks}A_{k}$-THA-GalNAc | 18 |
| 1220059 | $G_{ks}{}^{m}C_{ks}A_{ks}T_{dr}G_{dr}T_{dr}T_{dr}{}^{m}C_{dr}T_{dr}{}^{m}C_{dq}A_{dr}{}^{m}C_{dr}A_{dr}{}^{m}T_{ks}T_{ks}A_{k}$ | 18 |
| 1277252 | $G_{ks}{}^{m}C_{ks}A_{ks}T_{dr}G_{dr}T_{dr}T_{dr}{}^{m}C_{dr}T_{dr}{}^{m}C_{dq}A_{dr}{}^{m}C_{dr}A_{dr}T_{ks}T_{ks}A_{k}$-THA-GalNAc | 18 |
| 1220063 | $G_{ks}{}^{m}C_{ks}A_{ks}T_{dq}G_{dq}T_{dr}T_{dq}{}^{m}C_{dq}T_{dr}{}^{m}C_{dq}A_{dq}{}^{m}C_{dr}A_{dr}T_{ks}T_{ks}A_{k}$ | 18 |
| 1277253 | $G_{ks}{}^{m}C_{ks}A_{ks}T_{dq}G_{dq}T_{dr}T_{dq}{}^{m}C_{dq}T_{dr}{}^{m}C_{dq}A_{dq}{}^{m}C_{dr}A_{dr}T_{ks}T_{ks}A_{k}$-THA-GalNAc | 18 |
| 1237988 | $G_{ks}{}^{m}C_{ks}A_{ks}T_{dq}G_{dq}T_{dq}T_{dq}{}^{m}C_{dq}T_{dq}{}^{m}C_{dr}A_{dr}{}^{m}C_{dq}A_{dr}T_{ks}T_{ks}A_{k}$ | 18 |
| 1277254 | $G_{ks}{}^{m}C_{ks}A_{ks}T_{dq}G_{dq}T_{dq}T_{dq}{}^{m}C_{dq}T_{dq}{}^{m}C_{dr}A_{dr}{}^{m}C_{dq}A_{dr}T_{ks}T_{ks}A_{k}$-THA_GalNAc | 18 |

A subscript "d" indicates an unmodified, 2'-β-D-deoxyribosyl sugar moiety. A subscript "k" indicates a cEt. A superscript "m" indicates 5-methyl Cytosine. A subscript "s" indicates a stereorandom phosphorothioate internucleoside linkage, a subscript "r" indicates a phosphorothioate internucleoside linkage having the (Rp) configuration, and a subscript "q" indicates a phosphorothioate internucleoside linkage having the (Sp) configuration.

TABLE 127

| Compound ID | in vitro CXCL12 $IC_{50}$ (nM) | in vitro Caspase (% control) @ 20 μM | % nucleolar p54nrb |
|---|---|---|---|
| In vitro toxicity and activity of modified oligonucleotides | | | |
| 855156 | 40 | 1437 | 90 |
| 1277251 | 130 | 174 | 6.4 |
| 1277252 | 111 | 525 | 62 |
| 1277253 | 111 | 138 | 12 |
| 1277254 | 20 | 336 | 24 |

Example 60 Nucleosides with Two Chiral Phosphate Linkages in an Otherwise Stereorandom Phosphorthioate Nucleotide Modified oligonucleotides containing chirally-controlled phosphorothioate linkages at two positions of the central region were synthesized. The compounds in the table below are 100% complementary to mouse CXCL12, GENBANK NT_039353.7 truncated from 69/430,515 to 69/445,350 (SEQ ID NO: 1), at position 6877 to 6892. Each compound with an ID in the range of 1273959-1273967 has a kkk-d (10)-kkk sugar motif, wherein each "k" represents a 2'-constrained ethyl modified sugar moiety and each "d" represents a 2'-deoxy sugar moiety. Each compound with an ID in the range of 1276491-1276497 has a kkk-d-m-d(8)-kkk sugar motif, wherein each "k" represents a cEt and each "d" represents a nucleoside comprising an unmodified, 2'-β-D-deoxyribosyl sugar moiety and each "m" represents nucleoside comprising a a 2'-Omethyl modified sugar moiety. Internucleoside linkages are as indicated in the table below, wherein a subscript "s" indicates a stereorandom phosphorothioate internucleoside linkage, a subscript "r" indicates a phosphorothioate internucleoside linkage having the (Rp) configuration and a subscript "q" indicates a phosphorothioate internucleoside linkage having the (Sp) configuration. Each compound contains an "Rp/Sp" unit comprising an internucleoside linkage having the (Rp) configuration followed by an internucleoside linkage having the (Sp) configuration, from 5'-3'.

Compounds were tested in 3T3-L1 cells for caspase activation as described in Example 1 above.

TABLE 128

| Compound ID | Chemistry Notation | SEQ ID NO |
|---|---|---|
| Modified oligonucleotides | | |
| 1273959 | $G_{ks}{}^{m}C_{ks}A_{ks}T_{dr}G_{dq}T_{ds}T_{ds}{}^{m}C_{ds}T_{ds}{}^{m}C_{ds}A_{ds}{}^{m}C_{ds}A_{ds}T_{ks}T_{ks}A_{k}$ | 18 |
| 1273960 | $G_{ks}{}^{m}C_{ks}A_{ks}T_{ds}G_{dr}T_{dq}T_{ds}{}^{m}C_{ds}T_{ds}{}^{m}C_{ds}A_{ds}{}^{m}C_{ds}A_{ds}T_{ks}T_{ks}A_{k}$ | 18 |
| 1273961 | $G_{ks}{}^{m}C_{ks}A_{ks}T_{ds}G_{ds}T_{dr}T_{dq}{}^{m}C_{ds}T_{ds}{}^{m}C_{ds}A_{ds}{}^{m}C_{ds}A_{ds}T_{ks}T_{ks}A_{k}$ | 18 |
| 1273962 | $G_{ks}{}^{m}C_{ks}A_{ks}T_{ds}G_{ds}T_{ds}T_{dr}{}^{m}C_{dq}T_{ds}{}^{m}C_{ds}A_{ds}{}^{m}C_{ds}A_{ds}T_{ks}T_{ks}A_{k}$ | 18 |
| 1273963 | $G_{ks}{}^{m}C_{ks}A_{ks}T_{ds}G_{ds}T_{ds}T_{ds}{}^{m}C_{dr}T_{dq}{}^{m}C_{ds}A_{ds}{}^{m}C_{ds}A_{ds}T_{ks}T_{ks}A_{k}$ | 18 |
| 1273964 | $G_{ks}{}^{m}C_{ks}A_{ks}T_{ds}G_{ds}T_{ds}T_{ds}{}^{m}C_{ds}T_{dr}{}^{m}C_{dq}A_{ds}{}^{m}C_{ds}A_{ds}T_{ks}T_{ks}A_{k}$ | 18 |
| 1273965 | $G_{ks}{}^{m}C_{ks}A_{ks}T_{ds}G_{ds}T_{ds}T_{ds}{}^{m}C_{ds}T_{ds}{}^{m}C_{dr}A_{dq}{}^{m}C_{ds}A_{ds}T_{ks}T_{ks}A_{k}$ | 18 |
| 1273966 | $G_{ks}{}^{m}C_{ks}A_{ks}T_{ds}G_{ds}T_{ds}T_{ds}{}^{m}C_{ds}T_{ds}{}^{m}C_{ds}A_{dr}{}^{m}C_{dq}A_{ds}T_{ks}T_{ks}A_{k}$ | 18 |
| 1273967 | $G_{ks}{}^{m}C_{ks}A_{ks}T_{ds}G_{ds}T_{ds}T_{ds}{}^{m}C_{ds}T_{ds}{}^{m}C_{ds}A_{ds}{}^{m}C_{dr}A_{dq}T_{ks}T_{ks}A_{k}$ | 18 |
| 1276491 | $G_{ks}{}^{m}C_{ks}A_{ks}T_{ds}G_{ms}T_{ds}T_{ds}{}^{m}C_{ds}T_{ds}{}^{m}C_{ds}A_{ds}{}^{m}C_{ds}A_{ds}T_{ks}T_{ks}A_{k}$ | 18 |
| 1276492 | $G_{ks}{}^{m}C_{ks}A_{ks}T_{ds}G_{ms}T_{ds}T_{dr}{}^{m}C_{dq}T_{ds}{}^{m}C_{ds}A_{ds}{}^{m}C_{ds}A_{ds}T_{ks}T_{ks}A_{k}$ | 18 |
| 1276493 | $G_{ks}{}^{m}C_{ks}A_{ks}T_{ds}G_{ms}T_{ds}T_{ds}{}^{m}C_{dr}T_{dq}{}^{m}C_{ds}A_{ds}{}^{m}C_{ds}A_{ds}T_{ks}T_{ks}A_{k}$ | 18 |
| 1276494 | $G_{ks}{}^{m}C_{ks}A_{ks}T_{ds}G_{ms}T_{ds}T_{ds}{}^{m}C_{ds}T_{dr}{}^{m}C_{dq}A_{ds}{}^{m}C_{ds}A_{ds}T_{ks}T_{ks}A_{k}$ | 18 |
| 1276495 | $G_{ks}{}^{m}C_{ks}A_{ks}T_{ds}G_{ms}T_{ds}T_{ds}{}^{m}C_{ds}T_{ds}{}^{m}C_{dr}A_{dq}{}^{m}C_{ds}A_{ds}T_{ks}T_{ks}A_{k}$ | 18 |
| 1276496 | $G_{ks}{}^{m}C_{ks}A_{ks}T_{ds}G_{ms}T_{ds}T_{ds}{}^{m}C_{ds}T_{ds}{}^{m}C_{ds}A_{dr}{}^{m}C_{dq}A_{ds}T_{ks}T_{ks}A_{k}$ | 18 |
| 1276497 | $G_{ks}{}^{m}C_{ks}A_{ks}T_{ds}G_{ms}T_{ds}T_{ds}{}^{m}C_{ds}T_{ds}{}^{m}C_{ds}A_{ds}{}^{m}C_{dr}A_{dq}T_{ks}T_{ks}A_{k}$ | 18 |

A subscript "d" indicates an unmodified, 2'-β-D-deoxyribosyl sugar moiety. A subscript "k" indicates a cEt. A superscript "m" before a C indicates 5-methyl Cytosine. A subscript "s" indicates a stereorandom phosphorothioate internucleoside linkage, a subscript "r" indicates a phosphorothioate internucleoside linkage having the (Rp) configuration, and a subscript "q" indicates a phosphorothioate internucleoside linkage having the (Sp) configuration. A subscript "m" represents a 2'-Omethyl modified sugar moiety.

TABLE 129

| Compound ID | in vitro Caspase (% control) @ 20 μM |
|---|---|
| Caspase activation in 3T3L1 cells | |
| 1273959 | 1138 |
| 1273960 | 654 |
| 1273961 | 1036 |
| 1273962 | 752 |
| 1273963 | 1349 |
| 1273964 | 907 |
| 1273965 | 984 |
| 1273966 | 750 |
| 1273967 | 785 |
| 1276491 | 116 |
| 1276492 | 450 |
| 1276493 | 234 |
| 1276494 | 85 |
| 1276495 | 214 |

TABLE 129-continued

| Compound ID | in vitro Caspase (% control) @ 20 μM |
|---|---|
| Caspase activation in 3T3L1 cells | |
| 1276496 | 165 |
| 1276497 | 148 |

Example 61

Modified oligonucleotides were designed based on compounds 546108, 546118, 465178, and 694804, described in Examples 18, 18, 19, and 13, respectively. For sequences with a Tat position 5 (from the 5' end) in the parent kkk-d(10)-kkk oligonucleotide, the kkk-d-m-d(8)-kkk contains a 2'-OMe modified U at this position. For sequences with a $^{m}$C at position 5 (from the 5' end) in the parent kkk-d(10)-kkk oligonucleotide, the kkk-d-m-d(8)-kkk contains a 2'-OMe modified C at this position, lacking the 5-methyl group. Each of the modified oligonucleotides is conjugated with a THA-GalNAc conjugate group at the 3'-end. The oligonucleotides were evaluated for in vivo toxicity at a single dose after 72 hours.

Six week old BALB/C mice (purchased from Charles River) were injected subcutaneously once at 50 mg/kg with the modified oligonucleotides shown below or with saline control. Each treatment group consisted of 3 animals. The mice were sacrificed 72 hours following administration, and organs and plasma were harvested for further analysis.

TABLE 130

| Compound ID | Target | position of altered nucleotide in central region | modification of altered nucleotide | Chemistry Notation (5' to 3') | SEQ ID NO |
|---|---|---|---|---|---|
| Modified Oligonucleotides | | | | | |
| 1306441 | HDAC | N/A | N/A | $T_{ks}A_{ks}G_{ks}T_{ds}{}^{m}C_{ds}T_{ds}{}^{m}C_{ds}T_{ds}G_{ds}T_{ds}{}^{m}C_{ds}A_{ds}G_{ds}T_{ks}T_{ks}A_{k}$-THA-GalNAc | 105 |
| 1306442 | HDAC | 2 | 2'-OMe | $T_{ks}A_{ks}G_{ks}T_{ds}C_{ms}T_{ds}{}^{m}C_{ds}T_{ds}G_{ds}T_{ds}{}^{m}C_{ds}A_{ds}G_{ds}T_{ks}T_{ks}A_{k}$-THA-GalNAc | 105 |
| 1306443 | HDAC | 2 | MOP | $T_{ks}A_{ks}G_{ks}T_{ds}{}^{m}C_{dx}T_{ds}{}^{m}C_{ds}T_{ds}G_{ds}T_{ds}{}^{m}C_{ds}A_{ds}G_{ds}T_{ks}T_{ks}A_{k}$-THA-GalNAc | 105 |
| 1306444 | HDAC | 3 | MOP | $T_{ks}A_{ks}G_{ks}T_{ds}{}^{m}C_{ds}T_{dx}{}^{m}C_{ds}T_{ds}G_{ds}T_{ds}{}^{m}C_{ds}A_{ds}G_{ds}T_{ks}T_{ks}A_{k}$-THA-GalNAc | 105 |

TABLE 130-continued

| Modified Oligonucleotides | | | | | |
|---|---|---|---|---|---|
| Compound ID | Target | position of altered nucleotide in central region | modification of altered nucleotide | Chemistry Notation (5' to 3') | SEQ ID NO |
| 1306445 | HDAC | 3 | MOP | $A_{ks}{}^{m}C_{ks}{}^{m}C_{ks}{}^{m}C_{ds}T_{ds}{}^{m}C_{dx}A_{ds}A_{ds}G_{ds}T_{ds}{}^{m}C_{ds}T_{ds}{}^{m}C_{ds}{}^{m}C_{ks}T_{ks}G_{k}$-THA-GalNAc | 109 |
| 1306446 | FXI | N/A | N/A | $G_{ks}T_{ks}{}^{m}C_{ks}A_{ds}G_{ds}T_{ds}A_{ds}T_{ds}{}^{m}C_{ds}{}^{m}C_{ds}{}^{m}C_{ds}A_{ds}G_{ds}T_{ks}G_{ks}T_{k}$-THA-GalNAc | 89 |
| 1306447 | FXI | 2 | 2'-OMe | $G_{ks}T_{ks}C_{ks}A_{ds}G_{ms}T_{ds}A_{ds}T_{ds}{}^{m}C_{ds}{}^{m}C_{ds}{}^{m}C_{ds}A_{ds}G_{ds}T_{ks}G_{ks}T_{k}$-THA-GalNAc | 89 |
| 1306448 | FXI | 2 | MOP | $G_{ks}T_{ks}{}^{m}C_{ks}A_{ds}G_{dx}T_{ds}A_{ds}T_{ds}{}^{m}C_{ds}{}^{m}C_{ds}{}^{m}C_{ds}A_{ds}G_{ds}T_{ks}G_{ks}T_{k}$-THA-GalNAc | 89 |
| 1306449 | FXI | 3 | MOP | $G_{ks}T_{ks}{}^{m}C_{ks}A_{ds}G_{ds}T_{dx}A_{ds}T_{ds}{}^{m}C_{ds}{}^{m}C_{ds}{}^{m}C_{ds}A_{ds}G_{ds}T_{ks}G_{ks}T_{k}$-THA-GalNAc | 89 |
| 1306450 | DMN2 | N/A | N/A | $A_{ks}G_{ks}A_{ks}{}^{m}C_{ds}T_{ds}{}^{m}C_{ds}T_{ds}{}^{m}C_{ds}G_{ds}G_{ds}T_{ds}T_{ds}{}^{m}C_{ds}{}^{m}C_{ks}G_{ks}A_{k}$-THA-GalNAc | 49 |
| 1306451 | DMN2 | 2 | 2'-OMe | $A_{ks}G_{ks}A_{ks}{}^{m}C_{ds}U_{ms}{}^{m}C_{ds}T_{ds}{}^{m}C_{ds}G_{ds}G_{ds}T_{ds}T_{ds}{}^{m}C_{ds}{}^{m}C_{ks}G_{ks}A_{k}$-THA-GalNAc | 127 |
| 1306452 | DMN2 | 2 | MOP | $A_{ks}G_{ks}A_{ks}{}^{m}C_{ds}T_{dx}{}^{m}C_{ds}T_{ds}{}^{m}C_{ds}G_{ds}G_{ds}T_{ds}T_{ds}{}^{m}C_{ds}{}^{m}C_{ks}G_{ks}A_{k}$-THA-GalNAc | 49 |
| 1306453 | DMN2 | 3 | MOP | $A_{ks}G_{ks}A_{ks}{}^{m}C_{ds}T_{ds}{}^{m}C_{dx}T_{ds}{}^{m}C_{ds}G_{ds}G_{ds}T_{ds}T_{ds}{}^{m}C_{ds}{}^{m}C_{ks}G_{ks}A_{k}$-THA-GalNAc | 49 |

A subscript "d" indicates an unmodified, 2'-β-D-deoxyribosyl sugar moiety. A subscript "k" indicates a cEt. A subscript "s" indicates a phosphorothioate internucleoside linkage. A superscript "m" before a C indicates 5-methyl Cytosine. A subscript "x" indicates a MOP internucleoside linkage. A subscript "m" indicates a 2'-O-methyl-β-D-ribofuranosyl sugar moiety.

TABLE 131

| In vivo Toxicity of Modified Oligonucleotides | | | |
|---|---|---|---|
| Compound ID | position of altered nucleotide in central region | modification of altered nucleotide | ALT (IU/L) |
| PBS | N/A | N/A | 28 |
| 1306441 | N/A | N/A | 2371 |
| 1306442 | 2 | 2'-OMe | 37 |
| 1306443 | 2 | MOP | 30 |
| 1306444 | 3 | MOP | 38 |
| 1306445 | 3 | MOP | 51 |
| 1306446 | N/A | N/A | 1555 |
| 1306447 | 2 | 2'-OMe | 53 |
| 1306448 | 2 | MOP | 43 |
| 1306449 | 3 | MOP | 43 |
| 1306450 | N/A | N/A | 1058 |
| 1306451 | 2 | 2'-OMe | 34 |
| 1306452 | 2 | MOP | 25 |
| 1306453 | 3 | MOP | 23 |

Example 62 Effect of 2'-OMe Incorporation on Delayed Toxicity of Modified Oligonucleotides Complementary to HDAC2

Modified oligonucleotides were synthesized with 2' modifications as indicated in the table below. The compounds have the sugar motif kkk-d(10)-kkk ("parent") or kkk-d-m-d(8)-kkk, where "k" represents a cEt, "d" represents an unmodified, 2'-β-D-deoxyribosyl sugar moiety, and "m" represents 2'-OMe-β-D-ribofuranosyl sugar moiety. For sequences with a T at position 5 (from the 5' end) in the parent kkk-d(10)-kkk oligonucleotide, the kkk-d-m-d(8)-kkk contains a 2'-OMe modified U at this position. For sequences with a ${}^{m}$C at position 5 (from the 5' end) in the parent kkk-d(10)-kkk oligonucleotide, the kkk-d-m-d(8)-kkk contains a 2'-OMe modified C at this position, lacking the 5-methyl group. The modified oligonucleotides in the table below have a mixed backbone motif soosssssssssos or soososssssssos, wherein each "s" represents a phosphorothioate internucleoside linkage and each "o" represents a phosphodiester internucleoside linkage, as indicated by the chemistry notation in the table.

For the in vivo toxicity study in the table below, four female C57/B16 mice per group were administered 300 μg modified oligonucleotide by intracerebroventricular (ICV) injection. At 8 weeks post-injection, mice were evaluated according to 7 different criteria. The criteria are (1) the mouse was bright, alert, and responsive; (2) the mouse was standing or hunched without stimuli; (3) the mouse showed any movement without stimuli; (4) the mouse demonstrated forward movement after it was lifted; (5) the mouse demonstrated any movement after it was lifted; (6) the mouse responded to tail pinching; (7) regular breathing. For each of the 7 criteria, a mouse was given a subscore of 0 if it met the criteria and 1 if it did not. After all 7 criteria were evaluated, the FOB scores were summed for each mouse and averaged within each treatment group. The results are presented in the table below.

TABLE 132

| In vivo Activity and Toxicity of Modified oligonucleotides complementary to HDAC2 | | | | |
|---|---|---|---|---|
| Compound ID | Chemistry notation | HDAC2 mRNA (% control) Cortex | 8 week FOB | SEQ ID NO: |
| 1282276 | $G_{ks}A_{ko}{}^{m}C_{ko}T_{ds}{}^{m}C_{ds}T_{ds}{}^{m}C_{ds}T_{ds}G_{ds}A_{ds}T_{ds}G_{ds}A_{ds}T_{ko}A_{ks}{}^{m}C_{k}$ | 86 | 5 | 97 |
| 1282277 | $G_{ks}A_{ko}{}^{m}C_{ko}T_{ds}C_{ms}T_{ds}{}^{m}C_{ds}T_{ds}G_{ds}A_{ds}T_{ds}G_{ds}A_{ds}T_{ko}A_{ks}{}^{m}C_{k}$ | n.d. | 7 | 97 |
| 1282278 | $G_{ks}A_{ko}{}^{m}C_{ko}T_{ds}C_{mo}T_{ds}{}^{m}C_{ds}T_{ds}G_{ds}A_{ds}T_{ds}G_{ds}A_{ds}T_{ko}A_{ks}{}^{m}C_{k}$ | 72 | 6 | 97 |
| 1282280 | ${}^{m}C_{ks}T_{ko}A_{ko}T_{ds}A_{ds}{}^{m}C_{ds}{}^{m}C_{ds}A_{ds}T_{ds}{}^{m}C_{ds}T_{ds}{}^{m}C_{ds}T_{ds}{}^{m}C_{ko}A_{ks}T_{k}$ | 44 | 2 | 98 |
| 1282296 | ${}^{m}C_{ks}T_{ko}A_{ko}T_{ds}A_{ms}{}^{m}C_{ds}{}^{m}C_{ds}A_{ds}T_{ds}{}^{m}C_{ds}T_{ds}{}^{m}C_{ds}T_{ds}{}^{m}C_{ko}A_{ks}T_{k}$ | n.d. | 7 | 98 |
| 1282622 | ${}^{m}C_{ks}T_{ko}A_{ko}T_{ds}A_{mo}{}^{m}C_{ds}{}^{m}C_{ds}A_{ds}T_{ds}{}^{m}C_{ds}T_{ds}{}^{m}C_{ds}T_{ds}{}^{m}C_{ko}A_{ks}T_{k}$ | 68 | 0 | 98 |

TABLE 132-continued

In vivo Activity and Toxicity of Modified oligonucleotides complementary to HDAC2

| Compound ID | Chemistry notation | HDAC2 mRNA (% control) Cortex | 8 week FOB | SEQ ID NO: |
|---|---|---|---|---|
| 1282281 | $A_{ks}T_{ko}T_{ko}A_{ds}T_{ds}A_{ds}T_{ds}G_{ds}G_{ds}{}^{m}C_{ds}A_{ds}A_{ds}{}^{m}C_{ds}T_{ks}{}^{m}C_{ks}A_{k}$ | 70 | 4 | 101 |
| 1282627 | $A_{ks}T_{ko}T_{ko}A_{ds}U_{ms}A_{ds}T_{ds}G_{ds}G_{ds}{}^{m}C_{ds}A_{ds}A_{ds}{}^{m}C_{ds}T_{ks}{}^{m}C_{ks}A_{k}$ | 50 | 0 | 139 |
| 1282282 | $G_{ks}A_{ko}{}^{m}C_{ko}T_{ds}A_{ds}A_{ds}T_{ds}A_{ds}T_{ds}G_{ds}{}^{m}C_{ds}A_{ds}G_{ds}T_{ko}T_{ks}T_{k}$ | 107 | 0 | 102 |
| 1282628 | $G_{ks}A_{ko}{}^{m}C_{ko}T_{ds}A_{ms}A_{ds}T_{ds}A_{ds}T_{ds}G_{ds}{}^{m}C_{ds}A_{ds}G_{ds}T_{ko}T_{ks}T_{k}$ | 86 | 0 | 102 |
| 1282283 | $G_{ks}T_{ks}{}^{m}C_{ko}A_{ds}A_{ds}A_{ds}T_{ds}T_{ds}{}^{m}C_{ds}A_{ds}A_{ds}G_{ds}G_{ds}G_{ko}T_{ks}T_{k}$ | n.d. | 7 | 103 |
| 1282629 | $G_{ks}T_{ks}{}^{m}C_{ko}A_{ds}A_{ms}A_{ds}T_{ds}T_{ds}{}^{m}C_{ds}A_{ds}A_{ds}G_{ds}G_{ds}G_{ko}T_{ks}T_{k}$ | n.d. | 7 | 103 |
| 1282284 | ${}^{m}C_{ks}A_{ko}T_{ko}A_{ds}A_{ds}A_{ds}G_{ds}{}^{m}C_{ds}A_{ds}T_{ds}G_{ds}G_{ds}T_{ds}G_{ko}G_{ks}A_{k}$ | n.d. | 7 | 104 |
| 1282630 | ${}^{m}C_{ks}A_{ko}T_{ko}A_{ds}A_{ms}A_{ds}G_{ds}{}^{m}C_{ds}A_{ds}T_{ds}G_{ds}G_{ds}T_{ds}G_{ko}G_{ks}A_{k}$ | n.d. | 7 | 104 |
| 1224264 | $G_{ks}T_{ko}A_{ko}{}^{m}C_{ds}{}^{m}C_{ds}T_{ds}A_{ds}T_{ds}A_{ds}G_{ds}T_{ds}{}^{m}C_{ds}T_{ds}{}^{m}C_{ko}T_{ks}G_{k}$ | n.d. | 7 | 106 |
| 1282631 | $G_{ks}T_{ko}A_{ko}{}^{m}C_{ds}C_{ms}T_{ds}A_{ds}T_{ds}A_{ds}G_{ds}T_{ds}{}^{m}C_{ds}T_{ds}{}^{m}C_{ko}T_{ks}G_{k}$ | n.d. | 7 | 106 |
| 1282285 | $T_{ks}T_{ko}G_{ko}{}^{m}C_{ds}{}^{m}C_{ds}A_{ds}A_{ds}T_{ds}A_{ds}T_{ds}{}^{m}C_{ds}A_{ds}{}^{m}C_{ds}{}^{m}C_{ko}A_{ks}T_{k}$ | n.d. | 7 | 94 |
| 1282632 | $T_{ks}T_{ko}G_{ko}{}^{m}C_{ds}C_{ms}A_{ds}A_{ds}T_{ds}A_{ds}T_{ds}{}^{m}C_{ds}A_{ds}{}^{m}C_{ds}{}^{m}C_{ko}A_{ks}T_{k}$ | 59 | 0 | 94 |
| 1282623 | $T_{ks}T_{ko}G_{ko}{}^{m}C_{ds}C_{mo}A_{ds}A_{ds}T_{ds}A_{ds}T_{ds}{}^{m}C_{ds}A_{ds}{}^{m}C_{ds}{}^{m}C_{ko}A_{ks}T_{k}$ | 88 | 0 | 94 |
| 1282286 | ${}^{m}C_{ks}A_{ko}A_{ko}{}^{m}C_{ds}T_{ds}G_{ds}A_{ds}A_{ds}{}^{m}C_{ds}{}^{m}C_{ds}A_{ds}{}^{m}C_{ds}{}^{m}C_{ds}{}^{m}C_{ko}G_{ks}T_{k}$ | 68 | 3 | 95 |
| 1282633 | ${}^{m}C_{ks}A_{ko}A_{ko}{}^{m}C_{ds}U_{ms}G_{ds}A_{ds}A_{ds}{}^{m}C_{ds}{}^{m}C_{ds}A_{ds}{}^{m}C_{ds}{}^{m}C_{ds}{}^{m}C_{ko}G_{ks}T_{k}$ | 71 | 0 | 138 |
| 1282287 | $G_{ks}{}^{m}C_{ko}A_{ko}{}^{m}C_{ds}A_{ds}A_{ds}T_{ds}A_{ds}T_{ds}{}^{m}C_{ds}A_{ds}T_{ds}T_{ds}A_{ko}A_{ks}{}^{m}C_{k}$ | 74 | 0 | 96 |
| 1282634 | $G_{ks}{}^{m}C_{ko}A_{ko}{}^{m}C_{ds}A_{ms}A_{ds}T_{ds}A_{ds}T_{ds}{}^{m}C_{ds}A_{ds}T_{ds}T_{ds}A_{ko}A_{ks}{}^{m}C_{k}$ | 70 | 0 | 96 |
| 1282288 | ${}^{m}C_{ks}A_{ko}T_{ko}{}^{m}C_{ds}A_{ds}T_{ds}{}^{m}C_{ds}T_{ds}A_{ds}T_{ds}A_{ds}{}^{m}C_{ds}{}^{m}C_{ds}A_{ko}T_{ks}{}^{m}C_{k}$ | 16 | 2 | 99 |
| 1282298 | ${}^{m}C_{ks}A_{ko}T_{ko}{}^{m}C_{ds}A_{ms}T_{ds}{}^{m}C_{ds}T_{ds}A_{ds}T_{ds}A_{ds}{}^{m}C_{ds}{}^{m}C_{ds}A_{ko}T_{ks}{}^{m}C_{k}$ | 18 | 4 | 99 |
| 1282624 | ${}^{m}C_{ks}A_{ko}T_{ko}{}^{m}C_{ds}A_{mo}T_{ds}{}^{m}C_{ds}T_{ds}A_{ds}T_{ds}A_{ds}{}^{m}C_{ds}{}^{m}C_{ds}A_{ko}T_{ks}{}^{m}C_{k}$ | 70 | 0 | 99 |
| 1224263 | $A_{ks}{}^{m}C_{ko}A_{ko}{}^{m}C_{ds}A_{ds}T_{ds}T_{ds}T_{ds}A_{ds}G_{ds}{}^{m}C_{ds}A_{ds}T_{ds}G_{ko}A_{ks}{}^{m}C_{k}$ | n.d. | 2 | 100 |
| 1282635 | $A_{ks}{}^{m}C_{ko}A_{ko}{}^{m}C_{ds}A_{ms}T_{ds}T_{ds}T_{ds}A_{ds}G_{ds}{}^{m}C_{ds}A_{ds}T_{ds}G_{ko}A_{ks}{}^{m}C_{k}$ | 61 | 0 | 100 |
| 1282289 | $T_{ks}A_{ko}G_{ko}T_{ds}{}^{m}C_{ds}T_{ds}{}^{m}C_{ds}T_{ds}G_{ds}T_{ds}{}^{m}C_{ds}A_{ds}G_{ds}T_{ko}T_{ks}A_{k}$ | n.d. | 7 | 105 |
| 1282621 | $T_{ks}A_{ko}G_{ko}T_{ds}C_{ms}T_{ds}{}^{m}C_{ds}T_{ds}G_{ds}T_{ds}{}^{m}C_{ds}A_{ds}G_{ds}T_{ko}T_{ks}A_{k}$ | n.d. | 7 | 105 |
| 1282625 | $T_{ks}A_{ko}G_{ko}T_{ds}C_{mo}T_{ds}{}^{m}C_{ds}T_{ds}G_{ds}T_{ds}{}^{m}C_{ds}A_{ds}G_{ds}T_{ko}T_{ks}A_{k}$ | n.d | 6 | 105 |
| 1282290 | $T_{ks}{}^{m}C_{ko}A_{ko}T_{ds}G_{ds}T_{ds}A_{ds}{}^{m}C_{ds}{}^{m}C_{ds}T_{ds}A_{ds}T_{ds}A_{ds}G_{ko}T_{ks}{}^{m}C_{k}$ | 22 | 6 | 107 |
| 1282300 | $T_{ks}{}^{m}C_{ko}A_{ko}T_{ds}G_{ms}T_{ds}A_{ds}{}^{m}C_{ds}{}^{m}C_{ds}T_{ds}A_{ds}T_{ds}A_{ds}G_{ko}T_{ks}{}^{m}C_{k}$ | 60 | 0 | 107 |
| 1282626 | $T_{ks}{}^{m}C_{ko}A_{ko}T_{ds}G_{mo}T_{ds}A_{ds}{}^{m}C_{ds}{}^{m}C_{ds}T_{ds}A_{ds}T_{ds}A_{ds}G_{ko}T_{ks}{}^{m}C_{k}$ | 107 | 0 | 107 |
| 1282291 | $T_{ks}{}^{m}C_{ko}T_{ko}T_{ds}A_{ds}A_{ds}T_{ds}T_{ds}T_{ds}{}^{m}C_{ds}A_{ds}T_{ds}G_{ds}T_{ko}A_{ks}{}^{m}C_{k}$ | 64 | 0 | 108 |
| 1282636 | $T_{ks}{}^{m}C_{ko}T_{ko}T_{ds}A_{ms}A_{ds}T_{ds}T_{ds}T_{ds}{}^{m}C_{ds}A_{ds}T_{ds}G_{ds}T_{ko}A_{ks}{}^{m}C_{k}$ | 65 | 0 | 108 |
| 1282292 | $A_{ks}{}^{m}C_{ko}{}^{m}C_{ko}{}^{m}C_{ds}T_{ds}{}^{m}C_{ds}A_{ds}A_{ds}G_{ds}T_{ds}{}^{m}C_{ds}T_{ds}{}^{m}C_{ds}{}^{m}C_{ko}T_{ks}G_{k}$ | n.d. | 6 | 109 |
| 1282637 | $A_{ks}{}^{m}C_{ko}{}^{m}C_{ko}{}^{m}C_{ds}U_{ms}{}^{m}C_{ds}A_{ds}A_{ds}G_{ds}T_{ds}{}^{m}C_{ds}T_{ds}{}^{m}C_{ds}{}^{m}C_{ko}T_{ks}G_{k}$ | n.d. | 7 | 109 |

A subscript "d" indicates an unmodified, 2'-β-D-deoxyribosyl sugar moiety. A subscript "e" indicates a 2'-MOE-β-D-ribofuranosyl sugar moiety. A subscript "m" indicates a 2'-O-methyl-β-D-ribofuranosyl sugar moiety. A subscript "k" indicates a cEt. A subscript "s" indicates a phosphorothioate internucleoside linkage. A superscript "m" before a C indicates 5-methyl Cytosine. A subscript "x" indicates a MOP internucleoside linkage.

Example 63 Effect of Incorporation of 2'-OMe at Various Positions

Modified oligonucleotides were synthesized with 2' modifications as indicated in the table below. The compounds have the sugar motif of kkk-d-m-d(8)-kkk, kkk-d(8)-m-d-kkk, or kkk-mm-d(8)-kkk where "k" represents a cEt, "d" represents an unmodified, 2'-β-D-deoxyribosyl sugar moiety, and "m" represents a a 2'-OMe-β-D-ribofuranosyl sugar moiety. For parent sequences with a T at the 2'-OMe-modified position, modified sequences contain a 2'-OMe modified U at this position. For parent sequences with a ${}^{m}C$ at the 2'-OMe-modified position, modified sequences contain a 2'-OMe modified C at this position, lacking the 5-methyl group.

TABLE 133

Modified Oligonucleotides

| Compound ID | Target | position of altered nucleotide in central region | modification of altered nucleotide | Chemistry Notation (5' to 3') | SEQ ID NO |
|---|---|---|---|---|---|
| 936053 | CXCL12 | 2 | 2'-OMe | $G_{ks}{}^{m}C_{ks}A_{ks}T_{ds}G_{ms}T_{ds}T_{ds}{}^{m}C_{ds}T_{ds}{}^{m}C_{ds}A_{ds}{}^{m}C_{ds}A_{ds}T_{ds}T_{ds}A_{k}$ | 18 |
| 1244114 | CXCL12 | 9 | 2'-OMe | $G_{ks}{}^{m}C_{ks}A_{ks}T_{ds}G_{ds}T_{ds}T_{ds}{}^{m}C_{ds}T_{ds}{}^{m}C_{ds}A_{ds}C_{ms}A_{ds}T_{ks}T_{ks}A_{k}$ | 18 |
| 1306760 | CXCL12 | 1, 2 | 2'-OMe | $G_{ks}{}^{m}C_{ks}A_{ks}U_{ms}G_{ms}T_{ds}T_{ds}{}^{m}C_{ds}T_{ds}{}^{m}C_{ds}A_{ds}{}^{m}C_{ds}A_{ds}T_{ks}T_{ks}A_{k}$ | 19 |
| 895155 | SOD-1 | 2 | 2'-OMe | $T_{ks}G_{ks}A_{ks}G_{ds}G_{ms}T_{ds}{}^{m}C_{ds}{}^{m}C_{ds}T_{ds}G_{ds}{}^{m}C_{ds}A_{ds}{}^{m}C_{ds}T_{ks}G_{ks}G_{k}$ | 26 |

TABLE 133-continued

| Modified Oligonucleotides | | | | | |
|---|---|---|---|---|---|
| Compound ID | Target | position of altered nucleotide in central region | modification of altered nucleotide | Chemistry Notation (5' to 3') | SEQ ID NO |
| 1308544 | SOD-1 | 9 | 2'-OMe | $T_{ks}G_{ks}A_{ks}G_{ds}G_{ds}T_{ds}{}^{m}C_{ds}{}^{m}C_{ds}T_{ds}G_{ds}{}^{m}C_{ds}A_{ms}{}^{m}C_{ds}T_{ks}G_{ks}G_{k}$ | 26 |
| 1309002 | SOD-1 | 1, 2 | 2'-OMe | $T_{ks}G_{ks}A_{ks}G_{ms}G_{ms}T_{ds}{}^{m}C_{ds}{}^{m}C_{ds}T_{ds}G_{ds}{}^{m}C_{ds}A_{ds}{}^{m}C_{ds}T_{ks}G_{ds}G_{k}$ | 26 |
| 1133122 | HDAC2 | 2 | 2'-OMe | $T_{ks}A_{ks}G_{ks}T_{ds}C_{ms}T_{ds}{}^{m}C_{ds}T_{ds}G_{ds}T_{ds}{}^{m}C_{ds}A_{ds}G_{ds}T_{ks}T_{ks}A_{k}$ | 105 |
| 1308545 | HDAC2 | 9 | 2'-OMe | $T_{ks}A_{ks}G_{ks}T_{ds}{}^{m}C_{ds}T_{ds}{}^{m}C_{ds}T_{ds}G_{ds}T_{ds}{}^{m}C_{ds}A_{ms}G_{ds}T_{ks}T_{ks}A_{k}$ | 105 |
| 1309073 | HDAC2 | 1, 2 | 2'-OMe | $T_{ks}A_{ks}G_{ks}U_{ms}C_{ms}T_{ds}{}^{m}C_{ds}T_{ds}G_{ds}T_{ds}{}^{m}C_{ds}A_{ds}G_{ds}T_{ks}T_{ks}A_{k}$ | 145 |

A subscript "d" indicates an unmodified, 2'-β-D-deoxyribosyl sugar moiety. A subscript "e" indicates a 2'-MOE-β-D-ribofuranosyl sugar moiety. A subscript "m" indicates a 2'-O-methyl-β-D-ribofuranosyl sugar moiety. A subscript "k" indicates a cEt. A subscript "s" indicates a phosphorothioate internucleoside linkage. A superscript "m" before a C indicates 5-methyl Cytosine.

Six week old BALB/C mice (purchased from Charles River) were injected subcutaneously once at dosage 1.8, 5.5, 16.7, 50, or 150 mg/kg with the modified oligonucleotides shown below or with saline control. Each treatment group consisted of 3 animals. The mice were sacrificed 72 hours following administration, and organs and plasma were harvested for further analysis. The oligonucleotides were evaluated for reduction in target mRNA expression levels in vivo. P21 and Tnfrsf10b mRNA levels were also measured. The transaminase levels (ALT and AST) for each dose were also measured.

TABLE 134

| In vivo Activity and Toxicity of Modified Oligonucleotides | | | | |
|---|---|---|---|---|
| Compound ID | position of altered nucleotide in central region | ALT (IU/L) @ 50 mg/kg | ALT (IU/L) @ 150 mg/kg | ED50 (mg/kg) for target |
| 936053 | 2 | 11 | 109 | 3.5 |
| 1244114 | 9 | 9092 | death | 1.0 |

TABLE 134-continued

| In vivo Activity and Toxicity of Modified Oligonucleotides | | | | |
|---|---|---|---|---|
| Compound ID | position of altered nucleotide in central region | ALT (IU/L) @ 50 mg/kg | ALT (IU/L) @ 150 mg/kg | ED50 (mg/kg) for target |
| 1306760 | 1, 2 | 16 | 436 | 3.0 |
| 895155 | 2 | 29 | 110 | 11.0 |
| 1308544 | 9 | 2054 | 14507 | 27.7 |
| 1309002 | 1, 2 | 6 | 64 | 47.6 |
| 1133122 | 2 | 31 | 76 | 2.7 |
| 1308545 | 9 | 24695 | death | 0.9 |
| 1309073 | 1, 2 | 28 | 128 | 3.1 |

Example 63 Effect of Incorporation of 2'-OMe in a Modified Oligonucleotide with 11 Nucleosides in the Central Region Modified oligonucleotides were synthesized with 2' modifications as indicated in the table below. The compounds have the sugar motif of kkk-d(11)-kkk, kkk-d-m-d(9)-kkk, or kkk-dd-m-d(8)-kkk, where "k" represents a cEt, "d" represents an unmodified, 2'-β-D-deoxyribosyl sugar moiety, and "m" represents a a 2'-OMe-β-D-ribofuranosyl modified sugar moiety. For parent sequences with a T at the 2'-OMe-modified position, modified sequences contain a 2'-OMe modified U at this position.

TABLE 135

| Modified Oligonucleotides | | | | | |
|---|---|---|---|---|---|
| Compound ID | Target | position of altered nucleoside in central region | modification of altered nculeoside | Chemistry Notation (5' to 3') | SEQ ID NO |
| 1280764 | CXCL12 | N/A | 2'-OMe | $G_{ks}{}^{m}C_{ks}A_{ks}T_{ds}G_{ms}T_{ds}T_{ds}{}^{m}C_{ds}T_{ds}{}^{m}C_{ds}A_{ds}{}^{m}C_{ds}A_{ds}T_{ds}T_{ks}A_{ks}T_{k}$ | 125 |
| 1280763 | CXCL12 | 2 | 2'-OMe | $G_{ks}{}^{m}C_{ks}A_{ks}T_{ds}G_{ds}T_{ds}T_{ds}{}^{m}C_{ds}T_{ds}{}^{m}C_{ds}A_{ds}C_{ms}A_{ds}T_{ds}T_{ks}A_{ks}T_{k}$ | 125 |
| 1306440 | CXCL12 | 3 | 2'-OMe | $G_{ks}{}^{m}C_{ks}A_{ks}T_{ds}G_{ds}U_{ms}T_{ds}{}^{m}C_{ds}T_{ds}{}^{m}C_{ds}A_{ds}{}^{m}C_{ds}A_{ds}T_{ds}T_{ks}A_{ks}T_{k}$ | 146 |

A subscript "d" indicates an unmodified, 2'-β-D-deoxyribosyl sugar moiety. A subscript "e" indicates a 2'-MOE-β-D-ribofuranosyl sugar moiety. A subscript "m" indicates a 2'-O-methyl-β-D-ribofuranosyl sugar moiety. A subscript "k" indicates a cEt. A subscript "s" indicates a phosphorothioate internucleoside linkage. A superscript "m" before a C indicates 5-methyl Cytosine.

Six week old BALB/C mice (purchased from Charles River) were injected subcutaneously once at dosage 50 or 150 mg/kg with the modified oligonucleotides shown below or with saline control. Each treatment group consisted of 3 animals. The mice were sacrificed 72 hours following administration, and organs and plasma were harvested for further analysis. P21 and Tnfrsf10b mRNA levels were measured. The transaminase levels (ALT and AST) for each dose were also measured.

TABLE 136

In vivo Activity and Toxicity of Modified Oligonucleotides with an 11-base central region

| Compound ID | position of 2'-OMe nucleotide in central region | ALT (IU/L) @ 50 mg/kg | ALT (IU/L) @ 150 mg/kg | P21 mRNA @ 150 mg/kg | Tnfrsf10b mRNA @ 150 mg/kg |
|---|---|---|---|---|---|
| 1280764 | N/A | death | death | death | death |
| 1280763 | 2 | 109 | 112 | 236 | 460 |
| 1306440 | 3 | 5109 | 7614 | 7022 | 13361 |

Example 65 Effect of Incorporation of 2'-OMe in a Modified Oligonucleotide on Kidney Toxicity Modified oligonucleotides were synthesized as indicated in the table below. The compounds have the sugar motif of kkk-d(10)-kkk or kkk-d-m-d(8)-kkk, where "k" represents a cEt, "d" represents an unmodified, 2'-β-D-deoxyribosyl sugar moiety, and "m" represents a 2'-OMe-β-D-ribofuranosyl sugar moiety.

TABLE 137

Modified Oligonucleotides

| Compound ID | position of altered nucleotide in central region | modification of altered nucleotide | Chemistry Notation (5' to 3') | SEQ ID NO |
|---|---|---|---|---|
| 683702 | N/A | N/A | $A_{ks}C_{ks}A_{ks}A_{ds}G_{ds}G_{ds}A_{ds}{}^{m}C_{ds}A_{ds}{}^{m}C_{ds}{}^{m}C_{ds}A_{ds}A_{ds}G_{ks}A_{ks}T_{ks}$ | 147 |
| 1295373 | 2 | 2'-OMe | $A_{ks}C_{ks}A_{ks}A_{ds}G_{ms}G_{ds}A_{ds}{}^{m}C_{ds}A_{ds}{}^{m}C_{ds}{}^{m}C_{ds}A_{ds}A_{ds}G_{ks}A_{ks}T_{ks}$ | 147 |

A subscript "d" indicates an unmodified, 2'-β-D-deoxyribosyl sugar moiety. A subscript "e" indicates a 2'-MOE-β-D-ribofuranosyl sugar moiety. A subscript "m" indicates a 2'-O-methyl-β-D-ribofuranosyl sugar moiety. A subscript "k" indicates a cEt. A subscript "s" indicates a phosphorothioate internucleoside linkage. A superscript "m" before a C indicates 5-methyl Cytosine.

8-10 week old Sprague Dawley rats were injected subcutaneously at dosage 50 mg/kg/week for two weeks (3 total injections) with the modified oligonucleotides shown below or with saline control. Each treatment group consisted of 3 animals. The mice were sacrificed 72 hours following administration, and organs and plasma were harvested for further analysis. KIM-1, NGAL, P21 and Tnfrsf10b mRNA levels were measured. Primer probe set rHAVCR1 (forward sequence: GGGATTACAGAGATCGTGACTGATT (SEQ ID NO: 148), reverse sequence: TGCAGCTGGAAGAACCAAAA (SEQ ID NO:149), probe sequence CAGAGTAAAATACCCATTCCAGCTCCTGGG (SEQ ID NO: 150)) was used to measure KIM-1 and primer probe set RTS4389 (forward sequence: GATTCGTCAGCTTTGCCAAGT (SEQ ID NO: 151), reverse sequence: CGTCTGTTCAGTTGTCAATGCA (SEQ ID NO:152), probe sequence TCTGGGCCTCAAGGATAACAACATCGTTT (SEQ ID NO: 153)) was used to measure NGAL. The transaminase levels (ALT and AST) for each dose were also measured.

TABLE 138

| In vivo Toxicity of Modified Oligonucleotides in kidney | | | | | | |
|---|---|---|---|---|---|---|
| Compound ID | 2'-OMe position in central region | ALT (IU/L) | P21 mRNA (liver) | KIM-1 mRNA (kidney) | NGAL mRNA (kidney) | P21 mRNA (kidney) |
| 683702 | N/A | 393 | 1243 | 3449 | 741 | 439 |
| 1295373 | 2 | 39 | 92 | 122 | 142 | 98 |

Example 66 Nucleosides with Various Chemistries at Position 2 and 3 of the Central Region Modified oligonucleotides containing altered nucleotides at position 2 of the central region were synthesized. The compounds in the table below are 100% complementary to mouse FXI. The sequence of the oligonucleotides is GTTATTGTGGTTGGCG (SEQ ID NO: 81), GTTAUTGTGGTTGGCG (SEQ ID NO: 133), or GTTATUGTGGTTGGCG (SEQ ID NO: 154) as indicated in the table below. The compounds have the sugar motif kkk-d-Z-d(8)-kkk or kkk-dd-Z-d(7)-kkk, where "k" represents a cEt, "d" represents an unmodified, 2'-β-D-deoxyribosyl sugar moiety, and "Z" represents a nucleotide comprising a modification as indicated in Table 139 below.

Compounds were tested in 3T3-L1 cells for caspase activation essentially as described in Example 1 above.

TABLE 139

| Modified oligonucleotides and in vitro toxicity | | | | |
|---|---|---|---|---|
| Compound ID | position of altered nucleotide in central region | modification of altered nucleotide | SEQ ID NO | in vitro Caspase (% control) @ 40 μM |
| 464924 | N/A | N/A | 81 | 246 |
| 1326529 | 2 | cEt | 81 | 593 |
| 1326530 | 3 | cEt | 81 | 376 |
| 1326531 | 2 | 2'-MOE | 81 | 146 |
| 1326532 | 3 | 2'-MOE | 81 | 121 |
| 1133247 | 2 | 2'-OMe | 133 | 133 |
| 1326533 | 3 | 2'-OMe | 154 | 126 |
| 1326534 | 2 | 2'-FANA | 133 | 65 |
| 1326535 | 3 | 2'-FANA | 154 | 158 |
| 1326536 | 2 | 2'-ribo-F | 133 | 116 |
| 1326537 | 3 | 2'-ribo-F | 154 | 103 |
| 1326538 | 2 | F-HNA | 81 | 115 |
| 1326539 | 3 | F-HNA | 81 | 298 |
| 1351257 | 2 | LNA | 81 | 665 |
| 1351258 | 3 | LNA | 81 | 136 |
| 1351259 | 2 | α-L-LNA | 133 | 217 |
| 1351260 | 3 | α-L-LNA | 154 | 114 |
| 1351261 | 2 | ENA | 81 | 175 |
| 1351262 | 3 | ENA | 81 | 209 |

"cEt" has the meaning set forth herein. "2'-MOE" has the meaning set forth herein. "2'-OMe" has the meaning set forth herein. "2'-FANA" indicates a 2'-F-β-D-arabinofuranosyl modified sugar moiety. "F-HNA" has the meaning set forth herein. "2'-ribo-F" indicates a 2'-fluororibose. "LNA" has the meaning set forth herein. "α-L-LNA" has the meaning set forth herein. "ENA" has the meaning set forth herein.

Example 67 Nucleosides with Various Chemistries at Position 2 and 3 of the Central Region Modified oligonucleotides with 2'-5' internucleoside linkages in the central region were synthesized as indicated in the table below, "k" represents a cEt, and "d" represents an unmodified, 2'-β-D-deoxyribosyl sugar moiety, and "25s" represents a 2'-5' internucleoside linkage. An example of a 2'-5' internucleoside linkage is shown below:

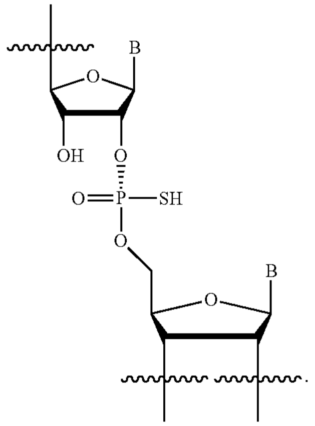

These modified oligonucleotides were compared to the otherwise identical modified oligonucleotide lacking an altered internucleoside linkage nucleotide in the central region, a 3-10-3 cEt gapmer, having three cEt nucleosides in each of the 5' and 3' regions and 10 DNA nucleosides in the central region (compound 558807). The modified oligonucleotides were also compared to a modified oligonucleotide having a 2'OMe at position 2 of the central region (Compound 936053). As demonstrated by the caspase activity, placement of a 2'-5' internucleoside linkage at certain positions in the central region reduces caspase activity compared to the otherwise identical modified oligonucleotide lacking an altered internucleoside linkage. The compounds in the table below are 100% complementary to mouse CXCL12, GENBANK NT_039353.7 truncated from 69/430,515 to 69/445,350 (SEQ ID NO: 1), at position 6877 to 6892.

The compounds were tested in Hepa1-6 cells for caspase activation essentially as described in Example 1 above and the results are shown in the table below.

TABLE 140

| Modified oligonucleotides complementary to CXCL12 | | | | |
|---|---|---|---|---|
| Compound ID | position of altered linkage in central region | Chemistry Notation (5'-3') | in vitro Caspase (% control) @ 20 μM | SEQ ID NO |
| 558807 | n/a | $G_{ks}{}^{m}C_{ks}A_{ks}T_{ds}G_{ds}T_{ds}T_{ds}{}^{m}C_{ds}T_{ds}{}^{m}C_{ds}A_{ds}{}^{m}C_{ds}A_{ds}T_{ks}T_{ks}A_{k}$ | 3843 | 18 |
| 936053 | n/a | $G_{ks}{}^{m}C_{ks}A_{ks}T_{ds}G_{ms}T_{ds}T_{ds}{}^{m}C_{ds}T_{ds}{}^{m}C_{ds}A_{ds}{}^{m}C_{ds}A_{ds}T_{ks}T_{ks}A_{k}$ | 148 | 18 |
| 1273969 | 1 | $G_{ks}{}^{m}C_{ks}A_{ks}U_{d25s}G_{ms}T_{ds}T_{ds}{}^{m}C_{ds}T_{ds}{}^{m}C_{ds}A_{ds}{}^{m}C_{ds}A_{ds}T_{ks}T_{ks}A_{k}$ | 538 | 19 |
| 1306771 | 2 | $G_{ks}{}^{m}C_{ks}A_{ks}T_{ds}G_{m25s}T_{ds}T_{ds}{}^{m}C_{ds}T_{ds}{}^{m}C_{ds}A_{ds}{}^{m}C_{ds}A_{ds}T_{ks}T_{ks}A_{k}$ | 526 | 18 |
| 1307546 | 3 | $G_{ks}{}^{m}C_{ks}A_{ks}T_{ds}G_{ms}U_{d25s}T_{ds}{}^{m}C_{ds}T_{ds}{}^{m}C_{ds}A_{ds}{}^{m}C_{ds}A_{ds}T_{ks}T_{ks}A_{k}$ | 164 | 20 |
| 1306773 | 4 | $G_{ks}{}^{m}C_{ks}A_{ks}T_{ds}G_{ms}T_{ds}U_{d25s}{}^{m}C_{ds}T_{ds}{}^{m}C_{ds}A_{ds}{}^{m}C_{ds}A_{ds}T_{ks}T_{ks}A_{k}$ | 210 | 21 |
| 1306777 | 5 | $G_{ks}{}^{m}C_{ks}A_{ks}T_{ds}G_{ms}T_{ds}T_{ds}{}^{m}C_{d25s}T_{ds}{}^{m}C_{ds}A_{ds}{}^{m}C_{ds}A_{ds}T_{ks}T_{ks}A_{k}$ | 4293 | 18 |
| 1309496 | 6 | $G_{ks}{}^{m}C_{ks}A_{ks}T_{ds}G_{ms}T_{ds}T_{ds}{}^{m}C_{ds}U_{d25s}{}^{m}C_{ds}A_{ds}{}^{m}C_{ds}A_{ds}T_{ks}T_{ks}A_{k}$ | 3744 | 39 |
| 1306759 | 7 | $G_{ks}{}^{m}C_{ks}A_{ks}T_{ds}G_{ms}T_{ds}T_{ds}{}^{m}C_{ds}T_{ds}{}^{m}C_{d25s}A_{ds}{}^{m}C_{ds}A_{ds}T_{ks}T_{ks}A_{k}$ | 3408 | 18 |
| 1306738 | 8 | $G_{ks}{}^{m}C_{ks}A_{ks}T_{ds}G_{ms}T_{ds}T_{ds}{}^{m}C_{ds}T_{ds}{}^{m}C_{ds}A_{d25s}{}^{m}C_{ds}A_{ds}T_{ks}T_{ks}A_{k}$ | 2162 | 18 |
| 1306931 | 9 | $G_{ks}{}^{m}C_{ks}A_{ks}T_{ds}G_{ms}T_{ds}T_{ds}{}^{m}C_{ds}T_{ds}{}^{m}C_{ds}A_{ds}{}^{m}C_{d25s}A_{ds}T_{ks}T_{ks}A_{k}$ | 4384 | 18 |
| 1306769 | 10 | $G_{ks}{}^{m}C_{ks}A_{ks}T_{ds}G_{ms}T_{ds}T_{ds}{}^{m}C_{ds}T_{ds}{}^{m}C_{ds}A_{ds}{}^{m}C_{ds}A_{d25s}T_{ks}T_{ks}A_{k}$ | 4769 | 18 |

What is claimed:

1. An oligomeric compound comprising a modified oligonucleotide consisting of 14 to 16 linked nucleosides, wherein the modified oligonucleotide has a 5'-region, a central region, and a 3'-region, wherein:

the 5'-region consists of 1-3 linked nucleosides, each comprising a 4'-to-2' linked bicyclic sugar moiety;

the 3' region consists of 1-3 linked nucleosides, each comprising a 4'-to-2' linked bicyclic sugar moiety;

and the central region consists of 9-10 linked nucleosides, wherein the central region has the following formula:

$(N_d)(N_x)(N_d)_n$ wherein $N_x$ is a nucleoside comprising a 2'-OMe-β-D-ribofuranosyl sugar moiety and each $N_d$ is a nucleoside comprising a 2'-β-D-deoxyribosyl sugar moiety;

and n is 7 or 8.

2. The oligomeric compound of claim 1, wherein the 5' region consists of 3 nucleosides.

3. The oligomeric compound of claim 1, wherein the 3' region consists of 3 nucleosides.

4. The oligomeric compound of claim 1, wherein each 4'-to-2' linked bicyclic sugar moiety of each nucleoside of the 5' region is independently selected from cEt, LNA, and ENA.

5. The oligomeric compound of claim 1, wherein each 4'-to-2' linked bicyclic sugar moiety of each nucleoside of the 3' region is independently selected from cEt, LNA, and ENA.

6. The oligomeric compound of claim 1, wherein each 4'-2' linked bicyclic sugar moiety of each nucleoside of the 3' region and the 5' region is a cEt.

7. The oligomeric compound of claim 1, wherein each nucleobase of each nucleoside of the modified oligonucleotide is independently selected from thymine, uracil, guanine, cytosine, 5-methylcytosine, and adenine.

8. The oligomeric compound of claim 1, wherein each internucleoside linkage is independently selected from phosphodiester and phosphorothioate internucleoside linkages.

9. The oligomeric compound of claim 1, wherein at least one internucleoside linkage within the central region is a modified internucleoside linkage other than phosphorothioate and each remaining internucleoside linkage in the modified oligonucleotide is independently selected from phosphodiester and phosphorothioate internucleoside linkages.

10. The oligomeric compound of claim 1, wherein the nucleobase sequence of the modified oligonucleotide is at least 85%, at least 90%, at least 95%, or 100% complementary to a target RNA.

11. The oligomeric compound of claim 10, wherein the target RNA is a target mRNA or a target pre-mRNA.

12. The oligomeric compound of claim 10, wherein the target RNA is not a mouse, rat, monkey, or human PTEN, SRB-1, MYD11, HTT, SOD1, or alpha-synuclein mRNA.

13. The oligomeric compound of claim 10, wherein the target RNA is expressed in the liver.

14. The oligomeric compound of claim 10, wherein the target RNA is expressed in the central nervous system.

15. The oligomeric compound of claim 10, wherein the target RNA is expressed in cancer cells.

16. The oligomeric compound of claim 10, wherein the target RNA is expressed in muscle cells.

17. The oligomeric compound of claim 10, wherein the target RNA is a MeCP2, DUX4, HDAC2, APP, Ataxin 1, Ataxin 2, Ataxin 3, Ataxin 6, Ataxin 7, C9ORF72, UBE3A, Prion, PMP22, Tau, LRRK2, LINGO2, GYS1, KCNT1, IRF8, Progranulin, or GFAP RNA.

18. The oligomeric compound of claim 10, wherein modulation of the expression of the target RNA is associated with treating a disorder or condition.

19. The oligomeric compound of claim 9, wherein the modified internucleoside linkage other than phosphorothioate is a methoxypropyl internucleoside linkage.

20. The oligomeric compound of claim 9, wherein the central region contains exactly one modified internucleoside linkage other than phosphorothioate.

* * * * *

SEQUENCE LISTING

<160> NUMBER OF SEQ ID NOS: 154

<210> SEQ ID NO 1
<211> LENGTH: 14836
<212> TYPE: DNA
<213> ORGANISM: Mus musculus

<400> SEQUENCE: 1
cctcccccgt gtctccccac acccgggttg gggttgtttt ggttgaccag agtggaacac 60
aacgatctat tggcagggct gaacaccaat gggtctattt gtaaagcgcc aatgaccact 120
ttctgaagca gggttttagg gagcggggcc ttagggaact ctttggtcct ttttagaaca 180
ctggactttc ttctggaaag gcaggaaaca ctgaagttta agaagttgtt tccagcttcc 240
attaactgaa cacacattaa aaccaagcac agagaatcag gacgtttcgc gggagtgaga 300
cccagtcatt tctcctccgt ttccattctg cagggtgaga gttgtaatca cccacccact 360
attcgtacca tccacccacc cccagtcgag agaatagggg tacagagggg aggtggcaaa 420
gaaaattcac gatactgagt atctctggga gacctgtttg gtctctttgc tcggtagcgc 480
agccctacgt tagaatgcat cttcccggga atgactgtag tgagactttg gctgggaatc 540
caagttattc taactgtaga ttggtccacg ttgccctaag cctagcagtc cactgcggca 600
cagacaccct ggacatgagg tgggtcagct taagttcctg gcacgaaaga aagggtactc 660
tggcaacttt tggatgcggc gaaacagact gtttcgtctc tcaggttctt atttcacggc 720
ttgtgccttt gacagcccct tagtttctct atctgcagga tgggagcatt aagctctacg 780
acccagcctc tttacaattc aggtccaaag agcccgccca agttggggac tgggaagatc 840
aaaggtctca gcacccagcg gagccgcgga cactgagggc gccaagaagg gggtgggtag 900
gtagggaact ggaagggcgg ctgctccgca ggggatgcgc gtcagagacc ccagccacac 960
tccaggcccg ccccttgatg agccccgccc cgccccgcct ggttttcgcc tctaaagcgc 1020
ccagcgctcg cctcccgctg ccgcactttc actctcggtc cacctcggtg tcctcttgct 1080
gtccagctct gcagcctccg gcgcgccctc ccgcccacgc catggacgcc aaggtcgtcg 1140
ccgtgctggc cctggtgctg gccgcgctct gcatcagtga cggtgagtgc aatccgcggc 1200
cgggcccggg aaaggctcgc agctctgcgc cggagctcct tcgggtccgc ggttcctctg 1260
cccgcgccga agtcgcggag aaagaactcg gtcggcgccg ttcactacaa gcgaacttgg 1320
ggcagtccac tttgcagggc gcactcccac cgggtgccct ttcccgtgtc ccacgggtcg 1380
caccgaggtt ttgtgctctg cgaagtgcgg ccataggacc tagagagggc tgcaggggag 1440
gacccgcagg attgttgggc aagagtgggt tcggcgcgga atggaagcgt gggcgattgt 1500
gtccggggct tgggccccgg agcgcgccag ctgcactcag ctagtgtcta ccggcgccca 1560
gatgtttcca gaggcgaagg gcagcgcggt cccggagttg accgtgcaag aggttcactc 1620
gggtggtgcg tgtgtcagca aactctcaaa gaccggtcaa gtagctcgaa gtgcatggct 1680
tggctatagg ttcagtggtg aggctgagtt tcgtcccctg cgggtgtagc gtgttctctt 1740
acagcaccct cgaggggctc agggccacca gcagcgcagc gcagctcttg aactcgcgct 1800
gccagccagg gccgcgcttc tgcacagttc gttggtccgt agcgacgcgg acctgagcac 1860
gcgtctcttc actgcccctt tttcttctta cccgggtcac tagacaaagg ctcagcagtt 1920
acccaagcta tatgcacacc tctccccaac ccccaaacac acctgcaaac gggcgctttt 1980
gtagccagcc ccggagtcct cagctctgga atgagagctg cagcggagtt cagtctccca 2040
gacccagggt ggtgtcttct ttcactggga aagggctttc attttgtttt cttttttga 2100
cactgaagag aaaactctca gcgctgttac aagacaccgt tgctgcaaaa caaaacaaac 2160
cattgcctct gaacacaaaa caaaatccta ctagtcgatc ccctgccttc ctccgcagtg 2220
gtgtttcctg gagagaactg agggacagtc ggggctcttg gtgagactga gctctaaatg 2280
ctgcccaagt acaccaactc gttcgtttgg gttctttccc tgtgacaacg gggtacggga 2340
atggttggag ttgcctagtc cgagggaaat gttctgtaaa agaatagtca gttgctgatc 2400
ggagtagtaa aaaaaaagaa atgaaaggca gtttcgattt tttttttttt tttttttttt 2460
ttttttgtta ccgagaacac ccgggaggct gagccttccc actggtcccc cagtgccccg 2520
tcatggagca cattgatttg ggcattaata attgaatgag ctggtgatgt tgcaagggtc 2580
acagcctctg gcaagttagg tatggggcaa gaatgtagga ctcaggtcct caaggttgga 2640
gtgcaattat ccagagtaaa agttgtctca ccctcaacat attctgaccc taggaagagt 2700
cggattgttg acagtgtctg gatcagacct gttctctagg caggacccca ttgtgctgcc 2760
cgaatgaact tttttacctc ctagtgcctg tgtgccctct gatcttacac agccctcaag 2820
ttgcagcacg gctaaccttg ctgtggttcc tgtcttttcc catcagctac tccaactcag 2880
aagctagata gtagacaccg gaggcttctt tggttaaacc cagagcagca ggcttgccag 2940
gcttgttaga ttgaatggac ccctggttcc ctaagccaag ctctctagat tcccaagtcc 3000
agggtggcag cagagctgga ttagactttg gtctgtacct gaagtctggt tttcctatgc 3060
tttagagtct aaagacacta cccttcctgg ggcatgcatc ccttagctaa ataatgcttg 3120
cagaagaaga taatcccatc atatatttaa ttcggtccac ttctccagct gcttcccaaa 3180
ggcagtgaac ttcagaatac ccagaagtct cctggaactc taaataagca aacttaaaat 3240
cctggggcta actattctca gtcatacttt taaactttgg tgaaaagacc cataaattga 3300
aacatttggg gatgctcagt agagctagga taaaaccctg ttgttggggg agcagctaca 3360
aatccagcag tcctcagggt ttgcaattct agacttaaag ggtggttctt aaggggggt 3420
tctaaaggag ccccttgcta atttacacta atgagtgtca attatagcat tttgcaaatt 3480
ggtgaattgg caaacaaagc tggtaatagg atccaggagg cctaggcatc caggtagtga 3540
ccataaaagc cacggttgac cccagctttt gggaaaagct ggatagaagg taaatccggg 3600
tcctcccctc tggattcttt tgtgatttcc agggcttagg atagggtgag tgggaggagg 3660

```
gaaaactgca ggtggtagaa gtgaagcccc ccacctccag gcctgcacca gagggccaca   3720
agggagccca gaactctgcc accccacttc tcctgggtcc ttttgtcctt tagaggctga   3780
gcccagtcag atctcactgt gatccctggc cgaggggatg gtctttgcaa gaaactttct   3840
gtaaccattc ctgctgatgt tcctgagtct tccccacaag agccaccaaa ccccctgcac   3900
caggcagata atgactggcc ccacttttct ctctacacct cctctaggta aaccagtcag   3960
cctgagctac cgatgcccct gccggttctt cgagagccac atcgccagag ccaacgtcaa   4020
gcatctgaaa atcctcaaca ctccaaactg tgcccttcag attgtgtaag tcctagccgc   4080
catcccccaa agaggagcat ggtatagaag cctcggactt ggcataacta ggggcagctg   4140
ttaccaccac caccacgggg acactgatat gccatcagac atgggtttca aaggatactt   4200
ttgttcccca gagccctgat gtcctcagtg tttctcactc ttgctttcca agctgtttct   4260
tgcagcacag tgggccgcct ctctacagaa aaagccatgg acttgatgga ggtcagccct   4320
cagctgacag ttgggtctgt cttgtcagtt tcaaggttct ggtgtccaaa gttaatcctt   4380
tctcacatag aaaaaaaaat tacaagaccc ggatggcacg gggggggggg gggttcagtt   4440
ttactcactt gcactcactt gctcagaggt catttttgtt ttagagtttt agagtttgct   4500
ggagtgtgat ggtagctgcc agtatttgat ttaaatttac ctgggaaata agaaaagccc   4560
aaaaaaggta taaatgatgt gaatatctca ctcagagtct ggtagacttg gcagagatgt   4620
gtcctgtgct agtctgtcct gctcactgcc ccccagcagg ggttcccatc ctcgggagac   4680
tcaacactaa caacagtata aggatgcagc agctggagca atgctagcct gacggctttg   4740
tcacccaacg gtgactgctt cagactttct gtgctcatca gccttcctct ccagcctccg   4800
ctgctgtgtt atgtacagta ggctttagag acctagatga tgaatattat ttttgctgtt   4860
ttgattaaaa tacaatactc tcccgagaaa gggattttaa agatgatgag tttacgtttg   4920
aataggctgt gctggtgcac tgtcccggga agggcccttg aacttagagg gtcaaataca   4980
actattgatt ctgggtgatc actaagttaa taaatggcag gatccagact gacacccctg   5040
atccctgttg aagttacatc cctctgaacg actggtcaac tgcagggcag cctgcttgaa   5100
gagggttacc tgtccctagg acactgaaca ggcatttgtt tttcctagaa gacagttcac   5160
cagctggaga ggagtcgtct cccgtagttt ctgtttggtt gcttttggtt tttgtttggt   5220
tttggttttt taattatctg gcatccagga cttgatggaa aataaccaga gctaagctca   5280
ccggttcatc tgcccattag gaagttctag ggatgggaga aagaacacgg cgtcaattaa   5340
caaatccaca aagctaagac cttgaagcat tctgtgaact tgtaaacgcg ctcaggcaac   5400
cattggacaa tttgtctaga ctgctccttg cccacctgaa ctgccctgtt cctccccttc   5460
tggactcctg ccgtcttcct ccagagctac ctttaaggtt gtcccatgta ctatcaaggt   5520
gctctgtcaa aagttcttag gctgcttctg gcactctcca gaattttcca agacctcccc   5580
cccaccatga tatcagtcat ccgcgccttc tgggtggttc ttcctccaca cccttttgggc  5640
actttgactc ctgtgggata ttcgtccttc cttttccttt agctttcctc acttgccaag   5700
ctccaacttg gccagaagct caaatgcctc cactgtggtc tcttctctgt gtcccctggg   5760
agacatcctt agcacgtccc taactctgcg gtggtggtcc caacacgatt caagtgctat   5820
gtcttccaaa actgaagctt ccgggagcag cagctgggcc ctgcagtgag gacctttagc   5880
tgggtgtgtt gggtgagccc acaggatcgc tttctcccgc ttggctgtac agcgtctctc   5940
cccttgtgtt ttggcagtgc acggctgaag aacaacaaca gacaagtgtg cattgacccg   6000
aaattaaagt ggatccaaga gtacctggag aaagctttaa acaagtaagc acaacagccc   6060
```

-continued

```
aaaggacttt ccagtagacc cccgaggaag gctgacatcc gtgggagatg caagggcagt   6120
ggtggggagg agggcctgaa ccctggccag gatggccggc gggacagcac tgactggggt   6180
catgctaagg tttgccagca taaagacact ccgccatagc atatggtacg atattgcagc   6240
ttatattcat ccctgccctc gcccgtgcac aatggagctt ttataactgg ggtttttcta   6300
aggaattgta ttaccctaac cagttagctt catccccatt ctcctcatcc tcatcttcat   6360
tttaaaaagc agtgattact tcaagggctg tattcagttt gctttggagc ttctctttgc   6420
cctggggcct ctgggcacag ttatagacgg tggctttgca gggagcccta gagagaaacc   6480
ttccaccaga gcagagtccg aggaacgctg cagggcttgt cctgcagggg gcgctcctcg   6540
acagatgcct tgtcctgagt caacacaaga tccggcagag ggaggctcct ttatccagtt   6600
cagtgccagg gtcgggaagc ttcctttaga agtgatccct gaagctgtgc tcagagaccc   6660
tttcctagcc gttcctgctc tctgcttgcc tccaaacgca tgcttcatct gacttccgct   6720
tctcacctct gtagcctgac ggaccaatgc tgcaatggaa gggaggagag tgatgtgggg   6780
tgccccctcc ctctcttccc tttgctttcc tctcacttgg gccctttgtg agatttttct   6840
ttggcctcct gtagaatgga gccagaccat cctggataat gtgagaacat gcctagattt   6900
acccacaaaa cacaagtctg agaattaatc ataaacggaa gtttaaatga ggatttggac   6960
tttggtaatt gtccctgagt cctatatatt tcaacagtgg ctctatgggc tctgatcgaa   7020
tatcagtgat gaaaataata ataataataa taataacgaa taagccagaa tcttgccatg   7080
aagccacagt ggggattctg ggttccaatc agaaatggag acaagataaa acttgcatac   7140
attcttatga tcacagacgg ccctggtggt ttttggtaac tatttacaag gcattttttt   7200
acatatattt ttgtgcactt tttatgtttc tttggaagac aaatgtattt cagaatatat   7260
ttgtagtcaa ttcatatatt tgaagtggag ccatagtaat gccagtagat atctctatga   7320
tcttgagcta ctggcaactt gtaaagaaat atatatgaca tataaatgta ttgtagcttt   7380
ccggtgtcag ccacggtgta tttttccact tggaatgaaa ttgtatcaac tgtgacatta   7440
tatgcactag caataaaatg ctaattgttt catgctgtaa acctcctacc gtatgtggga   7500
atttatttac ctgaaataaa atctactagt tgttagatgg agtgcacata catttctgaa   7560
gatggagaaa aacaggtgtg cctgctgatc aggtgctgtg ggctgccctg cagtcctggt   7620
gagcgacaga cactgaggca ggcttgtctc atgaacaggc tgcctctgca gtgaaagttt   7680
ttgtgtattt tttttaaccc aagctagttt tctaatgaat aatacttgac tcactaattt   7740
cccctcctcc tccttctcct cagttctcct aacatcctca tgtgatcccc agactcaact   7800
ccagtaatat caagctttcc tattttccca tgtaaaaaaa tcccatgact ctgggccatg   7860
ttaatatcag gcttttgtgg gaacaggtgg cctcacccca taaatcatta aataccattc   7920
agcttgaatc attttaatgt gacagtcaca aaccagttgc tctaataaaa actctgctaa   7980
ccatccttct ccttagctct ctagaacaat ctcagttatc cctagggatg ctccccagca   8040
tccagaaaag agaagtggga tcaatcatcc tgcctttctc cccctcctct cttggagggc   8100
tgcctgagcc cgtggcctcc acctcccctg ctttgtataa tttgaaatgc agatttgtag   8160
tgaaggcaga gttcacctct gcattgaaag ggaaggcagg cccagagctt ccttccctgc   8220
cctctgagat gtgcatttat gtctcaggat ggatgagctt tggtaggaat gctcaaaacc   8280
aggaccagcc agacaaactg gcagtccctg taagcggttc ccgggtcata gggttagggc   8340
acccctgttt aactttgggg tggggaaagt atctggtttt ctttgataaa ttgcttgtga   8400
```

accacatttg ccaagtggcc tccaggcctc aaactcaaag accgagctaa atcgactcgg 8460
aaggcaatgc tgaatgaaga ttgtgggaac tgagatagat acactcctct atgttgcaat 8520
gtgattaatg gttctactaa ttttatctaa gggggcgcag agaagaaaaa gtggggaaaa 8580
aagaaaagat aggaaaaaag aagcgacaga agaagagaaa ggctgcccag aaaaggaaaa 8640
actagttccc cgcttcctgc cgatggaccg cagtgcgctc tgctctggcg ctttgtaact 8700
cgctcctccc tcttcggggg cagaccccac actccgggca ggtgctcaaa cctgacggta 8760
aactcttccc tcttcggggg cagaccccat accccggggc gggtgcttag gctttcctgc 8820
cctggtggcc acaccagctg ctgtatttat gtgcttcata aggccctgct ctgtctgcta 8880
aagctatgaa gaaagatgtg cagagactgg ggtggagact aagccaaaga ggagctgcct 8940
agcctggcag cattgccccg agctgagccc ccttggccag gacttcacaa ggctcacacc 9000
tacaatccca tgaaggccag ggtggtctgc ttagccagga aagggcaagt gccttcccct 9060
cggccacact gccccttgtg gccttctcgg gacatgtggt aactgacttg ctctcaggcc 9120
cacccgcagc ttttccaaat acctgcagcc ttcagccctg ctgccctgcc tgtgggagca 9180
gctttgactc cagtccagaa gggtttctgc agactgtgtt gggtgagacg cagaaaggat 9240
gaaatctcag aacacatgtc agctgcttct caggaaatct tttctttgga caattcactt 9300
tagagtcttt aaacgggtct ctcgtgggga ggatagatgt gctctggaac tttctgaagg 9360
accagcagct tcagggactc ttagtctgtc cttccccact tttggtccca acatccctgg 9420
gatggtgtgc tgtctgggca ccacggtctc catcctcact cctgagagat ttctgccttc 9480
tgtgagttgg gttaaagctc tggaattatc tactatccca atccactacc ctcacctggc 9540
aatatttgtc tgtttttgtt tgtttgtttg tttgtttttg tcttttgcca gtttgaatta 9600
gaaggcaagg ctctgatttt agtagtgttt tggaaaagga ctttttttctt caccttcctc 9660
tttgcctcat gtgtacacac acacacacat cttgtacccc agacctctgg gtataatttt 9720
cataattggt gcagaaagaa gaaatgatct gaagatgtgt taaatggatt gcaggggaag 9780
gaaggcccag ggccctgtgt gtcatgccct cttgggttcc taagttctat gttccttaga 9840
ggttctagca ttaaacagat aaagcccttc atggtcctgg ctgaggaaga gtcttgctag 9900
ggggattcag ggaagacccg tgttaccagc tcttaccctt tatctggaca gctctcctac 9960
cctgtatctt ctcctcagat ctgaggatag caggctggac tattggtggg cacctttcaa 10020
gcccagggct actgtttgtc ctgtggcagc cggctacagt ctcgtctgag tggcctcatc 10080
tggacccttc ctgttattaa taaaacgctt ctggaggcca gatctgtgct caagccatag 10140
ttctgcttag aaagggatgc cccaccctta ccggacactg ggaagaactg ttggccccta 10200
gaaaccaaag gccaaactga ggctgccctg agttggaaga ccactttctg aaatgcccat 10260
ggactctgcc tcccaaccat tcgtctctca ctcctagcag agctgtctgt gcagactgtt 10320
tcttaggagg cacagcaagc tccagggaac cctctgtgct tatgaagctc gtctggtggg 10380
caaccccagc ccactggaca gagtcctcat ggaaatgcct gggaagctga tttcatctaa 10440
ggatgggttg aagtaggatg tgctcctgcg acttctcagg caggtgagag gggtagtcct 10500
tacactgtct agcataaacg ccttccggaa ggacctgcag ctccagagac cacctcctga 10560
gcaccaagac ctcttctggt ggtgtggaac cagccaagag atttcaagga agagtgatta 10620
tttgatgaat gctatgggaa tggcctcttc tcttggagtt ctgaggcctg gggatgccca 10680
ggaacactgg gcacctgctg ctgttagggc caatgcatag tctcagcacc ggtgtcctaa 10740
ggttaaggcg gtgcgccttg tcatgtgctc cttgtaccat gccatctgtg ccagtgtgtg 10800

-continued tctgcctcac cctgtgcttg acatgttcac ccatcttctc tgcttcccgc caccatccag 10860
atcctcagcg gccgccccgg ctgtgccctt ccctgctctc ccgctctctc aggcctcgga 10920
aggaagatcg gtggctgcga gctgaactaa ggagtagggc ctgtggctca gcgctaggcc 10980
acgcacgcag catcccaggc atgtggtgag aaactgcctt aatgtgtctc ctctgttctt 11040
gtcaacagga ggctcaagat gtgagaggtg tgagtcagac gcccgaggaa cttacaggag 11100
gagcctaggt ctgaagtcag tgttagggaa gggcccatag ccacttcctc tgctcctgag 11160
cagggctgaa gccgtttgca agggacttgc tttgcacagt tttgctgtac tttcacattt 11220
tattatgtag caagatacat ggtgattttt tttttttca tttagcctga ttttccaacg 11280
tcattggtga caggccaagg ccactatgtt atttcctttg ttctggtatc cttcccttgg 11340
aggaccttct ctgagtagtg gctccccagg tttgtccttt gagctgaggc aggaggctca 11400
cccattcttc tgaataggaa ctgggtgttc ccaccccca aggactgcag ggctttccca 11460
agctgaggca ggaacgtgag gccagggaag agtgagcttc accctcatcc cacgctgtcc 11520
tcctcaaccc accatgctca tcattctgtc tcatccatcc atccatccat ccattcatcg 11580
ccatgtgtcc gcaagactgt ctccatgacc ctgaaaaagg actctcgaga tgaaatcctt 11640
tattcaaatg ggacagcaag aaggaaaagc caatgtctgg tgtctctccc cccgccccta 11700
ccctgcgcgc atctatgtct tgtttggaat attgtctctt caaccccctg ttcatgtcct 11760
tctcactcat gatcgatgtc ttgtctgtgc actgtctcta acccaaatgc aaaggctgag 11820
tgtgaggtga tggccccgag gtccaggttg tagtcatgga aagagccctg ctgtctccct 11880
tctcaggggg cccattttag acacacaaag cccaaagaaa ggtggtttgc aacagtgctt 11940
agctcgagcc tccatatttc cataactgtt agcttaaaac tgtggggttt taccttcctg 12000
gaaccaaatg cattcttctg ttgaggagta acaggtctca attcttttca attaatttta 12060
aaagtcaatc actaagagca tcggctttgg gccctgatgg gcaggcattt ccctggaaag 12120
ggggtgaact acctacctct cctcaagaca gccgaagggt gggattggtg ccgctctggg 12180
aagcgtggcc ccaggagttt tgtcctctgc agtttttaat gcaagttcac tgccactttg 12240
acaaaagccc aattagaagc cagtctctag ttccttaaac aaaacagaca gagtaaggaa 12300
aggaaggagg gtggcagcca gctggctgga cactcgagaa agacggggaa gtaagctaca 12360
gaaagatagt cttcaaaaac aggtgtttga gagtgaatac tctgtagaat tgttagtggg 12420
gtgtgtgtgg tggtggtggg gggatttcta caaaatagtc ctttaagttg agtttacagc 12480
agatgaaaaa tccaaccagc aaaattttga tcaaatttga acaaaaaccc aaaaacctaa 12540
aactgttgag caggttgcga tgaggagcac agggctagct gcagagctgg atcctcagga 12600
ggatagcgaa ttattttcaa ccctggaata gaaaccacac actggcttgc tgtgcaccag 12660
ccactttgca tctaatccaa gctttgaagg gtgttgcttg ggaggaaaca aatacagcct 12720
tccatcttca ctccagttag ggatcctttc aaagtctcct tcacagtgag gaaaaagaga 12780
agggtagaaa ctttagggag ccggatttgt gtatcaattc ctccgctgac agtcagtttc 12840
tagatggaga cagcctgctt aaagcaaatc cgaatttaaa taggacattt acatcggaaa 12900
agtctctccc taccttaatc ccccattctc ttgctttcaa aatacaagca cagcagtcct 12960
tgaatggctg ttgacccagg gcacctagct gtccctgctg gtcctggggc tgccagaatt 13020
cccttgggcg ccaagcaacc tgccaggtag ccagtccctc tgttacaagc ctttgcatct 13080
ggatagggaa aggggtggag acatacagtc tgctttgtgt tgaaacccag atttgtaccc 13140
tgtgtttata cactgctgct ggctcccgag gacagtggga ctttagcaag gaagtgcagc 13200
cgaggggtaa agagccctct ggttcattgc ctgatcggct ttgagagagg gtttggaggg 13260
caaggggctg cattcctctg agggacttgg cctgaggcct ttcgggcctc tccagtgggt 13320
tctgtttatc ctctcatggg tgattatctc agtggtgtca ccaggggctt cctcccagaa 13380
gtcagtcatc cccaggccgt gcaccctttt cagctggatg agagccaggg atgcattctc 13440
tccaaacagc taccctggcc cattttaagg taatctcatt cttcaaaatg ttccatagaa 13500
tcctccaaat tcccccagca gacttctacc ctcgccaagt tcccaaaacc cactcagcaa 13560
agttgccaac ctcgacgggc tagcagtgtc taagcagcga tgggttcagt gttgtgtgtg 13620
gtgaatactg tattttgttt cagttctgtc tcccagataa tgtgaaaacg gtccaggaga 13680
aggcagcttc ctatatgcag cgtgtgcttt cttattctta tttttaatat atgacagtta 13740
tttgagaagc catttctact ttgaagtcat tatcgatgaa agtgatgtat cttcacctac 13800
cattttccta ataaagttct gtattcaaat atagctgcca agcatcctca gtgaatgtta 13860
ccatgtggaa ttttccacac ttggttttac cccctcaaac ctgactctga ccgtgcagtc 13920
ttagcagaag agcttagcag gtcctagtgt tcactcttgg tctaactgct ggtgtcagaa 13980
gatctctaca gggagaggtg ttccattttc tccacatgac ctggattgct ccttagaggt 14040
cagacagcct tgcactgtac aaggcaatgg cttagggtaa agtcccagga gttttcccta 14100
cagtcccaag aatttggaag aggaaggccc acactacaca tgcaggtcat ggtggaaggt 14160
gacagaggaa ggactctgtc cctgtaagac agctggaaac cacaatattc tgcatgttcc 14220
tatcctgggt gaggacgcta atggaagtca aaggggaatt tgctaactgc tgttggccag 14280
cttcctccaa gaatcctgct tccccaacag acagagcctt tgtctcttat agtttggtct 14340
tcagattctc tttatcccac attcagccat ttttgtaaaa gagaggctag caccagctcc 14400
aaatatccaa atctgcagtg tttgagatct cactgcgcct cctccatacc aacacatttg 14460
ccattactta tagggtagtt ttcatgtgag ttctaagttg attaacacac aagaattaga 14520
agggtgggag gctctaggaa aggcactgtg ggactatttg actgcatggg tgtgaaaatg 14580
taaggaacag gcaagagctt ggatcccatt ctctctgccc acattgtgac ttgagatata 14640
ctaattgctc ttgggggtct cagtcatata ccatccataa cagagttaaa ctgagagaga 14700
tacaggatca gctagaatga aaagcccacc ccatgcttcc agaaagtccc ctctttatac 14760
ctcctgtgat atgaactaga ggaaaagcaa ttgactttgc ttctcaaaca gcctacggca 14820
aagccctgtg agtttg 14836

<210> SEQ ID NO 2
<211> LENGTH: 25001
<212> TYPE: DNA
<213> ORGANISM: Mus musculus

<400> SEQUENCE: 2
aagggtttct ttggcttaca cttttcttat tgttgttcat tattgaagga agtcaggaca 60
ggaattcaaa caagtcagga tcaaggaggc aggagctgat gcagaggcca tggagggatg 120
ttacttacta gcttacaccc cccccccccc cccggcttgc tcagctttct tttttttttt 180
tttttttttt tttttttag atattttcta atttacattt caaatgctac cctgaaagtc 240
ccctatacca tccccccaca ctgctcccca acccacccac tcctgcttcc tggccctggc 300
attcctctgt attgttgctc agctttctta tagaacccag gaccaccagc ccaggaatga 360
caccacccat agtaggctgt gccttcctcc actgatcacc aacggagaaa tatgggcaac 420
agcttgccca taggatgggt cactagttgg gttggttact gttgggccat tccctcagtc 480
tctgctccat cccccatctc tacatttctt gtagacagaa tcaattttgg gtcaaaagtt 540
ttgcaggcag gttgttgtcc ctcttacatt tctcatggag gcatttcctc aacttatttc 600
ctctctctga tgtctccagc tcatgtcaag ttgacacagt tgttcgggac ccacatgaag 660
accaagctgt tcatctgcta catgtgtggg gaggcctagg tccaacccgt gtatgctgtg 720
gtagttcagt ctctgagagc caaaacagtc caggttagtt gactctattg atcttccttt 780
ggagttccat ccccttttggg gccctcaatc cttcccacaa ctctaccatc agagtcccca 840
agcttcatcc actgtttggc tgtgggtctc tgcatccgtc tgagtcagct gctgggtgga 900
gcctctcaga ggacaggctt tctagactcc tgtctgcaag catagcatta atagcatcag 960
ggattggtgc ttgcccatag gatggatcac tagttgggtt ggttactgtt ggccattccc 1020
tcagtctctg ctccatcccc catctctaca tttcttatag acagaatcaa ttttgggtca 1080
aaagttttgc aggcaggttg ttgtccctct tgctccactg aggttcctgc ctagctacat 1140
gaggtagcct ctttaggttt gatatcctca atgctgtgaa tcccaactaa gatcaccccc 1200
cattcattcc tggtgtctcc cctatctcag gtctcagata tgccttcaag atgccccccc 1260
cccacctctc cacctctgcc agctgcagat ttccattcat tctcatggcc atctggctat 1320
ctctcctgtt cctccccata cctggtcctg aaccccccttc accccactcc ccatcccctc 1380
tcccacccag ttcctttcct ccatcttcct cctatgactc ttttattccc tcttctaaat 1440
aagattcaag catcctcgct tggacattcc ttcttattta gcttctttgg gtctgtggag 1500
tggagcgtga gtattccaac ttctaaggca cacagacaac ctcagattct ccagcccttt 1560
gtgtgtgttg cttatttgaa caaacgggtg aaagaaaaca cacaaagttg gcgtgttgaa 1620
agagttagtc gatcttctgg ggtaggtttc agtacagaga ccaaagggac attctcagac 1680
actagacaca ctatgcaaag acaggatgtc acatgacaaa ggataacggc acaagtaaac 1740
atttaagcaa cagtgttcca taccggctca cgtagaaaaa ggacaagact ataggaaaga 1800
aagcaaacac tccgccgagg actacagcaa agacagaaag tatctgcagg tacggcttca 1860
aaaggagcat ttctctcagc aacttatatc tgttaatgcc ctgtcttctg gaataagggc 1920
ttagttttta tcagtagaga gagattgatt tttaagatgt atctgatttt acattgtaga 1980
tctccttagt cacccccctgt agtaaactaa ggaaaacttc cgtggaggga gaggggaaga 2040
ttagtaactc gtagtgagta agaattctct ttcaagaaaa agattcaaga gcaatacaag 2100
gcctagatat gaaggtgtgt gtgtgtgtgt gtgtgtgtgt gtgtgtgtgt cttaacagcc 2160
tgttcagaat ttagtaggtc acatacactt acaagtaatg aagacaatat attaatgaat 2220
ttgcagtaat tttttgtttt agaaatagaa actgttgtaa ggaggataat cattcagagc 2280
tctttgatat gtatcactca cattcacata catgcataca cacagagaga gagaaagaga 2340
gatacagaga tagacagaga gagaacccaa aaatgtaaag agaggaaatg agttgaaaga 2400
aaaaatggga aactgggtta gggaggggtt cagatgacag tgactggggg ctttcagagt 2460
tgggagtgag gcagcgatgg agagagggca gggaggaggg agtgtccatt gtgacctctg 2520
cagaactctg actagactga gcagctcaca ccgtgttgga gctgtcctaa cactaccaag 2580
gggacggggg agaccccatg aacaccacct agggagttgc tcctttcatt ctgtgtaaag 2640
tctgatgtct tcaaacttgt tgtaaattta tactctgttc taaaaacagt gacattcttc 2700
tctttgtagg atgacctcat tacatcaggt gttatatttt atctttttttg cctcagtttc 2760

-continued tagtggtaag ttgctgtatt tattttcccc taacataata ttttttatta cttgagagtt 2820
tcatacaatg caccctgatc acactcactt tccattcctt ctaagttcac cctcccactc 2880
ttgagccctg ccagctcact ccccccttct tgaaaaaaaa tcatcaagtc aatcaatttg 2940
tgttgagaat atatactcgt tgggaatgtg atcaaactcc caatggtcag cccccttaaag 3000
aaaagtgagt ctttttcctc ccccacttct ctccccactc ccttacccag ttggaagcca 3060
tcaactgtga agagttatac ttcagcatct ttactacaat tttaaaggac tctcttcagt 3120
atttaagtat ggcttagaaa tagctcattc cttgacctgt aatgtaggaa acagcctaag 3180
tccacaaaaa gaaattacac ttcagacccc atatattgtg gaataattcc atgctgtgaa 3240
ctccagggaa ggaaatagag tcgtttattt tccagtgaaa gctccccttt aatacatcaa 3300
agaaagaaag agatttaaat atagaattac aaagagtctt cacctatatc atctgaatgc 3360
tagtaatatc tgtctataga gttgcatctc tatctaccta cacaacacat tgccatgatt 3420
cctaggagca agattagaaa gagaagactc gactcacctc attgattatt attccataag 3480
ggattcagtc tagtatctct ctctgtctct gtctctctgt ctctgtctct gtctctctct 3540
gtctccgtct ctctctctct ctctttctct ctctctctct ctctctcacg cacacacaca 3600
cacacacaca cacacacaca cacactcacc aattcctgac tgaaaatgtt atagaaaaat 3660
taatgtgtgg cttacacatt tggttaattt accccttgca attatgcttc cattctacat 3720
tacatccagt aaatacattg cttaccattc agtagaatga aatgggaagt tacctcacca 3780
atactgatct taacaactta gtgtaagcac ttcttaaaat aatttattta tgttatattg 3840
aatgcctgag actgccattg acatattaag catagttagt tctttttggt gtgacacatg 3900
tgaacagtag cagatctaaa ataaaataaa catatgtaac atattaaatt atacagatta 3960
tagcttaatt tttctttgtg attagattga ttttcaggtt attccttcat tatcaatgtt 4020
ttgaaatccc attgttattt gtactgtctt gttcagtact gttttgacat gttgttgttg 4080
ttgttgttgt tgttgttgtt tgacacagag tttctatgtg tagccctggc tgtcctggag 4140
cttgatttgt agaccaagct gacctcaaac tcagagatct gcctgcctct acctccaagg 4200
gctgggattg aaggtgtgca ccatcatcgc tcggcagcct gtcttaacat cttaaacact 4260
gagttcaata actgtgtcga ttcacaagga cattctgaga attataagac tttttttgctt 4320
atgaatatat atatgcaaat gtaactgaca aaatattatc cattgtggtt gtatcacact 4380
taaaaatctc agagccgaga aagttggggc aagatgatta aaagttcgag gacaggatgg 4440
gctacataac aaggttctgt ctcaaattgg ctataccaaa ccgtccaaca catattttaa 4500
agaaaaataa atgggaggct agagagatgg ctcagtagtt aagagcactt agtgctcttg 4560
catgggatca gttcaattct cagcgcccat gttagatagt tcacaacttc ctatgactct 4620
aacttccagg aatacagcac cctcttctgg cttctgtagg tacacacaca cacacacaca 4680
cacagacggc atacgtacat acatacatac atacatacat acatacatac atgcctacat 4740
acacatgtac atgcatacac aataaaaaag tttttaaaat cttttttttt aaagaaagaa 4800
aattaaaaga ccaattacat tggcatattt tggccaagtt tgcttaattc taggaacaag 4860
gagttacttt aatctaagaa aaacaatcaa tggatgcaat gtagatccaa aggaagtgaa 4920
agaagagagt cctacagaga tttgtcattt gtcttcctgc tatcgggcag agaaccagca 4980
agagagaaac gtgggcattt gaagcccact cagccgtgtc atagcacaag ttgggtcttc 5040
accaatggac agaaggttaa acaaaatata atatcacagt atgcacatgc aacacaaaac 5100
aggatattac tcagcgtgtg aggaagaaaa ttctccctca tactggggca tagctgagcc 5160

-continued

```
ttcgtggttt tatactcaac gaaatgagtc atttacaaat gaacacatga ctgaacccct   5220

aacgtttggt tcccagagat gccgatttca ggaaaacaaa agaccgaaga gaactgacca   5280

ggggctaatg ctaatgacta tttaatgggt acaagttttc agttggaaaa gctgaaggaa   5340

ttctagaata gtggtggaaa ttgtacctaa ggtacatact tcattccaca actctagaga   5400

cctgaaaagg gccggagtga caaactttat gtcatatata ttttgccata gaagaacaaa   5460

attaaaataa tctaacacat cgaagatttt aaagattttc ataataaaat agtttagcaa   5520

actcagaact ttcccaatga ctaagtagta ctgtaaaaca acaacaacta gaaaaacatt   5580

caaaccaaaa gttttcaaga aatctcatat gtaatggtga ctgaaatagt gtttccctga   5640

ggtactgggg taaggcagga gtatccacaa cttggctcct gtgaatagga aacaaggaac   5700

agagagatgc aagcatcttc aaaaagttgt cataggatcc atcatggaca ttccaggagg   5760

ggttcagttc tacttttagt tttctgtgac atctcattac aggttttgat tttttccccc   5820

catagcttcg ccagcatgga aatttattca caagtaccaa gtcagggagt ctgcctatgt   5880

gtccatcaat agatgaatgc aaagagcaaa cactggatgt aggcacagtg cagggggcag   5940

ggaggggtgg catgttctgc atttagctaa aatggttgtt ttagttttta ctaattcttc   6000

aagaatgcca tataccatat tttgctaatt tttacctcga ctccccaaac tccatccaga   6060

accccccatt ctgtacccac ctaactctgt gttctccctg tttcatttgg ccacagtgag   6120

gaatgaaatc gtgccatttg tgtaacaatg gctgtgactg ggcatcatca ttattcagtg   6180

agataagtca gattgaagaa gataaatatc ccattttctc aaatttgtgg attctagacc   6240

ttatatggat acataaaatc cagtgtgtgt gtgtgtgtgt gtgtgtgtgt gtgtgtgtgt   6300

gtgtgtgtgc ttgagtgaca cactctaggc tccagagtct aggggaatga cagagactag   6360

aaggaaagag ggaaacgaaa agatatgaag aataaatata gtcgaagcac atgatacatg   6420

cctatgatat tatgatgtat acacacctat gcaggtgtcc catgaagccc cctgctatgc   6480

aacgaatacg tgtcaataaa tgtgttgaga gactatctac tgtcacttcc cttaaacatt   6540

atattagaga tcctgtgtag cacagtaggg aaggtcgaag gacctaagag tcaggagaaa   6600

gatggaaatt aactgactct tcccataaat gtggttatgt acatagaaaa attcaaagta   6660

atgaatgcac tgattatttc aggcagatca gcaaggagtt tacaaactcg atggaccccc   6720

gggagtggag gcacacactt gtaatctcat gactcaggag gcagagggca catcagagac   6780

cctaactcca gctcttccgt tcaaaatctt caatatacaa acagtagcca actctcgcca   6840

gtactaggaa ctgtactgag attatgaaag tcaatattat aggttaaatg attcaagtag   6900

tggctacatc ctaatcaaaa ctgcacattt attaatcctt taaaaatcaa ttcaacttat   6960

caaatcctgg tgttgtgctt gataagaaca ttttaatgtg ttatgatggc ttaatagtaa   7020

aatgttgcat ttcttagagt taacaggtaa actgtgaggt gggaatagac tgccaattag   7080

ctggaaacag acgcagtatg gtttggtggg agacaacact gaacttggaa aaagaagtcg   7140

gatctctatg tagctcctgg gatacttgcc tgtagtggag aaaaccatgt tccctaccaa   7200

gtctctgctg aattttggaa atggatctgt agtgaggttg ctcttcctcc ccacaaatcc   7260

cttccgaggc cccatggacg cagcggagcc tatccttgga ataacttttc taaaggcatg   7320

gactaaaaat atatagggtt gctggggaaa ttaattatat tgaaatatga gtagctaaag   7380

tggaaaatac tcagtacaga attagttgtg gctcggagtt aacaccttac atgacattag   7440

tggcatgccc aaaactgaat agaaataacc aacaaattat cgacaaatca taatgatgtt   7500
```

```
atatctcatc atcacataca tgacaaatac taatcatgtt aattgattac attaataata   7560
caggtatgta tgtaccacat tttggttagg gaatcaatga aaaaccacat gaggtttttt   7620
tgagctcgtt ggttatctag gtcctacaag cctcatagga gggttttgag actgctatgc   7680
acctacaatc ctctcaagac atgactgatg gctgttacag tagtctatat ttgagttaaa   7740
ttttattctt ctggaagtac ttccacgtga gtctggtaat gttttcaagt tataaagaga   7800
aatgggctag caacacctct ccatgggcat gtatggctgc atgaagtaat cttttattca   7860
gtcactaggc aacctactgt gtgaattatt agctatctct tctagcaaca gagcactttt   7920
gaatttttat gcattttggc tttttaaaaa ctaaagctga tgtaaggttt tcgctaaata   7980
gaactcagta agttttccct ggtaaatgtt ggtcatgaga ccatttttaa tgttcgcatg   8040
acatcataca agggcccctc agtcttggct tttagtttgt ggtagtgtca aaacaataaa   8100
tgaacgtaaa cacagcacac ccttgctgac cccctagagg ggtttcatgg ggaccgtgtt   8160
cttcttgccg gtcaacagct gagaaatcac tgagttgctc ctgcagcctt cccaagacaa   8220
tcactcataa atgtgacaac acggagggcc cccatgttgt ttgtgattta tagttccatc   8280
tggggctgtt cactgaagag cgttgcccga tctgatgtcc gaggtcaggc atatttagca   8340
ctgacttttt aacaaaccat gtaacgaggt aagtgcccac caacatctgc agtaatgtgc   8400
gcccgcgtgt ttttttcttc acagaatgcg ttactaaggt cttcaaagac atcagctttc   8460
aaggaggtga cctgagtact gttttcacac cgagcgccac atactgccgc ttggtctgca   8520
ctcaccaccc acggtgcttg ctcttcacgt tcatggctga gtcatcttcg gatgatccta   8580
ccaaatggta acagtttctg tttctctgaa gaggaactga tttccagtgc cagttactca   8640
ccaatgcaga ttaccttaca accccacttt tgtcatttta caaaagggga tgttagtggc   8700
tggaaagtga gtttccttcc acggaaatac taaatattac aggaaggata gcgcttaggc   8760
atattggtgg aaaaccgtaa taactcctgg gacctcaatc ttaaagtcac gtttttgctc   8820
ttcatccatg gtttgtctta cattcttttt ctgtcgtggc tattggctaa caatggtggg   8880
gttatctaga gcttccttct aacctttcaa ttagggggaa aatgtttaaa aagctacttt   8940
aaaaattatt acaacaattt tctaccccct ccaatatcct gtcatattat gtggctttct   9000
cggctcccat cagtggttca ataaggcatg cagactttta tataaaactt aaggcccttc   9060
attggggcag gcagactctc agctctcttc tctaatctta gatcgtctgc caagtagcta   9120
atgatttatc tcgtttccat tcctttccct atctgcctct gaatctccca cctctgcttt   9180
agttctctct ctctctctct ctctctctct ctctctctct ctctctctcc ctctctctct   9240
ctctctctct ctctctctct ctctctctcc ccctctctct gtcccacccc cagaagtccc   9300
acccttgtac ttcccgtccc actttaggca atatgagtgg gtgaggaagg acaagcactt   9360
acaaatcaga agctggtgat gggccataga catgacgata ccaaacatct gccagaactt   9420
agctctttgc cagtacagta atcaacaatt gcacaattga aagtacagag acacgcctta   9480
atacaatata aggaaggtca tcgcaacact gtcatatttg ctttacctac ctgtatatgg   9540
tcacagataa atactgaaag tgagtttaaa atatcatcga cctgcatatc taaatacttc   9600
aacatgaatt tcccaataag gaaactgtaa gaagcccaac aaagttaaac atacttgaaa   9660
tgttaatttt agctgttaat taaattctca tcaaatttca caggttccta tggctgtttt   9720
tccctctcta tcttattttt aaaatattgc atccatttct gtctctatgc taagcttgaa   9780
attttaatat ataaccttta atgcaaaatt aagctgccaa tatctttgtt attgctgttt   9840
tctcagatgg ttacatattg ctgtcaacat taaatattct tctgaaatct agaacagaga   9900
```

```
tcggcaagac aggaataaaa ctttaggctt tgttgaacca aatgcaaaaa gaacattctg   9960
tgtttctaac actgttttag aatgtaacca tgtgtgggct ggagggattg ctcagtggtt  10020
aagtttgctg gctgctcttc taaagggccc taggtttgtt accccaactt acagagattt  10080
gcaatcattg gtaactccag ctctagatgc catcttctgc ctttctcatg catgtgatca  10140
cacacacaca cacacacaca cacacacaca cagagagaga gagagagaga gagagagaga  10200
gagagagaga gagacagaga gagacagaga cagagacaga gacagagaca gagacagagg  10260
cagaggcaga gagagagaca gagagaggca gaggcacaga ctgagagaga gtgtgtgttt  10320
aaaatttaaa atgtagccat gtaaaaaata gaaaaccatt tctatctcaa ggataacaca  10380
aaaatggcag attttaagca acattttagc aataggttaa agtccttcca ttcttattca  10440
tgtcctgttg gaaaggaggg ccgtgtgtgt tcttttagat gtagggatgt tgtaataaaa  10500
aacaaagtca aatcttgcta attaaacatt tgttttggca ggaaacccag tcgtttgtct  10560
ccttctcttt gaccttagga tcccctcttt gaaagcatga attcctgctg aataatgtta  10620
ttttcatttt attttactat tttatttttt aaaaaagaac aggtttgcct gcatcctgaa  10680
ggacagcgtc acagaaatat tgccaatggt aaacatgaca ggcgcgatct ctggatattc  10740
cttcaagcaa tgccctcagc aattaagtag taagattttt tttatcaaat acaattaaaa  10800
ctagccatta gagtatatac gtgtaatcgt ttcagataca ggtttgtggc tataaaataa  10860
aatactacca cctaggacta aacttcccac caaggaacca tcttcctatg tagagtagag  10920
gacacagttt tctcccttcc tctccccata agcacactgt ctcgctttac catttcttag  10980
cctcataaag gcatgtcagc acctcagttc ttattattgc acacgaaagc cctcgttata  11040
aaagctaatt caaatcaaga ggagaaatgc agactgaagt ggcacatgtt ttaatagtgg  11100
aacgggcact tttcagtaag ttaaggggtg aaccagttgg tcagtgcggt ttgaggtcag  11160
aaagtcaaaa ttcaaattca caagctttct atttgttaaa aaaatttttt atttatttta  11220
tatgcattgg tgttttgcct ccatgtgtgt ttgcgtgagc gtgtcagatc ccctgaaact  11280
agagttacac acagttgtga gctgccatgt gggtgttggg aattggaccc aggacctctg  11340
gtagagcagc cagtggtttg aatcgctgag tcccctctcc agtctcaaat gtacaagctt  11400
aaagcggttc cagtctaaga ggcacattgg cttcctcgga atacctccta gtggaagtgg  11460
gaatcacagc tgagtgaaac aaaacataga acttccacgg gagagtgggc gagaagcgag  11520
cagtttccac gcgagagggc cagcagcgaa agcagcgtac tgtagttgcc cctcgcttct  11580
ggtgacgcct agattctccg cctttatttc cagcttgcag caaagatgtg tacgtgaacc  11640
tagacatgaa gggcatgaac tataacagct ctgtcgtgaa gaatgctcga gaatgccagg  11700
agagatgcac agacgatgcc cactgccagt ttttcacata cgcaacaggg tattttccca  11760
gtgtggacca tcggtgagtg agcgggagtc cgagccgctg gatataagcc tgcccaggga  11820
aagaaaaccg ctggttccgt aggtattttc atcaatttga agcctaaact tcttttttta  11880
aaccccaaga tatttgcata acaacaatca ctgttttgtc atgaaaaggt catagcgtgt  11940
ctaacacaca tttacgacat attcaaattt cagaactgga ggatggctcg gtgggtgcgt  12000
aaacacactg cttatgcagg gaccctgagt ttggatccca gcatgcacat aaaagccaga  12060
tatgggtgtg tatgccttta accccagtgc ttgggacatg ggcacgggac agagggagga  12120
tggttggagc tcactggtta gctccaggcc tttattatta ttattattat taaatattgt  12180
ctttatttac atttcaaatg ttatctcctt tccctgcccc ccccccaacc ccctctccca  12240
```

tcccctccc atttctacta ggttgtttac ccacacacca acccactcct gcctccctgc 12300
cctggcattc ccctacactg gggcatagag ccttcacagg accaagggac tctcctccca 12360
ttgatgcctg acaagaacat tctctttagc tccaggctta gggagagatc ctgtctggag 12420
gggaaaagac agagaggtca tagggcagga actctaacac cccccccca cttggacttc 12480
ctattctcac ttgcataccc acacccccac accccacaca caccatatac aatacataca 12540
gcgtggcctc acagattctg tgtatgttgt aaagcataca caagcttacc ctatctaact 12600
tcaaaaggca ttacattttc acgcttgtgg ttctgagagc tcggtttgct tggccatgct 12660
cttcccagtc taacaaatgt cctaacctaa aaatcatcaa aacttaaagt ttgtttctct 12720
atctacctac atgtacagtt ctgtccctta cccaagacga agtcattgga acccatgtgc 12780
aaagttttct cctgtttgat gtgggattcc aaactcctcc aaggaagaaa tctgttatat 12840
aaactaacga gagggaatga ctaaatctgc atcttcagtt taaattgttg ttagaaaagt 12900
atatgacttg ttcttttaca aacattttaa ttttgtgtgt gtgtgtgtat gtttatgtat 12960
gtgtgtgcct gtgcgtttag acacacacgt gtgcagataa ctatatagcc agaagagaca 13020
tctctcaatc tctcaaggtt catttttaga cttaggaatc tttgacatta tctagatttg 13080
cacagtaaac aacaggtatg tggtagttgg attttaacat tggctattcc tacttcactt 13140
tccataattc tggggggaa aagatgaatg ggaagtgaaa cattaaagat gtcttttaga 13200
atgaataata aaaaaatgga aagtagcctt ctatggctct ctttagctct cctcagagga 13260
catgttttat gtcttagact tcacagaatg ccaactgcag gctaggaaaa tgttcctagg 13320
gcttacacaa aagcgtattt ggagggctaa cgtgaacccg ttcacacaac cacctcacac 13380
cacatcaggt cttctgtgtt gtcctctcac tgatgagata acattattcc tgagtccaca 13440
gagcctccct gtggttagaa gagctgccag gactcatgca gccacctggc tctgcaggtg 13500
aacactcctg ggcagttcct ctgttattac agtcatttcc cccctgcgga ccgtaacttc 13560
ttatcctctc gtgtttttat acacttggaa agaacaatat tttgccattt ttgtttgtat 13620
tcagtaaaat gtgtcttttg aagtacaccc gaacggggac gccaaccaca ataacgaagc 13680
tcaatggcgt ggtatctgga ttttcactga agtcctgtgg actttcaaac ttgggtaact 13740
atcattttc tcaatgagat attggtacca ttaagcctga gtgaagcaga gactatgtgc 13800
aatgggtcta actttaaaaa cagctgatgg ttatacatga agcgaaccca gtaacctttt 13860
actgtcttca aagtgaaatg gttcactatg tcctggaaag catttccttc ttaaatttca 13920
aatttgttct ttttataaac aacaacaaca acaacaacaa cagcataaat aaataaataa 13980
ataaataaat aaataaataa ataaataaat aaataaggtc ttcggatgaa ctttccattt 14040
ataatacaat ttacaaaccc tgtctgggat gtctatgatt ttgctggtgc ccctgccttc 14100
ctaacacagt ttcttccctt ggacagcttg tatcagggac attttcccta acacggtgct 14160
ggcagacctt aacattgaca gcgtggtggc cccagatgct tttgtctgtc gtcgcatctg 14220
cacgcatcac cccacttgtt tgttcttcac attcttttcc caagcatggc cgaaagaatc 14280
tcagaggtaa ggcgttgtca ttaagggtca tctggtcttt ttaaaaaaac ggccaataaa 14340
aatgtgctgc acaatcaaga taggaaacgt ctaggcagca ggacacttct ggactccttg 14400
agatagattt gaattgcgga aaggaatggt accagcagga ggaaagactg ggaccacgga 14460
caatagggca aggttcaaaa gtgttttgaa aagttcttag tgacattaca atttacagaa 14520
cgcgacttgg tgattcaaga agcaatgtta ggatgaggtt gctattaaat gcttctctga 14580
gctaccttta tttgctatac ttgtaccaag tggtctttct ctttgctata ttttatctga 14640

```
tttattcata cactcccttt ggtcctttag acatctttgt ctccttaaaa cctctgaaag  14700
tggattacca agcacacgca ttacaaagag ccacgccctt tcgggcttca gtctccagca  14760
ctgcaggcac agtgtcccag gtaaacaatg caggctgtcc ctctctctga gctccacagc  14820
cccaaggaac tggatggctg tgaaggctac acacttcaaa cctggcgtgt gctttgttgt  14880
ctagtattct gccatccgtc cttttacaac gacactgatt tcttgggaga agagctggac  14940
atcgtcgatg tgaaaggcca agaaacctgt cagaaaacgt gtaccaataa cgcccgctgc  15000
cagttcttta cctactatcc atcgcacaga ctgtgcaatg agaggaagta aggcacaagt  15060
taggtggatg ctcttggagc atctccttgt aggatgagtt ttgcttacag agttttgttt  15120
tcagccgcag gggcagatgt tacctaaagc tttcctccaa tggatctcca acgagaatac  15180
ttcatgggag gggaggcatc tctggatact cactgaggct gtgcaaaatg gataatggtg  15240
aatacttgaa aaaatacaac tgaaggggaa tagtcaacct aacgttgcta gtctactaca  15300
cgaggctagt ctacaacaac catagagaga tggagacagc agcacaagga ggttgaggca  15360
ggagaatcag aaatttaata ccagattgga ttaaaaggca aaatcctgta taaaaaatga  15420
caacaaaata gacatggaag agagaacaaa gttaacaaat ttggaggttt tcccttacat  15480
atatgtatgt catatatata tatatactta tatatatatg tatatgtgta tgaatatgta  15540
tatgtatata tgtcatttca agtggcattt cctgtagaga cagacccaga gggccaattt  15600
ttgttttcaa gaagtgtttt ttttaattat cagagattaa actattaaac agtccattaa  15660
ataaattatt cattttcttc ccacttaata tttcagtgag ccatgattag atgctatgat  15720
atatgatatg atatatacac acacacatat atataatatc tctcatatat atatatatat  15780
atatatatat atatatatat atatatatat acatacacat acatacacac atgcatatat  15840
ataattccag atgttaagct atcctgtaaa ttgtgatgag atttcatcaa taaagtgtga  15900
ccctaattac tcctcgtgaa agtttcaaaa gtataaaacc tttttcatca gatcatttgc  15960
tattctagaa ggtgactcta tccttagttt cagaggacct gatttacagc acattgagat  16020
gttttatccc aacaactgca gtgccctaaa cagaaaacat gccttcctag aattcactgg  16080
tttgatagca atctctgggt ggcctgagcc tcttaagaca gttaattaag ttatagttca  16140
tacacactgt gttttgctca tgataaactt acctaataag aaggaacatt caagacaagt  16200
attgtcttaa ttctacttct tcatggtaga aggggcaact agaaagacgg ctaagtcatg  16260
tgagcatgct ttaaaaactg ggatccagaa cagatagctt gatacactga agattacatt  16320
tctcacccac ttctgccttc attatgtttg tctctgttga atttatagcc tggtctgtac  16380
aggtgacaga atggatcagt tgtagattga cagaagagaa aatgtggagg gtaataaacc  16440
tgtctgcctt ctcatgcata gagaagtggt tacactgtac aatattgggc tacaatactt  16500
acctttatgc aagagagaag atcgaactca gttgtttttc gtatttactc tgttgttggt  16560
ctctaatgta acttgacttc ctaaagacac ctagcaatgg acaccactaa aagaagtatt  16620
tcttcatccc caatgcaaag ttgagcacta taagttttca gcattctgtt caagttgatg  16680
gagcagacat cgagatagaa ctttttctga aggcttgcat tgggcttact gataatgtgt  16740
cctacttact gcttgcctgt taactttcta aaggttacct ttctgctgat ggactgaaag  16800
gtttctgagg gatttctcag aagcctttca ggacgaggga cattgaagcc taggtaactg  16860
ctaaccacac tctctctgtt gtagtgtgca caactaaaat caaccccaga gtggtaggag  16920
gagctgcgtc tgttcacggt gagtggccat ggcaggtgac tctgcacatc agccagggac  16980
```

acctgtgtgg aggctccatc attggaaacc aatggatact gacagcagct cattgtttct 17040
ctgggtgagt attattgcta ttctcctggg attgccatca tgaaggtgaa atctgggact 17100
atcataagag tcaataaaca ctttgaaaat gtaaatgatc ctgtttccta aattaattct 17160
ctctgtgtgg gcagggacga tggtgtagaa gagaccagtc ctcatcattt ggccacaata 17220
gaacaggggc aggagcagag cagattgccc acctctgcct tttcattcaa acgcaaatta 17280
tttccattgt cttcctgatg gtgcctggtg gcgaagcaca gggccagagt gaagcttaca 17340
atcctcagct ctctgaatcc tggttaccct agtctctctt tctctgcctc cgaatgctta 17400
gagttcagca cacaccatca gaccagatcc ccgcacttag cattgctttt cgatattggc 17460
caaatgtgaa catcttagcc ggggaagtgt gtatctcgag gaaattcggt tgagtgaaac 17520
ctttctgtgc tacttttagt gcctctgttg cttccagaca caggtttaga ggctaatcgt 17580
tttgttaatt tttttccatg catggatgca ttatgcacat aattcaatgc tacacttgag 17640
atcaatagtc ccctttgcaa gcacatatga aaaaacacag aaagtcccag tgacttttct 17700
ttaaattctg cccaagacaa ggttgagact aatacccaac tctcctgagc ttggagatgt 17760
gctggggagt agaaagacca tttatttaaa gtgtccaata ttagtgcaag aactaatcca 17820
gtgatttcac tgtagaggaa atatgtgact aaaagttttg agaataaaat cacttttttt 17880
accacctaaa ggtagaaaca gacacagagt ataaataact gtgaaacaca aatatttgga 17940
aattgcctag tgatagattt ttttttccat tctgtttgtt ccttaggata gagacaccta 18000
aaaagctgcg tgtctacggt ggcattgtaa atcaatcaga aataaatgaa gggactgctt 18060
tcttcagggt tcaagaaatg ataattcatg atcagtatac gacagcagaa agtgggtatg 18120
atattgccct gttaaaactg gaatcagcca tgaattacac aggtatatat atagagagag 18180
agagttttag gtgacctaga taaaacattc acgttaggag actcacagtc tcatctatgg 18240
ggtctaatca acagacagac aaggaaggtc tgaaaagatg gcctcactct gttgagacag 18300
agagtttgcc ttagaatact agattagcga tccatactta tctccttgta ctaaggtcaa 18360
atctaagtgg atcaaggaac ttcacataaa accagagaca ctgaaactta tagaggagaa 18420
agtggggaaa agccttgaag atatgggcac aggggaaaaa ttcctgaaca gaacagcaat 18480
ggcttgtgct gtaagattga gaattgacaa atgggaccta atgaaactcc aaagtttctg 18540
caaggcaaaa gataccgtca ataagacaaa aagaccacca acagattggg aaaggatctt 18600
tacctatccc aaatcagata ggggactaat atccaacata tataaagaac tcaagaaggt 18660
ggacttcaga aaatcaaata accccattaa aaaatggggc tcagaactga acaaagaatt 18720
ctcacctgag gaataccgaa tggcagagaa gcacctgaaa aaatgttcaa catccttaat 18780
catcagggaa atgcaaatca aaacaaccct gagattccac ctcacaccag tcagaatggc 18840
taagatcaaa aattcaggtg acagcagatg ctgtcgtgga tgtggagaaa gaggaacact 18900
cctccattgt tggtgggatt gcaggcttgt acaaccactc tggaaatcag tctggcggtt 18960
cctcagaaaa ttggacatag tactaccgga ggatccagca atacctctcc tgggcatata 19020
tccagaagat gccccaactg gtaagaagga cacgtgctcc actatgttca tagcagcctt 19080
atttataata gccagaagct ggaaagaacc cagatgcccc tcaacagagg aatggataca 19140
gaaaatgtgg tacatctaca caatggagta ctactcagct attaaaaaga atgaatttat 19200
gaaattccta ggcaaatgga tggacctgga gggcatcatc ctgagtgagg taacacattc 19260
acaaaggaac tcacacaata tgtactcact gataagtgga tattagccca aaacctagga 19320
tacccaagat ataagataca acttgctaaa cacatgaaac tcaagaaaaa tgaagactga 19380
agtgtggaca ctatgcccct ccttagaagt gggaacaaaa cacccatgga aggagctaca 19440
gagacaaagt ttggagctga gacgaaagga tagaccatgt agagactgcc atatccaggg 19500
atccacccca taatcagcat ccaaacgctg acacctttgc atacactagc aagattttat 19560
cgaaaggacc cagatgtagc tgtctcttgt gagactatgt cggggcctag caaacacaga 19620
agtggatgct cacagtcagc taatggatgg atcacagggc tctcaatgga ggagctagag 19680
aaagtaccca aggagctaaa gggatctgca acccaatagg tggaacaaca ttatgaacta 19740
accagtaccc tggagctctt gactctagct gcatatgtat caaaagatag cctagtcggc 19800
catcactgga aagagaggcc cattggacat gcaaacttta tatgccccag ttcaggggaa 19860
cgccagggcc aaaaaggagg agagggtggg taggggagtg ggggtgggtg ggtatggggg 19920
acttttggta tagcattgga aatgtaaatg agctaaatac ctaataaaaa tggaaaaaaa 19980
attaaaaaaa aagaatacta gattagactt tgagagtgca gacggagaga cttgccttca 20040
ggcttcttca ggtacataga atgacatcgt tttataaaat accgaagcaa taagaataat 20100
gattgatatt ttgctttagt aacaaagggc ttgacagcac agttgagcaa atgctacaga 20160
atattaaacc acattaaaaa tgaaaggtgg tgtaaagagg gcctgtctta ccctttccct 20220
tgtcccttct gcttgggaca tttcatatgt gccactgaac acatgacatg aaacacatga 20280
gaaaaagata acgaatatca taaagaaaga gagcatgatt aatgtcaggt gagataacac 20340
ccctttctgg gacaaatgat tggctttctt tctgcttcgg tcagcttttc gctactgtga 20400
caaaatgcct gatgtaacca ccctgtaaga aagaaaggtg atatgggctc tcttgatgtc 20460
agaggcttca gcctgcagtt gtgtgtgtgt gtgtgggggg ggggggtcca ctgctttgta 20520
gcccttggta agaaatgtgc agaggagcaa attttcacct cctggatgct gggaagcatt 20580
aatgaaggga cggggctcct gatagcccct tcaaaggccc accctcaatg acgtcacttc 20640
cttcctacac cttccccccc aacacacaca cacacacaca cacacacaca cacacacaca 20700
cacattctcc attatctcta agtagtgtca caggctggga tggagtcttt gaacatgggc 20760
ctttggggag acacctcaga tccaaaccgt agtggcctct gatgactaaa ctgtgatttt 20820
caaaattaga ttttcagcgg ccaatatgcc tgccttccaa aggagataga aacgcagtgc 20880
acacagaatg ctgggtgact ggatgggggt acacagcact aagaggtaac aaaccatgcc 20940
ttctatctct gctttattct gaagtcaaag aacagagctt aaccattgcc tctgttttct 21000
atctagtcat atggcccaaa cgtgagtcaa gtcacctact caataacagg aagactgata 21060
acaaagatca atacatctga tcagaaacgt taaatatgat taaacccctc taaagaccat 21120
tttaactgga gacttttagt ttgggaccta acactctatg taaaagttct agcctggttt 21180
ctaattattt tgtctgaaaa gaaattctac ttagtgtcag ttaattttga acttaataac 21240
attaatgaaa ttatgtacac aatagtagaa acaatgtctt ctttatactc catacttaca 21300
aaaattactt atgaatcaag cttagtaata ccaccccccc ccaggatttg tatgtacaat 21360
tttggctttt aaatataatt gtatataaac ctatagtaat tattcctcta aaacactaat 21420
atgacccttt tcaggtgaag tacaaagtac tcttcagaaa gccaaggttc cattggtgtc 21480
aaatgaagaa tgtcagacaa gatacagaag acacaaaata accaataaga tgatctgtgc 21540
aggctacaaa gaaggaggga aggatacgtg caaggtaagg cagtctcaag caatcagtca 21600
tgccagattg aagtgagagc ttaatgcatt tgtacaaacc actgtaccat tgagcagtgt 21660
ccgagtgtgc ttcctgttgc tgtgataaaa cactgaccaa acacaactca gggaaggaaa 21720
gggtttatca agcttacagg ttacacagtc caccatagcg gaaagtcaag gtaggcagga 21780
actgcagtag agacggtgga ggagtgctac ttcctggctt ctgtttagtc ttgtgttccc 21840
tacttttctt ttgtgacaat gtggttaaca attagcagtg gagaaagttc cccacagtcc 21900
aggctgatgg cagaggtgcc tcagctgtgt tccctcttcc caggtgtgtg aggttgacaa 21960
ctcagattag ccatcgcaag cagatcactt ggtgggttta ttttaggtaa actaaactct 22020
acaggaggaa ggaaagctgg ataaaggaga acaattggat gtttggatgc ttgtgagagg 22080
gccagaatat tatgtaaaat tgctgtgagc aatacttact taactcagga aatgcctacc 22140
atgatcccgg catgtgtctt ctttttctcc ccctttgaca gggagattct ggagggcccc 22200
tgtcctgcaa atacaatggg gtctggcact tggtgggcat cacaagctgg ggtgaaggct 22260
gtggtcagaa ggagagaccg ggggtctaca cgaacgtggc caagtacgtg gactggattc 22320
tggagaaaac tcaaacagtc tgaaagagtt caactggtat cactttgtgg ccctggaaga 22380
ttattccata gaaatgagct tgacgtctct gatgaagaca ctgggatact gactcttcca 22440
ctgtaaccaa ttgaatggcc ttgatgtacg taagaacacc cagaaagaaa actattattt 22500
tcagaattcc tgatctggga gaaccactgg ttgttttctg catccagcta ctactcaagg 22560
aaacaaatac agcaaggaga ttttaaaaat aaaaacacat cagatatata aggaaaatat 22620
caagtaaggg tgctgtctgc ctttttagtc tctgtgacaa atacctaaag tagttcacaa 22680
aaggaaaaat ttcttttgca cacctttcct caggtttcag cctacgatct ggttggctgg 22740
ccccattgct ttagcctgag gtgaggcaga accatatatc cataggaggc tgtggagaag 22800
gagtctgctc agttcatggt aggcaggaag caaatggaaa caggaatgta ttggggacac 22860
gaatggtcct tcaagaatat actgtcaatc atttacttct tccagagaca tcctgctccc 22920
taacctccct ttccttccca gataacacct ctgtcctagc tggccccaag agatcaggta 22980
gaaaggcaga ggaaaccata taaagagttg ttaagtgcaa aatcaaaacc agaaggaatg 23040
cagacaggag ctcaaaatgt ccatttataa gaatcttttt ttttctctgc ctatatgaat 23100
ccccctcctg tataaaggac tgactcaatt cagtgatggg ttttgagaag tctgtttgtg 23160
tgtgtgtgtg tgtgtgtgcg cgcgcgcgtg tgtgtgtgtc tgtctgtctg tgcacattca 23220
tgtttaggta tgtgcaggta cctggtgggg gcgatcaacc ttgcattatt tctcatgtgc 23280
catctaccct agcttttcaa agacagagtg tcttactggg attggagact tgggctaagc 23340
tagctatcta gcaagtccag ggaccattct gtctctacct ccccaaactg aaattaagaa 23400
gacatgccat ggtgcttaat ttaaacctct ctctgtcttt gtctctgtct ctgtctctgt 23460
ctctgtctct gtctctgtct cgctctctct ccttcctcct tctctccctc ccactctctc 23520
tttgggtgtg cacgtgcgca tgtgcaagtc atagtgtgtg tgcagggcag tggaccatct 23580
tcaggagtca atgctctcct tccatcatgt aaggtccagg gatggacatt aggtgttcag 23640
atttggtgac aaatgtctgt accttcttag ccacgtcaca agccagctgt tccgatttcc 23700
tacagatgct gggaatcaaa tctgagtcct cggggttgcc tggcaagcat cattactgac 23760
tgagctctcc agtggccttg tcagtcttct ctctgcattt tcccaaactg gcttggacaa 23820
gcaccattgc aggtgttaag tgcacacttc ctaatttcca catgggccga gtataggagg 23880
agcaattttc caggaagtgg tcccttgaag acacaccgta ctgatttgct tgcctcggaa 23940
agtatctcag cgtagcctgc actctttttg cagtgttagg ggaaagtaca ggtggatgga 24000
gataaggaag acaagccaaa acctaccaag atctgccagt gagtgggagt ttacaaagct 24060
gagtaatgaa tgtgctggac ggaaatgtgt gttgaaatcg tacatactac gggggggggg 24120

```
ggggggtgg ataatttggg agcaaatgtg gtttcaatag aggctgcagc ctcctcaaac  24180

agttctctgt attctgagta cctgactttt gtcctcacat ggggcaataa tgtagtattt  24240

ggactttgtc cccgtacttt tcagtcagcg ttgataacta tacaagttgt ccaaatgaaa  24300

agtatttatt gtgcccaatt atgtcagagt gtcttgttga gcttggggaa ctgaagcgcc  24360

agccaataaa ttatgaaggt ttcataaggt tttctgttga tttagtacga accgaagaga  24420

ggagctgcac aaaatctata ctttcaaaca aagatgacca tgacacaaag ggttctaaga  24480

aatgacaacg aagaagagtt agcagaagct aagagagtgg catggaaagg aagtggcccc  24540

aagcaagaca aagcaaagac agcaaacaag caaaagccag agatcgatgt cactgaaatg  24600

gcacgagcag gctggattca aaatgcttct agagtaagac agaattgaca tcaaatgggg  24660

tcacaacttc acaacccatg aacaagcagc gccttttata acctatttat tacatttcac  24720

ataggaaatc ttttataacc tatttattac atttcacata ggaaattgag gaggcattgc  24780

tgtcttctct gagaagtatt taaggaatgt tttcgtctta atttttttc agaacaagtg  24840

caacatctta attctgaata tctagtacct agaaaatgct atgagctata aggaataaga  24900

aattacgctg agcagattca catctccaca ccaacaagct gcgaatctgt atactttctg  24960

gcacttttct cacttaatct tctctctcct ggagctagct c                      25001
```

<210> SEQ ID NO 3
<211> LENGTH: 74000
<212> TYPE: DNA
<213> ORGANISM: Mus musculus

<400> SEQUENCE: 3

```
tgtaaactag atctccatct tagattaggc tgtgtgaacc gaatttattt acatcgttag     60

aaaccaaata gaggcctctc ggctattgtt ctcagattgc tctcattggt catccctgcc    120

ctccctctac tgaccagaac cttgccccaa aacagcctgt aataaacatc aacgctggct    180

tagcttgggc tgctatctct ggcggagaga tctttaaagg atgtatctaa atgcaatgtt    240

tgagtagctt cagagagctc taatagaact gtaaatatcc ccggtttaat tagcagtcct    300

gcagttcggt aatggcccat agctctctga gccgagcctc ttgaggtttc tagacttcag    360

aggctgcctg caactatgct gtgtggacct atgaaatttt ccttctcctg tactctaaac    420

ccccagctag cctttcctag acacctactc gcaattattg caaatccata actgactact    480

atcctccgga tttctaaaat gatccagtgt ttcagcttag gtctcaactc agagatactt    540

tagggctcag attggcatcc tgagaattaa gtcccctggg aaaagaacaa taaggaagaa    600

aactctacct acattggagt tgatgtcatt ttttttttcc ctccaagctc aaggtgatcg    660

cttgctttgt ggctggttgg tgggggagga ggggctgtac gctagttatc agcatttctg    720

aaccagctct ctcaaccgcg acaggtcagc caatcccggc agtaagcttt tacttgacag    780

gtttgttctg ggctgacagc cattgactag gtgctcagat aagtcacttg gctgagtcta    840

cggtaggtgg ggcgcgctca ccagttcagg ggcagtgact ggaagtttgt tgcaacatcg    900

gtaagcctaa ccagccagca gcaacaggag ataccctttt gccccgcgag tacagatcta    960

gaaagggttc acctcattaa gcgaaggaga tgcgtcaatc ccccccaccc ccgccccgcg   1020

cctcccccta gggcccggcc tcttctccca cggttgggaa cgcgcggtgt gggcagatcc   1080

agaacaggag tctcgtgtcc cggccttctg gctagctcta tgggttacaa gcgaaaggga   1140

ggaacagctt ggggactctc cgcgtcagcg tgcacaaacc ggcggcggcc agcagagagg   1200
```

-continued

```
ggtggcgggg gcacgtgctt ggatgtggct gcttgtgtaa ccagctcccc aggcgctcgg   1260
ccccgacagc gctcctgcgg acggctcgtg gatgctattc tctgctccga tccggcaaga   1320
gaggggtcca gcagaccaca cgggagaagg aggcgggggc gatcacctaa tagagcagag   1380
gggaccaagc tcctgcccca ggagcacaca gataggggaa tgggaatttg gaaagttccc   1440
caactaggac cacacgtgac ctcctcctga aagtagttcc gaccgcggct catgtatcct   1500
tccacctcgc ctttgagccc tcccaggcct gctcgccccg cccactcgct ggctgcagct   1560
tccgaacgtc ccatactcca cacccgggct cagtaaccgg gtcctcgaac atgcaaggtc   1620
cgacagggtc agaacctggc catcgcgatc caattctgcc gggttttcat agcggccacg   1680
aagtggggat tgggggtggg ggcttagctc tttgaagact gagcttggct gtgatccggt   1740
agacccaccg ctgcggggag ctgcgggtct catcaccggg cggtggaggg gtgtgtgtga   1800
ggtgcactct attcacggag acccactttg tccaaccagg ggtgtccttt gggccctgga   1860
aactcagggg agatgtgaat gtacacgccc cgtatgcaca atcatcatgc ttggctggga   1920
gcgttcatct ttcgggcaaa tgaacccagc tgcctgggaa gcaagaggcg gggcagggaa   1980
ccggagcccg atgaggtgac ccacgcggga gacacaatag gggttgttct ttgtgcaaag   2040
actgacacct tgaggacacc gtgagggggga gaggtgtgtt atctaggtaa agactgtcgc   2100
cgacaaatcc tagcgaagca ctgcaatctg accacagcgc agggcaggga atgaaagccg   2160
ttccgaagaa acgcagggac agacgcagga aggataatcc tgcccctgag gctcccggag   2220
caccgaccaa ggcggtcagc tagtgcgatc cacctgtgag cggtcagcga ttgtgctcag   2280
cgcaccctca ctcggcccca gcctgttgta cctttgccgg gtctctctgc gctgaggcca   2340
aagccggcgt agctccggga gcgagccgcg gacacactgg gcatgctccg cggcgttccc   2400
cgcccctgtc ccttccgacg ccccgccccg ccccgccccg tccccggctc agcgcccgcc   2460
tcccgcccgc ctcccgcctc ccctccggct ttccgaggcg ccctgctctc ccggcggggc   2520
ggcggagggg gcgggctggc cggcgcacgg tgatgtggcg ggactctttg tgcactgcgg   2580
caggatacgc gcttgggcgt cgggacgcgg ctgcgctcag ctctctcctc tcggaagctg   2640
cagccatgat ggaagtttga gagttgagcc gctgtgaggc caggcccggc gcaggcgagg   2700
gagatgagag acggcggcgg ccacggccca gagcccctct cagcgcctgt gagcagccgc   2760
gggggcagcg ccctcgggga gccggccggg cggcggcggc ggcagcggcg gcgggcctcg   2820
cctcctcgtc gtctgttcta accgggcagc ttctgagcag cttcggagag agacggtgga   2880
agaagccgtg ggctcgagcg ggagccggcg caggctcggc ggctgcacct cccgctcctg   2940
gagcgggggg gagaagcggc ggcggcggcc gcggctccgg ggagggggtc ggagtcgcct   3000
gtcaccattg ccagggctgg gaacgccgga gagttgctct ctccccttct cctgcctcca   3060
acacggcggc ggcggcggcg gcacgtccag ggacccgggc cggtgttaag cctcccgtcc   3120
gccgccgccg cacccccccct ggcccgggct ccggaggccg ccggaggagg cagccgctgc   3180
gaggattatc cgtcttctcc ccattccgct gcctcggctg ccaggcctct ggctgctgag   3240
gagaagcagg cccagtctct gcaaccatcc agcagccgcc gcagcagcca ttacccggct   3300
gcggtccagg gccaagcggc agcagagcga ggggcatcag cgaccgccaa gtccagagcc   3360
atttccatcc tgcagaagaa gcctcgccac cagcagcttc tgccatctct ctcctccttt   3420
ttcttcagcc acaggctccc agacatgaca gccatcatca aagagatcgt tagcagaaac   3480
aaaaggagat atcaagagga tggattcgac ttagacttga cctgtatcca tttctgcggc   3540
tgttcctctt tgcttttctg tcactctgat aacgtgggag tagacggatg cgaaaaattt   3600
```

```
ctgtagttgg ggtgactata acgtttaatt ctgggcgcat ttctagatcg tgcatattgt   3660
gtctcttcca gtgtattcaa cctagggagt gttcggctag acggaactca tgcctccttg   3720
caagtgtcaa ggcacggatt gttttcttgt cgagctctgt ggtctcttct taaaatctat   3780
tgtccggtaa tacagagtac tgtacactgg attagcgagc tcgtcaatcc agccttctaa   3840
atgaactaaa aaaaaaaaaa aaaatagacg ctttgggttg tgcatatttc gattagatcg   3900
tgacttgggc cctagatcta gggtgtagat gagattaaaa tgaaagtccg tgctgcacgt   3960
aggcatgttg cctcagaatc ttgcagtgat tgtttttagt ttcctgggtt gcattggaag   4020
atttttctga aatgtgactt gtggactgat ttgcataact ttataagcat agtcatcgtc   4080
agcatggacg gtgcacattt gagggtagaa gtagttttgt gtgtttaaac cgacgtaatt   4140
acaaatttgg agcctgcatt tggaagtttt gtagtttaaa atcaatagtg ccagaatata   4200
tatcattgga gcttttaata gaactttgtt aaattagact ttctttcctg atgagatgtg   4260
ggataggata tgaaatttgc atttcagtgg tatgttccat tcatttgacc tcgccacact   4320
tgatagaatg gagatcgaat agtttttgat cccagatgat gatgtctgtg agtccaggga   4380
tgcttgctgt gtgtggcaaa tgactgcaga ggttaaactc agttctcaca tgaaatttaa   4440
gtagtagcgt gaattcgctg ctcatatttt ttgtttcagg tgctctgact cgttggctta   4500
tcagtgggtt ttagcctgat ttgtgcagaa cgtcaagtat aatttagccc gctaatatcc   4560
agacaaactg gcaggaatgg atcactggct ccagattgta ggtatgctag ctctctgcat   4620
gcagtaattt actgagtcag cttgttgaat aagacagaaa cccaagaatt ttaacgttgt   4680
atagttctga ttgtctaaaa gttaggcctt tgtacttcaa aagttcgtgg tttaaagcat   4740
ttatctttgc agtttcaggt atggtgctgg ttatgatcag gggtaggaaa gagagccctc   4800
ctcttttgca gagtgggaag tgttgacaga aattgagagc tttggggagg ccagtgtgca   4860
aggtgtgcga aaacacaagt tgcaggtctg aagtgactga gcctttaaat gattgggcct   4920
tttggtacaa cccaaaattt tgttatgtga cttgtagcat tgaacagtat ttagttaaaa   4980
ttatgtaatt ttataattgg tggtaaggta ttctttgtaa aaattatttt ttagttaata   5040
ttagtagaca ttttcttaag gtggaagggc agcagcaact tgtctataca tgtcctgcta   5100
atagatcact atggagaact ttgtttatta attaatttat tatttttttt gaagaaatat   5160
tttcatttgg aagaggtttg atggattaca ttagtggcat ataaaatgca tagctaattt   5220
tgattgagtt ttttgttctg acatgaagat gaaactctca ctgaagagct ggcttcacac   5280
aggctaattt tctttcgagc taaaaataca gtttgaaagg aatctttaat ttccgagttt   5340
gcgttaattg agaagcttta ctcaggatga acttgaccaa aagataattg gtgagcattc   5400
tgagttgtca cttgcttcaa ggcagtttac tgttggtgtg aattaatgtt aataatctcg   5460
atctagaagg aattagtcag gtatctattt aattaaaaaa aaaaaaacat tcaaagaaaa   5520
gtctagaatg cctggtaggc agacttcttg tagagtccaa agtacacttc tgctttgcct   5580
tcctttcccc aaaggacttc aagattattt tgtaaatttt tttttttgt ctgagcagtg   5640
acgtgattgc agttccttat ttgatttcat actgcatggg cttctgcacg tgcagtttat   5700
gtggctgaag aaatccaaag ctctcccttt agttatggta tgcgtagaaa gcagcatcaa   5760
atactgcatc aaatgactaa taacaaactc ttaatttcta gagctgtggt ttgatggagc   5820
caaatgttga tgtgagaacg agtcaggagg ggaaaaagtc agcgagcctt gctcttctga   5880
gaggtgtgcg ccccttagtt ctgagaagct agggagaggg cttgcttggt tcctcatcag   5940
```

```
ggttttctgt gtttggggca gggattaaaa tggtcattga agatttgtgc tggtcagtgt   6000
tggcaatgag gttggccaag ttaaatttca ttatgaaagt agtaagttga atattttcat   6060
ttgctgaagg cacaattgaa ttactgtagg aatgtgttgg ttggaaatta ttattttttt   6120
tttaatatat aaaactctga agtctttttt tttttaaaga tttatttatt tttatttata   6180
caagcacgct gtagctctct tcagatacaa aagaagaggg catcagaccc cattacagat   6240
ggttgtgagc caccatgtgg ttgctgggaa ttgaactcag gacctctgga agagcagtcg   6300
gtgtgctctt acccgctgag ccatctctcc agcccaggaa atttttctta ccgtctggaa   6360
agtaggctga atgtgagaca gcaagagtta atgatgttaa agcacagaga aggttcaggt   6420
ttctggtaca gctttttttgt ttggtatatt tacttttcag atactgacca caggaatatt   6480
agtaccttgc agagagaata gtgattattg atattagctc ttttgttaaa ggcaagtgat   6540
tgttgcaggt aattatggtt tttctttata agtgactcta caaacttcat cttgcctttt   6600
tcatagtcat ttgtgtcttt cctgaaaaat acaactagta tagtaagttg caaatttcat   6660
ttttcctaaa acttaagagg agtaaagtgc atcaaaagga gtaattttca gttatgtgta   6720
attcaatata aggaaaagaa attttattac tgtcaatttt agaagtttac acagcaatag   6780
agatgtagac tgagattcct tataacgtat taaataaaga ttaaatgttt caagttaaat   6840
atgatgaata taatctggtt atttctagac atagatttag aaagtggaga ttcatggcct   6900
ttaaaaatct ttattttagt aacaggagaa aggcagatag tgtattttca tttttttgtg   6960
tggaacatta tgtctaattt atcataatta tataaaatat atacctaagt attatgaaat   7020
agcttacctc ctggaaatga attcagttct tatttttaaa tgttacaaca tgagttgttg   7080
gttttttttt tttttttttt tttttttttt ctgttcattt gtttatagag tgacagtatt   7140
tttttttttt ttttcccgag acagggtttc tctgtgtagc cctggctgtc ctggtactca   7200
ctctgtagac caggctggcc ttaactcaga aatccacctg cctctgcctc ccgagtgctg   7260
ggattaaaag cttgcgtcac caccgcccgg caagtgacag cattttaagc cacttctaaa   7320
atagtcactt taatgacttg attagaaaat tgttcatgta ggaaaataga aagtttgaac   7380
attcacttta gtaaatattc agttttcaat actttatgtc tcagtaagct ccaaatgtag   7440
gcagtgtttt tctattgata acttatgtaa attcagagtt gacagggata agtttagagt   7500
cctgagtatg taggtcaggt tttcatttct gtaggcctat tccatttaga agtattctgt   7560
tctatgaggc agtgttagtt attagtacag cttaaaaagt ttacttgctc gcattttttg   7620
tttttccatg ataaactact ggctcataaa acagaagttt ggctgcacag agctggtggc   7680
tcgcgttttg ttcccctttc ttctccctgt agataaaaaa gttgattttc agaaccagcg   7740
ttggagagtt ggttttgtga tccactcttt tgaaaagtta caggacttgt tccaaagatc   7800
atgatttagg tatgacactt tgtgtggttt tatcagaagt gatttctgta aatattcagg   7860
gtttttttgt agttgatttg tatgtggtag ttttgaagtt catgcagttg ctgagctatt   7920
agtgatgttg aatacagatt aaatagcttt atgttagtat ttgctgattt ttttttttat   7980
aggtcttgct gctgttgctt aaaagtgtct aattgtggga tgatggttct caggtcctga   8040
agctattggc agagatgaaa ttaggatcct ggctttgatg tcttaccttc ccattctgta   8100
ttctctgcta tggtttcaga agggacgata tagcagtttc agcttctaaa ataatttata   8160
ctggaacaaa aagcctgttt cttggaggaa ggttactatc agagtaaaca actaattttg   8220
cctgggaagt tttaattaca tttagaatag tcaggtatac tcttctattg caacggacat   8280
ttgtggacat ctttggagta ctaagactta acacttgttt gtggtgttaa ctttggagag   8340
```

-continued atgcaaactg cagttgcacc cactaatgac ctgtatgtgc gtggtgtgga aaagcttgca 8400
aatctgctgt tttgtgtaat tagtcaaaca gttataatca gaaagccaac gcttaatacg 8460
aacagtgact ttaacgtaaa tatttgaatt tttctatgtg taggcatgca tgtgagtatc 8520
aagttaacaa acttactagt ctggaaaatg gattttctcc ttaaagaaca gactactttg 8580
gaagccattt taaaccataa ttgagtcttt taaattacat tgaaatacgg ctggtcttat 8640
ctatactctg aagttataat tatttatctt agttttaggt agacagggtc cctgtcttgg 8700
ctctgtcaca gagctgggta actatgctat ttaatttctc ttagtcttac tttacctgaa 8760
ataaaggaag gataatgata cccaccacaa aagtttatct aataccagca aggcagagga 8820
aggaggctat tgctaattcc taggcagtag ccttcagtac tacatagtga atttgaggtc 8880
cactatagtt ctatactgtg agttccaagc cggctaaggc tccatagcga gaccatgtct 8940
gaacaagcaa caatcaaatc acatagttaa tccccctaca gggtttctct gtgtagctct 9000
ggctgtcctg ggactcactc tgtagaccag gctgacctcg aactcagaaa tccgcctgcc 9060
tctgcctccc gagtgctggg attaaaggcg tgtatcacca ctgtctggat gttttcaact 9120
tttaagggaa catgaaaact tccttagttt tcacataata actttaagaa ctatctgttg 9180
taagattaaa ttttcttagt attcaatata gatgaatata aatagcatga catttataat 9240
atgtgtgctt atatgatacg atacatagca tatatgatct atgatacagt tatggtatgc 9300
ttgtccttag gaggcagagc ctcaccatgt agccctggct tgtctggaac ttgtggccat 9360
gcttggtcag tatcacagtt ctttttcaca aagagtattc ctcaccacta agaagtagga 9420
cttcgaatat gtaactcagt tatataaact ctcaggaaag gtacattagc atttcctttc 9480
tgctcttcca gctcacatac atacagcaga caatacagtc tgcagtgagc tactatagga 9540
atttaaagtt actgttaaac cttgccctca gtttcacagt gagccaggat tttcagtata 9600
actacaactt tgaaatggga agaaagagct agagagattt ttttccttcc catactgcat 9660
ttttaaaaat tactcattta tttggggttg gggatgggag gaatggaaca gggcatacgt 9720
ttggaggtta gagaacagct ttcgggagtt gattctctca ttcctctctt tgacactggg 9780
aatggcagtc aggttgttag ggtagcagga agtgcctttt agccagctga gccatcctag 9840
aagctcacat gctttttctt tatctagggg agggaagaac ggagtaagct taaggctcac 9900
ctacctgcac gtgacaggga ctagtttttc cttcctgtgc ttgtggtttc ctgggaatgg 9960
agcgccttaa tttccagggc tgtttcttat ttattttgaa atgcagagtg gatgctgctg 10020
taattattca tgactgcgct cttgtaattt ttatttattt tttgctgagc tttccctgag 10080
tattttagct gttttttttt tttgtagcag attataaaat tgagttgcat atctttatat 10140
ctgaacctat ctcactgtct gaacgagttt ctatctttct cttctgtctg tgtacctgta 10200
ctataagcac ataggtgtta tatcactaga ggaccagtga ctttcattgc atggtaacac 10260
tcatgtaggt tttcaggctg aagtagaata atttcctccc tccctccctc cctccctccc 10320
tttttcttcc ttcctagtga tgcagacctc atttgtatgt ttgttcttga ccctaggagt 10380
aggatgcagt tactcaaggt gtatggaagg gtatgaattc tgctttgaaa cagcttatct 10440
tttaaggaga tatatttcta aaagtgaatt gtaaaaatca atatttgttt aacaacgcta 10500
gaagcaaatt tttgctttga aacaaaatgc agattttttc caataaattt tttctcttta 10560
atgagacttt aaaaaaaaaa aaggttggtt tattagtgta tatgagtaca ttgtagctgt 10620
ctacagacac accagaaggg ggcatccaat cccattacag atggttgtga gccaccgtat 10680

```
ggtttctggg aactgaactc aggacctctg gaagagcagt cagtgctctt aaccactgag  10740
ccatctctct agcctgagac ttgtttttg aatgttttat gtttctctca actaaataga  10800
attaaaattt ttcttttatg ttgagaatga agtttgggga gatattatta aagttgtcct  10860
taggactctg tattacatta tctcctatca aacaaacctt aatgtactat attctctgtg  10920
tatgtgtgtg tttatagttt ataggctagc aatcaacatt ggtgtctcct ctgttgctct  10980
gtgccttgtt tattgagaca gggtctctca ttgaacctgg agcttgccaa tttggcaaga  11040
ctgtcttctg tctgtgccct ccagtgctgg gatcacaggt gtacacacca tacatggttg  11100
tacacaccac acatagctgt acatactata catgggtgcg taccaccata catggttttg  11160
acattggtgc tagggctctg acctcagatc tttgtgcgtg catagtaaag tactttatcc  11220
actgagccat tccctcagct cccatgctat atactcattg agttaatagt atttacaggt  11280
gcattatatc aatagacata agtcctaaat accctaatgt aagaaatatg ttgatttgtt  11340
ttgtagacaa ggcccagtga attagaaagg cagcctgcta gaatgcaaag aacatagcct  11400
ggcattagcc aggccctgga attagattcc tgccctagtt cccatctttc taatgagggg  11460
taaagctgtg acttgtaggt gtttcttttt gttgatctga acttttggta atgtctagaa  11520
acattttggt gaacatggtc atacctgagg tgacagaagg cctacttgca cttagtgggt  11580
tgaggctact gggctcttag acatttgcag aacctgggat ctgtttaatg ttaggggaag  11640
tgtttgatat gtagatatag tacctttgcc aaggtcaact gttgctgggt ggtaaaaact  11700
gggcccacat aggttttctg actattgtgg ggcctttctc tctctctccc ccccccctc  11760
tcttttcttt cttcctttct tccttccttc cttccttcct ttcttccttc cttccttcct  11820
tccttccttc ctttctttct ttctttcttt ctttctttct ttctttcttt ctttctttct  11880
ttctttcttt ctttctttct ttctttcttt ctttctttct agacatggtt tctctgtaaa  11940
gacctggctg tcctggacct cactttgtag accaggctgg cctcgaactc agaaatccgc  12000
ctgcctctgc ctcctgagtg ctgggattaa aggcgtgtgc caccaccgcc cagcggggct  12060
tatgtttctt ctaacaactt tgtccactaa agatatctct aataagaaaa agatttattt  12120
gacaaggtct catgtctttt agcattttgt gggagtttga acctctgctg aaatgctgtc  12180
tttgtcgctg ttctgaagag tatgacaggg aatgcaaggt ggatgtgcag tcaggtgttt  12240
tgctccttga agctgaagca ggaggattat ttttatgttt gaggacagct tgggcaacct  12300
catactacac cttgagttct agggccaggt cagactgtct caaaggccag gttcgcgctc  12360
acccccactc agtgtttgaa cagttttctt tgtaattgtt tagggagtta ctttgctgct  12420
agtgtcttta atgttactgt tgtttaactg cttctttagt cttagatttt tttttttttt  12480
tttactctaa acctttgttt cttcagatgg ggtgaagtta aatgtgctca tgtgaagaag  12540
gggcaggttt ctgacaaaga ataagaaaaa tcatgaaatt tttccagatg aagagaatgg  12600
gttggcctga ctgaagttcc cgggtgctgg tcacctgctt ttctgagcct tacattggtt  12660
gttagcctgg ttactggaaa ttaccgtgat gctcctgaat tgggcatgcg agtttgcatt  12720
agtccaaaga tgcacagaaa ctaaagcagt aaaaaggaca gagaatttct tggtttattt  12780
ttagggatca caagcataat tataagtgtt ctaggaatag attagttgct atgttggttt  12840
ctttttcctg tttaatttta caatttcatt tgctgctcac tttacaacag aataaaatgt  12900
ccaaggcctt aatttttaat ttcttaggaa acttaagtac tgatttagag ttttggttct  12960
tgaagttgag ggcagtgttt aggtatgtat actgataaat gttttgaaac cgacatgact  13020
tgtcatgata gcttcatatt caccaagaaa agcaaatagt atccattgct actaaatact  13080
```

atccattgct aaattgaata gattaacagt gattaagtct gaattaagag ctcatttgct 13140
tactaaagaa aattcctttt ataaagagat tactaagaga aaaattttgt tgtttgctca 13200
tttgtttttt catttcttca aaacttcaag ttgttttcta attcttggtg aactcaaaga 13260
ggtatctttt ttgaataatt tatatagtgc ttcataattg aaattatcaa aaatacatat 13320
ttacctataa attaagattt ctccattttt ttctcttact attttttat atagtggact 13380
taaagtttca aatagggaca atttttatga ttgagatttt acacaaatca caatcaacaa 13440
gaacaaaaaa aacaattgaa atattagagc tttgaaatgc cttcatctga aattacttct 13500
aggccatcta ttgcacattt aatacttaat gtttatatta cttatgtgag atagcacaca 13560
cacatataat gttatatgtt acatataata tatattaaat atttgggaca actttccagt 13620
ttcctagacc atgctgccct cgaactcatt ataaacatcc cattttccct gcttctcaag 13680
ggctatggtt ataggtttat attagaattc caggctccaa atacttttga tatattaatt 13740
tcatttattt tggagtattt tgctgatttg aaattgaaat ggaatagaaa taatttgaac 13800
aattttcata ctaaagtggg catagctttg ttgctgtacc tttgaatcca taattattgg 13860
cttgccatga tgttacagtt gcagtttgaa taatgtggtt tatatttgta tagttggctt 13920
gtatttgttg tactatcaat taatcaatgt gcactgataa ctagtactag cttttggtga 13980
aaaatctgca tttaacagtt tgtcagattt tatttttaag tcagatacta aaagagaatc 14040
ttttttcat agatttttat tatttaaatg cattttatat atatcaaaca taataatact 14100
gagtatttta ggaatcaaat aatacataaa aatttgttca atttttatat tcatatctaa 14160
aagagaatct ttaaccatat cagctaacca ttaattcttt atcaataaat tatattaata 14220
tttttgtat aaacaattta aaacaaagtg atagaaacat cgttttttat tttataaaca 14280
aagttactac taggtgtgct ctgtggcctg tgaccttagc accctggagc tgtccccaag 14340
gaaaccagaa gtgcagttac tcttggccac attgtaaggt gaagcttagt ctagaccaaa 14400
agagacagaa ccaagacaga aaaacaaatt acctgcttat tattaagtac gattctttcc 14460
caaataaagt gaaacttaag cttgaaattt tcatctaggc ataaggttgc tatcttgggt 14520
tctaataaaa attagtggtg gcaaaaatct tttgttactg ttttcttgtt gctgcctggg 14580
gactgaagac ccagtcttca gtagctttgg tggtctggtt tgtagggcat ttgatgaaag 14640
aacagtattg gaaaactgtg aagcactttc tcctgcattg tgtccggatt gtggtcatga 14700
ttgcgtgagt ttgaaaatat gagaaggtcc ttagaaagat gtttgtttgt tattactgca 14760
aaggtcatag gttgtggttg tgccgtgtcc agatacccag gcctgccatc tgttcctcag 14820
atgtaggaaa aagttaaggt aatttagtgg tagtaagtgg ttttgacacc tttgtttttg 14880
gaatcatcta attataagtt ttaagaccta agattaagtt ttaggccttt gtaaaaatga 14940
aacttacaca gtatgctatc atttgtgcaa aaccactaag ggcctgcttc agagctgaag 15000
atggctgctc cgagcccaac tctttactga agtgtctgca tgcttcagca caggagtgtc 15060
acgtgtcacg tgtcatgctt tcacctgacg tactaaatta cacaaaatgt tggggttttt 15120
taaactaggt tttctaacac gttatgtaag aattgataat acagaactca gtgagggcac 15180
tgacttagta agcagtttta aacatttctt ttaagtattt ttttcaagcc ctgtgctttt 15240
tttctctcct acaacttaat tcttaatttt catctgcgtt tgaaggagct tcctcaggta 15300
aaccttttct cttgcattat acttgcatga aaatgatgtt agctatgctg tatttaaaat 15360
ctttaaaatg cctctatatg gcttaatata atctgatgag ttttgtatta tagttggagt 15420
ttttgatgtg ccaagtggtt attgtaaaaa taatgtctga agtttaaata tttgaatttg 15480
tattttttt taaagattta tttattgtat ttatatgagt acactgtcac tgtcttcaga 15540
cacaccagaa gaggacattg aatcccatta gagatggttg tgagccacca tgtggttgct 15600
gggatttgaa ctcaggacct ctggaacaac agtcagtgct cttaaccact gagccatgtc 15660
tccagcccga atttgtattt tcaaacccaa cttcgggcct ggggtctata gtttttgagt 15720
gcaagcttct tgtcaggtta atgtctggga ggaagaaggt tttgtcagta aagtttctga 15780
acttttgact agaataactg actttctgtg atgaagacta aactacaggc catgactgca 15840
caggagtcag ggcgtacata gatgatcctc agattttggg cagcttttac ccaaacattg 15900
agtttagaaa ctgttctcca ttcggctcac ttcgtatttg gatagcatgg agtattaaag 15960
gagttctcat tattgtcatt tttattgctt ccatttaact ggtatttttg tcttttgtgt 16020
attgagctct ctttctgtct ccccccctctc tgttagggcc tcactgtgta ggtctagttg 16080
gcctgaacct cacaagactc ccactgcctt tgcctccttg ggttacagga gggtgccacc 16140
tcacttcagc caaacaaacc ttgtatgttt cagcacttta tttatcagtt gaaaatactg 16200
actttcttct ttttttaaat tttagccttt ttttctatgg ctttaaaata tattctttga 16260
acataaggat gataaattac aaaggtgctt tctcccacag agccagtaat tattttctta 16320
taaaaattgt acccctccaa tcaatttctt taaaaagtag tttatttaaa tgtgcaccaa 16380
agactcattt cttttttttc caaatatttt tgtattttat atgtaagatt gttctgtctg 16440
catgtatgcc tgcatcaagt ccagtggttg tgagccacca tctgggtgtt gggaattgaa 16500
ctcaggatct ctgggagagc agccagtgtt cttaactgct gagctatgtt cccagcccct 16560
aaagacttgt tcttactttc catctatcaa tacagttaaa atgttaatag aaaagtttca 16620
tattctaaag tgaattttaa ctagcatatt ttaaaataca atttcacagt tcagggaata 16680
attttataat tcaaagttga ttataatgat ttaaatgttt tcagtgggaa taggaatcct 16740
tttacaatat taaaacaagg caattataaa atcatcaata tgactctact ctagtaatga 16800
gtgacagtat atatgtcttc atgatttaaa atctacataa ttacttccgg ttcattttat 16860
ttttcttcag tccaaaacag tccatagggg caaatttatt tataccactt gcaatagaaa 16920
cgaagccatt tcatttgatt tctatgttag taatacaggg taaagaaaca ttttatttca 16980
tgtattacat caaagtcata tgtaaagtga actaattcag cccacagatt tggagttttt 17040
ctgttttaaa tagtctcaaa gtctgctttg aagggtaaaa ttttgactgt taaaagcaac 17100
taaaaatttt gcaattttgg ctaaattgaa ggagactggt ccatcggcag gcaggacata 17160
ctgcgtgagg accctgagtc tcttcattct cagtgctgaa cttgctaagg cattgcaggt 17220
gaatgttttg ggtttttttt tatttttgca agatgcagct actactaagt taattggcac 17280
taaatatgac aggggctttg ttctcaagtt actggtccat ccttcaggca cataggaata 17340
tctctcctgt cgtaagttag agactttaat atcttttgaa tgattataaa gtagctaaaa 17400
cttagtgttt tgtttctaag cagcctgttg caggagtaac ttagaaatct aatatcaaat 17460
atgaagatta gagcattaga gagatatctc ttatagcttt atgttagtgt tgaatcaatt 17520
acagctttag tttttatagt cttgtgtgta ccattatgat ttttctgtag acagtttgga 17580
gtttgtgttt gccttagttc tcataaagtt gttaatatgc ctgatacatg ttgggcttct 17640
gcacttttgt gcatattttg tcattagtgg tcaatcttag atggcttttt tagtggcaag 17700
aaaaccaaag agatgccggg ctggtggcgc acgcctttga tcccagcatt tgggagctag 17760
aggcaggcga atttctgagg ccagcctggt ctacaaagtg agttctagga cagccagggc 17820

```
tacacagaga aaccctgtct cgaaaaacca aaaaaaaaaa aaagaaaacc aaagagtgtt  17880
atgcataaaa gtgtgtatgt gtgtgtgaac caaagagaca gcgttgtgtg tggatgtgtg  17940
cgcacacttg aatgtagtgt aaatgcagta gagctttgaa acaggaaacc agtcttttca  18000
tattttccag agacctagga agaagctaat tgttctatat aaactcatta gaaattaaaa  18060
gttttagagg ctcacatatg taggcttttg agcagttgca ggtacattat ttcataatta  18120
acttctagga agaaaaactg ggtgggaaac tagtagggat gactagtaag caagccatcg  18180
gtaaatatgc ccaataaacc ttactttgga tttcggagtt gctgacttta aaaggaactt  18240
aataaactaa gtaaacctta tttgaaattc agaatacttt tttcattgaa aaattgaaag  18300
ttttattgaa agtttttcat tgaatttatt catatccaga tataaataag attggaatca  18360
cttttaaaga gattctaaaa cttaaggatt cagtggaaaa aaatgtgctg gggataccca  18420
gggacttcca gatgtaaggc agagtgctct accattgagc tatgaaacca ttcctttctt  18480
tctttacttt ttttttaaa gagatttatt tattttatgt atatcagtat accattgctc  18540
tcttcagaca caccagaaga ggtcatcaga tcacattaca gatggttgtg agccaccatg  18600
tggttgctgg gaattgaact caggacctct ggaagaacaa gcagccagcg ctcttaaccg  18660
ctgagccatc tctccagccc tctttcttta cttttgagtc aagttttcct tcactgaccc  18720
aggctagtct taaaccctgg aggcccagaa cttgtgatcc tccagtctca ccctaccaaa  18780
tagctaagca ttatatagcc ctgcaccacc atgccaggtt gattctgttt caaagggtgt  18840
tactggcact tgggtgtggt gcctgtaatc ccagtattta gggaagacag gaggaacaag  18900
aggagttaaa ctttcctgct ggcaagttgc agaccagttc aggctaagac acccctcttc  18960
ccacaaaaag aaagtttgtc actggaaatt aagttagtta atgtatatgc ttacattctc  19020
atgtatgttg ttattgcata gccattgtca gtgtttgata cggttttctt ttcacaaaga  19080
gttttttttt tttttttggt ttttcgagac agggtttctc tgtgtctggc ctagtatttg  19140
tttttgtttg tttgtttttt ttttttttta ctttatttat tatatgtaac tacactgtag  19200
ctgtcttcag acactccaga agagggagtc ggatctcttt acggatggtt gtgagccacc  19260
atgtagttgc tgggatttga actcggaact ttgaaccttt ggaagagcag ttgggtgctc  19320
ttacccactg agccatttca ccagccctta tttatttatt tatttattta tttatttatt  19380
tattttttga gacagggttt ctctgtgtag ccctggctgt cctggaactc actcggtaga  19440
ccaggctggc ctcgaactca gaaatccgcc tgcctctgcc tcccaagtgc tgggattaaa  19500
ggcgtgcgcc aacacaccca gcttgccctt tctttcttaa gcattttctt tgtaatatgt  19560
tacatgcatg ttagggcttt cagtgtccct tgttgaaagc actccagtaa tggtaaatgt  19620
aggttgttct tgatgtctgc tgacttgaca ggccatgacg aggcttttcc ccttcaggct  19680
ttcccttgtt cttgactatg accccattta tgcatatatg cctgagtaaa ttgaactact  19740
tgacaggcat ccctaaacct gtgtctgttt tatgtaaatc ctgtcctttc tgtgtgtctt  19800
tatgagttgc attgggctct tgttcctgga tagatttctg tctctttcct gcagttctct  19860
gcttggactg ttctagccac ttaagtatat cttttctaat ataaatctta tttttatgt  19920
gtatgagtgt tatgcctgca aacatgtctc tttcccgtat gcgtgtctgg tcttcacttt  19980
gatatgggta cagggaacca aaccggatgc tctttctgca agagcagcaa gtatgtttaa  20040
ctgctgggtc atctctccaa acactcctgt gttttcttct gtcaccagaa ggcgtgtgtg  20100
agtgctaccc aacataatac tcacttggtg atgcttatac atacttccac ggatccctct  20160
```

-continued gaaaacatct tcatttaaaa aatacagtag tacttttagt gccatggtag gtctgtgtgc 20220
ctgtctttct tgaggacggt aaccactgcc cggccctaca gactttttaa tttgtctcat 20280
ttattcttgc ataatattat ttagcctgtc cctctatatt attcctataa gttaacattt 20340
tttttctcaa aggctttgag agttggtgtt aaagattctt ggccattaca gatgatgctc 20400
tgcctttgta gtacctatgg ccaaagcctt ctcatgactt ggagatcaat tactgagtta 20460
tatgtagaag gcaaatgtat ccagaatatg taggcggagg tcttaagtgg ttgttttaaa 20520
ggaggtaact tggtatagtt gatgtgaaaa tcttgtaggt agttatgaga tggaacccca 20580
gaacaaatga gagctagaaa gatggataaa attcatggaa gtgtagattt ttagttaatc 20640
ggaaataaat tctcccagaa tatagagatg ggtttttatg ttaactggtt ttgaattgaa 20700
actaaggaca tgctaaggac taattacact gatgagaaga aagcatgtag gcttgagcct 20760
cagtcgcgta ttctgacatc acagctgtca gggatgaggt tatcactgcc cgccgagtca 20820
ctgtgggcag taggaactta tagaagtcta aggatagtga gtggctgact gtccaggcta 20880
tagctcaagg agcagacaag tacatttgac gaccttttat aatcacagct agcgtgggaa 20940
aagctaatgt tttcaaatgc atgcatattt gtgtcattgt atattctagg tatttcctta 21000
acttaataat ttagatattt atccaaatat tattgctatg ggatttcctg cagaaagact 21060
tgaaggtgta tacaggaaca atattgatga tgtagtaagg taagcattct tgattttcta 21120
tttcttatat taataaatta ttttgatgtg ttttatttag aaaagatccc gaaaacacag 21180
accagtattt gcattttgat gtgttttggt aaaactctga aagttttaac ctaaagcacc 21240
tgacagctct cactcggctg gatgcgtcac tggatgagaa ctggctagtt atatagtcgt 21300
gtttgtttat gtcatgaaga tttttttttt tgtattccat aatatgtctc ttaccaggtt 21360
attctctggc ttgtattaca gtacaaggtt ttgactttgt atttgggtta ggccttgctt 21420
aagtaggttt gtttagttat tcaccctgcg gtatgagtga ccgatgtgtt ttatgtagca 21480
cttatacctg tagcagtgtt tgatacaatg attttggaga gacttgctgg acattcattc 21540
aaaagagtaa atgaagagta tcataatttt acaaaatttc caagtgtgat tgttgcttag 21600
ttcagaaaag tgtttctcaa ggcccactta aaaaatttag tttcagaata aaaatgcaat 21660
tgtatgagta aatgaacatt aaatttttgt tgcaaactat catagttttt aacaattcat 21720
taatactgag tcttgctgta tttgctatgc tggttctgaa gtactttaat gaatttaaaa 21780
gttaaaattc tggattattt ccttttttact cataagtgag catctttcct ggtgctttta 21840
actatgtgtg attatgcaga tttaaatagg tgggagagtg ctttgtaact tagagtgtca 21900
tgcagatgta ggatgctttt gtggtactgc atgactttat gtctttagat gagctagtag 21960
tcagtttcct aagtggctaa tttttactgt tttaaattgt gcttgtttgg ataatttatt 22020
ataatattgt ttatgttttg ttcaggttta aatttcacca tctataaaag tctaccaaaa 22080
ctaacaccaa accccttact gctttgtagt ttccattaaa ccttaggtta tcctgttaga 22140
ggtaactgtt taaaagcctt taacaatagg gaaatacatt tgccttctta taattaggta 22200
gaacacagtg gaaggatact tagcatggca ggcccacagg aacacagctc gataggaaca 22260
cagtgatgat gcagagaaaa tgaaatacgc cacagaaaaa aagtaagaga ggaaattttt 22320
tcattgaaag ttgcagagta tggttaagtg gcagtttggc cagataatta ttttctgctt 22380
tgatgcagaa ttgtttatgt ctttcatgtt atgcctcata agatacacta tttcacatca 22440
attttatatt cagccaagga ccaatttaac caaaccaaat tcagctgtat tgaaaagggg 22500
agcaagttct ttctttaagt ggaggggatc ttttctggcc atgtaatgtt cttttgacta 22560
atctggcatg ctaattttat attgatttct cttaagtatg aattagtaag tgagggtgat 22620
tagattatct ttaaggttac aattccagtt tctagacctt taccccctggt tattagacct 22680
tatactacag taacttagcc aaaaatatgt tgtgttgaaa aattagtttg gtcctgagtc 22740
ttctggtttc atgattccta tacttttgct tgcaaattaa gagaattgca cattcatttt 22800
tataattagt aactaagacg gaaattaatt ctatctagct ttatctatct agttttttta 22860
tttagcctta ggtgttctct ctcttttaaa gaaatctatc tgtattattt agcttgttct 22920
tttagcttct tactttaatg tttttataaa actgttctgt gtttggtttt tgttgtttgt 22980
ttgttaagat aaatgaccat taaggcctgg ataacttctg tttatcagtt ccccacccac 23040
ttttatagta aagtatgaat agtgactaga aaggaagata ggccttttcc tacaaactaa 23100
agtgactaaa aataactttt ttgtgatttg tttgtttgtt tgcttttttt tttttttttt 23160
ttgagatagg gtctgaatta agtaagtagc cttggctagc ctggaagtcc ttatgtagaa 23220
ctgtcttgtt ttgaactcat aggcatttgc ctctctgtct ccgcctcgga ggactgggat 23280
caaagccaac accattacat tagcccctac aaataatgaa ttacaatgcc ttttaggatt 23340
gccttctcca aagaacactt gtgtctaata tctaaataac tgattacttc agtttgttca 23400
cactatattg gtgatgttag ttttaatcaa tagtgagtgc ttccttttgc tttaaagttg 23460
ataacatctc agtacaagta tttttgtttt catatcacca gatagcccag aagaagcagg 23520
tgatgtaaga gggggttcgt ttgcctcatt gtttgagaag gctttctggc tgtggagggt 23580
gaggagggag ggcagaggcc ctccatccct ccatccatgg cttcctgagt ttggggcaga 23640
gttcatggtg gaaggagtgg aggcagtaac tcctcatggc tgtgaaagga agcaggaacc 23700
agagaaacct gcagataatt tgccctgact gactgatttc tgtcagccag atttcacttc 23760
caaaggctcc acaaccgggc tgggaggagg atttcagatt gaaactataa catgtttgct 23820
ttcttattaa taaacttttt ttttgcagtt aatttttctt tgctttgtct agtagggtat 23880
ccaaaagata ttttaaacta tttttctttt atctaattcc atatttttct tatatttccc 23940
ccaaacaaga aatatataaa acttaaatct ttgctattgt actatagcgt tacctggagt 24000
gaggtaaact taaattgcaa atattttcat gcttaaattg tcctatgcag aaaggtttgg 24060
aagatatagt gtgctatgat aagtaaaatt tcatagctga gatctacaaa atttgagaaa 24120
aatatttagc ttcttcattt gagatctggg attcatgtaa aaaatggaaa tggaggaaca 24180
ctgggcttgg aatttgcttt ctaattacag atgatttgct ttttttaatc taaggagtga 24240
gctgacaggg caggcagggc aggagggact gcggaggctc ccacagtagt tgttgtcgtt 24300
cctcttaact gcttccttct tttttttttt cctcattttt tgcaatgaag agggggtgat 24360
gcaccaccag cacttggctt gatttgtgct tttccagtgt cctttaggct ggtgggaaag 24420
ctctgtggct ttaaatctaa gcagtcgtga acagactggg gcatagtgtg tctaaggagc 24480
ttgtcttgta atctcttctg cccaatgact caggaaaatg tagatgtaac agaggcaaac 24540
tactttttac acaaaatgtt tagtacagtg ccaccaggta gacctttccc cacctttatg 24600
ttttctcttg gtttcctttt ataatttgct aactctcatc ttcctagaca gtgtttcatg 24660
gagctcaatt tggaaaatgt tgaaaatgaa aaagttatgt gtacagaatt gttctaagtt 24720
tgatatgttt tgaggtggag gcatgctata tgacccaggc tgacttatgt atagtccatg 24780
ctggtttcta attcatgatt tttacactcc tgcctatggg tgtccatcaa gcccagtttg 24840
tctatagctt ttataaggaa atgattagag ctcagtcttg tgacataatg atttaacaaa 24900

```
aagctattac tgttttgtaa acccatgtat aacctgttac aggttcaaga gtcttattgt  24960
ttcttgactg ctggcatata tattttcttt ctgaagaaac tttgcaaatg ttcaattctt  25020
ttttttttt ttttttttt ttttggtttt tttgagacag ggtttctctg tgtagctttg  25080
tttgtactgg aactcactct gtagaccagg ccggccttga actcagaaat ccgcctgcct  25140
ctgcctccca agtgctggga ttaaaggcgt gcaccaactc tgcacagccc tattcattac  25200
ttaatggccc tctgaataat gttttcaagt cttattttta attgatagtc aataatgatg  25260
ctagaataac aaatagttct ttctcattga aaatcaagaa aaaaaaatgt tgagcggtgg  25320
tggtgcacgc ctttaatccc agcacttggg aggcagaggc aggcggattt ctgagttcaa  25380
ggctggcctg gtctacagag tgagttccag gacagccagg gctacacaga aaaaccctgt  25440
cttggaaaac aaaaaaaaaa aaaaggaaat aattaataat aataataata aacaggaaag  25500
attacttctg tttttccatt ctaacatttt tttgcccctt tcctcatttt gccttcctct  25560
tttccatttt aaaaaaatta gtgagttaac ataatagtca ctgttttaaa ctgtaatttg  25620
agtgacattt aatattttca cagtatagcc agaggtaatg cagtcaccac cgataccaaa  25680
ttccagaacc tttttatcac tcctgaaagc tcctggctgc ccttcccttc tgctggctgt  25740
ctttcctgca catggggaga tttagtgtgt tggacaataa taatgttatg ggcacaaact  25800
agctttgcta tttaatagcg gatactgttt tctgtacatt tatttattta ctatttatat  25860
ctgttaacta ttgtataacg agcttgcata taccatctta ctaagtttgt agacggaatc  25920
taatccctat ttcactttta taagtgcctt aaaagaaatt agaatcttca gttgccacag  25980
cttagaagta gcaagaagct ggaagttgag tccgtgtctg tgagattcca aagttgattt  26040
tttttctttt ttgtttgtta ctgtatttaa ggcaaggtct cactgtgtag ctaaggccag  26100
tcttgaactc aaggtcctcc tggttccata ttctcagagt gctctgtgta taatcttatg  26160
gtgatctggc cagcaaaaat tcaattttta aaaagttttt taaccagggg agggatgcag  26220
tctggagttt gaactcagtc attactaggt acttcaccac tgggcattac ttaaagctgc  26280
ttcccttaat atctttttc tgtacatcaa aggacaaaat ctagaaacac ttggacaaat  26340
cgagactata cttaaaaatc atgaagcctc gtgcaaaacc ctgtatttct agcttatttt  26400
taaaagctga aagagctgtc aaaactgaat tcaacattcc tgtgtgatgg atcaagtatg  26460
gttgtgtaat gctctctggc attaaattgt taccatttct ccattaagga ctgtttctta  26520
gtgaggtttc cattgctgga aatgtgcctg gcccaaggaa tggcactatt aggaggtgtg  26580
gtcttgttga gggatgtgtg tgtgtcattt tggggttagg ctttgagacc ctctcataac  26640
tgcctgagga cagtctgctc ctggtgtcct ttggatgaag atatagaatc ctggacacca  26700
ccatgcttct tgctgtgata actttcatta tattgaaagt tgttatattt taataatact  26760
gttaatgttt taccttgcct agtttattca acttcattga taagtgtgta tatggaaaat  26820
gtacatacag tttgtcgctg tccaaagttt caggcagcca tatggaaggc gtgtgtatag  26880
tgtaaggttt cagctgagga tacattacat tccttgttaa accttagtgc tgcagatgtt  26940
ctctcacttc cacttgaagg gctgtctata gcatttcttt taagttttcg taacttttgt  27000
ttctctggga atatttcaat ttatttctca ttttttgaag gacagttttg ctggatattt  27060
tttatttcta ggaccttaaa tgttatattc ttacttcctg ttctgagggg gaaaaatctg  27120
ctgataccaa cgctcctttg tgacatgttc cttctctctg tatttgagac tgtgggtctt  27180
tctcaggaga gggtcttgca taatacaggc tagcctggag tccttgtata tatgcaagga  27240
tgtactaact gacttttgat cctcctgctt ccacttgact agtgctctga tttcaggagt  27300
```

gcaccaccat caaaggttta tgtagagatg gggacagatt tctcagagct ctgtttgtgt 27360
tatccaatga gatatgcccc cagcctgtct ttgtcttgtg atggtttgat tgcgatctgt 27420
cttagtaagt ctctgagttt ttgtgaattg tggttcattg agccagaagt tctttatatt 27480
cttttatcaa atttgagaag ttttgactgt acttctgtat ataattattt ttctggaact 27540
ttaaagatcc ctaaggtagt ccagttgctg ttgtctcaca ggttggttaa tctctttacg 27600
tttcttcagt aagttgcttt ctgtattttg atatttatcc tcctacccta gttcctgggt 27660
gtggaatgtg gtttactcca ggaaagaaga ttgactttct cactcttggt agccaatagc 27720
tccttagccg gggatgggac tttggtcatc actttcttt gcttggcttg tgctttcaca 27780
ggtcttgtgt atgctgttag ggttgctgtg agttcatatg tgcatctggc ctgttgtgtc 27840
tagcaagcgc tgtctccttg aagtcaccta tcattcttgc tcttacagcc ttcctgccct 27900
cttccacata gatgcctgag ccttgaaagg aagggtatga tgcagaatac catttgctct 27960
gaacattttg aagtctttct ttgcaggttg tatgtactaa ttgccatcaa cagaagcttc 28020
tctgatgagg gttgagctgt gcactgtctg tggtttattt agcagtagtc attagcaatc 28080
attctattgc tgtgtccact tacccgagga atattggtag gttttcccta ggctccatgc 28140
ccatctagct acaggctttt ggcctcattt tgacaatgtt agatgtggct tccatcttat 28200
agaacagacc taaatctaat caaaaggtgg ttggttattc ctataaacat ttttattcca 28260
cttgactgta cttttcagcc atggctagga ttacaagtat gaactactgt attgttctat 28320
ttaaattttt attaagagtt ttttcatata tcttgatgat attctttccc attcttcaac 28380
tcctcccagg tcttttccca cctcccattc cgacaaatgt catgttcttt ttttctttcc 28440
ttctcaagaa gaaaaaaaag aaaatcaaca aaacccaata agacaaaaag tgacaaaaca 28500
aaacagaaaa gcacaaaaac catggagtcc attctatgtt ggccaactac tcctgtgcat 28560
gagcgctgat tggagcgtag ttgatatgtt ggagaaaact gatcttctgt ttctcagtag 28620
gaatcaactg caaatcgttt cttggttaga ggcagggctt tgtgtctgct tcagatttag 28680
tgctgagatt ttgtttggtt tgacttgagc agatcttgca catgctgaaa caatctgtga 28740
gtttgtgtga cacccttgtt gtgtctggaa gatgctgttt gcttagactc atttactacc 28800
tctagctctt cccatctttc ttccctttcc tcggagtaga tccctgaacc ttgaggggag 28860
gggttcaata aatgcatccc atttagtact gagtgttcca aagcctctcc atttgtacgc 28920
tgtgttgatg tatatgctta atttcatgtg ggggttactg ctttagatca ttcagtttcc 28980
agataaaaaa cacaaacttt taaaaattat ttataagcct taatgagcac taaagctggg 29040
ctggtatcta ccttctaggc tattagtatc tacttcctta ttggtagccc tgagttataa 29100
cttgccatat ttcatctggg ccactcttaa ctccaattgg ccagccttca tgaccgagtt 29160
ttcatgaatc acttaacccc actgtggctt ctcctctctc tattgtttcc tgatcttctg 29220
cctcagaccc caagcctggg aacccaaacc ccacctaact ctcttcagcc tagctataag 29280
ctgtaggcat cttcattcac caatcaagga tagctttcag ggttatagag cattatttga 29340
tgtatgtgag gatcaccttg gcccagaggt aaccagggcc aatatttagc attacaatat 29400
ataacaacag accaaacctt aacggtttta aattaaggtg taaggtttat acagcaaagg 29460
ctggtaaatg tgaaattcac ttgtaggtct aaatctttta gtacagaatt cagcattgct 29520
atacatagca acagaccaaa cctcaacaca ctcttcagtt gtgggtctct gtgttaatca 29580
ccatctactg caaaaagaat tttctctgat gagtgacaca ctcatctata gggagagcag 29640

-continued

```
tatgttagga atatttctgt ttctttaata gaataatagt agtagtaggt tttcccctag  29700
gctcatgact tgtctagcct taaattctta gcctcactag cagtggcagg catgggttct  29760
attttaagga atgggtctta aattcagttt ttaaaaagtg gttgtttgtt cccataacat  29820
ttatgccaat attggatcaa tatatatgcc cgcgagcatg caggtctttg ttgtgggtca  29880
cagagtttgt agctgggtta tattgatgac tacttttatc ttccagtcgt gtgcaaaagt  29940
accttccagc accacgagtg ctagtcagta gtgctgaatc tctagttggc tgtcagctca  30000
atctctctgt gctcgatgac acaagtaagc agtatcttaa gcaacaggac taccatctgg  30060
ttgtggagga aaacagtagc cttggcagta gccatgatgt tgggattgca agtatgtgct  30120
atcgcacttt gttctttttt tcaagacagg gtttctctgt ataccccttg cttcctggaa  30180
ctcactctgt agaccagaaa tccacctgcc tctgcctccg aagtgctagg attaaaggcg  30240
tgtggcacca ctgcctggcc tgtgctttgt tctttatgtg ggttctggga ccctaaactt  30300
agactaaggt gccttcctag tcctggaatt ttcctttta aaattttttt atttgttttt  30360
gtatgttggg gtgtgtgtgt gctatgccat gccacacttt tagaggtcag aggacaactt  30420
ataattcttt ccttttactg catggttcag tttggtggca gttatctttt ttttatcttc  30480
tcagctaccc atcttgttaa taactcagaa gctgcacttt cctgcctcag ccttccgaat  30540
gctggcggac aagtgtgtac cactacacct agctctttgt ttctctttca ctttattgat  30600
acttctgttc atcatttttc ttgatcttac ccgtgtcttt tttttctttt tttgagacag  30660
ggtttctctg tgtagccctg gctgtcctgg aactcactct gtagatcagg ctggccttga  30720
actcagaaat ccgcctgctt ctgcctccca agtactggga ttaaaggcgt gcgccaccac  30780
gcctggcata cccctgtctt tcattagctt tctgagtatc attaagacca cacaaatctt  30840
tgcctagtaa atttgctttc tggtttttct gagagacagt ttgttgactt tttaacttat  30900
tcgatttttg agtatccaca catcttattt tggggtgtga gtatgcacac ttgtgtatgc  30960
atgtatgttt ttgtcttggt cttgtaaatg tgtgtgtatg tgtgtgtgtg tgtgtgtgtg  31020
tgtgtgtgca tgtggtgtgt gtgtgtgtgt gtgtgtgcat gtgcgcttgt gtgtgtgtgt  31080
gcatgtgtgt gtgtgtgcat gtgtgtgtgt gtgtgtatgt gtgtgtgtgt gtgtgtgcat  31140
gtgtgtgtgt gtgtatgggg ggaggtagct aaaaacaatc tggatcttgt agggtcgaag  31200
atcctctctc ttttcttgat ggcccagctt tcccttgttt tctgtattgg gtatctacta  31260
tgctatacct atgcaaagat taccatgcta aactcatgca aacttaagat ctttggggct  31320
ggagcagtgg ccgagtgttt ggggacactg gctgttctca caactgcctg ccaatctagt  31380
ctgagggtac ccgatagcct cttctaaact cgggtggcag gcactacatg ctagtggcat  31440
gcaagtggtg cacagacata cattcaggca aaatactaaa tacacaaaat cataataaat  31500
taaagatctt ttaggcttgg gctttttttc taggtatagg gaatgacttc ctaaattttt  31560
tttgtatgtg taattaatct cagttgttat tatctttaaa tgttgggttc tttgaaagat  31620
ccaaaggaag gaaaaagaag tgggcagggc gagtagattt aaaatccctt gatgtcttca  31680
gttggtgggc gacagcttcc tccatctacg tatgcgtgtt caaaagcagc aattagtgac  31740
cagcacacag atttaaaata ttggaacgta cggcatttat tattaacttt ggcttttgaa  31800
agttgtttgt aagtctctat agaggtatat caatgactgt atgagaagtc cttgttgtat  31860
aagagctaaa atcagggctg tggagatggc tcccttagta aagttcttgc tattctgagt  31920
tcccattgtt cttttttttt ttttaataga agaaaaggtt tattttactc acagttccat  31980
ataacagttc attatcaaaa gtaatgagga caggaactga aacagggcag gaacctggag  32040
```

gcaggagcca atgcagagag catgaagggg cactcctgac tggcttgctc agcatgcttt 32100
cttttctttt ctcttctttt cttttctttt cttttctttt cttttctttt cttttctttt 32160
aatatttttt attattacgt attttcctca attacattta gaatgctatc tcaaaaatcc 32220
cccatacccct ccccccacca ccacttccct acccacccat tcccattttt ttggccctgg 32280
cgttcccctg tactggggca tataaagttt gcgtgtccaa tgggcctctc tttccagtga 32340
tggctgacta ggccatcttt tgatacatat gcagctagag tcaagagctc cagggtactg 32400
gttagttcat aatgttgcac ctacagggtt gcagatccct ttagctcctt ggatactttc 32460
tctggctcct ccattggggg ccctgtgctc catccagtag ctgactgtga gcatccactt 32520
ctgtgtttgc taggccccgg cctagtctca ctgagttccc attcttagaa ctcatacaaa 32580
agccagcttg ctcagcatgt ttctgcgacc tctgtgacag gaagcaggca gagaagacta 32640
tcctgggggc ttgctggcca gttagcttag ccaaaataac tagctccgtg ttcagtgagg 32700
gaaccgttct caaaaacaga ctagttgcaa agtcatagag aaatacctgt tgttcccatg 32760
acacacacac acacacacac acacacacac acacctaaaa ttgtttaagt taaccttcat 32820
tttctgtcag agctgactca ctgaaagtgt cagcgtttgc ctagattccc tgggaaaggt 32880
tccgcaagtg cagtcggtgg tcagggctgg cttctggggc tgcttctctg tcctcttgaa 32940
ctactttggt ttctttgttt ctgttttgtg gggtttttta agatttgttt ttgttgtttt 33000
gttgtggatt tttggtaata ctttctagca tttgaaatac atgtttatat aaaataaatt 33060
taaaattcac tattgtggct tatctagatt tatttcctaa gaaatctttc atgctcatac 33120
atcagcctca gtttatctca gtgagacaga cacacagaca cagcacagtt ggaaaggagg 33180
ctcaacaggg ataggagggt gagagtggtg aggcgatgtg agacagacac acagacacac 33240
cacagttgga aaggaggctc aacagggata ggagggtgag agtggtgagg gcgatgtgag 33300
acagacacac agacacacca cagttggaaa ggaggctcaa cagggatagg agggtgagag 33360
tggtgagggc gatgtgcagt cagttccttc aaggaagatg cagttctagg aggtgtctta 33420
ggtcgtgcag ggttagggag cattgcctct cactgctgtc taatatttta gcctctacta 33480
tctaaataca tctctgtagg caagtttgcc catttctctt tggaatgtgc tgtttcactt 33540
gtctttcctc acttgtcttt ctatgtgtca gactgagaga acagtggggg aagtgcggaa 33600
tgtgtcccta agtaatcagt tctctttgag acagttatcc ccccacccct tcaaatgatg 33660
gaatgatgta ctgtacccat taaagggctg ctttcttctg ttagacttgc tgttgctcac 33720
atgctagcta agaaatcaga atgttcaact gttaaggggc acacagatag gatttcccta 33780
agcctaaggt aaacacacgg taggaaagac tcttgaaaga attatgagtt tttagttgca 33840
aatgacataa aatgtcttta ccagaaagga ataatgctct ggaggaagtt cccattgtgg 33900
aaagcagaag tttaggaaac gtggtgtagg ggctacagtc tgcttagaca ccaatgcatg 33960
gtcctacatc ctggttgctg tctgtgaatt cccaggtctt ccagtgagat ctttgaagaa 34020
tctactgttc tcttgtacct tgctgcccac tctgtaggag tgagtgtctc acaacaaggg 34080
aaagagaaaa gaaatacctg cctctgatct cagtgtttgc taactggttg acataagggt 34140
ggcacaattt ccttatgaaa tttttatact tcatccccct ttcagaaatt tgtagctgtg 34200
tttacatata agaagccgtg gtctttgttt gtttgtttgg gtgttcttgg actttctagc 34260
ttccaaagct tcggacagtt aacttctgtg gggcattgtg tgcatacgtg gtgtttactt 34320
tgtgttgact ttcttttcaa ctgagttttc ttttaaattg tttaaactgc tttgattcct 34380

```
tttgtagaca cagctttata atgctttata agtcctttct ttatgccttt ataatatagc  34440
ctttataaat cccttctgtg cccttagatt cagataaatg ttgactaaag aaattgatgg  34500
gttatatttt gctcagaata actgattgct aactctgctt tattgttgta tataattact  34560
atattttcta ttgctagctc ttaaataatc aagaagcagc tttgcttaaa ttatcaagta  34620
gaaaagattt aacttatgag gaattgttaa tatatctcct actactgact cggcattttt  34680
cttttggaca gagaatagag aagtgaaagg tttagggctc cctgcctttt tcctgtttcc  34740
agcattatac accagtcaag cgtatggaat tctagtttct ttttgttctg ttgctccact  34800
ccaaccttta gttgatactg tttttgtgtt ccttcttata caccactttg tgctgttctg  34860
atttcatctc tgagcactcc ttctgccatt gtgatgaccg tgttttaaaa tggagctttg  34920
tgagctctct gcagctaagt gttttttcct gaataatttg ttcattacaa aagagaattc  34980
tagagaatcc taccaagtcc atagcattgt tactgtgatt gctgttttga gatggtgtcc  35040
aactctaatc ccagctgact tcaaactcag ttctatagac ctggctgtgt ttacatgtgt  35100
gcggtggtaa catgcatggc acatgtcact tagtgggctt gacctttctt tctctctctt  35160
tctttctttc tttctttctt tctttctttc tttctttctt tctttctttc tttctttctt  35220
tctttctttc tttgaatcat caaagtatga cttcatgttt tgtcttttaa aaaattacat  35280
ttccctctgt gtttaaacaa atgagcctag tttatagttc cccatggatt acagttaaat  35340
cctctctgta gtcttctttt agattgggtt gtagattcct aggctgctgc tgaggcgaag  35400
catttgcaat gctttacagt ccagtatggt atctcactat gccagcattt ccttccttgt  35460
ctgatgtcag ctctagaatt acatgaacac tttccctctg tttcctgaca tttccagagt  35520
tgtagtttcc ttctaaaaat tatttataaa agagaactaa ccaaccattt caagattttt  35580
ttttttaaag aaaaacctca gaagttaaaa gaaccagatt cctaatattt tgctctattt  35640
ttcttgtaat tttataatgt attccgagga tgtgcccact ttggtaacct gactgtgaca  35700
caaatgtatt gtgtcatact gcttggtttt ctttctttaa ttgaaaataa aaaatagata  35760
ttttttcata caatattctg attatggttt ctcctatccc aactcctcct agtttccctc  35820
ccttctccca tacagattta caccctttct gtctctcatt agaaaacagg tgtctaaaaa  35880
ctaatagagt gaaataaagt aagcaaacaa actggaatag gacaaaacaa acaaacaaga  35940
aaaacacaag acccacgtag gctcagagac acgtgtttgc acacatagaa ctcttataaa  36000
atcacaactg gaaaccgtac tatgtgtcca ggagatctat gttctcggtt ttaatttaca  36060
cgcacacaca cacacacaca cacacacacc ctgctctgta aatctcacag tgattgagca  36120
catttggtgc tcatcagttt ctcgtactcc tgggtcttcc tgaccgacct aactctgacc  36180
taattgcctt ctgtgtgtgc agcctgaggt accccttgcg atccttgggg tcctcacttc  36240
ttttacaggt tgggctccct ggttcccaga accgattatg atttttcact ctcaacatct  36300
tttacaactg agatagtgta tgggaaacaa atgacttgtt gtagaacagt gcctttattg  36360
tattatatac tcacccacga tttatagtct gtcttgtata gcattctagg ctggaagtaa  36420
attttctgaa aaatcaaact ttgtataatt gtttttagga agctagtgtt aatggcagtg  36480
cgtttgtcgt tttgtcttat gctgtctact ttccatgcca actttagggt ctggtgttct  36540
ctttggcact tagaaataac gtagatatat atggctccat ttgcggctcc cctagacccc  36600
ctttttaaag tcaattttat tagctattta tgtcttcatc ttgggaactc atgttggacc  36660
tggagatgta aactgacaga atgttttgct gaggctctag gtttaattgc cagcactgca  36720
taaacccagg ttggtgatac agacctgtag tcccagcacc ccagaaatgg agggaggagg  36780
```

```
gtcaggaatt cagggccagc ccgggctaca tgaaactatt ttctcctttt gtctcattat  36840
taattcttca ccattatacc ttgctgagtc ttctgtttca ggcctgaagg ttaaacaaat  36900
ttacatacat aaagtactta aataatacct ggcatgtaat aggtgctttg gtacctgtga  36960
tcactgtgtg gtttcacagc tggttggaag gagtggcccc tgctctgact cttcatttac  37020
tagcttcaca ccttggacaa gcttcataat ctcttgaggt ttacttcctt ttcctgtaaa  37080
atgtaaattc catctctgcg atgttggtca gggacaagag aaagtataca tgtatacatg  37140
tgaaaaatgc ttacagaact acattgctat tgtacttttc agattgtggg tttttttttt  37200
tttccctgct aggaagatta cattttaagc tttttttttt ttttcatgga agtctgtgag  37260
ctgggtacac ttgaactgct aatatcgttt tgtcaagacg tgattgtaat ttattagact  37320
gaagacatag atatgaaaac agtttttgat aaagtcagct ctacttcaga atgtataaat  37380
ctgtgtaatg taataactat taatgaatga ggggatatgt atttgtgtta ttaatagtat  37440
gtgagataag ggtaaataaa tctgttttag tcctgtgcag cattaatgta atttgaaata  37500
ttagctcatt tttgttaatg gtgttttttt tgtttgtttt gttttaaggt ttttggattc  37560
aaagcataaa aaccattaca agatatacaa tctgtaagta tgcttttttt atttgtctct  37620
gttaaaataa ctaaataaaa gttatttctt tgttgaagat aaaaatatat ttagatattt  37680
ttatatttga ggaactggat tcctgaaaac agttgcagtc tgatagagag agttgttggg  37740
tctcgaagcg tggtgatgag gtgcagcagc ttggcacagc ctccggttac ttgatctgct  37800
tttacagact tggcacctcg cccatccttg agcccataat catgtgataa tttgaaatgt  37860
aatccacagc ggagctgctg ttagtattaa cgatggcttc taaggagaca gactccaggg  37920
tggatggaca gacttttgtt tcctctgtgc ttgttgatca atatactgaa acagctattt  37980
gaatattttc tgtgtataac ctagtaagtt atgcagcatt gtttagttat ctagtatagg  38040
atttgaggga ttgctcatta aaacttattg gcctatcttt aaaccttcac tttcttttga  38100
cttttggagt agtgacatga aaacaggaaa ggaagacaaa tcattaaaca ccctttgtct  38160
ttcaaaacca tttttatttt ccccaaatac tgagcatttt taaaaattta aaagataaat  38220
taccatgttt ctattatgtc ctttaatttt ctatgtctat gatttatata acaggagaat  38280
gttatgcaat ggtagaatac caattagtaa ttaaccattt tctgtagact ttatcaaata  38340
taactacaag tgttttctgt tctgcttcga gtggctattt gaattgctac ccagaaggat  38400
ggagaatttt ctatgtcttg ttatagtgct agatgttact tttatttttt cagtctttaa  38460
tgatatttct gttttgataa gacttcaaag tattcatgtg caatagttac caatattatt  38520
tctcttcgct tttgctgact tcagatcaga aaggtgcagc catggtgaaa catgcagata  38580
gagtgctcat atggctagtt ccagccctct agtagcctat agcttgatgt gaaagtagga  38640
gggagcagga gagaagtgtg gacaaagtaa ctggccccac aggaggcctc tgtaaaagac  38700
cagatgtgtg ggctgtgatt aacttctgat accttctttc ttctatccct gcttgttata  38760
tacttgtaag actaagagga gtttctgttt tatttctttt aattttaaga ttatttcttt  38820
gcaaacataa atttaaagat cttgaaatat ttccatggct tttctactaa tgaaaatcaa  38880
taggagttat ctattagacc tgggaggatg agccaaggca agtcagaaga ttgatagtat  38940
aatggtattt gaaatatggc agataactca ttttgggcag gtggtggtgt atgctggctt  39000
aggtggggtt gtgctaataa aaggtggata ggagaaccac aagactgttt ctgaacagct  39060
gcattcagaa ggtgactgaa aaaggacaag aactgttgaa agctggaatt gatgaaatga  39120
```

atcatttcag actcacactg tcaggtttgg ggatttagag aggtcccaat agggaagtag 39180
aaagacatta gaagacacat ttctgcctga gctgaaatct tatgcctgtt taacatatct 39240
aaagcacagg gaggaaattc ttttcattcc tgcctatagt gacttcctgc ccctagaatt 39300
tagggattag gtttatgctg tctcctttgt tgtatttcag tatagttaga ggtggcattg 39360
ggtggaccta ggaacttgat ttgagtttcc aagcatttga ttcccaattt aatgaaccat 39420
ctctttatta gttgagagca gcctttagtg catatgaact tattcccttg tcatttggaa 39480
ctgaggcttt cagaatggca aaggatctga agggtccttt tagcagtgcc ttcttatctt 39540
atagacaggg cattaggcct aggaagttaa atgaggtagc caaagacagg taggtgcata 39600
ataacagact acccactgtt tgcaccagaa tccctttttgt ttgctggtta gctcttcgtt 39660
ttatttactt caaaagtttt taaacatata caaaattgag tgttttaatt tgagtacccc 39720
ctctcccctg cctactgtgt atctgatttt aggcaagtga gactagccac aacagatgtt 39780
tttgttttat ttctttttgt cttaggatag gaattacagg tagtatgtat ttttttttc 39840
ttggaaatgt agatgtttga aggtcctaaa gtatttttca ctggacatct gtatagttag 39900
tagtttgtga gacctttttat agcagcagtg ttgcacatga atgaagaact atcagcctaa 39960
gctttctgat aatctagctt atctattatt attaatcagt tattttgaaa aagggcaaca 40020
ttaattaatc agttttatat gagtgttttt aaaatttctt tgttgctccc tgttcagaga 40080
atacaagatt ttaagttttt attatatttt agtgaatatt tgctgtactt ggcaaacatt 40140
taactgtgtt atttttctgt taagatttcc tttgtaaaac actgtagagt gaagaagaga 40200
gctccctacc atgtagttct atggcaaggc ctagttgtct gcaagtttgc ctttctggtt 40260
tcactcctcc tcttaatttc tgttgccacc ttgggaaacc tcattttcct tgtttttttt 40320
ttttttcatt tctcttttca tataagccaa tttaagataa ggacaaaaat atcgtttgag 40380
ttttaattac aaagaaaaat ttaaatccaa attgttattt gctatcttct attttagtat 40440
gtggagtgac ttactgctaa tatgccataa gaaatttaaa agaaactccg ctgtgaattt 40500
tggctatata ccagagattc taactaaggt ggaaggtttc ttcttgaccc tgtgaccctt 40560
tctttctctt gagcactgtt tcacaggcag ccctagcatg tcctcccaaa gcccctccgc 40620
ttgcctataa ggagctgcat gctcccctcc ccccccaagt caattgttag gtctgtcttc 40680
agtgacaaat actgctcatg tttgtgctgt aaaatttgtc actgcttttt catttaagac 40740
ttgaatgttt ctgttatgtt gaatgaaact gtaatagaag ttgttggatt tagttgagca 40800
aggatactaa gcttgagttc ctgtctcacg gtgacttcat gttgttatta ggaaagcttt 40860
taagggcctt tctaaatctt agcttttcca tatatacata tgcctcacat atacaatggg 40920
gatgtaaact gttacatgat tgtgagggtg aaaacatgga tgtcagctgt aaggtgccca 40980
tatcctgtag acttcagttg ttactgtgtt cctttcacct taactgatga tacatgacaa 41040
ccagtttgta atggtgatct taagcagtgc ttattaaacc aaacttttca gagtgtttgt 41100
tccatctttc tctggggtgg gaccctccct tcccctcctc tccccttccc tgcatcacct 41160
ccgcaggcaa ttgggatccc tgaccctaga ccagaaagtg tggcaaactg aaaaatctga 41220
cttgtaggac actaacaacc ggcttcttag ggtatgtgcc tagcttcctc ttgtttcctg 41280
attgtatcct taattcttga ctgtcttcca ctgtgggctc ttcaccacac agcacctctc 41340
agaagagcag aacctggctt ccctgtgtgg agttctaaca cttggaggtg gagggagaag 41400
ggaattcaga gccagtcttg ggtatatgag atcctgactc aaggaaaacc aaagaggaag 41460
ggaggaaaga gaatatagaa tatgtgatct tttgtatatg tgtcagtttt cttcttccta 41520
tctcattttt aggtaagcag acatttagca gagtatttag caaggatgca tacgtcatct 41580
aataaatttt ctcttttcaa aaacagtaca tcaggtaata cactaaaaga aaaacacatg 41640
tgtgtgtccg tgtctgtgtg tgtgtgtgtg tgtgtgtgtg tgtgtgaata cagaagttaa 41700
ttcccctcag gtctgctcca ttgggctgta gtttatggat aatttgttca atctttgtgt 41760
gaactgggtt ttgaaataca gttgagttgt acaaattcca gatgcccagt gcaggcccac 41820
agctatttat ttggaagtct tggatcagtt ttattttggt acatagaaaa tttcagtttt 41880
caaaaaacta aaaaactaaa taaaacaaga aaatccatat cttttgtgtt actctagtat 41940
ccactgtggt agactagtcg gtactcagca ggtatgttgg ttgaacaacc tcagattggg 42000
tcctgttcga gttgagatta cctatttata actttggagt ttgagatttg ggctaaggaa 42060
taatggaact ttgttttaaa acactaactt ttatttttca gtaatttctt tttgtttgtt 42120
tgtttgtttt ttttgagaca gggtcttgta tcccaggctg gcctaggact cactagatag 42180
caaaggctaa tcttaaagat ataatctttc ccagtaactc ttctgaagtg ctaggattac 42240
agcctgtggt aacactccta gcttatttga ataatgctta agtgtctgat ttccttagta 42300
gttggagtca ccaggatgct tctgacccca ctaatatgta ggataccctt catagtatca 42360
ctgattagtg ttattattga aaagctaagt gtttgtctta atgtgtcagt attttactat 42420
cagtgggttt tagttatttt attgtgatct ggtattaaat tttgtactct gagagattat 42480
tggaaatgag atttgtatat aaaagagtaa aggtctggct tacaattttt agtaagcatt 42540
gtgttaataa ttaaattagt atcattcagt tgtcttttac atttcctttg ttctttttct 42600
ttatttttaa catgtatgtt ttaagtaatg gtttaagatt gtatgtgatc atctgtcagg 42660
taaagataat agtaagagta gctatttatt cataggtatt tgtgaaataa aaaatacatt 42720
ctaaagccat gtatagtctt tatccaagaa attacagggt cagtgcagtt gaatttacag 42780
tgttgcatgt tgatgtcaca aattctgtga acaaatatat gcacacaaat tgcatgcatg 42840
cgtttaactt ttattaaagc tttggtctcc ttaattataa gaatgataat agtacctact 42900
tcagaattct tgaagttaac ggaaatagtg actgtaaaaa cacttagcgc agtgttttta 42960
catgatagaa aaggtggtat gatagaaagg gtggataaat attgctaata ttgatactct 43020
tccttccagt gtgaaaggta actttatgcc acatttaaac tttcttgtag atgtgctgag 43080
agacattatg acaccgccaa atttaactgc agaggtatgt ataaacataa ccacagcata 43140
ctgtataact aaagaccaat agacttgtct tttactgcct ggtgataatt atcaagatta 43200
gtgagataaa aatcttaaga atggcctttg acaattaaaa aaagtgtatt taatgttaga 43260
gttgttcttt aagacctatc tattgtcagg aaaactaaat cacagaatac ttggagaggt 43320
cccaagacta aactaggatt ggaggtgctt attgacggtg tgggacagct agcgctgctg 43380
gaaacaatca caagaagaga gcagaaccat tttaactttt ctacatcgaa gaatggcata 43440
aagttaggaa aagatgtagc attggtctgt ctgtctgtct gtctgcctgt ctgtcttctc 43500
agaatcatga agcactaagg agtaagtaag aacagtttct ggggaccgac agacctaggc 43560
tactgctcat taggaaacat gccatggttg aaggtcactt agctttaaat gtacatttta 43620
acagactctt gaatgttctt gtgtgccact ggggaaatga ggtcgggagc acagttagac 43680
agatggttaa gtaaaagctg gcctgcagcc tcttggtgaa tgtagtttgc cattgtttac 43740
cacagagctt tcctgtcatg gaaaggagta aatggatgga ttgttcttgt accattttac 43800
gatggcttgc tttaggataa gtcagagttt ttacatatta gataatatgg cagataatca 43860

```
gaacagtaat atcaccagga ttttttgttt taattttaag acaagggtct cagggtctca  43920
gtgtcccaga gtgaccctga actcaatgtt tagctgaggg tgactttgaa cttgtgatcc  43980
caattctcct gcttttactc ctcaagtatt aggattacag acttgcacca catcctcagt  44040
tgtgtgttta ctcaaggcag ggatgagccc agagctgagc atcctaagca agcactctgc  44100
gaactgagct acatcccaga gttcatacca ggatttaagg atctcaatag gatagaatca  44160
aaacagatac tagtaagata aaaaccagta gtgatagaac ggaagtcttg cttctagata  44220
atagcatctt gccttcaaaa acttaactct gactatagag aacaaagaca tcttagattc  44280
ttaattcatg tgaaaaaaat ctgaaactta atttgctata aactttactt cagttgtatg  44340
tttttctgtg agtgattaat ctcatgtata tggaaatata atgtttgtga gaccatttta  44400
aaaacaagtc actgggtaat tttattatgg gataggaaaa gtcagtcttt tccatagttg  44460
actctattag taattatact ttcttcggag catgtctggc aatgctgtag taatatctgc  44520
tattggtcct gatagaagtt actacttgac aagaggcctg ggtgacgtgc atttggattc  44580
agttgtactg ataggctatg acgtgttccc ttcatgcaca gattcatcct ccctggagtg  44640
aagagcacaa tgcttgtttc catgtctaat gaatgcattt aagaattaat aaaagacttt  44700
ctttaaaatc taggtttaat tagtaataaa ttaaaatttc ctgaaagtta ggcttctttt  44760
aagaaccagt aagtttatat ataacatttt gaaagttaac ctatgttttt aaataaaaaa  44820
tttaaaattt tcttacactg ggattatctt tttgcaacag ttgcacagta tccttttgaa  44880
gaccataacc caccacagct agaacttatc aaacccttct gtgaagatct tgaccaatgg  44940
ctaagtgaag atgacaatca tgttgcagca attcactgta aagctggaaa gggacggact  45000
ggtgtaatga tttgtgcata tttattgcat cggggcaaat ttttaaaggc acaagaggcc  45060
ctagattttt atggggaagt aaggaccaga gacaaaaagg taagctgttt actttttcct  45120
tcctccctct ttgtggacca agaatttatt gggaaacagg ttttctccct cttgctttat  45180
tgaggtataa ccaacaaagt cttaatctac ttacagtgtg atgctttgag aactgttata  45240
ttgtggttgt atccacttag tgtatccctc atccctggta tccccaccct cttccttagc  45300
tgtactgaga acatccaaga cctacctgga gtaggtgcta ggcacacagt atggattttg  45360
atgacaactt gaatgccatt acctagtaaa gcaaggtatt taatttgatg gtaaataaaa  45420
cattttctga tgggggtatt cactagtata gttaactaat caaagattca ttggttattc  45480
agaaaactaa agactgttga attagtggca tgttttgtct atggtacaat tgaaaacaaa  45540
agcaaattct tggactgctt tttcagagga ctcgtttagt tagtgtaaca ccaagattct  45600
ttgcatgttt ttctttctcc aagcacagca cctatagtac ttcagatgaa ttgaaagctc  45660
agggtagcag tgaaagtgcc ccaacataag gtcataaact cacttaacct ttgagttggt  45720
ttgcagtctt ttttgtagac attgtaagtg acaacatcag tttgcaatgc caagggttgg  45780
acatggctgc tctggggagt aagacatttg aaacttgatt ctagtattaa atttggactt  45840
gtgccccacc cccgcttctc ttctgcctcc tctcccttct gtctttctcc tcctctactc  45900
cattcttccc ccttctcctt tttttgagcc ctgattttat ctggatcaac tttgggccat  45960
gcccatcaca ctaaggtctg tggctgcagc ggtcctgggc cctgtacttc tctttcacct  46020
gctttttaaa aaccctgtcg ttataactct tttgagtttg tacaagaata tcaagactgt  46080
ttgttcattg gtgggagttc acaaaattac atctttaatg cagtaaaaaa gtcatgtgtt  46140
agaaaatcag atttaagcta gagactcctc aactctgact cccgatgaag tgttcagatg  46200
ttctgttatt cgatgtatgt ggtatataca taaccataaa ttgttgttgg tagcttccat  46260
```

ttgccttcag acaaaatata aaggaacttc taacaaatta tgtctcattt ctcccattta 46320
aaaaatcagt accccttacc tgagaacagt aggtatctaa atgggttgat tctgttcaat 46380
agtgaaattt atgataaaca agttttaaaa acaagttgaa agcttgccat tgtttgactc 46440
ttacatcatc cttgctctca gtgttatttt tattcttgtt tagtgaaaat aaattatgaa 46500
aactcttatt tcacctatga gagaaatatg gaacataata tgtttttgac caattaaagt 46560
aggctgtgtc agataaaatc tctaagacta gatacgatca tctattagtt tctttgcctt 46620
caagatcatt atctctgtgg ggcaggaaaa gattatggac cattttaatt ttcaggttaa 46680
agcattaaac tgcttgacag cacagcgttg tctggcttct agatatcagt ggacctgtgt 46740
gcagtgaaga gctttctagg tccttctgtc tgttgacaaa gcctcttgag attctcttgc 46800
ttgaaggtct tggctctctc ttgtgaattt gggtctttca cagcagtagg tttttcatga 46860
caaatcatca gcaggggaac ttttcacaac tgtagaagag agtctcctag gattaatgtg 46920
atcttgctac ccagtgcagc agtgagggcc agggcagaga tatcatccac ttttaccagt 46980
gcagggaaac cagaggagct gcagggaaag ctgctagagt gtggaggact cttagggcca 47040
gcgatgtgct cagccatttt tatttaactt ttttacatta agacttttca gttctttgag 47100
actgtaataa attatatcat gagtatgtat gtatgtgtag tacaacctgt ggatatgttt 47160
ttagggctta ccatttggat aacaaattgg catgctctct tagcatttct tagttaccag 47220
tagatctttg tctagggttg aggcttggtc agctttctcc cattctggca tgtcttttgt 47280
tctccttgct cagctcatgt ttggtagtca tgttgatgag actttatggg tgtagcttct 47340
gacattgcca gtagacaatc tcacagcaaa ctcccagatc ctctacctct tacagtctct 47400
aagccttcgt ctacaatggt ccctgagctg taggtgcagt tattgtgttg tagatggctc 47460
agttggaact gagttccaca actctgtgtt ttgaactgtt gtggttttct gcaatgtttt 47520
ccttatgcta caaagagaaa tttccttgat gagggataag cactatgctt atctattggt 47580
ataaatttag agcatagtta tggactatat atattattta gtaaattagt ggttgtaggt 47640
tctctgtcaa gaagcatgac ttccctagcc caaggtagtt ggctaggttt ccaataccag 47700
gcagtttctc tgtctttaag gggatttaaa atttttattt gtttatctgt ccatccatct 47760
gtccatctgt ctgaaatcta tctatccgtc cacccattta ggtgaggcct gagagacaga 47820
gtcaaggaaa tgtcaccatc tttaaaaaaa aaaattaaga aggacccttt ctttaaaaga 47880
ccttaaatta tttgctgatt atttattcat ttgtttttat tgccatgcat aattttgatg 47940
gaaactttga actgattaca ctaagagctt aattactagt aagtggtact cctgatactt 48000
ctatggcctg tcttgtattt tgagagagca atgtttgctt tggagaaatg gatgagaata 48060
tttgaagtcc tgcgactctc tcagccattt cctgccagga atctcagcta cttgacattt 48120
ttttctgttt ctgtttgttt gtttattgtt gttttgatgt tttcattttt ctctctttct 48180
ctcattcccc ttttgtaatg gtaaggattg agcctagggc cttgtacatg gacacatatt 48240
ctaccagtaa gctatatccc tcagcccttg tttgactcat tcatcatgtt aaactacatg 48300
accttttgtt ttgctttgtt tctgtttgtt tgctagttca gacaaggatt ttcacttgag 48360
acaaataatg gttgtgaaat ggtttaggct tctctaagct ctgctgtcaa tctccattct 48420
ttttccttca cttcttcaga attgccagcg tgtgtataga gtgataagat gctggggtgg 48480
tctgtttcct tatgttcaag ggtaagagca agacttgggc acttgaactt tcctgtaaat 48540
ttctctgttt ccaggccagg gtaaatgcag gaatccaggt tagacgcagg agtcaagtta 48600
ggtgcaggag acccatgtca gaaactgagg tcttgacaca ctagtcatta cagcctggtg 48660
gcaacagttc tgtttccctc tagaagggag gggagggtgt ttgtggaagt gacaagaagt 48720
cttgggaaat gttacaaggt agggggtatt tgtgagtgaa atgtgaagcc tctagtgtca 48780
tttggtaaaa tgtaataata atacttgtgt cctccataga acttttcttg gcactctcca 48840
tctcttgacc atttcttcca tgtgaaaatg atagactaat ggacatagaa gatgcagggc 48900
tgtgcacatt gttagagctg tagctggtgc atttgatgtt tagccattgc attatactaa 48960
gactccttaa gtaatttagc atcttacagc cacatcagta ggatctactg tacctgttgc 49020
atagttaata tacctagaca agtgttttgg ataagtttat acacggacct aaagcagaat 49080
ccttatgtgt atcctacctt tattctttcg attatttaaa aaacaagaaa gaacttatga 49140
acagatactg ttgaccaagc tgtgttttac taatggttgc ttttgcattt taagctacaa 49200
tagtattaga aacctacatc cagataaaag ctttcagata tccctactcc aggaatgctt 49260
ctttacagat gacatcaagg cccagaaaag tgaactgtag tgatcagaat tcgtgacggt 49320
gtcaatcagt tcatgacagc atttacagta aaaacaagtc ccttggtgtg ttgttaaatt 49380
tctttgtata ttatcaagct tacagattct gaactgcaaa aggttccata tttattgctg 49440
atggttttga aaggcttctc agttttatgc ttttctttac aaatcgtagt gtttaataac 49500
cctccaggtt aaaatcttgg agtgtttaac ctccagtcta agtttaaaat ctccagagag 49560
agattgctag ttttgtaact ataatgctgt gcatttcctt aaaattttta caatttaatt 49620
ttctcaaagc ttttaaatgt aaagaaaaat aaaatcatgg catttatagg aagagaatgg 49680
aactagaagt cattacttta agtaaaacaa atctgatcag aaaaacgtgt tttctctcat 49740
gggaagaacc tagcttggag gtatgcatac cctttggggg agggagatct gaagggaaga 49800
tggtgaaagg aagagtggaa cctgctccac acagaaatgc agaagaggaa ctgtttaggg 49860
agggaggtga ctcagaagga agtacaacgg tacctctatg aggaaatgtc atagtgaaat 49920
gcgctagtaa caaagaaaaa taataaaaca aaccttaaaa ggcaccgggc cttgggctgg 49980
tagagtggct gtggaatgat ggatgtgttt tagcttgctg agtataggaa agctgcttta 50040
gtacagctga ggaagtcttc ctagaagaat cttagagaat tgatgactca gtgtggcagt 50100
gtagacacac agtggacttg cagacttgta gactagctag gagtccctgt ggctacgttc 50160
gtgctgcttg ttgtgtttgc tgtttctgga tttatacttt gtgattgtaa atgtgaactt 50220
ctggagatta atacttaaat ctgctttgta gttaatcata ttagaattgt ctgtattatt 50280
ttgtttatat ttgtaatttt aactatggag ggaccataag aagctgaaga aatttgtgtt 50340
ctggtacaga atcctcatct tctttctttt atgttaaagg aggaggcaat tggcctgttg 50400
tgaaaaaatt gtagactttg cctaaaatgt gtgttttttt ttttttggct tttacttata 50460
gtactttctt tctcagagtc ctgtagttag gtcttgatat gatgcaggtt ggatttgcaa 50520
gctgaccata aaatgtagca ttgtgttctt aatgctggaa caatacttca ggttttgaat 50580
attgcaatga agttcaacag ttgctacttc ctataaagaa aaaatatctc aagggcgaag 50640
taactgctca agggaacaaa gacccatacc cttattcagt caaagaagtg tgttgcccac 50700
tttactggga attatttact tgtatagttg atattttcct ttgtgaaaag gtggcaaatt 50760
atccaaatcc aaagtcactg agggtgaatc ccgactgact gcacatgcgc gcgcgcgcac 50820
acacacacac acacacacac acacacacac accccgcgcc agcccctcct gctgtaaatt 50880
accttctggg gttggtttcc acgtgtgcct tgctgtttgc aaatgcactt agggttcagt 50940
gctgcaatac atggtttgcg ggatgtaaac tatgaggaga gtgtaagaaa gaccttttca 51000
gaatggcaat gagcgcaggt tttggagtaa ctttccaaac ttgagggaag acactgccac 51060
taaccatacg tagtgtctgt tctccctggc ctccagcagt ggcaaggaaa gtaaccttaa 51120
tgcttagttc tcttattaaa cttaggggag ggattgaaac gtttcagttt gccttttctt 51180
tgcttacaag ttggttatta ggtaggtgtg tgtgttttga ctacgtgagt gtgtgtgaga 51240
gagaatgtgt gtgtgtgatt agtttactac ctcagtttgt caactttact aaaataacaa 51300
tgccaagctt aattttaaga gatttcatta ttttctgtga gaagtgaact tttataacct 51360
actatcaagg ttatccccct acccctgttt tacttattaa atcccctcat cataaaattt 51420
tcttgcttag tccttatttt taaatcaaac aagttgtggt tgctgttgct aaaacaaaaa 51480
actcagtata attttcttgt aatgtcaatt atcatgtgtt ctcttctgat gcatactgtt 51540
tgggctatta tctactatct agcagtccac tgattcataa agctgtgcag ttttaggctt 51600
tgaaagattt aagcagttac ttaatacaaa cccatttgca aagaccacac tgccctgatt 51660
catagtcttt ctttgtcata ctcaacacct ggcttcctaa ttttgttcct tggattctct 51720
ctgctgtact aagctctact taatttttc cttttctttt tgattcctaa aatagaaacc 51780
aacaccaaaa aaaaaaaaaa aaagagagag agagagagag aaaaattgct gttttgaatg 51840
tgtgagtttt tcagttttag gtaagagaaa cccaagtagg agaaggagac agagaagaca 51900
caagggagat gtttattgac taatagaacc taaaaggtca ggtctggatc taaatgctca 51960
ataagtgtca ggaacctctc ctttctacac tcttcccttt tctttcttgg ctatgtttat 52020
tcagaaagga tctttgcaag taataccaag ctatggtccc gtagctttag gcttacactc 52080
ttgactaact gcagtggtaa aagaacaccc atttgactag aggttcctag aataggttct 52140
gatttccctg gcttaaaggg tgtgtctttt tatttttta ttttttgta agatttgttt 52200
atgtatatga gtatactgtc actgtcttca aacacaccag aagagggcat cagaccccat 52260
tacagatggt tataagacac catgtggttg ctgggaattg agctcttaac cactgagcca 52320
tttctccagc ccacatctac ctcttttttg aaacaaatac ttttgctagt gagtggaatc 52380
ctcttacaaa ttcatatatc tgaattgaag aataggccca acaccccaaa ccacaaaact 52440
gtcattatag cttctaaaga aaatccaggt gaggaaagag tgttggccag aaatgatctg 52500
tgtcactttt gtcacagaga ttctgtaagt taccatagaa ctcgaagcat tatgtattcc 52560
aaacttcaga ggttcttcat aaaggggaaa aactgaatta agagaagtta tggcttcatt 52620
cagatcgcat agcattcctg ttttcaggtc acctgagtca gattcattta ggtcctgtac 52680
tgcatttgag caagataaac atgtatagtc ctacttgttt cttattaaag tagaggcagc 52740
agggctggcc tcagtgtgcg tgggacccag cagttggcag gtagagttag gaggatcaag 52800
agtcaaagcc accatcagat cctgcagtgt gtttgaggcc agctctcccc tggggggaaa 52860
ttgaggttgt aatggttggc tgtggtgtca cagaggccta taatctccac tgttggagcc 52920
tgaagcaata gaatacctat tttgagacca ttctggggta cataatgaga ccctgtctta 52980
aaacataaga tatgtgataa tatatacctt gtaattttat gggaataata gaaatatgtt 53040
ttgaatatta gaaaatatct acaataacta ctattgtcat agtattagta accacattct 53100
tttgtttatt gaattactgc cttgtttatt gtggtcattc agaatgtagg tttttcctct 53160
tcaagcaaat actttttagg ttgaaacttt tatttatgag tttagacttg gaaaatattt 53220
tccagtttat taagaaagtt tgctcaaata gaaaattact tctttaagga ctctaagttg 53280
tgaatttacc ttctagaaga tcatctagaa tctgaatgca tagaggatga acatacatta 53340

-continued

```
tatatacata tatatataca cacacacact gtgttgttcc gtgctaatcc cgtatagtag  53400
tcttatgaca gtagtataga tctcaaagat gtatgtcctc catataagtc tgtttttcaa  53460
agagccagcc aggcatggtg gaacacacct taaatcccga gcacttggga agtatgagtt  53520
tcaagacaca aagaaactct tatcttgaaa accaaaaaga gaaaaagtaa ttagcatcaa  53580
gtagccaagg cttataaaag aagaattaat gaaaaataca ctaggaaaat gtaaaattcc  53640
aaggcaggct tttcttatcg gaatagcatt ataataaaaa ccataaaact gatcaaagat  53700
gtcattttac actcacacag gagacacttc atacggacac tgagctgtta cgaacgtctg  53760
tgccaaaagg agtcaacttt gttaagcaaa tgctagagaa ggaaaataaa aagctagact  53820
cggaggaggc gcaaagtaaa tatgtgcaca ctgaagacag tgatagagtc ggcacctgag  53880
tgctttgcag tgcccacttg cttaggttaa taactcacca gattaactac aaatcccaca  53940
agcttggaaa gtagagccct gttacctgtc ttgacagttg agtggaacta tagtttgaag  54000
tttaattcag gtcattatgg aaatttaaag ccattttctt caataatttt tgagccattt  54060
gaagaaagat acattgatta ttcaccagta gaaaatgaaa caaaaatata aaggagtgaa  54120
ctgaggaaat gctgaactat ttgggctagc aaatcgaaca ttgactacaa gaaagagaac  54180
tggtgttttt tttaatagtg tttagggtta aatctgggtt tttgtaactg tctcaaagat  54240
gaataatgta gcacatgttt gtgtttagct aggcagttaa gtcctagggg tgtacgatgc  54300
tctggcctcg ccttgctgcc taggccttag tatggtgcaa gcttccctct gtatcaccac  54360
tgcctgtgag ctctgtgagc tctattcaca caactgctgt tgatctgaga attgtttact  54420
tacatatcaa cccagctttt ttcaaaagga tgagcatata aatgcttgtg ataataggtg  54480
tccttcccat cacttgagaa tctgtttatt gctgtacaca agtgtgaaat gtgtaccaaa  54540
agctagagag caggagaaat gccatctgaa cattatcagc tactatattt ttttgtttat  54600
tttaacttct tttatataac tgaatttgct ggtttatcct catgtaaatt ctattaagga  54660
ggtttgtatt attgtattaa tttttttaaa gaagcaaatt ggaagtttat attttctcag  54720
aattcaaata taagctttga ctatttagta tgtgattttt cactctagcc aaagtcttaa  54780
attgccaatc atgatttcaa gtggtttata tccatttttg tttgtttgtt tttgtttttg  54840
agacggggtc tctctttgta gccctgttgg cttggaatgc acagagatcc accagcttct  54900
ttcttcctcc tgaattctgg aattaaagtt gtatactgcc acttatccat tttgatacac  54960
atatggagca gagaaacaga gaaagacaga gagaggggaa gagggtgggg tcagagttca  55020
tatacctgta tttgctagac atcgtattcc ttctatactt cttagcttgt atgctgtctt  55080
cttccccagc agaagggtgt ctgtgtctag agtccttatc acagtagaag ttgagaggcc  55140
atcagtaaac taaagagcat tgtaatacct ttttcttatt aacataaaat acctattttc  55200
tgcaattctg tttgttgaga ctgggcctca cataggtcaa gctggcctta aacttacgat  55260
tttggttgta cccaagtacc gagattacaa gagggtactg ccatgccaaa actgctgttt  55320
actttaaact gttagattaa atgcttatta tttgccttat attgactttt ttactgttat  55380
attgtgaata gaaaaatatt aactcattag tgaatgaatt gttacacata tggtatgtat  55440
gtctttgtgt gtgtgtgtct atatgtatat atgtatgtgt ctgtatgttc cttggatgtc  55500
catcctctgg tgccatctat cttgttcaga cagggtctct aattggtctg gaattcacca  55560
agtaggctag gccagcctgt gaatcccaag aatctgcctg tctctgctcc cccatgccga  55620
agttttaggc atatatatgg ttacgtggta ccttaaaaaa tgtatatagg catgggctag  55680
gttggctgaa gtgatagctg gtttaaagca ctgttgttct tgcagaggac ccaggttaac  55740
```

```
tcccagtacc cacacaatgg cttacaaaca tctgtaactc cagtttcatg gcatgccttc  55800
tggtttctgt gggcaccagg tatacatatg gcaaaacact cacaaaatat ttcaagaact  55860
aagaaaaaaa catatgcatg ggttttgggt catacatgcg attgattgat tgattgactg  55920
gtttccggct ggcctggaac tatataaacc ctgggctggt tcggaacagt cctctgcttc  55980
atccccttta gtggtaggat tacaggtgtg ggacaccatt cctggttagg gtcccctttt  56040
aaatgtcata tgaattatgt cttttaaata tttgtaatat tttctaagcc attttatgct  56100
tccctaatgt ctgcaaggag tggatatagc acaaggatac cgatacccct tactgcctct  56160
gttaacaagt tgtattgaat atgtttatca ttcagctgca tactctctct tttccttttt  56220
tttttggact ctaaggtcag aatctcattt ttcctgcaca gaggcaacac gtttctctag  56280
tgtactgatt ctgatatgat tttgcttaga aagtatgtaa acaggtttgt gaagacttgc  56340
ctagtaaacc catctttgag aggagacttg ggtatgtgta gctgcagtac agagaccatt  56400
gactgtctgt ttgaatacac agtggccttt gcttattggg ttcatagatc agagcattat  56460
ttaatatttg aataaatgag gtatttaata actacatttt aagaatattc ttttgttatt  56520
gctcttattt attctaatac tgagttagat ttgattgtta gccacttaaa ggagaaactt  56580
tgggataacc cagttatagc aattttgtat aataacttta atgaaacttt cctttttgaat  56640
ttgacttctc tttttctttt gtctccctcc tccctctgcc ccctgggcct atcagggagt  56700
cacaattccc agtcagaggc gctatgtata ttattatagc tacctgctaa aaaatcacct  56760
ggattacaga cccgtggcac tgctgtttca caagatgatg tttgaaacta ttccaatgtt  56820
cagtggcgga acttgcagta agtgctctaa attcttagct gtctgtgtgt cggaaaactt  56880
tttaaaacca tatctaaatg tatatgtaaa tgtttagaaa tacatttacc aggttaaaag  56940
gagtatattt ctgaagttgg aattaattag ttcagttgtt caactcactg ggttaagaaa  57000
gctaacccaa tgaattttgg tgttcttttt ttgtttgttt gtttttatgt ttttcgagac  57060
agggtttctc tgtatcgccc tggctgtcct ggaactcact ttgtagacca ggctgtccct  57120
gaactcagaa atctgcctgc ctctgcctcc caagtgctgg gattaaaggt gtgagccacc  57180
acacctggca attttggtgt tcttcaagtc aattatattt atgggagaaa tattctatgt  57240
tataaccacc agatgcagtc tctgttctga caaaataacc gagagactct tgacagatca  57300
gtgtgagaat ctgagagaca ctcttgacag atcagtgtga gaatggcctc tggctacaac  57360
caggtcctca tcagagggaa acatgttcac tgtcagagac agaaagagag gagcccttca  57420
aatatagaga ataaaagggt gtgtgaattg ggatgtgtgg agaaaaccta agtgtagctt  57480
tgaagtcaag ctctcagcct gtggcttgga cttgtcatct cctcactgag tttgcttgtt  57540
agtaaaataa agaaatcttg gtaagtatga cgtcatgaca tcagtgtgtg cttgtagtaa  57600
tttctcttac cttagtgaca cctgggagtg gtcagtcatg ttttacactt aagatatttt  57660
atttgtattt tcaatataac gtcatagtat cagatgtcac ttattagaat cccttgatat  57720
tattttatgg atgtttgcag tttgtcagtg attttagttt ttcgcctcca tgaaatactt  57780
cattaaatta acttgttctt tctaaaataa tttttatgta gagaatcagt ttcttcgtca  57840
gataggtgtg attgcccatg agtatggcaa ctttgttaag ggcccctaat ttatttatat  57900
agcttgttgg aaagttctaa ggaacttcca tactgattaa gtatattagt ataattttaa  57960
aagtgtgagt acaaggcaca atggactatt gaaagcaatt gacctaggaa cttcactagg  58020
ttcattgaga aggaaagggg ataggaactc atgttcttcc tatagtttag gcatcaatat  58080
```

agagctgtaa aggcggtatg gaggcaatac ggaaaagctc tgctcaggaa tctcactagg 58140
tactgacttt ttgtcagctc tactttgctt attgattaaa ctgctgttgg gcttttagtc 58200
ggacaacatt atgtttgcat ctctacgctt aaaaaatatt gactactaaa ttctttttaa 58260
tctttaaaaa tttctagtta cttatttatg tgctgggatt taacactata tgttgaagtt 58320
atattaaaat aaagctcatg agattcatat gtataaatta taactgccat gttcacaaaa 58380
ggttttggaa acaatttcat gaagaaagtc ggtcactgga gaacacatgc agtttggatt 58440
ggcattgagt gtgaaggaaa tattacaggc agtagaaata aggtgaccga aacacagcag 58500
aagaactgga cgagaaatag aagatgtgat tggctgtcac aggatcttga atgggatgta 58560
atagacttgg actattggtg tcacgataat tctaggaact tcagctgtgt tttaaggaca 58620
ggcccatgtt gtatagacag ttgtgatgta ggaggggtag tacagccagc tctgtgactt 58680
ggcagatgtt gctagagcga tggaatgtac tttgtttgga ttttctttag ttgttcatac 58740
ccagagtgca tttgagattt ggagatataa atattatcac tttgctttta agttatttta 58800
aatctgatga gatcaaggta cttgtgagga tctgcagtgg ggctgcagct ctgtcttggt 58860
ggtgtagtgt ttttctcaag ctagagtgca ggattgcctt cagtctccag cccgaggagg 58920
aggaggcatg agtgaaacag acagaactag tgataaaagg tttagtgtct tctgcagagg 58980
gaccaggaag tgtttgccaa gcgtttgtct tattacctta ctttttctac gtgaagagaa 59040
gttgctgtat aataaaaatg atcagtttgc ttttgtgtca ggatgcactc tcatccttgt 59100
ttttgtcaag tccagatcct gtcatttctt cagaacatag ttaattaaca tagcatatat 59160
ttcagatgtg catctcagaa gtcaagagga ctgtactaat attagaatat tgatgttaga 59220
acttccatcc ctcctgctgg gcgtggtggc acacaccttt aatcccagca cttgggagac 59280
agaggcaggc ggatttctga gttcgaggcc agtctggtct acaaagtgag ttccaggaca 59340
gccagagcta tacagagaaa tcctgtctcg aaagaccacc aaaaacaaaa acaaaaaaga 59400
aacaaacaca caaacaaaaa aaacaatttc caactcaatg ggaaactcat ggtctatagg 59460
aggtcgtttt gtctcagtgg tcttagaaaa agctgctgtt ttttcattac tgtacactac 59520
agctggggac attgtcaagg aaagatgcca tgacaaggca attcttataa aagagttaat 59580
tgggacttgc ttacactttc agaggatttg tccattatca acctatcagg aagcatggtg 59640
gcacacaggc agatacgctg agagttctac atccagaggc tggcagcctc tacctcctga 59700
gtgccagcac ttttaaaagc acgggctacc atcacccagc tatacatgtt ttttattttt 59760
ttaaacatat tatttttatt aattccttga gaatttcaga taagcattca gtgtatcttg 59820
atgtaactca tttcctactt ctcccaacag ccttgtctag ttccaggaca gccagggcta 59880
actaaacaaa gaaactctgt cttaaaatgc caaaaccaac aaacaaaaac ttgtgaactg 59940
gaggtcaaaa gaaagatgat cagtattgta tatttctata ttataaaggc ttaggtttac 60000
atcgtttatt aaaatattct tgtaaagttg cctctatgca gttcacaaaa gtcccaggaa 60060
attgttaaag ttattttatg cttaaagtag tttgtgatgt gtcttttgca tgttaatgta 60120
aagctttaat tgttaatatg ctgctagagt ctagtcttag aacttactgt ttgtgaagta 60180
gcaattgatt atcatatctg taatagaact ttacttaagg attcagattg aagaagtcct 60240
tacatgggtt ggttatgttt ttacatattt tatttctact gatttgtttt agataagcag 60300
tcaatatgaa gagttatcat tttgtgtata tttctgttta ttttatcatt aaagtagttt 60360
ttgataagtt gaagacattt cttgtgaaat gatcctatat gtatttaacc acacagatcc 60420
tcagtttgtg gtctgccagc taaaggtgaa gatatattcc tccaattcag gacccacgcg 60480
gcgggaggac aagttcatgt actttgagtt ccctcagcca ttgcctgtgt gtggtgatat 60540
caaagtagag ttcttccaca aacagaacaa gatgctcaaa aaggtttgca attcagttct 60600
attgtgtaga aatagccatt cctcaatgag taaccacaga ccttttgctt aaagcctttg 60660
gttaggaaat tattctgtaa ggagagacta tttctctgcc atctaccaaa ctgattactc 60720
ttttgttaga ttggcagact cttcatttct gtggcattga tgagacatgt aagcagactc 60780
acctgccccg acccttagtt tgttggcttt tttggtttgt tctatgttct tatgttgcac 60840
aagccatgtt ttacccattt gggtttatgt ttcttgagag tagactattt tatattttgt 60900
ttccccaggt tactgagtat ttagtcagta ctgagtattt agtcagtact gagtatttag 60960
tcagtattac ttagttgaaa gaagtggttg tgaagaagta atagtaatta aaaaaaaaaa 61020
aaaaaacata ccaaaaaaca aaagggtgga aacagctaag catatcctct gtccagggtt 61080
gctggggctt gagatacact tgggaggagg agagagctca ggtgcagtgt ccttggtgtg 61140
aacatttatc cttggtggct ttagtaccct tagttgaatg tgaacattaa aatgagtctt 61200
aaggtgtaga agttttagct ggatcagaag aagataccag ttttgtgcag aatcaattcc 61260
cgtgaagcac atagagcagt acatagtccg gaagggggtt ttataaaaag cagtaaaagg 61320
agagcttact tactataaaa ccttgcaatg tcagatcaat ttatcaggag agataatttc 61380
ttttttctag gatctacata gctaaagaag aaaaaaaatc acaaagttaa ccaaattaat 61440
gtttttatca tggacctctc atgaaacaaa aaagctaaat ataaatatct ttgagttact 61500
ggtttttttg tttattttct gagaccacaa taaatgtgag caaacatttc aaaaattagg 61560
tatttggaag gctttagttt ttttccctct tacttcattt gtttgtttgt ttgtttgttt 61620
gtttgagaga catggtctct ctgtctagct ctagctgtct cgaacttgtt ttgtagacaa 61680
ggctagtctc aaactcagag atcgattgcc tctgcatcct aaatgctggg attaaaggcc 61740
tgtgccatcc ctgcccgcta tctcttacat cttgtaagac tctgattcac ataagagtgt 61800
gtgtgtgctc acacttgtgt gtgtgcgtgc gctcacacat gcatatgttt ttctttcctt 61860
gtttgtttga agacagattc ttactctgta gctcaagctg gtctggaact cactaagtag 61920
ctcaggttgg cttcatataa aacagtcttt ttgctttaaa ttcccaagac aggagccgcc 61980
tctcttggct ttatattgct tgtaaaaaga gataattacc tcactgtctc cttgtagttt 62040
tagagatgtg ctgtttctta ctccagatct ctgaagattg gatatttata atatatttgt 62100
atattttaga ttactttcca taaatttcca tttatcatag gttttcctta ctaattatat 62160
gcctgttctg atttaaataa aaacagtttt agaaaatcag tgcacatcag tgagctacat 62220
ttgcaagttt aaataatatt accgtgtttt cttctaagta aaatatgatt gccaactgaa 62280
caactttgtt aaaataattg agatcaataa ggtttgaaaa gggctggaaa cacgactcag 62340
cagttaggag ggagcgctgg atgttctgga ggacacaggc ttggtcctca gcacccatct 62400
gttgtcttac agttgtctgt aataccagac ctgggggga atctgagtcc tacctcgggc 62460
ctccatggac actggacaga tacaggggcc agaaatgtag ttgccatagg gatcaactta 62520
ctagggcttc tgttgaagta gcaacacctg atctttgttt atatttacat atgcataaac 62580
tcagaatatt tttaaaatcc agtattagaa taagaagtag ttttcttagg attttaagat 62640
aaaagtaaga taccagattt tacatgatta tattttttat ttgaaatttt agaaaagata 62700
acttagtgaa taagaatatt ccacaaggtg tttgccttca cttaagaata tcaaataata 62760
tatggtttat atgttgacta tttgtggtac atttttaaat aagtgaaata catcttccat 62820
ttcttttctg tttaggacaa aatgtttcac ttttgggtaa atacgttctt cataccagga 62880
ccagaggaaa cctcagaaaa agtggaaaat ggaagtcttt gtgatcagga aatcgatagc 62940
atttgcagta tagagcgtgc agataatgac aaggagtatc ttgtactcac cctaacaaaa 63000
aacgatcttg acaaagcaaa caaagacaag gccaaccgat acttctctcc aaattttaag 63060
gtcagttaaa accatttggg ggtgggaggg tgtgttttat tctgattgtg aagctaagag 63120
ctagacattg ttctagtatt gttcaatatg taacattccc gagtggttgc gtagcctttc 63180
cttttctgtt tattactcca cttgctctcc ttatttcttc tcctccccc tccccatctt 63240
gagtctttcc tctttccttt ttccttttta aattcttttt tcattccatt gtatttgttt 63300
cattcacatg taacaaactc aaccatagat tattatatta ttattataac ataataatac 63360
tcctaatatt taaaatagaa aatgaccttc acacatgtta agtgaacata gacctaatat 63420
tcagtgcctt tggatctcaa gtatgtttta agtttccttt agaatcttca acttttcatt 63480
ttttcctttt ctctaaattt acatttctat caaccacctg cttcctgatt tttattttag 63540
ataggatctt ggtatatagg ctcaggctgg ccttgaactg gcatgtctct gcctcagcct 63600
cacctggcaa ccatttgctt ttaaaatgta tttctctcta gttttactgt tttaatattt 63660
ttctggcaat gtgcctcaat gcttgtctaa catgagaaat gccttgagtt gaacaccaag 63720
tcctacaaaa caaccagtaa aaaaataaag cataaaatag ttcgtgtaga taaaagctgt 63780
tttcattgtc actgtaaggt aagtcctatg aagcatgcag ctggcaaaga aagtctggtc 63840
aagtggatgg tctgtaaaga gggttgtctg cgtgaaatgg gtgcatttaa ttatgcaaat 63900
tgtatgcgac ctacagaaca gttatgtggg ggaaggagga agagtagaaa tgagaatctg 63960
aggcatgaat gagcttggta tattcagtgg ctgaagtcat ttccactgag tcacaggaac 64020
ccagtcttga tgtagcagtg tggagtgctg aacacagaga aggtataatc tgagcttttt 64080
aaccttccag ttcacttcct aaattgagac tggctcagaa actagggaga ggagaggccg 64140
tggggctgta gtggcaagga gcagtggtaa attactaact ttgaaggggg atttttaaag 64200
caaatgttgg ttataagaaa aacttataat gacttgcata atgggaaaag agcaaagata 64260
tgatttaaac ctggtctctg ccaattgttc actagagatt gtcctttagc atgtggccta 64320
gacttcaggg tttttgtttc ttacctttta aaatggaaat aacctaagaa ctgcagccat 64380
gcatgtaaag gctactgatc aatcctcaca gcacagagtg ctctgttagc ttgcaccatt 64440
ctctcgtcag atgactgttg tagagctagt tgaccttatt aatcagtatt gtgtagtgtc 64500
actaatgtaa acatagagtt gtctcagaga ttgcaagaga aatgtttttg aaacataagc 64560
acttgtaaat tgaattttgt gatttagtga gttcattgcc ttcagtttgc acttttatag 64620
aattatacag tgcttatggc tgatgtattt taaaaatagc tttcaactca tcattgtgtc 64680
ttttgagagc acagtagtca atcttcaggt catctgaaaa gcagtgccct tcagaattca 64740
ttttgttata gtactttcaa gtaaatctgc aaaacagaat gtctttgcta atacagaact 64800
cattctaatt gttcattttc atcttaaact ttctttctct aggtgaaact atactttaca 64860
aaaacagtag aggagccatc aaatccagag gctagcagtt caacttctgt gactccagat 64920
gttagtgaca atgaacctga tcattataga tattctgaca ccactgactc tgatccagag 64980
aatgaacctt ttgatgaaga tcagcattca caaattacaa aagtctgatt tttttttct 65040
tatcaagagg gataaaatac catgaaaaaa aaaaaacttg aataaactga aatggacctt 65100
ttttttttt ttttttttt aaatggcaat aggacattgt gtcagattgc agttatagga 65160
acaattctct tctcctgacc aatcttgttt taccctatac atccacaggg ttttgacact 65220

```
tgttgtccag ttaaaaaaag gttgtgtagc tgtgtcatgt atataccttt ttgtgtcaaa  65280
aggacattta aaattcaatt aggataaata aaagatggca ctttcccatt ttattccagt  65340
tttataaaaa gtggagacag gctgatgtgt atacgcagga gtttttcctt tattttctgt  65400
caccagctga agtggctgaa gagctctgat tcccgggttc acgtcctacc cctttgcact  65460
tgtggcaaca gataagtttg cagttggcta aggaagtttc tgcagggttt tgttagattc  65520
taatgcatgc acttgggttg ggaatggagg gaatgctcag aaaggaatgt ttctacctgg  65580
gctctggacc atacaccatc tccagctcct tagatgcacc tttctttagc atgctccact  65640
tactaatctg gacatccgag agattggctg ctgtcctgct gtttgtttgt gcattttaaa  65700
gagcatattg gtgctagaca aggcagctag agtgagtata tttgtagtgg ggtacaggaa  65760
tgaaccatct acagcatctt aagaatccac aaaggaaggg atataaaaaa agtggtcata  65820
gatagataaa agacacagca gcaatgactt aaccatacaa atgtggaggc tttcaacaaa  65880
ggatgggctg gaaacagaaa atttgacaat gatttattca gtatgctttc tcagttgtaa  65940
tgactgctcc atctcctatg taatcaaggc cagtgctaag agtcagatgc tattagtccc  66000
tacatcagtc aacaccttac ctttattttt attaattttc aatcatatac ctactgtgga  66060
tgcttcatgt gctggctgcc agtttgtttt tctccttaaa tattttataa ttcttcacag  66120
gaaatttcaa cttgagattc aacagtaagc aggttttgtt tttttttttt cctagagatt  66180
gatgatgcgc gtcctcagtc cagtggctgt cagacgttca gccccttga ccttacacat  66240
tctattacaa tgagttttgc agttttgcac attttttta aatgtcatta actgttaggg  66300
aattttactt gaatactgaa tacatataat gtgtatatta aaaaagtcat tgtttgtgtt  66360
aaaaaagaaa ttagagttgc agtaaattta cagcactgca cgaataataa ggcattgaag  66420
tttttcagta gaaattgtcc tacagatgct ttatcgactt gctattggaa gaatagatct  66480
tcttaaatgt gcagtgttga gtcacttcgt tatagtggta gagttgggat tagggcttca  66540
attttacttc ttaaatatca ttctatgttt gatatgccca gactgcatac aatttaaagc  66600
aagagtacaa ctactatcgt aatggtaatg tgaagatgct attacaaagg atctcctccc  66660
aacccctcgg gaatttggtg tctttcaaat tatatcttga ccttgacatt tgaatatcca  66720
gccattatta gatttcttaa tggtgtgaag tcccattttc aataacttat tggtgctgaa  66780
attgttcact agctgtggtc tgacctagtt aatttacaag tacagattgc ataggaccca  66840
ctagagaagc atttatagtt tgatggtaag tagattaggc agaacgccat ctaaaatatt  66900
cttagaaaat aatgttgatg tattttccat acctcatcag tttcactcaa ccaataaagt  66960
ttttaaaatt gtaacaaagc tcttaggatt tacacattta tatttaaaca ttgatacatg  67020
aatattgact gactgttgat aaagtcagag acaacttttc ctgagatctc accatggaaa  67080
tctgtacacc cccttgtctt tcctaaaagc tgaaagtggc tgactaaaat gcaaagcagc  67140
tgttgatgtt ttgaagatag tgataaacac tgttctttgt tagttttggg cacagcatgc  67200
taaactataa cttgtattgt tccaatatgt aacacagagg gccaggtcat gaataatgac  67260
attacaatgg gctgttgcac tgttaatatt tttcctttgg aatgtgaagg tctgaatgag  67320
ggttttgatt ttgaatgttt cagtgttttt gagaagcctt gcttacattt tatggtgtag  67380
tcattggaaa tggaaaaatg gcattatata tatattatat atatataaat atatatatta  67440
tacatactct ccttacttta tttcagttac catccccata gaatttgaca agaattgcta  67500
tgactgaaag ggttttgagt cctaattcaa actttcttta tgacagtatt cacgattagc  67560
```

ctgaagtgca ttctgtaggt gatctctccc gtgtttctgg aatgctttct tagactcttg 67620
gatgtgcagc agcttatgtg tctgaaatga cttgaaggca tcacctttaa gaaggcttac 67680
agttgggccc cgtacatccc aagtcctctg taattcctct tggacatttt tgccataatt 67740
gtaaaagggt agttgaatta aatagcgtca ccattctttg ctgtggcaca ggttataaac 67800
ttaagtggag tttaccggca gcatcaaatg tttcagcttt aaaaataaaa gtaggttaca 67860
agttacatgt ttagttttag aaaatttgtg caatatgttc ataacgatgg ctgtggttgc 67920
cacaaagtgc ctcgtttacc tttaaatact gttaatgtgt cgtgcatgca gacggaaggg 67980
gtggatctgt gcactaaacg gggggctttt actctagtat tcggcagagt tgccttctac 68040
ctgccagctc aaaagttcga tctgttttca tatagaatat atatactaaa accatccagt 68100
ctgtaaaaca gccttacccc gattcagcct cttcagatac tcttgtgctg tgcagcagtg 68160
gctctgtgtg taaatgctat gcactgagga tacacaaata tgacgtgtac aggataatgc 68220
ctcataccaa tcagatgtcc atttgttact gtgtttgtta acaacccttt atctcttagt 68280
gttataaact ccacttaaaa ctgattaaag tctcattctt gtcattgtgt gggtgtttta 68340
ttaaatgaga gtatttataa ttcaaattgc ttaaatccat taaaatgttc agtaatgggc 68400
agccacatat gattacaaag ttcctgtgca tttttctatt tttccccctc cttgctatcc 68460
ttccaagcaa agcatctttc tgtcatcttg gtagacacat acctgtctac tcatggttaa 68520
gaagagcact ttaagcctta gtcatcactt aataagttat tccaggcaca gtaaaaagtt 68580
caaggttctt ggaaaacggt gcttatttct cttcttataa gccagatgtc tgaagatagc 68640
cctaacccca agaacgggct tgatgtctca ggtctgttct gtggctttct gttttttta 68700
acactgcagt tggccatcag cacatgggag gtttcatcgg gacttgtcca gagtagtagg 68760
ctcaaatata ctatctcctt tctaatattc ttaaaggcta aggagtcctt tcaatataac 68820
agtaagataa cttgtgatgt tttagaagta agcagaccat taatgtcaat gtggagtctt 68880
aatgttacat gaagttgata gtttctctgt gacccattta aaaatacaaa ccgagtagca 68940
tgcaattatg taaagaaata tgaagattat atgtagtcac acattttctt tagaattctt 69000
agtttggtga aaacttgaat ataaaggtat tttgatttat atgacatttt gatgatattt 69060
gaaaaaaagg aatttcctga cattttgctt ttagatcatg tcccccattg tgctgtaatt 69120
taagccaact tggttcagtg aatgccatca ccatttccat tgagaattta aaactcacca 69180
gtgtttaaca tgcaggcttc tgagggctcc cggagaatca gaccttaagc ccagttgatt 69240
tacttctaac gtgaaacttc gagttcctgt atactttgct agataatttg tggtacatct 69300
aaagcttagt cttaagtggc ttgtgtgtgg attttattca acattcttgt tgctagggta 69360
gagagaaatg ttgctgagta gaaacaagag tacccagttc aatgtggtac agagagcagt 69420
ccctaaaatc tgtacacagt gtaatggacc actttaggag tcaagaggct gatttttcct 69480
atgaaattac attgcaacag gaagccttct agtatagttc cttttactgt tagaatatgt 69540
ttttatgcat acgctatagc tgctttccca tcttccaaca acaggtatca ggatgtaagc 69600
aagctttaaa cagtgtgaag atggcaggat agtgtcatcg gtaacagtcc tctgactcta 69660
aatgtagttg ctctgtaaca ctttgtgaat ataacatcac aattctcatg tccttggggg 69720
gggggggcat acccagtatt agtatgtttt agtgactaag caatcatttt tctgtttact 69780
catgtacatt ttctctttaa aactaaaacc tgtactgtgt atgtctccaa agccttttag 69840
cttagttttt aggaaatgaa cactgaatgg atcacttttt agtgtagcag gtatgggata 69900
tgtgcattat agagagacct tgtcagctct ctgggcctat ttgaatgttt attgttggtg 69960

```
tgaggatggt aggggaatca gtaaatacaa gttacgttgg tttagcagag caagctcagt  70020
gtgggtattt ctctttgaag cgtggtgcgt gacgcactgt gagtagagaa tttggtcacc  70080
ctttgagtcc tcttgcattt tgcaaacttg ctcagcaaat gcgtacctac cttgcccccct  70140
aggtaaaagc aggaactact actgatttat ctgtcactca gctgtcttta tatgtgtgct  70200
tctgtgactt gtatcacaca agaatcttaa agatttcaca aattgttacc ttttagctct  70260
gaatgttgag tattctggtg ggctaacaac aagacaaact cttgacagtc atttgagaat  70320
tttcatgaaa catttagctg aaaacatttt ataatttatg aaaaaaatgt gttaccttaa  70380
acttttacat atgtgggaga cattaactgc catatttgag catactgaat tttaaattta  70440
aaataaagct gcatattttt aaatgaaatg tttaacaagg attcatattt tttgtttttt  70500
aagattaaaa ataatttatg tcttctcatg tggaacctca tctgtcacaa tggttagatt  70560
atacagaatg gagcaaggct tgtagtggtt tagcttacag taaaattctt aatgtttaga  70620
tgtgtttact tactggctgt tatgtatact tttgagattt tccacctgtt ctgtgtagtt  70680
ttctaaatga tactcctact taaaaacagc attttagtat ctattttctg tctccattaa  70740
atggtcctca ttttctattg agtttggaag tgtgcacatt gtgtgtgtgt gtgtgtgtgt  70800
gtgtgtgcac acgtgtgcgc gcccgtgcgt gtgtctattt gtggagtttg tatgggagaa  70860
ttagttttga aagtgctaga atagagatga aatttggttc aagtaaaatt ttcccactgg  70920
gattttacag tttattgtaa taaaatgtta attttggatg accttgaata ttaatgaatt  70980
tgttagcctc ttgatgtgtg cattaatgag atatatcaaa gttgtatatt aaaccaaagt  71040
tggagttgtg gaagtgtttt tatgaagttc cgtttggcta ccaatggaca taagactaga  71100
aataccttcc tgtggagaat atttttcctt taaacaatta aaaaggttca ttatttttga  71160
tgatttgctt cttagctttt tattcatccg agaatcaatc cctgctatgt gtaacaggta  71220
tttggactat attacttagt gaaagaggaa catcctgatc ttactgttga aaagtttata  71280
cttcaccaga gtaaactacg taaaagctgt ggggtgtgct aggaagtatg agacctcatg  71340
gctcccttgc atgtccatcc tcagagttta gattctgttt actagagcat tactagagtg  71400
aaatagccat gaaagtgcag agaaacttcc aagtaaaggc agtgagagat ccctgtaccc  71460
tcctgtcttt ttccttccct agtgcagtgt cctgaagtgt gtcctagtgt gtgtcatggc  71520
tctgccagcc caggtcttga ggtaacacct gcagtggagc tcctgagggt cttcctctac  71580
ccccttttcaa cacaagcaag aaacaataat attttgggtt gctattctaa ccaatatgct  71640
ttgaaaaact tagctttctt gagcagcaaa gggaattaat aataaaaccc aacatattta  71700
gattagtttg tccaattaac aggatgcaag atgtccaaat gttttttttt ttgatgagta  71760
gttattgcgg tacgtcaggc attgtgaacg ctcggcatgc acttgggtga acagcagttt  71820
cctgtctgtg aagtttgcat tctagcaaga aaaatagagc aaagataaat gtgtcagctc  71880
acctcaagca gagtgacttc agtgttggat aggttatttg agagtggctt cagcaggtgt  71940
ggggggtttc agtagactgg tgcaatttgt acccagaaac ttccacaaaa ctttactcag  72000
acttggagtt tgaaaatgtt tagtatatct aaggagaatt tatagtaacc tcatcttaag  72060
tagccatgac cattctgttg tctaaattgg tttggtaaag cctgtttaaa caattggttc  72120
ctctttattc tcagagttaa ctttttagtg ttctctgtgt atgtttcaaa aacactaagt  72180
catttttcag aagttaaagg ctctattttg accttaaata gttttgtaat gttgaagagt  72240
catgccattt atgatttgtt gttggacagt gagttataaa tgttgagtta ctcaggatat  72300
```

gggtgtgatt tatgacctgg tgctctatgt attagttcct aacccataac caaacatcct 72360
gaaaaatacc attatctaag tatcagaagc agcatttcca cacaaagata aaaatcccca 72420
cctctcctgc ttcatctcaa agattgaagt caaagtgttt aataatctgc tacaatggac 72480
acttgaaaca ttttattcat tacatcatta acattttagt agtggcaggg tccactcctc 72540
agatcaggcc caggactaag ggtgaggtc ttttatttat ttgtttattt ctgtgtatac 72600
acgttcacat gtgtgggagc atgtatggca cgtgtatgta tatgtgggtg gagtcagagc 72660
ttaatgttag ttgccttcct ccatggctat tgaggaagcc atctcttcct aaaatcttcc 72720
taaatctctt cctaaacttg gtgcttggtg attcatctgc aattacagtt ggatgtacag 72780
cccagcatgt agtgttggga tcataacact agtcctcata gttgcaaagc aagtactttg 72840
ctcagtgagc catctcccca gtccctaggg aggaaatctt gaaagaaaat gttgactttt 72900 ttttttaat tcttgatttt aaaataggtt taaaagaatt tgatagtcat ctatagatag 72960
accatgaatc tgagcaagga gaggtatata ggaagatttg gaagggagga aggcaagggg 73020
agaaattatg taattaaatt acattatcgg gctggtgaga tggctcagag gttaagagca 73080
ccgactgctc ttcggaaggt cctgagttca aatcccagca accacatggt ggctcacaac 73140
catccgtaat gagatatgat gccctcttct ggtgtgtctg aagacagcta cagtacttac 73200
atataacaat aaataaatta aaaaattaca ttgtctcaaa aaataagaaa ataactaaaa 73260
attttaattt tacttaatgt tttcctgtga atattattga taagaaacct ttttgtgtgg 73320
ctgcctttaa cagaggagcc acaagctata ttcttgttac ttattacgtt tgtgtgtttt 73380
tgtatatgca aatgtttgcc atgatactcc atgtaggtta agaggacaac ttgtcaggag 73440 tctttttct ccttccacta tgtaggtccc agaagttaaa cttaggttgt caggcttggt 73500
gctcatctcc tgagccttct catctgccca taccaggtat tctttagcaa gtacttcagt 73560
aagtacagcc attgtaagtc acaagagcaa ttagacttct tcatggtaga aataattagc 73620
tgatggaaag attatatttt aggattataa atgttcttgg ggggggtttg tttttgtttg 73680
ggagtttttg gtttgttttg agacagggta cttaggctgg cattatactc acgatatagt 73740
tctggctgac ctgcagcaca tgatcctttg gcttcagtct cccaggtaag aatactggaa 73800
ttacagatgt gttgccaaca cctctggtta ttagtgatgt gtgtgtgtgt gtgtgtgtgt 73860
gtgtatacac acacagtgaa tgttttactc ttttggtaaa aatggaggtc tgaggtaaaa 73920
gtttcctatg tcagctgtcc atagggaaga cttaaaagac tttgcttcaa aagattgagg 73980
gctggtgaga tggctcagca 74000

<210> SEQ ID NO 4
<211> LENGTH: 9001
<212> TYPE: DNA
<213> ORGANISM: Mus musculus

<400> SEQUENCE: 4
ggcagatttc taagtttgag gccagcctgg tctacagagt gagttccagg acagtcaggg 60
ctacacagag aaaccctgtc tcgaaaaaaa aaaaaaaatc cctttctctg gctataagga 120
tggctcagtg gttaagagca ctgactgctc tgccagaggt cctgagttca agtcccagca 180
accatctgta atgggaaata atgcactctt ctagtgtgtg tctgaagaca gctgtagtgt 240
actcatataa ataaaaaata aatcctaaaa aaaaaaagaa ttcccttcct cttattgata 300
ccctttcttg tctctaggga ccccccatat atctttctag acatttctga gaactcatgt 360
aaatacatgc tgagccccct ctttgtagtt tgtaaccttt gctcattcca taccatttta 420

```
acaaatattt tccttgaaac actatttctc acccattgca tggaggtatc acataggact    480
ttatcaggca tcctgttctc cagtgtgtgg cttagagcca gtggaatgca cggcgtgtcc    540
gagaaccact tcacacaggg aagagaatac agatttttac tcagcaagta acaccagctg    600
ggaatggtgg ggcagacaag caatcctagt tactagggat gctgaggcag gaggatctta    660
aattcaagtt tagtccctat ctcaaaaatt aaaaaagaac ccctctaacc ccagcaactg    720
agaggcagag gccagggaga tctctgtgag ttcaaggtca gcctgtctgt tctacacaat    780
gagttccatg agagccaaag gtacacagtg tgatattttt aaaaaggtat gtgtgtcttt    840
ttttttttca aatttttatt attttcttca tttacatttc aaatgctatc tggggagtcc    900
cctataccac gccccccctgc tcccctcccc acccactccc acttcttggc cctggcattc    960
cactgtactg aggcatataa atttgcaaga ccaagggcct ctcctcccag tgattgtcga   1020
gttggccatc ttctgctaca tatgcagcta gaaacacgag ctccggaggt actgggtagt   1080
tcatattgtt gttccaccta tagggttgta gacccccttca gctccttggg tactttctct   1140
agctcctcca ttaggggccc tgtgttccat ccaatagatg actgtgaaca tccacttctg   1200
tatttgccag gcactggcaa agccttacac gagacagcta tatcagggtc ctttcagcaa   1260
aatcttgctg gcatacgcaa tagtgtctgc atttggtggc tgattatggc acggatctcc   1320
aggtggggca gtctctggat ggtccatcct tttgtctcag ctccaaactg tgtctctgta   1380
actccgtcca tgggtatttt gttcgttatt ttaaggagga atgaagtatc cacacgttgg   1440
tcttccttcc tcttgatttt cttgtgtttt gcgtgtgtgt gtgtgtgtgt gtgtgtgtgt   1500
gtgtgtctta actggcagag cacttgtctg tcatgcaggg ggcggggtgg ggggtgggga   1560
ctgtctaatc tccagctcta gtaacaaaaa taaaagaagt aaaaaataag taagaaacgg   1620
gggtgtgtct agagatagaa catgggcttt acacatttta gacatcatga gaaaataaag   1680
ctggaaatga cactgggcat ccatcttggc gcatctcaac tttcacactg caaccgaggc   1740
gcgctgtgca aagtcagtga caatccgcat ttccagacac agtgggttca gaccttccag   1800
gcgcgcacgc gggcctcgtg ttctcggttt ccgcggcgac tcggccgacg tcacagttag   1860
aagacaatag cgactttccc cgctcaggct cctcgggaac tttctcagtc cgcacgctcc   1920
aggagccgga gctaccctcc gccccgcccc cagcgtgccc cgcggccagg gagctccacg   1980
aagggcgggc ggaggccgcg ggtagcgatt ggttccgtgc caaggtgggc gtggtcagac   2040
tcaggcctat aaaagctccg tggcgccagg gcctcgtttt tttgcgcggt cctttcctgc   2100
ggcgccttcc gtccgtcggc ttctcgtctt gctctctctg gtccctccgg aggaggccgc   2160
cgcgcgtctc ccggggaagc atggcgatga aagcggtgtg cgtgctgaag ggcgacggtc   2220
cggtgcaggg aaccatccac ttcgagcaga aggcaaggcc cggggcgcgg ggcgcaggcc   2280
gcggtgacgc ggcgcacctg tgcgggagca cgccacgccc ccgccacggc ctgagcccgc   2340
taagtgctga gtcaccgtgg cctggggcag gggctgggcg ccgggaagcg aggcccgggg   2400
cgccgcgggg ccttccgggc gggcgggggc ctcccccgcgc cccggagcgg ctgggcctgc   2460
ccgggagagc cggcttggca tccgttatcc ttctggggct gctgcttttc cggtgtccgt   2520
gtcccacagg ctcagagccc cgtggccacc ggctgcgatt gttgtaagaa tatttgaacc   2580
cggtggtgcc agaccggact aaggccgcag gacgcgtttg cggcacttta aagcaaagtc   2640
ctgggctgtt ctgtactagg tcagggtcgt gtcgcaaggc ggaaagaaag agatggcctt   2700
ggacagccgt cccttgcttt gcactccaga gagagacccg gctgtgggtt ttttctacca   2760
```

```
cagcgagttt ctgagcacat tttggaaaag tacatagaga tattttcgaa aatactgtga   2820
ccctgcaaaa acacatgcgt cacagggaag atgtgtgtgg taaggttgtg tccagagcct   2880
tagggaggtt accgttgttg tattcacctt aatcccgaga gaatatttga taaatgagcg   2940
ttatgtgctc tctgaagtgg tggacatacg tgtgagaagg cagacaccat agtgaatccc   3000
aagtgtttgg tttacgacga gaactgataa cggcaattta gagtttttcg taactagcct   3060
cgtttccagc agtttcttgg cattgaaatg cgttttgttg ttttcctgtg gaagtttttt   3120
gtttttgtct ttttctcctc cccacgtaat tcactgtgag aaagacgaag ttcggctggg   3180
tcttacccct gtgtgtgggt ttctgtcatc ttccaccatg ccatgccaga gcagctcgca   3240
ctatttttgt gacgctgcaa actacacatc gctggtgccc tttgtaccca atgaaacgat   3300
agttaagcat tccagattgg cagttgtaat caaagctggt tgatttaacc tgttgccaac   3360
ttttcagaat cagattttc tacccaaagt tcatattccc ttattctgtt gcaaaagttg   3420
gacatttaaa aaaaaaaaaa cctaaaaaat gattgtcctt gcttgttggt cggttgctct   3480
tacattttct ccctattgct acactttctg gagcagtact aatttgaatt ttgggtgttc   3540
ttttcttttt tgttaagtgg caaattttct agatttggat agctaatgag attttttttt   3600
taaggtagct ctggttagac ccaaatggat ctccacaggc agtaggacaa aggcattttc   3660
tgaccactaa ataaaaatag gggaactgat aaaatcactg aatgtggaga acagggttct   3720
cggcagccag tgttctgtaa gagtcaagtc tgacagtgca gtagccatct cttccccagg   3780
cctggcattc agtagcccct gtttgttcca cctggtgctt tctaaatgct gttcagtcca   3840
ggtgcctgca cacatggcat ctggcagcaa gtgttaggag aagtgtgaca gggagagaga   3900
ggcctagagc tgagcgtctc cagagccacc ctgtaggaag tgggtctact tggatctgaa   3960
cataggtttg attttcactg ttgtgtgttt tgacttgagc tttttactgt gcttggttag   4020
ggtgtaaccc agcaacagcc ctggtgcagg agtatttaca ctcaaacttg atgtcttcat   4080
ttttgtattt ttttaaatca aggcaagcgg tgaaccagtt gtgttgtcag gacaaattac   4140
aggattaact gaaggccagc atgggttcca cgtccatcag tatggggaca atacacaagg   4200
taggtcctag gctggctagt gaccagtgat ggaaaggaac tgagtcagga cccaattact   4260
aaccatttaa aactatctcg tttgttttct ttttctttta gataaagtta aaatgaccac   4320
ttaggtcaac cttggaaagt agccacaaaa gtattttatt tagtatcaag tattgcttgc   4380
ttccttaagt gtgggaaggt aaagaaggtg atttttcttc attgtaatta taattaagca   4440
gcaccttgct tattctgggt gtttattggg tgcttatttg ggtgtttgga gctgggcgtt   4500
gaggatggat gcattaggca gagtgtctaa ggacaaccat gccttagcat gagaggcata   4560
gcgggacaga agtgacaaaa actgaagatt caatataaat gcttaagtaa gatttatttt   4620
ctctatttgg gattagaatc aagtcagtaa aaagtagtgg cttaaattgc agttagtgaa   4680
cttttaccat attggagtaa tgatctgaat ttgcttaccg tcatttaaga gcctcatcca   4740
tgttgcgaga gccttttcct ttcctctcct tctcccctgc cttcttccct tctccacata   4800
gcccacggtg gcctggaatt tagtcttgtg tgtgctgtgt taaaggcatg taccatcaac   4860
ctgtgtgcta tgtgccataa tttgttctac agttacttag gattgggttt gacccatttg   4920
ataattacta aagttacccc gagttgcctc tggcctggta gctttgattt gttaagctcc   4980
ttccagaatc ctgcccagtt cctattttct tggtctgagt aaacactgga agtcctgcat   5040
ataaaaggac ttgctgcatt gttgagctgt gccttgtgac tggcatccct tagcccacat   5100
gagtagtgtg gtacacctcc tggagttgag gacaccagcc ctggcccttg ggaacaagcc   5160
```

atctaacagt ctgcctgccc caagtaaaag ctagacaggt gagctgtttg gtggcacatg 5220
gtctagaaag ataagtattt ttatcatgaa gtatgctccc ttcttaaaag ccaaggtctt 5280
taaatgtggg actttaactt tagaagtgcc attaaagatc acatctgttc cagttacaag 5340
gaaggaacaa gagccaggca tgctgtcctg acactgccat ggccctaagg ctaaggtggg 5400
agggtcatag gtcgcagata tcctgagctg tagtagtgag acactgtctc aaaactcaaa 5460
agcaaacaaa aagaaaaatg tgacagtcta ggaaaaaaag gtagcctgag aatgtaaggc 5520
tatacagtgc agctacttac accagggcgc tgctgcctgt ttttatcgcc ccagcacata 5580
ccaggtcagt gtttgctatg ttggaggttg taagaatgcc tgtgttgtta catatagggg 5640
tttacttcat aatctgactg ctggtttctg gtaaataggc tgtaccagtg caggacctca 5700
ttttaatcct cactctaaga aacatggtgg cccggcggat gaagagaggt gagcagcacg 5760
ctctgtatgc atggtggagg agaggggtct gtggaggacc ccagtaagac agaactgcat 5820
ggcctcctgc ctctgctttt gtgtttgttt ccattcaccc aactcactcc cacaacccca 5880
cgtgctagaa tagcttctgt tgggtgaagg agctgacaaa tgtggactct taaagtgatt 5940
tggttttgta gcatttattg aagatgaact aatacaagtg ccaaaaggaa ccaatacaga 6000
aaatatcatg gataacagta ctgtcagtca ctggcaaagt aaatcattgt ataataggac 6060
gctaatgcag ataatgaaaa ctagttgaga ttccatttgt atgtgaaacc ttaggaaagt 6120
cctaaataaa gaagggctag cctgttttta gaatgggggc ctgggagcaa acctttgcta 6180
actcaggagc tggcatactt tactaaagcc ccagattatg actcttctca gagcactacc 6240
tttaaacttg aagaactgtc tgtcaaggta tcctgtagct acctgttttg aactttgtgt 6300
ttccagacct ttgccggtct ggaaaagcca tcatagttga taatgtatgt gtactttttc 6360
atccactcat acgtatttga cttagtcaga ttttaactta gttattgaac tctagtgatg 6420
tgaaatagac atcattgttc atccacctga tgctgtttta atgttaggca tgttggagac 6480
ctgggcaatg tgactgctgg aaaggacggt gtggccaatg tgtccattga agatcgtgtg 6540
atctcactct caggagagca ttccatcatt ggccgtacaa tggtggtaag tttttcatat 6600
aaggatatat acataggatt tcttctaaca tagttatgta ccttcccatg actttatggt 6660
ggttaaacta gtttctaaag agtcacataa attgttaaga gttcagggta ggaaaaaagt 6720
tcttttattg gctgtgatag taaagaatta atttgcctag gtcagttaag aacactgttg 6780
tgctgaaatg cagtagaaag cagttacatt tgatgagact ggatctgagt tgaggataca 6840
atagtcttta gtctaaaaca gccggatttt cttgccatga ttgccccccc ccttgcaaca 6900
tttcgttgag tctaaaatct gcgatggatg gcagtattca agtctgtagg ttatcgcttg 6960
gttaccatat gggagccgtc ttcccaagtt accctcggga gatgcatctg ggtcatgcag 7020
aacaccaagt agtaaaggct cttgcccacc tcgggcagct aacttttcag taggcacttc 7080
cttccttgca gttgaccctt tatccttaga atgctcttca gccctattgg tgaagcagaa 7140
cagtcattca taagtgttgt aaaataaagc tttagagtct tgttgctaag tagagatact 7200
tagaattgcc tcttatgtgt aggcctatag ttctttcaac atgagatttt gatagagaaa 7260
tttgtaagaa tgactactgt gtagttgggg aggagctaag atcagcatgt acctggtagt 7320
tacttgggtc ttagtatttc atctagaaat agccactagc aaggaaaaac ttagtggtct 7380
gctcttaact gctagtattt aagtctgtag tattgctggg aagaagtact agttacttga 7440
tcattcaaac ctaaatgttc ttcttttcaa aggtccatga gaaacaagat gacttgggca 7500

```
aggtggaaa tgaagaaagt acaaagactg gaaatgctgg gagccgcttg gcctgtggag   7560
tgattgggat tgcgcagtaa acattccctg tgtggtctga gtctcagact catctgctac   7620
cctcaaacca ttaaactgta atctgaagag ttgtaactgt gtgactcctt tgactgggct   7680
aaggacagca atgacagctg atggagactg tgtacaactc actgaattca aatctgtttc   7740
tgtgcctttc catattttgc cagactacac aggtgataag ctgaaattct catttgagcc   7800
tgttagtaaa tatgtgtggc acttatttg agcctattaa tgtgtacaaa aaaaaatttt   7860
aagttagctc tatacattga gcatcaataa cagactcaat gatgctaact catagtattt   7920
cattttgaaa gtgttttatg tgataccatc aaaatggtgg gtggtagccc aaacaaaatt   7980
tgagcagaaa attttctgcc ccttatcaga gaaattattg aaagctctca agattcagag   8040
tacttaacct tatattttaa aattgtatta ggattagatg tcatgattta agaaaaagcc   8100
ctttagtaaa cttgtatcaa actcatagaa ggcaaacatg gagcctcagc tagctctact   8160
agccaagtga agttggtacc acccatcttt aaggttggca ctcagggaaa acacaatagc   8220
tcggggaatg acaccaagtt tgactggagg ttctggctaa atcgactttt atagccccag   8280
gtaatgaaat tgagtgcctt aatacccaag aaagagtgcc tttgaaagga aatattaaca   8340
ggcttgtgac tatctgaaat agttcaattg aagtattttc aacaaattgg gtgtaaacca   8400
tagttctcac tgatatactg aagtcactga agaagagaca actaaattgg aaaagcacat   8460
aatttggtgt ttccaacctt aaaattttta agtttagatt tccaatctaa gattgctcat   8520
aatgcttttt caagtagtta tgttgaagtt ccaggtaaat cctatgtaac tgatttcctt   8580
aatgtagttt tgatgtgggg gatgactcaa tgcggattaa cttggtaatc acaaaccatt   8640
tagtggctca cgtctcagta tttttagttg gaaagacaag ctgcaagtct gtccttggaa   8700
tctgacattg gatcatcgtc ggatgcatgt tttatgatac tctaataagg acttaaaagc   8760
ctaagtaggg tcaccagaaa gctgaagcct ggcaaagcta cagacacatt tcttccatca   8820
ttaggaagag ctcagatcta aatgtcaaat gggaacatac aaaaaggaac ttctaggtac   8880
gataaagcta agtttgacaa gttttttgtt taacctagca ccttgtagtt ttaaaaatca   8940
tttttagggt gtgtgcacta agaggaaaac aagttcatat tcttccacct tttattgtcc   9000
c                                                                   9001
```

<210> SEQ ID NO 5
<211> LENGTH: 66001
<212> TYPE: DNA
<213> ORGANISM: Mus musculus

<400> SEQUENCE: 5

```
ggccttggcc tcactgagga aggaagtcac cccatgcctc agggtttttt tttttttttt     60
tttttttttt tttttttttt ttggctgtaa cacgaagcat ttagaattaa aggcttaaag    120
gctctggctg tggtctgaga acgagctaac tgggcactgg gcagagcagg gaaagacaga    180
gtccctacca ccctgctggt atcctgagtg gggttcatgg ccaaagaacg cataactgag    240
ctcaactgag ctggtggtgt ctctgggtga taaggaagag tcagcagaga gcatagccgc    300
caggcagtct gataagcccc tcgaacacat tcctggatgg agtcaggggc ccagcgcgtg    360
tctggggcct ggagttttga gtggagggta tgcttaaggc ctcgagggac acagaattct    420
gtacgaaggg tgtgcaaagg tcccgggaga catggaattc cgaggggaca gtgtgcaaag    480
gccacgaggg acacagaatg gagggtgtgc aaaagcccaa agggatatgg aattccgagt    540
gggggaagtg caaagggccc cgagggacac ggaattttga gtggagggcg ttcatggccc    600
```

```
agaggctggc ccgggctgac tgcaactgat tttaatgcag gggagcggga ggcattcgca    660
ggagtccgga agaaagaaga ggtcgcaggg gcgggggtag tggatgcaga cggtgccagg    720
gtcttctgcc ctctgtagag ggcacatcgg ttcccaccta gaccagcaac caccaggaaa    780
gcccagcagc tcggaggggc ggcgcccaaa ggaagccacg cccacgcctc accatcagag    840
caccgcccac tccccgcctc ttcccacccc tcgccggaat cccgcgccga actcgggggc    900
gggctgcccg ggccatggcg cataaagcct ctggccacct gcagggctac tgctgctccg    960
gccaccgcca ggcacacacc ttgctgctga gggagtctcg gcttctgtca tctctgtggc   1020
ctccgtcacc tctgtctccg tctccttcag gtcctgagcc ccgagagccc cttccgcgca   1080
cgcggacatg ggcggcagct ccagggcgcg ctgggtggcc ttggggttgg gcgccctggg   1140
gctgctgttt gctgcgctcg gcgttgtcat gatcctcatg gtgccctccc tcatcaagca   1200
gcaggtgctc aaggtgagtg aagtgtcttg gggagatggg ggttggggat cgggacgcag   1260
ggtgggacgg tggagctacc tcctcaccac cagggaggcc caggctcacc ccagaggctt   1320
ggtctgagtc accagcgtcc caggagccta aacctcactg aagcagaagt atggcctggt   1380
tgtccctgag tttcgactgt agctgtcgcg acctccagcc cttctgaacg cgccggccgg   1440
tgactgtacc tagtaacctc agagctgcgc gaaacccctg tacatctgtg aggctcccac   1500
gggctccagt tctttgggtg ctctgcctgt ttcctcccgc ccagatgccc cagagatgcc   1560
ctggctcgcc cccacactgc ctgccagtct cgagagttaa gctgctttct gccccccacg   1620
ctctggcaga ggtagacacg actcaggtct gccgaggata ggcagcccag cctctccctt   1680
gatctcagcc ttaggccctg ttttgccctt tcaaccgggc accgatatta ggcgggtggt   1740
gccggtccag ccacagactc tgccctggga tccggtgtcc ttctatttga gccgggagct   1800
cattaagtcc tggagattac cgagtaattg tgttttctga gacgcagggt tactgcggaa   1860
ggggaaacgg gggctggctc tcagggaaca tccagttaga actggatctg ggatccagaa   1920
ggggctgttg tcacagggtt tgactgacat ctttcctctt agcgggtttg tttactggga   1980
gtttaagaat ggcttcgtgt cccatgtccc atcgcccgct gaaaggaggg aatgaatgag   2040
ggatactccc tcttgggctg gccgctacct gccaggtcct ggcgggtctt caggatggag   2100
ccacaggtgg ctttcctgga gttgtggtgg gtatttccga gttctcttgg ccacactgtc   2160
atttctcttg cttagaattt tcaacccttg tacatgaagg tcccaggagt tgccctgtct   2220
tgggtagagg gaagatcctt cttgttggag catcagaatt gctctgggcc tttctgttag   2280
gtttggcaaa gtagtggtga cagccttgtc tcagtggcag cctgtggttt cagtaagaac   2340
ccagccctgt gcactccgca cgtggactgg gtttcctgct cagccagcct gtagtgggta   2400
gagtgagcag atatcccctg ttcttcgatt tgggggtgag ggggaatctg agctggttcc   2460
ttctcaaact cctttcggga atgttttctt ttgggggttg gcacagagac taaggatggg   2520
gggggttggt gtgtgtgggc gtgcacgtta gcgttgggac tgcgcaggcc tgctccatca   2580
gtcagggtcc catctgcccg tgcttgagaa agaccacgac tggcagaatt gccccatagc   2640
tggtagcttg gggcttcacg tttgagcgag cggcttccac aatcttactt gtgaaaatcc   2700
caaaggcgat tggttggggg ctgagtggcg tgaaggaagg aagagcctaa gacacgccta   2760
gcccaaaaca gcctcttctt agaggccctg gctggaagcc gacctcttga gggaggaaaa   2820
aaaagttcac ttcaggggat ggtgggagga tggcagcgag gggagcaggg agggaccctg   2880
gagttgactt tggattcttg cgttctgtgc tacttgaatg gaagccttgt ctttgtgtgt   2940
```

```
gtgtgtgtgt gtgtgtgtgt gtgtgtgttt ctttctttcc tttttttttt ttttttgtaa   3000
gttaaagaag ttgatttata aaagtcagga atactaggtt gtttaagaaa acaagttcag   3060
gacttggggt gtagctcagt ggtagagaac ttaccttgca ttcaacaggc cttgggttcc   3120
aacacacaca cacacacctt gcattcaacg gccttgggtt ccaacacaca cacacacaca   3180
gagagagaga gagagagaga gagagagaga gagagagaga gatttcactc ttattttctt   3240
ctgatgatat catttttga cataaattgt gtgtgtgtgt gtgtgtgtgt gtgtaggtca   3300
cctgatttct tcccttacag atagggtctc ttgatgagct agacagccat ccccctgtct   3360
ctggggttac aggtgcaatc ctatcgatgc acaatattgt atatgtcact gggagtttga   3420
actcaggtcc tcatgtttgc ctagcgtgga catcttttac aaaacccgag ttggatagta   3480
tgtggttttc ttcttttctt cctcctttct ttccttcctt tcttcttctt ttttctcctt   3540
tctcttgatt cgtggtctca ctagatagcc caggaactca gtgcatagtc caggctggcc   3600
tcaaactcag agatccacct acctttgcct cttgagtgtt aggattaaag gtctgtctac   3660
catgcctggc ttaaatagta tggtttttct gttcagtgtt agtattcaaa ggggtgtgtg   3720
tatgcctgtg tgtgtatgtg tgtatacacg cacacgtgta cacacacata catgcacgta   3780
tactcatgca cctgtatgga cgtgcttgcc acgcggtgag accagaggtt gaagtgcagt   3840
gtcttccaca gtgtctctcc accttatttt tttgagacag gctctctcat taaatatgag   3900
gtgtgccttc tctgctagcc actgaacaac aggtccctgg aatctgcctg tctccgcctg   3960
tcctggtact ggggttccag acatgtatca gacgtgctca gctatttttt tttctgcgtg   4020
tccctggcca tcctagaact ccctctgtag gctctccctg cctcctgagt gctgagacta   4080
aaggtatagg ccaccacccc tggctctgtg ttgagctttt gtttgggttt tgagaatcag   4140
aactcagatc ctccagcgag cactttaccc actgggcgat cttcccagcc cctttcaaag   4200
gttttgacag gccgaacatg ccaagtctgt tactgccttt tcccccctta ctgtgctggg   4260
attcctttgt ttacagttcc tctgttgact ggccatgtct ttgtctcaga ctccagagaa   4320
cacatagcgt cctgtgtgag tccaggaaca cttgcacggt ctgagcctta gctgtggacc   4380
cacaggtgcg ctctgtttgg aatttggaat tctctactat tgctcccgct gtcaagctgt   4440
gggaccatcc acttcgatgg caatgaagtg tcatttctaa accccatcac cctctttggc   4500
tacctgtggt tttgatttca catcttcagc gccacaaggt tgggcaggag gaacgtgatc   4560
cccgtgtagg tgacagtttt cagagctcag gggctcaggc ctactgtacc atgtgctagc   4620
tggagccggt tcatcactca agagagccaa gtttttcccc cagcagtgag acaggggtca   4680
gatctggttt gctgtccctg agggattagc aagttgcaaa ggagattaca agcggccttt   4740
ggaaatgccc tgtgagcttg cctgcttctg gactcaatct aaccacggca gcgttgtgaa   4800
acaggcagag gctgcgaatt cttcctctct acagataagg gatctggccc atagcaaagg   4860
tcggcagctg gttattaaac atggcctgtg gtgggctggg agggacttca agcggccatg   4920
ctcggtttac cttccatagg gaagtaggaa gcaagcaaga gccctctctt tctgtacagt   4980
gagctgctgg gcagtccaag aaaagaatta agaagggcca ggtttcagga agacatgcat   5040
gatagaaaaa aggctctgtt actattaaag tccctcttcc ccagcctctt acccggcatc   5100
ccagctactt ggagtctgag gcaggaggaa tgaatattca aagccggagg aagttcagag   5160
cctgcctggg ttgcacagga agctcagggg agcttagtga gacccctgtc tttatatcaa   5220
atgtaagcaa ggtgcattag tgcatatttt taaatcccag cgctcagaag gcagaggcag   5280
gcagatctct gagtcaagtc aagtgcctgg atagccaggg ctatagagag agatcctgtc   5340
```

tcataaagaa acaaacacac aaataaataa cacataaata agtaagtaaa taaataaata 5400
ggtaagtgga aaactgaaga tagagctcac tgattgatag actgcttccc agtatgtgca 5460
catccctggg ttcaatcccc agcactgcaa aacataaaga gaaacacaca cacacacaca 5520
cacacacaca cacacacaca cacacaccaa aatccctcag ccagtcggtg gtcgcagcgg 5580
cggctcatac ctttaatccc agcactcggg aggcagagac agagtgatct ctgtgtcagc 5640
cagggttaca cagagaaacc ctgtctcaag acaaaacaag tcaaccaacc aaccaaaccc 5700
aaaatgacaa gaatgacatc aaaaccctaa cagtattcta tattttcaac agactcgtgt 5760
tagtgccaaa atggtttaga aaaaggtgcg gaagggtgcg tgccagacac acaaggtaga 5820
taatgctggc tgcacgactc tctgtacatt tttgttttat tttatgtgta ggggtgtttt 5880
tcctgcatgt acctctgtgc atgcagtgcc cttgtagacc agacaggaca tcagatcctc 5940
tggaacttgg acttacagat ggttgtgagc caccatgagg gtgctaggaa tttcacgaac 6000
ccaggtcctg tatcagagcg gccagcctgg ctcttaacca ccgagcaatc tccaaaccat 6060
catgattctt tttgtaaaat attatgtgta tgtatttgtt ggtgtgtgag tggaggggtg 6120
gtgctgcaac atgcctatgc aggtcatggg acaactttga ggagtgattt ctctcctgct 6180
cctaagtggg gtcctaggga ttgaactcag gtcgtcaggc tgccgagccg tctcactgag 6240
cccaatggtt actatcttgt ttgtagttct ttagggcaag gtttcgttgt attactcagg 6300
ctttatttga aatcctcctg cctcagcttc ttgttcatca ctgttcatca tggaagggag 6360
tcagggcagg aactagaaca agggagggac ctggaggcag gagctggtgc agagaccatg 6420
gagggatgct gctacgaact ttctctttat gacttgctca gcttgctttc ttacagaacc 6480
gaggaccacc agctctgggg agacccctcc cacaataggc cacgcccttc cccatcaatc 6540
actaattaag aaaatgttct acaggcttgc ccattgccca gtcttttttt tttttttaa 6600
gatttactta tttatttaat gtatatgagt acaccgtagc tgtcttcaga cacaccagaa 6660
gagggcgtca gatctcatta cagatggtta tgagccacca tgtggttgct gggaattgaa 6720
ctcacgacct ctggaagaac agtcagtgct cctaaccact gagccatctc tccagccccc 6780
cccccccccc cccccagtct tatggaggaa tttgtcttaa ttgaggttac ctcctctcaa 6840
atgacaatag actgtgtcaa gttgacgcaa agctagccgg cacaggcagc gtggttgaca 6900
caggtccttg tcagttaagg aaacagctga aaatggtaag aagtaccccg tgactttctt 6960
ggagtgtgtg taagtgtcac acggagggaa acccaccagc cctggaaccc ctgtgtgtct 7020
cacctagaac ccagcctggc acgcggcttg cccgtccaca gggccaccgc cttcagcaca 7080
gagcctcata atctttccca agtctgggtc tgcatcagct ccactgtcct gacgtggcat 7140
ttcctgttgc actgtgcgtg atctgttcat ctgctgatgc ctccctcctc tgtcccatgt 7200
gtcccctagg tgcaaagcgg aagcctcagg ctgccctcac ctgctccgtt gttctttctg 7260
ctacctcata cctgcttcac cattaccttt tatgacccct ctacccccat ggccttactg 7320
cctgcttgga cccgtgtggt agtctatcct gctcttctag tgagggatgg tgcccaccct 7380
gctcagactc tctaacattc ccgtcttttt ctgagtgaac cccaaattcc tctcagcagc 7440
ttgaaggctc ccaatttgtt tctctttccc accctcaatt cagcacccca cccccacacc 7500
actatgctcc tggtttgagc ccattagacc tagtccctct tcagaggccc tggcgtgtcc 7560
ctttggtggc acatgccttt aattcccagc acttggaagg cagagaggta ggtggatctc 7620
tgagttcaag gccagcctgg tctatagagt gggttttatg acagccaggg ctacacagag 7680
aaaccctgtc tcaaaacgcc ctatccccct aaaaaaatga tttatttatt attttcagtg 7740
ttttgtctgt attcacgtgt gtggtgcttg aggagggtca aaagaggtgt caggattccc 7800
tggaactgtg acctgtcatg tgggtgctgg gaaccgaact cagattctct atgggtgcag 7860
ccagtgcttg taaacctcgg agccatccct ccagcccacc atccttattc tgtcacaggc 7920
ttggatgtgg ctcgctcttt ttcctgattg agaagttggt cagccaggtg aagggctagg 7980
gagctgactg gatgctggcc aatagctggc tctctacccc tccttgcctc aattctaatc 8040
tgatcccttc tcccacagct aggagttggg ctagcctggg atatctactc tgttcctgag 8100
ttgttttgtg acctctggca gagcccattg gcttgacact tggaaggtgt ccctgatggc 8160
agatagctcc ttgtagatag atactgtgtt acgatgctcc tcagagcctt ttattaagta 8220
tctaaacgac tacagttgct ctctgcttca tctagggaga gggacacaaa gagagattaa 8280
gtaaaacttg tcccctggtg tcccatgtct ccccacccca accctctacc tccgcattcc 8340
agatttaggt gacagaacca agatgtagcc tctgctaaaa gattgtaacc cttgaacagc 8400
tggccttgac tggccgttcc ttctttttct cccttctctt ccatcgatgt gcatggctag 8460
cgggtgtatt ccagggtttt ctcccacaag agaaggctgc agattcagca ccccttggta 8520
cctcctcagg aggactctta agtgggaagg tctgcctttt cccagtttgt accaccctgt 8580
gaccttggga tcaaggtctg cctgggccat cgtgggctgc tccccaagtg gagactgggg 8640
ccccagatgt caggatgggt gtccctgcaa gttccctgtt ctctgggccc tgggtaagaa 8700
tgcttgggtg tgctgggatt tcttctgttt tcttcctctt tcctgatgcc tggtttccgg 8760
ttcccatggc ttccggtccc cctggcatgt gtggaactat tttagttccc ttcagggtgc 8820
agctgtggct atagactacc tatttttagt cccaagcatt tatttctgtt cctttctggc 8880
tcctcgtaca tccacaagtc ctcatagctt cagtgtgtgt gtctgttggt atacacacct 8940
tttggtgcgg gtccacgtaa tagtgtcccc caggtatagt agcacacaga cagagcttgg 9000
tgtatgtatg gtccagtgct gacatccatg gatgtgagtg tttctgtgta ccgcacgagc 9060
tacaacctat ccacatggag aaaagccagg aaggggatgc aggcacatgg gtcattgtct 9120
gggcccatgt agacacatgc acatatgttg atgcctgttc catttgctgg gggtgggcag 9180
tggacatggc tgcatggcag aatgatggcc ttcgaggtgc aagccactgg gctccgacct 9240
tagcactgca gcagacagaa ggggtcacgg gcactgcatg gtcactgtgt gcagtagtta 9300
ggtgctggta ttttgaagcc agactctcct gttgcattcc tggaaggaag ttaccctggg 9360
acccttcctg gaaggatgga ttctttgcta tcttcccaca gtgactcatc ccctcattcg 9420
ctccaattcc tggagttcgg ctaccaggaa tcctgttctc tggccttgga tcccagcagc 9480
cgactctggg gccagtcctg gagagagcca cttggttctc tgcagagctt atcctaggtg 9540
catcttggtt cctaggaggc ttggcccagg ctgccagctc tgtggccttc tgtggctttt 9600
agggtacaga ggagtattca aatgtccttc cttggccagc aaaagagagg ccctgggcta 9660
ccgtgagctt ctccccaggt tgccactgga tgtttgacat ttcactctta aggaccatga 9720
gttcagctga gaggccttct gaatgagaga gggggggggg agagagagag agagagagag 9780
agagagagag agagagagag agagaagaaa acatggatgc tcttgggtat agtggaggag 9840
aaggtttatt gtagataaaa gggagaacgg gagaacatag ctagaggcag agaccgctgg 9900
aagagtccag agtggacatg accttgaacc ctgagctaga tgaggggagg gggagggaaa 9960
aggagaggag agaggggagc caggtgcaac tgccaagaag gagggagggc aatcaaaatg 10020
gttggattat cctggggaga gtagcccagc cctctgggct atagagttca gggtaggggg 10080
cagggtatgc cagcctgaag gggttctgaa actggtaggg actgagggat gctgggagaa 10140
cgtggcagcc aggtctgctt tgatatgtta actagccacc taaaccattt gtgcagggtt 10200
tgaaactcaa taccttcagt gccagatcct gtgccatcaa tttagtttga ggaggattta 10260
gcctggcagg ggtgggtggg ggtgtaggtg gggctctgcc caaaatagaa acaggttagg 10320
aggctaaagc agggggattg ctagttctag gccagcctgg gctaccctcc ccccaaaata 10380
aataaaaaaa attccataaa aatgaaaaac cagaaaacaa aaacacttga tccttttacc 10440
tctctcctct ctcctcactc tctccctcac tggtgacctt ggcctccact ggcctagggc 10500
agggtcaggc caggctgagc tacaaagaga aacaacaaca acaaaaaaac ccaggtctgg 10560
ctcagcctgg ctctgagtcc cagtggctga ggaggttcca tggctgccga gggaagattt 10620
ccacccctct cctcagatcc cgggctttct ggcctctccc cagctcccat ctcctctgct 10680
ttgtgatctt cagctgccta gggaggggaa ggaataggag tgacctgacc cttgcttgct 10740
tcctggcttt tcaatgaagt tccttccacc ctctctggaa gcttctagaa aagggtcttg 10800
gctggggcct ctctggctgt gggttgtctc catggttctc gtggggcagg ggttctcttt 10860
ccccctttgc ctcagccaga ctctggtgga atatgcccag gcccaattca cagctcaggg 10920
ccttaacttc ccccccaacc cccccacccc caccccctgc tcagccccaa actgtcccct 10980
cctgggcctt gacctcaaag gagtctggtg tgccaggtgg ctcaactttt tcctgacctt 11040
ccccttcaac tccaggcctg tccccttca ccttcctggt tagcttggcc tgtggtcttc 11100
tagcttgtgg cggcagcaag ccacgacctt ggcagcggcc ttccctcgcc ctctctgctt 11160
cccacacgtg agccctgggg aagtgagcgt ctcccacctt tttgtccgtt tcccgaggct 11220
gacttctgtc attttcttat ctggatcctt aaattccttt cctctgtctc ttgtgttcct 11280
cccagctccc agtacagcag ccagaaacag accctaggtc cttcccatgt gtcaagaggc 11340
cagtaccttg ccctctgata cctttctggc ttgcacaccc caccccttga ttcctctcgt 11400
gcgtgggcta ggtctatagt ctaatgtctg acatttccaa gtgggactcc gctgaggtca 11460
attcagaccc aatatgccac actagttaca tgtacattgg gctttttcc ttctgccacg 11520
ttgtccccat ggggagtccc caggctcagg agggcaagga cctctgtggt gtttgttctt 11580
tgtccccagc gttggaactg atgccagaca ctgggccttg ggttcccaaa tgtttaccca 11640
aagtggacag ggtcgaatca cagggtgttc tggtaccctg gcactaggaa gtcctgtgcc 11700
aggctagacc atgggtgccg tggtgctact gtcctgccat gggtgatccg gctgatccgg 11760
cacttccccc tgtcacagac agagtgctct ttcgaagaca cagtgcttta gtttaaagct 11820
gtttcaggat ccagctaggt gagatgatgt ggatttgatc cccagagccc acgtcaaaca 11880
agctggtaat tccatccctg gggaggcaga gacaggagac tccatggggc tcccgggatt 11940
cattcctgca acgcaactgg ggagctccag gctttagaaa gaatcgatct taaaaaaaaa 12000
gatagatagt gctggaggga gcacacctga ggttggattg gcctctggcc tctacatata 12060
tacatacaca cacacacaca cacacacaca cacacagaga gagagaggga gagagagaga 12120
cccacaccca cagaggcaga cagacagaca aacacacaca cccagagaga cagacagaca 12180
cacacaaaga gccaaacaca tacacccaca gagacacaca catagagaca tacatgcaca 12240
cagaggcata gagaaagata gacacacaca cacacacaca gagacggagg agagacatat 12300
agagacacac acacacacac acacacacac acagacacac atacaaagac agacagacag 12360
acagacagac acacgcacac actcactcac tcttgccccg atccatcagt cctttcttca 12420
caggctccaa cctgtctggc cagtcagcgg ttctgttcta agcccacaag tctctctcct 12480
cctccattct cacacgcgcc ggaagttcct tctgcccaga tacttttccc cttggctctt 12540
tcactcagtt cctctcctgt gtttcaaaat aaatgacacg tatttgtatt ttggggtgct 12600
tgggagggac acagagaggc actcatacta gacaagtgtt ctcacaccag tacacccaaa 12660
gcctgtgtgg ggatgttttt gaagacactt cctggtccca gcttccctga cctcccttga 12720
cctttggaag tttccttgcg cccatctcta gtgaactcat tcctttggtt gatgtcctac 12780
caggatgggg atctggtgtg ttttgtacat agctttactc ctgcagtggt ggcctggctg 12840
gggtgggacc ctagcagcca tcgctgaggt cacaagcctt gctgactgcc tctgctccat 12900
tggggggggg ggggctgtgc ctctgttttg ctttttttgtt tttgtttttt tgtttttgtt 12960
tttgtttttg tttttgtttt tttttttttt ttttttttgg tttttcgaga cagggtttct 13020
ctgtgtagcc ctggctgtcc tggaactcac tttgtagacc aggttggcct tgaactcaga 13080
aatctgcctg cctctgcctc ccgagtgctg ggattaaagg cgtgcgccac cactgcccag 13140
caagggctgt gcctctgtct ccagggggct gcctcctgat gccactacct aagcctcaga 13200
ccatgagcct ctgtcccctg gatgccattt cttgaagcca cctgggtgag ttggtgttca 13260
tatgtcccag accacaccca ctggcccgag tctctggcag gtgaccctag atccagggtc 13320
tgagtctctg catgttttct cttgactcca gcaactcctc actggtgtct gtgccagggc 13380
tgctggcttc ccccagtaac ctcttcctgt cccaccacaa aggcagtgga ccagaaggaa 13440
gagacccagt tctcagccat gtcatcggga tggctgtggg cggtggataa ataaatcaca 13500
cctgtcttag ccaagggcgg gagagaccag gaggtggggt gcaggtttgc aatgcacggc 13560
cttcgggagt gaacgggagt cttcagcagc cttggtttga cgtggtccgt gtacagtcct 13620
ccgcagggga caagtttagg tttatgaata aagcgaagtc acttcctccc cggagttcca 13680
gataacctgc cccagtgcgg gatgcagtgc gggatgcagt gcgggatgca gtgcggggtg 13740
cagtggacag ctgctttctc ctgccagtga tctatataga aggacctggg aggtgtggct 13800
cacaggtgcg aagaacaaaa ataaactggg tgccattaca cacctgtaat cctggcattc 13860
cagaggcgaa aacaagagaa ccaggtgtta agtcatcctg actacagagg gaattggagg 13920
ccagccctgg ctaaagaggc tgtctaaagg gttcagtgag taatgcttgc caccaagcct 13980
gttgattggc gttcgatcct gggacccaca cagtggaaga aaagaacagg ctctttcaag 14040
ttgtcctctg accgctgtgg gtgtacctca ggcacattca cactcctcac acatacactc 14100
aaataacaaa tgcaaaaaac aataacaaat gcaaagcaat gacgttaagg gctgggagaa 14160
gggggcgggg cttggggctg tccattgcct ctgattggct taggtcacat gctcatgttt 14220
gagccaatca gtgtgtgtca agaaagcttt ctttggaaag aggcgctctc tctgaggact 14280
caggagggga tggagcgatg ttctatgggt tggcaggagg caagggagac aggtagccag 14340
agtaaggaca gaacccttgg cccctagtta gcaccggatc accccaggtt ccgctcgctg 14400
cctcttatgt acgtacatgg gtgctttttt tgacgctggc tccaggcttt tttgattggg 14460
gaggcagcgc gccagggtaa attttataaa tcttaggttg ttgggtcttc aagtacttac 14520
ttgggtttct ctctttttat tttatttcat tcttatcctc attgttattt tggtttttttg 14580 aaacagggtt tctctatgta gtcctggctg gcctggaact tactttgtag accaggctgt 14640
cctcgaactc atagagatcc atctgcctct acctccctcc tgagtgctag gattagagta 14700
tttcaccacg cccagatttt gctacgggct acggctgctt ctgcttctcc ttcctattta 14760
ttattattat tattattatt attattatta ttattatttg aggcaggggc tcacactgta 14820
gcccaggctg gcctcacact tttggcaatc cttctgcctc tgcttcccaa atcctgggag 14880
taaagacatg tgccgtagtg cctggcccat ctttttgttt gttaaaatca catgtttgtt 14940
tatttgtgtg tattgtggag ggtaggggtg ccatatgtgt actacacatg tgtagagggc 15000
agaggacaac ttgcaagagt cagttttctt cttctaccat tatgcatggg gttgaactca 15060
ggcaggcttg gctgctgggg ctttattggc taagtcatct ctcctgccct catgcttttg 15120
tttttgtttt tattttgttt cttgagactg ggtttctctg tgtagccctg actgtcttag 15180
aactcaatca gtagaccagg ctggcctcga actcacagag atctgtctgc ctctgcctcc 15240
caagtgctgg aattaaatgt gtgtgccatc accgcccagc ttagcgcctg tgttttattt 15300
ttctctttaa ggacccagat ctcagaggga gctgtgatct gttcaaggcc atagttggta 15360
gccagtgtta gctggtcgtg ggccaggtta actgccaggc tggccgggga agtggggtgc 15420
tgggctaggg aaagataaga gatctcggta agtgagggct agtcatgttg ttttctggtg 15480
acttcgggca gtctcccagc tccctcccac ctacctcttc tttgctctca tctgactgta 15540
ggagtgggag gaggtgtttt gataaagtag gagagatgtc aggacccggt ataccaaagt 15600
tcaagctcta tgcgccttct ctgaggctct gagtgcgccg taggatgcaa acagcgagaa 15660
ccagcccaag cctccgcgcc cttcactaca ctcggcatca ggctcagatg cagaggaggt 15720
aatctgctct ggacgtgttc tgcaatatag ctcaggagtc ggctcacgcc ccagacagag 15780
cagctgttgg ctcttaccca agactctgag gtacgccatg tccttctgga gcagtatggg 15840
gactgaagct gagcttctgc tagtgtctct ttgtaagccg agctgggctc tctggctacc 15900
cacatgtttg ccgtctgcct ggaggagagg tgggaggtga gtgtgttcct ggagggtcac 15960
tgccaaggtt gtaaacccat tggaaagtct ctgggcttga gccttgcggg ggatggctct 16020
gccaattccc tgctgggtaa cctcgggcaa gtgccttaat tcctctgtgc cttttcaccg 16080
tgttcttaat agtgtcctgt gtctgaggag atcatacctg ttaaacacct agaataacaa 16140
gctgctgagt atcgctcagt atgctgatgc acacatcctc ggggacctgt catcaatgct 16200
tgcaactgac ttctcttcta catcctgctc tgagatgtca cagggcatgc tcatggcaca 16260
cccagctttc ccaccagcct taagagtggc tggggatgtc tcaagactga ttctgcagtt 16320
gcccaagtac cttgctggct agccatgtcc cagtaaactc agccaccggc tgttctccct 16380
ccccacgtct aggtttttct tttaaaaatt attgttttgg aaaaatcgct gacacaatgg 16440
gacagtgggt cacattggca ctcacccaaa cctcttggcc ctgcagagaa tgtgcgtaga 16500
cctctgttag agtcaaggtc acttatcctc ctgcccacag cctgcagcta caggctggcc 16560
cctgtgtgtg aggcctctgc ctccagctct gtccttttc cattcaaatc tgtcttactt 16620
atttctgcc agggtaggaa ctgaacctgg ggtctcctgc ttgatgtgcc atatccccag 16680
tcctttctcc ttaaaaacct ttttacactt acttatttaa agattttttt tttaaattat 16740
gtgtctttgt gtgggtatgt gcacatgagt gcaggtgcct gtggaggcca catgaaggcg 16800
ccagatcccc tggagcaaga gttctagtga gccacctgac tatagggtac tggaaatgga 16860
acttagggtc tctgcaatag cactccatgc ttttaactgc taagcggtct ctctggccct 16920
tatttttgtt tgtttgtttg tttgtttgta tagcgattag aggacatccc tagtttgtca 16980
gttccctttt ctgtcatgtt gacagcaagc acctttactt gctgagccat tttgaaagcc 17040
caactctttc ctaatattat tattaaagtt agtctcacta agtgtcccag gctagccttg 17100
gatgttcagt cctcctgctt tagcctgggg tggcaggctt gcccacagag tccatatttg 17160
gttgtagctg ttaagtttag aggtttgtcc tgtgtggatc tccttcctcc tatcagtggt 17220
acaaccaggc ctctcttgcc acctgttctg caagccttgt ttcccaggag ctgatggcca 17280
ccttctaggc agggcgccct ggttgtggtt gctatgtgct cttcccacag accctgcaca 17340
taaactgcct agggttatcc tggctgagca ggcagtgcga gcagcggggc ttagagtttc 17400
ttgcaccagc ttctgcttga gtttcctggc tttcccagcc ccacctccat gttcggagag 17460
gtgttgatcc ctctgacgac caggctgagg ccagctcagg gctcccaccc acccttgcag 17520
ctgtaggagt cctggcatgt cagagctggc cttctggagt tggaggccca ggaaggtggg 17580
acctgggggc tcatcctgct ctgctcccta ccgccacccc aacccccatc ctgacctctg 17640
agccctgcag aaattctaag ccctggccct ggtcccctca tctggcctct tagcccagga 17700
ggctcccctg ggctgagagc ccatcttagc cagtgctcca ttgtagctgg ggtcctgacc 17760
tgcgctggcc tcgggatctc cttctcctgt ctgttcccag ccctcactgt gcctcttgcg 17820
cttcctttct tattattgtg aaatagtaca aagttctaac aaaggtcata atacacatcc 17880
gtcaggttaa atcagcccca ggtgaaaaga tggagcctca tggtcccgag gccctgctgg 17940
agggagccac cacccttggg tgctccttgc cttttgtaga accatcccta tatatccgac 18000
ttggtctggt tttgaacttc ctttagtgtc tacaaactct gactttattg ctgtggcatt 18060
ttgctttcgt tgctttgttt gtttgtttgt ttggagacca agcctgctct gtagctcaga 18120
ctaacctggt atcagtcttt ctgtctcagt ctctggcatg caaggcccac agatgcgcac 18180
cgccaagcct gaccacattt gcatcctggc tgtggcccgt ttttttcaag ttcatctatg 18240
taatagcgta tacctgtgcc tcctaactct ctgtgactgg acaatgtttt gtgtgtgtgt 18300
gcggttttta atggtataga tgtcacattg tgtttatctg tctttagccg gtggcagcag 18360
gtagctagtg gctcttgtgg gtgtggggag cgtggtgctg tggggtgtgg acacatgctc 18420
acttgtcatg tcctctctct ctccttccct gtctcctcct gtcagtgtct ccctctgtgg 18480
ctcatcctct ctctggcttc gatcttgagt acgttcttcc atctgcttca gtcccatcca 18540
tccacatcac tgtgggtgag agcttacgtt ccgaggcctt gggctggggt ccaggtgttg 18600
gctcagcctt ctcccagcta tgtgacctag tgccattggc tcacctctct gccttaggtg 18660
acttgcttta ccaggccatc atcgtgaaag gccatcagct gtgtgactta agcaacatcc 18720
gcttcctttc tggctcttct ggaggctgca tgcccttggc tgccatggct gctcctgctg 18780
tctagcttgc agccactgcc tgcctttccc tgtctccctg ctgctatcct cagtatctct 18840
ctcctagctc ttcttgctgt agactccggt cacaccgcat cagggaccat cctgactaat 18900
ttattgcctc cttttttttt tttaacctac tgtggcccca tcatgggctc tgaatccagt 18960
acattccaat acagtttgag gcatgggggt ggggtagaca ggtgggagtg gttcggcacc 19020
tggaacgctt caggcaatga cgctatgtgg acaccttgaa atcagagtct ctgtgattag 19080
tggctgggac ccttgaaaga ctgggtcttg tgggaatgaa gaggtgccct ggagtagcca 19140
tgcagtaagc agttgctagg gatggggtgg ggtcacacag ctgcctttga gtcatccgtg 19200
cttctataag tgaccccagt atcattgctg caccccatct gatgggccag aatctcctct 19260
taggtcaggt gtcactttgg ggtgaataga aagagtctca aggaaaaatc acacaagaac 19320
agggggtttg ctgggcagtg gtggtggcgc acgcctttaa tcccagcact tgggaggcag 19380
aggcaggtgg atttcagagt tcgaggccag cctggtctac agagtgagtt ccaggacagg 19440
cagggctata cagagaaacc ctgtctcaaa aaaccacccc ccccaaaaaa aacccaaaaa 19500
aaaaccccag gggttttat gtttattttg tttatgtatt tacttgtgtg tgtacgtgca 19560

```
catgtatgtt tgtgtgtgtg tgcatgagtt tttgcgtatg cacgagtgtg tgtgtgtgtg  19620
tgtgtgtgtg catacagacc tacagaccca aagatgacat caggtgtctt ctttttctgt  19680
cattttctgt gggaataaag gtagattcta gtattctggt tacagtgtcc agggaggtgg  19740
tggcatatcc cagcactggc caatcactta gccaggtgtt accatcttat ctgggttgcc  19800
cgtgtgcata tctggctcct ggctccttgc tgttgcctgg tctccctgtt taatgtctgt  19860
gagagcttgt ctgttaccat ggtgacagat gccctggttt ttccaactct atcaaccata  19920
tacagcatac gcaacacact tcctgggacc tgccacattg ggtggcttca gattggtccc  19980
tgggatgttt gagtaggcag ctggctgcct actgttagca ggctggttac acaagtgtcc  20040
attcaccctc tcagagttct gtgtgaccag ccttcttgaa gaagacgacc tgtgggtgtt  20100
tcagtttgca tttctgaggt gtgtgtgtgt gtgtgtgtgt gtgtgagcat acatctatga  20160
gtgtgtgtat atgtgtaggt gggtgcattt ctgtgtactt gtggatacca gagtctaggt  20220
tgggtgttct cccccatgat tctcaagttt gcatgtttgt ttattctgag gcaagctctt  20280
attgtgtagt gtaggctgac caggaactca ctgtgtagat caggctagcc tcggaactca  20340
ctatgtagat caggctagcc tcgaacttac agagatgcac ctgccttttc ctcctaagtg  20400
ctgggattaa tggcatgcac caccacactt gatcgtaaat tatgtgtgtg tatataaatt  20460
atatatttat ataaatctac aaaatgtata ctatatttat gttatatata tttatatata  20520
taagtaaatg tatatttggt ggtgccggag tttgagccca gagcttcgta ggtgctagtt  20580
aagctctctg ccactctcct acctcccatg ccagtttatt tatttattta tttatttatt  20640
tatttattat ttatagattt atctttagat ttatttattt tatgtaagta cactgtagct  20700
gtcttcagac actccagaag agggcgtcag atctcattac ggatgggtgt gagccatgtg  20760
gttgctggga tttgaactca ggaccttcag aagggcagtc agtgctctta cctgctgagc  20820
cacctctcca gccctgccag tttatttttg actcagggtc tctcactgaa tctggagctt  20880
gctgattgtc tagactgtct gaccatcaag cttcaggaac cctcctttct ccactgatcc  20940
caatgcccag agtgctgtag ttatagacct gtatgtctgg gtttgatgac ccacttggct  21000
ttttcatggg tgctggggcg agggtccgca ctcgggtcct cagcttgaac ggctggtact  21060
tgtgtctaga gccgtctgtg cagcctgctg agcctcgctg gcttgtgagt aaggctctga  21120
gaacttgaag gactttaaca ggctaacctg aggtttgggc ttcacttctt cagagcattt  21180
gtgttgcgct gagcatgtgg ctcactttgt agctgcttgc ctggcacaca cgaggccccg  21240
ggggcagccc ccaggacccc atgaacttta tatgatggtc cctatctgtc atctcagatt  21300
ctgcttggct actctaggga gtaggaagcc aatctgggct agagagacac tggcccccaa  21360
aaaggaatct gtgatgaagg tcatggggct caggagtgtc tgcatcttgc ctgggatgac  21420
agtttgatag aggccagcag aaacgtcccg ccaagggcta gaggccaagg acgagtctgt  21480
cccatcacca gagctgaaat cagggtgtgt ttctttcagt ggtggtgccc cagcctccta  21540
gagaggcctg tgttagtcac ctaggtctaa acttgtgtcc ttaagccgtg ggaacttcat  21600
ggctaggctg ggcgcttcta gtgtcttgag ggctcttggc tctctccatt cctggaggtg  21660
ttcaccgttc ctcagttgac ggcatcaatg ctcctgtttc tgtctctatc tctgtctcaa  21720
cgtggcctcc tttgtatttt ccatttcctc ttcaaaactg agttattagt attatttatg  21780
tgtatgtgca tatgcctgca tgagtttatg tgcatagcat gcgtgcttgg tccccatgaa  21840
ggccggagga catcagagcc cctggacctg gagttacaga tagtgtgagc caccacgtag  21900
```

```
ctgctgggaa ccgaacaccg atgcctgcat ccatcgagcc atctttccag ctcccctgct  21960
cttctttgag acccaaccta agtccaaaca ctttgacatt cattcctatt ttgagttaag  22020
agtctcaccg tgcagcccag gcaggcttta aattcacaat cctcctgcct cagcttccca  22080
agtgctgaag tgacaggcct gtgccactgc gctgatctga tatttttaac ttgacatctg  22140
gccagaccct atttccgatt aaggtcacac agggcacagt caagtatctt aggatcacca  22200
cctacataga tgcatggcag agtacctttt gcccagacag cccctactgt gaaaataaac  22260
tacaggacaa aaatcaccag tctgtcctga tagccggctc tcagcacttg aaggtaggaa  22320
gcaagaggat cagaagttca aggtcatctc tgctaatagt gagtttgaag ccagtccaga  22380
ggggaatgac cctctgggaa gacaaaggtg acatgacact cgcgtccccc agcgtcccaa  22440
gcacagaggt aactttggtt catggctctt tgttccttgc tgcaaaaaac atgtttgtgt  22500
ttagaagagc ccctccctgc cctccctggc ctccctctcc tggcccccgg tacccgtgcg  22560
cacttcctgc actttgcagt ctcggattgg gcactcagat ggctctgggt ctccccctto  22620
tttccagagc gctggaggga tcagccgtgt ttcccatcag ccaaggccgc ggggaatggc  22680
tgtgcattca atagcatgtc tctgggaaat tgggcctatt ccagcaccat cttcccgtgt  22740
cttccggagc tttctcagga gatatatttg tttctacaga cgccactaat tactcctggc  22800
tgggtgcctg gaaatcacat ctgtggatta aggtgccacc agatctgagc ttcctctagg  22860
gccccaggag tcctgacata tcccccattc agcatacttg ctcgcttgct tgcttgagct  22920
cagtttgatt tctccactca tacagcccag gacccottgc ctagggaatg gggccgccaa  22980
tggtggacta ggtcttctca ggtcagataa gctaatcatt tagacaatcc ccacaggcca  23040
atccaaatgt aggcaggccg tccttcactg agaccctctt cccaggggaa tctacgttgt  23100
gtcaggttgc cagagctaac cgctgcaagg ttataatttt aaaggacaag acacatcatt  23160
gggcgtgctt agctcaaagt tgtggcttaa gtacgtaaaa gagtaaaggt taatcaacac  23220
agaatttggt ccccgaagtc acttgccgtg tttagtcacc ctcagagctt cacagtaaga  23280
acttttctca aagaaaaaaa aaaaaagaac agccgggcag tggtgtcgca tgtctttaat  23340
cccagcactt gagaggctca tatttctgag ttcaaggcca gcctggtcta ccctccaggt  23400
accatgctgt gtgaggtcca ggcaagctca ccagatccag atccgctccc atctactgag  23460
gtccactcaa ggcattttct gcaagtggag gctcacaggc actgaggtag aggtacccgt  23520
gtgaggccag atgagtgaac cttgactcaa atccccatgt ccaggaactt gctgtgcatc  23580
aagatggcag gatttatgtg gcagcccctg gcagagctgt cccottaagg atcttgatct  23640
ttagaccatc tcctctctgg atggtcatct ctggtgtgtg gctgagggca agaacttgat  23700
tccttgcgcc tttggtttcc tgcttgtcag tggggctggg gctgagagag ataaatgggt  23760
atcattgggg aatcagagag gtgttgccgg gatcggatcc agctgctggc tggcatgggt  23820
agcaaggtgg ccaattcaaa tcgacagtga agagggccag agagacggct catcacgggg  23880
aagggttctt gctgctaagc ctagtaaccg gaattggatc tctggaaccc acatggtgga  23940
aggacagaca gactcctata agttatctat cctctggctt ccacacgtgt gctgtggtgc  24000
atctgtgcct gtgcacataa taaataaata cacaaataag taaatgtgat ttaaaaaaat  24060
aattgaaagg gtctaagaag tgtcctgtgt tttctgtaat tctccactaa gtttatggcc  24120
gatggccgta tggagtagaa tggaggaggc gggcccaggt ctagcttccg actcagtcag  24180
ggtctcatct cccaaggact cagtttcccg gtctgcagag tggttggtgt taattcctgt  24240
atccagttgt caggacttag gggtcagccc acctacctat aaggctgttg tctggggtgg  24300
```

gagtcattga tgatgatgaa ggtgtccccg gggacctctc acacaagggg acgagtcaaa 24360
gaaaggtgag gagaagaggc cagccaggga aatggccatg gctgtgggcg ggaggctgca 24420
gtggactgag cagcctggcc ttcgaggtct ccccacagct gaccttccca gtctgggctt 24480
tcatggtgtg tggtccagga gcagataagt ggaccgagct atcagcagtc agggtcaccg 24540
agtcctcatg tggaagtgga ggcgggggag aaggggaagg gagatataga atgggctttg 24600
tttcaaggta gaggccaatg gagagccatt gtggaagaac cctatatgta tagcctggcc 24660
tcagagagtg ccattgcccc ctacccagac ccacagcggg gtctagctga gctctggctg 24720
aaaaaaaaaa ccaaaacccc ccaaacaaca ataacaacac aaaacctgtg ggattggaag 24780
gtgcctgtct cctagcagct gggataccca caaactccag ctctaagtgt cgatttaaga 24840
cacttggtgc cttaagtcac ctccaggtgt ctttcagtcc caccaaaacc ttggggatta 24900
ttgatctggc agatgggaca gacacagagg agcagggtag agaggaggag gagtctgagg 24960
ctcttctggg gaagcaggtg ttccctcttc ctgttgagct gactgccccg ttgcatgctg 25020
ggcccctccc aggccctgga gttgcatggt gggcagagaa acagggtctt gatggactgt 25080
ctgcaggact tgacacctgc acaagagggg cagtgtgact ggcctgtggt gagtgtggct 25140
aacaaggcca ctggtgaggg aggggcctct ggtgctgagg agaagcaggc ccctctgagg 25200
gccaggcaag gagcatttcc acctgacaga aaacgaaatg agtatccgaa gtagtttaca 25260
ggtggtgaga gccctggagc agatagatgc tcaggacacc tgtcactggg ctgcaggttg 25320
ctgaaggtca aaggtcgtgc aaacccacaa ggacagcctc tgttgaactt agtaggtcgt 25380
aggtgatgtt gctggtactg taaaagggtg cagctgccat gagaagctgg tgtcaggtca 25440
ctgtcccgtg cagccgtcct cctggggagt ctggacacca cacaacagct gaaggtagaa 25500
gggtcccaat acttagtgat gctggatggg cagataggaa aagcagatga aatacagaga 25560
ggtgagctgg agagggtttc agaggtcagg agctcacatg gctcttccaa aggaccagag 25620
ttcagttccc tgcacccaca tcaggcgagt cacagctact tgtaatatca gctccaggag 25680
atctgacacc cttctgggag cctctttagg gactgtgctc atgtgcacag agcaacacac 25740
acattaataa aattaagatt aaatcttcag aaatgaaaag agggctctcc aagagggaat 25800
agtatgcagc cgtataaagg aagagagaga ttccatttat ttatttattt atttatttat 25860
ctatctatct atctggagac agggtttcat tatatagtcc ccaggtaaat agttcaaact 25920
cgtggtcctc ctgcctcagc tttaaagtcc tgcgatagct gctgcagagg agagaattct 25980
cccacacact ggaacatgga tgaatgctga agttagattc tgagagacgg caggatggtt 26040
gcagcgtgat ttcgtttact ggggccccta gagtacctat tgatgaggtt ggagaaatgg 26100
gacactaagg aggtagtggg aggggaaagg ggccagggag agtgttaagt ggagacaggg 26160
tctcagaagg acatggaagg gcgtggccat tggtggggac agttgcccaa gccatgggtg 26220
tacttaacac catcagaatg gatgctataa aatggcactg cctttaatcc tagcagtgga 26280
agcagaggca ggcagatctc tgagttcaag accagcttgg tctacagatg gcgttccaag 26340
acagctgagg ctacagagaa accatgtctg gggttggggg cttgggggga gagtgacaaa 26400
acaaaaccca agtctggaga ctttagcatg ataaaaatga ataaatcatt atggctgatg 26460
tcccctgaag ggacatgggt cacagccctc cttactctgg tttgtaaaag gggggacccag 26520 tggccatagt gactatgttc cagcctgatg agtgtcttag aaaaaaccca gttccctgga 26580
aatatggccc tgagctgata gctgatgctg gctgccactg cccttcctct gaggtttggc 26640

-continued agggctctgg gattgttctt gaaccccagc cagtctacag ctggaggctc tgtgatatgt 26700
cttccttgaa gtgtctggga gttggtatct tcctagggac agccttgtgc cccaggctat 26760
tgcatgcagt gccactggaa ggagccctaa ggggaccagg caacagcctg gggattaggc 26820
tgtagagacc tgaggatggg gcccctggcc aaccccaacg gccttgtgtg gcactggctc 26880
aatggagaac tcacacgttt ctaatgtctg tagctgctac tgaaagcatt ctctagaagt 26940
ctcccaaaga cttctcactc agtctaaagt cagggctacc ttccctgtat ggttgggctc 27000
tacccaacag gtgaaccaca tgtgtttcta gaggggtagg aggcagagag gccttgggtg 27060
ggcaacaagg taatctgctt ctgtgtcaat ttcttatctg gcatgtggct gtcgagaagc 27120
agagaccgga ggatcatggg catgagctat acactgaggt ccaggctagc ctgggtgaca 27180
taacctgtca gaaaaactac aagaaaagat tcgcattcac catctggctt ggaccttggt 27240
taagtgataa ccattgtcat tagcctgaca cttaggcgcc aggatcaaga aacaagaact 27300
cccagaatcc tttggggcac cagaaagcct ttcattttga gataggctct ggctgtgtct 27360
ctggctctcg tggaagtcac acagcaatcc ctttgcctta gcctaagtgc agagattgta 27420
gacgtgagtt atactagcct cctctgcatg gattggcttg acctaaactg agctgggctc 27480
tccatcgact tgcttctgcg atttcagagt ggcagcctga cctagctctg cagtggcttg 27540
gtgcagctca gcctgaggct ggtgagatgc ttacaagtca tagctggttg ctgcttggtg 27600
ctggtggtca tgttatgagc aaactggtcc ctggtcagtg ggctccggat tagggctgtg 27660
atggaggcct ctaggaatct cgctaagtct ctcactggtt gttttcatct ctctgagcga 27720
tgtgtaggat tgagtgacag atggcagata attgggagtg ggtgacaggc ttcagtattc 27780
tactttaatg gctgttaccc ggtgatgccg gcataggcgt ctgatgctct gagtacttcc 27840
tctcatgtcc ctgagtcatg cagacttagg aggcctcttc tccactcaca accgtttccc 27900
tgagggcaga atccagttcg gttaactttg cttcgtagta ctaaatacca gtttggggcc 27960
tcgacagtgc gggggagtgg ggcgggttag aatgaaaaaa aaaggagcaa acaggttcat 28020
taacagctaa atgaatgaat gactgatgaa aggatgaatg aatgaagtgt tctcagcctg 28080
tgctgttctg ggtcagggct gagtgggaat gtcaaagggt gtggccacta tgtgagccat 28140
ggagttgggg ttagagggaa ggctgcctgt gggctgcacc agtgttgggg tgcaaccctt 28200
gttgggcagc acctagtttt ccaaagggag tcagaaacga ggcttttgag actaaccttg 28260
gttatgtctg acagggtttg ggggtggggt gggcacatag acactcttgc tttttgtttg 28320
tttccttttc ttttctgggg agtgtgtggt gtcaacttga cagggtctag aatcaccttg 28380
gagacaaatc tctggatgtg tctgtgatgg agccatccta actgctggag cagagaaaaa 28440
ggagaaagat cctagcagtc attcacccct ccctgcttcc tgactgtgga cacagcctgg 28500
caagctgccc ctggcttctt cctctattgc ctttccacca agatggactg cggctttgat 28560
cagtgagcca gattagcctt ccttaagctg cttctgtcct acgtatgtat gtatgtatgt 28620
atgtatgcat gtatgtatgt atgtagcaag ccaggggcct gtgcacatac cacacaagtg 28680
ctccgatgtt agcatttggc ccttgagact tgagcgttgg agtttctatc gagtctggga 28740
aaattactgc acaccagaag cctgttaaac agtaacaggc cccagagcga gagccaacct 28800
cacacgcctc ccgtaagctt ctcccactga cagctgtctg tgggccagac acggttgata 28860
tgcgcacctg ctccctggtc agcatggtag gggttctcct ctgagggact ttattggggt 28920
agcccttggg agcagaagga atatggtccg gggattgaca tacacatagg tgcccacgtg 28980
tttgcgtcca gtccagtcca accagggagc ttcctaagaa ccctggagtg gctctcactc 29040

```
cacttgtctc cagggaaact cactaggtcc tgatgttgcc ctagaggatg ctgggacctt  29100
ctgatggagc caccttagcc ctctttcctg gggctctgac ttttatagct ggacaggctc  29160
tctgctttgt caagctgggg tcaaagtgag gtcacaaggc ttataccttg aggacacctt  29220
tctacttctg tccctaagat gtatctgcct gctctggtgt gtcaccggag cagaaaccag  29280
tttccccata gcccgaggga ctcaccggcc acaccctttg acgtctaggg atcatttgag  29340
gatgagatta tgcatctccc agccactcaa tcggacgtcg gcttcaccct tgtgtattaa  29400
gctactgtag caaaaccctt gaaaacattt atggataacc agcgggcagg tgctggcgtt  29460
tccccaggat gtacagtgaa caggtactta gctctagcag gcaaaccatg gcgccgacac  29520
agttccaccg acatcgtgca tgcattctgg ttgccccaga gccttgccaa cacttgtgat  29580
tatcaatccg tctccttttg gctgtgctgg tatacgtcat agagattctt gtgaatttgg  29640
gggatatgtc cagagttggg gagggcttta tgatgtcaca ggccaccagt ctttatgctc  29700
tgtcatcctt tgggtatggt tttcagtctc aaagctttcc catgatccaa ggtagctctg  29760
tagctctctc catcaggacc gaatttctgg gtgggggtgg cgggtgtttc actgaaacca  29820
ccggaacttt tagtgtggtg ggaggggctg ctgttacaaa gattggtcct gtccattttc  29880
ttttttcttt ttttaagatt tatttattta ttacatgtaa gtatactcag acacctacag  29940
tatgcatagg gcatcagatc tcattacgga tggttgtgag ccaccttgtg gttgctggga  30000
tttgaactca ggacctttgg aagagcagtc agtgctctta actgctgagc catctctcca  30060
gcccttgtcc attttcttcc ctgctgtggt ttaggcctag cacacagcct cttgtgcact  30120
gggtgctcag cagaggcctc gtggatgcca ggaactgaac ccaggtcctt tgtaagagca  30180
gccagtgctc ctaaccactg agccatctct ccagccattc ctggtgtgtt cctggtgtgt  30240
ggtgtcttca tgccctaggc tggattgtcc tttggggccc atccttcctg tatacatagt  30300
aactctacag ggctagtaca ttgcgactgg ctggctggct cagagctgac aggatatgtg  30360
tctcaaccca gatccagggc tggtgaaccc agtggcaatg accagaactg tttcctctcc  30420
ctcctcctcc tccctctcct cctcctcctc ctcctccttc tcttcttctt cctcttctct  30480
ccttcctctt cttcctcctc ttgtttggag atagggtttc tttctgcatc cctagctgcc  30540
ctggtagacc accaggttag ccttgaacac agagatccac ctgcttctgc ctcctaagag  30600
ttggattaaa ggtgtgagcc gacctctgtc agcctggctc aaaaacctgg tttttttttg  30660
aacctgaaat gtgtttgctg tgattcttgg gggaggaggg actggatttt gcaatttccc  30720
aggtcagatt aatgattgct ttgcgagggc tgcagcacct gagctgagcc acactgagca  30780
gggcctggag aggctaggta cagtgtcctg gagatcctgt gcagtcctgt gtggggatag  30840
aggctggggg agcttccatc tctgtgatct tcatgaacca gaggcctctg agcctgatgc  30900
ctgtgcacct gggatatatg gtcagagagt taaagaggtg tagtgaccag aagtgtcctg  30960
ttacccacac agagggtctg ttgggtccct agcacctcat gtggcggcct tgatcagctc  31020
cagctgcctt tttgtttgtt tttcttttga atggagcctc tgatgtccaa gtgtgttcgg  31080
ttcctgcaga ctgacctata tcctggccat cagagaaccc gctaaccccc ggattatggt  31140
gctcactccc agtttggctt gcccagaccc cacctcagac tcaaagcctt tgtttctctg  31200
atgcccagcc accctaccca atccctctct ggaaggcaga tggcttattc tgtgcttatt  31260
ctgtacccag gtcactgctg ccaagcacat gcctagtatg tactggggtc gtgggggagc  31320
aggggtccaa gcaaatgatc agaatgctca cagacctttg tggtgtggag catggagatt  31380
```

-continued

```
gctccagttt tcctgtctct cgggcacttg gtgtgcattt tggacatccc caaggcttgc  31440
agaatggagt cgaggtagcg tatggctccc cacggaagga ggaaacctca gtgcattagt  31500
ctgtcggtat tgctgtaatg aaagacacag gcttggtgtt agcatcacat ctgatggggc  31560
cacttcatgt tgttgcgaac tgcttggagc agctatgagc cgagagatta cagtggggaa  31620
gccagaaggc aaagaaagtc tgcaccatcc ccaccaccaa tccccagccc tttcccagtg  31680
gggctaagcc tcctgagggt cccctcccaa ggcttcatgt cagagaccaa gtctccaact  31740
gccaccgaaa gcacgagaat aaagtgtttg cagagcagac atttttaagg taatgatctg  31800
gtgggccaat gagtgtcctt tagagaagac agaaaagaat gtgcagtgga gaggagggga  31860
cagagaagca ggggtgggag ccaagaggct gtacgaggct gagaggctca ccgctggagc  31920
tcagggatgc tttggtgaca gctggcccag gaagtgggag ctgtggtcat ttattttaga  31980
aatataaatg tgtgtgtgtg tgtgtgtgtg tgtatctgtg cacatgtgca tactcggtga  32040
ctttggaggc cagaggatga tgtcatatcc catggaacta gagttacaga tgattgtgag  32100
ccaccaagtg ggtcctggga tttgaacctg ggtcctctgg aagaacccag ccaatgctct  32160
aaccaatgaa ccacctcact ttgttgttca aaggcagggt ctctcactag gatgtgagtc  32220
tcgccatttt taggctagcc tggctggcca gcaagccctg ggcattatcc cgctgtctcc  32280
acctctccag agctgggatc acaagcatac accaccatgc ctggctttgt atgggggcca  32340
aactcggctc cttccactta tgaagcaagc actttatggc tgagccatct ccctagaatt  32400
ccaaactctg ttctcaagaa cacactatgt caaaggtgcc cacaggatgc tgggggtttg  32460
tttcctacaa tgatggatta tggcgctcca gaattggctt gggctccttc ctccaagtcc  32520
tctgaggtcc ttccaggtgc ctggcactgc tcagagttca cggatccagc atgagcatca  32580
ttggtggggt ttatggcctg gcagagagac gtgagcacaa tacacaggat gagtcattaa  32640
cgtaatcggg aagaaggcag ggagagcctc ggaataaaca agagtttaag agggagccca  32700
gggctcgggg tgggctctgt gggggttcct gagcacagac acaggatccc aggaggcttc  32760
ctctgcaaac atggaaggca gaagaagcga cgaccagtgc aagggcctgg tgggtgagag  32820
tgtgtgaaca ggcaaggcag agcaagcatg ccaggctggt ctaaaggact aatgggggta  32880
tcagtaagac acagccctag agatgccact gagccagatg ggcaaaggct tataggtcag  32940
tgttagcatg gtaaaattta caataaataa ataaacaaac aatccatttg gtttggggat  33000
ggccatacat atgccagggt gcatgtagaa gacacagaac aatgtcttgg agtcttctgt  33060
tctgttgtgt gggtcctggg gatccagctc tggtccttag gcttggtgat taagctcctt  33120
tattttgcag gccacaatct gaaagatgct gggccctggg cttcagatag gggaaggcca  33180
ctccccacag gcattccatt ccccactctg gtggctgtac atgaggtacc tcgtggttca  33240
gcctcccgca acaccccaac cacctgcttg cagagggaac cgcccatcac cccatggttt  33300
tcagtgagat tctgcctagt cctctgtgcc aaaaaagcca agcagaatct ttggggaggc  33360
tgcctttcct gctctcctga gagttctctg ggtggcgaag ggagacaatc tgtctgagat  33420
gaggaccttc gggcgctctc caccgctctg ttggcctctc aaaccttgag aatccctccg  33480
gggcagagtt ttcaaactgg gatgttatct ttctgatatc ggttgtgaca tccctggggt  33540
gtgtgggcaa ctgatgttta aaacatggcg ggagtgtgct ggtgatgatg gggtgataaa  33600
gaaatggctc agaggttatg aggagtatgt ctcatctcac acacacacac acacacacac  33660
acacacacac acacatacac acacacacac acgcgcacgc acatttgagt gtggggtgct  33720
aggaactgaa ttcagtctcc tggaacagcc tcaagtgctt ttaaccacta agccagctcc  33780
```

ccaccccac cccaccccg caaattaaaa acaagcaaat atataaaagt ctaaaacaca 33840
gtgtgagcca ggtgtaatga taccccaggc tccctataat ctggacattg aagaggcgga 33900
ggcagaaaga tcaggagttt cagagtcatc ctcagctaca tatcaaatca gaaatcctgg 33960
agttggggtg gaaatcattt tgtactggag aggttgccct gggtggcagg cagcatttgg 34020
gagctggtat tcggggtgtt gtcccaggta gaggctccgc agagccatag ggcactgcac 34080
agatatgatc tatgttagaa gtgcacacaa gtacccgctg gctgcccggg ctgtgtacct 34140
cacccatgcc ctcacttatt tagcttcagc ttcctattgc agtgttctgg ggaagtatag 34200
tctacttgac tttacagctg acctttaaa aatgatgggt gcatttcagt ttcggtattc 34260
aatggagggc gcagcaagat ggctcagtgg gtgaaggcac ttgctgccaa gcctaatggc 34320
ctgagttcga tccctggggc ccatatggtg gaaggaggga gaactgtcct ctgacctcca 34380
cacatgcacc ctggcgtaag caaacccaca cacataccca tatacacaaa taagtaactg 34440
cagagattaa aagaatataa aaacctttat tgagacacgc cagccttgtt tattctggaa 34500
tttctcacag taggactcac aacgccctgt gcatatttcc ttctgtattc tctcccccag 34560
tagtatactg agtccttccc cttcccctcc ctttttcttt ttgagatggt cttacgtagc 34620
ccaggctagc cctgaattca ctatgtagct gaggatggcc tgggactcct gctcctcctg 34680
cctgtgcttc tggagggctg gggtggcaga ggtgggcact gtgcccactt tgttcagggc 34740
tggggatgga tctaatttaa tccaccaggt cacacacaca cgagtggagc catgagcacc 34800
cgtgggactt gtctcgtgtt ggcagaggca ggttggtaat ctcccagcag ctccacagat 34860
gtttcctaga gtctcggttt ataaacactc ctgtcatggg tggacacgga gccccgcacg 34920
cttgctcggc aggccagcct ttgctggaac accctcctgg gaccttttcc tggcaaagcc 34980
tgttttgtct ttgttttgtc ctcttgctgt tgtgaagcgg gtgattgcca tgcagcaagg 35040
ctggcctcag aaagccagtc aaccctctgc cttagctgcc tgagcgctaa agtgactggc 35100
gtgtgctcca acagcgtgca ccccgagagc cagctcttaa tttttttttt tttttagttt 35160
tccaccatgt gttgatttgg ttgtggtggt agggattgaa cccagggcct tgcacgggct 35220
gggtaagctc ttttccactg agctgcatct atgtcttctc ttcttttaaa tgtaaaatcg 35280
tttattcagt ctttgagaac cacaacattc atacaacgta tttcaatgat acacgcttgc 35340
tactcctccc agatcccccct acaggccact cctgatttta tatccatttt ggttttggtt 35400
ttggttttgt tcaccccttc gagacaggat ctcactagat agtgctggct ggtcttaaac 35460
tcacatagat ccttgtgcct ctgcctccca agcgttggaa gtaaagtcac gtgccaccac 35520
agccagtact ttcttcttgt cttttctttt tccccttat ttacccactc aatccaattg 35580
ctgtggccca tatacatatt gtaggggcag ttttacactg tgtggcagta agcaaaatag 35640
tagttctggg gtcatggggg aacagcaccc ccagagcctg tctcagccat ttgattctca 35700
gccagattta tagtatcggg catgtttttc gtcctatgga gaaggcctta aatccagtca 35760
gagagtattg gctaaaccca taatatccgt gccactaatg cgtccgtggg cagatcttac 35820
caggctgata agctgcaggg tagtttgcag gagtcacagc tgcctaaggg tgccagggtc 35880
ttgaaatgcc tctctgtttt tgccagatgt tcaggctgtg ggtgaccaac ggaaggtgcg 35940
gcaggacatc tcttaggtgg actcagcagg ggatttttct ttcagtgggt cccgaggagg 36000
acaggccaga cccagccatg gctttcatga ctccggcctt gcagtactca aggacaaacc 36060
ccaggcccag agagccaagc taggcctgag agagtgtggc ccagtgtccg cctgcctcgg 36120

```
agtctactct gacgtggggc tgggcttgac ctgccagttc tggcttgcca cctcccctgg  36180
agcctctgcc tgttgtttct ggctgtttgg ggacagtggg gtggttgtct ttgtcctggc  36240
aggtcgagtt caaagtcaaa gctgtttggc ttttggacac tgctatctct gatgagctgg  36300
gggtggtgac tcttagctct gtggcattag cagaggtccc aggtcaggga atggtccacc  36360
tcttcctcct agccttggag aaaatcagta gttctgtttt gagacagagt gtctcattca  36420
ctgtgtatcc caggctgacc tcaaagttac catctaactc cttcagtgtc ccaagtgcta  36480
ggatgacagc cctgcatgac tggacccagg gctgcctgca cactaggcaa tcactaagcc  36540
ccgcccccgg tcctgcttac tgtcttctgt ccctcactgc tggtgactca agaatcatcc  36600
tcttccctct ccctgctcct cagtacatca cacagcactg gctctgcccc cgctccaccc  36660
ccccccaccc ccaccccccc acccggtgca taaagccctt gtcttcccga tttggtaaaa  36720
gcttcacggg actggagaca gccagcctgt ctacttccca ctcctgtctg ctactgcggg  36780
aacctcatct gtcaaaaatg aatgaatgag tgaccaaatg aatgaatgaa gaaaagaaca  36840
aaagaatgcg ggagtaaatg tgaaatgatc agtgaataat gaatgaatga acgaacgaac  36900
ggctttctgg atgagttatt gactgaaaga atggagagac agccacctgt gcagagctcc  36960
agccctagga gcacctccct cgatgagcac tacctagcca gtgttctgtt ttgctgtgaa  37020
gagagaccac aacgaagaca actctgtatt ataaagcatt taactggggg cttgtttaca  37080
gtttcagagg cttagtccgt tatcctcatg gcagggagca tggtgcaagt taggtggagt  37140
tagtgttgga gcaagttagt gttggagcag tagctgagat cacaggcaga gagggagaga  37200
gagagacagg gagggaggga gaccaatgga ccctgtgctt ggagtgagct tttgtaacct  37260
caaaccctgc ccctagcgac acacctcctt caacaaggcc acacctcctc cgacaaagac  37320
acgcctcttc ctccgacaag gccacacctc ctccaacgac acaccccccta atccctgccc  37380
atagcgacac gcctcctccg acaacgacac acctcctaat ccttccaagc cgttctccaa  37440
ctaaaggcta agctgcaaat atctgagcct gtggggcctt tctcattcag accaccccag  37500
acacccttcc agatgagcct tggagggtcc atggcgcagg ccaagtctca ggcagctgtt  37560
gcagagccgt aaagtgggga agcccctcct cacactcctc cctgtgtctc cccacagaat  37620
gtccgcatag acccgagcag cctgtccttc gggatgtgga aggagatccc cgtccctttc  37680
tacttgtctg tctacttctt cgaagtggtc aacccaaacg aggtcctcaa cggccagaag  37740
ccagtagtcc gggagcgtgg accctatgtc tacaggtgag gccaggcagg gtggggtggg  37800
actgtgtgtg ggtgtgtggg tgtggagggg ggtgttctgc catgctgagt tttggagatt  37860
gattgctcca gagacagaag tcggacagac accgcctctc cacagactgt cagccacaca  37920
gagaagccgg aggccacagt ggctgacagt ctgtggagag gcggtgtctg tccgaggcga  37980
gtgcatactc gcatgcgtgt cctggggtga gggctaatgt gagtgtaaat gtgttgtcat  38040
gggggcgggg cacagaggac ccaacagcgc acaaaatggg caaaatggct gctgttgagt  38100
cagaaaagtc aaacaaacat gcagaagtga agccagttac gcagcatcta agaagtgagc  38160
ggtgctgggt agtggtggca cacaccttga atcccagcac ttgggaggca gaggcaggtg  38220
gaattctgag ttgaaaactg gatccaggag cggctgcctg gtcctccacc ttggacagag  38280
agttttaact tccataatgc ctattttagc cccatctgtg agacagaggt aatggtaccc  38340
actgtgggta ggttcaagga taagatgaga tagttagttg gagccactta agctctgtct  38400
gccatgccat aaactctcag taaacgctgc ctgtgtggat atctgctcca tgctggttgt  38460
caagtgaaag ggagacgtgg ggggtggggg cagcagttgg agttgttttc cagagaggct  38520
```

```
caaagagcct tatggctcac cagggaaagc agagaagagc tgattggtgg tggcagtgtc  38580
ttgccctgga cagacagcga ggatataaac aagaggtggc aagcttgatt tggtggcctt  38640
ggtgctgttg ggtatcagtg taccatcacc ccagggcatg ctgggagatg atgggtgctt  38700
tcatgtgacc tcacagagcc acagctgact caatgccttt ttacagggag ttcagacaaa  38760
aggtcaacat caccttcaat gacaacgaca ccgtgtcctt cgtggagaac cgcagcctcc  38820
atttccagcc tgacaagtcg catggctcag agagtgacta cattgtactg cctaacatct  38880
tggtcctggt gagactgtgg ccctgtgtca accccatgcc aaccctgctt cctcccagct  38940
tagccttcag gagtcagaga gcaagggcca cctcagcccc actgtctcca tggtgaccat  39000
cccctccttc tcattgcctt acctcccatc tgagactccg ggacctccac tgtggtccct  39060
ggggaagcat gaaggtcaga gccactgggg gccagagggc aggtgggagt ccggaagagc  39120
aggcatttat tgagcacact gtgtggggtc gctgagtctg tcctttggtg tatgcgggga  39180
tctactcaac cctgctgttc aggggaggaa gcaaaagcca ggcagaggca gggaatttac  39240
acaggggcca gaaggaccct ccccaaggac aaaatcccag ataccaattg ggccagtgtt  39300
accaaggcag gatcggatcc tgtggtcaga catcacggcc ctcgctggaa gtttgaggac  39360
agggtacacg gtggttggta gtggggggac agtcaaggca tgatgtcacg aggtaagcat  39420
taccattccc agtgacacta acttgagaga ttggaactgt gagctttgtg tgattttcat  39480
gctttttaga agattcttct gatctccccc cacccccacc ctcaaccata ggaaactgtt  39540
gaaaacacca gctttcctgc agttgatgcg ggccgatgct gactggattg gtcctttagc  39600
caccttgcct cgagtccatt ttcagaggtg tcccccgggt ccgatggggc tggagggaca  39660
ctttttgttt ttattaattt attatattac tactatcatt atcattattt tgagataggg  39720
tgttactggg cagccatagc tgccctgtat ctcattatgt agaccaggcc agccttgaac  39780
tcacagagat ctgccagcct ctgcctcaag tgctgggtgt gagccaccac atttgtcata  39840
ttaattccag tttttaaaaa ttatttattt tatgtatatg agtacactgt agctggcttc  39900
agacacacca gaagaggtca tcggatccca ttacagatgt ttgtgaacca ctttgtggtt  39960
gctgggaatt gaactgagga agtagtactt taaccactga gccatctctc cagcccttaa  40020
ttccattttt gatattgaaa aagcaacagc attctgtgct gggccagcag gatggctcag  40080
taggtaaaag gtgcctgtca ctaagtcgga tggcctggct ttaatctcca ggacccacat  40140
gactgcctca cattgtcctt tgacctctat acgtgcacta tagcacccct caataaatat  40200
aataaaagcc ctgtgttgaa ggagacctgt aagtgttggt gggtaggcat catgcgcttg  40260
cttgatggaa agaacctgga gacaccagcc atgcgttgcc caggaggtgg aaggtggctt  40320
ttggttgaat ggcctttggg aaaaaacaag agcccagatg ctccatacgg aggaagaaca  40380
aacaagaaaa ctataaactc aactgaactt ggggcagtta gaccctgggg gggcttcggg  40440
ggagtagata ttctgggctc ccagtgttga ggtggggcag ggacatgaga agtgaggtgg  40500
aatccctgtg aggagactgc ggcaggagaa tgctgatttc caagccagcc cagattaatc  40560
attgagacct tgctgtaaac atgttcaaaa ggaggccacg gggagtcggg gaggctttct  40620
ccatatgctg tgtttctagg ctcatgttac tgatagaata gggttcacgt cctagctata  40680
aaccgggtat ccaaggggct ggcgagatgg ctcagcgggt aagagcacta ctgactgctc  40740
ttccagagat cctgagttca aatcccagca accacatggt gactcacaac cacctgtaat  40800
gagatctgac accctcttct ggtgtgtctg aagacagcca cagtgtactt atttataata  40860
```

```
ataaatgaat ttgggaacaa gaagaggccc taaaaattca attcccaaca acatgaaggc  40920
tcacaaccat ctgtacaact acagtgtagt catatacatt aaaataaata aataaatctt  40980
taaaaatcaa aaacaaaaca aaacaaggta ttcatatctt tgctggcccc cttctgtgtt  41040
aggttttctc ttaaccttgg ctccagcctc atccgttcgc ttggtgaggg atggcatggg  41100
agcctccttc tctgtgcccc ggctctgcgg agtgtctctg gtggttcact ggttccattt  41160
aggcctcagg tgtggctcta cagacacagt ggctcaggaa ggcttccgga ggtcaggcct  41220
gagcttcgtg tatgcctctg agtccttgta gagttcactc aatctgaacc catcatcggg  41280
tgttctcgag agtacaggtt accctggcaa caaggaccag agaaaggtcc atcctgaggg  41340
cctgagctct ttgcctgaag cctggttgaa agtgggggat ggtgtcctac catgtccttt  41400
accctaatcc catgtccttg gctttccagg ggggctcgat attgatggag agcaagcctg  41460
tgagcctgaa gctgatgatg accttggcgc tggtcaccat gggccagcgt gcttttatga  41520
accgcacagt tggtgagatc ctgtggggct atgacgatcc cttcgtgcat tttctcaaca  41580
cgtacctccc agacatgctt cccataaagg gcaaatttgg cctgtttgtt ggggtaagtg  41640
tcttctgtcc cttcagagag tcaggttatc tctcaaggac cctaactcaa accagcttaa  41700
acaaaaattg ggaaattatc agctcatata acaggagatg ccaggattac attcaggtgc  41760
ggcttgatcc agttcgagtg gggggatatg gctggggttt aacttagaag atttgaggca  41820
cagcttgcgg ggaggaggag gaggactgga tcttcgaagc acacctctca aatgtcccca  41880
tcagtgtgac ttagaggcac ccactatttc tcacagttga cctttggtaa cctgagctaa  41940
ggtttggtct ctgacccctg accccaactc tctggttcag ctcagctttc tctgtgggga  42000
tctactgacg gggtgtgctt gcagtaacgt tacccacacc ctccaggacc tgttattact  42060
gagttcacgt gagatttact acccagtggt tagagcactg gctgttcttc aagaggaccc  42120
aggttcgatt cccagcaccc acatgacggc tcacacccca tctgtagctc cagttccagg  42180
ggatctgaca ccctcttctg gctcactcag gcactgcagt gcaggcaatg cacagaccta  42240
catgcaggca aaaagactca gacacataaa ataaaaatat gtccaatctt gtggagagga  42300
gacggggtaa ggcactgtgt ctcccagtga ccagatgggg accccatggg gtgaacacat  42360
aacgagggcg gcaggctgaa tacccagtct taaagctttt acagagttag aggccctggg  42420
taaagccctg tacctgtctg tacctgccct tcccagtacc ccatagagac tgccatccct  42480
ctcttcctga caattgaggt ggggcccttc tactgagctt ctagatcgtt cctgtcagaa  42540
atttgtatta aattctttct ttctttttat ctttgtttta ttatttttat tgagtcaggg  42600
tctctctatg cagtcctggc tgtcctggaa ttcactttgt agaccaggct ggcctcaaac  42660
agatgtctgc ctacctctct ctcctgagtg ttgggagtaa gggtgtgtgc cactaaaccc  42720
ccgctaaaat gcctttttac tttattagct gttggccctg attgagtaga cttgtcatct  42780
gtgtacatgg gagtatgagg caggagtatg gcaaattcaa aaccagcctg gacaaccctg  42840
tctgaaaatg tgcaataaaa aagaatgctg gatggagggt ggagctggag agatggctca  42900
gcagttaaga gcactgactg ctctaccaga ggtcctgagt tcaattccca gcaaccacat  42960
ggtagctcac aaccatctgt aatgagatct gatgccctct tctgatgtgt ctgaagagag  43020
ctacagtgta ctcacataaa attttttaaa gggtgggggg aagctggggg tgtgactcag  43080
tggatgagta cttgcccaca tgtgtaaggc actgggttct gtccccatca tttatgcagc  43140
aacagtgagg ggacatacct atagctgaag aataggtggg cttgtgccta tgttgtgatc  43200
tatgcccagg gctaaaggtg ctgttccctg cctgtctgta gatgaacaac tcgaattctg  43260
```

-continued gggtcttcac tgtcttcacg ggcgtccaga atttcagcag gatccatctg gtggacaaat 43320
ggaacggact cagcaaggtg agcaggaggg cagacagtcc ccatcgattg gtgtggggac 43380
tacaccagaa caagccttgg cagagggtgt ccgggtcacc cgaggacttc acggatccca 43440
caactgtccc tgcggtattt ctgtcgggaa ctcttttctg ttcctgagtt gtcatttcta 43500
aggctgacag gaagacattc ccataaagat aagacaatga ggtccagcac cttgcctagg 43560
cccacccgga aatcccccaa cactgcttat agaacccagc ttcctggcca tttacccacc 43620
accacgcctc tgtgtaccca gagaaatgtg ttttccttcc ttcttcgaat acacagaaat 43680
cctgtcatgt gctattttgc tgctggcttt tctccttagg ggcatcttta tggataatgt 43740
gtttttgttc tgttgtgttg tccagaggcc caggtactaa agatggaacg caggccatgt 43800
gaatctttga caaggacacc actgctgagc tagacttctg cccttcactg ggggaattct 43860
aggcaggggc tctaccactg agccacgccc ccagcccctc actgggggat tctaggcagg 43920
tgctctacca ctgagccaca cccttaaatt tttttattct gaaataaggt ctctgtgtat 43980
cccaggctag cttcaaaaat tcaatcctcc tgtctctgtt gccttgtaag tgtttaattc 44040
atagatgtgt gttaccacac ccagccaaca gctattctta gtgggtgctg ttcacattaa 44100
ccagctgctg ttttatatgc attggcattt tgtctgcatg tatgtctgtg tgagggcctt 44160
ggatcccctg gaactggaat tatagacagt tgtgagctgc catctgggtg ctaggcattg 44220
aacctgggtc ctctggaaaa acagccagtg ctcttaacca ctgagccatc tctccagccc 44280
ctaatcgtct cctttctact atgagaaggg ctgattgaaa gctcttacgg cagagtggga 44340
agtgcgttta gttttgctgt tgctgttgct gttttgtttt gttttgtttt ggaagcaggg 44400
tctcagtgta gtcctggcta gcctggaact cgatattgta caggtgactt aactgagtcc 44460
ccacaatact gtatgttctg tccccactgt ggggaacagg aagctgggct agaacctctg 44520
tgcacacagc ctgctcacgg gcttggatat gatgatgtct gtactagggc acacattggg 44580
tgtagatctt ggctgtccct caaggctata tctcatcctg tcctgcagat cgattattgg 44640
cattcagagc agtgtaacat gatcaatggg acttccgggc agatgtgggc acccttcatg 44700
acacccgaat cctcgctgga attcttcagc ccggaggcat gcaggtaagc cctgtgtagg 44760
gactccctgc ctcctaccag gaaactctgc ttctgagatg gttcagggtc cactcaggta 44820
gctccctgga agtgtgctca aagtgtctgg ccttctgtgt actatgcctc aatggttttt 44880
cttgtcactg tgacaagata cctgacagag gtgacttgcg aggtgtctgg ggactcagtc 44940
atggtggcag tggtgaaggg tactggtagg aaagtgttaa agtcttgtag cttgggctcc 45000
accatcccca gggtcctaac tgtggcctag gaagacatgg tgggtcttca gagacccatt 45060
tccaggtggt gccctagcct gtgcatccat tctggccaca ccagagatga ctctggcctg 45120
gggactcact gggctgatct ttgagccctc ttcctctcta gctcacacag gcagccatgc 45180
ttcatgccag gtgtgaacac agccacgacg gggtgagcaa agtctgtgtg ctctggtgga 45240
ctttcaaaag cagaacttcg ggtttggttt tgttttgttt ttacatttta tttattactg 45300 gtttttttaat tttgtgtatc tgtgtgtgtg cacatgagtg caggtgcctg aggaggccag 45360
cagagggcgt cagatcacct ggagctcctg taagaggtgg ctgtgagctg ccctacgagg 45420
atgctgggac tcaaacgttt tgttttgttt tgttttgttt tttgagacag ggtttctctg 45480
tatagtcctg gctgtcctgg aactcacttt gtagaccagg ccggcctcga actcagaaat 45540
ccgcctgcct ctgcctccca agtgctggga ttaaaggtgt gctgcgccac cacgcccggc 45600

-continued tgctgggact cgaacttaag tgttgctcta aactactgag ccacctctcc agcccattta 45660
tttgtgtgtg tgtgtgtgtg tgtgtgtgtg tgtgtgtgtg tgtgtgctga taatggaacc 45720
cagggcctca cacactctaa gtaagtggcc tgatactgag tcatgccgca gacactaaat 45780
aggatttcag cctggcagaa ttatatgaga gcagggtgca ggccaggtgt ctctttcctt 45840
cagtccttca tggggttatc tccagaaaca aaggcctctt cttacacaat cacaaggatc 45900
gaaatcagag aatttaacat cgccctaata agagcctcta agctggtgct gctgcataaa 45960
ataacaaaac aaactgtgct tataatttca gattaggggc catctttgtg gctggtggtg 46020
gggggagatc aaagcaggaa ctccaggcag ctaatcaatc cacttacagg aacagagtca 46080
cactgaatgc actcatgcct atagctcaga tggctgtctc cattcttata cagtccatga 46140
gccaaaccta gggaatagtg ccgcccacag tgggctggct cttcccacat caattagggg 46200
aatccagaca atttcacaca gtgagagtct cttcacagga gattctaact atgtcaaatt 46260
gacatttaaa aacttaccac cagactgtgt gaaaagattt tctgagaaga gcttttgctt 46320
agtgttgggt cttagaaatc tgggtgtcgg tcaggtgtgg cagtgcttgc atttaatcct 46380
agcactcaag gcagaggcaa gggaatcctt gggagtctaa ggccagcctg gtctacatag 46440
ctatttccag ttctttacat agagagacta tagaactaca taaggaaggg gcagagggag 46500
ggagggaggg ggagagagag agagagagag agagagagag agagagagag agagagagag 46560
agagagagag agagcgccaa tgtcttatcc tcttttttttt ggttcatccc aattggtttc 46620
ctcttgtttt gctttgttgt tttgagttgg gggggggggt ctcactgtgt agcctggcaa 46680
aaaagtatcc tcctgcctca gcctgcacag tcctaggatt gaagccatga gccacagacc 46740
gagttctgcc ctggactctc tttgttttga ggattgagca gacatgtgtg tgtgttatgg 46800
tgttgaccat ggacagtgtg ggtcacccgg gccttgtttc ccatcagaag agtgtttgag 46860
gccagacagt gggagtgaat ggatgaagag gagtcagggt ggacaaggga gactgggaaa 46920
gccgaagtct gggctgaggg agaggtggga tccggaggtt caggggcagg aagggacatg 46980
actaaggccc tggcaggtac agtgagacag gaagtggaga gggaagctgt ggatggcatc 47040
tgtggatggc atcgcactgc agggtgactg cagggccatg gtggttgctc atccctccgc 47100
atgcacagaa aaccattgcc caaagccttg gtttccacag tcctcatcag ctctcaagcc 47160
cctatcaaga gaacatggca catcgttgta agtgtaaggg aactctgtaa acttcagatt 47220
atctcaagtg actgacacag ctactgcaga catgtgctgt gcatgtttta gcttgctttc 47280
tttctttctt tctttcttcc tttctttctt tctttctttt tttttgtgtg gtttttcgag 47340
acagggtttc tctgtgtagc ccttgctgtc ctggaactca gtctgtagac ccaggctagc 47400
ctggaactca gaaatccgcc tgcctctgcc tcccaagtgc tgggattaaa ggcgtgtgcc 47460
accactgccc ggctgctacc gtactgttat gaatcataat ggaaatgtct gcgttttcca 47520
gtgggctttt gtgggcggtt acgacccaca ggttgagaac ctccggccta gggcatgctg 47580
gccaaactgt gctaaactgt gctgagttct ggtttttaat ttgcctcatt gggaggatgg 47640
attagtgagt ggggagccaa gggagcaggc agaacattga gggaccgctg aagtttcctc 47700
agcaacaggt gactagtgtc attgctggtc cctgtggttt cttctgcagg ggtgccccag 47760
cctctgtgct caaggcacag ttctcaccct gcctcccctc tgcaggtcca tgaagctgac 47820
ctacaacgaa tcaagggtgt ttgaaggcat tcccacgtat cgcttcacgg cccccgatac 47880
tctgtttgcc aacgggtccg tctacccacc caacgaaggc ttctgcccat gccgagagtc 47940
tggcattcag aatgtcagca cctgcaggtt tggtgagtgt cctctaagtg ttctccacct 48000
ctaggctgag gtgagagggt ggtaccggga ttttatctgc tgccagcttg ctgtcccatt 48060
aatctctggt ctctgcaccc atgatgatct cagtgctaca gatagggagc taaaggtaac 48120
tggaaaaaag ataacagcca ccctgataaa tgtcccaccg gcacgcgtta tccacaagcc 48180
gtgtcgctcc gaagtccgaa gggtcctgcc ccgaggttaa gattccatca gtgggcactg 48240
cttcttggcc aaggagagga gcctgccctc atcctttcct gcttccggag gcaccacatt 48300
ccttggcttg tggtcccttc ctttctcaac ctagcatcca gcttgagact gggtagcgcg 48360
ttgtggccca agttagcttc aaacttgcgc atccttcctg cctctgcctt cagaggtatc 48420
gggatagaag gcatgtaccc agacaccaga tccccccaaa acactccgtt ctatgaccac 48480
ctcctcctcc tctatccagc ccatagcttt caggacccca gagactgact gggtagaggc 48540
cactgggata acctggtctg ttatcctggt ggctctaact tctttgccca ctaggacgag 48600
gctggaaaca ttccctgtgg ccattcacct gctgggagca aaagctagag tcctgccctt 48660
cactcaaact ggccacgctc ctattgtgtc aaactctcct ctttagccaa gttgggtgtg 48720
aatcttggta ctggctgtgg ccccctggca catctgctct gtgttctaat cctgggccct 48780
accctgctgc tattgctcaa gtctgctccg tgcctcaccc ctcacctggc agtcaggccc 48840
aggctgctct aagcacctcc cacacagtct ttctccttcc cacccacctt cttcccgtgt 48900
cactcgggtg cccttgctct ctcgccagct cgtattgcac cagatgtcaa tcaaactcaa 48960
atgaaatgct tcctctgatc ctgatcagat cctcccagac actctccctg atcttccgtc 49020
ccctctggct ctccagccgc tctctggtac actctctctt atgccttcct gttgcctgct 49080
catggctgtc gatgttattt actgaaccct cccctgcttg tctcctcctt ggactgcaaa 49140
ccctgtggcc atgtcccagt aggatattgg gagtcaaact tctaaggccc ctacacagac 49200
gtgggatcca gggcttgcct gcggacagga agtttcactc acaactgcac ctccgccttc 49260
ccctccttgt accagcaaaa atcccagggc ttggttgaac tggtccagct ctgacctagt 49320
cattaggctg tgttaattgg ccaggctggg tcccacacac cgcaggggca gcaacaggcc 49380
cacatcacac agaactctgc tgtcaggaac agaatttcag ctgtgaaaga gaatctaagt 49440
gtagttgtgt ctgtagcttg ttcttttgtt ttgttttgtt ttgttttccg gagacagtgg 49500
gtttaagtat gcgtgtgcgt gtcgcacacg cgtggaggga ggtataaaca ggtgcatcga 49560
tggatggaga ccggaagtga gtgtcttcct tcatcactct ttgtttgttt gtttgtttgt 49620
ttattgatgc agatttttca atcactaatc ctggatcttg ggaggtccag ggatccacct 49680
gtctctgcct cccagttaca gatgtggcgc tgctgggaac ccgaattcgg gtcctcacac 49740
ttgcacagga ggctcttaac tgactaaact gttttcccag cccctaaagc ttgccccttg 49800
taaatcgggt gagaacaaga aaggggaaga ggaacaggga ttcgagtgat agggaacacg 49860
gccatgtgac caacaacccc acaaagaggc aactcttacc acacccaaca tctccccttc 49920
ctgctcctcc tgcccactgg cctgactttt ggtctctcgg ctctctgcct ggcattactg 49980
tttacataga tggagtcaca actgttcttt ctccctcgat ccctgatgcc tcccatgatg 50040
gctctcatga ttatatggta aatctgcaag atagcgggtg atagcctaga ttgttgggtg 50100
gtgttccatg gtggggctaa ctctgcttgc cttactcctt cctggctcac ggagctttct 50160
tttggcattt caccactaca aggatgcttc tagaacattc tcgcacctgc tgtaggagga 50220
gtgcacctga gttcgaattt ctgtggcatt ttatcttaag ataaagaata cacataggtt 50280
tccctttctg ggtcacgaga ctttcttgga ctcaggactc cccgtgtttc ctgtccttgt 50340
cttgggagca ccttggatct tccctgaagt ggtccttaat caccacgcgg gtaatcctga 50400
gcagttaagt ctggatacac gggccataaa gctataaatt aattatactt attgcccggg 50460
tgcgtctctc tgagggtgtt tggaaatcaa aagaaaagat gagccacacc tattgttaga 50520
aagccacggg catgccacct gcagcaggtc tgtgctggca gccttgacat cctgttggaa 50580
tctgtgcttc caggtctggt taggtggggg cttcatctcc cggggatcca tggcatccct 50640
ctgaaagaaa tggggttctc tctgatcttt gctggtgtct cctttcacag tatggttgga 50700
aggatgggta gggttttcca agtagaaggc agcatatctc agcgtgactt tagaagggtc 50760
cacagaggtg acgttaggcc tcagggattg atcaggtctc ttttctgttc tgttgtatcc 50820
ttggtgttgt gtttccatga gggcttgaag gccaccctga ggatccttcg cctgtctttc 50880
tgacaggacc aggtgtgtct ctggagcctc gaaggtgcta gggttcacct ggactctcag 50940
tgatccgggt tctctgctgc atccctgccc acgtgcacct cctggctagg ccatttctct 51000
gccaaggctg tcacaggtgc agcactcttg tgtctgacac ctgcacttga agatgcccat 51060
agcagccggt tcaggggttg ggagcaagag gtaggggttg gggcttcaa gcagtggatg 51120
tcctggagac cagactcgga tggaactcag agatccacct gcctctggct cccaattaaa 51180
gaggtatgct agcctgtctg gctttggatt ttaaagaaat gttttctttt ttttaaaagg 51240
tttattattt attttattta tgagtacacc atagctgtct tcagacatgc cagaagaagg 51300
catcggatcc ccattacaga tggttgtgag ccaccatgtg attgctggga attgaactca 51360
ggacctatgg aagagcagtc agtgctctta accactgagc catctctcca gccctgtttg 51420
ttgtgttttt gagacagagt ttctttttgt agtcttagct gtcctggaac tcactatgta 51480
ggccaggctg gcctcaaact cagagatctc cttgcctctt cctcctaggt gctgggattc 51540
aaggtgtgca ccaccagacc cagctaaaac acaatgcccc ccctgtggat ctgttgccct 51600
gggagcctct tgtggcctcc ccagggagac tcagaactcg gaactcccca ggcccttgtc 51660
ctgagatctc tgggttgagc cactttggct ggttggtggt aaagtcccac ctcagggccc 51720
tgggtgggaa tatctcattg gtgctgtccc ttccattcct gtgatgtcag agacccactc 51780
acgtgtaccc ctgagctaca atgtctccaa aagcagtctg tgtgcctggc ttgacattca 51840
gactccgctt ccactcctaa attcatatgg tgttaatttt cctttccact ttcatctccc 51900
atgattccct gctgcacctc cagacctgga ggggtggggg tggggggttg aaaatcacgt 51960
ccaagctctc acctcttgct acactcccac ccggaatgcc tttcccttgc cgggtagcag 52020
ctgctctctc ccttcctcca cccacccacc cacccacccc caacactgta atcggccact 52080
ctggctccat ccacccttcc caggtcctgt gtgtgctcag cttggtcccc agtgttagca 52140
tccctgcatc cctggcaccg aggcaggcca acgtgacgct cccgtcttct aacgcctctc 52200
ttcccctcct ccaggtgcgc ctctgtttct ctcccacccc cacttttaca acgccgaccc 52260
tgtgttgtca gaagctgttc ttggtctgaa ccctaaccca aaggagcatt ccttgttcct 52320
agacatccat ccggtaagct ccgtgtcctg ctagtggctg gggcccattc ccagagattg 52380
ccactggccg ctgggcaccc gccccgctcc ccccaattcc ccaggacaga gcgggttcca 52440
actgaggcag gggagttcag ttccttccac agcggctgct cctagaactt caagtcatca 52500
aagtcttact ttaccccaat tccagagttc agtgatatca ttaccttttt tattggggcc 52560
tataaaaaga tataagatag taaattaatt aagacctatc agccgggacg tctccttcac 52620
cagagacaga taccettgac agtgtcaaga cactaaagac atcatcgtgg gccagtgtct 52680
cacagagaaa tcagggggag gaatttgtcc tctgttaact tctctctgcc tctggtcact 52740

```
gtaagatgtg tccagtccag ggttcctgcc ctacgtgacg ccctgaaggc attccgtgaa  52800
gaactctttt ttgttttact gggtggggat ggaagcctgg gttttgaaca cacaaggccc  52860
caggctctga tgccgagctg tgcctgcagc tggccttgaa cttgcaaatc ctcctgcctc  52920
ggcttccagt gtttcttcac acctggctca tagctgaggg ttatcgcaga ggaagggtgg  52980
gcacatgggg cacagtcgtc tgaagtcttt cccaggttgt gcctagctcc ccagcaagga  53040
acttgacata gaggtgtttt atatcaggaa agcccctcag aatagggggg cctagttgtc  53100
gactggggac ctgtcctgtg agcctctctc cctggggcag atccatgctt catcccagag  53160
gacgaaggtg tttggtatta ttaactgtct atgcaaatgg cacagtgagg ccaacacact  53220
agcttagaga atggggcacc ctcacctcac cccccagaac ttaggttcca agaccaacac  53280
tgggcaccta ccctggacga cttctaggga gggttgccgg gcccacccat ggtatgcgtg  53340
gttatcacat ccatgcctct gtccaaaagt cataccaggt ttctggaggc ctttgccctg  53400
ggggcaggag ggatctgggc gtcctgggca aaacgtgtcc tggccttcta ctgtgggtga  53460
ttacaatctg agaggtggcc tccggcctcc catcaatctt tcaagagtct catgatctgg  53520
gcagggctaa aggcatcaaa cggtggtctc ttttcaccaa ccttttccat tctagaactt  53580
tcttcctgat ttaaataata cctgtgaatt ctcctagtga ttttttggtt gttgttgttt  53640
ttaattttat gtatgtgagt acactgtcac tctcttcaga cacaccagaa gaggacattg  53700
gatccaattc cagatggttg taagccacca tgtggtggct gggaattgaa ctcagcacct  53760
ctggaagagc cgtcagtgct cttaaccgct gagccatctc tccagcgaga ttttttttta  53820
aaagcatcac attttaaaaa gagagctgca agcaggcagc tctctgtggc tacctctgtt  53880
agggagcgcc aggatgctac atagtgggaa actggctcga ttaaacctac tcaccctgga  53940
ccaggccctt cctttggttc cctgggctat taggaaatgt aaacaggaga aaaaagacat  54000
ccttactgcg catgccccac acttgggagg cactgtctta ggcagcttcg tgagggctgg  54060
gaggatagct tagtaggtag ggtgctcccc tgccctgcac agagccctgg cttccatccc  54120
agcaccatgt aaagttaggc ataagccagt cctcagaagg tagagacagg aagatttgga  54180
gttcaaggtc atccttggct acatagcaaa ttggagtcca acctggacca catgaaatct  54240
gtccccaaac gaacatgcag atgtgggggg cggggggtgt catccctctg gcaacaagtg  54300
tctagagagg ggatcttgcg atagctgatc cctttgggag caggtatttc ctgagggaga  54360
gcccagtggg tgtgtgggaa atttctagaa gggtggatgc cccagcaggt attatctggt  54420
ttaagttgga taagaaaccc cagggctgga gcaggctgga gcaggctgga gcaggctgga  54480
gcaggctggg aggctcccca caggatctta catctcctca ctgtatttat gctctaggtc  54540
actgggatcc ccatgaactg ttctgtgaag atgcagctga gcctctacat caaatctgtc  54600
aagggcatcg ggtgagtgga gttgggacgg gagcttctga aagcttcagg ggccaggagg  54660
tttcatgcat tggtgatgca aggcacagga cagggcgagg cccaagcgtt gggatccaac  54720
cacctctttt cctgggattg catcattgct ctggatggag actcagaccc aggctgcatc  54780
ctgacactac ctccatcctc cacgcccaag ggctcttctg ccattagtcg cattggtaat  54840
cttgtctccc ccacagtagg atggatttgc ctgcttgtat gtctgtgcac catgtaagtg  54900
caagagccgc cgaggccgga agagggcata gggacctgga gttagacgga gttgtgagcc  54960
actgaatgga tgctgagact tgaacctggg tcctgccagt gttctcaacc acaattccct  55020
gggtttactt tatgtttagc tttgtgtaac gtacagagtg agactgagag tcctcctgcc  55080
```

-continued

```
cccattccct gcttgcccgg cagaaacatg gtggtaggag tccagccttg gggctggaga  55140
gatgtcttag cagttaagag cactgacggc tcttccagag gtcctgagtt caattcccag  55200
caaccacatg gtggctcaca accatctcta atgggatctg atgccctctt ctggagtgtc  55260
tgaaaacact aaagtgtact tatgcaaata aaataaataa ttctttgaac gaaaggaccc  55320
acatgctggt cactcctcag catcgcagat cacatgcctg ggaaccactg aggaagaggt  55380
ggactctggg cttcatggtg aaaactaagt ccgggaattg ctggactcag ctaggcttct  55440
gtacacacac acaccctggg actcctgcat gccagaaaac actctttcac tgaattacat  55500
cccagccctc ttcacttttt aggtctcact agattaccca ggctgccctt aatctctctg  55560
tagcccatca tggccttgaa catgcgccac ttgatctgac tcatctgggc tcttgaaacc  55620
ggaggccaaa gtgggctggc cacgggcttg agttcctgag gtcagcagcc aaacattgat  55680
ttgctccact gcctcaaata ctctttagaa atctttatag atttatggag aggtgtcaga  55740
gacgcaagca aatctttgtt ctctgtcccc ggtgcattca gtactgtccg ctcctggcag  55800
tatctgtcac ggtaaggaac caaagtctag tgcagcgtta ttgccacaac tgcagcttct  55860
cagcacgaga tgccgcccgc tcacgcctca cgcccggctc ccgtggctgt gatgggttgt  55920
tttgttttgt ttttttcttt taatctttgt ttcttgttgg tgttgtgagt tttgggattt  55980
tgttttggtt tttggagggg aaggtggttc atacagaggc caaaagagga tgccatgtgt  56040
cctcttttat ccctcttccc tttcttccct cgcggcagga attctcaccg aagccccagc  56100
tagcttctac ctgtctcagc cctggggtca caggttcaaa gccacacaca gcttttagcc  56160
tgggttcagg ggtctcacct cgggttcatt tgcttgagca gcaaatgctt tccccactga  56220
accatcccca gcacagtgat agtttctcct ctagcttttg gggtgttaaa gtacttgctg  56280
gacctgggtg tgtgtggtgc gatcaggttc ccctgtagat agtaacaggg gcagccaccc  56340
aggctttggt gggaggagac tcattattat tttattatta ttggtattat tattattatt  56400
attattatta ctactactac tactactact actactacta tttggctttt tgagacaggg  56460
tttctctgtg ttaataacct tggctgtcct ggaactcact ttgtagacca ggttgacctc  56520
aaactcacag agatccacct atctctgcct tcccaagagc tgggattaaa ggcattgtgc  56580
caccacatac acagatatta ttatttattt ttaaagttgt atttatgtat tttatgaatg  56640
agtggtctgt ctgaatgtac acctgtgagc cagaggaggg catcagatgc catgatagat  56700
ggttgtgagc caccatgtgg tggctaggaa ttgaactcag gaccttttaa ccgttgagtt  56760
atctctctag ccccattttt agttgtgttt agtgtgtgtg tgtgtgtgtg tgtgtgtgtg  56820
tgtgtgtgtg tgtgtgtata ggtgcatgcc acaatgaaca tgtgaaggtt gggacaactt  56880
tagggagcct gttccacctt ctgggtcccg gggatggaac tcaggtcttc aggcttagca  56940
gcaagcactg tcacccactc agctgagcct tgccacgccc cttaattaat tttttgcatc  57000
agggtttcct gtagcccagg ctagcctcaa acttggctaa ggatagtcaa ctgtacgtag  57060
cgttacaggc tcccctttat ctttctgtct cattttcttg tgaagtggtt tcgactgagc  57120
gaaggccttt cacatggtaa ccagtagctc tcccactgac accccaagcc ccaaacatag  57180
ctccattgcg agggtcacat cacccctggt cactcacttt gtgtcccatg tttccaggca  57240
aacagggaag atcgagccag tagttctgcc gttgctgtgg ttcgaacagg tgagtctatg  57300
aaggtagaag ggagtctggg gtctctgtat gttagctgag gcttttagtt cgctttgatg  57360
ctaatgttat gttaacttcc ggtacctaaa tttagctatt tgtatgttta gcctgcccat  57420
atgtatgtat gtatggttat catgtgagtg cccggtaccc gcagaagccc agagagcatc  57480
```

-continued

```
aggtctccta gaactggaat tacagatggt tgtgagccgt caagtctgaa acgtgggctc  57540
tcttgaagag cagccagcgc tcttaaccac agagccattt ccaggttttg ttaatggccc  57600
ctgagagggg ggagtggaga tggaattccg caccaggcca ccctgcaggc atcctgatct  57660
cgtcgccctt caggtcctaa gactagattc taaccagcga aagagatgac tgttaggcga  57720
ggaggcttgg ggccagatcc acctcccatt agccagtgcc tcatttcatg ggcgtgccaa  57780
cagcaagggc gtctgggaaa tgtagttctc tttggacttc tagccaaagc gcccgaggct  57840
ctctgttctg atttggggcg gggcacggca cagtgggatg ggtgccttgg agacgcagcg  57900
tgcagcccga cctttcttct gcagagcgga gcaatgggtg gcaagcccct gagcacgttc  57960
tacacgcagc tggtgctgat gccccaggtt cttcactacg cgcagtatgt gctgctgggg  58020
cttggaggcc tcctgttgct ggtgcccatc atctgccaac tgcgcagcca ggtaagtagg  58080
aggggcggcc acgcctcgga ctcggctcgg gtttcagccg acctctgttt cctgcagcta  58140
gctcttgttc tacctcctct ctcgcaccct gcagtaactt ttctctacaa gtcctggaag  58200
gcccaggacc ctcccaggtc ggggctaggc tgaggctagg tacccagtca tttggccaac  58260
aagtgggtgc cacttggtgc ccgctctgga aagtgcctgc cgaaggtaga ggtggggggt  58320
cagggctggg ctggttagag aagcaaagga aagccaggtt aaaccaaaca gagaagatag  58380
tttttcccaa ggaaaatgct ctgggctgga gttgggtgtg agatggaagt gggaggagcc  58440
acgtgtggaa ccatgaactt agattttcta agtccagaga aaaaagtgaa agaaattagt  58500
tataaatttt gcttgaccca aatatatcag catatgaggc tgaagtttta catcagccat  58560
agagcacttg tttagccagt gtgaggcctt gtattcaggc ctcagcgctg acaggaaaaa  58620
aaaataatca aaaataatga aaatatttaa aaaagaagaa gaaaagaaaa gaaggtctgg  58680
agagatagct cagtgattat gagcacttac tgcttgcagg gacccaggtt cgattcccag  58740
cacctacctg gtgttctgca accaactgta acccttgttc tgtaacccta gttctgtaac  58800
cctagttcca ggtgatctca aggcacacac acagtgcata tacttgcatg gagaacactc  58860
atacacataa actaatacag gtgcctataa tcccagcact caggaaggaa ggaggccagg  58920
ggagaaggat ccggttcaaa atcatccctg gttacatgta gggtttgatc aaggccagcc  58980
taggatacgt gacatcttgt ctccgaaaat caattaaact tcaaaaaaag aatagtgtgg  59040
gcgactggag agatggctca gcagttaaga gcactggctg ctcttccaga ggtcctgagt  59100
tcaagtctca gcaaccacat ggtggctcac aaccatctgt aatgggatcc gatgcctgca  59160
gagcaacagt gtacttgtat acataacata aataaataaa tcttaaaaga caagaatagg  59220
gctggtgaga tggctcagtg ggtaagagca cccgactgct cttccaaagg tcaggagttc  59280
aaatcccagc aaccacatgg tggctcacaa ctatccgtaa cgagatctga ctccctcttc  59340
tggagtgtct gaggacagtt acagtgtact tacaataaat aaataaataa ataaataaat  59400
aaataaataa atctttaaaa aaaaacttta aaaagaaaaa gacaagaata gtgtggttca  59460
gacaggggta ggggtcactt ccataaagaa aggatgactg aggaatgtaa catcagggca  59520
tgcagcccct gaaagcagga agcaaagggg tcatgactag aaccttcgtt cccttctggc  59580
ctcaggagta ccggctcgtg catgagatct tggggttacg acattggtca agtcccctgg  59640
ggtgcttgct gatagctgta gttgtgaagc agggaatttg aggacaggac tgtgatcagc  59700
tgtgattcaa gagggctgct gtctgcaaac aggggagcca ctggccacct ttgaacactc  59760
gtacaagagc cactcacagg gtcccacctg agatgtcctg ggccacaggc ctgggctttc  59820
```

```
tgtgcgtgct tggtgtgtgt gttggggggg tcttcccacc tgctctcctg cagtcagcca  59880
gctggctgcc tttcttcttt aaggcttgct tgcttgcttg cttgcttgct tgcttgcttg  59940
cttgcttgct ttgggaagaa cggatccctg tggagtcccc agcacccggc ttccctttcc  60000
aaacacaggc cccaagtctc ttgtcatcac caaggggtgt ctggttgcct ctggctctcc  60060
atgttgactg tagctatgag gatctggagg acatcacggt ctgggcttcc gggctggtgt  60120
tcctccctgc tgctgcccag tgagaactga gccaggcttt ttcagtcaac cattggagga  60180
gagaccccaa aatagaaggc aggcgtctcg ctggggtctg ggggcaaggt tgtttgtcct  60240
gcgggtttca tcagagagag gccaaagaag ccttgtcctg acaaagctag gcctcacctg  60300
tgtgttcctg tccttgagca tctgggggcg ggggggttaa ctgcttgctg gtaaagaaca  60360
tactcagtca tacgccattc ataaatcaag agtatgttaa tgtttccctc agattgacaa  60420
ataccatgga cttggagaag aggttaagag agagattgta cccagtaggc tccaggccct  60480
aggttcaaat ccagccccac cagaccagac cagagaaatt caaacactca gcaggccagt  60540
cccgctgtgg ccacctccgc cactctcttc ctgtcggtga ctttctgctt gccggacttc  60600
cggggcgctt cgcccacagt gcagggtgga acaagactct gcaatcttgt tctcttctgt  60660
ccctttgctt ctggggggac ccagcgtcac cccagtgaca cggcatgcca tataaactag  60720
cttggttgtc ttccaggaga aatgcttttt gttttggagt ggtagtaaaa agggctccca  60780
ggataaggag gccattcagg cctactctga gtccctgatg tcaccagctg ccaagggcac  60840
ggtgctgcaa gaagccaagc tataggtgcg taccaggtaa ccccccctct tcaccccacc  60900
tactcatagc cagtagacct accgtctcta cctatagcat cttcctggat gttattcaca  60960
tggagagcag ttaccctcct gcctctcacc ctcctgcgag atgggaatct tgcctcggtt  61020
tcttggaccc tttcagtcat tgactctcat ttacaaagtc ctgttagaag atgacagtta  61080
gggctggtga gatggctcag tgggtaagag cacccgactg ctcttccaaa ggtccggagt  61140
tcaaatccca gcaaccacat ggtggctcac aaccatccgt aacgagatct gacgctctct  61200
tctggagtgt ctgaagacag ctacagagta cttacatata ataaataaat aaataaatct  61260
ttaaaaaaaa aaaaagaaga tgacagttag gccagttgct tctcagtgtc ctatcccctg  61320
caggttgcta aatacaggtc cctgggcatc ccggaaagcc aagagactct cctagcccaa  61380
aaggtttgaa aactttttttt ttttttggac ttcaagggca tgtaaaagga cacactgact  61440
ccagttcaga atagagagac tgaaaatgaa gacgtttaaa catcagttaa gcaccagcta  61500
catactcagt cagggcctga ggatagaatt tcatggtcaa gtacacaggg tgtgcgacag  61560
actgctcaat acagtctgaa tttagatgga gtcgtgtgtc cgccctgtgc tttgctgcga  61620
tgggtggtcc aggtggtgag ccaccgagtc aggtatagct ggcgtcctgg tttacttagt  61680
agccatctcg caaggatcca ggaccgtact tctccaagat ctccaggtcc tgtagggatc  61740
aaggctcagg agagaggctg agccctacag ggtgtgtccc tgcctgggaa gggactggaa  61800
gagctgtggt ccctgcaatt tggggttagc agaggtgagt gagtgtctca atagaagctg  61860
ctattttagc ttgtgagcca acttgggtgt gagcactttc ttggagggag ctgggggtgg  61920
ggggtggagg cggggcttgg gggggcgggg aggggaggcc acagctcagc tcctggaggc  61980
cagctgacta tttgctgcaa tgtcatttgc ttgagaagca aataaggcag aactctggtg  62040
actgtgtgat tgtcctggtg agtgccacct ccctggagga ggaagaagct ctgcagctca  62100
gtgggtcccc atatgtccct ggagctgaga aagggtcctg ccaggaagag gtggggagat  62160
ggttagtgtc tgccagtcat ggtgatgttt gggtattgcc agagtgcgag gggacaaatg  62220
```

```
taggctccga gcagaggctc cgcagtccct ttagcccaga tggagcccat aggtacacag  62280
ccatagccct gtccagaccc taatagaatg aacaagattg ggcttacctc tttactttcc  62340
cagcttggtc taatcctcgt ttggcttcaa gattcccctg ggtgcccct agtcctggcc  62400
atgtgctagg gagggcagtg tcctctgagg atcagctaca gcacatgggt ccttgcatag  62460
ggacctcacc ctcccccccc cgacccccca gtgcctggct aagtgaaatt cggtggggcc  62520
ccacactctg ccatgcacct gggtgtgggg gtggtcccta gaggctgctg ctgattgcta  62580
tagaatggaa acagacgtgc cgctagacca aagggtatta ttatatgaat aacgtccctc  62640
tgggtggatg ggcatttctg taaggcaagg gggttggggg ttggcaggca gggttggctg  62700
tccggccagc tgctgtgaac acagtagcct ttaagaaaat gacctgatcc tctgcttctt  62760
tttggtctgt ctctcattct gaattctcct ctgtcagaca cagtacaggg aggagccagg  62820
acagaggagg ggaaatctgc ccacccgccc tggctgccca gagccttgtg gctttgtgtg  62880
tgttttcatg ggagagacca agctacagag ttaactcttg ctttattctc tggcaacaag  62940
ggcgttctgg gccactcacg ctggcttcga acttgtggac atcctcctgc ctctgtctcc  63000
cgagtgcgga gattccaagc atgcaccact actgtgcctt gtgtcccctt ccccatttta  63060
cttctgtttt ggttttggtt ttgtgttttg ttgttttcgt tttttgggtt ttggttttgg  63120
gtttttgaga cagggtttct ctgtgtagcc ctggctgtcc tggaactcac tctatagacc  63180
aggctggcct cgaactcaga aatctgcctg cctctgcctc ccaagtgctg ggattaaagg  63240
cgtgcgccac cactgtccgg ccttttactt ctgttttttt gtctgtccat ttgtctgtct  63300
gtctgtgtgt ggtgaagcca gggccttttg cttagtgtag tccacctctg agcttcaccc  63360
cagcacttcc tgttttactt ctgagtgaga ctatctggaa tgctggggtg ctgtgtcggg  63420
ggtggaggag tgggatgggg ggtgctcgtt ggctttgatc caaagagaag acgcctccct  63480
gcagtttcct tccctgccac taggggggatc ggtatggggg ttgcagggca ggggtgccca  63540
gtgttcttaa acccggcctt ccattcattt tcctaagttg ggaagtcttt tcaagtcaga  63600
gtctcccaac ttaccaagcc atcctttcct gttctgcacc ctttgcccaa catcctactg  63660
tccctaaggc ccgaggccac cattacagca gtctggtgag agtgtgtctc tcttacctct  63720
atgaacaaga gccagtttta atagctgttc ctggcccgtc aggtgacagc attttaaaca  63780
tgtgggcaga catttaagcc attcctagtt tctttgtgcg gcggtgttat ctacccactc  63840
cggactctgc ccccttcact gtaacaggcc agtctccctg gcctcagttt tcccatctct  63900
aaagggagag gttggaacca agagacctac atgactgagg agtccccgtg tctatagagt  63960
ggcatctctg ggttcatggc agacagggct ggatgtgtca ggaagtggtt tctgtgctgg  64020
tgggatgtgc ggtgggacta ggggaggtag gcagggcagg gctaggtgac aggcttgtga  64080
ctcagcttcc ttttttctcc acagggtcct gaagacacta taagcccccc aaacctgata  64140
gcttggtcag accagccacc cagtccctac accccgcttc ttgaggactc tctcagcgga  64200
cagcccacca gtgccatggc ctgagccccc agatgtcaca cctgtccgca cgcacggcac  64260
atggatgccc acgcatgtgc aaaaacaact cagggaccag ggacagacct gctgccaagt  64320
gagcctgatg ggccacaggt gtgctcttct aaatggcctg tgagccaggc tgtgggaact  64380
ctagctgctg tcagcccctc ctgtaggagc tggccctgcc caggctcctg acttccctca  64440
ggaagtcttt ctgtctttct ccatcagtct gaaagcctta gttcccacag aggacggatc  64500
tgtcactcct aggggctggg catatgtcgg cctcttgtgc caaggccagg caagcagctc  64560
```

caggtcctga ccagtttgca cacacactct ggagctgtat ctggcgcttt ttctatcgtc 64620
tctgctatgt cactgaatta accactgtac gtggcagagg tggcaggccc ctcagggtcc 64680
ttatttttca ggcatggggt caaagctaga ggtatgggcc gtctacaccc ccccgccccc 64740
cggcatctag tgtacctcac cagagggtat tcggaggccc agcatcctgc aaccgacccc 64800 tttttctac tggaagagaa attttatcat cttttgaaag gaagtcatga ctgaagcaat 64860
aaaccttttc actgattcaa caacactggc ttctgtgact gttttctggg cagggctggg 64920
tctccagaat ccaggccaca tcagtaggtg ttcccatgac tgccagcgag tctcctggtg 64980
tgaggccagc accggccact agccatgttt ccacctcaag gctaatgtgg tatgtggctt 65040
ggatgcacca ggacaggcta gctctgtcct ttctctgtcc cgtggaacct tctgggcctt 65100
ccagcagtct gtgtccaaga tcagaacatc cttgtgaccc caagtgacaa gcctgcagcg 65160
tctgggggag ggctggaagg gagggtctaa cttttgtccc aagttcaagc aggggttcta 65220
cctggcatct ctgagagtaa aaccatgttt tgcccttaag ggacccacta ggaactgggc 65280
aatagatttt cactgtgaac attaaaaact acatagccgg gctggagagg tggctcagtg 65340
gttaagagca ccgactgctc ttccaaaggt cctgagttca attcccagca accacgcgat 65400
gactaacaac catctaatgg gatctgatgc cctcttctgg tgtgtttctg aagacagcta 65460
cagtgtactc atataaaatg aataaataat taaaaaaaaa actacataga cactcactcg 65520
gtggttgtaa tggtcttcac ccttcccttt cttagaaaag aatttgaatt attgtgtgtg 65580
ggtccatgcc atggcataag tcagagggtg agctctaaga gttggttctt ttctcaccat 65640
gtgggtcccg ggcatcgaac tcaggtcccc aagtttggca gcaagctcct ctagctgcgg 65700
agccatctcg ctggccttgc acttccttaa tgagcactgt tctctacctg ccctggaagc 65760
attgaaagtt tcctacctca tactataaac tgcattataa tcgtgagaca taaacttcta 65820
tataaggcaa acatttttag tcttgtaaga cggggtctag ctttgtaggc caagctgggc 65880
tggacctcat catccgcttg ccttctgctc ctaatgctgg ggtgacaggc acaccctcac 65940
catagccaga tttcttttt tccaagacag gatttctctg tgtatcctta gctgtcttgg 66000
a 66001

<210> SEQ ID NO 6
<211> LENGTH: 70000
<212> TYPE: DNA
<213> ORGANISM: Mus musculus

<400> SEQUENCE: 6
agtgtcctca gaggccagaa gagggtatac ggtccctcat aactcaagtt acagaggatt 60
gagagccacc aagtggaggt gaaacagagt ccaggagctg gatcctcagc aagagcagcc 120
tctgcccata actgttgagc ctcgtcttca gccctttcat ttttccaccc aagaaaaatg 180
aaaaatgaaa ggcctagggc agccacacag taaacctcag cagaagaccg gagttcagtt 240
cccagaatct atacagagcc gctcacaacc acctctaact ccagctcctg agacctagtg 300
ccctcttcta acctgagggc acccacacat ccgtgaacac agataaaaag ctttaaaatc 360
tttaagaata aataaataaa tagatagata ttttaaaaac aaaactccta atgacagagc 420
ttcttgcctc acctgtttcc tctacccccca gaggctctgt cacctaccta ggcatcaact 480
gggcacagcc cagacttatc tgaggacata acatgagggg aattgcctca ttcaattggc 540
ctgtggcaca tctgtgggag tagctcaatt ggtagggtac tcaacatcct ggccattgtc 600
tccagcacca cacagacctg gcacaatgga gcacatctgc agtcccagta tgggcaggta 660

```
gtggcaggtg atcaggagtt caaggtcact cttggctacg tcacgagtac cagaccaaca    720
tgcactactt ctcaaagaat ggtagggtgg aggggcagga gcactcactg gacactcttg    780
ccgaggaccc aagttcaagt attcctagca tccagatggt agttcacaag catttgtgca    840
tggagcctta tctgtgtatg ttcgtgagtg tgtgtgtgta ccatttcctg ctgagccatg    900
tctctggccc tgacttcatt tcctagggta ggaaactgag gcttacacgg gaccaggagg    960
ggctcacact gacacaccta gccctggtct tgtggcttcg attgtttctt ctctgggata   1020
gtaaacactg ccaactttcc tttcactggg tgctcgggaa ggcaaggcag aagaaaacag   1080
tggagtggcc cccaaagtgg gacaggcagg gtacatttca caggacattt tcactctctg   1140
gtgggaacag cgggacacag aagaagcctc atggactcca agtttctttt cccacactcg   1200
ttggcagcct tgggtttgtt atccttgcga caatgccact gtcctcatga aacctggtga   1260
cgttggctga gcaaatacta cctccgatat tgactcaaaa cgtgtacagg ggctcaaagt   1320
tcaagttcag tggggcctga ggcttggagg aggaggggaa aacactgcct cctgtgatta   1380
caacattctt tagtatgaag tagagttccc tcaaaactag gtctcatagc caagtcccca   1440
aacgtcttaa gcactttgga tagatatcta ttgagtcctg ccaaccggaa aggaggctag   1500
agagaatgac catggagcag ccatcctctt ggcaaaacag tgggggctgt gaaaattccc   1560
tgtcacatat attaggtggg atagttaggg ttgggatgtt gtttggcctt ctacacataa   1620
gaccttggct tccagctcta gtactgaaaa aaaaaccaaa ccaaaacaaa acaaaacaaa   1680
caaacaaaca aacaaaaaaa cgagggctgt ggtagctccg tggcagagca cctgactagc   1740
atgcatgcaa ccctacgatt aatcagctta tcttattctt tccattgtcc tcaaacttga   1800
tatgtggcca aggacaattt gaacttcttg ctgggatcac aagtgtgcat cattataccc   1860
tctttatgtg gtgtggggga tgggatctag gacttcatgc ctgctagaca agcgctgtaa   1920
tactgagcca catccccagt tgtggtttgt tttttagatt aaaaataatg tgtatgggaa   1980
tgtatgaaca tataaatgca ggtgcccatg atggccagaa gggggagcaa gatccccagg   2040
agctggagtt ataggtgttt gtgaacattg agacttggat gccgggaacc aaactgtggt   2100
cttgggcaag agtagtattc gtacttagtt actgagcaat ttcctccaac tctgtttttg   2160
ttttgtttg ttttgtttg ttttggtttg gtttggtttg gtttggtttg gtttggtttg   2220
gtttggtttg gtttttgaga caggctcacg ctgtaaccca ggctggtctc caactcatat   2280
atgatcctcc tgcctcagtc tcccaagtaa tgaaattaca gatgtgagcc accacacagg   2340
gcaaacgtat ccatcgtgag cagctggcac agtctatggg attgaaactg agaaagaatg   2400
tgaaaaataa acaggcgagc ttgagaaagg ttattctagc cttggtgcca gttcctggta   2460
tattttcagc gctcagggag tttaggttaa tgccccaagc ttccccatcc ccaccccgag   2520
gggcgagggg gaggttaagc tctttattaa tagccactcc gggagctaca gtccttggga   2580
aaagggctat ggtgagggta gaggaaggaa aatgaggtcc ccacaggata aaaccaggtg   2640
caggcggctc tggctcatta tggtgcctcc ccaaggcacg aggtgtctga gagttccttc   2700
tgatgttgtc tccgcccctg ctcctgtccc tcctggccgg cagggagggc ctgctgtcaa   2760
ggccgctgag cctcctggac agacagggca cagggccaat ccagagggac gcaaagcagg   2820
acgccaagaa aagaggaagt gtccttgggg aggggaccgg ttaggactgg ggttctaggg   2880
agagaaggaa gggcatttaa ggtgagtcca acagtccagg acttaaaagg agccttaagt   2940
agggggcagc aagaggtgac actagagcca tcgaggccga tgaggcccgg gggacagcag   3000
```

aaagtgtttc cagatagcac ctctgcagtg ccagccacat gtcacactgg tctctgcttc 3060
cacgctcagg aacaggtgct cagataagga tgcttaagaa gatggaaggc gtttgggtgt 3120
gtcagaacaa tgaaggcaag tgaaagaccc cgattctcta tgagtccctt cacataaact 3180
aaaaatctca aagttacacc caacaatcgc ctgtcctttt aaataataga ggtgtagggg 3240
gagatgagat acagcaacag ttaactacag ttgggggcgg gatcaagggg aactttcatt 3300
ttctctatgg aacccttcca cggcaaggca gagaaagatg gaggcaaaca gggctcttcc 3360
atgaccaggc gtgcttgacc tcagagctgc gactcttcct tcttcagcgc atttatggag 3420
agcttgctac acgcagggcc tggagctgca gcctgggagg gcgccccatc tggcgggtag 3480
agtgctttgc catgtctggc ccgacttctc tacaccctgt tcacaactca ccctgcaacc 3540
ttcgttcccc gtgtgctgcc agcgatcccc ctccagaagc cactctgtcc gaggttccaa 3600
tcactcccct attgacacct attcgttctc agcgttcaaa gagtacttcg attccgttgc 3660
ttttgggcgc agagacttga atccaggacc ttacacaggc aaggaatgca cggcattgtg 3720
agctacccac acaccctaat tgttccgcag atgagggttc ccccgccccc tgacgatttt 3780
atcccaggga gactatgagt gtgttggcct ctggcgccaa cctgcccccg gatgtcaaac 3840
atctgttctc aaacttggaa cctgagctta cttcttcatt ctctgatgtt agacaagccg 3900
ttcttcccaa caccacccca agcgtcccac tccccttttt taaaaaaaaa aataatcaac 3960
caaacaacca aacaaaccaa aagtctggag caaaatcagc ataactcccg cagggttgca 4020
gagaagttta cgggcggatt agtgtaaacc gcgagtgtaa gccaagtatg gtgcaaagag 4080
ctgttttgga catggcttta atgagttggt cccttttgta tatgaagaaa ctgaggctct 4140
cagggtaagg aatgttgtcc taggtctgcc gttggcaagc tcgggactta gcctcagttt 4200
ccttactgac ctcctccccg cagccccgcc ccgtccaggc cccgccccgt cctgcccgcg 4260
ctgcagccca gctgggctca gccaatcacc cgcggcgcgc gtcggtgagc ctggcctcgc 4320
ccgccccggc ccggactccg ctcgctcatt ccgccgccgc cgtctgcaga ctcggtaaga 4380
caccgcgagg gcagcgctgc ggcaccgccc tgggctgggc gcgcgggtgt cattcttaag 4440
agtgtggagg gagacccaga ctgtgcccgt agggtacgcg tgagccgcgc attggagaag 4500
cagagggcac tccctccccc gcgcagtgac ggatctgggg gatcccggga cgggaggaaa 4560
gatgcttggt ccccagactg ggcaaaatgc ctccactcgg gacgcgtggg acctcggctc 4620
gtggtgtccc gccccacggt ggattcactc accgcgtggg tttggggtct tcattgctct 4680
gtgaaagatg cttatgatta ggcgtgactc cttggtccct gaccagtagg agtgtcaact 4740
ccctttctga cccctgctca ctccccactc cgcgggtggc ttggggccag tgtggacgcc 4800
gagcgttctc caggctcttt ccacccgcta ctctgcaggt ggattggttc tcggggtccg 4860
tgagggtcgg gctcggcagt aggaaggatg ctcgcacagg ggacttggca ggtggccggt 4920
gccctctctt cgtgcgggtc cctgcagtat agccttcggg acacaccctt ggcgcagaga 4980
cttaagtgtt ttgcacccct caccgcggtt ttgcccgggg ttcaagggca ggtgggtgtc 5040
agagactgcc caaggtcgcg ccgggaccag agcccgggag ggtgggggcg tcacgtgacc 5100
tggcctgagc gaacttggcc tgggacagcc ggacagcacg gtctgggcaa ccaggctgtg 5160
cggtaacagc gggtaccctt cgtttttctt catcttattg tgaatcgggt ctggttttcg 5220
ttgatgtcac agaacacaga tgaacgctca agtttttaag gagttaaaaa gttcctagtg 5280
tgaaccaggc tacatacaat caagctcagt actctcagct ctgggccgac tctcgttccg 5340
tgcatttaaa tagttgtcca aaaacagatt ttagtcggaa actgctaact ttggaagttc 5400

```
gcaaataaaa tgaaagtgag tttagaagcc tttcggaacg cgtatttagt tacagcattt   5460
tgttgcacag gcgtctggtt tctggtcatt cctgatattc aagcgtgttt atcactgtca   5520
aaaccacaag ccaaatgact aaaacacagc tttggccttt tatttgtgcc agcaagcata   5580
catcaccacc accccttcc tagtcggtcg actcaggact cagtgaggac ctaaagcaga   5640
ggactgtggt gtggggagga cagtgcttgc tccggggcag tgcagagtag taggtaggtc   5700
tgggcagcgt ccgcattcag agtcctgggc tagactggtt ttgctgcagc acccggagct   5760
cttttgtcat gtaaattatt gcttttctta actaaagcct cgctagactt aaccttacac   5820
ttgaattttc tcttttatct atttatttac ttttaaaaaa tgagatagga tctcatgtaa   5880
cacaggctgc cctccagcct gctctgtacc caaggttggt tttgaacccc cgatctcctt   5940
cctgcaccca cccataagtg cggtgattat aggcgagcac caccacgccc ggctttgaac   6000
tccttaaccg tctttggaat caagctccgg ttaggttttg tatcaaaagt ggccgaagcg   6060
gcttcctgca caagacaaaa cctttcgagt ttgagctaga aagccacctg actgcagatg   6120
aggggtggaa cgcctccctt ccgccgccgc tgcgcttggc cctgacccag tggtcacgaa   6180
accggcaggc ctgattctct cgggagtttg gggcgctggc cggggtttag ccaaccctga   6240
ttcctcttgc ccattttgcc cattcataaa agcgctgcaa tttttacttt attttcccct   6300
tgggtttcgc agcgaaaccc ttcgaggcac ggtgccggct ggctgttttg ttgtatgcga   6360
cagctgtcct cggacaaagc ggatcggtga ctccgggatg gcagcggcga cgcgtcgctc   6420
cggaaggcct gcgtgggctc ggccggtgga acaggatccg agcgccccgg acgcgccagc   6480
acgggggcgg ggcacccgta acctttcccc tacttttctc agccgtcacg tgacccggct   6540
gggtagggga aggggcgggg cgggaagccg ctgttgttag tgcccttccc ttccccagcg   6600
ccttgaactt gcagtctgga tctgcaggcg gctagagcca cgcgactttc ctgtactttg   6660
accgtttgaa ggtttttttt ttttttggt tagaaaatat gtttagtcac tcttcagtca   6720
ctcttcatag atatttaccg gtaggcccga gtcttaaagc tggtggaagt ctgcatttga   6780
actagtttag aataaaatgg tagtccaagg tggataattt taaagtgtgt ttagcagact   6840
ggacagtccc ctgaaggagg gagagtcgct cgaatctggg agttaaggga cagcctggga   6900
ataggcaaag atccatcctc agctcgggaa agaagaaaaa gggaggtggg gttttaagcc   6960
ggtggcggtg gcgcgcctag taggcttaaa aaggattact gcacacttga attaatgcca   7020
atttaagctc ttagtgcaag aatttttgtt gtttggaaaa taagcctgct gccaagcctg   7080
actaccctaa ctcgaagggt gaaaatgatc ccgacttctg cacaccgtgc tatagtgtgc   7140
actcaaccgc caccataaat aaataagata catggttttg ttttaagtaa aaagcaatac   7200
aagcatattg tgcaaaatta gaaaggcaaa aatggggtgc gatgcagtca cctacttact   7260
cagtagttac tgcaaaggcc accactgtga gcagttcatt caggactgtg atggtgtgta   7320
cctgtaccat ctagctcttc ggaggtggac agaggagagc cggacttaag gccagctacc   7380
accatccgtg agttggagtc ctgtgtggga tacacaagaa cttgtctcta aaccaaacct   7440
agactgcaaa gtttgtttat ttttttaatc tcttacctaa cacaaggagt gagttctcct   7500
tgttgatttc aaatatctgt tgccttttgt actcttcacc ttgaaccccg tgcaaatatt   7560
gaggcggaca ttgggtcccc acaggccctg ggctaaggcc agctttgctc tgttgaggta   7620
acgtggcagc ctggttctga gaagtgccca ccctttgccc tttttgtgcg agttgttctg   7680
accttcagga atgtttttcg gaagttaata gcagcaggca cactgcccgt ttcgcgcccc   7740
```

```
gacacctggg taactgccac tttagaaggt tgggaaatag gatggctact gaccttgcct   7800
ctgaggagtg ttgcacaccg accatttagg tagaaatgta agagaagctt ggtgtggtac   7860
aaaacactta taatcctagg gtttggggga tggtgctgag gcaggattcc gtgactccat   7920
agtgagacct tgactcaaaa aacaaaatta accaaaccaa acccagcaaa gaccggatta   7980
ggctgggttg tccatgccta taatcccagt ccttagtagg tggagacaaa attagtagtt   8040
caagatcagc atcagtgatg tacctggttt agggctagca tggactacat aagacctgtc   8100
tcaaaaacaa gacaaaatac tgtatgcact ggtattaatg cactggtgat atatattgga   8160
gttatgcact ggtgctgtgc actggtgtga atgcactggt gctgtgcact ggtgctgtgc   8220
actggtgtga atgcactggt gctgtgcact ggtgtgaatg cactggtgcg aatgcactgg   8280
tgctgtgcac tggagttgtg cactggtgtg aatgcactgg tgctgtgcac tggtgctgtg   8340
cactggtgtg aatgcactgg tgctgtgcac tggagttgtg cactggtgtg aatgcactgg   8400
tgctgtgcac tggtgctgtg cactggtgta aatgcactgg tgctgtgcac tggtgtgaat   8460
gcactggtgt gaatgcactg gtgctgtgca ctggtgctgt gcactggtgt aaatgtactg   8520
gtgctgtgca ctggtgctgt gcactggtgt aaatgcactg gtgctgtgca ctggtgctgt   8580
gcactggtgt gaatgcactg gtgctgtgca ctggtgtgaa tgcactggtg tgaatgcact   8640
ggtgctgtgc actggtgctg tgcactggtg tgaatgcact ggtgtgaatg cactggtgct   8700
gtgcactggt gtgaatgcac tggtgctgtg cactggtgct gtgcactggt gtgaatgcac   8760
tggtgctgtg cactggtgtg aatgcactgg tgtgaatgca ctggtgctgt gcactggtgc   8820
tgtgcactgg tgtgaatgca ctggtgtgaa tgcactggtg ctgtgcactg gtgtgaatgc   8880
actggtgctg tgcactggag ttgtgcactg gctgtggcac ttaggaaaac aaaggtcatc   8940
tatactcttt ctgtctcctc ctcctccatg tgtggtccaa ggagctgagt ctcacttctg   9000
tttcttaagt cccactagaa tttgtcttcc tcagtctccc tgaccctatg caggcctgca   9060
aatcattgct gaaggaagga caggtttggg gcgccctttc tccgctggac tgaaccagcc   9120
tactgatatt aagggggtga gggccttttg gaagtttcac tggctacacc cctagaaatt   9180
aatgcccgag agggagggct tagaggaagt ggttgggccc ctagctcagt gtgcttccat   9240
ggtacgtggc tctgggatga cttgcctgac atctctgtcc ccatccaggc cacatgctct   9300
ctgcagtgac cacgtccaca cccacctctc ttcttttagg gtttccttgg ctttgggtaa   9360
agccatgaaa agagaattca acaagcctcg ttatcatggc ctgaagggat attcgtatgt   9420
ctacaggaca gggacactga gtaactcccc acaaccctat ccccccttgta gtcctggcta   9480
gcctgaaact cactatgtag accaggatga ctttgaactt gtgatcctct tgctccactt   9540
cagataaaaa cttggccctt tatgaaactg gctggtttat taacatactc acccctagct   9600
tccagcagct gctcctggaa atgctacaag gaaggtccag ccccggagcc cattgcgtcc   9660
tgcgggcctg tgaaggtatt ctgaaaagat atgaatgagc tgcccatgtt agtcagttag   9720
aagataggct gaggtaccat atgctcgccc tgaagcattg agctgggtgg gccttggggg   9780
atagagccag gacagacacc cactttcttg aaggacaggt gttgactgct caggctcctg   9840
gtgggataac agagtgtggc cttgtattaa agaacacgtt ctgtgtttgc acactctagt   9900
atccttcgat tgatgggagc tgaggcagtc tgttctgccc tgtgctgata aagcatagga   9960
gagaggctga tgtttgtcag tgagctgcag atctggaagt gaacccagat ctgtgttgta  10020
gccactctct cacctgctgt catagagcag ggctcttagt ggcagccatc acctctatat  10080
atgcagactt agactgatat cgaagtgcgg gcatgtctgg gtgttcattt ccttctctgt  10140
```

```
caaatggcag ctctgatacc tgctctcctg tgtcccttga gtcccaggag actccattaa  10200
ggagtgagac ctcagtctta gcattcaggt gacaaagata ggctgatctc taggtttgag  10260
gctggctttg tcttcccgca gtatgaccta tgcaaaatcg tgaactttat ataaaaaaag  10320
gatttatttt attcatcttt tttgtttttt gtttttttgtt ctttgttttg ttttaggatc  10380
gctatgtata tagcctttac tagcctggaa cttgctacat agaccaggct agtcttgaac  10440
tcacagatat ctacctgtct ctcgctccag agtgctggga ttaaagtgta ccaccacaca  10500
cagtgctttt tacattttta acttttttat ttacgagtat gctatgcatc tccgtgtgcg  10560
cacctccgat ggctgggggc atcagctccc caggggctgg agacaggcag ttataagctg  10620
cagaggcact aggagctgtg ctcactcctc tgaagagcct caggcactct tagcctccct  10680
ctagcctggt ccctgatgcc tgaaaacacc acacatccca tggaaagtga atttagaagg  10740
ttgactttgg atcttctcct ggggctaatg aggtgaagtg ccatcttcca tgtgagtctg  10800
ggtgacttca gcatgaccca caactgtgag gaggaccaga agcccttcac aggacattat  10860
gttgttaagg tgtgaaggtg tgacagacaa gcagtagatt gaatggactc cgtgcttttt  10920
cctttttttt ttcccactgc atggagactg gctatgagga ttattgacga acttgtgcaa  10980
gcagcagaca ttcttaagcc ctaagccatg tctccagccc cacctaacag cattttctac  11040
ctggaggtgg cctgtggcat gtgacccctg ccccacacat caaaacattt gtagatacag  11100
gttctagacg ccagtgtcag gactgcaccc gggcgggttt tctggtggtc agatctcagg  11160
ttgctgaggt gacaaacata gacaggatgt ttagaacagt ccctgaggat ttgggaacgt  11220
gtatagggac agtggtatga ggagaagttc agttttcttg agctaacaga ttcatgccac  11280
ttcctggcag tcaagagttc aggctggcat cctgttctgg caagattgga cccatgtgct  11340
gtttcagaat ggatggggta gactgttagc cttgttaaag tgtatttcac gtcttattac  11400
aaatttttac atgttttgtt gttgttgttg ttgttgtttt ggtattgtga ggcagaggtg  11460
tgtgtgtgtg tgtgacctgt ggggaggtca gaggacagtt tgtgggactt ggttctcttc  11520
ctctcctgtg cgggtctctt gaagattgaa ctcagttgac ttggcagcaa gagccttctc  11580
ctgctgaatc atgttgctgg tcctctttgt tactttgttt tgcagttttt gagacagagt  11640
cttagatatg cttggtgagc ttgaactcac tatgtagttg aggacaatct gatcctcctg  11700
cctccccctc ttgagtactg ggattacagg tctgtgccac caagcctgct ttagtggtgt  11760
tagagatgca gggtcattcg gacttacccc atgctagaca agcactctgt caactaagcc  11820
atgtccccag tcgtggctac ttcccttaga agtgtgtcct ctgctggctt ccccatgtgt  11880
cacatttctc tgattgccat ttcttaatga tgtgctgcag tcgcctaaat tggattttgc  11940
tttactttga actttctttt actaagtagc tctagctggc ttagaactgg agatgtagac  12000
caggctggcc ccaaatgtac agcagtccct ctgcctgctc ggattacggg caagctccac  12060
cacacccggc ttttatttca ttattattgt tatcatttta aatggaggca gggtctctgt  12120
agcctcagct ggctttatgg ccacagagcc tttgcattcc tgattctgtt gtcttcagct  12180
cccaagtgct ggagctggaa cgattcggca tcctgtctag catgggtttt tacagtgtgt  12240
ggtaggcggg acttctcttg ttattttggg ggaatgtaga ctgaattgaa aatagattaa  12300
aaaaaaaaaa gaaaatagat ggaaatctta cttttaccat ccaaaaacta accctgctta  12360
gcttctttta aaaatcagac catttaaaat ggtatggcca gggctggaga gatggctcag  12420
cggttaagag ccgactgctc ttccaaaggt cctgagttca attcctagca accacatggt  12480
```

ggctcacaac cacctgtaat gggatccaat gccctcttct ggtgtgtctg aagacagcaa 12540
actatgtact cacatatgta aaataaataa ataaatcttt tttaaaaaat taataataaa 12600
atagaatgat atggccatag accagaattt gttttctaac ctgatctgaa ctattgtgtt 12660
cagccaaaca gcacaaatgg cttatggtga tatgccatga tgtgggaaag tcacctaggg 12720
ctaaattaca taatgcaaat gaagactgtt caggcatgaa ttccaaattt aacctttcag 12780
ggtgagttcc tgtgacctct ccacctatac agtaagttaa caacaacaaa ttgaaatctg 12840
gtagccaatg tgacagtttc caaggtggag tctttcaagc agggtctagt gtcttggtct 12900
ggattcgttc ttagattgga ttaattctca taggtacagt gccttgggcc tgctttctct 12960
cctccacact cttccactct tgcccacgct ccaacccctc cagtgccttc tcccatccca 13020
ggacatagca taaggctctc accgagaagg agtgatcctg aactctccag tctctggagc 13080
tatgagaccc ataactctct ttataaagta cccacccttg gcaactctgt tacagcaact 13140
gtaaatctac taagacattc cttcaccttc ctcatacccc aagccagccc acagaaggca 13200
caaggtgcaa aggtctcatt tctatttggg tatagcagtt gtactcagat ttttaagtct 13260 ctttttttatt tttgatgtgt gcgcatttca catgtgtatg tagcccagag gccacaggca 13320
gtgtcatctg cagttactct tcggctttct tttttttttc tttgaaagga aggttacccc 13380
taccaagtct ttcttgttta ttttagattt gaagtgattt acagaactta gatataaggc 13440
tttgaaacct ttctttcatc ctagagaagc tcacatgtat ttgtcttttt aaaaatattt 13500
ttattaggta ttttcctcat ttacatttcc aatgctatcc caaaagtccc ccataccctc 13560 cccccccac tcccctcccc acccactccc cctttttggc cctggcattc ccctgtactg 13620
tggcatataa agtttgcaag tccaatgggc ctctctttcc agtgatggct gactaggcca 13680
tcttttgata catatgcagc tagagacatg agctctgggg tactggttag ttcataatgt 13740
tgttccacct atagggttgc agatcacttt agctccttgg gtactttgtc tagctcctcc 13800
attgggggtc ctgtgatcca tccaatagta tttttttttc tttgaaacag gagtgtgtgt 13860
gtgtgtgtgt gtgtgtgtgt gtgtgtaatg gccttggcta acgtggactt atttattgac 13920
caggctggcc tcgaactcac agagctccac ctgcctctgg ctcttgagtg gtatgctcga 13980
ccatgcccag cctctctaag ttacagccat ttctgtttag cggagcagag cgctcccaga 14040
agttagatcc cagcagcagc atctgtccag gggcaaggcc cagggttcat cagcctggtg 14100
ctgttccttg tgagggatgc ctgccatgtt cctggatgtc ctgcctagaa ttctgttaag 14160
gtgccacttc ctgtgggtaa ccctttctct caggatttcc agaggttgtt tactgctagt 14220
caagatggac agctggtgag ggattagagc tgcaggcaga gcctgtgtct gcctggcaat 14280
gaatgatgtg attctggtgg gcacctaggt cacactgata agagtcatta gccttggtcc 14340
gagtttgtag taatcaagtt ttcctgttgg ctaccatcta tcattttggc tacagcagtg 14400
acgtaagctg gtgtgtgttg caactgcagg aatcttttgc tagcctttgc tgtcacagct 14460
gctactgcac tttggaaggt aaggacatgc ccactggagc tgagcctgga cctgattcct 14520
gctttacagt tggctagcta tgaccttacg caagcgtttg acatctgagt cttgttttcc 14580
tcgtcagtga atggggacaa ccggggattc attaattaga gttgtagtta gaatttaaca 14640
agctgatgga tgagaaacaa attaataata ataataaaac cggcaggtgg cccatgccct 14700
taattccact tggtaagcag aaggtggaat ctgtgagtct caggccaggc agggcctccc 14760
tcatagaccc tgtcagaaga agaagagaaa aggcttggga tgaggatacg gttcggtgag 14820
ttatgtgctt gccgtgcaag catgaggagc tgagtacgga tcccagggcc cacataagaa 14880
gccgggagca gtggtgcata tctgtaatgc taaccctggg attagagaca gagaccggag 14940
gaaccctggg gctcgctggt tagccagcct ccccacatcg gcggtctctg ggctccgagg 15000
gagacccttt ctcaaacaat aaggtaaaga gtgatggaca ccgatttgga cacaggcatt 15060
catgcacaaa atagggaggg cattgtttgg tttgtgccaa gcagttatta ggcaaacccc 15120
acaccttctt ggccatgaaa acaagcctgc taaccatcca tgctagtata cggtgagtca 15180
cctgcttgcc tgttgtcttg tctaccgacc tatctggctc cccatctgtg ggctgcaggg 15240
ctgtgttgca atactccctg gggcccagaa tccatttgca taattcagtt actcagaagc 15300
ctgtcatccc tgggtaggtc ttattgtttg atttatatgg tggacacggt tttctcattg 15360
cagtttctct ggcatgtgcc agtttctggc ggtgtgctgg gcctctcctg aacttcgccc 15420
tcctttccta gctgactgcc tctcaactct gcagccctgg ggagctacag gaagagcaga 15480
gaggctgaga gggcctggtc gtggggtggc agcttggtgg catggccatc gttagggctc 15540
atgggctgac ctcagaggtg aaatggtttt gatgcaggcg gcttgactgt ggagaaagca 15600
agcccagtag ataagtccat cagccaagct cagaggactg gcgcttgaca ccaagccatg 15660
ttattaaaat gaagacagtc tcaagtcagc aagaagcctc agcagataaa gtgcttgctg 15720
cgcaagcttt gtgacctgag acaactccct gatcccacat acatgtagaa gataagagac 15780
tccacagagc tgtccactgc ctctgcacat gctcagtagc gtgtgtcccc accccacccc 15840
accccctcca tgcacaaaca ctagaacaat actaaagaca aattaaaaaa atgaagacag 15900
ttgtggcaga ggtaattgtg ctgcagcctg cagggttctc atgatttgat caagagcatt 15960
aagctttggg gtctttgaaa agctttcagc ttattggggg gggggtgatt agacacggct 16020
tggaaagggg gaatcctttg ccagagagca gaggtgagtg cttgagtgcc atcttgtgca 16080
tctctgtgct ttgggaatgt gaagtcagta gctgtccaaa accgggtcct gagggggcta 16140
actgtgatga aggtaagaac aggtatgacc cagtaggggc taaggaaatg gaacagacag 16200
tgaagtgctt gccttgcaag cgtggggacc caagaaaggt caggtgtggc agtgcacagt 16260
tgcaacccca gctcaggaga ggtgaattca ggagaacctc tggggctcac caccagccaa 16320
accagcctcg ctgaattagc cagggagaga agcttggccc ttcaggaaca acacccagga 16380
ttgatctcag gtacacacac acacacacac acacacacac acacacacac accaagagca 16440
tagtgcaggc agagatacaa catagcaagc aggtgccagt taagcaccag acctaatatg 16500
tgtccttagt ttttggtgga ggtctcttgt tctgcattgc agtgaggggc ttaggagact 16560
aaagtagccc tctttgggag ttcctccttg gcaagtgagg ttcgaggctg gtatgtaggc 16620
agggttgggc ctggaagcat ggggacacct gcgacaagga agttggcagg taggatttgg 16680
gagtgagcag tcacccacca cactaacact gccacttggg gcagagcaag agcacaggtc 16740
tccacgggag catctttgtg ttctctctga caccagaaac caagcctagt catacaccta 16800
acggaggttt taactctagg ctttgtgggt gtattcctgt ccgtgtctaa ctctaggcct 16860
tgtgggtgca tccctggcca tgtcctcctg ggacctgggc tagggtagag gtttctgtca 16920
cagaaaccac ctgcagtttt gccctgagcc attgtgagga cacagggcaa gacactgtgt 16980
tgtgttagga acaatcccag aggggccttt cctgtgtacc tggccagact tgcttctggg 17040
ttgaagctgt ccgtgtgttt accctacagg gtgtgtccca tgtaaccctt ttcctctggt 17100
tttgatttct aatccaaagg ctaaagctag gtgtggtggt tatatatact gtaatcccaa 17160
tatgagggca gccacaaggt caaggccagt ctggtgtaga cactgagttg tccttgctga 17220
gcagcttggg agggacagtg agtggcagag ggcaggtcaa agcccttctc tctgtgccca 17280
tgtgtctcca tcatgcttct gtccagtgtg tgctcttgtg gccctctttg aacttgggtc 17340
ccaggtgcat gccctacagg tatagtccct gtggtcctgg tgctgtgatg gctcagcccc 17400
tgggggaata tacaaagcag agcttcatgg ggcacttggg acatcttgtg agcagtaata 17460
gaggtcgggg agttgggggg gggcactgaa aagccgagtc tatacccagg caaagaaggg 17520
tgcaggttga ggaggtgctg gtgggctaac acacctcctt cctctgtggg ttctgtgcct 17580
gggtgagtga agcagaggca gggagattat tttgggtaac tgatggttcc tgtgtgcccc 17640
actgaggcag gccaagtagg ggagaggtca ggtcgagagg gtgcagcttg agagatgggc 17700
tgatgtccag tctctgtagt ttgggtcttg gaaggtgggt ttgtaacatc tgatcacatg 17760
cacaggttgt agaggtctgg ttagggacag gggccctggc tagctcctag ggtaaagaga 17820
gccaaagaag ctcctattag tgcagacaga gatcggggct ggaggtctag cagacaatgt 17880
ggtgggcctg gcctgtgtaa tcgaggactg gttgtgggaa ggcagtgctt tagtgccccc 17940
tgcatggagc caccatggag gtctgccggg ccctccctgc aacagccttt ggaagggagg 18000
aagcagctgc ccaatgtcag tggtctgtat ccaggcacag ctggcttgcc agacagaatg 18060
gctgggacag ttggccccga gggcctttct tccaggacgt caggttccca gcttggtaga 18120
cacaagaatg cagccttgtg cccaggctgg gcagggtgtg atggcaggaa gggagagtgg 18180
gaagggagag tgggagtcag agcagtcagg gctcttactc tccggcctca ggtgccagct 18240
ggggaatgga ttggctttct attggcaagg gcacaccaaa gaagaatggg ggatacggca 18300
agatttgtgg accacatgca catacatgct tgcatgtaca aatgtgtaca ctcacacagg 18360
tagcccatgg ctgctcagaa gcccagggtt ccagggaaga ggtgtctgaa atgtctgcgt 18420
gtgtgtatca tgtgcattgc agtggccttg gagcctagaa gaagacattg ggccctctgg 18480
agttggagtt caggcagcta ttgagcctca tagtgttggt gctgggaact gaacttgggt 18540
cctctgcatg aacagagtgt gtttttaact acctagccac ctctccagcc cgaggtgttc 18600
ttatttattt atttttactt tttattgatt ctttgtgagt ttcacactgt gcaccccagt 18660
cccactcatc ttcctgtccc ctcaggtcag cccttgtaac cccaaaataa cacacacaca 18720
atagaaaaaa catctcatca cataagctgt agtgtgttag tgtgtcccac agtatatccg 18780
tctgtccaca catattccct tgcaacaagg agtcattgga agtgtctggc ttctgtgaca 18840
ccatcaatac tgggtcctca ctgggtctcc tccaggttat gctgttgtta ccctgtgtcg 18900
tggaggttct gcacctttgg atcagtagta ccagcttttc catgcatccc agcgattgac 18960
agatgataca gattttgggg tgggccaatt cagtgccctg ggtctgggcc tgggcagtag 19020
ctgagctgat ggtcagcaca ctggctcttc ctcaccagca ccactagggc aagttctcca 19080
gcattgtttc agctaagcca tccaatgcca ccatcagcag gaggcagagc tatgccctca 19140
ggctggttca cccacaccca tgccttcaga gccagctcca ctgtgctgcc cagtcaaggt 19200
gcagggccca ctttccccag ggctgcaacc agtaaggggg cagggccagt tctcccgctc 19260
tcacactctt ggagctggct ccccccttgcc tttgccatca gagccagctc cactgagttg 19320
cccaggcaag gtgcagggcc cactcttccg agtgctatag ccagtgaggg tgcagagcta 19380
ggtctcccac tctcatccct agggaccaac taactaccct aactgctgag atggtaaggg 19440
aaggagggaa ggcatcaccc ccgcatcctt gccatctccc agcagacaag tggcagagcc 19500
tgcctccccc ccttgctctt gtcctcaggg ttggagcacc cacacactct tgaccagggc 19560
cagcccttct gtgttgtcca ggtgaggggc aggaccagct catctgctct cacagccctg 19620
tggtcagctc tcccaactgc cacaggtggc aagagaggag ggaagtgcat cacggccaaa 19680
accacatcac ctcctggcaa cgtggggcca gctctccccc acccccaccc ccatccccac 19740
cccactccac tcttaccctc aggggaccag ctcacctgtg ctcccaccac cagggccagc 19800
tctgctgtgc tgtccagggg aggggcaggg cctgctctcc cgagggctgc agctggtgag 19860
ggacggggct agctctcgtg agtccactgc cagagtcaac tctccccact ctcacaccat 19920
gagggccagc tctccagagt gctgtagcca atgaggggca gggccagttc tgcacagccc 19980
ttggtcagcc ttatggtccc ctatggctgt cccaactagg aacttgccca tgtcctctag 20040
tggtaatatg agtcaaggat agaaacaccg gcccctgcca ctgggtagcc attgactcag 20100
acttggccct taacagcagc aagctgggac ctgtaacaag ctcaggtggc agggctggcc 20160
actcacaaca ggcgactcct ctccaccctc gagtctccag tcccatctct tcataatact 20220
caagctgctg cgcttctccc tctcttccct ctgaccaccc attcctgcga attgtggtgg 20280
ctcctgctgc aggctggtca tgcagttggt ggcccctggg tgacatcctc agtctgtaca 20340
acagagcagc agcctgtgct gtgtgccaga gggcagtcct gtgggtggca ttgtggtctg 20400
caggccttgt cttccttctc gttacactgc gtggtgacag gcggggctct gtgtgtctgt 20460
ggcctgcctg tgccacgggg cagctctggc caccaagcca ggcatcaaac taggatgaac 20520
aaatgactgc cctaacccta taaggttaga ctgctataag gacagcaagg tgtctcttcg 20580
cctttggctg gggggttgggg ggtgctgtat tattaattga agaggaccag attgccatag 20640
gtctgtgtca ccaacaggcc attgctggag caggtacaca ggtgaagttc tgtactgacc 20700
tgtatgtgtt gtgttttata actgagcatt tgaggaagtg ttcagttaag gccaagttca 20760
tggaggcttt gggggaactc ttgcaagctc cttggatttg tgggcatttt gcttcctcca 20820
tgggactgtg tataccccag taccttctcc ccacacatcc agccggctct gccaggtgca 20880
ccaggcctcc aatcccacgc ttgagggtga actcgctttt ggtgctttgc agagagctac 20940
tcattctacc acagtggctt caaatggtag gtgaggggga ccgagggtgt ctgacccgca 21000
gcctgtgggg cacatgcagc taaggctatg aaaacagccc agcacatgct ccatagcatt 21060
gagtagaggt tagaagacag ctttcagggg ttggttcgct tatcccaccc acccgtatat 21120
tctgggaatt gactgtgagt gggcaggact tggcagcatg cacctgtccc cggtagcaat 21180
cttgctggcc caggatgttt ttcctttttt ctttttcgta acttgattga ttgttgtaga 21240
taagtaatgt tctgttgaaa gtcaaaacgt gagacaccct gcctacggtt actttccctc 21300
gagggcctct gggatgctgg ctctgagtca gggatgaaga gagccttccc cacacgggcc 21360
tgggatcagg tttactaagc agaactgtgg tgactgggtt gggactctct gggactactg 21420
tttctggggt cacagagcct cccacaggga catctgtgcc cacctgaaaa ggagggagct 21480
gcaggtggca gtttctgcca ggtgtggggt gtggtctcca gggcaggaag agaatggcag 21540
gaccagcgtg catcccgacc agcaggtgtc attgggtctg gtcaaagtgg agagtggcgt 21600
atgtacacac atgaactcaa tccagatcag gccacaaaag cccaactggg caaaacagtg 21660
atttttggcg gggagaggta tttacgggaa tataggggag ggattcctta ctggagcaga 21720
aattactcaa agacagctgc cttcccaagg cacaccccag catgggtgac agcccacaaa 21780
gctgggaact tagagcacac tgcacacact gatggcccct cacacattgg agagagttct 21840
ttccaggagc ctcggttagt ctaaacctct atcagttagc ttggctggtt tctgcttctt 21900
ttaggcagct ggtctctaga ggcttctttg aagcttgtct tgtctttgtc ttagtagcag 21960

-continued ctctgttgtt gggctagtct cagagggacc caccgctttt attgctttct ctgtcagtga 22020
gtgcctagtg gatctggtca gtttcaggga cttcctggag gtgtttaccc ttgttaagga 22080
gcctgcctgc atgatggggt gttttggagg aaatggatac acaagaagtg ggcatgggat 22140
gggagttggg agcttgggtt gctgcagctg ccttcccctc cctcctgact ccacttgcag 22200
gagtctgctg tgctgtacgt gggtggagca agtgcttact tcacagcaag catgggcacc 22260
cagttctgct tagcatccat gagagctctg gcttactgaa cagacagctg tgtgggtaca 22320
ttcagagctg tggggagacg atagacttga acagaggaag agctcagagg atggggcttc 22380
ctgtggtcac tgcccacctt tccgggctct cactgaagct ttgcccactc ttcctcaccc 22440
aagccctagg tgccatggaa tccatgctgg gattcgtgtg ggtcagaggt cagccgtgat 22500
tgtcattcct tgcacagtct gccttgtttt tttgaggcag ggttgaagca ggctggctgg 22560
tgagcccaag ggatcctcct gtgtctgcct cccagtgttg ggattacatt gtgcctggct 22620
tttttgtag attgagctca gatcttcatt ccgctcagca agggacgcgc ctaacagtct 22680
gagctgtctg cagatgcttt ggtatctgtc ctaccgcacc aggggatccc tgaaaaatta 22740
cttagttctg gagggtgata tttgttctga atgaagcctt ggtgggaaca gtggtggggt 22800
ggcctgctag agccactcct tccacactga tggccgcaac tgtgtgacca gagatggatt 22860
tgatgcttaa gtgtaagtgt taagaagaca acatttgtgt tttgtgagag gacatttcct 22920
ttttttcctt tctttcttca cagtttttttc tttgtgaatg tgcagtatat tcatgtgtat 22980
gcgtgccttc atgtgtgtgc atgtggaggt cagaggtcaa ttgtcttagc agtggtcagt 23040
tttctttcca cttaaaaatt ttagtttagc actggggagg cagaggcagg aggatttctg 23100
agctcgaggc cagcctggtc tacagagtga gctccaggac agccagggct atacagagaa 23160
accctgtctc aaaaaacaaa aaacaaacaa acaaacaaaa ttttagttta ctattactgt 23220
gtacatgatg tgtgtgagag agagtgggga tgcatgcacc ataatgtatg gagggcagag 23280
gacagctctg gaagtcagtc ctttcctttc aaattttttt ccttttaatt aaaagaaatt 23340
tggggggggg gtgtgcacgc gcatgtgtgc acatgagtgt aagtgtcctc agagagcagg 23400
attaggaccc aactcgggct gttttcttca ggtgcttcac aactgaacca cctccctgtt 23460
ctgtttttttg tttctttgtt tgtttatttt ttaaagacag tttcttactt ctgtaggttt 23520
cacagcaaac ctcctgcctc aaccactcag agtctgggat tgcagatgtg aactaccatg 23580
cccagctgag acagggttgg ttttttttt ccccctaagtg atatgtttag cagggcgtgg 23640
tggtgcccac actttaatcc cagtactggg gagaaagagg cagaggggtc gctggaagtc 23700
caagaccatt ctggtttaca gagtaagttc caggataact agggctacat ataaagaccc 23760
tgactcaaac taccaagaca aaacaaaaaa gataagttta tgcatcaatt tttaaaattt 23820
attttttatt gattgattga ttggtttttc aagacagggt ttctctgtat agccctggct 23880
gtcctggaac tcactttgta gatcaggctg acctcgaact cagaaatcca cctgcctctg 23940
cctcttggtg ctgggattaa aggcgtgtgc caccatgccc ggcaaaattt atttattttt 24000
ctgtgtttgg atagtttgtc tgtatgcaca gctatgcacc atgtgagtgg agtgtctggt 24060
ggccagggag accagaggaa ggcatcacat cccctgggac aggggtcaca gatggttgtg 24120
agctaccata tgggtgctgg gaatctgacc caggtcactt agaagagcaa ccagtggctg 24180
ctgagccatc taggaagaga agctcaattt aaatttctct ttatttattt gtgtatgtaa 24240
cgcgcacgtg tgtgtgtgtg tgtgtgtgtg tgtatgtgtg tatgtgtgtg tgccacataa 24300
gtgcagtgcc catagaggcc agaagaaggc atcaaatatc ctggaactat aattacaggt 24360
ggttgtgagc tgcttgataa gggttctggg aactgaactc agatcttcgg gaagagcagt 24420
aagctctctt aatgactgag tctctgagac tatattttta aataacaacc tcaatgaggt 24480
gtgcctaagc tagttttata tgaacttgac acagggtata gtcagtcatc tgagagggag 24540
gaggaaacct cagttgagaa aatgcctcta taagaccagg ctataaggga ttttcttaat 24600
tagtaattga tgggggaggg cccagcccca gcctattgtg ggtggtacca tccctgggct 24660
gtaagaaagc agactgagta agccatgcag agcaagccag taaacaacat gcactgtggc 24720
ctctgcatca gctcctgcct ctaggtttgg agtgagttcc tatcccaact tcctttgatg 24780
atgtactgtg atacagacgc ttgtgccaaa taaacctttt cctccccagc ttgttttgtt 24840
catgtgtttc attgaagcag ccgaatccta agacggtgga gaattcacag aaggaattca 24900
cccatctaaa gtgtgttttg gtgatctttg atttattcac agcaacgtgc cactgtgtag 24960
cattgtaacc agttagggaa catttttatc aaccctccca aatactcctt cttagcctca 25020
tccagcctcc cctggtgtgt ccctggctgc tctggtcttt ccttctctgt aggtttgttc 25080
tgttctggac acgtcatgta aatggagtga gacattggct tccttggctt cctgccatgc 25140
tggtttggtt tgtcttggtt ttgtgagaca gggtctcctg tagctcaggc taacttctag 25200
ctaaggatga tttgaacatc tgatcctccc acctcctctc tcaagtgctc tgacctcagg 25260
agagtgccac catgctgtgt tcatgtgtcg ctgggatgga accctgcacc atgtatgtgt 25320
aaggtgaacc ctctgctgtg tccccagacc ctggtgccat gctatcatct gtgtcactgc 25380
gtgtgttggt gctgctgtcc ttcttaggat agagtcatgt tcctggtgtg tggctgcatc 25440
agtttaccca cgctcttcct ctgtggaagg ggctggctgt actttcctct cctgctgtaa 25500
ttttgtctgt catgagcatt gtgaacgtgt gtgtgtgtgt gtgtgtgtgt gtgtgtgtag 25560
gttttcctga gaacttgttg gggttagctt agccaaggag aggttgctgg gttccatggg 25620
ttttagtttt gatttgttgt tgttgttgtt gttgagatga tggtcattta gtgtagccca 25680
ggctagcctg gaattagctt tatgcttagc ctttcaggaa aggacaggct gtcttccaga 25740
atgacctgaa cctgtcacat ttctttgaca gtggcgtagg taggggacag ggtggggtgg 25800
gggagagctc ctgatctctc tcctccctct gacagcacct gtcactcatt gtttgcattc 25860
tagccattcc tgtgggtagt atgtgctgtg atttgattgt acttctggaa gcagtcagag 25920
aatttgaatt agtctgtgaa gccaacatgg aggctgtggc cgcctcatta gatctgtagg 25980
cctgagtttc tcaggctcat gttttctggc accagtgcct gcttaatgac ttgaagcagg 26040
gaggctgtga gggcagagtg cattgttcat gcatgcccac ggagcagcag gagtgcctgc 26100
tatcgggggc ctttattaag gcctttatta agtttaggca ggtcttttta gtctgttgga 26160
ggcagggttt tatgtagacc aggctggtct tgaattcact gtgtagccaa agataacctt 26220
gaagagcctc ttgcttctac atcgataatg ttaggtttat aggcttgtgc cgtcacacct 26280
ggtaggttcg ggtggttctg aacattagac tcaggtcatg tgacagggct atttcaccct 26340
ggaaaggaca ccataaatat tcccaggccc catgattgtc ctgagaccag gtttggtttc 26400
cgggcaaaca tggggttcat gactttggat agaattaatt gcaacactgt gtttaatcca 26460
ctgctgttaa caaccccctt gtgagctggg gagatgactc agtgggtaaa gtgcaggctg 26520
ggcttgaggg cctgagtttg agcctcagta tccatggaaa gtgctgagaa cagaagcgca 26580
ggtcagtttc cagtgctggg gttggtggtg ggagcaggag gttcctcggg ttcacggatc 26640
actcagccag tcagcgtgct ccaggtcctg tgagagacct tgcctccaaa cagtaaggtt 26700

-continued

```
ataagccaca gaagaatgca tctcgtgttg aactcaggcc tgcaggtatg cacacccacg  26760
aacgcatgtg cactcacata cacatacaga aaagtttgca tcgaaatagt tccccggtgt  26820
ttcaaaagtt cattaatgta tttattgagt tcgtttgttt ttgttcttgc tacaagatct  26880
gtctgtagtc cagcctggaa ttcactgttg agcccacagg ctggctttga acttgaaaca  26940
atactcctgc ctctgcctta taactagtgg gattacagag tatgagccat tgtgcctggc  27000
tcacccttga ggttgtataa aagattggcc aggtggccag ccacagagct ctgttgccaa  27060
gattgatgcc aaatgtagac attcaccatg gctaggcctt gttgccctct tcctgcctgt  27120
cacaggatgt agatacacag gaacttccct tgggctctaa attatcttca gtaccaggct  27180
gtctccacct caacctttct gaggtcagaa cagcactcaa aggccagttt ccaggtgtgc  27240
cacccacagg cattgtcctc ttcctcccac atccacctgt ccctagccgc cccacctagg  27300
tgtcctagat gacactgtgc catttccaac acagcaggcc cacaggtgca ttgtctgatg  27360
tctgctcctg ccaccccagg aatggctccg cagagcacaa tagttcaagg ctggagggtc  27420
cctttgatca gcttgtccag ctcacaggtc tcagacctgt tcattagggt ggcatcttca  27480
tcttcactag caccacactg ggccagggct gtctgctctc cttttcagag tggcctgctg  27540
agctgtgtgg tgtcctgcct ggccctcttt ctctaactac tatgtaggca ttgcttgctc  27600
tttgcctctc agctctgcca caggagggca gaagggtcgt ttctgcgagg gtctagttcc  27660
tcacctcttg agttcacggg acgcagacag caagtatttg ttgaatggac aagtgattga  27720
cagttgatac catctcattc tgcagcttaa gctggtagat cactcaagct ggcctcaaac  27780
ttgtggcaat catcctcctg aggtgcatgt caccacacac agctagcttt ggttgatatc  27840
tttgagttgt attgatgtgt gtgtgtgtgt gtgtgtgtgt gtgtgtgtgt gtgtgtgtat  27900
tatttattta cttatttatt tataatttct tttgcagtgc tggggttaaa acccaggcct  27960
cacatacatt agcaaatgat ccaaccactg agctacatcc ccaattctgc ttgttgatat  28020
catgtagccc aggctggcct ctaactttcg atataaccaa ggataacact gaactcctga  28080
ttttcttgcc tccatctcct gagtgctgga attacaggca tgtactacca cacacaataa  28140
taagcatcac accgagggct cgtgcaagct aaacaggcat tcttctatct gagctacagc  28200
ctagaaccct gactgctgat tttctaaaaa ggcacatatt taaagttttt tttaaaatct  28260
gagtgttttg cctacatgca tataaatatg cagcatatat aagtcgtacc taggaaagac  28320
agaagacagt gtgtgatcct atggaactga agatacagat ggttgtgagc caccatttaa  28380
atgctgggaa ctaaagacag gtcctctgta agaccagtaa gtacttttaa aagctaaacc  28440
atctctctag tcctgatacc tattggtttt gacaggtttc tcagactatc tgggcctcag  28500
taggaaagtt actatctgat gagaacatac ccataaattt gattttatta ttgttctgca  28560
tagtttttac cttgtatctt ttatatattt gtgtgtatac aaatacatat atgtatacac  28620
attttatatg tatatagtat atacaaagtg tgtgtatata tagatacaca cacacataca  28680
cacactttgg acacacactt tgtaacaaac agctttggaa aacagaggga ttgcacactt  28740
tcagaagagg ggatacctca ggcagtgctg gggagtgagg gaagccagga aggggtgata  28800
cgtctgctgt actgagtgtg gagggggttg gaagctgttg attctgaaga caacaggagt  28860
aaatgaagaa gagagggaaa gaatgcattg tagatccctc ttgttctatt ttttacctgt  28920
attagtgtac actgtgtgta tgtgcatgtg agtgtagtac ccacagaggc cagaagaggg  28980
catcagatct catggagctg gaggtataga tggcagtgag ctagctgctt gtcttgggtt  29040
ctgggaattg aactcaggtc ctctgcaaga gcaggaaaca ttgttcccag ccaagccatc  29100
```

-continued tcttcagctc cagatcctct tattttgggg ggttggggat ctaacctggg cttcacacat 29160
gacaggtatt gagatagcac ctgtagattt ctaagattta ctgtattgag ttgggcaaag 29220
tacagaagag gccttgtttt gtgcagggat gacgaaggcc ccatacatgg gtgcttaaga 29280
ccagtttgac tttaggactg gcctcagagg atcaggacca gagggtgtct gtgcagtttg 29340
tagggtgcta gtggagtctt tttcattttt cttgttgggt tttgttttgt tttgtttttt 29400
aagtttttgt tggttttttt gagtcagggt ttttctatgt agtcctggct gtcttggaac 29460
ttccactgta aaccaggctg gcctcaaact cagaaatctg ccttcttctg cctcctaagt 29520
gctgggatta aaggcataca tcaccacaac cagtgttaaa agcattttta tttattacgt 29580
gggggtgggg cagggcatgc acaccacagt gttgttgtga aggtcaaagg acaactttgt 29640
ggagtcggtc ctctccttcc acctttcctg gattctggga tggagctcac atttgtcagt 29700
ctttggagga ctgagcttgt ccagccgagc tatctcacca ccccacttgg agtctttata 29760
gcaccatcca aagctggagg tgcagtggtc ctgtctgaag gccagggttc agggccactg 29820
ggggcgtgtt tgtggctact ccaggtgtct tcacaaaaac tgaaggggat gagctgcaag 29880
aagctgccat ctctgcagtt caggtcaatg catggccacc aatgtccttt gccatgctgg 29940
ctgagaatgc cagtggaggt gtggctctgt gggataggta gagagggttg gtgagcccac 30000
accatcaccc cgggtctcta aatggagcag gcctgttggg agctacacag tgaggtgtgt 30060
ggtgtgaggg gcaaaactgt atctattgag catgagtctg ttgggccaca gggttcactt 30120
cgagagtgtc ttctcctgct gcttcctggt gccaggcttc tcaaagccat ctcttgcccc 30180
tcctccaggt caccactcaa gatggcagag gctcaccaag ctgtggcctt ccagttcaca 30240
gtcacccctg atggcatcga tctccgcctg agccatgaag ccctcaaaca gatctgcctg 30300
tcagggctgc actcctggaa gaagaagttc atccgattca aggttagttg gttgatcgtc 30360
tctgcagcac ttgcttgcat gcacctccct gggtcccgct gaagaaggaa tgtgtcttag 30420
gtgggtctct gacagagcag tggtctcagt gctggctaag gcttgtggag gacacagata 30480
tataaaatgg cctcatcgct tcatagctcc ttcttattgt tgggttttgg gctttttgtt 30540
tgtttgcttc tgttttttaa gacacagtct ctctgcatcc ctcactctcc tggaactcac 30600
tcagtagacc agactggcct tgaactcaca gagatccgct tgtttctgcc tcccaagtgc 30660
tgggataaca agcctatgct accatgccct ggaaggcaac tggagctcat cagattaatg 30720
taaaacaggc caagcacctg atgccagagc agggggccca cttatgggga gtcagtgtcc 30780
aaataggaac acaggcctgc cctctgcccc tcagctggat tccttgcacc ttactgaaga 30840
ggattatttt caaactttaa tgaatttgtg tcttatttgc ttaaagaaaa gttctcaggt 30900
agctcaggct agcctgaaat tctccatgta gctgaggatg gccttgtata tctggttctt 30960
ctgcctctgt cctccctggt gctgaaccac agacatgtct gttgggtttt attaggtttc 31020
ttagggtttg gttggcatca gggatgccag gggtttgctc aggctaggca gtcatacatg 31080
ttacatgtgt cacaaaaacg aaaggttctc agaggtcagt gtgatgtgac ctgtcatccc 31140
agcactttag aggctgaggc aggactgtct agcttggact acaatgagac cctatcttaa 31200
aaattgcttt taattatgta gatctctgtg tgtctgtgta tgggtaggtg cctgcagagg 31260
ccagaggcat gtgatcccct gaatctggca ttataggtgg tcaccagcta cctgacatgg 31320
gtgttaggaa ttcaactcgg gtctctacaa gagcaagtgc tcttaactac tgagccttct 31380
ctagccccaa gaatgtgtgt cttagttagg tttttactgc tgtgaacaga caccatgacc 31440
aaggcaagtc ttataaaaac aaaaacaaaa aacatttaat tggggctggc ttacaggttc 31500
agaagttcag tccattatca tcaagatggg aacatgacag catccaggca ggcatggcgc 31560
aggcagagtt gagagttcta cgtcttcatc caaaggctgc tagtggaaga ctgactttca 31620
ggcaactagg atgagagtct taagcccaca cccacagtga cacacctatt ccaaccaggc 31680
cacacctcca gatgttgcca ctccctggtc cgaaaatata caaaccatca caatgtgttt 31740
ttagttgaaa ggtttttctt cttggttttg tttgcctgtg tttacaggag tgggggggaga 31800
gagagagtgt gtgagagtga gtgtgtgtga gcacacgagt gtgtttatgc atggaggccc 31860
aacctttaca gcagatgtct tcttctctag cttcatttat tgagatgagt ctctcacaga 31920
acctgagatc actgattctg gctagtctag agtctggcta gtctagagtc tggctagtct 31980
agttagccag cttgcctctg gagcactggg gttacataca ggtgaaagcc attcctgcct 32040
ggcttttaca ttgattctag agatccaaat gccaggcctt cccccagctt gtgtgctaag 32100
tgctttaccc actgagccat gtcccagcct agttttactt ttttgagacg gtgtctgacc 32160
ctagccaggc tcctctgtaa ctaaaggcag ttctcctttc ttagcctctc aagtgcttgg 32220
aggatgtgtg agcccccaca ccgtgcttgg acagttgttg ttattgttgt taatatcaat 32280
attattgagt taggatctca ctgtgtactc atggctgacc cggatctcac ggtggagacc 32340
agactgccct caaactcaca gagctccatc tgcctctgct tcccaagtgc tgaggtgaaa 32400
tgtgtgtatc cattaagaat ttattatgca gggctggaga gatggcttag cggttaagag 32460
cactgactgc tcttctgaag gtcctgagtt caaatcccag caaccacatg gtggctcaca 32520
accatctata atgagatctg actccctctt ctggagtgtc agaagacaac tgcagtgttc 32580
ttacatataa taaataaatc tcttttttaa aagaatttat tatgctgggt gtggtggcac 32640
acttctctaa tcgcagcatt caaaaaacaa aaccaaaaaa aacaacaaaa tagaattaac 32700
tttttgtaag actcaaacat ccaacaaagc agaaaaaaca gctctccctc cccattaccc 32760
tcctcctggt tcccagagct ggcggagtct gggcagtgtt gagtcacgca agccttctct 32820
ccccaaacct cagttcttta gaccagtttt ttaatcgggt gggcaagatt gcagcccagc 32880
tgatgacctg agtttgaccc aaagttccac aaaataggag gagagatctg acctctgacc 32940
tccacctttg cgccttatgg tccttgcatg cacctacgta caataaataa atgtaacaac 33000
aaaaaattaa tgtaaacttt attttgctgg gttattttgc agcaatggta tgggggctcc 33060
tgtaaacaca tcttgactca ggaacagggc aagggtagtt tgggagctgg ggttcctgac 33120
tggcagatag tggcagtgta ggaatgggac ctcacagtgc ccaggctgcc agtcaccata 33180
tggagacctg tatggtaagt caggcctggc tgttttacca acctggagtc cctttcttgg 33240
agaatcttcc aagatgcatt tggctcaga agtcagggga gagaatagac tgtgtaaaga 33300
aaggtaaggc agttgtgact ccaggcagag acacagctac tgggctttgg tctttggtgg 33360
cctgcatata tggcaccttc tccctgctgc ctgatgtccc aactgcctgt tgccacaggg 33420
ctgctgacag gtagtgatgg tgacctcggg gaggatgcag ctcacagctc acatgtcttt 33480
ccagaatggc atcatcactg gtgtgttccc cgcgagtccc tccagctggc ttatcgtggt 33540
ggtgggtgtg atatcatcca tgcataccaa agtggacccc tccctgggca tgattgcaaa 33600
gatcaatcgg accctagaca ccacgtgagt aacccacctc caccctctgc atcttgaaga 33660
agatggtggt acctctgttg actgtcctcg ctctgaaatg tctgagtaca actatgctat 33720
cgctgttttt ccgcatgctc tttgccctcc tgacctgcta ttgaaagtct gcagacactg 33780
ccacccttct tctgaagact aggctaagag tggcagaggc acggggacct gccttccagg 33840
tgtctgtctc ctgaggtcaa gatggagaca gtgatgacct cagagggcat ctctgcccca 33900
gaagatggct ccaagtgtgg ctgttgccct ggagttggtc catccagtga tctggtcctc 33960
tgaacttact gccggtcatt gcttagggac aactcagccc ttggcccctt cacagtggct 34020
tagatgcctg cagggaagtg cgttactcct tggctttgag ttttagttta ttctgggaac 34080
ttaaaaaagt agatgtcatc ctgtctaggg acaaatcctg gccatcttct ggtttttctt 34140
tttcttttct tttcttttct tttcttttct tttcttttct cttctcttct cttctgttct 34200
ctttctttct ttcttccttt ctttctttct ttctttcttt ctttctttct cccttccttt 34260
cttccttcct tccttccttc cttccttttt ttttttttga gacagggtct caccgtatag 34320
ctccagctgt tctggcctag aactcaggga tcttatctct gtctgtctct gtctgtctgt 34380
ctgtctctct ctctctctct ctctctctct ctctctctct ctctctctct cctggttgtt 34440
cagctgtaga tactgtatgc taggaaggat tgcacaagca aacagatgag agagtggccc 34500
cagggaacac tcacagctgg aggagttggt ttctgctgac tcagagcaac tagcagattt 34560
aacccagcag tgtggcatgt ttaagacagc ttgaataggt gctcgggaat cctggaggtc 34620
agtctttaat gggtctgcat gccctgcctt ctgattgaga cacccaggag tgactgagaa 34680
gccagccagc tcctcagcct ccagccctcc tggcagcatt ggtcattcct ttgtaagcaa 34740
ctgtaggaaa caagataaaa atgcctgtcc aggcatcctg ccaagggtcc tgtctgcctg 34800
gggcctggaa catcgagctg gggctaggtt ctcagaagca gctggcagag ctggtcacta 34860
aagactggac ctgtgctgtc ctgagaggtg aggaaagtcc tgtgaacgct caccctgctt 34920
ccctgagtgt tgagctggct gccaggccca aggcagctgt gaggccaaca gccaagcttt 34980
gctcttacat gggctgtgtg tctcaaagcc ggattgcaca cagccacgcc agctactaaa 35040
accttgctta atctcagtct ttatacgatt tgtttcttg tcccttagac tctattttcg 35100
taaactgggt catgtctggc tcaaatttag aaaggtcagg tgaaggctca gagacttgca 35160
gcctgagggg ctgttctgga agcatctttc cagtgtgggt ggagtgcctg tgtctcctag 35220
gctgctttgg ttttgtttgc tgagatctga aaggaaggcc atagaggtta tcagcacagc 35280
tgaaagtgaa attacttttt tgtccttatt ggattttttt tttttttttt ggtttttttga 35340
gacagggtct ctgtgtagcc ctggctgtcc tggaacttgc tatgttgcta tgttgaccaa 35400
ccttgtctca tgaactcata gagatctact tgcctctaca tgtgacacca tgcccagctt 35460
ggatttttttc tttaaatttt attctgtgtg tatgtgtact atacgtgtgc ctggtgcctt 35520
cagaggtcag aagagggcat cagatcccct gagaccagag tttcagatga gtgtgagcca 35580
ctgtgtatct gttcccatca gctgcaggag gaagcatctt ccaatgacag ttgtgctagg 35640
cacccatcct gttcttctgg gaggcgaggc ctccagagca taggtctctc acatgatgtt 35700
aatgttttcc aatatcagag ctctgaaggt tagatatgct actactttga tcatttggga 35760
cctcttatgt tatgttttgc ttttagattt atttattttt atgtattatg tgttagtcac 35820
atattatgca tatatgtttt taagaattgt ctatttattt tagtacacta tagctgtcct 35880
cagacacacc tgaagagagc atcagattcc tttacagatg gttgtgagcc accatgtggt 35940
tgctgggaat tgaactcagg acctctggaa gagcagtcag tgctcttaac ctctgagcca 36000
tctctccagc ctcatattat gcatatatta tgtatgtatg tgtgtatgtg tgtatgtatg 36060
tatgtatgtg cctgcaggcc agaagagggc accagatctc attatagatc agccaccatt 36120
tggttgctgg gaattgaact taagataact ggaagagcag ccagtgtgct taacctctga 36180
gccagactcg atctctttta tttgttcctt gacaattgca tacacgtcaa caggatacct 36240
tgatttaacc catcccaact ctccactcaa accttttttaa aaacccgctg agttccctta 36300
gcgccccctg ctggaggatc cctggtcggc cagctggctt ggtccacttc tcagtgagtc 36360
ttgtctgcag cagccatgtt gtgttcacat ctggctgcac cctttccacc ccttcttcca 36420
tgatgtcccc tgagccatga aggggaaggg ctagttttta tttttgtcac tatttttcct 36480
tttctaaaac aactgaaata acccctcaaa tagcagcact ttgttttgag ttttctttca 36540
tagtcggtga ctttgatttt taactattta aaaatctttt aagtttttta aaagatttat 36600
ttatttttat ttatgtgggg attttttggc tttgttttgt tctgtttttg tgtttgagac 36660
aaggtcttat gtagaccatg ctagtcttga actcacagag gtctacctgc ctctgcctcc 36720
agcttgctgg gatatttgag tttcttataa ataaagacag catttaaggt tatatctgag 36780
gactggggat ataactcagg ggttgagccc ctgcctagaa agcatgaagc ccatagttca 36840
cccctgggca cagcaaaacc cagcaaatgc tagcaaagta tgtttgagag actggcaaag 36900
cattataatc tgaagaaaac gggccaggat ccctttgagc agcagttggc aggtcccacc 36960
cactgggagc agttgccatc gtgagcagct ctctgcccca caggagcctc tccaccattc 37020
ctccagagac tggaaaaact gtgtgttgtt caagactgct caggtcgctg gccggcctct 37080
tgattcttcc ttgggcctcc agagacaggc cactctgctg cacccagcca aggctggccc 37140
attttgagag gaatagagac tgccagggcg cttggagaac tggggtccct caggcttctt 37200
ctgcagcctg ctcactcctg tcgctgggag ggtgcttggt cagcccgctt tctggtagct 37260
gccattacca ccttccatgc tgacgtctta gctccttgtc tgctccatcc tcacagtggc 37320
cgcatgtcaa gccagacgaa gaacatcgtg agtggcgtcc tctttggcac agggctctgg 37380
gtggcgatca tcatgactat gcgctactcg ctgaaggtgc tgctctccta ccatggctgg 37440
atgtttgcag agcacggcaa aatgagccgc agcaccagaa tctggatggt aaccacccgt 37500
cacccaccag gggacccgct ccgagtcaga gcaggaccct tgcctcctta gacctttcct 37560
cctctgttcc ttggtgtgta acctgtcccc agcctctggc tatgggagag ctatggctca 37620
tgacacttgc atggatggag ccagggctgc ttttgctaat ggtttctggg agttctgcca 37680
tctctctgtt cacctctgtg tgacctgtgg ttcaggctgg atattgagca taagtaccac 37740
ccaggaggtc tttgtagcct taggggccac tttgcaggca gacaccagac ggtttttctga 37800
gttggtcaga tcacatgatt taccctaatc cgtcagtgtt ctctatttct tcgtgacctt 37860
aaggccaagg caccatgttt aagagagaga gagggttata ccatatacat gtgtgtttgt 37920
taaattataa ctggttgtga aggcttttgt tgttgtttag ttttggtttt tgagatgggg 37980
gctcatgtca ccctggctgg ccatttcctg actgtagcca atgatgacct tgagtttctg 38040
gttctcctgc accaccatgc ctgatgttta tgagatgcca gtgaccaaac ccagagcttc 38100
atgcctggct tacccagatg agccgtctgc ccagggaagg acatccaaag ccccaacgag 38160
ctgcttttat aagcttagct ctctggagta gggggaggag gatgacggat cactcctggg 38220
acctccctct ttggcactca gaccccagcc tttccttccc acacacacca ttgtatggct 38280
gtcacatatc ccccacccac ccacccacat attgtcaccc ctcttggctt ctgattttta 38340
taaagaaaag gtcattttct gcacccaagg tttgtaaagg atttcagtga atctggttct 38400
ggtaacattg cctttcaaat gcttgttact ggagctcctc ctttgtgcat gggaggagta 38460
ggtcagcttg gccttgactt gcgggccagt gtgcccccat gcccgcactt gtgaacgtct 38520
tcaaggtccc tttgctgccc accacgcact cctggcctcc atctttcaca aaccagcttc 38580
caccttatat attagttttt taatgtctag agtagcaaaa cttaaccaac aggcttaaca 38640
cagtgtcctc taggatggcc ctgtggctgc tgttgagctg agtcccagca cttcctgagc 38700
atcgcaaatg agaatcaccg actacacctt gaacccttag agatgcccta gctcctgcca 38760
gcaggaggca gctgccttcc atagctggcc tgcaaaatct tcctacaggc tgtgggggga 38820
gctcactctc taggctgctt gacctgatgg gcagggacac actgctgccc ctgggggtgg 38880
cttgagggtc aggcacctca gctgatccta ctccctatgt gcagagcggg caccagcctc 38940
aaatcaagga ccttccagga ggaggcagac agccctcctg cagaatcggg aaggacagta 39000
ggcagccaca ccagaagact tctcttttca gctgagctct cggtgggacc ggagcctgat 39060
ggtgtagacc agggatggct ctgtcataaa acactcagag agtcaaacgc agttgaaccc 39120
tggctttggt tctttaacac agcctcatct ttgaaaacgt aacttgtatc tccaggctat 39180
ggtcaaggtc ttctcgggtc gaaagcccat gttgtacagc ttccagacgt ctctgccgcg 39240
cctgcctgtc ccagctgtca aagataccgt gagcagggta ggtattatcc acactcctgc 39300
tgagatgcca gtgtccttgg gatccatgtt tctgcctaat tgtgactgta aattaaagtt 39360
cttaatcttt gttattgctc tgcagtctct cctgtagggt tattataaga atgttcccct 39420
gtctcccacc ccacagagtc cttgcactgg ctagacaagt gttctaccag tgagctacat 39480
ccacagccct ttgatatata tatatatatt ggatacaggt ctttctagtt agcacacact 39540
ggccttgaat ctttttttgt ttgcttgttt ggttggggct tttgttttgt tttgtttttc 39600
tcgacagggt ttctccatgt agccttgact gtcctggact gactttgtac actgggctgt 39660
cctagaactc ccagagatcc tcctgcctct gcctcctaag cactggtatt aaaggcatgc 39720
gcaaccactt ctggtgaaca ttttaagatc tactcacctt ttgctttata tgtgggagtg 39780
tttgactttg tgtatgtatg tacaccatat gctcgcagtg cctgaggagg ccagaagagg 39840
gtgttggatt ccctgggact ggggttacag atgactgtga gcctccaagt gaatgttagc 39900
gacagagcct gggtcctctg caagagtagc cagtgttctt ccctaccatc catccctcag 39960
ccccatgacc ttgaactcct gatctcttgc tgtagcctcc tgatggtaga cgagtttcac 40020
tatccatggc ttgatactgt tttctctaga gcattattgc atctgcagtg tttaaagtgc 40080
tgtgtcccac ctattggggc atgatcactt ttttgtttgt ttgtttggtt ggttggtttt 40140
gttttgtttt tttgagacag ggtttctctg tattagccct ggctgtcctg gaactcactt 40200
tgtagaccag gctggcctca aactcagaaa tctgcctgcc tctgccttcc gagtgctggg 40260
attaaaggcg tgcaccacca ccacccggct gcatgattgc tttttaatgg tgttactgag 40320
atgcagttta ggactgtata gtgtccttga ttaatgtgca gagttcagtg atttgagttt 40380
gtatccatta ttttaaactg gaaaatacat acaaagacca catttattat ttttttttaag 40440
gctgggcatg gtggcactag ccacctttta atcttttaat cttagcaccc aaaaggcaaa 40500
ggaaggcaga tctcttgtga gttcagacca gccagggcta cacagtgaaa cactttccaa 40560
aaaaaagaaa aaaacagaag gaagaaaatg gttaaggaga tggctcagtc ggtaaaacgt 40620
ttgcctggca aacatgagag cctgcattct gcatttgatt tgtcagcacc catacatgat 40680
agcgacagat ttgcagcata cactggtaat cccagtactg gggagtggag gcagggggat 40740
gcctgtggct cactgcccag taagcctagc ctgactggtg aacttcaggc ggcttccagg 40800
gaggtggata gcctgtgtca ggctgactcc tgagtgccac cacacatggg ttcatctttt 40860
cgctctggct ctcgggcacg tgtgcacata cacagaattg ttttaactgt ttccaagtgt 40920
acgcccagca gtgcaactct ctgtgcttta gggtgtcaag gagttgtgac caccctggat 40980
tgtcaggctt ttttatagcc ttgggcagaa gccacaaaac tccctgccac aggcctgcca 41040
gcttctgttc cactttctgt ttctagttct gcctcgagag ggagtatggt aggaatggga 41100
ttatgtaatc tgtgactttt gtgaggggtt ccccctacta gcgtttattt ttctttgagt 41160
caggatctta accgaagcta gcctcagact tgtaatcctc ctgtctcagc ttcccaggca 41220
ggatgatttc aagcttcatc actgactttt gtttttttgtt tttttgtttt ttttttttg 41280
tttttgcttt tgtttttgtt tttcaagacg ggtttctctg tatagccctg gcttcatccc 41340
tttcttaaca aagctatgct tcttcccctt ttgtggctga taacgctcct cgctcgtcgt 41400
gtgggtagac cagttatctg tccatctgat ggtgtgaatg tgggttgtgt tgtaagcagg 41460
gaagctggga atatctatgc atgtttttta tctgggtact tgaccgcctc tggttgatag 41520
cagagtccat cacatcacag agtaagtagc agaggctggc tctgtcatga tcctgatctg 41580
ctgtaaaatg gcagcaccct agttctttcc agcttccaat gctggagggc acccatattg 41640
ttatgacttc tgccctcttc tcagaactgt aaatcaaaaa caccttggct tcaggtgttg 41700
gttcctggct tagggattta gtccttattg ccccttggcaa gttcctttcc atctctcatc 41760
tcccagattg gggcacaaac gagactccca gccttggctt gggggtggtg cagccaccta 41820
cctgccccac tcttcttctt aaaacaggat ctcacattgc ccagactggt tttgaacttc 41880
ctagactccc tatatagctg agaacgacct agaacctcag gttcttcagt atctgccacc 41940
tgagtgctgg gtcacaggct ggcctattac actcagtttt atgcagtgct ggggatagaa 42000
tccagggcct tgtgtgtgct aggcaagtga tctgccagct tagccatgga gagtccaacc 42060
tttgttttat cagtttggag ttagccagac agttgcagct ggctctgacc cttcattgtg 42120
caaagctggc cctatgtagc ctctgttgcc ctggaatttt ccatgtagac caggctggac 42180
ttgaaccctc attggttcct gctacttcac ttcctaaatg ctgggattat aggtattgtc 42240
caccacaccc tgctcaaact ttgtttcctg accaatcagg cttggcggca gttctgcttc 42300
ctggaactca ctcagtatag gtgggagctt tcagaatcct cagaaagagc cacacttagc 42360
caagcgtggt ggcacatgct gtcaccccaa cacttgggag ataaaggtag gaggaggatc 42420
aggagttcaa gaccagcctc agttatattg tgagtttgag tccaaaaaag ggggctggag 42480
agatggctca gcagttactc ttccagaggt cctgaattca atttccagca accacatggt 42540
ggctcacaac catctgtaat gggatctgat gccctctttt ggcatgcaag tgtgcatgaa 42600
ggtagagcac tcatatgcat aaatctttag gaaaaaagaa gattgcgtgt gagatgttcc 42660
tgtatgtttt acccccaagc ctgttcaagg tgtgtgtctg ccagtctgtg tgagctgagg 42720
atctagaccc taaacatggc ctgtgtcatg actgccttgt tgagcacctg cctggcctca 42780
ctgggctgtc agggttccca cccatctcac cacaccaacc caggtcatca ctgaagcaat 42840
ggctaggtgt cttggtacct ccatcaggaa gccgtgacct taattatcat ccacctgcag 42900
ccctgctcag ccctgcaggg gactgtcttg tccggtctat ctgcctatgt aaaagcagag 42960
aggacagact gacttaggga agcttttcta accttttcta caccgtctta cttttctgag 43020
gcatttgaag tgatgcacgg cttggagaag ggtgtttaac tctgcccgtg ttttctctct 43080
ccagtacctg gagtctgtga ggccactgat gaaggaggga gacttccaac gcatgacagc 43140
actggcccag gattttgctg tcaaccttgg acccaaattg cagtggtatt tgaagctaaa 43200
atcctggtgg gccacaaatt atgtaagtaa ttctgcatgt agtgctgtga aagttcttac 43260
ttgggtacca gggctcacag agttctagct gtggctgagg gcagccatac tttcccctga 43320

-continued gagctgtgct cagagatgct agcatctctt ccctcctgca agctccttag cagcctttgc 43380
accctgctca gggcagggag ctgctttgga ccctctagtc ccgacctggc ataccacagg 43440
ctgttctctc ctgtggtggc ccagccaccc cacctccctt tgtggcatct tctccatcca 43500
agagtatcac ttctgagtgc tctggtcaga gttcagatgc tgttgacagt ggcagctgtc 43560
tgctgggagc cagctaagcg tctgtgtgtg gtgttggggg tgggggtagc aagtgggcac 43620
actgcaggat atgaagccaa gagggggaat tcaggtgtca tgaataactt gatggaaggg 43680
aagggattga aaataaccta tgggagccag acacatgcct ataggcaaga taggtacatg 43740
cctatagtcc cagcactcag aaggcagagg caggagaact gtgggctcaa actaaccagg 43800
gtcacacagg gataccagac cctatctcaa gaaaaactct taaatttaaa aaattattta 43860
cttattcatg tatatatttg cctaggtgag tttatatgta ttacacaaat gcagatgaca 43920
tggaaactag agggcattgt atctcctaac agttgcaggt gattgtgtgc tgcccaacac 43980
aggtgctggg agccaaacta gggtcctctg taagagcagc acacactgag ccagctctgt 44040
agtccatcaa aaagaagtct caagagctgg gaatgaagct cagttggagt ctctgcctct 44100
ggtgcacaat gccctgggtt cagtctccag caccacacct gttctgtccc acacgcatgt 44160
atcccgaggg cttgagagat agaggcagaa agatcaaagt tcaaggttgt ctgtgcttct 44220
atagagttta aggtgagcct gaactgcttg agaccctgct ttaaaaataa aaccaggagc 44280
tggagagaag gctcagcagt taagagcatt tgccattctt gctgaagacc tgggtttggt 44340
tcccagcact cacaaggtgg ctcacaacta tctataactc cagggccagg ggatccaaca 44400
tccttttctg acttctatag gtgccatgca cacacatggt gcacatactt tatatgtaga 44460
caaaacacac acatgaaaga catcttagtg cacaccttta gtcccagcac tgggaaggca 44520
gagagaggca ggtgggtctc tgagttcaaa gccagggcta cacagagaaa ccctgacccc 44580
tggcccctca aaaaagaaaa attattttaa aaacacaaat aataagtaga caaaaatcaa 44640
cagagaaagt agacaaaaag aaacaagaga agagccagca gatggtgcca gacccaggca 44700
ctgtgcccag cagggcagga ggccacagca cctgggtcat caggactggg tctaatccta 44760
agcagctggc ccgctgtgca tttagactct cgtgcaagcc ttttctcagg tgtgcgctcc 44820
agcacgatgc tcaaatcatc acaggttgta gatcagcagc ccctgggtgg ctagggcagc 44880
ttgctgggta acattgccat ggtcactctg gagaatcgag acagcacatg ctggcctcag 44940
gcttagttct gtggctgaga tgtaccaggc atcaggaaga tcgatctttg gggagatctg 45000
ggttattttt tttttcctgc agtgctgggg atgggactgg gacccaaggc ctggtgaata 45060
tcagacaagc attcggcaca gcactttggc agttaagggt ttttggaaat atggccccca 45120
ggctagcctt aaagttgcta catagcagtc ttgaacttgc tataaccttg aattcctgat 45180
cctcctgccc atgtgtgcac tgctatatag ttctatgcct agttttatac attccaacag 45240
ttgagctaaa acccagcccg actcttttta tttatttatt taaacgcaat atgaaactat 45300
gctctatagt ctagccaggt ctccctttaa gaccagtgtg tctctcaatt ccttatggcc 45360
tgtctgcttg agacaacttt gttttggagc ctgtcataca ctggaatttt ccagaaagat 45420
ttgcatacat ctgggcatga ctgctcagcg tgctgacttg tcgtgtttgt accataggtg 45480
agtgactggt gggaggaata catctacctg cggggccgag ggccgatcat ggttaacagc 45540
aactactacg ccatggtgag ttggtcttcc attcccactg cagccaagat gggtttgtcc 45600
tgctgggtgg cctgggaaag ctcctcttgc tcctgcttct tttgtccaag tcttcatgtt 45660
gctgtgaaga gcccacctgg ggcccatgtg ttagaccccc ctgtgtctta acgggcccct 45720
gccctccacc caacagtgca aatacatttt cattgcaaac aacacttgct atgtaagtgc 45780
aggctgacct tgaacctgtg gtagaacaac aggaagctgg cgttgtaata gagcaataac 45840
aaaattaggg cttgtggtgt ctcatgcctg ccaggcaagc actggggagg tggagacagg 45900
gggattagtt cagggtcatc cttggctaca taggtagttc aaggccctcc tagattgtat 45960
gagatactct ttcaaaaaag taagtctgag ccaggcgtgg gggcgcacgc ctttaatccc 46020
agcactcggg aggcagaggc aggcagattt ctgagtttga ggccagcctg gtctacagag 46080
tgagttccag gacagccagg gctacacaga aaaaccctgt ctcgaaaaac caaaaaaaaa 46140
aaaaaagtaa gtctggcgct agaaggatgg tttagcagtt taagagccct tactgctctt 46200
ccagaggacc tgagttcggt ttccagtaca cacctcaagt ggttcagaac catctgtaac 46260
tccagttgca ggaaatctga tgccctcttc tggccactct gggtacctgc acacacatat 46320
acacttaacc ccacacaatc acacacatac acatagagag aaaaaacata tccaatttgc 46380
cagaaaaaca aatggaccta aaacagtaac aaaagtgtcc aaagttgtaa agtcaggcat 46440
agtgacacat agctttaatc ctagcactca gggacctggg gtaggagaat tgcctgaaag 46500
ctacataacc tgctcccaac aacaacaaaa gccaaaagcc cacctaaaac aaatacaaaa 46560
ggcggctgta acttagcaca gctgtcaggg agcaccccc ccacacacac acacaccttg 46620
tatacagacc gccgtgtcac cccatgagcc ctcttttctg tctcatcctc acaggagatg 46680
ctctacatca ccccaaccca tattcaggca gcgagagctg gcaacaccat ccacgccata 46740
ctgctgtatc gtcgcacggt agaccgtgag gaactcaaac ctgtatgtca acttgccttt 46800
aaaaatatct cttgggaggc tagagaggcg gctcgattaa taaagtgctt gctttgagaa 46860
gagtgttcag acttggccca gaggtgccca gctagatgca gcagtgcacg gttgtaatcc 46920
cggcactggg gagccagagt cagacaacgc tggggcttcc cagtcagtga ggcccaggtg 46980
cagcgagggg cttgtcgagg cctgggtgtt caatcccggg aatccacatg gtgggctgag 47040
agaaccagct cctgcaagct gtcctctgac ccccacatgt actgatacac gggtaaactc 47100
ctcaggagaa cggtttcttc ataacatcag gtggcttaag tgtttatctg gaaggaactt 47160
cagtagcctg gccctgctcg gcaagtcccc caggtgctac cctagggatg ctgagtgatg 47220
tggtcagact gggcagtgtg cacaggaaac aaaccgcatt ttaatcagtt cattgcaaag 47280
ctttcctctg ggattttgcc tgttggttta aaacacattt ttactacaga ttcgtcttct 47340
gggatctaca attcccctct gctctgctca gtgggagcga ctcttcaata cttcccgcat 47400
ccctggggag gagacaggtg ggtagtgctt actggggtct ccgctgggag ccagcatttg 47460
ccattttgct gctcggaacc aggaatagtt ggggaacgtt gggaacagaa tggtctacag 47520
ggtctgtccc aagagcgtct gactctgatt gttcctcctc ttggaatcgc tttgtctttt 47580
gtcattgggg gtggtttggg aatgggatct cacatgttcc aggctggcct aaaataatat 47640
gcagctaagg atgacccttt tgcctcccag tggattctag acatgtgtca tcatgcccag 47700
agtatatatg ttgctcaaat tgaaactctt ggcttcatat atattagaca acccaactga 47760
accgaagttc agctctggcc tgaatttcct ttgtccacta ggcctgtaca acaggcccgt 47820
ttccagattt tagtgtttct tctgttgaga gtttctttcg ttgggcattt tcctcagacc 47880
tgctggaata ttttcacatg actccttggg caccttgttc tggcccatgc agggtttgct 47940
gtaagatacc cttgagaacc aatgtgcctg agaggctcga tggaggccca gctgctgctg 48000
ctggcagcct ggcctgggct gggctcatct catctgcttc taacctagga catccttgga 48060
aaaggatgga gggagggaga cggatgccag atggtgccat gcaggcctgc tggggtcaag 48120
tgtacagcat tggtcacttt taaacttggt gacaaataac gtgagcaaaa ccacttaggg 48180
aggaaagatt tattctacct cctggagcca gagcctggag cctattgttg ctgggctatg 48240
gaagggcaaa gcatcatggg tacaggacat gtgagggagc agagcattta cctctaacag 48300
gaaggacaca gctcaagaaa agggactaga gtcaaaggtc cccttcaggc tgacaggtga 48360
ctcagcgcct gaatgagcct gtctgtaaac cgggtgcttg tacttgatgc caggctctct 48420
tgtggtaaaa ggagacaaca gactcccagg agctgtcctc tgccatctac acatgtatgg 48480
ggcatgcttg tcctcacaca tatttgagct cacacaagat aaataaataa attccattta 48540
tttattttat ccttgaggga gctggttttc ttcttgtcca ggccaggcag caagtgtctt 48600
tgccacctga gccatttcac tggctccagc atggtcttca atagtagtga tcacaaatat 48660
taactaaaat ctgggtaaca ctgggtatgg tggcatatgc ctttaatcct agcattcagg 48720
aggctgaaac aggtagattt cagtgagtgt gagcccagtc tggtctatac tatgtctaca 48780
tagtgagtta caggccagct aaagcttctt aatgaaccct tgccacaaag acaagttatc 48840
atttatgaaa atgtagtatg ctcggtgagg tcgtacagcg catgctagct gtcagaggcc 48900
tctcctgctc tgtggtgggc tctgattgtt tgcgtcttct gagacaggat ctcctgaaac 48960
cctggctctt ctgaattccc tagctagacc aagttaactc acagagatcc acctgcctct 49020
gcctcctcag tgctgggatt aaaggtgtgt gccaccacaa ccggcctttt gctatcaatt 49080
ctctttaaga tttttcactg tgtttgtgtg taggaaggac acagccacac tatagcagtc 49140
atgtgcaggt cagatgacag tgccgtgagg ctgcagatca aacgagggcc attggcttac 49200
acggcaaggg ttacccacaa gtcatctccc aggtcctctt ccccccccttt gagacagggt 49260
cttatgtagc ccagactagc ctctaatttg ttatgtagaa gctggctttg agctcctgat 49320
ccttccaagt ggtacaccat tgtgcctggc taaaacattc cttttttttt aagatttatt 49380
tttgcttttt atttttatgt atgtgttgcc tctttatgtg tatatgcact gagcatatga 49440
agtgcccaca gaagccagaa gagggcacca gatccccgga gctggagatc cgggaggctg 49500
taaaccacct gatgtgggta ctgggacctg aactctgcct gtgacttatg ggagagatct 49560
cattcaatac tacgtgtgcc aaccttgttt catagatagg aaactgactt aggttatagg 49620
ggctggttaa gccaaaggga gtgactcagt atggagtcaa gggccacaca gcagtattcc 49680
cagaactcag gaggtggagg cagaagaatc gggagttcaa ggtcaccctt ggctacatag 49740
acagtttaag accagcctgg gatacatgag atcctcacga agcaaaccgg tcaggtcaga 49800
tgagcccaag gctttctgac ttcttgtcac tccttcgtct cctcaccacc tcagacacca 49860
tccaacacgt caaggacagc aggcacattg tcgtgtacca cagaggccgt tacttcaagg 49920
tctggctcta ccatgacggg aggctgctga ggccccgtga gctggagcag cagatgcagc 49980
agatcctgga tgacacctca gagccgcagc ccggggaagc caagcttgcc gccctcactg 50040
ccgcagacag gtgcgtgtgt gcgtgcgtgc gtgcatggcc tcgcacaccc ttcccggtgt 50100
gtttgagggc ctcagtccaa tgccttaatc ctggggtcct ccgttcctcc acctcctata 50160
agcttggatc aaagtcctgt atcacggcat tcagttaact tccttcgttt ctttttctga 50220
ggtaagtgct ccaccactga gcagccaggg agactctgtg tgtgtgtgtg tgtgtgtgta 50280
atgtagtgta tgtgcatgtg tgtcaatgct gggtgtcttc atctgttcct ctccatctta 50340
tattatgcag acaaggtcac tcccaaagcc tggagctcac tgactggctt gtctggcaga 50400

-continued

```
ccagtgagtt ctagggataa tcttgtctct gccttctcag tactaggata ataggtcagg  50460
gccccagatc ctcatgctta tgcagagagt actttaccca cactccccaa cacacaccaa  50520
aggagcatgc gtatctttaa gaccagcatt gtggggttgg actgtgggaa agagaaactg  50580
ccctgtgccc tgtgccctgt gccctgtgcc ctgtgccctg ctttgaacag ggtaagaaac  50640
aggtagagtg agttggtggg gagaggattt tgctctctgg ggccaaaagt atacagcact  50700
tcacaaaaga ccatctttca cagaaccctg agctgctcta agctctaact ctttaataaa  50760
gagttgctcc aggcactcag gagataacaa ggctgtgtgt tgtttggagc ctgggactga  50820
gaaggaaaac cagaaagcga ggaaggccat agtctatgct tcatctcctg ccttgagggc  50880
tggggtgcac tgggggcctg cggcatttgt gggtgttgat accaaaagtt gttgagagag  50940
gtgggtagtg gatgggaggc agcacagaag gcctgaggct gagaactgtg ggagggaccc  51000
aggatccata ggaggaagct acttcagggt agctctgaag agagaccaag gtgagcatca  51060
tggtgggcac atggaggtca ttgtgggagt gtcatgtgac cagtcctggt ctggggtcag  51120
gggccagatg gtgtcgttcc ttccctgccc caaagtagtt gtggcatgat ctctgtgcct  51180
caggtttcct catctgacaa atgggtctgt ggtgctgaag acatcagtgg actgattgat  51240
gcctgagaga ggctcaggtc agagcctggc tccagggcca ggtccttcgg catttgttat  51300
aacttctgct ggggatgtct ggggcagaga agggtgcttc tccctggctg ctgcagagac  51360
aggttggatt tcattctgag cagtgtgtgt gtgtgtgtgt gtgtgtgtgt gtgtgtgaat  51420
atgttgttcc tcgggtacta gctgtcgaca ctgatgttgg agacagggtc cctcactagc  51480
ctggagcata tccatttagg tgacctgtct ggctaacaag ccctggggat cctgattttg  51540
tctctcagac ctgagattag gagcacatac caccacacct ggctcctcta catgggctgt  51600
gggggtgaaa ttcaggttct cgggctgaca agcaagcact attgcctact gagccatctc  51660
cccaccctgg acaactgatt ttagatgcgt ttactccttg ccacagagtg ccctgggcga  51720
agtgtcggca gacctatttt gcacgaggaa aaaataagca atctctggat gcggtagaaa  51780
aggcagcatt cttcgtgacg ttggacgaat cggaacaggg atatagagag gaggaccctg  51840
aggcatctat tgacagctat gccaaatctc tgctgcatgg tagatgtttc gacaggtaac  51900
tcccattttt aatctctgag gttgatgggg ggttgtggga gatgtttctg gggggtacctg  51960
tgagcagcct ccccaaatct gacccctgct atggggttgt actaggaagg aataagcatc  52020
caaccagaaa gctctgcttt cttccctcca cacaaactca gacacagttg taggcccggt  52080
agttttgagg tcccctcctt tgcttaccca ccacccttct taactgtggg ttacctggct  52140
cccagcagaa ctgtgggagg ggcccaggat acatggagga agcacatagg acagtcctgg  52200
gaaccatcac tggccttgtg cagttgctgt gaccctgccc tcctggatcc cctttctgta  52260
ggtgtaaagt gaggaggtac ctcccaggcc tggctggaga gggcatggcc ccagactcct  52320
tgttacagta gtctacacgc ctctggaccc agggctcaca cacatgctat attgtatctc  52380
tgatacaaga agctatgaat ggctctgtgt tctctgtgcc cccttgagtc accttcctag  52440
gatgtagaag cctggagaat tgtcagggtg gagagaagca acggtctctg cagaaagaag  52500
cacccatgta gcttttgggt tcccatgtcg atataaccct ggaagcccat gatcatgttg  52560
tctccctgta ggtggtttga caagtccatc acctttgttg tcttcaaaaa cagcaagata  52620
ggcataaacg cagagcattc ctgggcggac gcgcccatcg tgggccatct gtgggaggtg  52680
agccacacca ttgttacctg tctgaatgtg gaaggtgctt tgggaaagaa acccaacgca  52740
ggcccacttg aactctgcag tatttgtcta attctgtatt ggttacattt ctctctccct  52800
```

```
gatgaaatac cttggagagg gaggagtgag tgtgtgtgag agtgagtatg agtgtgtgtg  52860
tgtggggggg gtgctaggga tggaacccag ggcctgcctc atacttgctg ggcagctgct  52920
ccacaccaag gctgtataac cttagccttt attttggaga caaggtctca ctagatagaa  52980
acatgctaga cttgaactca ctgtgttgcc cagactggcc tcagacctgg aatcctcctg  53040
cctcagcgtg ttgagtatca gagattacag gtatgtgcca ccgggcctgg gttagcatct  53100
tggcttataa aatggcagtg tcctggagcc agagagatgc tagtagggta gagtctgacg  53160
atctgagttc aacccctggc acccatgtga cagtagaagg gcagcacccc atgtgcaccc  53220
tcacttcaca caccccatgt gcaccctcac ctcacacacc ccatgtgcac cctcacctca  53280
cacaccccat gtgcatcctc acctcacaca ccccatgtgc accctcacct cacacacccc  53340
atatgcaccc tcacacaccc catgtgcacc ctcacacacc tcatgtgcac cctcacctca  53400
cacaccccat gtgcaccctc acacacctca tgtgcaccct cacacacccc atgtgcaccc  53460
tcacctcaca caccccatgt gcaccctcac ctcacacacc ccatgtgcat cctcacctca  53520
cacaccccat gtgcaccctc acacacccca tgtgcaccct cacacacctc atgtgcaccc  53580
tcacacaccc catgtgcatc ctcacctcac acaccccatg tgcaccctca cctcacacac  53640
cccatgtgca ccctcacaca cctcatgtgc accctcacac accccatgtg caccctcacc  53700
tcacacaccc catatgcacc ctcacacatc ccctatgcac cctcacacac ctcatgtgca  53760
ccctcacctc acacacccca tttgcaccct cacacatccc ctatgcaccc tcacacacct  53820
catatgcacc ctcacctcac acaccccatg tgcaccctca tacatcctaa tagttaaatc  53880
aaaaaaaatt aaggcaatgt atcttactga aaatatttca gttactaaaa tgaccaggtt  53940
acttaaagac caccaaatct ctgtccccct ttctcctaac ccagctttca aaaacacaga  54000
gttgggtgtg gtgacacatg tcaccctagt acaggagcct gaggcaggag gatcaggaac  54060
ttgaggccag cttggactat aaaacgaagt catttcaaaa cagagagagg caaagcaaaa  54120
gaaagggtca gacccagact gcagatctgg tgcctttgtg gacttctcag tcaaatagct  54180
gtattgcagg aatctgaaat ttattaaata ttgacgtaac tctcaacgaa gttttaaatt  54240
tttgtaagat tttggacttc aggctaggga tgctctctct ctttccctcc cttcctctct  54300
cttccagggt ctcaccattt agcccaagcc aaatggcact gctcttgcct cagcctcggg  54360
agtgctgctg gtttcgggtt gcccggccac ccccagctaa gactttgcat cttagttttt  54420
ccttgcagtg ctgtgccagc gatttctttt cctgtggtgc agagtcaact gcagggtgca  54480
gattgtgtct gcttgtttgt gcgcatgctc tggcctccct ccctccctcg atcactcacc  54540
ctctcatccc ttgggtgctc ggacctctgc ttggggtctt ggcagagtcc cagctgctcg  54600
gcttcagcca gggaagagtt cctacacgag acagcctggg aaaggaagaa gcaggcagtc  54660
tggatctaag acaccagcgt gctccgctga gacaccaatt ccaatggcga agtgcaaggg  54720
ctcgtgtccc tgcgaggcag cccctgaact gatgccagca gcagcctcag tccagatgca  54780
gatacctcac ctccattagc tcccagaccc tgcggctcac acacagatct ctgggaagct  54840
ctgcaaagcc caacagtata ggcccatgag aatatcccag ggacttttca gataacacat  54900
gcacagctgc cgttgggtaa tgagggtctc tgaggcccag gcaacttgca gcatacacag  54960
caccgttctc aagggcagac atagagggca catagtggca catgcctata attccagcac  55020
tccagaggct gagatgggag aattactgaa aagcctgagg acaatcaggg ctacataata  55080
aaaaacaaaa ccaaacaaaa ggttgaaaag agatgaagaa gaaatttcag caagatatcc  55140
```

-continued

```
acaaggtctg gctgatgtta aggtttcttg tgtgtctaca tgtatgtgct catgagtgca  55200
gtacatgcag caaccaaagg ggggcgatag atcccttgga gctggggtta aaggtagttg  55260
tgagctggga cccaaacccc aaacttctgc tagagcagca ggcactttta acagctgagt  55320
tggctctcca gccctcgggc taatatttta aagtaactga tcaagataag gctaaggagg  55380
ccaagatcaa gataaggcta aggccaaggc cacaagtaga atcagtattt agtttcctgt  55440
ctgcctggtg gaatgaggag gactcttgaa tggagcctag gttcccagga tagtgctggg  55500
cacccagctc tcatcttgga gggacagtgc cccagtaaca atgggctgat tctgagatgt  55560
gaaaccaggt ggggacaact tcgtagtagc atcctgtgtg ctgtgggtcc agcatcctga  55620
gaactgagga tcctcccatc agccctgatt caaggtttct ccgcttacct tctcttgaca  55680
gattcatctc ctagagcagc tctggctcgg ggagacgcct atgcttctct cttattacaa  55740
agggcgcaga aggctgtggc aggtgggctc cagagatgca gaggttcaga gccacggtgt  55800
taccctccct ggtttctaga aaccacccat cagttagctt tctggggcct tcctgctctt  55860
tgccctctgg tgtgtgtgtg tgtgtgtgtg tgtgtgtgtg tgtgtgagag agagagagag  55920
agagagagag agagagagtg tgacagagac tggagaaggt gcttggtgtg tggagattcc  55980
gcccttactc ccaggattgg tcccaggagt gtggagtgtc tgtcctgagc gcagtaggaa  56040
ggaaacactg ctcactcgtg gcttctactc catctctgct tctttgtctc agtatgtcat  56100
ggccaccgac gtcttccagc tgggctactc agaggatgga cactgtaaag gagacaagaa  56160
ccccaacatc cccaaaccca ccaggctaca gtgggacatt ccaggagaag taagtctggt  56220
gtcccagaga ccatcactca cctgggtggc aatcttgttc ctgagctctg gtgataggca  56280
agctctctac caaacagaaa gctgtttgcc cagagttggg gaaggggcct gggatgctga  56340
gagaaatggg acttccgttc tcagttgaga tttcagctga aaagtagctg ggcttctgta  56400
aattccctgt aaacagggat aaaaaactta atcctagtca ggcaatggtg gtacactccc  56460
gtaatcccag cactcaggag gcagtagcag gcagatcttt ttgagttcca ggccagcctg  56520
gtctacaaag ctagttccag gacaataagg actacataga aaaacctagt cttagagatt  56580
ttggggctgt gtaaagatgg cctgtttctg tcatcccaac ccctgtggct gaggccagag  56640
aattctgtga ccgtgtctca acaaccaaca acagattctg agattcagtc cactcaagta  56700
ggagccctga gaagagatgt tagggttgga accataactc cagcctgtct gatccaagtg  56760
tgagtttctg gggcctgaga agtacttttt cgtgtggtaa agtccagcac tctgaggacc  56820
caggacagtg tgtgatccat agaggaacaa tacctctgtg gaggcctgac cttggggccg  56880
ggctgactgg accaccaggg ctcactggct ctcttcaaca cacctgtaat agagccatgc  56940
tgggttcatg gcagaatttt gagaaagatg caggtatttc ctggaaaccc acggtctgcc  57000
ccctcagcat cctcactagt ggtctgtcag gcctcctggc acatcccagg tttacacagc  57060
gtcgcctgga tgggattggg tgtgtagtgt cacgtgacta gtgcccagag tcagatggca  57120
gtgacattgc tataaacacc atggcctccg cctctcatcc agctccttcc tggcccctgg  57180
ccaccgtgga tccctgtgtt tgtcctttaa aaaacaatat tatttgtgct tctagaattg  57240
aacacatgta aacaatgtgt cttgattata tccatggctt cctcctccag ccagctcccc  57300
taaggcccta gactagagac tgaagtgcag acttccagac tgttccgccc tgcttccttc  57360
tcctcctgct gtgcttcccc actaagcaga gctgccttct tcctctgcag tgccaggagg  57420
tcatagagac atccctaagc agtgccagtt ttttggcaaa tgatgtggac ctgcattcct  57480
tcccatttga cacctttggc aaaggcttga tcaagaagtg ccggacgagt cccgatgcct  57540
```

tcatccagct ggcactgcag ctcgcacatt acaaggtaag aagggcactc actgtgggca 57600
ctctggagct gtttccctag tgggcagagg ctataaagcc cagcatggag ggcagctgac 57660
accaaacacc agccctgggg ctacctgcgg taccaaggtg tgaaatgcta gactgcagag 57720
cagatcaccc ttggttttgt gacatccctc tcaggctcct atcacagatg agagcttggg 57780
acataagcaa atgaacagtg taacctggac tggagagatg gcctggcggt tcagaccacg 57840
tgctacctct gcagaggacc ccattcggct cttggcacct tcacatagcg gctcacagcc 57900
acctgtaact gcagttccat gggatctggt gccactcttc tgccttctgt gaactacaca 57960
tagttacaca tatgcacaaa ggcaagcaca cacataaaat gttaaaatat aaatcttgta 58020
aaacaacccc ataataagct ctgactctta cagtattgtt aagaaatact taggacaaat 58080
tgcttaatgt gtctgacttt tgacaggcct ttccttaaag cagaagttat gagctcctca 58140
ttgctctagg ctgagtcaga tttctgtatc cacccaggac tgtgtgccaa ttctatcgtt 58200
tccctgagca gtgctaaagg gtggcagaag caatctgtac ctgtgtgagg atgtggaagg 58260
aactttagtt cttggtagag gtcagcctac tccagacaga agcattcagt tgctggcaat 58320
gcagaagtca ttgtggcacc agatctagaa gtgcacagtg ggagggtgga catcccaggg 58380
gctcagcttc aggtgccacc agctgtgtcc accacccttg cctccccagg agctcttcct 58440
gccccacccc taccctgttt ctcttcttgt tctctctggc acaactccca aggcctctgt 58500
aatcacttct aaccccagct tcctcgactc tctccctagc cacgcccccct gaccactccc 58560
ctgctgcctt ttccccagcc ctagccacac tctcctccag ccaggagcct ctcatctctt 58620
cctgaagctc atcgccagct tctactctgc ttccagaaag gcagccttac ctgcagacac 58680
ctttgcttca agctaaggag tgctggctgc agtagccttc cacctgtgat acctcccatc 58740
ctgccttcca caggtggccc ttctgtccca tccagacaat aggcttttcc catctgcatc 58800
tgctcgctcc tcctggctac tgtcttgtcc atggccatag tgactgaact cctcctcatt 58860
ccctagtcct gccctcttgc ctgtccctcc cctgtgtctc tcagacctca gaccttgctg 58920
tgtgccttgt cctttctcct aaaaattcac atcagctgga gggctttctg gaggacattg 58980
tggccttagt catgtcttgg accagaaacc atgcaaagac aaactccagg aggctggaga 59040
gacggctcag cagttaagag caccgtctgc acttccaggg gatttgagtt caatttctag 59100
cactcacatg gcagctcaca gtcatctgta actccagtcc tcagggatcc agtgccctct 59160
tctggcctct ggacaccagg tttatccttg ttggtcagat gtatgtgccg gcaacacaca 59220
cacacacaca cacacacaca cacacagtgg gggaagcaga ctgccacctc ctctcagatc 59280
cattccaggt cccttctccc ttagacttag atggccactc ccacctgtta gcctgttagc 59340
cctaagctag ttttccttcc ttcccaggac atgggcaagt tctgcctcac gtatgaggct 59400
tccatgactc ggctcttccg agaggggagg acagagactg tacgctcctg cactacggag 59460
tcctgcaact ttgtgctggc catgatggac cccacaacaa cggtaagacc atggtggcag 59520
aacatggcat ggtgcatggt ttctggacga cactagaaca gtggttctca acttgtgggt 59580
cgtgacccca ttggggtcac atatcagata tcctacacat cagatactta cactgtaatt 59640
cataaagtag caaaattaca gttatgaagt agcaatgaaa taattgtatt cattatgagg 59700
aaccatgtta cacaacatga ggaactgtgt taaagggaga cagcaagagg aaggttgaaa 59760
gtcactgccc tggaagctga ccatgaagct ccatagcccc tccagctcca cccttcctcc 59820
ctcaacccct cctccccctg ctcctccacc cttaccctac ttctgcatcc cctcccccag 59880

```
ctccttatgc ataggaacag aaagcattta agaggacata cagaagagag tattgctcgc  59940
tgagctttgg gaatgagatt atatgtatcg agacccttca catgcgactg gacatggcac  60000
agacacagga aaccggacac ccatccctgg ggtcagagcc tgtctgacca atctaccaga  60060
tactacagag tactacagta tgttctgcct cttaggagcc ctgcagtggc cttgggaaaa  60120
tgaactcaga tgaatccaat gcattgctgg tcccagctgg cacatggcca cattcagagc  60180
tatgcctagg ttccccaagc cctgagacag gcgtttacca ccaacagaca acagactgca  60240
tttttctttt ttttttttt ttactctaga gagaggaaaa aaaaaaaagc aagcggctac  60300
ttctgtcact agaacttcca ggaggctcct atgaggctgg gtctgtcata ggaaggccag  60360
tgccttgaca tacctccatg tagaggccac gtgtctcagg tggtgttgta atgtccagaa  60420
gattccaaag cagcctatat gtctgtgttt gttatgtgtg aacacatgtg tatgtatgta  60480
cttgtgttat gttgtacatg tgtatacaca tgtgtagtga ggccggaaat gtgcgctgtt  60540
gtcttcatcc attacgctcc accctgtact ttgagccagg gtctctcccc gaatgtagag  60600
ctgctactta ggctagactg gctgctcagc aagcctcccc cttgggtcat aaggaagccc  60660
tcacatttta gcagagtagc caaggagggt tagcgttcat ccctgtgaca aaataaactt  60720
ggggtcagag ctgggataga gctccaggtt tggcaagaac tcttaacagc ttgagtggtc  60780
cacatttggc tctctgtgta catagcacac acaccgtcac agggtgcctc tccatcaacc  60840
tacctactgc ccagcagccc ttctgaggca agaatctgga aagggatcgt gggctggtgg  60900
ggctctgtca agtatattgg tcacagcacc ctgcctttta cagaccactg aagagaaagt  60960
ggcccgacgc acaacctgaa ccatgcaaag catgtccttc tcctgttgac ccttaggcag  61020
agcagaggtt caagctgttc aagatagctt gtgaaaagca ccagcacctg taccgcctcg  61080
ccatgacggg cgctggcatc gaccgccacc tcttctgcct ctatgtggtg tccaagtatc  61140
tggcagtcga ctcacctttc ctgaaggagg taagtgcttg gactgtgtgt gtccagcctg  61200
gcttttctgt gttgagacag gatcttactc tgtagcctag gctagcctta aatagcaatc  61260
ctcctgcttc agcctcctga atgctgggac tacaggcatg catcagcata ctggctttta  61320
acagtggctg catagaatga gctagaaaag cccttgagaa cctagaggtg ggtttgtaga  61380
ggctacctta gaccccacgg gctgtcctct gccttccctg tgagaggcag tttggtcaag  61440
gggaggggct cagatacttt aaccttagtg tggccctgag ggcttggag aaatagtctc  61500
tgaccacgca gtttttcctt gcctccctct taggggatcc tcagacaaaa aggaggtatt  61560
ctgcattgct ctctgcattg ctctctgcat tgctctctgc attgctctct gcattgctct  61620
ctgcattgct ctctgcattg ctctctgcat tgctctctgc attgctctct gcattgctct  61680
ctgcattgct ctctgctgct gtataaagca ctctgaccac ttgccccttg gaagtcaggg  61740
caggaactta agcaggaaca gagtcagaag ctgtggagga aggcttcttg ccggcctgtg  61800
cacgggctca catttggtta actttcttta caaatataat tttacatgtg tgctttgcct  61860
tcatgtgtag gtgtatgttt ggtgtgtgtg cagtgcctag agggatgtct aggaactaga  61920
gttacaggtc cactatgtgg gtgctagcaa tcaaagctgg gtgctcttag ccactgagcc  61980
ctctctctag tcctctccag ctagatggac acctgtccag ggacagaacc cacctaccct  62040
gagctggacc ttcctgcagc aagacaattt cccacagaca tgtctgtctt aatgagtgtt  62100
ttgggcagaa agtgtttatt cagcttacat gtccatatca tagtccatta ctgaaggaag  62160
tcaggataga aacccaagca gaggtggacc tgtgaggtgg gacctggcgc ataggccatg  62220
gaggggtgct gcttgctggc ttgctgcccc tggttcactc agcctttcct atagaactca  62280
```

gcatcaccag cccagggatg atcccatcca gaatgggctg ggcctcccta aattgatgga 62340
taattgagaa aatgccttac atctggatct cactgaggca gttcctcaac tgaagttcct 62400
tcctctatga tgactctagc ttgtgtcaac ctgacacata aaacaagcca ggacagtgtc 62460
cacaaatcag tgtgatggca gatagtcact cagttgagaa tgtcttgtgg ttcctcccag 62520
gtgattgtca gcagtgtcag gttgacagtc ggtgctcact aggagaagcg agtagggaag 62580
tcatgtggac attttttgct ttgtcgcagg tactgtctga gccatggagg ttgtccacga 62640
gccagactcc tcagcagcag gtggaactgt ttgactttga gaaataccct gactatgtgt 62700
cctgtggcgg gggctttggg ccggtaagtg cagccaggcc cacccactaa cttcaagccc 62760
atcccattgt ccccaggctg gcctcaaact cactcactgt aaagtccagg ctggccatca 62820
ccatcctcct gcctcagcct cttcagtgcc cagacttaca ttgagaacag gaagtcgccg 62880
tccacgttat ctcatttcct agtgataaaa ctgccctttc tctctctgca ggttgctgat 62940
gacggctatg gtgtttccta cattattgtg ggagagaatt tcatccactt ccatatttct 63000
tccaagttct ctagccctga gacagtgagt atattgggca ctactttttc tagacatgag 63060
gtaaatttct ttttggaggg agcacatctt taaccaaaac attcatttca ggtgtcatcc 63120
tttttttagc ttagtttcac atcgatgaat ttcacccatt tgaaagacat atatttattt 63180
catttacctg cctttgatgg tagcagtggt cttaagtctc aatgtgtctg tgtttctgtc 63240
attctttcta ctctaaacaa ctccgtgagc aggttctggc cttccgtagg gagtaagtct 63300
ctgagggagc ctcttgggaa cctctaatgg tggccctccg cagtatcagc ctagccagtg 63360
ctacaaaatc ttccaggctg cccactccca cccacagacc ccgagtcctc aggaagctag 63420
gcatgagtta cacacctcta atcctagcat tatttaggaa gctgaggcag gaactgagag 63480
ttcagggata gcctggggtg tagtacagag tgacagggag gcctcagatc tgacccatcc 63540
atgcatatat caagccacct atggctgtcc cccactgagt gctcagggtg cttttattgc 63600
tcctccacta attccctcag agcttggaga gtgggaagac aggaggttgg cctaacccag 63660
ggacagatga taatgggcaa ttccaaaagt gagacttgct gcgtgccaga gcttttcctt 63720
ctctgtgtct ctgtctctgt ctctctctgt ctctctctct ctctctctcc ctctctctct 63780
ctctctctct ctctctctct ctctctctgt gtgtgtgtgt gtgtgtgtgt gtgtgtgtgt 63840
gtgtgcttgc acaagcactt tatccactga gccatctccc caactcctct catttggttc 63900
tttttttttt ttttccattt tttattaggt atttagctca tttggttctt ttttttccat 63960
tttttattag gtatttagct catttacatt tccaatgcta taccaaaagt cccccatacc 64020
cacccacccc cactccccta cccacccact ccccctttt ggccctggcg ttcccctgta 64080
ctggggcata taaagtttgc gtgtcctatg ggcctctctt tccagtgatg gccgactagg 64140
ccatcttttg atacatatgc agctagagtc aagagctccg gggtactggt tagttcataa 64200
tgttgttcca cctatagggt tgcagatccc tttagctcct tggctacttt ctctagctcc 64260
tccattggga gccctatgat ccatccatta gctgactgtg agcatccact tctgtgtttg 64320
ctaggccccg gcatagtctc acaagagaca gctacatctg gatcctttcg ataatatctt 64380
gctagtgtat gcaatggtgt cagcgtttgg atgctgatta tggggtggat ccctggatat 64440
gggtctctac atggtccatc ctttcatctc agctccaaac tttgtctctg taactccttc 64500
cctgggtgtt ttgttcccaa ttctaaggag gggcatagtg tccacacttc agtcttcatt 64560
cttcttgagt ttcatgtgtt tagcaaattg tatcttatat cttgggtatt ctcatttggt 64620

```
tcttgaagac agagtcttgc tatatagccc aggctgggtt tgaacttgct gcagttgatg  64680
ctcctgcctc agttttcagg cgctgggatt tatttgcccg gctgctgatg tgctgttcgg  64740
cttctttctt ttaggactca caccgctttg ggaagcactt gagacaagcc atgatggaca  64800
ttatcacctt gtttggcctc accgccaatt ccaaaaagta actgtcggag ccgcacggaa  64860
ggaaaatgga ctctagtgat acaaaccaaa tgaataggtg ttgctcctga ccataggaca  64920
ggcagaaaat tgttcttata aaactcagtt ttccttccag aaggtttacc gtcggtctcc  64980
ctagaacaac cgtaggctcc accgtttgac ttgtgaccct actacatcca gagatgcctt  65040
ggctccagga atattgggca cagtcccccg aagtcttttg aatcggctcc taatggataa  65100
agggatttaa atgctggtga atccctggat tttgggggtt gtatcaatat gtgttggagg  65160
tgacagactt cctcagtggt gaccctgtgg atacttggga cttgacttca cccaggcagt  65220
gagagcatca ccttgtggaa agagaaagtg gcttcagagc cagtggaggt aacagctcta  65280
gctaacacac ctgtaacaca ctaatggaat ggttaggcct ggggattaag gttctgctat  65340
gaatgacagc caccatcgct ttgggagtcc acatttgact ccacatttcc tggaagcagg  65400
ataccacctc ctcagtgcca ccttcgaaac ccagtgcctt aacgatggga gcccattggc  65460
aagtggggcc atagagaagg cttagcatgt gaagcctttg ggtggatatg tgagggtgct  65520
gcttcccctc acaagttcct gcatagagat gtccctaagt aagcacttcc cccaccctag  65580
aagatgaggt ccctggtgga gggagcgatg cagaatctca ttggccacca gttccattaa  65640
gcaacaaaat aacagatgtg tccacagagg gaagtgaggg gcttggtagt caaaggctac  65700
caagttggac accagctgga gagtgtggca gccattggca aggagagtga gaccctggtc  65760
actgagtcag gcatactgac acaggcagcc aaagccttgt catggcagcc aggagataga  65820
gatcctggca gatacaccaa cgggctcatc ttctaatccc acccagtcag attccaacca  65880
gagcaaattc gatagaaggc taggtcattt tggtgacaga ctcgggggtc tcaagtaatg  65940
ggtgctttgt acccaaatac catccctctg tgagagtgcc tttcttgaca acatccaata  66000
gactgtaaag caactccgtt tggtattcca tgtaaacata gcataatgga gtggcctccc  66060
ctacctgtta ccatcctgtc ctgacaagtt tagctcttcg tgttttaaat catgtattta  66120
ttttccagtg ccccttttggc cttgcttgat tcctactcgt gtgctagctg taacagaagt  66180
gagggtgggg tggccagaag tacagagagg tgctggctga acagctcatg cgtgttttat  66240
aagtatccat gaatacaaaa aaaagaatca cacctacaag ggccaaagtt tttttcctac  66300
taaaaacaag aaaacaaaag gcaacataaa tatatagcag agacaactgt aagtcaaagc  66360
cgcctgaccg cgctcttagg actacttgct aacctctgtt actcggagta ttcctgctag  66420
tacccaagtg tgacattcct ctctcaggtc tccagtgtcc ttccttgctg ctcctgagca  66480
gttaccaatg caatttttta ctccttccaa ggcagaagag tgggctttca ctgtaagtgt  66540
tcaaaggagg aggtaagact actatgtatt taatgtggaa caaaacatag tcttaccgca  66600
gccaaggttc gaatttggtt ttctaatctg tccattgcat gtaaatacca tatgctgttt  66660
ggatataaat cttagaaatg catgtgtgaa cgaatatagc tgaccattaa taaaacatta  66720
atcccgccta ctacatcatc tgtccctgtc tcccttgtca tactaatcag ggttatacta  66780
tcaggtactg gctgtgagcc tgcagtgtgc agggcaccac tgtcatgtac ttgaccaagg  66840
agcagcacac agtggagcta tcctccattc ctgtgtgggt gcctggcacc acagaggtgc  66900
tatagtgcat gttcagtgaa tgataacact tcctttttag aaacatgtaa tgtgtgtgcc  66960
tgtgtggcat atgcacattg gcatacggct gcaggtacat gaagaggcca gaggagttgt  67020
```

```
ccggcattct tcaccccctt tctttgagac agggtctgta tctaaacctg gagcttatat  67080
ttttttggca atgccagtgg ccagcaagcc ccaggagtgc tgactcggtc ccacttcagt  67140
gatgggtttt aggcatgtgt acaagcacac ctaccatgtt aagggatgaa ctctggtatc  67200
tgaactctgg tcctcatgtc atctgtgtct taactgctga gccatctctc cagaccagca  67260
ctgagtttct tcatcaggct cttccaagca tctgctctag gcacggagaa taaagaacta  67320
gctccctgcc tctagttctg gatgttagct ccagttccaa gacagccaac tgaaggaagg  67380
atcctaagta ttgcaactcg agtgaggtct gggcacgatg tcatggacct cgaatcccag  67440
tactaggaag gtgaaggtag gaagatcatg actatgaggc caacctaggc tacatagaga  67500
gttccagact aacctgatct atatagtgaa accctgtctc atagaatgaa acaacatgaa  67560
actggacata gcaattaaga acacttgttg ctcttccaga ggacctgggg tcaatgccca  67620
gcactcatgg taacttgcaa ccacctgtaa ctccagttca gagcatctga caccctcttc  67680
tgacctccaa cacaggcatg cacatggtgc acatacagac agacaaaaca tccattcaca  67740
taaaattttt tttttttttt ggtttttcga gacagggttt ctctgtatag tcctggctgt  67800
cctggaactc actctgtaga ccaagctggc ctctaattca gaaatctgcc tgcttctgcc  67860
tcccgagtgc tgggattaaa ggggtgcgcc accaccacct ggcaaaaata aatctttaaa  67920
aaatgtaaaa ataaacaaga gccccaagag ccagatgtag gaagtggaag ctggcacaag  67980
gaagtgccca gctgggcatg ggttagaact gtgaccaaca agaataacaa gacagaggca  68040
gctttagcca acctactggg acagcagcag tcatggaggt gccaggcttc attctgacca  68100
gcttggtgac ataccagtgt ctgtgtttat ctggtggata ggtgtctgag actccttacc  68160
attctttctt ggcaattttt gattgaatgc actaggattc tcaggctagc ccttaatgca  68220
gtgtgcttat tacagctgtg gaacatgtgt gcacagaccc aggagagcat agggagatac  68280
gagccattgt gacagtctgg tgcacgacaa gatgtcagcc tcaccttcca tttaaacagt  68340
tggtgagaga ctttcatagt atgtaactga gtcggggctc gcctcatttt aactggaaga  68400
agccgccaga gcactgtata gaatccttct caacgatatg ggaatgcaag gtgcaaagga  68460
attcttgctg ccgactgtgg gatgtggatt agcttacaga gtgcttgcct ggcatgcaag  68520
aagccctggg tttaattccc atactaaata agctgatgat agtggtgcat acctattatc  68580
ctagcactca gtaggcagag gcaggaaaat gagaagttca agattgcctt tgattacata  68640
gtaaattcaa ggaagtctgg gccacatgag accttacctt taaaagatat aagtaaaaca  68700
tgagttggaa gccaacctgg actaaatagt gatcaccagg tcaactagag tcacgcaaca  68760
agaccctgtc tcaaacagac taacaagaaa ctaaaatggc tgatgaggta gcttagtggg  68820
taaaggtgtg tgctgccaag tctgacaacc tgagtttgat cccagaagcc gcacagggaa  68880
ggagagacaa ctctcgactc tggaacgttt tcctttcctt cagattaatg ccatggtgtg  68940
tccacaaatg tatatgcaaa tacgcattaa gtgtaaataa acaaaaccct gaaagcaaaa  69000
cctgatggca caggatttta attgcaacta ctgagactga gacaaggtaa cacgttcaag  69060
ggcagagttc ccagcatgta ggaggcccta gattcaatct ccagtactgc ctgagcaata  69120
atagataaat gtactggaag tgactcacag gttaatagca cttttttttcg ctgaggaccc  69180
aaactcactt cccagcacct attaactcag tttcgtaatg cccccccccc ccccaggttg  69240
gaccgttagg gaagggggcg gggccatctc tgcctggaca gggcgggcct taacaggggt  69300
gggtggggcc tcccacctag cactgcttca aatttcctgg agtattagtc atgtttttaa  69360
```

-continued

```
ccccaatttt tgggaggcag aggcaggtgg agctctgtga gttccaggcc agcttggtct  69420

acgtaaagag ttctaagcca gccaagtcta cctactaaga ttctgactta aaaacaaaaa  69480

cagatgaaaa ggaggggtga aaatgatgta aatacagtac tcaccaatga aattttcaaa  69540

gtttaaaaaa agagagaaag aaccaccacc tgggagcctc agtttccccc actaggtgca  69600

ggagaggttg gctgataccc agtccctcca gcctccatcc aagcataccg aaaggctgcc  69660

ttgtgggcca accacagccc aggtcccatc catcatgctc aggcccccgcc caccaagagc  69720

caaagcccaa cctccatggc aaggccccgc ccaccataga cacccaccta ccacaaccca  69780

ggctcctgtc atcttggcag aggccccacc caccgcagcc caggctccgc cccgttcagt  69840

cagagacggg ccccgcccct ttccctaacg gtcaacggtc gtccagcctc tcagaagcaa  69900

ggcgagctgg acggccgcgt cgtgtcgctg ttctcgggtc ccagtggcca tggaggacgc  69960

gctgctcggc gccatgactg gccccgaaga cgagctgggc                        70000


<210> SEQ ID NO 7

<400> SEQUENCE: 7

000


<210> SEQ ID NO 8

<400> SEQUENCE: 8

000


<210> SEQ ID NO 9
<211> LENGTH: 20
<212> TYPE: DNA
<213> ORGANISM: Artificial sequence
<220> FEATURE:
<223> OTHER INFORMATION: Primer

<400> SEQUENCE: 9

ccagagccaa cgtcaagcat                                                 20


<210> SEQ ID NO 10
<211> LENGTH: 20
<212> TYPE: DNA
<213> ORGANISM: Artificial sequence
<220> FEATURE:
<223> OTHER INFORMATION: Primer

<400> SEQUENCE: 10

cagccgtgca acaatctgaa                                                 20


<210> SEQ ID NO 11
<211> LENGTH: 29
<212> TYPE: DNA
<213> ORGANISM: Artificial sequence
<220> FEATURE:
<223> OTHER INFORMATION: Probe

<400> SEQUENCE: 11

tgaaaatcct caacactcca aactgtgcc                                       29


<210> SEQ ID NO 12
<211> LENGTH: 20
<212> TYPE: DNA
<213> ORGANISM: Artificial sequence
<220> FEATURE:
<223> OTHER INFORMATION: Primer
```

<400> SEQUENCE: 12
gccctcagaa agctctggaa 20

<210> SEQ ID NO 13
<211> LENGTH: 21
<212> TYPE: DNA
<213> ORGANISM: Artificial sequence
<220> FEATURE:
<223> OTHER INFORMATION: Primer

<400> SEQUENCE: 13
tagggtcgag gctctgcttg t 21

<210> SEQ ID NO 14
<211> LENGTH: 30
<212> TYPE: DNA
<213> ORGANISM: Artificial sequence
<220> FEATURE:
<223> OTHER INFORMATION: Probe

<400> SEQUENCE: 14
ccatcggtgc aaacctacag aagcagtatg 30

<210> SEQ ID NO 15
<211> LENGTH: 23
<212> TYPE: DNA
<213> ORGANISM: Artificial sequence
<220> FEATURE:
<223> OTHER INFORMATION: Primer

<400> SEQUENCE: 15
tgatggtgtt gaggaagctt ttt 23

<210> SEQ ID NO 16
<211> LENGTH: 21
<212> TYPE: DNA
<213> ORGANISM: Artificial sequence
<220> FEATURE:
<223> OTHER INFORMATION: Primer

<400> SEQUENCE: 16
tccctcaagt ctcctgttcc a 21

<210> SEQ ID NO 17
<211> LENGTH: 26
<212> TYPE: DNA
<213> ORGANISM: Artificial sequence
<220> FEATURE:
<223> OTHER INFORMATION: Probe

<400> SEQUENCE: 17
acaacagatc gcgtgatgac cgtctc 26

<210> SEQ ID NO 18
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 18
gcatgttctc acatta 16

<210> SEQ ID NO 19

<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(5)
<223> OTHER INFORMATION: bases at these positions are RNA
<220> FEATURE:
<221> NAME/KEY: misc_feature
<222> LOCATION: (8)..(8)
<223> OTHER INFORMATION: bases at these positions are RNA
<220> FEATURE:
<221> NAME/KEY: misc_feature
<222> LOCATION: (10)..(13)
<223> OTHER INFORMATION: bases at these positions are RNA
<220> FEATURE:
<221> NAME/KEY: misc_feature
<222> LOCATION: (16)..(16)
<223> OTHER INFORMATION: bases at these positions are RNA

<400> SEQUENCE: 19
gcaugttctc acatta 16

<210> SEQ ID NO 20
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(3)
<223> OTHER INFORMATION: bases at these positions are RNA
<220> FEATURE:
<221> NAME/KEY: misc_feature
<222> LOCATION: (5)..(5)
<223> OTHER INFORMATION: bases at these positions are RNA
<220> FEATURE:
<221> NAME/KEY: misc_feature
<222> LOCATION: (7)..(8)
<223> OTHER INFORMATION: bases at these positions are RNA
<220> FEATURE:
<221> NAME/KEY: misc_feature
<222> LOCATION: (10)..(13)
<223> OTHER INFORMATION: bases at these positions are RNA
<220> FEATURE:
<221> NAME/KEY: misc_feature
<222> LOCATION: (16)..(16)
<223> OTHER INFORMATION: bases at these positions are RNA

<400> SEQUENCE: 20
gcatgtuctc acatta 16

<210> SEQ ID NO 21
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(3)
<223> OTHER INFORMATION: bases at these positions are RNA
<220> FEATURE:
<221> NAME/KEY: misc_feature
<222> LOCATION: (5)..(5)
<223> OTHER INFORMATION: bases at these positions are RNA
<220> FEATURE:
<221> NAME/KEY: misc_feature
<222> LOCATION: (7)..(8)
<223> OTHER INFORMATION: bases at these positions are RNA
<220> FEATURE:
<221> NAME/KEY: misc_feature
<222> LOCATION: (10)..(13)
<223> OTHER INFORMATION: bases at these positions are RNA
<220> FEATURE:
<221> NAME/KEY: misc_feature
<222> LOCATION: (16)..(16)
<223> OTHER INFORMATION: bases at these positions are RNA

<400> SEQUENCE: 21
gcatgtuctc acatta 16

<210> SEQ ID NO 22
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 22
gtctgtgcat ctctcc 16

<210> SEQ ID NO 23
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: bases at these positions are RNA
<220> FEATURE:
<221> NAME/KEY: misc_feature
<222> LOCATION: (3)..(3)
<223> OTHER INFORMATION: bases at these positions are RNA
<220> FEATURE:
<221> NAME/KEY: misc_feature
<222> LOCATION: (5)..(9)
<223> OTHER INFORMATION: bases at these positions are RNA
<220> FEATURE:
<221> NAME/KEY: misc_feature
<222> LOCATION: (11)..(11)
<223> OTHER INFORMATION: bases at these positions are RNA
<220> FEATURE:
<221> NAME/KEY: misc_feature
<222> LOCATION: (13)..(13)
<223> OTHER INFORMATION: bases at these positions are RNA
<220> FEATURE:
<221> NAME/KEY: misc_feature
<222> LOCATION: (15)..(16)
<223> OTHER INFORMATION: bases at these positions are RNA

<400> SEQUENCE: 23
gtctgugcat ctctcc 16

<210> SEQ ID NO 24
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 24
atcatggctg cagctt 16

<210> SEQ ID NO 25
<211> LENGTH: 16
<212> TYPE: DNA
<213> ORGANISM: Artificial sequence
<220> FEATURE:
<223> OTHER INFORMATION: Synthetic oligonucleotide
<220> FEATURE:

<221> NAME/KEY: misc_feature
<222> LOCATION: (1)..(1)
<223> OTHER INFORMATION: bases at these positions are RNA
<220> FEATURE:
<221> NAME/KEY: misc_feature
<222> LOCATION: (3)..(8)
<223> OTHER INFORMATION: bases at these positions are RNA
<220> FEATURE:
<221> NAME/KEY: misc_feature
<222> LOCATION: (10)..(14)
<223> OTHER INFORMATION: bases at these positions are RNA

<400> SEQUENCE: 25
atcauggctg cagctt 16

<210> SEQ ID NO 26
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 26
tgaggtcctg cactgg 16

<210> SEQ ID NO 27
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (2)..(8)
<223> OTHER INFORMATION: bases at these postitions are RNA
<220> FEATURE:
<221> NAME/KEY: misc_feature
<222> LOCATION: (10)..(13)
<223> OTHER INFORMATION: bases at these postitions are RNA
<220> FEATURE:
<221> NAME/KEY: misc_feature
<222> LOCATION: (15)..(16)
<223> OTHER INFORMATION: bases at these postitions are RNA

<400> SEQUENCE: 27
tgaggucctg cactgg 16

<210> SEQ ID NO 28
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 28
ttcagtcatg acttcc 16

<210> SEQ ID NO 29
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (3)..(8)
<223> OTHER INFORMATION: bases at these positions are RNA
<220> FEATURE:
<221> NAME/KEY: misc_feature
<222> LOCATION: (10)..(12)
<223> OTHER INFORMATION: bases at these positions are RNA
<220> FEATURE:
<221> NAME/KEY: misc_feature
<222> LOCATION: (15)..(16)
<223> OTHER INFORMATION: bases at these positions are RNA

<400> SEQUENCE: 29
ttcagucatg acttcc 16

<210> SEQ ID NO 30
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (5)..(5)
<223> OTHER INFORMATION: I
<220> FEATURE:
<221> NAME/KEY: misc_feature
<222> LOCATION: (5)..(5)
<223> OTHER INFORMATION: n is a, c, g, or t

<400> SEQUENCE: 30
gcatnttctc acatta 16

<210> SEQ ID NO 31
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 31
gcatattctc acatta 16

<210> SEQ ID NO 32
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 32
gcatgatctc acatta 16

<210> SEQ ID NO 33
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (5)..(5)
<223> OTHER INFORMATION: p

<400> SEQUENCE: 33
gcatuttctc acatta 16

<210> SEQ ID NO 34
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (6)..(6)

<223> OTHER INFORMATION: p

<400> SEQUENCE: 34
gcatgutctc acatta 16

<210> SEQ ID NO 35
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (4)..(4)
<223> OTHER INFORMATION: p

<400> SEQUENCE: 35
gcaugttctc acatta 16

<210> SEQ ID NO 36
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (5)..(5)
<223> OTHER INFORMATION: p

<400> SEQUENCE: 36
gcatuttctc acatta 16

<210> SEQ ID NO 37
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (6)..(6)
<223> OTHER INFORMATION: p

<400> SEQUENCE: 37
gcatgutctc acatta 16

<210> SEQ ID NO 38
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (7)..(7)
<223> OTHER INFORMATION: p

<400> SEQUENCE: 38
gcatgtuctc acatta 16

<210> SEQ ID NO 39
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(3)
<223> OTHER INFORMATION: bases at these positions are RNA
<220> FEATURE:
<221> NAME/KEY: misc_feature
<222> LOCATION: (5)..(5)
<223> OTHER INFORMATION: bases at these positions are RNA
<220> FEATURE:
<221> NAME/KEY: misc_feature
<222> LOCATION: (8)..(13)
<223> OTHER INFORMATION: bases at these positions are RNA
<220> FEATURE:
<221> NAME/KEY: misc_feature
<222> LOCATION: (16)..(16)
<223> OTHER INFORMATION: bases at these positions are RNA

<400> SEQUENCE: 39
gcatgttcuc acatta 16

<210> SEQ ID NO 40
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (5)..(5)
<220> FEATURE:
<221> NAME/KEY: misc_feature
<222> LOCATION: (5)..(5)
<223> OTHER INFORMATION: n is a, c, g, or t

<400> SEQUENCE: 40
gtctntgcat ctctcc 16

<210> SEQ ID NO 41
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 41
gaggatggca agcaca 16

<210> SEQ ID NO 42
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 42
cacctgcggg aagctc 16

<210> SEQ ID NO 43
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 43
tgtgccccag cccatt 16

<210> SEQ ID NO 44
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 44
cttccacagt atatct 16

<210> SEQ ID NO 45
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 45
tactggtagt gttgct 16

<210> SEQ ID NO 46
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 46
ttgacacaaa gggagt 16

<210> SEQ ID NO 47
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 47
gaatctcctt ttccag 16

<210> SEQ ID NO 48
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 48
tttacacgct tccgcc 16

<210> SEQ ID NO 49
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 49
agactctcgg ttccga 16

<210> SEQ ID NO 50

<400> SEQUENCE: 50

000

<210> SEQ ID NO 51
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 51
cttttctatc agtctc 16

<210> SEQ ID NO 52
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 52
cttcttgatg tctttc 16

<210> SEQ ID NO 53
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 53
aagtgtcact aaaacc 16

<210> SEQ ID NO 54
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 54
ggactgaaat agcaga 16

<210> SEQ ID NO 55
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 55
aggctggccc ccactg 16

<210> SEQ ID NO 56
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 56
ggtttttgat tcttcc 16

<210> SEQ ID NO 57
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 57
gcatgccgcc ccgtcc 16

<210> SEQ ID NO 58
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 58
tcttcataca atagca 16

<210> SEQ ID NO 59
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 59
cgttcaaatt ccgtct 16

<210> SEQ ID NO 60
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 60
tccggctgcg gctcag 16

<210> SEQ ID NO 61
<211> LENGTH: 18
<212> TYPE: DNA
<213> ORGANISM: Artificial sequence
<220> FEATURE:
<223> OTHER INFORMATION: Primer

<400> SEQUENCE: 61
agaggagacc gagcgaat 18

<210> SEQ ID NO 62
<211> LENGTH: 23
<212> TYPE: DNA
<213> ORGANISM: Artificial sequence
<220> FEATURE:
<223> OTHER INFORMATION: Primer

<400> SEQUENCE: 62
catggtttgt gttgatgtac gac 23

<210> SEQ ID NO 63
<211> LENGTH: 24
<212> TYPE: DNA
<213> ORGANISM: Artificial sequence
<220> FEATURE:
<223> OTHER INFORMATION: Probe

<400> SEQUENCE: 63
cctacatcag ggagcgagaa ggga 24

<210> SEQ ID NO 64
<211> LENGTH: 21
<212> TYPE: DNA
<213> ORGANISM: Artificial sequence
<220> FEATURE:
<223> OTHER INFORMATION: Primer

<400> SEQUENCE: 64
gtcaagacta caacacacag c 21

<210> SEQ ID NO 65
<211> LENGTH: 23
<212> TYPE: DNA
<213> ORGANISM: Artificial sequence
<220> FEATURE:
<223> OTHER INFORMATION: Primer

<400> SEQUENCE: 65
aaaactataa ggaggggtga agg 23

<210> SEQ ID NO 66
<211> LENGTH: 33
<212> TYPE: DNA
<213> ORGANISM: Artificial sequence
<220> FEATURE:
<223> OTHER INFORMATION: Probe

<400> SEQUENCE: 66
ctgaaggact tttaaatgta gcctgctcac taa 33

<210> SEQ ID NO 67
<211> LENGTH: 20
<212> TYPE: DNA
<213> ORGANISM: Artificial sequence
<220> FEATURE:
<223> OTHER INFORMATION: Primer

<400> SEQUENCE: 67
tgcagggagc cactctgagt 20

<210> SEQ ID NO 68
<211> LENGTH: 24
<212> TYPE: DNA
<213> ORGANISM: Artificial sequence
<220> FEATURE:
<223> OTHER INFORMATION: Primer

<400> SEQUENCE: 68 agaacccca ctgacttatc tgaa 24

<210> SEQ ID NO 69
<211> LENGTH: 26
<212> TYPE: DNA
<213> ORGANISM: Artificial sequence
<220> FEATURE:
<223> OTHER INFORMATION: Probe

<400> SEQUENCE: 69
cacagagcct aagatgtgca cgcctg 26

<210> SEQ ID NO 70
<211> LENGTH: 20
<212> TYPE: DNA
<213> ORGANISM: Artificial sequence
<220> FEATURE:
<223> OTHER INFORMATION: Primer

<400> SEQUENCE: 70
ccggagctag aagcgatcaa 20

<210> SEQ ID NO 71

<211> LENGTH: 24
<212> TYPE: DNA
<213> ORGANISM: Artificial sequence
<220> FEATURE:
<223> OTHER INFORMATION: Primer

<400> SEQUENCE: 71
cctttagctt ctcagcctct tcct 24

<210> SEQ ID NO 72
<211> LENGTH: 17
<212> TYPE: DNA
<213> ORGANISM: Artificial sequence
<220> FEATURE:
<223> OTHER INFORMATION: Probe

<400> SEQUENCE: 72
ctcgagtcag ggagatg 17

<210> SEQ ID NO 73
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 73
aatgtgcctg ctgtccttga 20

<210> SEQ ID NO 74
<211> LENGTH: 20
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(2)
<223> OTHER INFORMATION: bases at these positions are RNA
<220> FEATURE:
<221> NAME/KEY: misc_feature
<222> LOCATION: (4)..(8)
<223> OTHER INFORMATION: bases at these positions are RNA
<220> FEATURE:
<221> NAME/KEY: misc_feature
<222> LOCATION: (10)..(11)
<223> OTHER INFORMATION: bases at these positions are RNA
<220> FEATURE:
<221> NAME/KEY: misc_feature
<222> LOCATION: (13)..(13)
<223> OTHER INFORMATION: bases at these positions are RNA
<220> FEATURE:
<221> NAME/KEY: misc_feature
<222> LOCATION: (15)..(16)
<223> OTHER INFORMATION: bases at these positions are RNA
<220> FEATURE:
<221> NAME/KEY: misc_feature
<222> LOCATION: (19)..(20)
<223> OTHER INFORMATION: bases at these positions are RNA

<400> SEQUENCE: 74
aatgugcctg ctgtccttga 20

<210> SEQ ID NO 75
<211> LENGTH: 21
<212> TYPE: DNA
<213> ORGANISM: Artificial sequence
<220> FEATURE:
<223> OTHER INFORMATION: Primer

<400> SEQUENCE: 75
agatcaatcg gaccctagac a 21

<210> SEQ ID NO 76
<211> LENGTH: 18
<212> TYPE: DNA
<213> ORGANISM: Artificial sequence
<220> FEATURE:
<223> OTHER INFORMATION: Primer

<400> SEQUENCE: 76
cagcaccttc agcgagta 18

<210> SEQ ID NO 77
<211> LENGTH: 24
<212> TYPE: DNA
<213> ORGANISM: Artificial sequence
<220> FEATURE:
<223> OTHER INFORMATION: Probe

<400> SEQUENCE: 77
aagaggacgc cactcacgat gttc 24

<210> SEQ ID NO 78
<211> LENGTH: 20
<212> TYPE: DNA
<213> ORGANISM: Artificial sequence
<220> FEATURE:
<223> OTHER INFORMATION: Primer

<400> SEQUENCE: 78
acatgacagg cgcgatctct 20

<210> SEQ ID NO 79
<211> LENGTH: 25
<212> TYPE: DNA
<213> ORGANISM: Artificial sequence
<220> FEATURE:
<223> OTHER INFORMATION: Primer

<400> SEQUENCE: 79
tctaggttca cgtacacatc tttgc 25

<210> SEQ ID NO 80
<211> LENGTH: 26
<212> TYPE: DNA
<213> ORGANISM: Artificial sequence
<220> FEATURE:
<223> OTHER INFORMATION: Probe

<400> SEQUENCE: 80
ttccttcaag caatgccctc agcaat 26

<210> SEQ ID NO 81
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 81
gttattgtgg ttggcg 16

<210> SEQ ID NO 82
<211> LENGTH: 16
<212> TYPE: DNA

<213> ORGANISM: Artificial sequence
<220> FEATURE:
<223> OTHER INFORMATION: Synthetic oligonucleotide

<400> SEQUENCE: 82
attctgtgtg cactgc 16

<210> SEQ ID NO 83
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 83
tcttgtctga cattct 16

<210> SEQ ID NO 84
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 84
ttttgtgtct tctgta 16

<210> SEQ ID NO 85
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 85
ctgtttgagt tttctc 16

<210> SEQ ID NO 86
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 86
caaagtgata ccagtt 16

<210> SEQ ID NO 87
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 87
aatcttccag ggccac 16

<210> SEQ ID NO 88
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 88
tcatttctat ggaata 16

<210> SEQ ID NO 89
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 89
gtcagtatcc cagtgt 16

<210> SEQ ID NO 90
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 90
ggttacagtg gaagag 16

<210> SEQ ID NO 91
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 91
tctgggtgtt cttacg 16

<210> SEQ ID NO 92
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 92
tttccttgag tagtag 16

<210> SEQ ID NO 93
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 93
tctccttgct gtattt 16

<210> SEQ ID NO 94
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 94
ttgccaatat caccat 16

<210> SEQ ID NO 95
<211> LENGTH: 16
<212> TYPE: DNA
<213> ORGANISM: Artificial sequence
<220> FEATURE:

<223> OTHER INFORMATION: Synthetic oligonucleotide

<400> SEQUENCE: 95
caactgaacc acccgt 16

<210> SEQ ID NO 96
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 96
gcacaatatc attaac 16

<210> SEQ ID NO 97
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 97
gactctctga tgatac 16

<210> SEQ ID NO 98
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 98
ctataccatc tctcat 16

<210> SEQ ID NO 99
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 99
catcatctat accatc 16

<210> SEQ ID NO 100
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 100
acacatttag catgac 16

<210> SEQ ID NO 101
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 101
attatatggc aactca 16

<210> SEQ ID NO 102
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 102
gactaatatg cagttt 16

<210> SEQ ID NO 103
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 103
gtcaaattca agggtt 16

<210> SEQ ID NO 104
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 104
cataaagcat ggtgga 16

<210> SEQ ID NO 105
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 105
tagtctctgt cagtta 16

<210> SEQ ID NO 106
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 106
gtacctatag tctctg 16

<210> SEQ ID NO 107
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 107
tcatgtacct atagtc 16

<210> SEQ ID NO 108
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 108
tcttaatttc atgtac 16

<210> SEQ ID NO 109
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 109
accctcaagt ctcctg 16

<210> SEQ ID NO 110
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 110
cagatatagg actgga 16

<210> SEQ ID NO 111
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 111
gacgcgcctg aaggtt 16

<210> SEQ ID NO 112
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 112
ggacacattg gccaca 16

<210> SEQ ID NO 113
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 113
ggccaccacg ctgtca 16

<210> SEQ ID NO 114
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 114
tgccaccgta gacacg 16

<210> SEQ ID NO 115
<211> LENGTH: 16

<212> TYPE: DNA
<213> ORGANISM: Artificial sequence
<220> FEATURE:
<223> OTHER INFORMATION: Synthetic oligonucleotide

<400> SEQUENCE: 115
gctagcctct ggattt 16

<210> SEQ ID NO 116
<211> LENGTH: 20
<212> TYPE: RNA
<213> ORGANISM: Artificial sequence
<220> FEATURE:
<223> OTHER INFORMATION: Synthetic oligonucleotide

<400> SEQUENCE: 116
gauaauguga gaacaugccu 20

<210> SEQ ID NO 117
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 117
aggcatgttc tcacattatc 20

<210> SEQ ID NO 118
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 118
ggctactacg ccgtca 16

<210> SEQ ID NO 119
<211> LENGTH: 19
<212> TYPE: DNA
<213> ORGANISM: Artificial sequence
<220> FEATURE:
<223> OTHER INFORMATION: Primer

<400> SEQUENCE: 119 tttttgcgc ggtcctttc 19

<210> SEQ ID NO 120
<211> LENGTH: 22
<212> TYPE: DNA
<213> ORGANISM: Artificial sequence
<220> FEATURE:
<223> OTHER INFORMATION: Primer

<400> SEQUENCE: 120
gagggaccag agagagcaag ac 22

<210> SEQ ID NO 121
<211> LENGTH: 19
<212> TYPE: DNA
<213> ORGANISM: Artificial sequence
<220> FEATURE:
<223> OTHER INFORMATION: Probe

<400> SEQUENCE: 121
cgccttccgt ccgtcggct 19

<210> SEQ ID NO 122
<211> LENGTH: 21
<212> TYPE: DNA
<213> ORGANISM: Artificial Sequence
<220> FEATURE:
<223> OTHER INFORMATION: Primer

<400> SEQUENCE: 122
tggagactct cagggtcgaa a 21

<210> SEQ ID NO 123
<211> LENGTH: 22
<212> TYPE: DNA
<213> ORGANISM: Artificial Sequence
<220> FEATURE:
<223> OTHER INFORMATION: Primer

<400> SEQUENCE: 123
ggcgtttgga gtggtagaaa tc 22

<210> SEQ ID NO 124
<211> LENGTH: 20
<212> TYPE: DNA
<213> ORGANISM: Artificial Sequence
<220> FEATURE:
<223> OTHER INFORMATION: Probe

<400> SEQUENCE: 124
cggcggcaga ccagcatgac 20

<210> SEQ ID NO 125
<211> LENGTH: 17
<212> TYPE: DNA
<213> ORGANISM: Artificial sequence
<220> FEATURE:
<223> OTHER INFORMATION: Synthetic oligonucleotide

<400> SEQUENCE: 125
gcatgttctc acattat 17

<210> SEQ ID NO 126
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(14)
<223> OTHER INFORMATION: bases at these positions are RNA
<220> FEATURE:
<221> NAME/KEY: misc_feature
<222> LOCATION: (16)..(16)
<223> OTHER INFORMATION: bases at these positions are RNA

<400> SEQUENCE: 126
caccugcggg aagctc 16

<210> SEQ ID NO 127
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(6)
<223> OTHER INFORMATION: bases at these positions are RNA
<220> FEATURE:
<221> NAME/KEY: misc_feature
<222> LOCATION: (8)..(10)
<223> OTHER INFORMATION: bases at these positions are RNA
<220> FEATURE:
<221> NAME/KEY: misc_feature
<222> LOCATION: (13)..(16)
<223> OTHER INFORMATION: bases at these positions are RNA

<400> SEQUENCE: 127
agacuctcgg ttccga 16

<210> SEQ ID NO 128
<211> LENGTH: 16
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: bases at these positions are RNA
<220> FEATURE:
<221> NAME/KEY: misc_feature
<222> LOCATION: (5)..(6)
<223> OTHER INFORMATION: bases at these positions are RNA
<220> FEATURE:
<221> NAME/KEY: misc_feature
<222> LOCATION: (8)..(8)
<223> OTHER INFORMATION: bases at these positions are RNA
<220> FEATURE:
<221> NAME/KEY: misc_feature
<222> LOCATION: (10)..(12)
<223> OTHER INFORMATION: bases at these positions are RNA
<220> FEATURE:
<221> NAME/KEY: misc_feature
<222> LOCATION: (14)..(14)
<223> OTHER INFORMATION: bases at these positions are RNA
<220> FEATURE:
<221> NAME/KEY: misc_feature
<222> LOCATION: (16)..(16)
<223> OTHER INFORMATION: bases at these positions are RNA

<400> SEQUENCE: 128
ctttuctatc agtctc 16

<210> SEQ ID NO 129
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: bases at these positions are RNA
<220> FEATURE:
<221> NAME/KEY: misc_feature
<222> LOCATION: (4)..(5)
<223> OTHER INFORMATION: bases at these positions are RNA
<220> FEATURE:
<221> NAME/KEY: misc_feature
<222> LOCATION: (7)..(8)
<223> OTHER INFORMATION: bases at these positions are RNA
<220> FEATURE:
<221> NAME/KEY: misc_feature
<222> LOCATION: (10)..(10)
<223> OTHER INFORMATION: bases at these positions are RNA
<220> FEATURE:
<221> NAME/KEY: misc_feature
<222> LOCATION: (12)..(12)
<223> OTHER INFORMATION: bases at these positions are RNA
<220> FEATURE:

```
<221> NAME/KEY: misc_feature
<222> LOCATION: (16)..(16)
<223> OTHER INFORMATION: bases at these positions are RNA

<400> SEQUENCE: 129

cttcutgatg tctttc                                                     16

<210> SEQ ID NO 130
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(9)
<223> OTHER INFORMATION: bases at these positions are RNA
<220> FEATURE:
<221> NAME/KEY: misc_feature
<222> LOCATION: (11)..(16)
<223> OTHER INFORMATION: bases at these positions are RNA

<400> SEQUENCE: 130

ggacugaaat agcaga                                                     16

<210> SEQ ID NO 131
<211> LENGTH: 16
<212> TYPE: DNA
<213> ORGANISM: Artificial sequence
<220> FEATURE:
<223> OTHER INFORMATION: Synthetic oligonuclotide
<220> FEATURE:
<221> NAME/KEY: misc_feature
<222> LOCATION: (1)..(14)
<223> OTHER INFORMATION: bases at these positions are RNA
<220> FEATURE:
<221> NAME/KEY: misc_feature
<222> LOCATION: (16)..(16)
<223> OTHER INFORMATION: bases at these positions are RNA

<400> SEQUENCE: 131

aggcuggccc ccactg                                                     16

<210> SEQ ID NO 132
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(2)
<223> OTHER INFORMATION: bases at these positions are RNA
<220> FEATURE:
<221> NAME/KEY: misc_feature
<222> LOCATION: (5)..(5)
<223> OTHER INFORMATION: bases at these positions are RNA
<220> FEATURE:
<221> NAME/KEY: misc_feature
<222> LOCATION: (8)..(9)
<223> OTHER INFORMATION: bases at these positions are RNA
<220> FEATURE:
<221> NAME/KEY: misc_feature
<222> LOCATION: (12)..(12)
<223> OTHER INFORMATION: bases at these positions are RNA
<220> FEATURE:
<221> NAME/KEY: misc_feature
<222> LOCATION: (15)..(16)
<223> OTHER INFORMATION: bases at these positions are RNA

<400> SEQUENCE: 132

ggttuttgat tcttcc                                                     16
```

<210> SEQ ID NO 133
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: bases at these positions are RNA
<220> FEATURE:
<221> NAME/KEY: misc_feature
<222> LOCATION: (4)..(5)
<223> OTHER INFORMATION: bases at these positions are RNA
<220> FEATURE:
<221> NAME/KEY: misc_feature
<222> LOCATION: (7)..(7)
<223> OTHER INFORMATION: bases at these positions are RNA
<220> FEATURE:
<221> NAME/KEY: misc_feature
<222> LOCATION: (9)..(10)
<223> OTHER INFORMATION: bases at these positions are RNA
<220> FEATURE:
<221> NAME/KEY: misc_feature
<222> LOCATION: (13)..(16)
<223> OTHER INFORMATION: bases at these positions are RNA

<400> SEQUENCE: 133
gttautgtgg ttggcg 16

<210> SEQ ID NO 134
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: bases at these positions are RNA
<220> FEATURE:
<221> NAME/KEY: misc_feature
<222> LOCATION: (4)..(6)
<223> OTHER INFORMATION: bases at these positions are RNA
<220> FEATURE:
<221> NAME/KEY: misc_feature
<222> LOCATION: (8)..(8)
<223> OTHER INFORMATION: bases at these positions are RNA
<220> FEATURE:
<221> NAME/KEY: misc_feature
<222> LOCATION: (10)..(13)
<223> OTHER INFORMATION: bases at these positions are RNA
<220> FEATURE:
<221> NAME/KEY: misc_feature
<222> LOCATION: (15)..(16)
<223> OTHER INFORMATION: bases at these positions are RNA

<400> SEQUENCE: 134
attcugtgtg cactgc 16

<210> SEQ ID NO 135
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: bases at these positions are RNA
<220> FEATURE:
<221> NAME/KEY: misc_feature
<222> LOCATION: (3)..(3)

<223> OTHER INFORMATION: bases at these positions are RNA
<220> FEATURE:
<221> NAME/KEY: misc_feature
<222> LOCATION: (5)..(5)
<223> OTHER INFORMATION: bases at these positions are RNA
<220> FEATURE:
<221> NAME/KEY: misc_feature
<222> LOCATION: (7)..(9)
<223> OTHER INFORMATION: bases at these positions are RNA
<220> FEATURE:
<221> NAME/KEY: misc_feature
<222> LOCATION: (14)..(14)
<223> OTHER INFORMATION: bases at these positions are RNA
<220> FEATURE:
<221> NAME/KEY: misc_feature
<222> LOCATION: (16)..(16)
<223> OTHER INFORMATION: bases at these positions are RNA

<400> SEQUENCE: 135
ctgtutgagt tttctc 16

<210> SEQ ID NO 136
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(2)
<223> OTHER INFORMATION: bases at these positions are RNA
<220> FEATURE:
<221> NAME/KEY: misc_feature
<222> LOCATION: (4)..(5)
<223> OTHER INFORMATION: bases at these positions are RNA
<220> FEATURE:
<221> NAME/KEY: misc_feature
<222> LOCATION: (7)..(16)
<223> OTHER INFORMATION: bases at these positions are RNA

<400> SEQUENCE: 136
aatcutccag ggccac 16

<210> SEQ ID NO 137
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (2)..(3)
<223> OTHER INFORMATION: bases at these positions are RNA
<220> FEATURE:
<221> NAME/KEY: misc_feature
<222> LOCATION: (5)..(5)
<223> OTHER INFORMATION: bases at these positions are RNA
<220> FEATURE:
<221> NAME/KEY: misc_feature
<222> LOCATION: (7)..(7)
<223> OTHER INFORMATION: bases at these positions are RNA
<220> FEATURE:
<221> NAME/KEY: misc_feature
<222> LOCATION: (9)..(9)
<223> OTHER INFORMATION: bases at these positions are RNA
<220> FEATURE:
<221> NAME/KEY: misc_feature
<222> LOCATION: (11)..(14)
<223> OTHER INFORMATION: bases at these positions are RNA
<220> FEATURE:
<221> NAME/KEY: misc_feature
<222> LOCATION: (16)..(16)
<223> OTHER INFORMATION: bases at these positions are RNA

<400> SEQUENCE: 137
tcatutctat ggaata 16

<210> SEQ ID NO 138
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(15)
<223> OTHER INFORMATION: bases at these positions are RNA

<400> SEQUENCE: 138
caacugaacc acccgt 16

<210> SEQ ID NO 139
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: bases at these positions are RNA
<220> FEATURE:
<221> NAME/KEY: misc_feature
<222> LOCATION: (4)..(6)
<223> OTHER INFORMATION: bases at these positions are RNA
<220> FEATURE:
<221> NAME/KEY: misc_feature
<222> LOCATION: (8)..(13)
<223> OTHER INFORMATION: bases at these positions are RNA
<220> FEATURE:
<221> NAME/KEY: misc_feature
<222> LOCATION: (15)..(16)
<223> OTHER INFORMATION: bases at these positions are RNA

<400> SEQUENCE: 139
attauatggc aactca 16

<210> SEQ ID NO 140
<211> LENGTH: 16
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (1)..(9)
<223> OTHER INFORMATION: bases at these positions are RNA
<220> FEATURE:
<221> NAME/KEY: misc_feature
<222> LOCATION: (11)..(11)
<223> OTHER INFORMATION: bases at these positions are RNA
<220> FEATURE:
<221> NAME/KEY: misc_feature
<222> LOCATION: (13)..(14)
<223> OTHER INFORMATION: bases at these positions are RNA
<220> FEATURE:
<221> NAME/KEY: misc_feature
<222> LOCATION: (16)..(16)
<223> OTHER INFORMATION: bases at these positions are RNA

<400> SEQUENCE: 140
acccucaagt ctcctg 16

<210> SEQ ID NO 141
<211> LENGTH: 17
<212> TYPE: DNA

<213> ORGANISM: Artificial sequence
<220> FEATURE:
<223> OTHER INFORMATION: Synthetic oligonucleotide

<400> SEQUENCE: 141
ggcatgttct cacatta 17

<210> SEQ ID NO 142
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 142
ggactgaaat tgcaga 16

<210> SEQ ID NO 143
<211> LENGTH: 16
<212> TYPE: DNA
<213> ORGANISM: Artificial sequence
<220> FEATURE:
<223> OTHER INFORMATION: synthetic oligonucleotide
<220> FEATURE:
<221> NAME/KEY: misc_feature
<222> LOCATION: (1)..(1)
<223> OTHER INFORMATION: bases at these positions are RNA
<220> FEATURE:
<221> NAME/KEY: misc_feature
<222> LOCATION: (3)..(5)
<223> OTHER INFORMATION: bases at these positions are RNA
<220> FEATURE:
<221> NAME/KEY: misc_feature
<222> LOCATION: (7)..(9)
<223> OTHER INFORMATION: bases at these positions are RNA
<220> FEATURE:
<221> NAME/KEY: misc_feature
<222> LOCATION: (11)..(11)
<223> OTHER INFORMATION: bases at these positions are RNA
<220> FEATURE:
<221> NAME/KEY: misc_feature
<222> LOCATION: (13)..(13)
<223> OTHER INFORMATION: bases at these positions are RNA
<220> FEATURE:
<221> NAME/KEY: misc_feature
<222> LOCATION: (15)..(16)
<223> OTHER INFORMATION: bases at these positions are RNA

<400> SEQUENCE: 143
gtcugtgcat ctctcc 16

<210> SEQ ID NO 144
<211> LENGTH: 16
<212> TYPE: DNA
<213> ORGANISM: Artificial sequence
<220> FEATURE:
<223> OTHER INFORMATION: synthetic oligonucleotide

<400> SEQUENCE: 144
acatcttcag atcatt 16

<210> SEQ ID NO 145
<211> LENGTH: 16
<212> TYPE: DNA
<213> ORGANISM: Artificial sequence
<220> FEATURE:
<223> OTHER INFORMATION: synthetic oligonucleotide
<220> FEATURE:
<221> NAME/KEY: misc_feature
<222> LOCATION: (2)..(5)
<223> OTHER INFORMATION: bases at these positions are RNA -continued

```
<220> FEATURE:
<221> NAME/KEY: misc_feature
<222> LOCATION: (7)..(7)
<223> OTHER INFORMATION: bases at these positions are RNA
<220> FEATURE:
<221> NAME/KEY: misc_feature
<222> LOCATION: (9)..(9)
<223> OTHER INFORMATION: bases at these positions are RNA
<220> FEATURE:
<221> NAME/KEY: misc_feature
<222> LOCATION: (11)..(13)
<223> OTHER INFORMATION: bases at these positions are RNA
<220> FEATURE:
<221> NAME/KEY: misc_feature
<222> LOCATION: (16)..(16)
<223> OTHER INFORMATION: bases at these positions are RNA

<400> SEQUENCE: 145

taguctctgt cagtta                                              16

<210> SEQ ID NO 146
<211> LENGTH: 17
<212> TYPE: DNA
<213> ORGANISM: Artificial sequence
<220> FEATURE:
<223> OTHER INFORMATION: synthetic oligonucleotide
<220> FEATURE:
<221> NAME/KEY: misc_feature
<222> LOCATION: (1)..(3)
<223> OTHER INFORMATION: bases at these positions are RNA
<220> FEATURE:
<221> NAME/KEY: misc_feature
<222> LOCATION: (5)..(6)
<223> OTHER INFORMATION: bases at these positions are RNA
<220> FEATURE:
<221> NAME/KEY: misc_feature
<222> LOCATION: (8)..(8)
<223> OTHER INFORMATION: bases at these positions are RNA
<220> FEATURE:
<221> NAME/KEY: misc_feature
<222> LOCATION: (10)..(13)
<223> OTHER INFORMATION: bases at these positions are RNA
<220> FEATURE:
<221> NAME/KEY: misc_feature
<222> LOCATION: (16)..(16)
<223> OTHER INFORMATION: bases at these positions are RNA

<400> SEQUENCE: 146

gcatgutctc acattat                                             17

<210> SEQ ID NO 147
<211> LENGTH: 16
<212> TYPE: DNA
<213> ORGANISM: Artificial sequence
<220> FEATURE:
<223> OTHER INFORMATION: synthetic oligonucleotide

<400> SEQUENCE: 147

acaaggacac caagat                                              16

<210> SEQ ID NO 148
<211> LENGTH: 25
<212> TYPE: DNA
<213> ORGANISM: Artificial sequence
<220> FEATURE:
<223> OTHER INFORMATION: Primer

<400> SEQUENCE: 148

gggattacag agatcgtgac tgatt                                    25

<210> SEQ ID NO 149
```

<211> LENGTH: 20
<212> TYPE: DNA
<213> ORGANISM: Artificial sequence
<220> FEATURE:
<223> OTHER INFORMATION: Primer

<400> SEQUENCE: 149
tgcagctgga agaaccaaaa 20

<210> SEQ ID NO 150
<211> LENGTH: 30
<212> TYPE: DNA
<213> ORGANISM: Artificial sequence
<220> FEATURE:
<223> OTHER INFORMATION: Probe

<400> SEQUENCE: 150
cagagtaaaa tacccattcc agctcctggg 30

<210> SEQ ID NO 151
<211> LENGTH: 21
<212> TYPE: DNA
<213> ORGANISM: Artificial sequence
<220> FEATURE:
<223> OTHER INFORMATION: Primer

<400> SEQUENCE: 151
gattcgtcag ctttgccaag t 21

<210> SEQ ID NO 152
<211> LENGTH: 22
<212> TYPE: DNA
<213> ORGANISM: Artificial sequence
<220> FEATURE:
<223> OTHER INFORMATION: Primer

<400> SEQUENCE: 152
cgtctgttca gttgtcaatg ca 22

<210> SEQ ID NO 153
<211> LENGTH: 29
<212> TYPE: DNA
<213> ORGANISM: Artificial sequence
<220> FEATURE:
<223> OTHER INFORMATION: Probe

<400> SEQUENCE: 153
tctgggcctc aaggataaca acatcgttt 29

<210> SEQ ID NO 154
<211> LENGTH: 16
<212> TYPE: DNA
<213> ORGANISM: Artificial sequence
<220> FEATURE:
<223> OTHER INFORMATION: synthetic oligonucleotide
<220> FEATURE:
<221> NAME/KEY: misc_feature
<222> LOCATION: (1)..(1)
<223> OTHER INFORMATION: bases at these positions are RNA
<220> FEATURE:
<221> NAME/KEY: misc_feature
<222> LOCATION: (4)..(4)
<223> OTHER INFORMATION: bases at these positions are RNA
<220> FEATURE:
<221> NAME/KEY: misc_feature
<222> LOCATION: (6)..(7)
<223> OTHER INFORMATION: bases at these positions are RNA
<220> FEATURE:
<221> NAME/KEY: misc_feature -continued

```
<222> LOCATION: (7)..(10)
<223> OTHER INFORMATION: bases at these positions are RNA
<220> FEATURE:
<221> NAME/KEY: misc_feature
<222> LOCATION: (13)..(16)
<223> OTHER INFORMATION: bases at these positions are RNA

<400> SEQUENCE: 154

gttatugtgg ttggcg                                                16
```